US010851137B2

(12) United States Patent
Kelly et al.

(10) Patent No.: US 10,851,137 B2
(45) Date of Patent: Dec. 1, 2020

(54) POLYPEPTIDE AND IMMUNE MODULATION

(71) Applicant: 4D Pharma Research Limited, Aberdeen (GB)

(72) Inventors: Denise Kelly, Aberdeen (GB); Angela Patterson, Aberdeen (GB); Edouard Monnais, Aberdeen (GB); Imke Mulder, Aberdeen (GB)

(73) Assignee: 4D Pharma Research Limited, Aberdeen (GB)

(*) Notice: Subject to any disclaimer, the term of this patent is extended or adjusted under 35 U.S.C. 154(b) by 0 days.

(21) Appl. No.: 15/704,245

(22) Filed: Sep. 14, 2017

(65) Prior Publication Data

US 2018/0072778 A1  Mar. 15, 2018

Related U.S. Application Data

(62) Division of application No. 14/249,710, filed on Apr. 10, 2014, now Pat. No. 9,796,762.

(30) Foreign Application Priority Data

Apr. 10, 2013 (GB) .................................. 1306536.2

(51) Int. Cl.
A61K 39/02 (2006.01)
C07K 14/195 (2006.01)
A23P 10/30 (2016.01)
A61K 38/16 (2006.01)

(52) U.S. Cl.
CPC ............ *C07K 14/195* (2013.01); *A23P 10/30* (2016.08); *A61K 38/164* (2013.01); *A61K 39/02* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,683,202 A | 7/1987 | Mullis | |
| 4,816,567 A | 3/1989 | Cabilly et al. | |
| 5,589,168 A | 12/1996 | Allen et al. | |
| 5,599,795 A | 2/1997 | McCann et al. | |
| 5,674,707 A | 10/1997 | Hintz et al. | |
| 5,741,665 A | 4/1998 | Kato et al. | |
| 5,925,657 A | 7/1999 | Seed et al. | |
| 5,951,977 A | 9/1999 | Nisbet et al. | |
| 6,348,452 B1 | 2/2002 | Brown et al. | |
| 6,468,964 B1 | 10/2002 | Rowe et al. | |
| 6,645,530 B1 | 11/2003 | Borody | |
| 7,101,565 B2 | 9/2006 | Monte | |
| 7,485,325 B2 | 2/2009 | Swain | |
| 7,625,704 B2 | 12/2009 | Fredricks et al. | |
| 7,749,494 B2 | 7/2010 | Renaud et al. | |
| 7,998,474 B2 | 8/2011 | Kelly | |
| 8,197,805 B2 | 6/2012 | Lin et al. | |
| 8,287,932 B2 | 10/2012 | Rosales et al. | |
| 8,460,648 B2 | 6/2013 | Borody | |
| 8,557,233 B2 | 10/2013 | MacSharry et al. | |
| 9,011,834 B1 | 4/2015 | McKenzie et al. | |
| 9,314,489 B2 | 4/2016 | Kelly et al. | |
| 9,371,510 B2 | 6/2016 | Moore | |
| 9,376,473 B2 | 6/2016 | Gleiberman et al. | |
| 9,539,293 B2 | 1/2017 | Kelly et al. | |
| 9,610,307 B2 | 4/2017 | Berry et al. | |
| 9,662,381 B2 | 5/2017 | Honda et al. | |
| 9,796,762 B2 | 10/2017 | Kelly et al. | |
| 9,808,519 B2 | 11/2017 | Honda et al. | |
| 9,839,655 B2 | 12/2017 | Mulder et al. | |
| 9,855,302 B2 | 1/2018 | Gajewski et al. | |
| 9,974,815 B2 | 5/2018 | Mulder et al. | |
| 9,987,311 B2 | 6/2018 | Mulder et al. | |
| 10,046,015 B2 | 8/2018 | Mulder et al. | |
| 10,058,574 B2 | 8/2018 | Grant et al. | |
| 10,080,772 B2 | 9/2018 | Crouzet et al. | |
| 10,086,020 B2 | 10/2018 | Bernalier-Donadille et al. | |
| 10,086,021 B2 | 10/2018 | Jeffery et al. | |
| 10,086,022 B2 | 10/2018 | Bernalier-Donadille et al. | |
| 10,086,023 B2 | 10/2018 | Bernalier-Donadille et al. | |
| 2003/0147858 A1 | 8/2003 | Renaud et al. | |
| 2004/0005304 A1 | 1/2004 | Brudnak | |
| 2004/0106564 A1 | 6/2004 | Nilius et al. | |
| 2006/0062774 A1 | 3/2006 | Davis et al. | |
| 2006/0073161 A1 | 4/2006 | Breton | |
| 2006/0115465 A1 | 6/2006 | MacFarlane et al. | |
| 2007/0167423 A1 | 7/2007 | Bergauer et al. | |
| 2007/0258953 A1 | 11/2007 | Duncan et al. | |
| 2007/0286913 A1 | 12/2007 | Swain et al. | |
| 2008/0069861 A1 | 3/2008 | Brown et al. | |
| 2008/0206212 A1 | 8/2008 | McMahon et al. | |
| 2008/0260906 A1 | 10/2008 | Stojanovic | |
| 2008/0299098 A1 | 12/2008 | Se et al. | |

(Continued)

FOREIGN PATENT DOCUMENTS

CA 2768301 A 1/2011
CA 2768301 A1 1/2011

(Continued)

OTHER PUBLICATIONS

Girard (Vaccine. vol. 29, Issue 38, 2 Sep. 2011, pp. 6695-6703).*

(Continued)

*Primary Examiner* — Jennifer E Graser
(74) *Attorney, Agent, or Firm* — Wilson Sonsini Goodrich & Rosati

(57) ABSTRACT

The present invention relates to *Roseburia* flagellin, and/or a polynucleotide sequence encoding said *Roseburia* flagellin, and/or a vector comprising said polynucleotide sequence, and/or a host cell, including bacteria, comprising said vector, and/or a host cell, including bacteria, comprising said polynucleotide sequence, for use in modulating the inflammation of a tissue or an organ in a subject.

17 Claims, 66 Drawing Sheets

Specification includes a Sequence Listing.

(56) References Cited

U.S. PATENT DOCUMENTS

| | | |
|---|---|---|
| 2009/0217401 A1 | 8/2009 | Korman et al. |
| 2010/0028449 A1 | 2/2010 | Prakash et al. |
| 2010/0047209 A1 | 2/2010 | Stanton et al. |
| 2010/0247489 A1 | 9/2010 | Saur-Brosch |
| 2010/0284973 A1 | 11/2010 | Schiffer-Mannioui et al. |
| 2010/0303782 A1 | 12/2010 | Cobb et al. |
| 2010/0311686 A1 | 12/2010 | Kasper et al. |
| 2010/0316617 A1 | 12/2010 | Renaud et al. |
| 2011/0053829 A1 | 3/2011 | Baumhof et al. |
| 2011/0086011 A1 | 4/2011 | Kasper et al. |
| 2011/0280840 A1 | 11/2011 | Blaser et al. |
| 2012/0020943 A1 | 1/2012 | Lin |
| 2012/0107279 A1 | 5/2012 | Arigoni et al. |
| 2013/0022575 A1 | 1/2013 | Cassity |
| 2013/0130988 A1 | 5/2013 | Blareau et al. |
| 2013/0195802 A1 | 8/2013 | Moore |
| 2013/0280724 A1 | 10/2013 | Ramadan et al. |
| 2013/0316032 A1 | 11/2013 | Itoh et al. |
| 2013/0336931 A1 | 12/2013 | Wadstroem et al. |
| 2014/0037716 A1 | 2/2014 | Nowill et al. |
| 2014/0056852 A1 | 2/2014 | Guglielmetti et al. |
| 2014/0112897 A1 | 4/2014 | Pyne et al. |
| 2014/0147425 A1 | 5/2014 | Henn et al. |
| 2014/0154218 A1 | 6/2014 | Kohno et al. |
| 2014/0179770 A1 | 6/2014 | Zhang et al. |
| 2014/0193464 A1 | 7/2014 | Lin et al. |
| 2014/0199281 A1 | 7/2014 | Henn et al. |
| 2014/0227227 A1 | 8/2014 | Qin et al. |
| 2014/0328803 A1 | 11/2014 | McKenzie et al. |
| 2014/0335131 A1 | 11/2014 | Mazmanian et al. |
| 2014/0341921 A1 | 11/2014 | Honda et al. |
| 2014/0363397 A1 | 12/2014 | Allen-Vercoe et al. |
| 2015/0044173 A1 | 2/2015 | Jones et al. |
| 2015/0071957 A1 | 3/2015 | Kelly et al. |
| 2015/0104418 A1 | 4/2015 | Flint et al. |
| 2015/0132264 A1 | 5/2015 | Kelly et al. |
| 2015/0284781 A1 | 10/2015 | Klumpp et al. |
| 2016/0058804 A1 | 3/2016 | Jones et al. |
| 2016/0067188 A1 | 3/2016 | Cade et al. |
| 2016/0184370 A1 | 6/2016 | McKenzie et al. |
| 2016/0199424 A1 | 7/2016 | Berry et al. |
| 2016/0223553 A1 | 8/2016 | Sears et al. |
| 2016/0279177 A1 | 9/2016 | Kelly et al. |
| 2017/0143772 A1 | 5/2017 | Mulder et al. |
| 2017/0143773 A1 | 5/2017 | Mulder et al. |
| 2017/0143774 A1 | 5/2017 | Mulder et al. |
| 2017/0143775 A1 | 5/2017 | Mulder et al. |
| 2017/0319634 A1 | 11/2017 | Grant et al. |
| 2017/0326184 A1 | 11/2017 | Patterson et al. |
| 2017/0326202 A1 | 11/2017 | Kelly |
| 2017/0354695 A1 | 12/2017 | Grant et al. |
| 2017/0360856 A1 | 12/2017 | Grant et al. |
| 2017/0368110 A1 | 12/2017 | Grant et al. |
| 2018/0055892 A1 | 3/2018 | Mulder et al. |
| 2018/0078585 A1 | 3/2018 | Mulder et al. |
| 2018/0078587 A1 | 3/2018 | Crott et al. |
| 2018/0133265 A1 | 5/2018 | Stevenson |
| 2019/0000892 A1 | 1/2019 | Mulder et al. |
| 2019/0015459 A1 | 1/2019 | Grant et al. |

FOREIGN PATENT DOCUMENTS

| | | |
|---|---|---|
| CN | 1863540 A | 11/2006 |
| CN | 1917946 A | 2/2007 |
| CN | 1954066 A | 4/2007 |
| CN | 101590081 A | 12/2009 |
| CN | 102304483 A | 1/2012 |
| CN | 102031235 B | 7/2012 |
| CN | 102093967 B | 1/2013 |
| CN | 102905558 A | 1/2013 |
| CN | 102940652 A | 2/2013 |
| CN | 102373172 B | 3/2013 |
| CN | 103037876 A | 4/2013 |
| CN | 103142656 A | 6/2013 |
| CN | 103146620 A | 6/2013 |
| CN | 103156888 A | 6/2013 |
| CN | 103652322 A | 3/2014 |
| CN | 103781487 A | 5/2014 |
| CN | 103820363 A | 5/2014 |
| CN | 103849590 A | 6/2014 |
| CN | 103865846 A | 6/2014 |
| CN | 103930117 A | 7/2014 |
| CN | 103981115 A | 8/2014 |
| CN | 103981117 A | 8/2014 |
| CN | 104160014 A | 11/2014 |
| CN | 104195075 A | 12/2014 |
| CN | 103509741 B | 2/2015 |
| CN | 102940652 B | 3/2015 |
| CN | 104435000 A | 3/2015 |
| CN | 103037876 B | 4/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |
| CN | 104546942 A | 4/2015 |
| CN | 104560820 A | 4/2015 |
| CN | 105112333 A | 12/2015 |
| CN | 103820363 B | 2/2016 |
| CN | 103865846 B | 3/2016 |
| CN | 105982919 A | 10/2016 |
| DE | 19826928 A1 | 12/1999 |
| DE | 10206995 A1 | 9/2003 |
| EP | 0120516 A2 | 10/1984 |
| EP | 0238023 A2 | 9/1987 |
| EP | 0433299 A1 | 6/1991 |
| EP | 0449375 A2 | 10/1991 |
| EP | 0581171 A1 | 2/1994 |
| EP | 0778778 A1 | 6/1997 |
| EP | 0888118 A1 | 1/1999 |
| EP | 1141235 A2 | 10/2001 |
| EP | 1227152 A1 | 7/2002 |
| EP | 1383514 A1 | 1/2004 |
| EP | 1448995 A1 | 8/2004 |
| EP | 1481681 A1 | 12/2004 |
| EP | 1765391 A1 | 3/2007 |
| EP | 1675481 B1 | 11/2008 |
| EP | 1997499 A1 | 12/2008 |
| EP | 1997905 A1 | 12/2008 |
| EP | 1997906 A1 | 12/2008 |
| EP | 1997907 A1 | 12/2008 |
| EP | 2044436 A2 | 4/2009 |
| EP | 2103226 A1 | 9/2009 |
| EP | 2133088 A3 | 1/2010 |
| EP | 1280541 B2 | 3/2010 |
| EP | 2236598 A1 | 10/2010 |
| EP | 2286832 A1 | 2/2011 |
| EP | 2308498 A1 | 4/2011 |
| EP | 2217253 B1 | 6/2011 |
| EP | 1940243 B1 | 8/2011 |
| EP | 2359838 A1 | 8/2011 |
| EP | 1855550 B1 | 10/2011 |
| EP | 1871400 B1 | 10/2011 |
| EP | 2124972 B1 | 6/2012 |
| EP | 1773361 B2 | 9/2012 |
| EP | 1945234 B1 | 12/2012 |
| EP | 2323493 B8 | 12/2012 |
| EP | 2323494 B8 | 12/2012 |
| EP | 1629850 B2 | 5/2013 |
| EP | 2203551 B1 | 8/2013 |
| EP | 2140771 B1 | 12/2013 |
| EP | 2687227 A1 | 1/2014 |
| EP | 2179028 B1 | 8/2014 |
| EP | 2650002 A4 | 8/2014 |
| EP | 2164349 B1 | 9/2014 |
| EP | 2134835 B1 | 10/2014 |
| EP | 2810652 A2 | 12/2014 |
| EP | 2305838 B1 | 1/2015 |
| EP | 2832859 A1 | 2/2015 |
| ES | 2408279 A2 | 6/2013 |
| JP | H08259450 A | 10/1996 |
| JP | 2003261453 A | 9/2003 |
| JP | 2005097280 A | 4/2005 |
| JP | 2006265212 A | 10/2006 |

(56) References Cited

FOREIGN PATENT DOCUMENTS

| | | |
|---|---|---|
| JP | 2007084533 A | 4/2007 |
| JP | 2007116991 A | 5/2007 |
| JP | 2008195635 A | 8/2008 |
| JP | 2009507023 A | 2/2009 |
| JP | 2010246523 A | 11/2010 |
| JP | 5031249 B2 | 9/2012 |
| JP | 2013005759 A | 1/2013 |
| JP | 5183848 B2 | 4/2013 |
| JP | 2013527240 A | 6/2013 |
| JP | 2013201912 A | 10/2013 |
| JP | 2014196260 A | 10/2014 |
| JP | 2014534957 A | 12/2014 |
| JP | 2015500792 A | 1/2015 |
| JP | 5710876 B2 | 4/2015 |
| JP | 5792105 B2 | 10/2015 |
| KR | 100468522 B1 | 1/2005 |
| KR | 20100128168 A | 12/2010 |
| KR | 1020100128168 | 12/2010 |
| KR | 101017448 B1 | 2/2011 |
| KR | 101057357 B1 | 8/2011 |
| KR | 20130021764 A | 3/2013 |
| KR | 101250463 B1 | 4/2013 |
| KR | 20140037544 A | 3/2014 |
| KR | 20140061328 A | 5/2014 |
| PL | 229020 B1 | 5/2018 |
| RU | 2078815 C1 | 5/1997 |
| TW | I417054 B | 12/2013 |
| WO | WO-8807865 A1 | 10/1988 |
| WO | WO-9117243 A1 | 11/1991 |
| WO | WO-9611014 A1 | 4/1996 |
| WO | WO-9720577 A1 | 6/1997 |
| WO | WO-9730717 A1 | 8/1997 |
| WO | WO-9735956 A1 | 10/1997 |
| WO | WO-9843081 A1 | 10/1998 |
| WO | WO-9855131 A1 | 12/1998 |
| WO | WO-9857631 A1 | 12/1998 |
| WO | WO-9919459 A1 | 4/1999 |
| WO | WO-9942568 A1 | 8/1999 |
| WO | WO-9945955 A1 | 9/1999 |
| WO | WO-0116120 A1 | 3/2001 |
| WO | WO-0158275 A2 | 8/2001 |
| WO | WO-0185187 A1 | 11/2001 |
| WO | WO-0193904 A1 | 12/2001 |
| WO | WO-0207741 A1 | 1/2002 |
| WO | WO-0242328 A2 | 5/2002 |
| WO | WO-02070670 A1 | 9/2002 |
| WO | WO-02085933 A1 | 10/2002 |
| WO | WO-02094296 A1 | 11/2002 |
| WO | WO-03010297 A1 | 2/2003 |
| WO | WO-03022255 A2 | 3/2003 |
| WO | WO-03045317 A2 | 6/2003 |
| WO | WO-03046580 A1 | 6/2003 |
| WO | WO-03053220 A2 | 7/2003 |
| WO | WO-2004003235 A3 | 6/2004 |
| WO | WO-2004085628 A1 | 10/2004 |
| WO | WO-2005007834 A1 | 1/2005 |
| WO | WO-2005030133 A2 | 4/2005 |
| WO | WO-2005032567 A2 | 4/2005 |
| WO | WO-2005058335 A1 | 6/2005 |
| WO | WO-2005032567 A3 | 7/2005 |
| WO | WO-2005093049 A1 | 10/2005 |
| WO | WO-2005107381 A2 | 11/2005 |
| WO | WO-2005121130 A2 | 12/2005 |
| WO | WO-2006012586 A2 | 2/2006 |
| WO | WO-2006033949 A1 | 3/2006 |
| WO | WO-2006033950 A1 | 3/2006 |
| WO | WO-2006033951 A1 | 3/2006 |
| WO | WO-2006102350 A1 | 9/2006 |
| WO | WO-2006102536 A2 | 9/2006 |
| WO | WO-2006091103 A3 | 10/2006 |
| WO | WO-2006110406 A2 | 10/2006 |
| WO | WO-2006130205 A1 | 12/2006 |
| WO | WO-2007027761 A2 | 3/2007 |
| WO | WO-2007056218 A2 | 5/2007 |
| WO | WO-2007064732 A1 | 6/2007 |
| WO | WO-2007064749 A1 | 6/2007 |
| WO | WO-2007098371 A2 | 8/2007 |
| WO | WO-2007136719 A2 | 11/2007 |
| WO | WO-2007140230 A3 | 2/2008 |
| WO | WO-2008031438 A3 | 5/2008 |
| WO | WO-2008055702 A1 | 5/2008 |
| WO | WO-2008055703 A2 | 5/2008 |
| WO | WO-2008064489 A1 | 6/2008 |
| WO | WO-2008073148 A2 | 6/2008 |
| WO | WO-2008076696 A2 | 6/2008 |
| WO | WO-2008053444 A3 | 7/2008 |
| WO | WO-2008083157 A2 | 7/2008 |
| WO | WO-2008134450 A2 | 11/2008 |
| WO | WO-2008153377 A1 | 12/2008 |
| WO | WO-2009027753 A1 | 3/2009 |
| WO | WO-2009030481 A1 | 3/2009 |
| WO | WO-2009055362 A1 | 4/2009 |
| WO | WO-2009059284 A2 | 5/2009 |
| WO | WO-2009072889 A1 | 6/2009 |
| WO | WO-2009079564 A1 | 6/2009 |
| WO | WO-2009043856 A3 | 7/2009 |
| WO | WO-2009080862 A1 | 7/2009 |
| WO | WO-2009100331 A2 | 8/2009 |
| WO | WO-2009116864 A1 | 9/2009 |
| WO | WO-2009128949 A2 | 10/2009 |
| WO | WO-2009138220 A1 | 11/2009 |
| WO | WO-2009149149 A1 | 12/2009 |
| WO | WO-2009151315 A1 | 12/2009 |
| WO | WO-2009154463 A2 | 12/2009 |
| WO | WO-2009156301 A1 | 12/2009 |
| WO | WO-2010002241 A1 | 1/2010 |
| WO | WO-2010036876 A2 | 4/2010 |
| WO | WO-2010037402 A1 | 4/2010 |
| WO | WO-2010037408 A1 | 4/2010 |
| WO | WO-2010037539 A1 | 4/2010 |
| WO | WO-2010048481 A1 | 4/2010 |
| WO | WO-2010063601 A1 | 6/2010 |
| WO | WO-2010081126 A3 | 9/2010 |
| WO | WO-2010129839 A1 | 11/2010 |
| WO | WO-2010130659 A1 | 11/2010 |
| WO | WO-2010130660 A1 | 11/2010 |
| WO | WO-2010130662 A1 | 11/2010 |
| WO | WO-2010130663 A1 | 11/2010 |
| WO | WO-2010130697 A1 | 11/2010 |
| WO | WO-2010130699 A1 | 11/2010 |
| WO | WO-2010130700 A1 | 11/2010 |
| WO | WO-2010130701 A1 | 11/2010 |
| WO | WO-2010130702 A1 | 11/2010 |
| WO | WO-2010130704 A1 | 11/2010 |
| WO | WO-2010130710 A1 | 11/2010 |
| WO | WO-2010130713 A1 | 11/2010 |
| WO | WO-2010/143940 A1 | 12/2010 |
| WO | WO-2010139531 A1 | 12/2010 |
| WO | WO-2010142504 A1 | 12/2010 |
| WO | WO-2010143961 A1 | 12/2010 |
| WO | WO-2010147714 A1 | 12/2010 |
| WO | WO-2010133475 A3 | 1/2011 |
| WO | WO-2011000620 A1 | 1/2011 |
| WO | WO-2011000621 A1 | 1/2011 |
| WO | WO-2011005756 A1 | 1/2011 |
| WO | WO-2010133472 A3 | 2/2011 |
| WO | WO-2011020748 A1 | 2/2011 |
| WO | WO-2011036539 A1 | 3/2011 |
| WO | WO-2011043654 A1 | 4/2011 |
| WO | WO-2011044208 A1 | 4/2011 |
| WO | WO-2011058535 A1 | 5/2011 |
| WO | WO-2011075138 A1 | 6/2011 |
| WO | WO-2011096808 A1 | 8/2011 |
| WO | WO-2011096809 A1 | 8/2011 |
| WO | WO-2011110918 A1 | 9/2011 |
| WO | WO-2011121379 A1 | 10/2011 |
| WO | WO-2011149335 A1 | 12/2011 |
| WO | WO-2011152566 A2 | 12/2011 |
| WO | WO-2011153226 A2 | 12/2011 |
| WO | WO-2011157816 A1 | 12/2011 |
| WO | WO-2012012874 A1 | 2/2012 |
| WO | WO-2012016287 A2 | 2/2012 |
| WO | WO-2012024638 A2 | 2/2012 |
| WO | WO-2011153226 A3 | 3/2012 |

(56) References Cited

FOREIGN PATENT DOCUMENTS

| | | |
|---|---|---|
| WO | WO-2012055408 A1 | 5/2012 |
| WO | WO-2012062780 A1 | 5/2012 |
| WO | WO-2012071380 A1 | 5/2012 |
| WO | WO-2012076739 A1 | 6/2012 |
| WO | WO-2012105312 A1 | 8/2012 |
| WO | WO-2012122478 A1 | 9/2012 |
| WO | WO-2012140636 A1 | 10/2012 |
| WO | WO-2012142605 A1 | 10/2012 |
| WO | WO-2012145491 A2 | 10/2012 |
| WO | WO-2012158517 A1 | 11/2012 |
| WO | WO-2012165843 A2 | 12/2012 |
| WO | WO-2012170478 A2 | 12/2012 |
| WO | WO-2013005836 A1 | 1/2013 |
| WO | WO-2013008039 A2 | 1/2013 |
| WO | WO-2013008102 A2 | 1/2013 |
| WO | WO-2013037068 A1 | 3/2013 |
| WO | WO-2013050792 A1 | 4/2013 |
| WO | WO-2013053836 A1 | 4/2013 |
| WO | WO-2013063849 A1 | 5/2013 |
| WO | WO-2013080561 A1 | 6/2013 |
| WO | WO-2013124725 A1 | 8/2013 |
| WO | WO-2013144701 A1 | 10/2013 |
| WO | WO-2013153358 A1 | 10/2013 |
| WO | WO-2013154725 A1 | 10/2013 |
| WO | WO-2013171515 A1 | 11/2013 |
| WO | WO-2013175038 A1 | 11/2013 |
| WO | WO-2013181694 A1 | 12/2013 |
| WO | WO-2013182038 A1 | 12/2013 |
| WO | WO-2014001368 A1 | 1/2014 |
| WO | WO-2014019271 A1 | 2/2014 |
| WO | WO-2014020004 A1 | 2/2014 |
| WO | WO-2014032108 A1 | 3/2014 |
| WO | WO-2014036182 A2 | 3/2014 |
| WO | WO-2014043593 A2 | 3/2014 |
| WO | WO-2014053608 A1 | 4/2014 |
| WO | WO-2014064359 A1 | 5/2014 |
| WO | WO-2014067976 A1 | 5/2014 |
| WO | WO-2014070014 A1 | 5/2014 |
| WO | WO-2014070225 A1 | 5/2014 |
| WO | WO-2014075745 A1 | 5/2014 |
| WO | WO-2014078911 A1 | 5/2014 |
| WO | WO-2014082050 A1 | 5/2014 |
| WO | WO-2014093622 A2 | 6/2014 |
| WO | WO-2014093635 A1 | 6/2014 |
| WO | WO-2014093655 A2 | 6/2014 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014130540 A1 | 8/2014 |
| WO | WO-2014137211 A1 | 9/2014 |
| WO | WO-2014145958 A2 | 9/2014 |
| WO | WO-2014150094 A1 | 9/2014 |
| WO | WO-2014152338 A1 | 9/2014 |
| WO | WO-2014153194 A2 | 9/2014 |
| WO | WO-2014121302 A3 | 10/2014 |
| WO | WO-2014167338 A1 | 10/2014 |
| WO | WO-2014182966 A1 | 11/2014 |
| WO | WO-2014200334 A1 | 12/2014 |
| WO | WO-2014201037 A2 | 12/2014 |
| WO | WO-2015003001 A1 | 1/2015 |
| WO | WO-2015006355 A2 | 1/2015 |
| WO | WO-2015013214 A2 | 1/2015 |
| WO | WO-2015017625 A1 | 2/2015 |
| WO | WO-2015021936 A1 | 2/2015 |
| WO | WO-201503305 A1 | 3/2015 |
| WO | WO-2015038731 A1 | 3/2015 |
| WO | WO-2015057151 A1 | 4/2015 |
| WO | WO-2015077794 A1 | 5/2015 |
| WO | WO-2015095241 A2 | 6/2015 |
| WO | WO-2015077794 A4 | 7/2015 |
| WO | WO-2015156419 A1 | 10/2015 |
| WO | WO-2015156519 A1 | 10/2015 |
| WO | WO-2015168534 A1 | 11/2015 |
| WO | WO-2015169944 A1 | 11/2015 |
| WO | WO-2015095241 A4 | 12/2015 |
| WO | WO-2016019506 A1 | 2/2016 |
| WO | WO-2016033439 A2 | 3/2016 |
| WO | WO-2016036615 A1 | 3/2016 |
| WO | WO-2016057671 A1 | 4/2016 |
| WO | WO-2016065324 A1 | 4/2016 |
| WO | WO-2016069795 A2 | 5/2016 |
| WO | WO-2016069801 A1 | 5/2016 |
| WO | WO-2016070151 A1 | 5/2016 |
| WO | WO-2016086161 A1 | 6/2016 |
| WO | WO-2016086205 A2 | 6/2016 |
| WO | WO-2016086206 A1 | 6/2016 |
| WO | WO-2016086208 A1 | 6/2016 |
| WO | WO-2016086209 A1 | 6/2016 |
| WO | WO-2016086210 A1 | 6/2016 |
| WO | WO-2016102950 A1 | 6/2016 |
| WO | WO-2016102951 A1 | 6/2016 |
| WO | WO-2016118730 A1 | 7/2016 |
| WO | WO-2016139217 A1 | 9/2016 |
| WO | WO-2016149449 A1 | 9/2016 |
| WO | WO-2016149687 A1 | 9/2016 |
| WO | WO-2016203218 A1 | 12/2016 |
| WO | WO-2016203220 A1 | 12/2016 |
| WO | WO-2017085520 A1 | 5/2017 |
| WO | WO-2017091753 A1 | 6/2017 |
| WO | WO-2017148596 A1 | 9/2017 |
| WO | WO-2018011594 A1 | 1/2018 |
| WO | WO-2018/112365 A2 | 6/2018 |
| WO | WO-2018112363 | 6/2018 |
| WO | WO-2018112363 A1 | 6/2018 |
| WO | WO-2018112365 A2 | 6/2018 |
| WO | WO-2018215782 A1 | 11/2018 |

OTHER PUBLICATIONS

Synott et al (Biotechnol. Prog., 2009, vol. 25, No. 2 552-558).*
Vijay-Kumar et al (J Immunol. Jun. 15, 2008;180(12):8280-5).*
Honko et al (Infect. Immun., Feb. 2006,74(2): p. 1113-1120).*
Mizel et al (J.Immuno. 2010. 185(10): 5677-5682).*
Altschul et al. 'Basic local alignment search tool.' Journal of Molecular Biology. 1990, vol. 215, No. 3, pp. 403-410.
Aminov et al. Molecular diversity, cultivation, and improved detection by ftuorescent in situ hybridization of a dominant group of human gut bacteria related to *Roseburia* spp. or Eubacterium rectale. Applied and environmental microbiology. 2006, vol. 72, No. 9, pp. 6371-6376.
An et al. (1985) "New cloning vehicles for transformation of higher plants," EMBO J. 4:277-284.
An et al. (1986) "Transformation of Tobacco, Tomato, Potato, and *Arabiodopsis thaliana* Using a Binary Ti Vector System," Plant Physiol. 81:301-305.
An et al. (1988) "Binary Vectors," Plant Molecular Biology Manual. A3:1-19.
Archer et al. (1997) "The Molecular Biology of Secreted Enzyme Production by Fungi," Critical Reviews Biotechnology. 17(4):273-306.
Atarashi et al. Induction of colonic regulatory T cells by indigenous *Clostridium* species. Science 331(6015):337-341 (2011).
Ausubel et al. (1999) Short Protocols in Molecular Biology. 4th edition. pp. 7-58 to 7-60, and Chapter 18. pp. 18-1 to 18-23.
Aziz et al. The RAST Server: rapid annotations using subsystems technology. BMC Genomics. 2008, vol. 9, No. 1, pp. 75.
Barcenilla et al. "Phylogenetic relationships of butyrate-producing bacteria from the human gut" Applied and environmental microbiology. 2000, vol. 66, No. 4, pp. 1654-1661.
Beggs (1978) "Transformation of yeast by a replicating hybrid plasmid," Nature. 275:104-109.
Berg et al. (1996) "Enterocolitis and colon cancer in interleukin-10-deficient mice are associated with aberrant cytokine production and CD4(+) TH1-like responses," the Journal of Clinical Investigation. 98(4):1010-1020.
Brasel et al. (2000) "Generation of murine dendritic cells from ftl3-ligand-supplemented bone marrow cultures," Blood. 96(9):3029-3039.

(56) References Cited

OTHER PUBLICATIONS

Butcher et al. (1980) The role of tissue culture in the study of crown-gall tumorigenesis. Tissue Culture Methods for Plant Pathologists. Eds.: Ingrams, D. S.; Helgeson, J.P. pp. 203-208.
Carvalho et al. (Jan. 2011) "TLR5 activation induces secretory interleukin-1 receptor antagonist (sll-1 Ra) and reduces inflammasome-associated tissue damage," Nature. 4(1 ):1 02-111.
Cereghino et al. (2000) "Heterologous protein expression in the methylotrophic yeast *Pichia pastoris*," Fems Microbiol Review. 24(1 ):45-66.
Chevreux et al. 'Genome sequence assembly using trace signals and additional sequence information.' German Conference on Bioinformatics. 1999.
Chothia et al. The relation between the divergence of sequence and structure in proteins. EMBO Journal. 1986, 5(4):823-826.
Christou (1994) "Genetic engineering of crop legumes and cereals: current status and recent advances," Agro-Food Industry Hi-Tech. pp. 17-27.
Chung et al. 'Microbiota-stimulated immune mechanisms to maintain gut homeostasis.' Current Opinion in Immunology. 2010, vol. 22, No. 4, pp. 455-460.
Co-pending U.S. Appl. No. 15/359,144, filed Nov. 22, 2016.
Crellin et al. (2005) "Human CD4+ T cells express TLR5 and its ligand ftagellin enhances the suppressive capacity and expression of FOXP3 in CD4+CD25+ T regulatory cells," Journal of Immunology. 175(12):8051-8059.
Davis et al., Genetic and Microbiological Research Techniques, Methods Enzymol. 1970; 17A:79-143.
De Paepe et al. 'Trade-off between bile resistance and nutritional competence drives *Escherichia coli* diversification in the mouse gut.' PLoS Genetics. 2011, vol. 7, No. 6, e1002107.
Dennis et al. 'David: database for annotation, visualization, and integrated discovery.' Genome Bioi. 2003, vol. 4, No. 5, pp. 3.
Duck et al. 'Isolation of flagellated bacteria implicated in Crohn's disease.' Inflammatory Bowel Diseases. 2007, vol. 13, No. 10, pp. 1191-1201.
Duncan et al. (2002) "*Roseburia intestinal* is sp. nov., a novel saccharolytic, butyrate-producing bacterium from human faeces," International Journal System Evolutionary Microbiology. 52:1615-1620.
Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441.
Duncan et al. "Lactate-utilizing bacteria, isolated from human feces, that produce butyrate as a major fermentation product" Applied and environmental microbiology. 2004, vol. 70, No. 10, pp. 5810-5817.
Eckburg, PB. et al., Diversity of the human intestinal microbial flora.Science. Jun. 10, 2005;308(5728):1635-8. Epub Apr. 14, 2005.
Elkins et al. 'Genes encoding bile salt hydrolases and conjugated bile salt transporters in Lactobacillus johnsonii 100-100 and other *Lactobacillus* species.' Microbiology. 2001, vol. 147, No. 12, pp. 3403-3412.
Ely et al. (2000) "A family of six flagellin genes contributes to the Caulobacter crescentus flagellar filament," Journal of Bacteriology. 182(17):5001-5004.
Extended European search report and opinion dated Aug. 23, 2016 for EP Application No. 16166001.4.
Falony et al. In vitro kinetics of prebiotic inulin-type fructan fermentation by butyrate-producing colon bacteria: Implementation of online gas chromatography for quantitative analysis of carbon dioxide and hydrogen gas production. Applied and Environmental Microbiology. 2009, vol. 75, No. 18, pp. 5884-5892.
FDA Orphan Drug Designations. Total Orphan Drugs website. Aug. 2014. Available at http://www.orphan-drugs.org/2014/09/01/fda-orphandrug-designations-august-2014. Accessed on Apr. 13, 2016.
Flores-Langarica et al. (2012) "Systemic flagellin immunization stimulates mucosal CD1 03+ dendritic cells and drives Foxp3+ regulatory T CELL and IgA responses in the mesenteric lymph node," Journal of Immunology. 189 ( 12):57 45/5754.
Fraley et al. (1986) "Genetic Transformation in Higher Plants," Critical Reviews Plant Science. 4:1-46.
Frame et al. (1994) "Production of fertile transgenic maize plants by silicon carbide whisker-mediated transformation," The Plant Journal. 6:941-948.
Frank, D. et al., Molecular-phylogenetic characterization of microbial community imbalances in human inflammatory bowel diseases. 2007. PNAS. 104(34):13780-5.
Gaboriau-Routhiau et al. 'The key role of segmented filamentous bacteria in the coordinated maturation of gut helper T cell responses.' Immunity. 2009, vol. 31, No. 4, pp. 677- 689.
Gait, M.J., (1984) Oligonucleotide Synthesis: A Practical Approach. Irl Press. pp. vii-xiii.
GB Search and Exam report dated Apr. 20, 2016 for GB application 1510468.0.
GenBank Accession No. AB148297.1 (Jul. 20, 2007) "Fia1 flagellin [*Roseburia hominis*]".
GenBank Accession No. ABY J02000000 (Nov. 8, 2013) Version 2. "Roseburia intestinal is L 1-82, whole genome shotgun sequencing project".
GenBank Accession No.'s ABY J02000001-ABY J02000409 search results page (Last Updated Apr. 24, 2015).
GenBank accession No. AJ312385 (Oct. 9, 2002) "Roseburia intestinalis 16S rRNA gene, strain L 1-82".
GenBank Accession No. CP003040 (Aug. 5, 2011) Version 1. "Roseburia Hominis A2-183, complete genome".
GenBank Accession No. DQ789141. (Jul. 20, 2007) "Roseburia hom in is Fla2 flagellin gene".
GenBank Accession No. M20983. (Apr. 26, 1993) "R.cecicola ftagellin gene".
Gennaro, A.R., Remington's Pharmaceutical sciences, Mack publishin co. 1985.
Geraedts et al. 'Release of satiety hormones in response to specific dietary proteins is different between human and murine small intestinal mucosa.' Annals of Nutrition and Metabolism. 2010, vol. 56, No. 4, pp. 3018-313.
Geuking et al. 'Intestinal bacterial colonization induces mutualistic regulatory T cell responses.' Immunity. 2011, vol. 34, No. 5, pp. 794-806.
Gewirtz et al. (2001) Cutting edge: bacterial flagellin activates basolaterally expressed TLR5 to induce epithelial proinflammatory gene expression. The Journal of Immunology. 167:(4)1882-1885.
Giraud et al. 'Dissecting the genetic components of adaptation of *Escherichia coli* to the mouse gut.' PLoS Genetics.2008, vol. 4, No. 1, pp. e2.
Greenspan et al., Defining epitopes: It's not as easy as it seems. Nature Biotechnology 7: 936-937, 1999.
Hapfelmeier et al. 'Reversible microbial colonization of germ-free mice reveals the dynamics of IgA immune responses.' Science. 2010, vol. 328, No. 5986, pp. 1705-1709.
Hayashi et al. The innate immune response to bacterial ftagellin is mediated by Toll-like receptor 5. Nature. 2001, vol. 410, No. 6832, pp. 1099-1103.
Hedayat et al. (Mar. 1, 2012) "Prophylactic and therapeutic implications of toll-like receptor ligands," Medicinal Research Reviews. 32(2):294-325.
Higgins et al. (1988) "CLUSTAL: a package for performing multiple sequence alighment on a microcomputer," Gene. 73(1 ):237-244.
Hinchliffe (1993) "Yeast as a vehicle for the expression of heterologous genes," Yeasts. 2nd edition. Rose, A. R.; Harrison, J. H.: Eds. Academic Press Ltd. 5(9). pp. 325-356.
Hinnen et al. (1978) "Transformation of yeast," Proc. Natl. Acad. Sci. USA. 75:1929-1933.
Hoekema (1985) The Binary Plant Vector System Offset-drukkerij Kanters BB, Alblasserdam. Chapter V. pp. 63-71.
Hold et al. 'Oligonucleotide probes that detect quantitatively significant groups of butyrate-producing bacteria in human feces.' Applied and environmental microbiology. 2003, vol. 69, No. 7, pp. 4320-4324.

(56) References Cited

OTHER PUBLICATIONS

Holland et al. (1990) "Secretion of Heterologous Proteins in *Escherichia coli*," Methods Enzymology. 182:132-143.
Hollenberg et al. (1997) "Production of recombinant proteins by methulotrophic yeasts," Current Opinion Biotechnology. 8(5):554-560.
Hooper at al. 'Molecular analysis of commensal host-microbial relationships in the intestine.' Science. vol. 291, No. 5505, pp. 881-884.
Hossain et al. "Flagellin, a TLR5 agonist, reduces graft-versus-host disease in allogeneic hematopoietic stem cell transplantation recipients while enhancing antiviral immunity," Journal of Immunology. Nov. 2011; 187(10): p. 5130-5140.
Hoyles L. et al. Gastrointestinal Tract, Chapter 56. Handbook of Hydrocarbon and Lipid Microbiology Springer Verlag Berlin 2010, 3120-32.
Ibrahim et al. (1985) "Method for the isolation of highly purified Salmonella flagellins," Journal of Clinical Microbiology. 22(6):1040-1044.
Inaba et al. (1992) "Generation of large numbers of dendritic cells from mouse bone marrow cultures supplemented with granulocyte/ macrophage colony-stimulating factor," J. Exp. Med. 176(6):1693-1702.
Interational Search Report for International Application No. PCT/GB2012/052495, dated Mar. 25, 2013.
International Preliminary Report on Patentability corresponding to International Patent Application No. PCT/GB2014/051123, dated Oct. 13, 2015.
International Search Report dated Aug. 21, 2014 for International Application No. PCT/GB2014/051123.
International Search Report dated Aug. 26, 2016 for International application No. PCT/GB2016/051774.
Ito et al. (1983) "Transformation of Intact Yeast Cells Treated with Alkali Cations," J. Bacteriology. 153:163-168.
Ivanov et al. 'Induction of intestinal Th17 cells by segmented filamentous bacteria.' Cell. 2009, vol. 139, No. 3, pp. 485-498.
Jarchum et al. (Jan. 2011) "Toll-Like Receptor 5 Stimulation Protects Mice from Acute Clostridium difficile Colitis," Infection and Immunity. 79(4):1498-1503.
Kang et al. (201 0) "Dysbiosis of fecal microbiota in Crohn's disease patients as revealed by a custom phylogenetic microarray," Inflammatory Bowel Diseases. 16(12):2034-2042.
Kelly et al. 'Commensal anaerobic gut bacteria attenuate inflammation by regulating nuclear-cytoplasmic shuttling of PPAR-y and ReiA.' Nature Immunology. 2003, vol. 5, No. 1, pp. 104-112.
Kinnebrew et al., Interleukin 23 production by intestinal CD1 03(+)CD11 b(+) dendritic cells in response to Interleukin 23 production by intestinal CD1 03(+ )CD11 b(+) dendritic cells in response to bacterial flagellin enhances mucosal innate immune defense, Immunity. 2012; 36(2): 276-287.
Lakhdari, et al. Identification of NF-KB Modulation Capabilities within Human Intestinal Commensal Bacteria. J Biomed Biotechnol. 2011; 2011: 282356.
Lavallie et al. (1995) "Gene fusion expression systems in *Escherichia coli*," Current Opinion Biotechnology. 6 (5):501-506.
Letran et al. 'TLR5-deficient mice lack basal inflammatory and metabolic defects but exhibit impaired CD4 T cell responses to a ftagellated pathogen.' The Journal of Immunology. 2011, vol. 186, No. 9, pp. 5406-5412.
Lilley et al. (1992) Methods in Enzymology; DNA Structure Part A: Synthesis and Physical Analysis of DNA. vol. 2011. pp. v-vii.
Louis et al. 'Diversity, metabolism and microbial ecology of butyrate-producing bacteria from the human large Intestine.' FEMS Microbiology Letters. 2009, vol. 294, No. 1, pp. 1-8.
Louis et al. 'Diversity of human colonic butyrate-producing bacteria revealed by analysis of the butyryl-GoA: acetate GoA-transferase gene.' Environmental Microbiology. 2010, vol. 12, No. 2, pp. 304-314.
Louis et al. 'Organization of butyrate synthetic genes in human colonic bacteria: phylogenetic conservation and horizontal gene transfer.' FEMS Microbiology Letters. 2007, vol. 269, No. 2, pp. 240-247.
Machiels et al. (Feb. 14-16, 2013) "Predominant dysbiosis in patients with ulcerative colitis is different from Crohn's disease patients," Inflammatory Bowel Diseases. 8th Congress of ECCO. (This Abstract is in 7th Congress 2012).
Machiels, K. A decrease of the butyrate-producing species *Roseburia hominis* and *Faecalibacterium prausnitzii* defines dysbiosis in patients with ulcerative colitis.Gut. Aug. 2014;63(8):1275-83. doi: 10.1136/gutjnl-2013-304833. Epub Sep. 10, 2013.
Macpherson et al. 'IgA adaptation to the presence of commensal bacteria in the intestine.' Gut-Associated Lymphoid Tissues. Springer Berlin Heidelberg, 2006. 117-136.
Macpherson et al. 'IgA responses in the intestinal mucosa against pathogenic and non-pathogenic microorganisms.' Microbes and Infection. 2001, vol. 3, No. 12, pp. 1021-1035.
"Macpherson et al. The functions of mucosal T cells in containing the indigenous commensal flora of the intestine. Cellular and Molecular Life Sciences CMLS. 2002, vol. 59, No. 12, pp. 2088-2096."
Mahowald et al. 'Characterizing a model human gut microbiota composed of members of its two dominant bacterial phyla.' Proceedings of the National Academy of Sciences. 2009, vol. 106, No. 14, pp. 5859-5864.
Mallya et al. 'Characterization of the five novel Ly-6 superfamily members encoded in the MHC, and detection of cells expressing their potential ligands.' Protein Science. 2006, vol. 15, No. 10, pp. 2244-2256.
Martin et al. (1988) "Cloning, Nucleotide Sequence, and Taxonomic Implications of the Flagellin Gene of Roseburia cecicola," Journal of Bacteriology. 170(6):2612-2617.
Mazmanian et al. 'An immunomodulatory molecule of symbiotic bacteria directs maturation of the host immune system.' Cell. 2005, vol. 122, No. 1, pp. 107-118.
Mcintosh et al. 'Mechanism of conjugated linoleic acid and vaccenic acid formation in human faecal suspensions and pure cultures of intestinal bacteria.' Microbiology. 2009, vol. 155, No. 1, pp. 285-294.
"Mclaughlin et al. 'Fatty acid chain length determines cholecystokinin secretion and effect on human gastric motility. Gastroenterology. 1999, vol. 116, No. 1, pp. 46-53".
Meyer et al. (1992) "The use of cassava mosaic virus as a vector system for plants," Gene. 110:213-217.
Mikayama, et al., Molecular cloning and functional expression of a cDNA encoding glycosylation-inhibiting factor. Proc.Nati.Acad. Sci. USA, Nov. 1993; vol. 90: 10056-1 0060.
Monteleone et al. (2008) "IL-10-dependent partial refractoriness to Toll-like receptor stimulation modulates gut mucosal dendritic cell function," European Journal of Immunology. 38(6):1533-1547.
Neish et al. (2006) "TLRS in the Gut. II. Flagellin-induced inftammation and antiapoptosis," American Journal of Physiology—Gastrointestinal and Liver Physiology. 292:G462-466.
Neville et al. (Jul. 10, 2012) "Characterization of pro-inflammatory flagellin proteins produced by Lactobacillus ruminis and related motile Lactobacilli," PloS one. 7(7):e40592.
Neville (Jan. 15, 2013) "Functional genomics of motile commensal intestinal bacteria" PhD Thesis. University College Cork. 15 Cork, Republic of Ireland. p. 87. paragraph 1.2.2.4.
Neyrinck et al. 'Dietary modulation of clostridial cluster XIVa gut bacteria (*Roseburia* spp.) by chitin-glucan fiber improves host metabolic alterations induced by high-fat diet in mice.' The Journal of Nutritional Biochemistry. 2012, vol. 23, No. 1, pp. 51-59.
Ng et al. (2006) "Archaeal flagella, bacterial flagella and type IV pili: a comparison of genes and posttranslation modification," Journal of Molecular Microbiology and Biotechnology. 11:167-191.
Notice of Allowance dated Feb. 3, 2016 for U.S. Appl. No. 14/349,907.
Nutsch et al. (2012) "T cell tolerance and immunity to commensal bacteria," Current Opinion in Immunology. 24 (4):385-391.
Office Action dated Jan. 11, 2005 for U.S. Appl. No. 10/285,224.
Office Action dated Jan. 26, 2009 for U.S. Appl. No. 10/275,706.

(56) References Cited

OTHER PUBLICATIONS

Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office action dated Jul. 8, 2015 for U.S. Appl. No. 14/349,907.
Office Action dated Aug. 21, 2013 for U.S. Appl. No. 12/760,926.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 6, 2006 for U.S. Appl. No. 10/285,224.
Office Action dated Nov. 23, 2015 for U.S. Appl. No. 14/232,475.
Office Action dated Dec. 13, 2012 for U.S. Appl. No. 12/760,926.
Office Action dated Dec. 19, 2005 for U.S. Appl. No. 10/275,706.
Olivera et al. 'Nutritional and physiological responses of young growing rats to diets containing raw cowpea seed meal, protein isolate (globulins), or starch.' Journal of agricultural and food chemistry. 2003, vol. 51, No. 1, pp. 319-325.
Overstreet et al. 'Dysbiosis Characterized by Reduced Abundance of Roseburia is Associated With Increased Severity of Colitis in IL-10-/-Mice'. Gastroenterology. 2011, vol. 140, No. 5, Suppl. 1, pp. S-696.
Peterson et al. 'Catecholamines increase conjugative gene transfer between enteric bacteria.' Microbial Pathogensis. 2011, vol. 51, No. 1, pp. 1-8.
Polak et al. (1990) In Situ Hybridization: Principles and Practice, Oxford University Press. pp. vii-viii.
Potrykus (1991) "Gene Transfer to Plants: Assessment of Published Approaches and Results," Annu. Rev. Plant Physiol. Plant Mol. Bioi. 42:205-225.
Prakash et al. (Sep. 15, 2011) "Complete genome sequences of rat and mouse segmented filamentous bacteria, a potent inducer ofth17 cell differentiation," Cell Host & Microbe. 10(3):273-284.
Pryde et al. 'The microbiology of butyrate formation in the human colon.' FEMS Microbiology Letters. 2002. vol. 217,No. 2, pp. 133-139.
Punt et al. (2002) "Filamentous fungi as cell factories for heterologous protein production," Trends Biotechnol. 20 (5):200-206.
Qin et al. 'A human gut microbial gene catalogue established by metagenomic sequencing.' Nature. 2010, vol. 464, No. 7285, pp. 59-65.
Reiff C. et al. IBD, Gut Bacteria and Probiotic Therapy. Int J Medical Microbiology 300:25-33, 2010.
Rhee et al. (2008) "Toll-Like Receptor 5 Engagement Modulates Tumor Development and Growth in a Mouse Xenograft Model of Human Colon Cancer," Gastroenterology. 135(2):518-528.
Roe et al. (1996) DNA Isolation and Sequencing: Essential Techniques. John Wiley & Sons, New York, New York. pp. v-vii.
Round et al. 'The Toll-like receptor 2 pathway establishes colonization by a commensal of the human microbiota.' Science. 2011, vol. 332, No. 6032, pp. 974-977.
Rudinger et al., Characteristics of the amino acids as components of a peptide hormone sequence. Peptide Hormones. Biol. Council. Jun. 1976; pp. 5-7.
Rusell et al. 'High-protein, reduced-carbohydrate weight-loss diets promote metabolite profiles likely to be detrimental to colonic health.' The American Journal of Clinical Nutrition. 2011, vol. 93, No. 5, pp. 1062-1072.
Salminen et al. 'Probiotics: how should they be defined?.' Trends in Food Science & Technology. 1999, vol. 10, No. 3, pp. 107-110.
Salonen et al., Gastrointestinal microbia in irritable bowel syndrome: present state and perspectives. Microbiology. 2010; 156: 3205-3215.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Schulke et al. (Aug. 26, 2011) "A fusion protein of ftagellin and ovalbumin suppresses the 25TH2 response and prevents murine intestinal allergy," The Journal of Allergy and Clinical Immunology. 128(6):1340-1348.
Scott et al. 'Substrate-driven gene expression in Roseburia inulinivorans: importance of inducible enzymes in the utilization of inulin and starch.' Proceedings of the National Academy of Sciences. 2011, vol. 108, Supp. 1, pp. 672-4679.
Sczesnak et al. (Sep. 15, 2011) "The genome of th17 cell-inducing segmented filamentous bacteria reveals extensive auxotrophy and adaptations to the intestinal environment," Cell Host & Microbe. 10 (3):260-272.
Shevach et al. (1992) Current Protocols in Immunology. John Wiley & Sons. New York, New York. Table of Contents only, as accessed online at URL: http://www.4ulr.com/products/currentprotocols/immunology_toc.html. [Last Accessed Jun. 18, 2015].
Skountzou et al. (2010) "Salmonella flagellins are potent adjuvants for intranasally administered whole inactivated influenza vaccine," Vaccine. 28(24):4103-4112.
Sokol et al. 'Faecalibacterium prausnitzii is an anti-inftammatory commensal bacterium identified by gut microbiota analysis of Crohn disease patients.' Proceedings of the National Academy of Sciences. 2008, vol. 105, No. 43, pp. 6731-16736.
Sokol et al. 'Low counts of Faecalibacterium prausnitzii in colitis microbiota.' Inflammatory bowel diseases. 2009, vol. 15, No. 8, pp. 1183-1189.
Spor, A. et al., Unravelling the effects of the environment and host genotype on the gut microbiome. Nat Rev Microbiol. Apr. 2011;9(4):279-90. doi: 10.1038/nrmicro2540.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.
Tatusova et al. (1999) "BLAST 2 Sequences, a new tool for comparing protein and nucleotide sequences," FEMS Microbial. Lett. 174(2):247-250.
Tatusova et al. (1999) "Erratum to 'BLAST 2 Sequences, a new tool for comparing protein and nucleotide sequences' [FEMS Microbial. 174 (1999) 247-250]," FEMS Microbial. Lett. 177(1):187-188.
Tilg, H. et al. Roseburia hominis. Gut 63(8)1204-1205, Oct. 14, 2013.
Travis, et al. Complete genome sequence of the human gut symbiont Roseburia hominis. Genome announcements. 2015; 3(6):e01286-15.
Tremaroli et al. (201 0) "A role for the gut microbiota in energy harvesting?" Gut. 59(12):1589-1590.
Trueman (1995) "Heterologous Expression in Yeast," Methods Molecular Biology. 49:341-354.
Turnbaugh et al. (2006) "An obesity-associated gut microbiome with increased capacity for energy harvest," Nature. 444(7122):1 027-1031.
Turnbaugh et al. (2008) "Diet-induced obesity is linked to marked but reversible alterations in the mouse distal gut microbiome," Cell Host & Microbe. 3(4):213-223.
Turner (1994) "Vectors for genetic manipulation," In; Martinelli, S.D.; Kinghorn J. R.: Eds. Aspergillus: 50 years on. Progress in industrial microbiology. vol. 29. Elsevier. Amsterdam, The Netherlands. pp. 641-666.
Ukena et al. (2007) "Probiotic *Escherichia coli* Niss!e 1917 inhibits leaky gut by enhancing mucosal integrity," PloS one. 2(12):e1308.
Untergasser et al. (2007) "Primer3Pius, an enhanced web interface to Primer3," Nucleic Acids Res. 35(Web Server issue):W71-74.
Van Immerseel et al. 'Butyric acid-producing anaerobic bacteria as a novel probiotic treatment approach for inflammatory bowel disease.' Journal of medical microbiology. 2010, vol. 59, No. 2, pp. 141-143.

(56) References Cited

OTHER PUBLICATIONS

Vijay-Kumar et al. (2007) "Deletion of TLR5 results in 10 spontaneous colitis in mice," The Journal of Clinical Investigation. 117(12):3909-3921.
Vijay-Kumar et al. (2008) "Fiagellin Treatment Protects against Chemicals, Bacteria, Viruses, and Radiation," The Journal of Immunology. 180(12):8280-8285.
Walker et al. 'Dominant and diet-responsive groups of bacteria within the human colonic microbiota.' The ISME Journal. 2010, vol. 5, No. 2, pp. 220-230.
Watson et al. (2005) "Signal transduction in Campylobacter jejuni-induced cytokine production," Cellular Microbiology. 7(5):655-665.
Weigel et al. (2002) "Comparative analysis of murine marrow-derived dendritic cells generated by Flt3L or GMCSF/IL-4 and matured with immune stimulatory agents on the in vivo induction of antileukemia responses," Blood. 100 ( 12):4169-4176.
Werth et al. (201 0) "The transcription factor grainyhead-like 2 regulates the molecular composition of the epithelial apical junctional complex," Development. 137(22):3835-3845.
Wilson et al. (Nov. 2012) "The Toll-like receptor 5 ligand ftagellin promotes asthma by priming allergic responses to indoor allergens," Nature Medicine. 18(11):1705-1710.
Xu et al. (2007) "Differential development of murine dendritic cells by GM-CSF versus Flt3 ligand has implications for inftammation and trafficking," J. Immunol. 179(11 ):7577-7584.
Yoon et al. (Feb. 2012) "Structural basis of TLR5-ftagellin recognition and signaling," Science. 335(6070):859-864.
"Amedei, A. et al. Multiple sclerosis: the role of cytokines in pathogenesis and in therapies. Int J Mol Sci. Oct. 19, 2012;13(10):13438-60. doi: 10.3390/ijms131013438."
Atlas, R. Handbook of Microbiological Media, Fourth Edition. CRC Press. 2010.
Ausubel, et al. Current Protocols in Molecular Biology. 1987. Supplement 30.
Ausubel et al., Short protocols in molecular biology. Fifth edition, 2002.
Azad, M.B. et al., Probiotic supplementation during pregnancy or infancy for the prevention of asthma and wheeze: systematic review and meta-analysis BMJ 2013; 347 :f6471.
Balato, et al., Effects of adalimumab therapy in adult subjects with moderate-to-severe psoriasis on Th17 pathway. (2014) J Eur Acad Dermatol Venereol. 28(8):1016-24.
Birdi, K.S. Handbook of Surface and Colloid Chemistry, 2nd Edition. CRC Press. 1997.
Brand et al., Collagen-induced arthritis, 2007; Protocol 2(5):1269-1275.
Cheluvappa, R. et al., T helper type 17 pathway suppression by appendicitis and appendectomy protects against colitis. Clin Exp Immunol. Feb. 2014;175(2):316-22. doi: 10.1111/cei.12237.
Colowick, S. and Kaplan, N., Methods of Enzymology. Academic Press, Inc. 1996.
Co-pending U.S. Appl. No. 15/915,885, filed Mar. 8, 2018.
Co-pending U.S. Appl. No. 15/915,889, filed Mar. 8, 2018.
Co-pending U.S. Appl. No. 15/916,167, filed Mar. 8, 2018.
Co-pending U.S. Appl. No. 15/916,202, filed Mar. 8, 2018.
Co-pending U.S. Appl. No. 15/916,205, filed Mar. 8, 2018.
Co-pending U.S. Appl. No. 15/969,543, filed May 2, 2018.
Co-pending U.S. Appl. No. 16/022,207, filed Jun. 28, 2018.
Co-pending U.S. Appl. No. 16/022,256, filed Jun. 28, 2018.
Co-pending U.S. Appl. No. 16/022,484, filed Jun. 28, 2018.
Co-pending U.S. Appl. No. 16/022,577, filed Jun. 28, 2018.
Day, J.G. et al., Cryopreservation and Freeze-Drying Protocols. Springer. 2007. 2nd edition.
Fabro, A. et al., The Th17 pathway in the peripheral lung microenvironment interacts with expression of collagen V in the late state of experimental pulmonary fibrosis. (2015) Immunobiology. 220(1):124-35.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Gennaro, A.R. "Quality Assurance and Control," from Remington: The Science and Practice of Pharmacy, 2000, Lippincott Williams & Wilkins, 20th ed., pp. 980-983.
Goldin, B.R. et al., Clinical indications for probiotics: an overview. Clin Infect Dis. Feb. 1, 2008;46 Suppl 2:S96-100; discussion S144-51. doi: 10.1086/523333.
Jiao et al., Blockade of Notch Signaling Ameliorates Murine Collagen-Induced Arthritis via Suppressing Th1 and Th17 Cell Responses. 2014; Pathology, 184(4):1085-1093.
Kailasapathy, K. Microencapsulation of Probiotic Bacteria:Technology and Potential Applications. Curr. Issues Intest. Microbiol. (2002) 3: 39-48.
Kingsley M. A Personalized Approach to Managing 18D. Gastroenterology and Hepatology 12(5)308-315, May 2016.
Koenders, M.I. et al., Interleukin-17 Acts Independently of TNF-a under Arthritic Conditions. (2006) J. Immunol. 176:6262-6269.
Leslie, et al., Trehalose and sucrose protect both membranes and proteins in intact bacteria during drying. (1995) Appl. Environ. Microbiol. 61, 3592-3597.
Macpherson, AJ. et al., IgA responses in the intestinal mucosa against pathogenic and non- pathogenic microorganisms. Oct. 2001. 3(12). 1021-1035.
Macpherson, AJ., et al., The functions of mucosal T cells in containing the indigenous commensal flora of the intestine.Cell Mol Life Sci. Dec. 2002;59(12):2088-96.
Masco, L., et al., Identification of *Bifidobacterium* Species Using rep-PCR Fingerprinting. Systematic and Applied Microbiology 26(4):557-63 • Dec. 2003.
Mitropoulou, G. et al. Immobilization Technologies in Probiotic Food Production. (2013) Journal Nutr Metab. (2013) 716861.
Miyamoto-Shinohara et al. Survival of freeze-dried bacteria. J Gen Appl Microbiol 54(1):9-24 (2008).
Monteleone, I. et al., Th17-related cytokines: new players in the control of chronic intestinal inflammation. (2011) BMC Medicine. 2011, 9:122.
Notice of Allowance dated Mar. 6, 2017 for U.S. Appl. No. 14/249,710.
Notice of allowance dated Jun. 16, 2017 for U.S. Appl. No. 14/249,710.
Notice of allowance dated Sep. 6, 2017 for U.S. Appl. No. 14/249,710.
Notice of Allowance dated Nov. 17, 2016 for U.S. Appl. No. 14/249,710.
Notice of Allowance dated Nov. 24, 2017 for U.S. Appl. No. 15/070,605.
Office Action dated Jan. 2, 2018 for U.S. Appl. No. 15/357,936.
Office Action dated May 25, 2016 for U.S. Appl. No. 14/249,710.
Office Action dated Jun. 26, 2017 for U.S. Appl. No. 15/357,936.
Office Action dated Jul. 6, 2017 for U.S. Appl. No. 15/070,605.
Office Action dated Jul. 31, 2017 for U.S. Appl. No. 15/359,988.
Office Action dated Aug. 10, 2017 for U.S. Appl. No. 15/357,850.
Office Action dated Sep. 4, 2015 for U.S. Appl. No. 14/249,710.
Office Action dated Nov. 2, 2017 for U.S. Appl. No. 15/700,007.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Schieck, M. et al., Genetic variation in TH17 pathway genes, childhood asthma, and total serum IgE levels.(2014) J Allergy Clin Immunol. 133(3):888-91.
Shabgah, A.G. et al., Interleukin-17 in human inflammatory diseases. Postepy Dermatol Alergol. Aug. 2014; 31(4): 256-261.
Smith, et al. Comparison of Biosequences. Advances in Applied Mathematics. 1981;2: 482-489.
U.S. Appl. No. 15/700,007 Office Action dated Jun. 1, 2018.
Srutkova, D. et al., Efficiency of PCR-based methods in discriminating *Bifidobacterium longum* ssp. longum and *Bifidobacterium longum* ssp. infantis strains of human origin.J Microbiol Methods. Oct. 2011;87(1):10-6. doi: 10.1016/j.mimet.2011.06.014. Epub Jul. 2, 2011.

(56) References Cited

OTHER PUBLICATIONS

Strobel, H.J. Basic laboratory culture methods for anaerobic bacteria. Methods Mol Biol. 2009;581:247-61. doi: 10.1007/978-1-60761-214-8_16.
Tamanai-Shacoori, et al., *Roseburia* spp.: a marker of health?. Future Microbiology Review 12(2), 157-170 (2017).
Tesmer, L.A. et al., Th17 cells in human disease. Immunol Rev. 2008;223:87-113.
U.S. Appl. No. 15/359,144 Office Action dated Apr. 10, 2018.
U.S. Appl. No. 15/359,972 Office Action dated Apr. 4, 2018.
U.S. Appl. No. 15/631,945 Office Action dated Jul. 5, 2018.
U.S. Appl. No. 15/631,952 Office Action dated Feb. 16, 2018.
U.S. Appl. No. 15/673,270 Office Action dated Apr. 10, 2018.
U.S. Appl. No. 15/679,857 Office Action dated Feb. 14, 2018.
Yang, J. et al., Targeting Th17 cells in autoimmune diseases. Trends Pharmacol Sci. Oct. 2014;35(10):493-500. doi: 10.1016/j.tips.2014.07.006. Epub Aug. 14, 2014.
Ye, X. et al., The Role of IL-23/Th17 Pathway in Patients with Primary Immune Thrombocytopenia. (2015) PLoS One. 10(1):e0117704.
Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.
Miossec et al., Targeting IL-17 and TH17 cells in chronic inflammation, 2012; Nature Drug Discovery 11, 763-776.
Co-pending U.S. Appl. No. 16/100,349, filed Aug. 10, 2018.
Co-pending U.S. Appl. No. 16/147,551, filed Sep. 28, 2018.
U.S. Appl. No. 15/704,245 Office Action dated Sep. 17, 2018.
Jan. 17, 2019 First Office Action for CN201680041407.6 (Translated).
Jan. 17, 2019 Notice of Allowance for U.S. Appl. No. 15/803,721.
Dec. 21, 2018 Notice of Allowance U.S. Appl. No. 15/700,700.
Jan. 30, 2019 Notice of Corrected Allowability for U.S. Appl. No. 15/803,721.
Jan. 30, 2019 Final Rejection for U.S. Appl. No. 15/842,635.
Feb. 1, 2019 Non-Final Office Action U.S. Appl. No. 16/040,356.
Mar. 4, 2019 Final Office Action for U.S. Appl. No. 15/704,245.
4d Pharma Plc: "Clinical Update—RNS—London Stock Exchange", Jul. 19, 2016.
4D Pharma:"4Dpharma PLC clinical update on blautix (TM), a novel treatment to irritable bowel syndrome," 4DPharma, Jan. 19, 2016, XP002769874, Retrieved from: https://www.directorstalkinterviews.com/4d-pharma-plc-clinical-update-on-blautix-a-novel-treatment-for-irritable-bowel-syndrome/412689588. [Retrieved on May 5, 2017].
Ahanchian, Hamic, A multi-strain synbiotic may reduce viral respiratory infections in asthmatic children: a randomized controlled trial; Sep. 2016, vol. 8, Issue 9, pp. 2833-2839, DOI: http://dxdoi.or/10.19082/2833.
Alp, G., and Aslim, B. (2010). Relationship between the resistance to bile salts and low pH with exopolysaccharide (EPS) production of *Bifidobacterium* spp. isolated from infants feces and breast milk. Anaerobe 16(2), 101-105. doi: 10.1016/j.anaerobe.2009.06.006.
Anonymous: "4D pharma's Blautix for Irritable Bowel Syndrome shows positive impact—pharmaceutical daily news", Dec. 13, 2016.
Appleyard, Caroline B. et al., Pretreatment with the probiotic VSL#3 delays transition from inflammation to dysplasia in rate model of colitis-associated cancer; Am J. Physiol. Gastrointest. Liver Physiol. 301:G1004-G1013, 2011, Sep. 8, 2011:DOI:10.1152.ajpg.00167.2011.
Arenberg, et al., Interferon-γ-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92.
Atarashi et al., Th17 Cell Induction by Adhesion of Microbes to Intestinal Epithelial Cells. Cell, vol. 163, No. 2, Oct. 8, 2015. pp. 367-380.

Atarashi, et al., Treg induction by a rationally selected mixture of Clostridia strains from the human microbiota. Supplementary Information. Nature 500, 232-236 (Aug. 8, 2013) doi:10.1038/nature12331.
Atarashi, K. et al., Treg induction by a rationally selected mixture of Clostridia strains from the human microbiota. Nature. 2013; 500(7461):232-236.
ATCC Catalog, https://www.atcc.org/search_results.aspx?dsNav=Ntk:primarysearch%7cbacteroides+thetaiotaomicron%7c3%7c,Ny:true,ro:0,N:1000552searchterms=bacteroides+thetaiotaomicron&redir=1, Accessed on May 2, 2018.
Awadel-Kariem, Mustafa et al., First report of Parabacteroides goldsteinii bacteraemia in a patient with complicated intra-abdominal infection, Anaerobe, vol. 16, Issue 3, Jun. 2010, pp. 223-225.
Aziz, R.K., Bartels, D., Best, A.A., DeJongh, M., Disz, T., Edwards, R.A., et al. (2008). The Rast Server: Rapid Annotations using Subsystems Technology. BMC Genomics 9, 75. doi: 10.1186/1471-2164-9-75.
Bagge, et al., Diversity of spore-forming bacteria in cattle manure, slaughterhouse waste and samples from biogas plants. Journal of applied microbiology. 2010;109: 1549-1565.
Banfield, J. & Murphy, K.R., Non-Th2, Late-onset, non-allergic asthma. Copd & Asthma for NPs, A peer-reviewed newsletter, Aug. 2016; 14: 8 Pages.
Barry, et al., Criteria for Disksusceptibility tests and quality control guidelines for the cefoperazone-sulbactam combination, Journal of clinical microbiology, Jan. 1988;26(1):13-17.
Beaucage, et al. Deoxynucleoside phosphoramidites—A new class of key intermediates for deoxypolynucleotide synthesis. Tetrahedron Letters, vol. 22, 1981, pp. 1859-1869.
Begley, M., Hill, C., and Gahan, C.G.M. (2006). Bile Salt Hydrolase Activity in Probiotics. Applied and Environmental Microbiology 72(3), 1729-1738. doi: 10.1128/AEM.72.3.1729-1738.2006.
Berger, B., Moine, D., Mansourian, R., and Arigoni, F. (2010). HspR Mutations Are Naturally Selected in Bifidobacterium longum When Successive Heat Shock Treatments Are Applied. Journal of Bacteriology 192(1), 256-263. doi: 10.1128/jb.01147-09.
Berger, S. Gideon guide to medically important bacteria. Gideon E-book Series. 2017 edition. 4 pages.
Bergonzelli, G.E., Granato, D., Pridmore, R.D., Marvin-Guy, L.F., Donnicola, D., and Corthesy-Theulaz, I.E. (2006). GroEL of Lactobacillus johnsonii La1 (NCC 533) is cell surface associated: potential role in interactions with the host and the gastric pathogen Helicobacter pylori. Infect Immun 74(1), 425-434. doi: 10.1128/IAI.74.1.425-434.2006.
Bernalier, A., et al., "Diversity of H2/CO2-utilizing acetogenic Bacteria from Feces of Non-Methane-Producing Humans", Current Microbiology vol. 33 (Aug. 1996), pp. 94-99, Springer-Vertag New York Inc., USA.
Bernalier et al., "Acetogenesis from H02 and Co-2 by Methane and Non-Methane-Producing Human Colonic Bacterial Communities" Fems Microbiology Ecology. vol. 19. No. 3. 1996. pp. 193-202. XP000979130.
Bernalier et al. *Ruminococcus hydrogenotrophicus* sp. nov., a new H2/CO2-utilizing acetogenic bacterium isolated from human feces. 1996 Arch. Microbiol. 166 (3), 176-183.
Bertram, J. et al. Establishment of a cloned line of Lewis lung carcinoma cells adapted to cell culture. (1980) Cancer let. 11:63-73.
Blandino, G., Fazio, D., DiMarco, R. Probiotics: Overview of microbiological and immunological characteristics (2008). Expert Review of Anti-Infective Therapy, 6 (4), pp. 497-508.
Bond, John H., Jr., et al., "Factors Influencing Pulmonary Medicine Excretion in Man: An indirect method of studying the in situ metabolism of the methane-producing colonic bacteria"; Journal of Experimental Medicine, Oct. 29, 1970, pp. 572-388.
Born, P., et al., English Abstract "Carbohydrate substitutes: comparative study of intestinal absorption of fructose, sorbitol and xylitol", "Zuckeraustauschstoffe: Vergleichende Untersuchung zur intestinalen Resorption von Fructose, Sorbit and Xylit", Medizinische Klinik 89, Technischen Universitat Munchen (Munich) Nov. 15, 1994; 89 (11): 575-8 (Article in German), Urban & Vogel, Munich, Germany.

(56) References Cited

OTHER PUBLICATIONS

Born, P., et al., "Fecal bacterial activity in symptomatic carbohydrate malabsorption: Effect on the fecal short-chain fatty acid ratio", intervention during the week "Digestive Diseases Week" from May 16 to May 19, 1999, Orlando, Z. Gasteroenterol2000: 38:623-626, Georg Thieme Verlag Stuttgart, New York, USA.

Bottacini, et al., Comparative genomics of the Bifidobacterium brevetaxon. BMC Genomics, 2014; 15:170. DOI:10.1186/1471-1471-2164-15-170.

Bottacini, F., Morrissey, R., Esteban-Torres, M., James, K., van Breen, J., Dikareva, E., et al. (2018). Comparative genomics and genotype-phenotype associations in Bifidobacterium breve. Scientific Reports 8(1), 10633. doi: 10.1038/s41598-018-28919-4.

Bottacini, F., O'Connell Motherway, M., Kuczynski, J., O'Connell, K.J., Serafini, F., Duranti, S., et al. (2014). Comparative genomics of the Bifidobacterium breve taxon. BMC Genomics 15(1), 170. doi: 10.1186/1471-2164-15-170.

Bressa, et al., Differences in gut microbiota profile between women with active lifestyle and sedentary women. Plos One, 2017; 12(2): 1-20.

Bry et al. A model of host-microbial interactions in an open mammalian ecosystem. Science 273(5280):1380-1383 (1996).

Buffie et al., Precision microbiome restoration of bile acid-mediated resistance to Clostridium difficile. Nature, 517(7533):205-208 (2015).

Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.

"Campeau, J.L. et al., Intestinal Epithelial Cells Modulate Antigen-Presenting Cell Responses to Bacterial DNA. Infectionand Immunity. Aug. 2012; 80(8): 2632-2644."

Candela et al. 'Interaction of probiotic Lactobacillus and Bifidobacterium strains with human intestinal epithelial cells:Adhesion properties, competition against enteropathogens and modulation of IL-8 production'. International Journal of Food Microbiology. 2008, vol. 125, No. 3, pp. 286-292.

Candela, M., Bergmann, S., Vici, M., Vitali, B., Turroni, S., Eikmanns, B.J., et al. (2007). Binding of human plasminogen to Bifidobacterium. J Bacteriol 189(16), 5929-5936. doi: 10.1128/JB.00159-07.

Candela, M., Biagi, E., Centanni, M., Turroni, S., Vici, M., Musiani, F., et al. (2009). Bifidobacterial enolase, a cell surface receptor for human plasminogen involved in the interaction with the host. Microbiology 155(Pt 10), 3294-3303. doi: 10.1099/mic.0.028795-0.

Candela, M., Centanni M Fau-Fiori, J., Fiori J Fau-Biagi, E., Biagi E Fau-Turroni, S., Turroni S Fau-Orrico, C., Orrico C Fau-Bergmann, S., et al. (2010). DnaK from *Bifidobacterium animalis* subsp. lactis is a surface-exposed human plasminogen receptor upregulated in response to bile salts. Microbiology 156(6), 1609-1618.

Caruthers, et al. New chemical methods for synthesizing polynucleotides. Nucleic Acids Symp Ser. 1980;(7):215-23.

Casey et al. 'Isolation and characterization of anti-Salmonella lactic acid bacteria from the porcine gastrointestinal tract'. Letters in Applied Microbiology. 2004, vol. 39, No. 5, pp. 431-438.

Caspi, P.R. Experimental autoimmune uveoretinitis in the rat and mouse. Curr Protoc Immunol. May 2003;Chapter 15:Unit 15.6. doi: 10.1002/0471142735.im1506s53.

Cekanaviciute, et al., Gut bacteria from multiple sclerosis patients modulate human T cells and exacerbate symptoms in mouse models. PNAS. Jun. 30, 2017; 1-6.

Charriot, et al., Future treatment for ashtma, Eur Respir Rev 2016; 25: 77-92.

Chen, S. et al., Live combined bacillus subtilis and enterococcus faecium ameliorate murine experimental colitis by immunosuppression. International journal of inflammation. 2014(878054). 7 Pages.

Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.

Chi, W. et al. Upregulated IL-23 and IL-17 in Behcet patients with active uveitis. Invest Ophthalmol Vis Sci. Jul. 2008;49(7):3058-64. doi: 10.1167/iovs.07-1390.

Chiu, et al., Monocolonization of germ-free mice with bacteroides fragilis protects against dectran sulfate sodium-induced acute colitis. Biomed Research International 2014. vol. 2014. Article ID 675786. 9 Pages.

Christiaen, S.E., O'Connell Motherway, M., Bottacini, F., Lanigan, N., Casey, P.G., Huys, G., et al. (2014). Autoinducer-2 plays a crucial role in gut colonization and probiotic functionality of Bifidobacterium breve UCC2003. PLoS One 9(5), e98111. doi: 10.1371/journal.pone.0098111.

Christmann, et al., Human seroreactivity to gut microbiota antigens. J Allergy Clin Immunol 136(5):1378-1386; available online May 23, 2015.

Cintas LM, Casaus MP, Herranz C, Nes IF, Hernandez PE. Review: bacteriocins of lactic acid bacteria (2001). Food Sci Technol 7(4):281-305.

Claesson, et al. Gut microbiota composition correlates with diet and health in the elderly. 2012. Nature, 488, 178-184.

Claims to be granted in European Application No. 15817513.3.

Clarridge III, J.E. Impact of 16S rRNA gene sequence analysis for identification of bacteria on clinical microbiology and infectious diseases (2004). Clinical Microbiology Reviews, 17 (4), pp. 840-862.

Clinical Trials for Thetanix, EU Clinical Trials Register, Date of commencement of clinical trial: Oct. 16, 2015. Available at: https://clinicaltrialsregister.eu/ctr-search/search?query=Thetanix.

CN Office Action dated Jan. 17, 2019, for CN 201680041407.6 (translation not yet available).

Colin, et al., GIC-1001, A Clinical Stage, Orally Administered Colonic Analgesic Drug Proposed as a Cost-Effective Alternative to I.V. Sedation Used in Colonoscopy. Canadian Digestive Diseases Week, 2014; 2 pages.

Collins, M.D., et al., Enterococcus avium nom. rev., comb. nov.; E. casseliflavus nom. rev., comb. nov.; E. durans nom. rev., comb. nov.; E. gallinarum comb. nov.; and *E. malodoratus* sp. nov. (1984) Int J Syst Evol Microbiol. 34: 220-223.

Constantinescu et al. Experimental autoimmune encephalomyelitis (EAE) as a model for multiple sclerosis (MS). 2011. Br J Pharmacol. 164(4):1079-1106.

Co-pending U.S. Appl. No. 16/206,250, filed Nov. 30, 2018.
Co-pending U.S. Appl. No. 16/219,667, filed Dec. 18, 2018.
Co-pending U.S. Appl. No. 16/240,644, filed Jan. 4, 2019.
Co-pending U.S. Appl. No. 16/247,834, filed Jan. 15, 2019.
Co-pending U.S. Appl. No. 16/248,857, filed Jan. 16, 2019.
Co-pending U.S. Appl. No. 16/251,462, filed Jan. 18, 2019.
Co-pending U.S. Appl. No. 16/265,238, filed Feb. 1, 2019.

Cotter, P.O., Hill, C., Ross, R.P. Food microbiology: Bacteriocins: Developing im1ate immunity for food (2005). Nature Reviews Microbiology, 3 (10), pp. 777-788.

Cronin, M., Knobel, M., O'Connell-Motherway, M., Fitzgerald, G.F., and van Sinderen, D. (2007). Molecular Dissection of a Bifidobacterial Replicon. Applied and Environmental Microbiology 73(24), 7858-7866.

Cummings, M., Breitling, R., and Takano, E. (2014). Steps towards the synthetic biology of polyketide biosynthesis. Fems Microbiology Letters 351(2), 116-125. doi: 10.1111/1574-6968.12365.

Dahya V. et al., Clostridium ramosum Osteomyelitis in an immunocompetent patient after traumatic injury, Infectious Diseases in Clinical Practice 20150312 Lippincott Williams and Wilkins USA, vol. 23, No. 2, Mar. 12, 2015, pp. 102-104, XP009193312, ISSN: 1056-9103 the whole document.

Darfeuille-Michaud et al. High prevalence of adherent-invasive *Escherichia coli* associated with ileal mucosa in Crohn's disease. .2004. Gastroenterology 127(2):412-21.

Darlington, G.J., Liver Cell Lines. (1987) Meth Enzymol. 151:19-38.

Database UniProt [Online] Jun. 1, 2003 (Jun. 1, 2003), "subname:Full= possible pirin family protein {ECO:0000313|EMBL:AAO75294. 1};", XP00275366,retrieved from EBI accession No. UNIPROT:Q8ABC3 Database accession No. Q8ABC3.

(56) References Cited

OTHER PUBLICATIONS

Davis et al. (1971) "Genetic and Microbiological Research Technqiues," Methods Enzymol. 17A:79-143.

De Ruyter, P.G., Kuipers, O.P., and de Vos, W.M. (1996). Controlled gene expression systems for Lactococcus lactis with the food-grade inducer nisin. Applied and Environmental Microbiology 62(10), 3662-3667.

Deangelis, M., et al., Selection of potential probiotic lactobacilli from pig feces to be used as additives in pelleted feeding (2006). Research in Microbiology, 157 (8), pp. 792-801.

Delgado, S., Ruiz, L., Hevia, A., Ruas-Madiedo, P., Margolles, A., and Sanchez, B. (2018). "Evidence of the In Vitro and In Vivo Immunological Relevance of Bifidobacteria," in The Bifidobacteria and Related Organisms.), 295-305.

Demarche, et al., Detailed analysis of sputum and systemic inflammation in asthma phenotypes: are paucigranulocytic asthmatics really non-inflammatory?, BMC Pulmonary Medicine, 2016; (16)46:1-13.

Distrutti, et al., 5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity. The Journal of pharmacology and experimental therapeutics, 2006;319(1):447-458.

Distrutti, et al., Gut Microbiota role in irritable bowel syndrome: New therapeutic strategies. World Journal of Gastroenterology. Feb. 21, 2016; 22(7): p. 2219-2241, XP002769875.

Distrutti, et al., Hydrogen sulphide induces u opioid receptor-dependent analgesia in a rodent model of visceral pain. Molecular Pain, 2010; 6(36):1-16.

Divyashri et al. Probiotic attributes, antioxidant, anti-inflammatory and neuromodulatory effects of Enterococcus faecium CFR 3003: in vitro and in vivo evidence. (2015) J Med Microbiol. doi: 10.1099/jmm.0.000184.

DMSZ: Opening of Ampoules and Rehydration of Dried Cultures; (http://web.archive.org/web/20000 52411541 O/www.dsmz.de/open.htm); updated of website on Mar. 2000.

Dong, H., Rowland I Fau-Yacioob, P., and Yacioob, P. (2012). Comparative effects of six probiotic strains on immune function in vitro. Br J Nutr 108(3), 459-470. doi: 10.1017/S0007114511005824.

Drago, Lorenzo et al., Immunomodulatory Effects of Lactobucillus salivarius LS01 and Bifidobacterium breve, Alone and in Combination on Peripheral Blood Mononuclear Cells of Allergic Asthmatics; Allergy Asthma Immunol. Res. Jul. 2015: 7(4):409-413.

Duncan, et al. *Roseburia intestinalis* sp. nov., a novel saccharolytic, butyrate-producing bacterium from human faeces. Int J Syst Evol Microbiol. Sep. 2002;52(Pt 5):1615-20.

Durand et al., "Reductive Acetogenesis in Animal and Human Gut." Physiological and Clinical Aspects of Short-Chain Fatty Acids, 1995. pp. 107-117, XP000979817 Cambridge University Press ISBN 0-521-44048-3.

Elhenawy et al., Preferential packing of acidic glycosidases and proteases into bacteroides Outer membrane vesicles. mBio 5:e00909-14, pp. 1-12, 2014.

Elmadfa, 1., Klein, P., Meyer, AL. Immune-stimulating effects oflactic acid bacteria in vivo and in vitro (2010). Proceedings of the Nutrition Society, 69 (3), pp. 416-420.

Embl sequence AAO75294.1 (2003)—provided within the Office Action dated Feb. 16, 2018 in U.S. Appl. No. 15/631,952. 2 Pages.

Eren, A. Murat et al., "A single genus in the gut microbiome reflects host preference and specificity," The ISME Journal (2015) 9, 9-100 (2015).

ESR Dated Dec. 17, 2018, Appl. 18189521.0.

Estelle Devillard et al., Metabolism of Linoleic Acid by Human Gut Bacteria: Different Routes for Biosynthesis of Conjugated Linoleic Acid, Journal of Bacteriology, Mar. 2007, vol. 189, No. 4, pp. 2566-2570.

European Communication dated Jun. 14, 2017 for EP Application No. 15817513.3.

Evelo Biosciences, Inc. Clinical Trials (Rank 1): A Study of EDP1503 in Patients With Colorectal Cancer, Breast Cancer, and Checkpoint Inhibitor Relapsed Tumors, https://clinicaltrials.gov/ct2/show/NCT03775850?spons=evelo&rank=1.

Evelo Biosciences, Inc. Clinical Trials (Rank 2): A Study of EDP1815 in Healthy Participants and Participants With Mild to Moderate Psoriasis and Atopic Dermatitis, https://clinicaltrials.gov/ct2/show/NCT03733353?spons=evelo&rank=2.

Evelo Biosciences, Inc. Clinical Trials (Rank 3): A Study of EDP1066 in Healthy Participants and Participants With Mild to Moderate Psoriasis and Atopic Dermatitis, https://clinicaltrials.gov/ct2/show/NCT03542994?spons=evelo&rank=3.

Evelo Biosciences, Inc. Clinical Trials (Rank 4): Pembrolizumab and EDP1503 in Advanced Melanoma, https://clinicaltrials.gov/ct2/show/NCT03595683?spons=evelo&rank=4.

Evelo Biosciences, Inc. Portfolio: https://evelobio.com/portfolio/.

Evelo Biosciences, Inc. website: https://evelobio.com/science/.

Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.

Faith et al. Identifying gut microbe-host phenotype relationships using combinatorial communities in gnotobiotic mice. Sci Transl Med 6(220):220ra11 (2014).

Faith et al. The long-term stability of the human gut microbiota. 2013. Science, 341(6141): 1237439.

Falony, et al., Coculture Fermentations of *Bifidobacterium* species and bacteroides thetaiotaomicron Reveal a mechanistic insight into the prebiotic effect of inulin-type Fructans. Applied and environmental microbiology, Apr. 2009;75(8):2312-2319.

Fanning, S., Hall, L.J., Cronin, M., Zomer, A., MacSharry, J., Goulding, D., et al. (2012). Bifidobacterial surface-exopolysaccharide facilitates commensal-host interaction through immune modulation and pathogen protection. Proc Natl Acad Sci U S A 109(6), 2108-2113. doi: 10.1073/pnas.1115621109.

Farmer, et al., Gut pain & visceral hypersensitivity. British journal of pain, 2013;7(1):39-47.

Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.

Fenner, et al., *Bacteroides massiliensis* sp. nov., isolated from blood culture of a newborn. International Journal of systematic and evolutionary microbiology, 2005. 55: 1335-1337.

Ferrario, C., Milani, C., Mancabelli, L., Lugli, G.A., Duranti, S., Mangifesta, M., et al. (2016). Modulation of the eps-ome transcription of bifidobacteria through simulation of human intestinal environment. FEMS Microbiol Ecol 92(4), fiw056. doi: 10.1093/femsec/fiw056.

Frick, et al., Identification of commensal bacterial strains that modulate Yersinia enterocolitica and Dextran sodium sulfate-induced inflammatory responses: implications for the development of probiotics. Infection and immunity, Jul. 2007;75(7):3490-3497.

GB Exam and search report dated Aug. 30, 2016 for GB Application No. 1520638.6.

GB Search and Exam report dated Mar. 31, 2016 for GB application 1510469.8.

GB Search and Exam report dated Mar. 31, 2016 for GB application 1510470.6.

GB Search and Exam report dated Apr. 15, 2016 for GB application 1510467.2.

GB Search and Exam report dated Apr. 20, 2016 for GB application 1510466.4.

GB Search and Exam report dated Aug. 30, 2016 for GB application No. 1520631.1.

GB Search and Exam report dated Nov. 17, 2016 for GB application 1520502.4.

GB Search and Exam report dated Sep. 13, 2016 for GB application 1520497.7.

GB1612190.7 International Search Report dated Apr. 12, 2017.

GB1809729.5 Examination Report dated Oct. 15, 2018.

GenBank Accession No. NR_044054.1 (Feb. 3, 2015) Blautia wexlerae strain SSM 19850 16S ribsomal RNA gene, partial sequence.

(56) References Cited

OTHER PUBLICATIONS

GenBank Accession No. NR_117867.1 (Feb. 3, 2015) Blautia stercoris strain GAM6-1 16S ribosomal RNA gene, partial sequence.
Genbank NCBI Reference Sequence: NR-044054.1, Blautia wexlerae strain DSM 19850 16S ribosomal RNA gene, partial sequence.
Genbank NCBI Reference Sequence: NR_117867.1, Blautia stercoris strain GAMC6-1 16S ribosomal RNA gene, partial sequence.
Genbank NCBI Reference Sequence: NR_026314, Blautia hydrongentrophica strain S5a36 16S ribosomal RNA gene, partial sequence.
Ghadimi, D. et al., Epigenetic imprinting by commensal probiotics inhibits the IL-23/IL-17 axis in an in vitro model of the intestinal mucosal immune system. JLB. 2012;92(4):895-911.
Gonzalez-Rodriguez, I., Sanchez, B., Ruiz, L., Turroni, F., Ventura, M., Ruas-Madiedo, P., et al. (2012). Role of extracellular transaldolase from Bifidobacterium bifidum in mucin adhesion and aggregation. Appl Environ Microbiol 78(11), 3992-3998. doi: 10.1128/AEM.08024-11.
Gopal, P.K., Sullivan, P.A., Smart, J.B. Utilization of galacto-oligosaccharides as selective substrates for growth by lactic acid bacteria including Bifidobacterium lactis DR10 and Lactobacillus rhamnosus DR20 (200 1 ). International Dairy Journal, 11 (1-2), pp. 19-25.
Gousia, P., et al., Antimicrobial resistance of major foodborne pathogens from major meat products (2011). Foodborne Pathogens and Disease, 8 (1), pp. 27-38.
Groeger, D., O'Mahony, L., Murphy, E.F., Bourke, J.F., Dinan, T.G., Kiely, B., et al. (2013). Bifidobacterium infantis 35624 modulates host inflammatory processes beyond the gut. Gut Microbes 4(4), 325-339. doi: 10.4161/gmic.25487.
GT Biologics obtains FDA orphan drug designation for paediatric crohn's drug, pharmaceutical-technology.com news, Oct. 8, 2013. Available at: http://www.pharmaceutical-technology.com/news/newsgt-biologics-obtains-fda-orphan-drug-designation-for-paediatric-crohns-drug?WT.mc_id=DN_News.
Guide for the care and use of laboratory animals: 8th edition. The national academic press; 2011.
Haabeth et al. A model for cancer-suppressive inflammation. (2012) OncoImmunology 1(1):1146-1152.
Hammerich, L. et al., Interleukins in chronic liver disease: lessons learned from experimental mouse models. (2014) Clin Exp Gastroenterol. 7:297-306.
Hansen, et al., The role of mucosal immunity and host genetics in defining intestinal commensal bacteria. 2010. Curr. Opin. Gastroenterol., 26(6): 564-571.
Heberle, H., Meirelles, G.V., da Silva, F.R., Telles, G.P., and Minghim, R. (2015). InteractiVenn: a web-based tool for the analysis of sets through Venn diagrams. BMC Bioinformatics 16(1), 169. doi: 10.1186/s12859-015-0611-3.
Heuvelin, E., Lebreton, C., Grangette, C., Pot, B., Cerf-Bensussan, N., and Heyman, M. (2009). Mechanisms Involved in Alleviation of Intestinal Inflammation by Bifidobacterium Breve Soluble Factors. PLOS ONE 4(4), e5184. doi: 10.1371/journal.pone.0005184.
Hidalgo-Cantabrana, C., Lopez, P., Gueimonde, M., de Los Reyes-Gavilan, C.G., Suarez, A., Margolles, A., et al. (2012). Immune Modulation Capability of Exopolysaccharides Synthesised by Lactic Acid Bacteria and Bifidobacteria. Probiotics Antimicrob Proteins 4(4), 227-237. doi: 10.1007/s12602-012-9110-2.
Hidalgo-Cantabrana, C., Sanchez, B., Alvarez-Martin, P., Lopez, P., Martinez-Alvarez, N., Delley, M., et al. (2015). A single mutation in the gene responsible for the mucoid phenotype of Bifidobacterium animalis subsp. lactis confers surface and functional characteristics. Appl Environ Microbiol 81(23), 7960-7968. doi: 10.1128/AEM.02095-15.
Hidalgo-Cantabrana, C., Sanchez, B., Milani, C., Ventura, M., Margolles, A., and Ruas-Madiedo, P. (2014). Genomic overview and biological functions of exopolysaccharide biosynthesis in Bifidobacterium spp. Appl Environ Microbiol 80(1), 9-18. doi: 10.1128/AEM.02977-13.

Holdeman, et al., Eubacterium contortum (Prevot) comb. nov.: Emendation of description and designation of the type strain. International journal of systematic bacteriology. Oct. 1971;21(4): 304-306.
Horn, et al., Synthesis of Oligonucleotides on Cellulose. Part II: Design and Synthetic Strategy to the Synthesis of 22 Oligodeoxynucleotides Coding for Gastric Inhibitory Polypeptide (GIP). 1980. Nuc Acids Res Symp Ser 225-232.
Horwell, et al., The 'peptoid' approach to the design of non-peptide, small molecule agonists and antagonists of neuropeptides. 1995. Trends Biotechnol. 13(4):132-134.
Hougee, et al., Oral treatment with probiotics reduces allergic symptoms in ovalbumin-sensitized mice:a bacterial strain comparative study. Int Arch Allergy Immunol. 2010; 151:107-117.
Hughes, K.R., Harnisch, L.C., Alcon-Giner, C., Mitra, S., Wright, C.J., Ketskemety, J., et al. (2017). Bifidobacterium breve reduces apoptotic epithelial cell shedding in an exopolysaccharide and MyD88-dependent manner. Open Biol 7(1). doi: 10.1098/rsob.160155.
Hytönen, J., Haataja, S., and Finne, J. (2003). *Streptococcus pyogenes* Glycoprotein-Binding Strepadhesin Activity Is Mediated by a Surface-Associated Carbohydrate-Degrading Enzyme, Pullulanase. Infection and Immunity 71(2), 784-793.
Hytonen, J., Haataja, S., and Finne, J. (2006). Use of flow cytometry for the adhesion analysis of *Streptococcus pyogenes* mutant strains to epithelial cells: investigation of the possible role of surface pullulanase and cysteine protease, and the transcriptional regulator Rgg. BMC Microbiol 6, 18. doi: 10.1186/1471-2180-6-18.
International Preliminary Report dated Mar. 1, 2017 for International Application No. PCT/GB2015/054113.
International Preliminary Report on Patentability for International Application No. PCT/GB2012/051686 dated Jan. 14, 2014.
International Search Report dated Jan. 27, 2017 for International Application No. PCT/GB2016/053622.
International Search Report dated Feb. 10, 2016 for International Application No. PCT/GB2015/054113.
International Search Report dated Feb. 17, 2017 for International Application No. PCT/GB2016/053676.
International Search Report dated Mar. 7, 2016 for International Application No. PCT/GB2015/054112.
International Search report dated Mar. 15, 2003 for International Application No. PCT/GB2002/05255.
International Search Report dated Aug. 26, 2016 for International application No. PCT/GB2016/051776.
International Search Report dated Sep. 6, 2016 for International application No. PCT/GB2016/051768.
International Search Report dated Sep. 6, 2016 for International application No. PCT/GB2016/051773.
International Search Report dated Sep. 6, 2016 for International application No. PCT/GB2016/051770.
International Search Report dated Feb. 2, 2017 for International application No. PCT/GB2016/053620.
International Search Report dated Mar. 6, 2017 for International Application No. PCT/GB2016/053677.
International Search Report for International Application No. PCT/GB2012/051686 dated Jan. 31, 2013.
International search report with written opinion dated Feb. 26, 2018 for PCT/GB2017/053722.
International search report with written opinion dated Jun. 8, 2017 for GB Application No. 1616016.
International search report with written opinion dated Sep. 29, 2017 for GB Application No. 1621123.
International search report with written opinion dated Oct. 16, 2017 for PCT/GB2017/052076.
Inturri, R., Molinaro, A., Di Lorenzo, F., Blandino, G., Tomasello, B., Hidalgo-Cantabrana, C., et al. (2017). Chemical and biological properties of the novel exopolysaccharide produced by a probiotic strain of Bifidobacterium longum. Carbohydr Polym 174, 1172-1180. doi: 10.1016/j.carbpol.2017.07.039.
Ishikawa, et al., Effect of bifidobacteria to suppress Th17, Food Science and technology institute, 2008, 5 Pages.

(56) References Cited

OTHER PUBLICATIONS

Ispirli, H. et al., Characterization of functional properties of Enterococcus faecium strains isolated from human gut.Can. J. Microbiol. 61: 861-870 (2015) dx.doi.org/10.1139/cjm-2015-0446.

Israel, E. et al., Supplementary Appendix, Severe and difficult-to-treat asthma in adults. N. Engl J Med 2017;p. 377:965-76. DOI: 10.1056/NEJMra1608969.

Israel, et al., Severe and difficult-to-treat asthma in adults, The New England Journal of Medicine, Sep. 2017; 377(10):965-976.

Issue Notification dated Feb. 20, 2019 for Co-Pending U.S. Appl. No. 15/631,945.

Ivanov, D., Emonet, C., Foata, F., Affolter, M., Delley, M., Fisseha, M., et al. (2006). A serpin from the gut bacterium *Bifidobacterium longum* inhibits eukaryotic elastase-like serine proteases. J Biol Chem 281(25), 17246-17252. doi: 10.1074/jbc.M601678200.

Jackson MS, Bird AR, McOrist AL. Comparison of two selective media for the detection and enumeration of Lactobacilli in human faeces (2002). J Microbial Methods. 51 (3), pp. 313-321.

Jawad, S. et al., Elevated serum levels of interleukin-17A in uveitis patients. Ocul Immunol Inflamm. Dec. 2013;21(6):434-9. doi: 10.3109/09273948.2013.815786. Epub Aug. 19, 2013.

Jenq, Robert R., Intestinal Bluatia is associated with reduced death from graft versus-host disease, Bio Blood Marro Transplant. Aug. 2015; 21(8): 1373-1383. doi:10.1016/j.bbmt.2015.04.016.

Jeon, S.G., Kayama, H., Ueda, Y., Takahashi, T., Asahara, T., Tsuji, H., et al. (2012). Probiotic Bifidobacterium breve induces IL-10-producing Tr1 cells in the colon. PLoS Pathog 8(5), e1002714. doi: 10.1371/journal.ppat.1002714.

Joblin K N., "Ruminal Acetogens and Their Potential to Lower Remnant Methane Emissions." Australian Journal of Agricultural Research. vol. 50. No. 8. 1999, pp. 1307-1313. XP001010439.

Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.

Kanauchi, et al., Eubacterium limosum (probiotic) and its metabolites showed anti-inflammatory effects and increased mucosal barrier function in colitis. Gastroenterology, 2005;128: p. A281, XP009193489.

Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.

Karaffova, et al., Interaction of TGF-B4 and IL-17 with IgA secretion in the intestine of chickens fed with E. faecium AL41 and challenged with S. Enteritidis. Research in Veterinary science. 2015;75-79.

Karin, M. Nuclear factor-kappaB in cancer development and progression. Nature. May 25, 2006;441(7092):431-6.

Keller et al.. "DNA Probes", 1994. Stockton Press. New York. XP002158943 108660 pp. 594-596.

Kelly, et al., Commensal gut bacteria: mechanisms of immune modulation. TRENDS in immunology, 2005;26(6):326-333.

Kinoshita, H., Uchida, H., Kawai, Y., Kawasaki, T., Wakahara, N., Matsuo, H., et al. (2008). Cell surface Lactobacillus plantarum LA 318 glyceraldehyde-3-phosphate dehydrogenase (GAPDH) adheres to human colonic mucin. J Appl Microbiol 104(6), 1667-1674. doi: 10.1111/j.1365-2672.2007.03679.x.

Kirsty Minton: Mucosal immunology: The ins and outs of gut inflammation, The journal of immunology, 4(2), Feb. 1, 2004: pp. 81-81, XP055252701.

Kishimoto, M., Nomoto, R., Mizuno, M., and Osawa, R. (2017). An in vitro investigation of immunomodulatory properties of Lactobacillus plantarum and L. delbrueckii cells and their extracellular polysaccharides. Bioscience of Microbiota, Food and Health 36(3), 101-110. doi: 10.12938/bmfh.17-001.

Kitahara et al., *Bacteroides plebeius* sp. nov. and *Bacteroides coprocola* sp. nov., isolated from human faeces, 2005; Int J Syst Ev Microbiol 55: 2143-47.

Kitahara, M. et al., *Bacteroides plebeius* sp. nov. and *Bacteroides coprocola* sp. nov., isolated from human faeces. International journal of systematic and evolutionary microbiology. 2005; 55: 2143-2147.

Kogyo, S. Lactic Acid Bacteria, Intestinal Flora ad Health II; Physiological effects of heat-treated lactococcus "EF-2001" and application to food. Mar. 30, 2001 vol. 44, No. 6, pp. 35-39.

Koh, Gar Yee et al., Parabacteroides distasonis attenuate toll-like receptor 4 signalling and Akt activation and blocks colon tumor formulation in high-fat-diet-fed azoxymethane-treated mice, International Journal of Cancer, pp. 1-30. Accepted Article, doi: 10.1002/ijc.31559.

Korhonen, J.M., Sclivagnotis, Y., Von Wright, A Characterization of dominant cultivable lactobacilli and their antibiotic resistance profiles from faecal samples of weaning piglets (2007). Journal of Applied Microbiology, 103 (6), pp. 2496-2503.

Kumolosasi, E., Salim, E., Jantan, I., and Ahmad, W. (2014). Kinetics of Intracellular, Extracellular and Production of Pro-Inflammatory Cytokines in Lipopolysaccharide-Stimulated Human Peripheral Blood Mononuclear Cells. Tropical Journal of Pharmaceutical Research 13(4), 536-543. doi: 10.4314/tjpr.v13i4.8.

Kverka, M. et al., Oral administration of Parabacteroides distasonis antigens attenuates experimental murine colitis through modulation of immunity and microbiota composition. Clinical & Experimental Immunology. 2010; 163:250-259.

Lahteinen, T., et al., A Pro biotic properties of Lactobacillus isolates originating from porcine intestine and feces (20 10) Anaerobe, 16 (3), pp. 293-300.

Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9, 2015.

Law, J., Buist, G., Haandrikman, A., Kok, J., Venema, G., and Leenhouts, K. (1995). A system to generate chromosomal mutations in Lactococcus lactis which allows fast analysis of targeted genes. Journal of Bacteriology 177(24), 7011-7018.

Lebeer, S., Claes, I.J., Verhoeven, T.L., Vanderleyden, J., and De Keersmaecker, S.C. (2011). Exopolysaccharides of Lactobacillus rhamnosus GG form a protective shield against innate immune factors in the intestine. Microb Biotechnol 4(3), 368-374. doi: 10.1111/j.1751-7915.2010.00199.x.

Lebeer, S., Verhoeven, T.L., Francius, G., Schoofs, G., Lambrichts, I., Dufrene, Y., et al. (2009). Identification of a Gene Cluster for the Biosynthesis of a Long, Galactose-Rich Exopolysaccharide in Lactobacillus rhamnosus GG and Functional Analysis of the Priming Glycosyltransferase. Appl Environ Microbiol 75(11), 3554-3563. doi: 10.1128/AEM.02919-08.

Lee, et al. Intestinal microbiota in pathophysiology and management of irritable bowel syndrome . 2014. World J Gastroenterol. 20(27): 8886-8897.

Lejeune, FJ. et al., Efficiency of Recombinant Human TNF in Human Cancer Therapy. (2006) Cancer Immun. 6:6.

Leser et al. 'Culture-independent analysis of gut bacteria: the pig gastrointestinal tract microbiota revisited'. Applied and Environmental Microbiology. 2002, vol. 68, No. 2, pp. 673-690.

Li, C.Y., Lin Hc Fau-Lai, C.-H., Lai Ch Fau-Lu, J.J.-Y., Lu Jj Fau-Wu, S.-F., Wu Sf Fau-Fang, S.-H., and Fang, S.H. (2011). Immunomodulatory effects of lactobacillus and Bifidobacterium on both murine and human mitogen-activated T cells. Int Arch Allergy Immunol 156(2), 128-136. doi: 10.1159/000322350.

Li, et al,. Screening and Identification of Lactobacillus animalis strain and characteristics of its bacteriostatic protein, Weishengwuxue Tongbao 2009; 36(7): 1001-1007.

Liu et al. Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., Blautia hansenii comb. nov., Blautia hydrogenotrophica comb. nov., Blautia luti comb. nov., Blautia producta comb. nov., Blautia schinkii comb. nov. and description of *Blautia wexlerae* sp. nov., isolated from human faeces. 2008. Int J Syst Evol Microbiol 58,1896-1902.

(56) References Cited

OTHER PUBLICATIONS

Liu, Y., et al., Human-derived probiotic Lactobacillus reuteri strains differentially reduce intestinal inflannuation (20 10). American Journal of Physiology—Gastrointestinal and Liver Physiology, 299 (5), pp. G1087-G1096.

Ljungh, A, Wadstrom, T. Lactic acid bacteria as probiotics (2006). Current Issues in Intestinal Microbiology, 7 (2), pp. 73-90.

Lodemann, U. et al., Effects of the Probiotic enterococcus faecium and pathogenic *Escherichia coli* strains in a pig and human epithelial intestinal cell model. Hindawi publishing corporation scientifica. 2015(235184) 10 pages.

Lopetuso et al. Commensal Clostridia: leading players in the maintenance of gut homeostasis. 2013. Gut Pathogens, 5: 23.

Lopez, P., Gonzalez-Rodriguez, I., Sanchez, B., Ruas-Madiedo, P., Suarez, A., Margolles, A., et al. (2012). Interaction of Bifidobacterium bifidum LMG13195 with HT29 cells influences regulatory-T-cell-associated chemokine receptor expression. Appl Environ Microbiol 78(8), 2850-2857. doi: 10.1128/AEM.07581-11.

Lopez-Boado, Y. S. et al., Bacterial Exposure Induces and Activates Matrilysin in Mucosal Epithelial Cells. J Cell Biol148, 1305-1315 (2000).

Lozupone. Diversity, stability and resilience of the human gut microbiota. 2012. Nature. Sep. 13, 2012; 489 (7415): 220-230.

López, P., Gonzalez-Rodríguez, I., Gueimonde, M., Margolles, A., and Suarez, A. (2011). Immune Response to Bifidobacterium bifidum Strains Support Treg/Th17 Plasticity. PLOS ONE 6(9), e24776. doi: 10.1371/journal.pone.0024776.

López, P., Gueimonde, M., Margolles, A., and Suarez, A. (2010). Distinct Bifidobacterium strains drive different immune responses in vitro. International Journal of Food Microbiology 138(1), 157-165. doi: https://doi.org/10.1016/j.ijfoodmicro.2009.12.023.

Luger, D. and Caspi, R.R., New perspectives on effector mechanisms in uveitis. (2008) Semin. Immunopathol. 30(2): 134-143.

Álvarez-Martin, P., O'Connell-Motherway, M., van Sinderen, D., and Mayo, B. (2007). Functional analysis of the pBC1 replicon from Bifidobacterium catenulatum L48. Applied Microbiology and Biotechnology 76(6), 1395. doi: 10.1007/s00253-007-1115-5.

Lyons, et al., Bacterial strain-specific induction of Foxp3 T regulatory cells is protective in murine allergy models. Clinical & Experimental Allergy. 2010; 40:811-819.

Macsharry et al., Immunomodulatory effects of feeding with bifidobacterium longum on allergen-induced lung inflammation in the mouse. Pulmonary pharmacology & Therapeutics. 2012; 25:325-334.

Manni et al., A tale of two cytokines: IL-17 and IL-22 in asthma and infection. Expert Rev Respir Med. Feb. 2014 ; 8(1): 25-42. doi:10.1586/17476348.2014.854167.

Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.

Martin R. et al., Isolation of lactobacilli from sow milk and evaluation of their probiotic potential. J of dairy research 76(4)418-425. Nov. 2009.

Matthes, et al., Simultaneous rapid chemical synthesis of over one hundred oligonucleotides on a microscale. Apr. 1984. EMBO Journal, 3(4): p. 801-805.

Maya, J.R. et al., Emerging Therapies for Noninfectious Uveitis: What May Be Coming to the Clinics. (2014) J. Ophthalmology. 310329.

Mazmanian, SK., An immunomodulatory molecule of symbiotic bacteria directs maturation of the host immune system.Cell. Jul. 15, 2005;122(1):107-18.

McCarville, J.L., Dong, J., Caminero, A., Bermudez-Brito, M., Jury, J., Murray, J.A., et al. (2017). A Commensal Bifidobacterium longum Strain Prevents Gluten-Related Immunopathology in Mice through Expression of a Serine Protease Inhibitor. Applied and Environmental Microbiology 83(19), e01323-01317. doi: 10.1128/AEM.01323-17.

McClymont, S.A., Putnam Al Fau-Lee, M.R., Lee Mr Fau-Esensten, J.H., Esensten Jh Fau-Liu, W., Liu W Fau-Hulme, M.A., Hulme Ma Fau-Hoffmuller, U., et al. (2011). Plasticity of human regulatory T cells in healthy subjects and patients with type 1 diabetes. Journal of Immunology 186(7), 3918-3926. doi: 10.4049/jimmunol.1003099.

Menard, S., Laharie D Fau-Asensio, C., Asensio C Fau-Vidal-Martinez, T., Vidal-Martinez T Fau-Candalh, C., Candalh C Fau-Rullier, A., Rullier A Fau-Zerbib, F., et al. (2005). Bifidobacterium breve and *Streptococcus thermophilus* secretion products enhance T helper 1 immune response and intestinal barrier in mice. Experimental Biology and Medicine (Maywood) 230(10), 749-756.

Meyza, et al. The BTBR mouse model of idiopathic autism—Current view on mechanisms. 2017. Neurosci Biobehav Rev.;76(Pt A):99-110.

Milani, C., Mangifesta, M., Mancabelli, L., Lugli, G.A., Mancino, W., Viappiani, A., et al. (2017). The Sortase-Dependent Fimbriome of the Genus Bifidobacterium: Extracellular Structures with Potential to Modulate Microbe-Host Dialogue. Appl Environ Microbiol 83(19). doi: 10.1128/AEM.01295-17.

Miossec, P. et al. Targeting IL-17 and TH17 cells in chronic inflammation. Nat Rev Drug Discov. Oct. 2012;11(10):763-76. doi: 10.1038/nrd3794.

Miraglia Del Giudice, M., Indolfi, C., Capasso, M., Maiello, N., Decimo, F., and Ciprandi, G. (2017). Bifidobacterium mixture (B longum BB536, B infantis M-63, B breve M-16V) treatment in children with seasonal allergic rhinitis and intermittent asthma. Italian Journal of Pediatrics 43(1), 25. doi: 10.1186/s13052-017-0340-5.

Miyake, T. et al., Phylogenetic Analysis of the Genus *Bifidobacterium* and Related Genera Based on 16S rDNA Sequences. Microbiol. Immunol. 1998; 42(10):661-667.

Miyauchi, E., Control of multiple sclerosis by gut microbiota. Journal of clinical and experimental medicine. 2015. vol. 253 No. 5.2, pp. 445-450.

Molecular Biology Techniques, 1st edition. An intensive laboratory course. 1998.

Mortaz, E. et, al., Anti-Inflammatory Effects of Lactobacillus Rahmosus and Bifidobacterium Breve on Cigarette Smoke Activated Human Mcrophiages, PLoS ONE, Apr. 21, 20i15, 10(8):e0136455.DOI:10.1371, Journal.pone.0136455.

Mucientes, A. et al., Specific association of IL17A genetic variants with panuveitis. (2015) Br J Ophthalmol. 99(4):566-70.

Mukai et al., SH3BP2 Gain-Of-Function Mutation Exacerbates Inflammation and Bone Loss in a Murine Collagen- Induced Arthritis Model, 2014 PLoS ONE 9(8): e105518.

Mulder et al. 'Environmentally-acquired bacteria influence microbial diversity and natural innate immune responses at gut surfaces'. BMC Biology. 2009, vol. 7, No. 1, pp. 79.

Murofushi, Y., Villena, J., Morie, K., Kanmani, P., Tohno, M., Shimazu, T., et al. (2015). The toll-like receptor family protein RP105/MD1 complex is involved in the immunoregulatory effect of exopolysaccharides from Lactobacillus plantarum N14. Mol Immunol 64(1), 63-75. doi: 10.1016/j.molimm.2014.10.027.

Narushima, et al., Characterization of the 17 strains of regulatory T cell-inducing human-derived Clostridia. Gut Microbes Mar. 18, 2014; 5:3, 333-339.

Naughton PJ; Grant G. (2005) Modelling of salmonellosis in: Microbial Ecology of the Growing Animal Holzapfel WH, Naughton PJ. (Eds). London, Elsevier. pp. 235-257.

Neeser, J.R., et al., Lactobacillus johnsonii Lal shares carbohydrate-binding specificities with several enteropathogenic bacteria (2000). Glycobiology, 10 (II), pp. 1193-1199.

Neish, A. S. et al., Prokaryotic Regulation of Epithelial Responses by Inhibition of IκB-α Ubiquitination. Science 289, 1560 (2000).

Nemeth et al. 'Inhibition of *Salmonella*-induced IL-8 synthesis and expression of Hsp70 in enterocyte-like Caco-2 cells after exposure to non-starter lactobacilli'. International Journal of Food Microbiology. 2006, vol. 112, No. 3, pp. 266-274.

Nicolau, D.P. Current challenges in the management of the infected patient (2011). Current Opinion in Infectious Diseases, 24 (SuppII), pp. SI-S10.

(56) References Cited

OTHER PUBLICATIONS

Notice of Allowance dated Mar. 30, 2011 for U.S. Appl. No. 10/285,224.
Notice of Allowance dated Apr. 25, 2016 for U.S. Appl. No. 14/232,475.
Notice of Allowance dated Aug. 23, 2016 for U.S. Appl. No. 14/232,475.
Notice of allowance dated Sep. 1, 2017 for U.S. Appl. No. 15/357,850.
Notice of Allowance dated Nov. 22, 2017 for U.S. Appl. No. 15/359,988.
Notice of Publication dated Dec. 27, 2018 for U.S. Appl. No. 16/022,256.
Nuala Moran: 'Microbial wealth', chemistry and industry, 78(6), Jun. 1, 2014, pp. 20-23, XP055252922.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189.
Numasaki, M. et al., Interleukin-17 promotes angiogenesis and tumor growth. Blood. Apr. 1, 2003;101(7):2620-7. Epub Oct. 31, 2002.
O'Connell Motherway, M., Kinsella, M., Fitzgerald, G.F., and Sinderen, D. (2013). Transcriptional and functional characterization of genetic elements involved in galacto-oligosaccharide utilization by Bifidobacterium breve UCC2003. Microbial biotechnology 6(1), 67-79. doi: 10.1111/1751-7915.12011.
O'Connell Motherway, M., O'Driscoll, J., Fitzgerald Gerald, F., and Van Sinderen, D. (2009). Overcoming the restriction barrier to plasmid transformation and targeted mutagenesis in Bifidobacterium breve UCC2003. Microbial Biotechnology 2(3), 321-332. doi: 10.1111/j.1751-7915.2008.00071.x.
O'Connell Motherway, M., Zomer, A., Leahy, S.C., Reunanen, J., Bottacini, F., Claesson, M.J., et al. (2011). Functional genome analysis of Bifidobacterium breve UCC2003 reveals type IVb tight adherence (Tad) pili as an essential and conserved host-colonization factor. Proc Natl Acad Sci USA 108(27), 11217-11222. doi: 10.1073/pnas.1105380108.
Odamaki, Toshitaka et al., "Age-related changes in gut microbiota composition from newborn to centenarian: a cross-sectional study," BMC Microbiology (2016) 16:90, pp. 1-12, DOI 10.1186/S12866-016-0708-5.
Office Action dated Mar. 19, 2019 for U.S. Appl. No. 16/031,024.
Ohashi, Y., Ushida, K. Health-beneficial effects ofprobiotics: Its mode of action (2009). Animal Science Journal, 80 (4), pp. 361-371.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Olivares, M., Castillejo, G., Varea, V., and Sanz, Y. (2014). Double-blind, randomised, placebo-controlled intervention trial to evaluate the effects of Bifidobacterium longum CECT 7347 in children with newly diagnosed coeliac disease. British Journal of Nutrition 112(1), 30-40. doi: 10.1017/S0007114514000609.
O'Sullivan et al., "Bacterial Supplementation in the Irritable Bowel Syndrome. A Randomised Double-Blind Placebo-Controlled Crossover Study", Digest Liver Dis. 2000. pp. 294-301.
Overbeek, R., Begley, T., Butler, R.M., Choudhuri, J.V., Chuang, H.-Y., Cohoon, M., et al. (2005). The Subsystems Approach to Genome Annotation and its Use in the Project to Annotate 1000 Genomes. Nucleic Acids Research 33(17), 5691-5702. doi: 10.1093/nar/gki866.
Pace et al. Macrophage activiation: Priming activity from a T-cell hybridoma is attributable to interferon. (1983) PNAS. 80:3782-6.
Pang, et al., Crystal structure of human pirin: an iron-binding nuclear protein and transcription cofactor. Journal of Biological Chemistry, 279(2); Jan. 9, 2004:1491-1498.
Parabacteroides distasonis (Eggerth and Gagnon) Sakamoto and Benno (ATCC 8503). Sep. 19, 2017. 2 Pages.
Park, S.K. et al., *Blautia stercoris* sp. nov., isolated from human faeces. International journal of systematic and evolutionary microbiology. 2012; 62(4): 776-779.
Patel., R. et al., Determination of 16S rRNA sequences of enterococci and application to species identification of nonmotile enterococcus gallinarum isolates. Journal of clinical microbiology, 1998; 36(11):3399-3407.
Paustian, C., Taylor, P., Johnson, T., Xu, M., Ramirez, N., Rosenthal, K.S., et al. (2013). Extracellular ATP and Toll-like receptor 2 agonists trigger in human monocytes an activation program that favors T helper 17. PLoS One 8(1), e54804. doi: 10.1371/journal.pone.0054804.
Coakley M et al: Intestinal bifidobacteria that produce trans-9, trans-11 conjugated linoleicacid: A fatty acid with antiproliferative activity against human colon SW480and HT-29 cancer cells, Nutrition and Cancer, Taylor & Francis Group, US vol. 56, No. 1, Jan. 1, 2006 (Jan. 1, 2006), pp. 95-102, XP008087265, ISSN: 0163-5581, DOI:10.1207/515327914NC5601 13 cf. abstract, p. 101, last para. of the right-hand col.
PCT/EP2017/025038 International Preliminary Report on Patentability dated Jun. 6, 2018, 8 Pages.
PCT/EP2017/025038 International Search Report and Written Report dated Jun. 12, 2017.
PCT/EP2017/025038 Written Opinion of the International Preliminary Examining Authority dated Jan. 1, 2018.
PCT/EP2017/025038 Written Opinion of the International Preliminary Examining Authority dated Jan. 25, 2018.
PCT/GB2017/052076 Written Opinion of the International Preliminary Examining Authority dated Jun. 21, 2018, 11 Pages.
PCT/GB2017/052077 International Search Report dated Oct. 16, 2017.
PCT/GB2017/052077 Written Opinion dated Oct. 16, 2017.
PCT/GB2017/052077 Written Opinion of the International Preliminary Examining Authority dated Jun. 21, 2018, 10 Pages.
Database WPI, Week 201801, Thomson Scientific, London, GB; AN 2017-834299, XP002787097, & WO 2017/209156 Al (Morinaga Milk Ind Co. Ltd) Dec. 7, 2017 (Dec. 7, 2017) * abstract * of WO2017/2019156, Kobayashi, Youdai et al.
Devillard, E. et al., Metabolism of Linoleic Acid by Human Gut Bacteria: Different Routes for Biosynthesis of Conjugated Linoleic Acid, Journal O. Bacteriology, 2007, vol. 189, No. 4, p. 2544-2570.
Pearson, WR. An introduction to sequence similarity ("Homology") searching. Current protocols in bioinformatics/editoral board, Andreas D Baxevanis. [et al]. 2013; 0 3:10. 1002/0471250953.bi0301s42. doi:10.1002/0471250953.bi0301s42.
Petersen et al. Intestinal colonization with phylogenetic group B2 *Escherichia coli* related to inflammatory bowel disease: a systematic review and meta-analysis. 2015. Scand J Gastroenterol. ;50(10):1199-207.
Petsuriyawong et al. 'Screening of probiotic lactic acid bacteria from piglet feces'. Nature Science. 2011, vol. 45, pp. 245-253.
Hoarau, Cyrille et al., Supernatant from Bifidobacterium Differentially Modulates Transduction Signaling Pathways for Biological Functions of Human Dendritic Cells, PLOS ONE, Public Library of Science, US, vol. 3, No. 7, Jul. 1, 2008 (Jul. 1, 2008), pp. e2753-1, XP009139666,ISSN: 1932-6203 *cf. abstract and conclusion, furthermore discussion part at p. 3, col. at the right side*.
Pinto-Sanchez, M.I., Smecuol, E.C., Temprano, M.P., Sugai, E., González, A., Moreno, M.L., et al. (2017). Bifidobacterium infantis NLS Super Strain Reduces the Expression of α-Defensin-5, a Marker of Innate Immunity, in the Mucosa of Active Celiac Disease Patients. Journal of Clinical Gastroenterology 51(9), 814-817. doi: 10.1097/mcg.0000000000000687.
Database WPI,Week 201801, Thomson Scientific, London, GB; AN 2017-834299, XP002787097,& WO 2017/209156 Al (Morinaga Milk Ind Co Ltd) Dec. 7, 2017 (Dec. 7, 2017) * abstract *.
Hoarau et al: "TLR2 Activation by Supernatant From Bifidobacterium Breve Modulates Maturation and Survival of Human DCs Via Differential Effects on PI3Kinase, p38 and ERK Pathways",Journal of Allergy and Clinical Immuno, Elsevier, Amsterdam, NL, vol. 119, No. 1, Jan. 1, 2007 (Jan. 1, 2007), p. S258, XP005756921, ISSN: 0091-6749, DOI: 10.1016/J.JACI.2006.12.377 *cf. abs.No. 1008 at p. S258*.

(56) References Cited

OTHER PUBLICATIONS

Liu, Chang-jian et al., Antioxidant and Cholesterol-Reducing Properties of Enterococcus gallinarum m661, Bioengineering (Food Science), vol. 34, No. 7, Dec. 31, 2013, pp. 157-161.

Matsuda F et al: Evaluation of a probiotics,BBG-01, for enhancement of immunogenicity of an oral inactivated cholera vaccine and safety: A randomized, double-blind, placebo-controlled trial in Bangladeshi children under 5 years of age,Vaccine, Elsevier, Amsterdam, NL, vol. 29, No. 10, Dec. 26, 2010 (Dec. 26, 2010), pp. 1855-1858, XP028147184, ISSN: 0264-410X, DOI: 10.1016/J.VACCINE.2010.12.133 [retrieved on Jan. 7, 2011] *cf. abstract*.

Scuotto, Angelo et al., In silico mining and characterization of bifidobacterial lipoprotein with CHHP domain secreted in an aggregated form, International J. of Biol. Macromolecutes 82(2016), 653-662.

Rajilic-Stojanovic, et al. The first 1000 cultures species of the human gastrointestinal micriobiota. FEMS Mlcriobiol Rev, vol. 38, 2014. pp. 996-1047.

Reddy, K.B.P.K., et al., Role of cryoprotectants on the viability and functional properties of pro biotic lactic acid bacteria during freeze drying (2009). Food Biotechnology, 23 (3), pp. 243-265.

Remington. Remington: The science and practice of pharmacy. 20th Edition. Gennaro, Eds. Lippincott Williams & Wilkins, 2003.

Reuter, G. (2001). The Lactobacillus and Bifidobacterium microflora of the human intestine: composition and succession. Current Issues in Intestinal Microbiology 2(2), 43-53.

Rhee, Young-Kyung et al.., Antihumor Activity of *Bifidobacterium* Spp. isolated from a healthy Korean, Arch Pharm Res vol. 23, No. t, 482-487 2000.

Riquelme. Will 4D Pharma be UK's next Microbiome leader? Feb 2, 2015, LABIOTECH.eu [online].

Robertson, J.M.C., et al., Lack of flagella disadvantages *Salmonella enterica* serovar Enteritidis during the early stages of infection in the rat (2003). Journal of Medical Microbiology, 52 (1), pp. 91-99.

Robinson, et al. Inside information—The unique features of visceral sensation. 2008. Mol Interv, 8(5): 242-253.

Rockwell, S.C. et al., Characteristics of a Serially Transplanted Mouse Mammary Tumor and Its Tissue-Culture-Adapted Derivative. (1972) J Natl Cancer Inst. 49:735-49.

Rong, Y., Dong, Z., Hong, Z., Jin, Y., Zhang, W., Zhang, B., et al. (2017). Reactivity toward Bifidobacterium longum and Enterococcus hirae demonstrate robust CD8(+) T cell response and better prognosis in HBV-related hepatocellular carcinoma. Experimental Cell Research 358(2), 352-359. doi: 10.1016/j.yexcr.2017.07.009.

Roseburia. Ubiome, 2018. Accessed on Jun. 25, 2018; Available at: https://shop.ubiome.com/pages/roseburia-1.

Ruiz, L., Delgado, S., Ruas-Madiedo, P., Margolles, A., and Sanchez, B. (2016). Proteinaceous Molecules Mediating Bifidobacterium-Host Interactions. Front Microbiol 7, 1193. doi: 10.3389/fmicb.2016.01193.

Ruiz, P.A., Hoffmann, M., Szcesny, S., Blaut, M., and Haller, D. (2005). Innate mechanisms for Bifidobacterium lactis to activate transient pro-inflammatory host responses in intestinal epithelial cells after the colonization of germ-free rats. Immunology 115(4), 441-450. doi: 10.1111/j.1365-2567.2005.02176.x.

Sagar, et al., Bifidobacterium breve and lactobacillus rhamnosus treatment is as effective as budesonide at reducing inflammation in a murine model for chronic asthma. Respiratory Research. 2014; 15(46):1-17.

Saiki, et al., Primer-directed enzymatic amplification of DNA with a thermostable DNA polymerase. 1988. Science, 239. pp. 487-491.

Sakamato, et al., *Parabacteroides faecis* sp. nov., isolated from human faeces. International Journal of Systematic and Evolutionary Microbiology (2015), 65, 1342-1346.

Sakamoto, et al., *Parabacteroides gordonii* sp. nov., isolated from human blood cultures. International Journal of Systematic and Evolutionary Microbiology (2009), 59, 2843-2847.

Sakamoto, et al., *Parabacteroides johnsonii* sp. nov., isolated from human faeces. International Journal of Systematic and Evolutionary Microbiology (2007), 57, 293-296.

Sakamoto, M. et al., Reclassification of Bacteroides distasonis, Bacteroides goldsteinii and Bacteroides merdae as *Parabacteroides distasonis* gen. nov., comb. nov., Parabacteroides goldsteinii comb. nov. and Parabacteroides merdae comb. nov. International journal of systematic and evolutionary microbiology. 2006; 56: 1599-1605.

Sakamoto Mitsuo et al., Reclassfication of Baceroides distasonis, Bacteroides goldsteinii and Bacteroides merdae as *Parabacteroides distasonis* gen. nov., comb. nov., Parabacteroides goldsteinii comb. nov. and Parabacteroides merdae comb. nov., International Journal of Systematic and Evolutionary Microbiology (2006) 56, 15-99-1605. DOI 10.1099/ijs.0.0641920.

Salix Pharmaceuticals, Inc. FDA Highlights of Prescribing Information—Xifaxan (rifaximin tablet). Revised Nov. 2015.

Scher et al., Expansion of intestinal Prevotella copri correlates with enhanced susceptibility to arthritis. 2013; eLIFE 2, e01202, 20 Pages.

Schiavi, E., Gleinser, M., Molloy, E., Groeger, D., Frei, R., Ferstl, R., et al. (2016). The Surface-Associated Exopolysaccharide of Bifidobacterium longum 35624 Plays an Essential Role in Dampening Host Proinflammatory Responses and Repressing Local TH17 Responses. Appl Environ Microbiol 82(24), 7185-7196. doi: 10.1128/AEM.02238-16.

Schiavi, E., Plattner, S., Rodriguez-Perez, N., Barcik, W., Frei, R., Ferstl, R., et al. (2018). Exopolysaccharide from *Bifidobacterium longum* subsp. *longum* 35624 modulates murine allergic airway responses. Benef Microbes, 1-14. doi: 10.3920/BM2017.0180.

Schleifer, K.H. et al., Transfer of *Streptococcus faecalis* and *Streptococcus faecium* to the Genus *Enterococcus* nom. rev. as Enterococcus faecalis comb. nov. and Enterococcus faecium comb. nov. Int J Syst Evol Microbiol, Jan. 1984 34: 31-34, doi:10.1099/00207713-34-1-31.

Schmitz, S. et al., A prospective, randomized, blinded, placebo-controlled pilot study on the effect of Enterococcus faecium on clinical activity and intestinal gene expression in canine food-responsive chronic enteropathy. J Vet Intern Med. Mar.-Apr. 2015;29(2):533-43. doi: 10.1111/jvim.12563. Epub Mar. 16, 2015.

Schouten, et al., Cow milk allergy symptoms are reduced in mice fed dietary synbiotics during oral sensitization with whey. Nutritional Immunology. 2015; 139(7):1390-403.

Schreiber, O, et al., Lactobacillus reuteri prevents colitis by reducing P-selectin-associated leukocyte- and plateletendothelial cell interactions (2009). American Journal of Physiology—Gastrointestinal and Liver Physiology, 296 (3), pp. G534-G542.

Schwiertz, et al., Quantification of Different *Eubacterium* spp. In Human Fecal Samples with Species-Specific 16S rRNA-Targeted Oligonucleotide Probes. Applied and environmental biology, vol. 66, No. 1, Jan. 1, 2000; pp. 375-382.

Severijnen, A. J. et al., Chronic Arthritis Induced in Rats by Cell Wall Fragments of *Eubacterium* Species from the Human Intestinal Flora. Infection and Immunity, 1990, vol. 58, No. 2, 523-528.

Severijnen, et al., Chronic Arthritis Induced in Rats by Cell Wall Fragments of *Eubacterium* Species from the Human Intestinal Flora. Infection and Immunity, Feb. 1990; 58(2): p. 523-528.

Sgadari, C. et al., Interferon-inducible protein-10 identified as a mediator of tumor necrosis in vivo. (1996) PNAS. 93:13791-6.

Sgadari et al. Mig, the Monokine Induced by Interferon-g, Promotes Tumor Necrosis In Vivo. (1997) Blood. 89:2635-43.

Simon, et al., Peptoids: A modular approach to drug discover, Oct. 1992. PNAS, 89(20):9367-9371.

Simpson-Herren, L. et al., Kinetic parameters and growth curves for experimental tumor systems. Cancer Chemother Rep. Jun. 1970;54(3):143-74.

Sisson, G. et al., Randomised clinical trial: a liquid multi-strain probiotic vs. placebo in the irritable bowel syndrome—a 12 week double-blind study. Aliment Pharmacol Ther. 2014; 40: 51-62.

Sivan, A., Corrales, L., Hubert, N., Williams, J.B., Aquino-Michaels, K., Earley, Z.M., et al. (2015). Commensal Bifidobacterium promotes antitumor immunity and facilitates anti-PD-L1 efficacy. Science 350(6264), 1084-1089. doi: 10.1126/science.aac4255.

Sivieri, K. et al., Probiotic enterococcus faecium CRL 183 inhibit chemically induced colon cancer in male wistar rats. Eur Food Res Technol. 2008; 228:231-237.

(56) References Cited

OTHER PUBLICATIONS

Skolnick, et al. From genes to protein structure and function: novel applications of computational approaches in the genomic era. Trends Biotechnol. Jan. 2000;18(1):34-9. Review.
Smith, C.L., et al., Lactobacillus fermentum BRII and fructo-oligosaccharide partially reduce jejunal inflammation in a model of intestinal mucositis in rats (2008). Nutrition and Cancer, 60 (6), pp. 757-767.
Song et al., Impact of Schistosoma japonicum Infection on Collagen-Induced Arthritis in DBA/1 Mice: A Murine Model of Human Rheumatoid Arthritis. 2011; PLoS ONE 6, e23453, 10 pages.
Song, Yuli et al., *Bacteroides goldsteinii* sp. nov. Isolated from Clinical Specimens of Human Intestinal Origin, J. Clinical Microbiology, Sep. 2005, p. 4522-4527. DOI:10.1128/JCM.43.9.4522-4527.2005.
Sonnenburg, et al., Genomic and Metabolic Studies of the Impact of Probiotics on a Model Gut Symbiont and Host. PLoS Biol 4(12): e413. https://doi.org/10.1371/journal.pbio.0040413.
Catherine A. Lozupone et al: "Diversity, stability and resilience of the human gut microbiota", Nature, vol. 489, No. 7415, Sep. 1, 2012 (Sep. 1, 2012), pp. 220-230, XP055499616.
U.S. Appl. No. 15/915,889 Notice of Allowance dated Jun. 4, 2018.
Written Opinion for PCT/US2017/066709 (Published as WO2018/112365) owned by Evelo Biosciences, Inc.
Stokholm, et al., Maturation of the gut microbiome and risk of asthma in childhood. Nature Communications, 2018; 9(141): 1-10.
Stoll et al., Altered microbiota associated with abnormal humoral immune responses to commensal organisms in enthesitis-related arthritis, 2014; Arthritis Res Ther. 16:486.
Strasser, S. et al., Influence of lyophilization, fluidized bed drying, addition of protectants, and storage on the viability oflactic acid bacteria (2009). Journal of Applied Microbiology, 107 (1), pp. 167-177.
Strickertsson, J.A. et al., Enterococcus faecalis Infection and Reactive Oxygen Species Down-Regulates the miR-17-92 Cluster in Gastric Adenocarcinoma Cell Culture. Genes 2014, 5(3), 726-738.
Strus et al. Distinct effects of Lactobacillus plantarum KL30B and *Escherichia coli* 3A1 on the induction and development of acute and chronic inflammation. 2015. Cent Eur J Immunol.40(4):420-30.
Sun, D. et al., The role of Th17-associated cytokines in the pathogenesis of experimental autoimmune uveitis (EAU). (2015) Cytokine. 74(1):76-80.
Sun, et al., Exploring gut microbes in human health and disease: Pushing the envelope. Genes Dis. Dec. 2014; 1(2):132-139.doi:10.1016/j.gendis.2014.08.001.
Supplement to: ISRAEL, et al., Severe and difficult-to-treat asthma in adults. N Engl J Med 2017; 377:965-76.
Tahoun, A., Masutani, H., El-Sharkawy, H., Gillespie, T., Honda, R.P., Kuwata, K., et al. (2017). Capsular polysaccharide inhibits adhesion of Bifidobacterium longum 105-A to enterocyte-like Caco-2 cells and phagocytosis by macrophages. Gut Pathog 9, 27. doi: 10.1186/s13099-017-0177-x.
Tan, Hai-Qin et al., *Parabacteroides chartae* sp. nov., an obligately anaerobic species from wastewater of a paper mill, International Journal of systematic and Evolutionary Microbiology (2012), 62-2613-2617, DOI 10.1099/ijs.0.038000-0.
Tanaka, K. and Watanabe, K., In Vitro tebipenem activity against anaerobic bacteria. Japanese Journal of Chemotherapy. Mar. 2009. vol. 57 S-1.
Tap et al. Towards the human intestinal microbiota phylogenetic core. 2009. Environ Microbiol, 11(10):2574-84.
Tatusova et al., BLAST 2 Sequences, a new tool for comparing protein and nucleotidesequences, FEMS Microbiology Letters 174 (1999) 247-250.
Tatusova et al., Erratum to BLAST 2 Sequences, a new tool for comparing protein and nucleotide sequences, FEMS Microbiology Letters 177 (1999) 187-188.
Teng, L. J. et al., PCR Assay for Species-Specific Identification ofBacteroides thetaiotaomicron. J Clin Microbiol38, 1672-1675 (2000).

Terciz, Janos et al., Inflammation and Colon Cancer, Gastroenterology, 2010: 138: 2101-2114.
Tomas, M.S.J., et al., Stability of freeze-dried vaginal Lactobacillus strains in the presence of different lyoprotectors (2009). Canadian Journal of Microbiology, 55 (5), pp. 544-552.
Tomosada, Y., Villena, J., Murata, K., Chiba, E., Shimazu, T., Aso, H., et al. (2013). Immunoregulatory Effect of Bifidobacteria Strains in Porcine Intestinal Epithelial Cells through Modulation of Ubiquitin-Editing Enzyme A20 Expression. PLOS ONE 8(3), e59259. doi: 10.1371/journal.pone.0059259.
Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670.
Tsukinowa, et al., Fecal microbiota of a dugong (*Dugong dugong*) in captivity at Toba Aquarium. J. Gen. Appl. Microbiol., 54, 25-38 (2008).
Turnbaugh et al. A core gut microbiome in obese and lean twins. Jan. 22, 2009. Nature, 457(7228): 480-484.
Turroni, F., Taverniti V Fau-Ruas-Madiedo, P., Ruas-Madiedo P Fau-Duranti, S., Duranti S Fau-Guglielmetti, S., Guglielmetti S Fau-Lugli, G.A., Lugli Ga Fau-Gioiosa, L., et al. (2014). Bifidobacterium bifidum PRL2010 modulates the host innate immune response. Appl Environ Microbiol 80(1098-5336 (Electronic)), 730-740.
Tzortzis, G., et al., Modulation of anti-pathogenic activity in canine-derived *Lactobacillus* species by carbohydrate growth substrate (2004). Journal of Applied Microbiology, 96 (3), pp. 552-559.
Udayappan, et al., Oral treatment with Eubacterium hallii improves insulin sensitivity in db/db mice. NPJ Biofilms and microbiomes, vol. 2, Jul. 6, 2016; p. 16009.
Udayappan et al., PS4-5. Administration of Eubacterium hallii improves insulin sensitivity and degree of liversteatosis in male db/db mice. Nederlands tijdschrift voor diabetologie, vol. 11, No. 4., 23 Nov. 2013.pp. 145.
Untergasser, A., Nijveen, H., Rao, X., Bisseling, T., Geurts, R., and Leunissen, J.A. (2007). Primer3Plus, an enhanced web interface to Primer3. Nucleic Acids Res 35(Web Server issue), W71-74. doi: 10.1093/nar/gkm306.
U.S. Appl. No. 15/357,936 Notice of Allowance dated Apr. 18, 2018.
U.S. Appl. No. 15/359,144 Notice of Allowance dated Sep. 4, 2018.
U.S. Appl. No. 15/359,972 Notice of Allowance dated Aug. 8, 2018.
U.S. Appl. No. 15/359,988 Notice of Allowance dated Mar. 2, 2018.
U.S. Appl. No. 15/359,988 Notice of Allowance dated Mar. 16, 2018.
U.S. Appl. No. 15/592,178 Notice of Allowance dated Apr. 12, 2018.
U.S. Appl. No. 15/592,178 Notice of Allowance dated Jul. 12, 2018.
U.S. Appl. No. 15/631,945 Notice of Allowance dated Oct. 18, 2018.
U.S. Appl. No. 15/700,007 Notice of Allowance dated Oct. 17, 2018.
U.S. Appl. No. 15/915,885 Notice of Allowance dated May 23, 2018.
U.S. Appl. No. 15/916,167 Notice of Allowance dated May 31, 2018.
U.S. Appl. No. 15/916,202 Notice of Allowance dated Jun. 11, 2018.
U.S. Appl. No. 15/916,205 Notice of Allowance dated May 30, 2018.
U.S. Appl. No. 15/431,393 Office Action dated Jul. 30, 2018.
U.S. Appl. No. 15/631,945 Office Action dated May 15, 2018.
U.S. Appl. No. 15/631,952 Office Action dated Jul. 19, 2018.
U.S. Appl. No. 15/679,857 Office Action dated Aug. 6, 2018.
U.S. Appl. No. 15/803,723 Notice of Allowance dated Feb. 13, 2018.
U.S. Appl. No. 15/842,635 Office Action dated Aug. 27, 2018.
Van De Bogert, et al., Immunomodulatory properties of *Streptococcus* and veillonella isolates from the human small intestine microbiota, Plos One, Dec. 2014: 1-20, DOI:10.1371/journal.pone. 0114277.

(56) References Cited

OTHER PUBLICATIONS

Van de Pot, M.A. et al., Sybiotics reduce allergen-induced T-helper 2 respond and improve peak expiatory flow in allergic asthmatics, Allergy 2011;66:39-47.
Van De Veerdonk, et al., The Anti-CD20 antibody rituximab reduces the Th17 cell response. Arthritis & Rheumatism. Jun. 2011; 63(6):1507-1516.
Van Nevel et al., "Conrol of Rumen Methanogenesis." Environmental Monitoring and Assessment. vol. 42, 1996, pp. 73097, XP000979267.
Van Tilburg, M. Can we treat visceral hypersensitivity in functional abdominal pain? Lancet Gastroenterolhepatol, 2017; 2 Pages.
Verheijden, K.A.T. et al., The development of allergic inflammation in a murine house dust mite asthma is suppressed by symbiotic mixtures of non-digestible oligosaccharides and Bifidobacterium breve M-16V; Eur. J. Nut. (2016) 55: 1141-1151, DOI 10.1007, 500394-015-0928-8.
Vetrovsky, T. and Baldrian, P., The variability of the 16S rRNA gene in bacterial genomes and its consequences for bacterial community analyses. Plos One. Feb. 2013; 8(2): e57923.
Viaud, Sophie et al. "The intestinal microbiota modulates the anticancer immune effects of cyclophosphamide." Science (New York, N.Y.) vol. 342,6161 (2013): 971-6. doi:10.1126/science.1240537.
Wang, Chun-Sai-Er, et al., VSL#3 can prevent ulcerative colitis-associated carcinogenesis in mice, Oct. 7, 2018, vol. 24, Issue 37, pp. 4254-4262.
Wang et al. 16S rRNA gene-based analysis of fecal microbiota from preterm infants with and without necrotizing enterocolitis. 2009. ISME J. 3(8): 944-954.
Wang, Feng, Bifidobacterium can mitigate intestinal immunopathology in the context of CTLA-4 blockade, PNA, Jan. 2, 2018 vol. 115, No. 1, pp. 157-161.
Wang, G., Xia, Y., Cui, J., Gu, Z., Song, Y., Q., C.Y., et al. (2014). The Roles of Moonlighting Proteins in Bacteria. Current Issues in Molecular Biology 16, 15-22.
Wang, R.F., and Kushner, S.R. (1991). Construction of versatile low-copy-number vectors for cloning, sequencing and gene expression in *Escherichia coli*. Gene 100, 195-199. doi: https://doi.org/10.1016/0378-1119(91)90366-J.
Wang W., Lyophilization and development of solid protein pharmaceuticals. International J. Pharmaceutics 203: 1-60, 2000.
Wei, X., Yan, X., Chen, X., Yang, Z., Li, H., Zou, D., et al. (2014). Proteomic analysis of the interaction of Bifidobacterium longum NCC2705 with the intestine cells Caco-2 and identification of plasminogen receptors. J Proteomics 108, 89-98. doi: 10.1016/j.jprot.2014.04.038.
Welman, A.D., and Maddox, I.S. (2003). Exopolysaccharides from lactic acid bacteria: perspectives and challenges. Trends in Biotechnology 21(6), 269-274. doi: https://doi.org/10.1016/S0167-7799(03)00107-0.
Wendler, et al., Identification of a pirin, a novel highly conserved nuclear protein. J. Biol Chem. Mar. 28, 1997; 272(13):8482-9.
Wenzel, S.E., Asthma phenotypes: the evolution from clinical to molecular approaches, Nature medicine, May 2012; 18(5):716-725.
Westermann, C., Gleinser, M., Corr, S.C., and Riedel, C.U. (2016). A Critical Evaluation of Bifidobacterial Adhesion to the Host Tissue. Front Microbiol 7, 1220. doi: 10.3389/fmicb.2016.01220.
Williams, N.T. Probiotics (2010). American Journal of Health-System Pharmacy, 67 (6), pp. 449-458.
Workman et al. Guidelines for the welfare and use of animals in cancer research (2010) Br. J. Cancer. 102:1555-77.
Written Opinion for PCT/US17/066709 (Published as WO2018112363) owned by Evelo Biosciences, Inc.
Wrzosek, et al., Bacteroides thetaiotaomicron and Faecalibacterium prausnitzii influence the production of mucus glycans and the development of globlet cells in the colonic epithelium of a gnotobiotic model rodent. BMC biology, 2013;11(61):1-13.
Wunderlich, P.F. et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.
Xie et al. Short communication: Modulation of the small intestinal microbial community composition over short-term or long-term administration with Lactobacillus plantarum ZDY2013. 2016. Journal Dairy Sci. 99:6913-6921.
Xu, et al., A genomic view of the human-Bacteroides thetaiotaomicron symbiosis. Science. Mar. 28, 2003; 299(5615):2074-6.
Xu, et al., The endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.
Xu, J. et al., "Message from a human gut symbiont: sensitivity is a prerequisite for sharing", Trends in microbiology, 12(1), Jan. 1, 2004: pp. 21-28, XP055253932.
Yang, Changa et al., Non-invasive imaging of toll-like receptor 5 expressing using 131 labelled mAb in the mice bearing H22 tumors, Oncol. Lett. 2014., 7(6).1919-1924., Published online Apr. 12, 2014. DOI: 10.3892/01.2014.2025.
Yao, W., et al., Cultivation-Independent Analysis of the Development of the *Lactobacillus* spp. Community in the Intestinal TractofNewbomPiglets (2011)Agricultural Sciences in China, 10 (3), pp. 438-447.
Yq et al. Therapeutic Modulation of the Gut Microbiota in IBD—More Questions to Be Answered. (2016). J. Dig. Dis., Oct. 15, 1751-2980, 12422, Epub ahead of print.
Yu, Dah-Shyong et al., Bacille Calmette-Guerin can induce cellular apoptosis of urothelial cancer directly through toll-like receptor 7 activation, Kaohsiung Journal of Medical Sciences (2015) 31,391-397.
Yu, et al., Utilization of major fucosylated and sialylated human milk oligosaccharides by isolated human gut microbes. Glycobiology, 2013; 23(11):1281-1292.
Yu, N.Y., Wagner, J.R., Laird, M.R., Melli, G., Rey, S., Lo, R., et al. (2010a). PSORTb 3.0: improved protein subcellular localization prediction with refined localization subcategories and predictive capabilities for all prokaryotes. Bioinformatics 26(13), 1608-1615. doi: 10.1093/bioinformatics/btq249.
Yun, J.H., et al., Isolation and characterization of potential pro biotic lactobacilli from pig feces (2009). Journal of Basic Microbiology, 49 (2), pp. 220-226.
Yurdusev, N. et al., Antagonistic Effect Exerted by Three Strictly Anaerobic Strains Against Various Strains of Clostridium Perfringens in Gnotobiotic Rodent Intestines. Can J Microbiol 33, 226-231 (1987).
Yurdusev, N. et al., InfectInunun 57,724-731 (1989).
Yutin, N. and Galperin, M.Y., A genomic update on clostridial phylogeny:Gram-negative spore formers and other misplaced clostridia. Environmental microbiology. Oct. 2013; 15(10): 2631-2641.
Zhang, B. et al., Oral administration of enterococcus faecalis FK-23 suppresses Th17 cell development and attenuates allergic airway responses in mice. International journal of molecular medicine. 2012; 30:248-254.
Zhang, B. et al., The Prevalence of Th17 Cells in Patients With Gastric Cancer. 2008. Biochem Biophys Res Commun 374 (3), 533-537.
Zhang, et al.,The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.
Zheng, B. et al., Bifidobacteriu breve attenuates murine dextran sodium sulfate-induced colitis and increases regulatory T cell responses. PLOS one. May 2014; 9(5).
Zheng, B., van Bergenhenegouwen, J., Overbeek, S., van de Kant, H.J., Garssen, J., Folkerts, G., et al. (2014). Bifidobacterium breve attenuates murine dextran sodium sulfate-induced colitis and increases regulatory T cell responses. PLoS One 9(5), e95441. doi: 10.1371/journal.pone.0095441.
Zheng, Bin et al., Bifodobacterium breve Attenuates Murine Dextran Doium Sulfate-Induced Colitis and Increases Regulatory T Cell Responses, PLOS ONE, vol. 9, Isue 5, e95441, May 2014.

(56) References Cited

OTHER PUBLICATIONS

Zhongyuan, T. et al., The inflammation regulation effects of enterococcus faecium HDRsEf1 on human enterocyte-like HT-29 cells. Animal cells and systems. Mar. 2016;20(2):70-76.
Zhou et al. Central and peripheral hypersensitivity in the irritable bowel syndrome. 2010. Pain. 148(3): 454-461.
Zhu, S. and Qian, Y., IL-17/IL-17 receptor system in autoimmune disease: mechanisms and therapeutic potential. Clinical Science (2012) 122, 487-511.
Zitomersky, N. et al., Characterization of Adherent Bacteroidales from Intestinal Biopsies of Children and Young Adults with Inflammatory Bowel Disease. PLOS one. 2013; 8(6).
Zitvogel, et al., Type I interferons in anticancer immunity. Nature Reviews. Jul. 2015:405-414.
Daniel Garrido et al., "Utilization of galactooligosaccharides by *Bifidobacterium longum* subsp. infantis isolates", Food Microbiology, 33 (2013) 262-270.
Dheeraj Mohania et al., "Modulation of expression of Programmed Death-1 by administration of probiotic Dahi in DMH-induced colorectal carcinogenesis in rats", Acta Biomed 2013; 84: 102-109.
Dong-Hyun Kim and Young-Ho Jin, "Intestinal Bacterial B-Glucuronidase Activity of Patients with Colon Cancer", Arch Pharm Res vol. 24, No. 6, 564-567, 2001.
Federico E. Rey et al., "Dissecting the in Vivo Metabolic Potential of Two Human Gut Acetogens", The Journal of Biological Chemistry, Vol. 285, No. 29, pp. 22082-22090, Jul. 16, 2010.
Jagveer Singh et al., "Bifidobacterium longum, a lactic acid-producing intestinal bacterium inhibits colon cancer and modulates the intermediate biomarkers of colon carcinogenesis", Carcinogenesis vol. 18 No. 4 pp. 833-841, 1997.
Kari Shoaf et al., "Prebiotic Galactooligosaccharides Reduce Adherence of Enteropathogenic *Escherichia coli* to Tissue Culture Cells", Infection and Immunity, Dec. 2006, vol. 74. No. 12, p. 6920-6928.
Laetitia Rodes et al., "Microencapsulated *Bifidobacterium longum* subsp. infantis ATCC 15697 Favorably Modulates Gut Microbiota and Reduces Circulating Endotoxins in F344 Rats", BioMed Research International, vol. 2014, Article ID 602832, 11 pages.
Laureen Crouzet et al., "The altered gut microbiota of IBS patients plays a key role in visceral hypersensitivity: specific role of sulphate-reducing bacteria", INRA Symposium, 2012.
Mincheol Kim et al., "Towards a taxonomic coherence between average nucleotide identity and 16S rRNA gene sequence similarity for species demarcation of prokaryotes", International Journal of Systematic and Evolutionary Microbiology (2014), 64, 346-351.
Odile Menard et al, "Gnotobiotic Mouse Immune Response Induced by *Bifidobacterium* sp. Strains Isolated from Infants", Applied and Environmental Microbiology, Feb. 2008, p. 660-666.
Parfenov A.I., "Pain syndrome in the practice of a gastroenterologist", "Breast Cancer" No0 from Jan. 25, 2008, 5 pages, https://www.rmj.ru/articles/bolevoy_sindrom/Bolevoy_sindrom_v_praktike_gastroenterologa-.
Choji Kaneuchi et al., "Clostridium coccoides, a New Species from the Feces of Mice", International Journal of Systematic Bacteriology, vol. 26, No. 4, Oct. 1976, p. 482-486.
Pedro Berraondo et al., "Cytokines in clinical cancer immunotherapy", British Journal of Cancer, 2019, 120:6-15.
Ping Dong et al., "The role of intestinal bifidobacteria on immune system development in young rats", Early Human Development 86 (2010) 51-58.
NCBI Reference Sequence: NR_026314.1, Blautia hydrogenotrophica strain S5a36 16S ribosomal RNA gene, partial sequence (Feb. 3, 2015), 3 pages.
Sudha B. Singh and Henry C. Lin, "Hydrogen Sulfide in Physiology and Diseases of the Digestive Tract", Microorganisms 2015, 3, 866-889; doi:10.3390/microorganisms3040866.
Suzanne L. Topalian et al., "Survival, Durable Tumor Remission, and Long-Term Safety in Patients With Advanced Melanoma Receiving Nivolumab", Journal of Clinical Oncology, vol. 32, No. 10, Apr. 1, 2014, pp. 1-12.
Takashi Nakamura et al., "Evaluation of the Effects of Dietary Organic Germanium, Ge-132, and Raffinose Supplementation on Caecal Flora in Rats", Bioscience of Microbiota, Food and Health vol. 31 (2), 37-45, 2012.
U.S. Appl. No. 15/700,007 Non-Final Office Action dated Jun. 10, 2019.
U.S. Appl. No. 15/842,635 Non-Final Office Action dated May 29, 2019.
U.S. Appl. No. 16/022,577 Non-Final Office Action dated Jul. 9, 2019.
Yoshinori Kohwi et al., "Antitumor Effect of Bifidobacterium Infant's in Mice", Gann, 69, 613-618; Oct. 1978.

\* cited by examiner

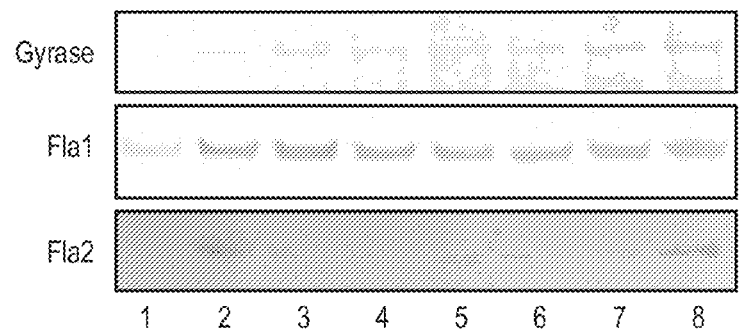
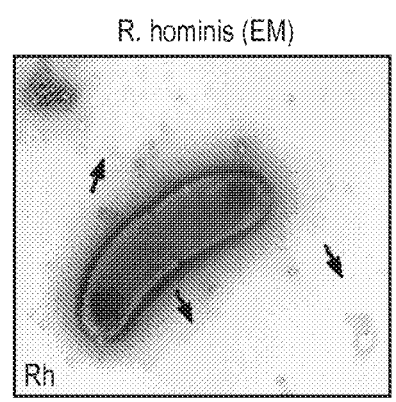
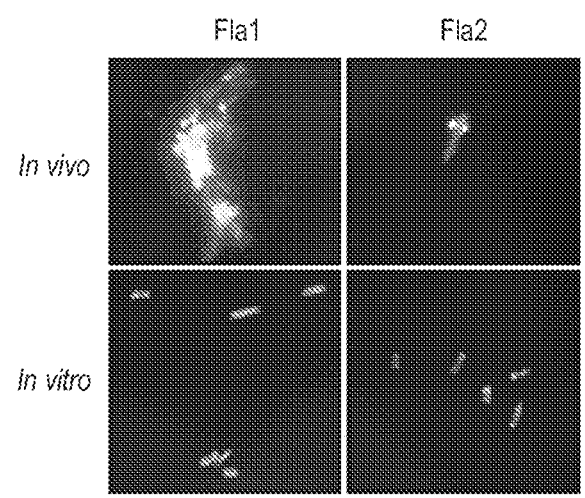
FIG. 2C

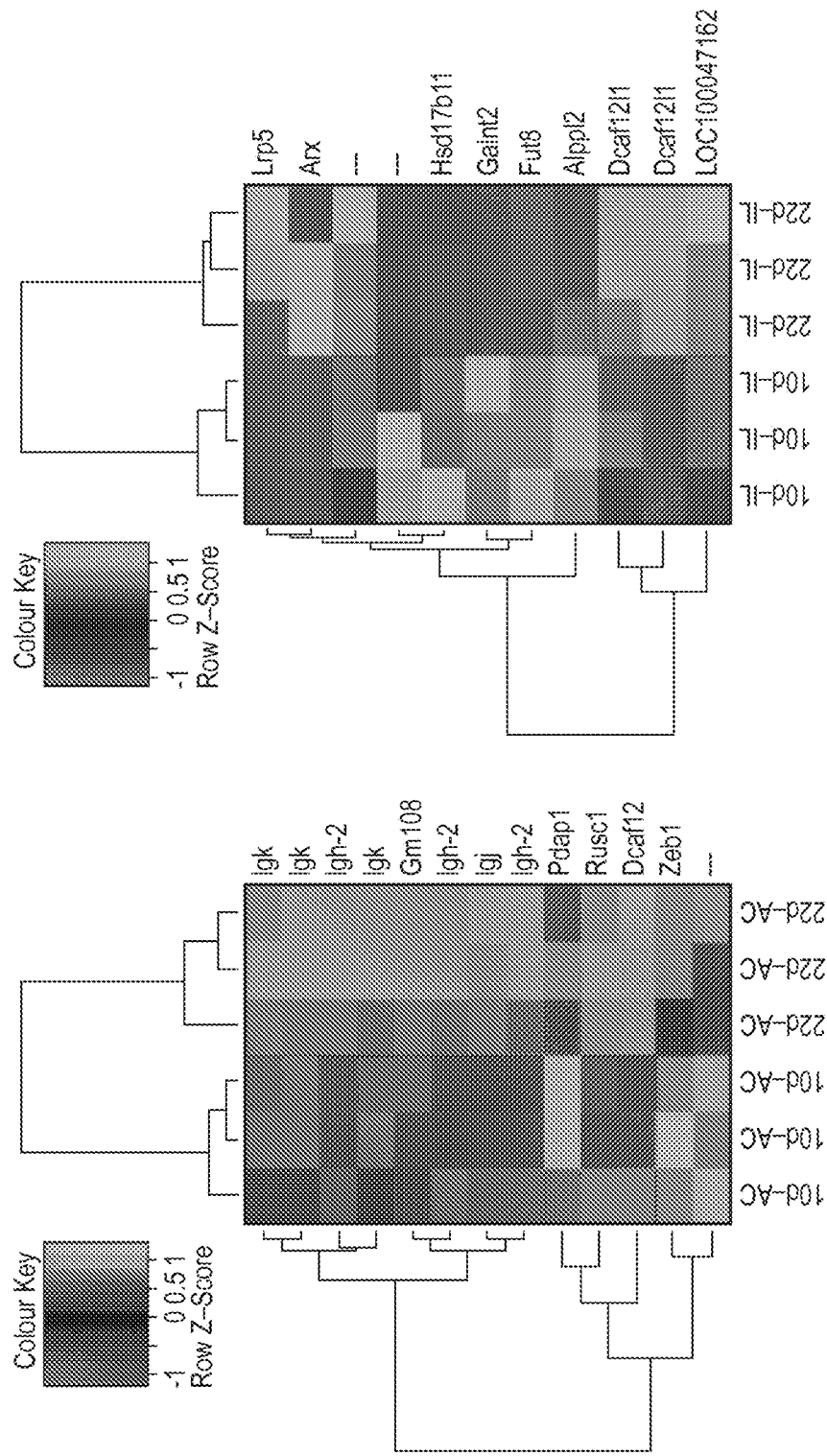

FIG. 18A
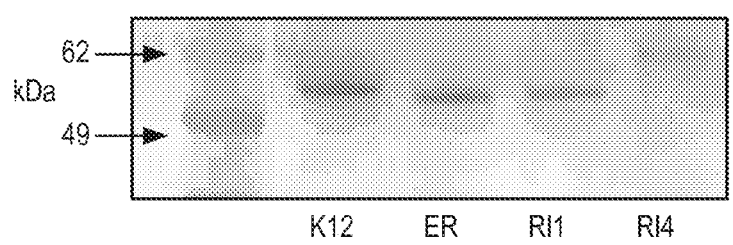
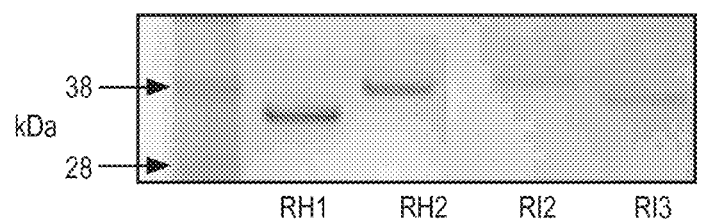
FIG. 18B

Figure C1
CLUSTAL 2.1 multiple sequence alignment confirming flagellin nucleotide sequence and accession number.

```
RIFla1 (SEQ ID NO: 33)      ATGCGTGGCGGAGACAATAGAAGGAGAAACAGAATGAGAATTAATTACAATGTGTCAGCA 60
RIEEV02820 (SEQ ID NO: 33)  ATGCGTGGCGGAGACAATAGAAGGAGAAACAGAATGAGAATTAATTACAATGTGTCAGCA 60

RIFla1       GCGATTGCGAATAAACATTTACTTGGAATTGAGGATAATTTAAGTGCATCGATGGAACGG 120
RIEEV02820   GCGATTGCGAATAAACATTTACTTGGAATTGAGGATAATTTAAGTGCATCGATGGAACGG 120

RIFla1       CTTTCATCGGGACTTAAGATCAACCATTCCAAGGACAATCCGGCAGGAATGGCTATTTCC 180
RIEEV02820   CTTTCATCGGGACTTAAGATCAACCATTCCAAGGACAATCCGGCAGGAATGGCTATTTCC 180

RIFla1       AACAAGATGAAAGCACAGATTGATGGTTTAAACCGGGCTTCCCAGAATGCATCGGATGGT 240
RIEEV02820   AACAAGATGAAAGCACAGATTGATGGTTTAAACCGGGCTTCCCAGAATGCATCGGATGGT 240

RIFla1       ATTTCTGTTATTCAGATCGCAGATGGTGCGCTGAGTGAAACGACCAGTATTTTACAGCGT 300
RIEEV02820   ATTTCTGTTATTCAGATCGCAGATGGTGCGCTGAGTGAAACGACCAGTATTTTACAGCGT 300

RIFla1       ATGAGAGAACTTTCCGTGCAGGCAGCGAGTGATGCAACAATGACACCGGCGGATAAAGAA 360
RIEEV02820   ATGAGAGAACTTTCCGTGCAGGCAGCGAGTGATGCAACAATGACACCGGCGGATAAAGAA 360

RIFla1       GCAATCCAGAAAGAAATCACTTCATTAAAAGATGAAGTTGACCGTATTTCTACAGATACA 420
RIEEV02820   GCAATCCAGAAAGAAATCACTTCATTAAAAGATGAAGTTGACCGTATTTCTACAGATACA 420

RIFla1       GAGTATAACAGCAAAACACTTTTAGATGGTTCATTAGATACCAGGGTTTACACCAAAAAT 480
RIEEV02820   GAGTATAACAGCAAAACACTTTTAGATGGTTCATTAGATACCAGGGTTTACACCAAAAAT 480

RIFla1       GCAACAAGAGTGGACATTTCTGATCATGTGAAAGCAGGACAGTATCAGCTTTCCATTGAT 540
RIEEV02820   GCAACAAGAGTGGACATTTCTGATCATGTGAAAGCAGGACAGTATCAGCTTTCCATTGAT 540

RIFla1       ACTGCAGCTACACAGGCCGGACCGGTAACAGCAAATCAGAATTATAATTCCACAGCACCG 600
RIEEV02820   ACTGCAGCTACACAGGCCGGACCGGTAACAGCAAATCAGAATTATAATTCCACAGCACCG 600

RIFla1       GTCGGTGCGTCCGGAACAATGAGTATTAATGGTTCTAAAGTAGAGATAGAGGCAGCCGAC 660
RIEEV02820   GTCGGTGCGTCCGGAACAATGAGTATTAATGGTTCTAAAGTAGAGATAGAGGCAGCCGAC 660

RIFla1       ACCTATGCGGAGGCTTTTGAGAAGATCAGAAATGCAGCAGAGACTGGTGAAACAACCGTT 720
RIEEV02820   ACCTATGCGGAGGCTTTTGAGAAGATCAGAAATGCAGCAGAGACTGGTGAAACAACCGTT 720

RIFla1       AAGATTGAAAAGAATGGAGCACTTTCATTTACCGCAGAACAGTACGGAATGTCAAGCATC 780
RIEEV02820   AAGATTGAAAAGAATGGAGCACTTTCATTTACCGCAGAACAGTACGGAATGTCAAGCATC 780

RIFla1       TTAGAGATCGCATTTGATGATAAGCAGCTTGCTAATGCACTTGGATTTACAGCAGACGGA 840
RIEEV02820   TTAGAGATCGCATTTGATGATAAGCAGCTTGCTAATGCACTTGGATTTACAGCAGACGGA 840

RIFla1       GGAAACAGTGTTGTAGAAGATCCAGAGAATAAAGGCAGCTATGTATACGGACAGATTCAG 900
RIEEV02820   GGAAACAGTGTTGTAGAAGATCCAGAGAATAAAGGCAGCTATGTATACGGACAGATTCAG 900

RIFla1       AATGGCAAAGTGATCGTACCTTCCGGTACAGATGCCGAAGTAACGCTCACAAAACCGAGT 960
RIEEV02820   AATGGCAAAGTGATCGTACCTTCCGGTACAGATGCCGAAGTAACGCTCACAAAACCGAGT 960

RIFla1       GATGGAACCGGATTTGGTGATACAGCTACGGTAAAAACAGATGGAAATAAGATTACGGTT 1020
RIEEV02820   GATGGAACCGGATTTGGTGATACAGCTACGGTAAAAACAGATGGAAATAAGATTACGGTT 1020

RIFla1       ACAGACAGAGCCGGATTTGAGATGTCATTTCTTGCTGATGCAGGTTATACGGGTAAGCTG 1080
RIEEV02820   ACAGACAGAGCCGGATTTGAGATGTCATTTCTTGCTGATGCAGGTTATACGGGTAAGCTG 1080

RIFla1       GATTTTGATGTCACGGATATCGGAACGATGGCACTTCATATTGGAGCAAATGAGGATCAG 1140
RIEEV02820   GATTTTGATGTCACGGATATCGGAACGATGGCACTTCATATTGGAGCAAATGAGGATCAG 1140

RIFla1       GAAACAAGAGTGCGTATTCCGGAGGTTTCCTGCAAGAGCCTTTACATTGATGATGCAGAC 1200
RIEEV02820   GAAACAAGAGTGCGTATTCCGGAGGTTTCCTGCAAGAGCCTTTACATTGATGATGCAGAC 1200
```

```
RIFla1       GTGACGACTGTAAATGGAGCAGGCAGAGGTATCACACAGTTTGACGATGCCATTTCAAAG 1260
RIEEV02820   GTGACGACTGTAAATGGAGCAGGCAGAGGTATCACACAGTTTGACGATGCCATTTCAAAG 1260

RIFla1       GTCAGTGAAGTGCGTTCAAGACTTGGTGCATACCAGAATCGTCTTGAGAGTACGGTATCA 1320
RIEEV02820   GTCAGTGAAGTGCGTTCAAGACTTGGTGCATACCAGAATCGTCTTGAGAGTACGGTATCA 1320

RIFla1       AGCCTGGATACGTTTGAAGAAAATATGACAGGAGCCCAGTCACGACTGACAGATGCGGAT 1380
RIEEV02820   AGCCTGGATACGTTTGAAGAAAATATGACAGGAGCCCAGTCACGACTGACAGATGCGGAT 1380

RIFla1       ATGGCATCGGAAATGACAGATTATACACATCAGAATGTATTAAATCAGGCAGCAATCTCT 1440
RIEEV02820   ATGGCATCGGAAATGACAGATTATACACATCAGAATGTATTAAATCAGGCAGCAATCTCT 1440

RIFla1       GTTTTGACACAGGCAAACGATCTGCCACAGCAGGTATTGCAGATTCTGCAGTAA 1494
RIEEV02820   GTTTTGACACAGGCAAACGATCTGCCACAGCAGGTATTGCAGATTCTGCAGTAA 1494
```

CLUSTAL 2.1 multiple sequence alignment

```
RIFla2 (SEQ ID NO: 7)     ATGGTAGTTAATCATAATATGGCATTGATCTGTGAGAGTAGACAGTTACGATGTAATGTG 60
RIEEV02466 (SEQ ID NO: 7) ATGGTAGTTAATCATAATATGGCATTGATCTGTGAGAGTAGACAGTTACGATGTAATGTG 60

RIFla2      AAGAACATGGAGAAGTCTTCAAAAAAGCTGGCAACAGGTTATAAATTGCTTGGAGCAAAT 120
RIEEV02466  AAGAACATGGAGAAGTCTTCAAAAAAGCTGGCAACAGGTTATAAATTGCTTGGAGCAAAT 120

RIFla2      GATGATGCAGCAGGATTACAGATATCAGAAACCATGCGTCATCAGACCAGAGGTCTTAAC 180
RIEEV02466  GATGATGCAGCAGGATTACAGATATCAGAAACCATGCGTCATCAGACCAGAGGTCTTAAC 180

RIFla2      AAAGCATCCAGAAATTCGCAAGATGGAATTAGTATGCTGCAGACAGCAGATGCAGCATTA 240
RIEEV02466  AAAGCATCCAGAAATTCGCAAGATGGAATTAGTATGCTGCAGACAGCAGATGCAGCATTA 240

RIFla2      CAGGAGACACAGGAAGTGTTGGATCGAATGACGGATCTGACAACACAGGCAGCTAATGAT 300
RIEEV02466  CAGGAGACACAGGAAGTGTTGGATCGAATGACGGATCTGACAACACAGGCAGCTAATGAT 300

RIFla2      ATCAATACGGATGCGGATCGTCGTGCAATTCAGGATGAAATCGATCAGTTAAATCAGGAA 360
RIEEV02466  ATCAATACGGATGCGGATCGTCGTGCAATTCAGGATGAAATCGATCAGTTAAATCAGGAA 360

RIFla2      GTGGATCGTATTGCATATACGACGAATTTTAATCAGCAGTATATATTAGCGGATGGAACT 420
RIEEV02466  GTGGATCGTATTGCATATACGACGAATTTTAATCAGCAGTATATATTAGCGGATGGAACT 420

RIFla2      CCGCAGGCAAGACCAGGATACTATATGATACAGACAGGAAGTCTTGCGGGACAGGGAATA 480
RIEEV02466  CCGCAGGCAAGACCAGGATACTATATGATACAGACAGGAAGTCTTGCGGGACAGGGAATA 480

RIFla2      GAGATTAAGTTTGTTAATGCGAGCAAAGAGAGCTTGGGTGTGGACAAGGTTGATGTATCA 540
RIEEV02466  GAGATTAAGTTTGTTAATGCGAGCAAAGAGAGCTTGGGTGTGGACAAGGTTGATGTATCA 540

RIFla2      TCGCATGCAAAAGCGACAGAATCTATAGCAGTGGTACAGAATGCAATTGAAAAGGCAGCT 600
RIEEV02466  TCGCATGCAAAAGCGACAGAATCTATAGCAGTGGTACAGAATGCAATTGAAAAGGCAGCT 600

RIFla2      TCGTTTAGAGATACATTTGGGGCACAACAGGAGCGGTTAGAACACGCATTGCGTGGAACG 660
RIEEV02466  TCGTTTAGAGATACATTTGGGGCACAACAGGAGCGGTTAGAACACGCATTGCGTGGAACG 660

RIFla2      GATAATACATCAGAAAGTACACAGAGGGCAGAATCAAGTAGACGCGATACCAACATGAAT 720
RIEEV02466  GATAATACATCAGAAAGTACACAGAGGGCAGAATCAAGTAGACGCGATACCAACATGAAT 720

RIFla2      ATGGAGATGGTACAATATTCTACAAACCGTATTTTAGTACAGGCATCTCAGAGTATTTTA 780
RIEEV02466  ATGGAGATGGTACAATATTCTACAAACCGTATTTTAGTACAGGCATCTCAGAGTATTTTA 780

RIFla2      GCACAGTACAATGATGATGCAAAATATGTGTTGGAAATGTTAAAATAG 828
RIEEV02466  GCACAGTACAATGATGATGCAAAATATGTGTTGGAAATGTTAAAATAG 828
```

FIG. 20

Figure C3
CLUSTAL 2.1 multiple sequence alignment

```
RIFla3 (SEQ ID NO: 9)     ATGGTAGTACAGCACAATATGACCGCAATGAATGCGAACAGAATGTTAGGCGTTACAACA 60
RIEEV00779 (SEQ ID NO: 9) ATGGTAGTACAGCACAATATGACCGCAATGAATGCGAACAGAATGTTAGGCGTTACAACA 60

RIFla3      AGCGCACAGGCAAAATCTTCAGAGAAATTATCTTCTGGTTACAGAATCAACCGTGCAGGT 120
RIEEV00779  AGCGCACAGGCAAAATCTTCAGAGAAATTATCTTCTGGTTACAGAATCAACCGTGCAGGT 120

RIFla3      GATGACGCTGCTGGTTTAACAATTTCTGAGAAGATGAGAAGCCAGATCCGTGGATTAAAC 180
RIEEV00779  GATGACGCTGCTGGTTTAACAATTTCTGAGAAGATGAGAAGCCAGATCCGTGGATTAAAC 180

RIFla3      AAAGCTTCTGACAACGCACAGGATGGTATTTCCTTAATCCAGGTTGCTGAGGGTGCATTA 240
RIEEV00779  AAAGCTTCTGACAACGCACAGGATGGTATTTCCTTAATCCAGGTTGCTGAGGGTGCATTA 240

RIFla3      TCTGAGACACATTCTATCTTACAGCGTATGAATGAGTTAGCTACTCAGGCTGCTAACGAT 300
RIEEV00779  TCTGAGACACATTCTATCTTACAGCGTATGAATGAGTTAGCTACTCAGGCTGCTAACGAT 300

RIFla3      ACCAATACAACTGCTGATAGAGGAGCTATTCAGGATGAGATCAACCAGTTAACATCTGAG 360
RIEEV00779  ACCAATACAACTGCTGATAGAGGAGCTATTCAGGATGAGATCAACCAGTTAACATCTGAG 360

RIFla3      ATTAACAGAATCTCTTCTACAACTCAGTTCAATACTCAGAACCTCATCGATGGTACATTC 420
RIEEV00779  ATTAACAGAATCTCTTCTACAACTCAGTTCAATACTCAGAACCTCATCGATGGTACATTC 420

RIFla3      GCAAATAAAAACCTTCAGGTTGGTTCTATCTGTGGACAGAGAATTACTGTTTCTATCGAC 480
RIEEV00779  GCAAATAAAAACCTTCAGGTTGGTTCTATCTGTGGACAGAGAATTACTGTTTCTATCGAC 480

RIFla3      AGTATGTCTGCTGGTAGCTTAAATGTATCTGCTAACTTAGTAAAGGTTAACACTTTCAGT 540
RIEEV00779  AGTATGTCTGCTGGTAGCTTAAATGTATCTGCTAACTTAGTAAAGGTTAACACTTTCAGT 540

RIFla3      GCAGCAGGTGAAGCAATGTCCAATATTCAGGGTGCTATTTCTGCAATTTCTACACAGCGT 600
RIEEV00779  GCAGCAGGTGAAGCAATGTCCAATATTCAGGGTGCTATTTCTGCAATTTCTACACAGCGT 600

RIFla3      TCTTACTTAGGAGCTCTTCAGAATCGTCTGGAGCATACAATCTCCAACTTGGACAACATT 660
RIEEV00779  TCTTACTTAGGAGCTCTTCAGAATCGTCTGGAGCATACAATCTCCAACTTGGACAACATT 660

RIFla3      TCTGAGAATACTCAGTCTGCTGAATCTCGTATCCGTGATACAGATATGGCTGAAGAGATG 720
RIEEV00779  TCTGAGAATACTCAGTCTGCTGAATCTCGTATCCGTGATACAGATATGGCTGAAGAGATG 720

RIFla3      GTTACTTACAGCAAGAACAATATTCTTGCTCAGGCAGGACAGTCTATGCTTGCTCAGGCT 780
RIEEV00779  GTTACTTACAGCAAGAACAATATTCTTGCTCAGGCAGGACAGTCTATGCTTGCTCAGGCT 780

RIFla3      AACCAGTCTACTCAGGGTGTACTTTCTCTGTTACAGTAA 819
RIEEV00779  AACCAGTCTACTCAGGGTGTACTTTCTCTGTTACAGTAA 819
```

FIG. 21

Figure C4
CLUSTAL 2.1 multiple sequence alignment

```
RIFla4 (SEQ ID NO: 11)    ATGGCAATGGTAGTACAGCACAACATGTCCGCAATGAATGCGAACAGAAATTTAGGTGTT 60
RIEEU99488 (SEQ ID NO: 34) ATGGCAATGGTAGTACAGCACAACATGTCCGCAATGAATGCGAACAGAAATTTAGGTGTT 60

RIFla4      ACAACAGGAATGCAGGCAAAATCATCAGAGAAGTTATCTTCCGGTTACAAGATCAACCGT 120
RIEEU99488  ACAACAGGAATGCAGGCAAAATCATCAGAGAAGTTATCTTCCGGTTACAAGATCAACCGT 120

RIFla4      GCAGCAGATGATGCAGCAGGACTTTCTATTTCTGAGAAGATGAGAAGCCAGATCCGCGGT 180
RIEEU99488  GCAGCAGATGATGCAGCAGGACTTTCTATTTCTGAGAAGATGAGAAGCCAGATCCGCGGT 180

RIFla4      TTAAATAAAGCATCTGACAATGCACAGGATGGTATCTCTTTAATCCAGACCGCTGAGGGA 240
RIEEU99488  TTAAATAAAGCATCTGACAATGCACAGGATGGTATCTCTTTAATCCAGACCGCTGAGGGA 240

RIFla4      GCATTAAATGAGTCCCACTCTATTTTACAGAGAATGAGAGAGTTATCCGTACAGGCAGCC 300
RIEEU99488  GCATTAAATGAGTCCCACTCTATTTTACAGAGAATGAGAGAGTTATCCGTACAGGCAGCC 300

RIFla4      AACGGTACAGAGACAGATGACGACCGCGAGGCAGTACAGAACGAGGTTTCCCAGTTACAG 360
RIEEU99488  AACGGTACAGAGACAGATGACGACCGCGAGGCAGTACAGAACGAGGTTTCCCAGTTACAG 360

RIFla4      GAAGAGCTGACAAGAATTTCTGAGACAACAGAGTTCAACACGATGAAGCTGCTGGATGGT 420
RIEEU99488  GAAGAGCTGACAAGAATTTCTGAGACAACAGAGTTCAACACGATGAAGCTGCTGGATGGT 420

RIFla4      TCTCAGAGTGGAAGTACATCTTCAACCGGGTCAGGTCCGAAGTTTGGTGTTGTAGATGCA 480
RIEEU99488  TCTCAGAGTGGAAGTACATCTTCAACCGGGTCAGGTCCGAAGTTTGGTGTTGTAGATGCA 480

RIFla4      ACATTAGACGGTGCACTTGTAACATCTAACGTGAAAGGTATTAAAGTAGCAACAGCAGCT 540
RIEEU99488  ACATTAGACGGTGCACTTGTAACATCTAACGTGAAAGGTATTAAAGTAGCAACAGCAGCT 540

RIFla4      GCCACAACAACAAAGGCAGGTCAGGAGACTGCTATCTGGGCTGCTGATGGAAAGACATTA 600
RIEEU99488  GCCACAACAACAAAGGCAGGTCAGGAGACTGCTATCTGGGCTGCTGATGGAAAGACATTA 600

RIFla4      ACTTTAAATCTTTCGAAAAATAAGGTATATACACAGGACGAAATTGATGACTTGATCGCA 660
RIEEU99488  ACTTTAAATCTTTCGAAAAATAAGGTATATACACAGGACGAAATTGATGACTTGATCGCA 660

RIFla4      AATGCAAAACAGGAAGACAGTTCTGCAACGGGTGCACCGGCTGAAGTGAAAGTATCTTTA 720
RIEEU99488  AATGCAAAACAGGAAGACAGTTCTGCAACGGGTGCACCGGCTGAAGTGAAAGTATCTTTA 720

RIFla4      AAGAATGGTATTTTTAATGCAGATGCAGACACAACTGCCGGAACTGTAACAGCCGGTGGT 780
RIEEU99488  AAGAATGGTATTTTTAATGCAGATGCAGACACAACTGCCGGAACTGTAACAGCCGGTGGT 780

RIFla4      GTGAAGGCAGTATCTGATGAAGGAACAGTAACTGGATTTGTTGGTGCAGATACAATTTCA 840
RIEEU99488  GTGAAGGCAGTATCTGATGAAGGAACAGTAACTGGATTTGTTGGTGCAGATACAATTTCA 840

RIFla4      TTTACGGCAAATAAGTATGGAGCAGAGTTCAATGATACTGTATTTAAATTCAAATTTGAT 900
RIEEU99488  TTTACGGCAAATAAGTATGGAGCAGAGTTCAATGATACTGTATTTAAATTCAAATTTGAT 900

RIFla4      AAGGCAGCAGGCAAAGAAGAAGTAGAGACAAATACAGCAATTGAAATTGATGGAGCAAAT 960
RIEEU99488  AAGGCAGCAGGCAAAGAAGAAGTAGAGACAAATACAGCAATTGAAATTGATGGAGCAAAT 960

RIFla4      GCGGTAACAGCAGGTGAATATACAATTCATCTTGCAGCAGGCAAAGAATATACGGCAGAA 1020
RIEEU99488  GCGGTAACAGCAGGTGAATATACAATTCATCTTGCAGCAGGCAAAGAATATACGGCAGAA 1020

RIFla4      GATTTAGAAGATGTTCTTAAAACGGCAGGATTCGACTTTGATGTTAAATTAAGTGGAAAT 1080
RIEEU99488  GATTTAGAAGATGTTCTTAAAACGGCAGGATTCGACTTTGATGTTAAATTAAGTGGAAAT 1080

RIFla4      ACACCAGATGAGCCAAATACTTTATTTGCAACCAGTGGCGCATCAACTGTGACTGATATT 1140
RIEEU99488  ACACCAGATGAGCCAAATACTTTATTTGCAACCAGTGGCGCATCAACTGTGACTGATATT 1140

RIFla4      ACAATGGGTGCTGGCACCGCCGGAGCTGGTCTTGGAAGTACAGATGCTATGTGGGGGCAA 1200
RIEEU99488  ACAATGGGTGCTGGCACCGCCGGAGCTGGTCTTGGAAGTACAGATGCTATGTGGGGGCAA 1200
```

```
RIFla4      GCTGGTTATGACAGT-TATCTTCTGGTGCTGGCATTACCTTGCAGATTGGTGCAAATGAA 1259
RIEEU99488  GCTGGTTATGACAGTGTATCTTCTGGTGCTGGCATTACCTTGCAGATTGGTGCAAATGAA 1260

RIFla4      GGTCAGACCATGAGTTTCTCTATCGATGACATGAGTGCAAGAGCACTTGGCGTAGATGGC 1319
RIEEU99488  GGTCAGACCATGAGTTTCTCTATCGATGACATGAGTGCAAGAGCACTTGGCGTAGATGGC 1320

RIFla4      AACAAAGTTGATTTAAGCACACAGGCTGGCGCACAGAAAGCAACTGATACCATTGATGCA 1379
RIEEU99488  AACAAAGTTGATTTAAGCACACAGGCTGGCGCACAGAAAGCAACTGATACCATTGATGCA 1380

RIFla4      GCAATCAAGAAAGTATCTGCACAGCGTGGTAGAATGGGTGCGATCCAGAACCGTCTGGAG 1439
RIEEU99488  GCAATCAAGAAAGTATCTGCACAGCGTGGTAGAATGGGTGCGATCCAGAACCGTCTGGAG 1440

RIFla4      CACACCATCAGCAACCTTGATACAGCAGCAGAGAATACCCAGACTGCAGAGTCCCGTATC 1499
RIEEU99488  CACACCATCAGCAACCTTGATACAGCAGCAGAGAATACCCAGACTGCAGAGTCCCGTATC 1500

RIFla4      CGTGATACAGATATGGCAGAAGAGATGGTTGAGTACTCCAAGAACAACATTCTTGCACAG 1559
RIEEU99488  CGTGATACAGATATGGCAGAAGAGATGGTTGAGTACTCCAAGAACAACATTCTTGCACAG 1560

RIFla4      GCAGGTCAGTCTATGCTTGCACAGGCGAACCAGTCTACACAGGGTGTACTCTCCTTATTA 1619
RIEEU99488  GCAGGTCAGTCTATGCTTGCACAGGCGAACCAGTCTACACAGGGTGTACTCTCCTTATTA 1620

RIFla4      CAGTAA 1625
RIEEU99488  CAGTAA 1626
```

FIG. 22 Cont'd

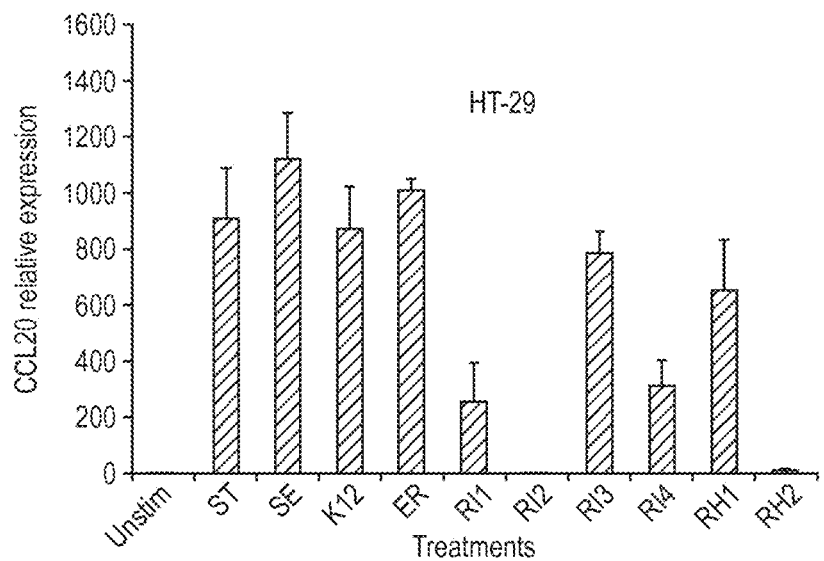
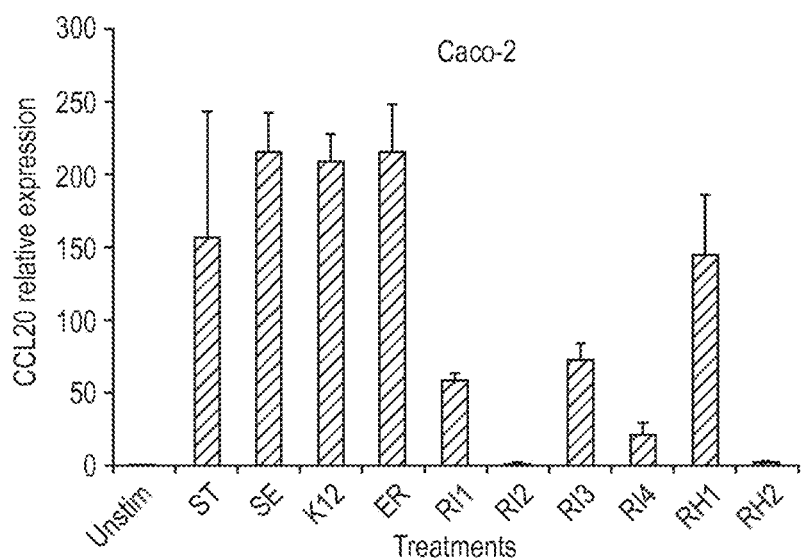
FIG. 23

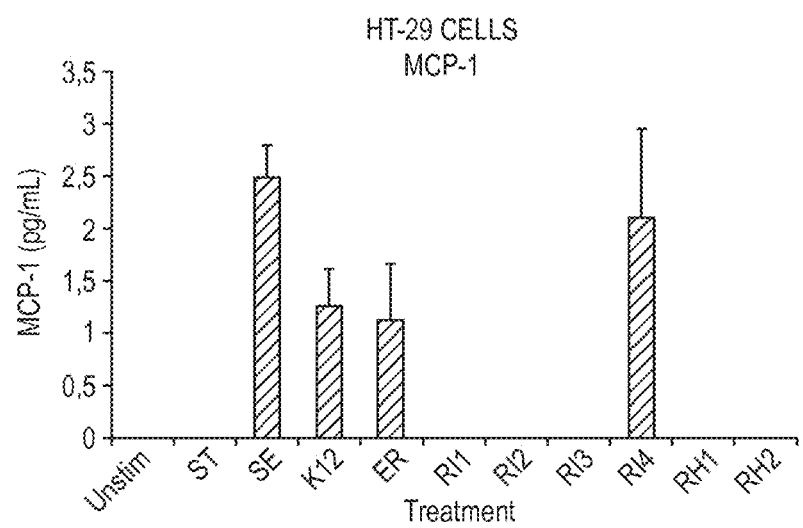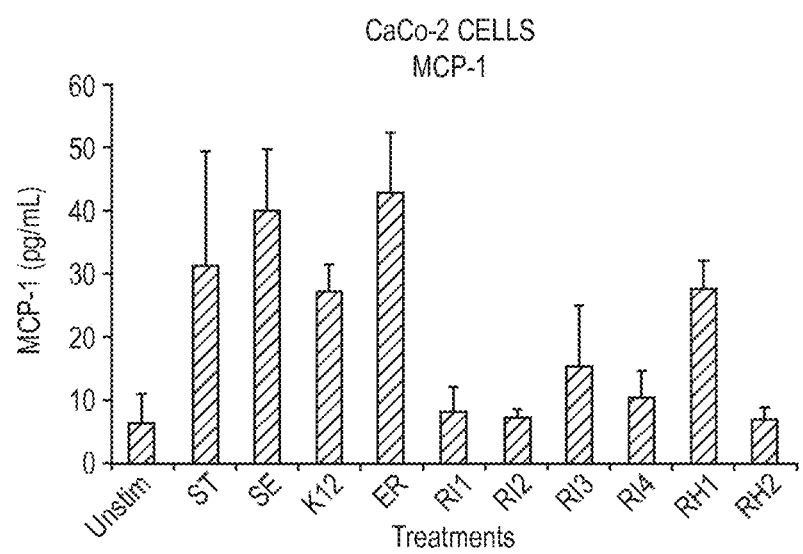
FIG. 24 Cont'd

FIG. 28

```
                              SEQUENCE LISTING

<160> NUMBER OF SEQ ID NOS: 34

<210> SEQ ID NO 1
<211> LENGTH: 813
<212> TYPE: DNA
<213> ORGANISM: Roseburia hominis

<400> SEQUENCE: 1
atggtagtac agcacaatct tacagcaatg aacgctaaca gacagttagg tatcacaaca      60
ggcgcacagg ctaagtcttc tgagaagtta tcttctggtt acaagatcaa ccgcgcagca     120
gatgacgcag caggtcttac gatttccgag aagatgagaa gccaggttag aggcttaaat     180
aaagcttctg acaacgcaca ggatggtgta tcccttattc aggtagctga gggtgcatta     240
agtgagacac actccatctt acagcgtatg aatgagttag caactcaggc agcaaacgat     300
accaatacaa cctcagacag aactgcagtt cagcaggaga tcaaccagtt agcatctgag     360
atcaccagaa tcgcttctac aactcagttc aacacaatga acctgatcga tggtaacttc     420
acaagtaaga agcttcaggt aggttccctt tgcggacagg ctatcacaat cgatatctct     480
gatatgtctg ctacaggtct tggcgttagc ggattagtag tatcttcctt ctctgcagct     540
ggtaaggcaa tgtctgcagc tcaggatgct atcagctacg tatcttctat gcgttctaag     600
ctgggtgcat tacagaacag acttgagcac acaatctccc acctggacaa catttctgag     660
cacacatctt ctgcagagtc tcgtatccgt gatacagata tggctgaaga gatggttgag     720
tacagcaaga caacatcct tgctcaggca ggacagtcta tgcttgctca ggctaaccag     780
tctactcagg gtgtattatc cttattacag taa                                  813

<210> SEQ ID NO 2
<211> LENGTH: 270
<212> TYPE: PRT
<213> ORGANISM: Roseburia hominis

<400> SEQUENCE: 2

Met Val Val Gln His Asn Leu Thr Ala Met Asn Ala Asn Arg Gln Leu
1               5                   10                  15

Gly Ile Thr Thr Gly Ala Gln Ala Lys Ser Ser Glu Lys Leu Ser Ser
            20                  25                  30

Gly Tyr Lys Ile Asn Arg Ala Ala Asp Ala Ala Gly Leu Thr Ile
        35                  40                  45

Ser Glu Lys Met Arg Ser Gln Val Arg Gly Leu Asn Lys Ala Ser Asp
    50                  55                  60

Asn Ala Gln Asp Gly Val Ser Leu Ile Gln Val Ala Glu Gly Ala Leu
65                  70                  75                  80

Ser Glu Thr His Ser Ile Leu Gln Arg Met Asn Glu Leu Ala Thr Gln
                85                  90                  95

Ala Ala Asn Asp Thr Asn Thr Thr Ser Asp Arg Thr Ala Val Gln Gln
            100                 105                 110

Glu Ile Asn Gln Leu Ala Ser Glu Ile Thr Arg Ile Ala Ser Thr Thr
        115                 120                 125

Gln Phe Asn Thr Met Asn Leu Ile Asp Gly Asn Phe Thr Ser Lys Lys
    130                 135                 140
```

Leu Gln Val Gly Ser Leu Cys Gly Gln Ala Ile Thr Ile Asp Ile Ser
145                 150                 155                 160

Asp Met Ser Ala Thr Gly Leu Gly Val Ser Gly Leu Val Val Ser Ser
                165                 170                 175

Phe Ser Ala Ala Gly Lys Ala Met Ser Ala Ala Gln Asp Ala Ile Ser
            180                 185                 190

Tyr Val Ser Ser Met Arg Ser Lys Leu Gly Ala Leu Gln Asn Arg Leu
                195                 200                 205

Glu His Thr Ile Ser His Leu Asp Asn Ile Ser Glu His Thr Ser Ser
        210                 215                 220

Ala Glu Ser Arg Ile Arg Asp Thr Asp Met Ala Glu Glu Met Val Glu
225                 230                 235                 240

Tyr Ser Lys Asn Asn Ile Leu Ala Gln Ala Gly Gln Ser Met Leu Ala
                245                 250                 255

Gln Ala Asn Gln Ser Thr Gln Gly Val Leu Ser Leu Leu Gln
                260                 265                 270

<210> SEQ ID NO 3
<211> LENGTH: 828
<212> TYPE: DNA
<213> ORGANISM: Roseburia hominis

<400> SEQUENCE: 3
atggtggtta atcataatat ggcggcaatc tgtgagagca ggcagctgcg ctataacgtg      60
aagaagatgg aaaaatcttc caaaaagctt gcgacagggt acaagctgaa cacagcaaat     120
gatgatgcgg caggcttgca gatatcagag acgatgcggc atcatgtgaa agggctgaac     180
aaagcctccc ggaattcaca ggacggcatc agtatgctgc agacggcgga tgcagcgctc     240
caagagacgc aggatgttct cgatcgtatg gtggagctga cgacgcaggc agccaatgac     300
atcaacacag actcggatcg cagggctatt caggatgagt tggatcagct gaacaaggaa     360
gtggaccgca tcgcctatac gacgcacttc aatcagcagt atatgttggc ggagggaacg     420
ccgcaggcgg caccgggata ttaccgcata cagtccgggg cactgaacgg acaggcgata     480
gatatccatt ttgtaaatgc gagcaaggag agccttggca gacaaaagt gaatgtatct      540 tcgcatgcga aggcgtcgga atccatcacg atggttcagg acgcgattga acaggcggcg     600
ctctggagag acgagttcgg cagccagcag gagcgtctgg aacatgccgt gcgcaatacg     660
gacaacacat cacaaaatac gcagagtgcg gagtcaggga tcagagacac caacatgaat     720
atggagatgg tattatattc gaccaaccgg attctggtgc atgcatccca gagtattctg     780
gcacagtata tgatgatgc aaaatcagtg cttgagattt tgaaatag                   828

<210> SEQ ID NO 4
<211> LENGTH: 275
<212> TYPE: PRT
<213> ORGANISM: Roseburia hominis

<400> SEQUENCE: 4

Met Val Val Asn His Asn Met Ala Ala Ile Cys Glu Ser Arg Gln Leu
1               5                   10                  15

Arg Tyr Asn Val Lys Lys Met Glu Lys Ser Ser Lys Lys Leu Ala Thr
                20                  25                  30

Gly Tyr Lys Leu Asn Thr Ala Asn Asp Asp Ala Ala Gly Leu Gln Ile
            35                  40                  45

Ser Glu Thr Met Arg His His Val Lys Gly Leu Asn Lys Ala Ser Arg
        50                  55                  60

```
Asn Ser Gln Asp Gly Ile Ser Met Leu Gln Thr Ala Asp Ala Ala Leu
 65                  70                  75                  80
Gln Glu Thr Gln Asp Val Leu Asp Arg Met Val Glu Leu Thr Thr Gln
                 85                  90                  95
Ala Ala Asn Asp Ile Asn Thr Asp Ser Asp Arg Arg Ala Ile Gln Asp
            100                 105                 110
Glu Leu Asp Gln Leu Asn Lys Glu Val Asp Arg Ile Ala Tyr Thr Thr
        115                 120                 125
His Phe Asn Gln Gln Tyr Met Leu Ala Glu Gly Thr Pro Gln Ala Ala
    130                 135                 140
Pro Gly Tyr Tyr Arg Ile Gln Ser Gly Ala Leu Asn Gly Gln Ala Ile
145                 150                 155                 160
Asp Ile His Phe Val Asn Ala Ser Lys Glu Ser Leu Gly Thr Asp Lys
                165                 170                 175
Val Asn Val Ser Ser His Ala Lys Ala Ser Glu Ser Ile Thr Met Val
            180                 185                 190
Gln Asp Ala Ile Glu Ala Ala Leu Trp Arg Asp Glu Phe Gly Ser
        195                 200                 205
Gln Gln Glu Arg Leu Glu His Ala Val Arg Asn Thr Asp Asn Thr Ser
    210                 215                 220
Gln Asn Thr Gln Ser Ala Glu Ser Gly Ile Arg Asp Thr Asn Met Asn
225                 230                 235                 240
Met Glu Met Val Leu Tyr Ser Thr Asn Arg Ile Leu Val His Ala Ser
                245                 250                 255
Gln Ser Ile Leu Ala Gln Tyr Asn Asp Asp Ala Lys Ser Val Leu Glu
            260                 265                 270
Ile Leu Lys
        275

<210> SEQ ID NO 5
<211> LENGTH: 1496
<212> TYPE: DNA
<213> ORGANISM: Roseburia intestinalis
<220> FEATURE:
<221> NAME/KEY: misc_feature
<222> LOCATION: (795)..(796)
<223> OTHER INFORMATION: n is a, c, g, or t

<400> SEQUENCE: 5
atgcgtggcg gagacaatag aaggagaaac agaatgagaa ttaattacaa tgtgtcagca      60
gcgattgcga ataaacattt acttggaatt gaggataatt taagtgcatc gatggaacgg     120
ctttcatcgg gacttaagat caaccattcc aaggacaatc cggcaggaat ggctatttcc     180
aacaagatga agcacagat tgatggttta accgggctt cccagaatgc atcggatggt     240
atttctgtta ttcagatcgc agatggtgcg ctgagtgaaa cgaccagtat tttacagcgt     300
atgagagaac tttccgtgca ggcagcgagt gatgcaacaa tgacaccggc ggataaagaa     360
gcaatccaga agaaatcac ttcattaaaa gatgaagttg accgtatttc tacagataca     420
gagtataaca gcaaaacact tttagatggt tcattagata ccagggttta caccaaaaat     480
gcaacaagag tggacatttc tgatcatgtg aaagcaggac agtatcagct ttccattgat     540
actgcagcta cacaggccgg accggtaaca gcaaatcaga attataattc cacagcaccg     600
gtcggtgcgt ccggaacaat gagtattaat ggttctaaag tagagataga ggcagccgac     660
acctatgcga aggcttttga aagatcaga atgcagcag agactggtga acaaccgtt     720 aagattgaaa agaatggagc actttcattt accgcagaac agtacggaat gtcaagcatc     780
```

```
ttagagatcg cattnntgat gataagcagc ttgctaatgc acttggattt acagcagacg    840
gaggaaacag tgttgtagaa gatccagaga ataaaggcag ctatgtatac ggacagattc    900
agaatggcaa agtgatcgta ccttccggta cagatgccga agtaacgctc acaaaaccga    960
gtgatggaac cggatttggt gatacagcta cggtaaaaac agatggaaat aagattacgg   1020
ttacagacag agccggattt gagatgtcat ttcttgctga tgcaggttat acgggtaagc   1080
tggattttga tgtcacggat atcggaacga tggcacttca tattggagca aatgaggatc   1140
aggaaacaag agtgcgtatt ccggaggttt cctgcaagag cctttacatt gatgatgcag   1200
acgtgacgac tgtaaatgga gcaggcagag gtatcacaca gtttgacgat gccatttcaa   1260
aggtcagtga agtgcgttca agacttggtg cataccagaa tcgtcttgag agtacggtat   1320
caagcctgga tacgtttgaa gaaaatatga caggagccca gtcacgactg acagatgcgg   1380
atatggcatc ggaaatgaca gattatacac atcagaatgt attaaatcag gcagcaatct   1440
ctgttttgac acaggcaaac gatctgccac agcaggtatt gcagattctg cagtaa       1496
```

<210> SEQ ID NO 6
<211> LENGTH: 479
<212> TYPE: PRT
<213> ORGANISM: Roseburia intestinalis

<400> SEQUENCE: 6

```
Met Arg Ile Asn Tyr Asn Val Ser Ala Ala Ile Ala Asn Lys His Leu
1               5                   10                  15

Leu Gly Ile Glu Asp Asn Leu Ser Ala Ser Met Glu Arg Leu Ser Ser
            20                  25                  30

Gly Leu Lys Ile Asn His Ser Lys Asp Asn Pro Ala Gly Met Ala Ile
        35                  40                  45

Ser Asn Lys Met Lys Ala Gln Ile Asp Gly Leu Asn Arg Ala Ser Gln
    50                  55                  60

Asn Ala Ser Asp Gly Ile Ser Val Ile Gln Ile Ala Asp Gly Ala Leu
65                  70                  75                  80

Ser Glu Thr Thr Ser Ile Leu Gln Arg Met Arg Glu Leu Ser Val Gln
                85                  90                  95

Ala Ala Ser Asp Ala Thr Met Thr Pro Ala Asp Lys Glu Ala Ile Gln
            100                 105                 110

Lys Glu Ile Thr Ser Leu Lys Asp Glu Val Asp Arg Ile Ser Thr Asp
        115                 120                 125

Thr Glu Tyr Asn Ser Lys Thr Leu Leu Asp Gly Ser Leu Asp Thr Arg
    130                 135                 140

Val Tyr Thr Lys Asn Ala Thr Arg Val Asp Ile Ser Asp His Val Lys
145                 150                 155                 160

Ala Gly Gln Tyr Gln Leu Ser Ile Asp Thr Ala Thr Gln Ala Gly
                165                 170                 175

Pro Val Thr Ala Asn Gln Asn Tyr Asn Ser Thr Ala Pro Val Gly Ala
            180                 185                 190

Ser Gly Thr Met Ser Ile Asn Gly Ser Lys Val Glu Ile Glu Ala Ala
        195                 200                 205

Asp Thr Tyr Ala Glu Ala Phe Glu Lys Ile Arg Asn Ala Ala Glu Thr
    210                 215                 220

Gly Glu Thr Thr Val Lys Ile Glu Lys Asn Gly Ala Leu Ser Phe Thr
225                 230                 235                 240

Ala Glu Gln Tyr Gly Met Ser Ser Ile Leu Glu Ile Ala Phe Asp Asp
                245                 250                 255
```

```
Lys Gln Leu Ala Asn Ala Leu Gly Phe Thr Ala Asp Gly Gly Asn Ser
                260                 265                 270

Val Val Glu Asp Pro Glu Asn Lys Gly Ser Tyr Val Tyr Gly Gln Ile
            275                 280                 285

Gln Asn Gly Lys Val Ile Val Pro Ser Gly Thr Asp Ala Glu Val Thr
        290                 295                 300

Leu Thr Lys Pro Ser Asp Gly Thr Gly Phe Gly Asp Thr Ala Thr Val
305                 310                 315                 320

Lys Thr Asp Gly Asn Lys Ile Thr Val Thr Asp Arg Ala Gly Phe Glu
                325                 330                 335

Met Ser Phe Leu Ala Asp Ala Gly Tyr Thr Gly Lys Leu Asp Phe Asp
            340                 345                 350

Val Thr Asp Ile Gly Thr Met Ala Leu His Ile Gly Ala Asn Glu Asp
        355                 360                 365

Gln Glu Thr Arg Val Arg Ile Pro Glu Val Ser Cys Lys Ser Leu Tyr
    370                 375                 380

Ile Asp Asp Ala Asp Val Thr Thr Val Asn Gly Ala Gly Arg Gly Ile
385                 390                 395                 400

Thr Gln Phe Asp Asp Ala Ile Ser Lys Val Ser Glu Val Arg Ser Arg
                405                 410                 415

Leu Gly Ala Tyr Gln Asn Arg Leu Glu Ser Thr Val Ser Ser Leu Asp
            420                 425                 430

Thr Phe Glu Glu Asn Met Thr Gly Ala Gln Ser Arg Leu Thr Asp Ala
        435                 440                 445

Asp Met Ala Ser Glu Met Thr Asp Tyr Thr His Gln Asn Val Leu Asn
    450                 455                 460

Gln Ala Ala Ile Ser Val Leu Thr Gln Ala Asn Asp Leu Pro Gln
465                 470                 475

<210> SEQ ID NO 7
<211> LENGTH: 828
<212> TYPE: DNA
<213> ORGANISM: Roseburia intestinalis

<400> SEQUENCE: 7
atggtagtta atcataatat ggcattgatc tgtgagagta gacagttacg atgtaatgtg      60
aagaacatgg agaagtcttc aaaaaagctg gcaacaggtt ataaattgct tggagcaaat     120
gatgatgcag caggattaca gatatcagaa accatgcgtc atcagaccag aggtcttaac     180
aaagcatcca gaaattcgca agatggaatt agtatgctgc agacagcaga tgcagcatta     240
caggagacac aggaagtgtt ggatcgaatg acgatctga caacacaggc agctaatgat     300
atcaatacgg atgcggatcg tcgtgcaatt caggatgaaa tcgatcagtt aaatcaggaa     360
gtggatcgta ttgcatatac gacgaatttt aatcagcagt atatattagc ggatggaact     420
ccgcaggcaa gaccaggata ctatatgata cagacaggaa gtcttgcggg acagggaata     480
gagattaagt ttgttaatgc gagcaaagag agcttgggtg tggacaaggt tgatgtatca     540
tcgcatgcaa aagcgacaga atctatagca gtggtacaga atgcaattga aaaggcagct     600
tcgtttagag atacatttgg ggcacaacag gagcggttag aacacgcatt gcgtggaacg     660
gataatacat cagaaagtac acagagggca gaatcaagta gacgcgatac caacatgaat     720
atggagatgg tacaatattc tacaaaccgt attttagtac aggcatctca gagtatttta     780
gcacagtaca atgatgatgc aaaatatgtg ttggaaatgt taaaatag                  828
```

<210> SEQ ID NO 8
<211> LENGTH: 282
<212> TYPE: PRT
<213> ORGANISM: Roseburia intestinalis

<400> SEQUENCE: 8

Met Val Val Asn His Asn Met Ala Leu Ile Cys Glu Ser Arg Gln Leu
1               5                   10                  15

Arg Cys Asn Val Lys Asn Met Glu Lys Ser Ser Lys Lys Leu Ala Thr
            20                  25                  30

Gly Tyr Lys Leu Leu Gly Ala Asn Asp Asp Ala Ala Gly Leu Gln Ile
        35                  40                  45

Ser Glu Thr Met Arg His Gln Thr Arg Gly Leu Asn Lys Ala Ser Arg
    50                  55                  60

Asn Ser Gln Asp Gly Ile Ser Met Leu Gln Thr Ala Asp Ala Ala Leu
65                  70                  75                  80

Gln Glu Thr Gln Glu Val Leu Asp Arg Met Thr Asp Leu Thr Thr Gln
                85                  90                  95

Ala Ala Asn Asp Ile Asn Thr Asp Ala Asp Arg Arg Ala Ile Gln Asp
            100                 105                 110

Glu Ile Asp Gln Leu Asn Gln Glu Val Asp Arg Ile Ala Tyr Thr Thr
        115                 120                 125

Asn Phe Asn Gln Gln Tyr Ile Leu Ala Asp Gly Thr Pro Gln Ala Arg
    130                 135                 140

Pro Gly Tyr Tyr Met Ile Gln Thr Gly Ser Leu Ala Gly Gln Gly Ile
145                 150                 155                 160

Glu Ile Lys Phe Val Asn Ala Ser Lys Glu Ser Leu Gly Val Asp Lys
                165                 170                 175

Val Asp Val Ser Ser His Ala Lys Ala Thr Glu Ser Ile Ala Val Val
            180                 185                 190

Gln Asn Ala Ile Glu Lys Ala Ala Ser Phe Arg Asp Thr Phe Gly Ala
        195                 200                 205

Gln Gln Glu Arg Leu Glu His Ala Leu Arg Gly Thr Asp Asn Thr Ser
    210                 215                 220

Glu Ser Thr Gln Arg Ala Glu Ser Ser Arg Arg Asp Thr Asn Met Asn
225                 230                 235                 240

Met Glu Met Val Gln Tyr Ser Thr Asn Arg Ile Leu Val Gln Ala Ser
                245                 250                 255

Gln Ser Ile Leu Ala Gln Tyr Asn Asp Asp Ala Lys Tyr Val Leu Glu
            260                 265                 270

Met Leu Lys Gln Val Leu Gln Ile Leu Gln
        275                 280

<210> SEQ ID NO 9
<211> LENGTH: 819
<212> TYPE: DNA
<213> ORGANISM: Roseburia intestinalis

<400> SEQUENCE: 9
atggtagtac agcacaatat gaccgcaatg aatgcgaaca gaatgttagg cgttacaaca      60
agcgcacagg caaaatcttc agagaaatta tcttctggtt acagaatcaa ccgtgcaggt     120
gatgacgctg ctggtttaac aatttctgag aagatgagaa gccagatccg tggattaaac     180
aaagcttctg acaacgcaca ggatggtatt tccttaatcc aggttgctga gggtgcatta     240

-continued

```
tctgagacac attctatctt acagcgtatg aatgagttag ctactcaggc tgctaacgat      300
accaatacaa ctgctgatag aggagctatt caggatgaga tcaaccagtt aacatctgag      360
attaacagaa tctcttctac aactcagttc aatactcaga acctcatcga tggtacattc      420
gcaaataaaa accttcaggt tggttctatc tgtggacaga gaattactgt ttctatcgac      480
agtatgtctg ctggtagctt aaatgtatct gctaacttag taaaggttaa cactttcagt      540
gcagcaggtg aagcaatgtc caatattcag ggtgctattt ctgcaatttc tacacagcgt      600
tcttacttag gagctcttca gaatcgtctg gagcatacaa tctccaactt ggacaacatt      660
tctgagaata ctcagtctgc tgaatctcgt atccgtgata cagatatggc tgaagagatg      720
gttacttaca gcaagaacaa tattcttgct caggcaggac agtctatgct tgctcaggct      780
aaccagtcta ctcagggtgt actttctctg ttacagtaa                             819
```

<210> SEQ ID NO 10
<211> LENGTH: 272
<212> TYPE: PRT
<213> ORGANISM: Roseburia intestinalis

<400> SEQUENCE: 10

```
Met Val Val Gln His Asn Met Thr Ala Met Asn Ala Asn Arg Met Leu
1               5                   10                  15

Gly Val Thr Thr Ser Ala Gln Ala Lys Ser Ser Glu Lys Leu Ser Ser
            20                  25                  30

Gly Tyr Arg Ile Asn Arg Ala Gly Asp Asp Ala Ala Gly Leu Thr Ile
        35                  40                  45

Ser Glu Lys Met Arg Ser Gln Ile Arg Gly Leu Asn Lys Ala Ser Asp
    50                  55                  60

Asn Ala Gln Asp Gly Ile Ser Leu Ile Gln Val Ala Glu Gly Ala Leu
65                  70                  75                  80

Ser Glu Thr His Ser Ile Leu Gln Arg Met Asn Glu Leu Ala Thr Gln
                85                  90                  95

Ala Ala Asn Asp Thr Asn Thr Thr Ala Asp Arg Gly Ala Ile Gln Asp
            100                 105                 110

Glu Ile Asn Gln Leu Thr Ser Glu Ile Asn Arg Ile Ser Ser Thr Thr
        115                 120                 125

Gln Phe Asn Thr Gln Asn Leu Ile Asp Gly Thr Phe Ala Asn Lys Asn
    130                 135                 140

Leu Gln Val Gly Ser Ile Cys Gly Gln Arg Ile Thr Val Ser Ile Asp
145                 150                 155                 160

Ser Met Ser Ala Gly Ser Leu Asn Val Ser Ala Asn Leu Val Lys Val
                165                 170                 175

Asn Thr Phe Ser Ala Ala Gly Glu Ala Met Ser Asn Ile Gln Gly Ala
            180                 185                 190

Ile Ser Ala Ile Ser Thr Gln Arg Ser Tyr Leu Gly Ala Leu Gln Asn
        195                 200                 205

Arg Leu Glu His Thr Ile Ser Asn Leu Asp Asn Ile Ser Glu Asn Thr
    210                 215                 220

Gln Ser Ala Glu Ser Arg Ile Arg Asp Thr Asp Met Ala Glu Glu Met
225                 230                 235                 240

Val Thr Tyr Ser Lys Asn Asn Ile Leu Ala Gln Ala Gly Gln Ser Met
                245                 250                 255

Leu Ala Gln Ala Asn Gln Ser Thr Gln Gly Val Leu Ser Leu Leu Gln
            260                 265                 270
```

```
<210> SEQ ID NO 11
<211> LENGTH: 1625
<212> TYPE: DNA
<213> ORGANISM: Roseburia intestinalis

<400> SEQUENCE: 11
atggcaatgg tagtacagca caacatgtcc gcaatgaatg cgaacagaaa tttaggtgtt      60
acaacaggaa tgcaggcaaa atcatcagag aagttatctt ccggttacaa gatcaaccgt     120
gcagcagatg atgcagcagg actttctatt tctgagaaga tgagaagcca gatccgcggt     180
ttaaataaag catctgacaa tgcacaggat ggtatctctt taatccagac cgctgaggga     240
gcattaaatg agtcccactc tattttacag agaatgagag agttatccgt acaggcagcc     300
aacggtacag agacagatga cgaccgcgag gcagtacaga acgaggtttc ccagttacag     360
gaagagctga caagaatttc tgagacaaca gagttcaaca cgatgaagct gctggatggt     420
tctcagagtg aagtacatc ttcaaccggg tcaggtccga agtttggtgt tgtagatgca     480
acattagacg gtgcacttgt aacatctaac gtgaaaggta ttaaagtagc aacagcagct     540
gccacaacaa caaaggcagg tcaggagact gctatctggg ctgctgatgg aaagacatta     600
actttaaatc tttcgaaaaa taaggtatat acacaggacg aaattgatga cttgatcgca     660
aatgcaaaac aggaagacag ttctgcaacg ggtgcaccgg ctgaagtgaa agtatctta     720 aagaatggta tttttaatgc agatgcagac acaactgccg gaactgtaac agccggtggt     780
gtgaaggcag tatctgatga aggaacagta actggatttg ttggtgcaga tacaatttca     840
tttacggcaa ataagtatgg agcagagttc aatgatactg tatttaaatt caaatttgat     900
aaggcagcag gcaaagaaga agtagagaca atacagcaa ttgaaattga tggagcaaat     960
gcggtaacag caggtgaata tacaattcat cttgcagcag gcaaagaata tacggcagaa    1020
gatttagaag atgttcttaa aacggcagga ttcgactttg atgttaaatt aagtggaaat    1080
acaccagatg agccaaatac tttatttgca accagtggcg catcaactgt gactgatatt    1140
acaatgggtg ctggcaccgc cggagctggt cttggaagta cagatgctat gtgggggcaa    1200
gctggttatg acagttatct tctggtgctg gcattacctt gcagattggt gcaaatgaag    1260
gtcagaccat gagtttctct atcgatgaca tgagtgcaag agcacttggc gtagatggca    1320
acaaagttga tttaagcaca caggctggcg cacagaaagc aactgatacc attgatgcag    1380
caatcaagaa agtatctgca cagcgtggta gaatgggtgc gatccagaac cgtctggagc    1440
acaccatcag caaccttgat acagcagcag agaatacccca gactgcagag tcccgtatcc    1500
gtgatacaga tatggcagaa gagatggttg agtactccaa gaacaacatt cttgcacagg    1560
caggtcagtc tatgcttgca caggcgaacc agtctacaca gggtgtactc tccttattac    1620
agtaa                                                                1625

<210> SEQ ID NO 12
<211> LENGTH: 541
<212> TYPE: PRT
<213> ORGANISM: Roseburia intestinalis

<400> SEQUENCE: 12

Met Ala Met Val Val Gln His Asn Met Ser Ala Met Asn Ala Asn Arg
1               5                   10                  15

Asn Leu Gly Val Thr Thr Gly Met Gln Ala Lys Ser Ser Glu Lys Leu
            20                  25                  30

Ser Ser Gly Tyr Lys Ile Asn Arg Ala Ala Asp Asp Ala Ala Gly Leu
        35                  40                  45
```

```
Ser Ile Ser Glu Lys Met Arg Ser Gln Ile Arg Gly Leu Asn Lys Ala
 50                  55                  60

Ser Asp Asn Ala Gln Asp Gly Ile Ser Leu Ile Gln Thr Ala Glu Gly
 65                  70                  75                  80

Ala Leu Asn Glu Ser His Ser Ile Leu Gln Arg Met Arg Glu Leu Ser
                 85                  90                  95

Val Gln Ala Ala Asn Gly Thr Glu Thr Asp Asp Arg Glu Ala Val
                100                 105                 110

Gln Asn Glu Val Ser Gln Leu Gln Glu Leu Thr Arg Ile Ser Glu
                115                 120                 125

Thr Thr Glu Phe Asn Thr Met Lys Leu Leu Asp Gly Ser Gln Ser Gly
130                 135                 140

Ser Thr Ser Ser Thr Gly Ser Gly Pro Lys Phe Gly Val Val Asp Ala
145                 150                 155                 160

Thr Leu Asp Gly Ala Leu Val Thr Ser Asn Val Lys Gly Ile Lys Val
                165                 170                 175

Ala Thr Ala Ala Ala Thr Thr Thr Lys Ala Gly Gln Glu Thr Ala Ile
                180                 185                 190

Trp Ala Ala Asp Gly Lys Thr Leu Thr Leu Asn Leu Ser Lys Asn Lys
                195                 200                 205

Val Tyr Thr Gln Asp Glu Ile Asp Asp Leu Ile Ala Asn Ala Lys Gln
210                 215                 220

Glu Asp Ser Ser Ala Thr Gly Ala Pro Ala Glu Val Lys Val Ser Leu
225                 230                 235                 240

Lys Asn Gly Ile Phe Asn Ala Asp Ala Asp Thr Thr Ala Gly Thr Val
                245                 250                 255

Thr Ala Gly Gly Val Lys Ala Val Ser Asp Glu Gly Thr Val Thr Gly
                260                 265                 270

Phe Val Gly Ala Asp Thr Ile Ser Phe Thr Ala Asn Lys Tyr Gly Ala
                275                 280                 285

Glu Phe Asn Asp Thr Val Phe Lys Phe Lys Phe Asp Lys Ala Ala Gly
                290                 295                 300

Lys Glu Glu Val Glu Thr Asn Thr Ala Ile Glu Ile Asp Gly Ala Asn
305                 310                 315                 320

Ala Val Thr Ala Gly Glu Tyr Thr Ile His Leu Ala Ala Gly Lys Glu
                325                 330                 335

Tyr Thr Ala Glu Asp Leu Glu Asp Val Leu Lys Thr Ala Gly Phe Asp
                340                 345                 350

Phe Asp Val Lys Leu Ser Gly Asn Thr Pro Asp Glu Pro Asn Thr Leu
                355                 360                 365

Phe Ala Thr Ser Gly Ala Ser Thr Val Thr Asp Ile Thr Met Gly Ala
                370                 375                 380

Gly Thr Ala Gly Ala Gly Leu Gly Ser Thr Asp Ala Met Trp Gly Gln
385                 390                 395                 400

Ala Gly Tyr Asp Ser Val Ser Ser Gly Ala Gly Ile Thr Leu Gln Ile
                405                 410                 415

Gly Ala Asn Glu Gly Gln Thr Met Ser Phe Ser Ile Asp Asp Met Ser
                420                 425                 430

Ala Arg Ala Leu Gly Val Asp Gly Asn Lys Val Asp Leu Ser Thr Gln
                435                 440                 445

Ala Gly Ala Gln Lys Ala Thr Asp Thr Ile Asp Ala Ala Ile Lys Lys
                450                 455                 460
```

```
Val Ser Ala Gln Arg Gly Arg Met Gly Ala Ile Gln Asn Arg Leu Glu
465                 470                 475                 480

His Thr Ile Ser Asn Leu Asp Thr Ala Ala Glu Asn Thr Gln Thr Ala
                485                 490                 495

Glu Ser Arg Ile Arg Asp Thr Asp Met Ala Glu Glu Met Val Glu Tyr
            500                 505                 510

Ser Lys Asn Asn Ile Leu Ala Gln Ala Gly Gln Ser Met Leu Ala Gln
        515                 520                 525

Ala Asn Gln Ser Thr Gln Gly Val Leu Ser Leu Leu Gln
    530                 535                 540

<210> SEQ ID NO 13
<211> LENGTH: 8
<212> TYPE: PRT
<213> ORGANISM: Artificial Sequence
<220> FEATURE:
<223> OTHER INFORMATION: FLAG peptide

<400> SEQUENCE: 13

Asp Tyr Lys Asp Asp Asp Asp Lys
1               5

<210> SEQ ID NO 14
<211> LENGTH: 25
<212> TYPE: DNA
<213> ORGANISM: Artificial Sequence
<220> FEATURE:
<223> OTHER INFORMATION: Roseburia hominis specific primer

<400> SEQUENCE: 14
cccactgaca gagtatgtaa tgtac                                             25

<210> SEQ ID NO 15
<211> LENGTH: 17
<212> TYPE: DNA
<213> ORGANISM: Artificial Sequence
<220> FEATURE:
<223> OTHER INFORMATION: Roseburia hominis specific primer

<400> SEQUENCE: 15
gcaccacctg tcaccac                                                      17

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Cys Arg Ser Gln Val Arg Gly Leu Asn Lys Ala Ser Asp Asn Ala
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Ile Asp Gly Asn Phe Thr Ser Lys Lys Leu Gln Val Gly Ser Leu Cys
1               5                   10                  15
```

-continued

```
<210> SEQ ID NO 18
<211> LENGTH: 15
<212> TYPE: PRT
<213> ORGANISM: Artificial Sequence
<220> FEATURE:
<223> OTHER INFORMATION: Synthetic peptide

<400> SEQUENCE: 18

Ala Gln Tyr Asn Asp Asp Ala Lys Ser Val Leu Glu Ile Leu Lys
 1               5                  10                  15

<210> SEQ ID NO 19
<211> LENGTH: 14
<212> TYPE: PRT
<213> ORGANISM: Artificial Sequence
<220> FEATURE:
<223> OTHER INFORMATION: Synthetic peptide

<400> SEQUENCE: 19

Gly Leu Asn Lys Ala Ser Arg Asn Ser Gln Asp Gly Ile Ser
 1               5                  10

<210> SEQ ID NO 20
<211> LENGTH: 18
<212> TYPE: DNA
<213> ORGANISM: Artificial Sequence
<220> FEATURE:
<223> OTHER INFORMATION: Bacterial probe Eub338

<400> SEQUENCE: 20
gctgcctccc gtaggagt                                                       18

<210> SEQ ID NO 21
<211> LENGTH: 23
<212> TYPE: DNA
<213> ORGANISM: Artificial Sequence
<220> FEATURE:
<223> OTHER INFORMATION: R. hominis A2-183 specific probe

<400> SEQUENCE: 21
gtacattaca tactctgtca gtg                                                 23

<210> SEQ ID NO 22
<211> LENGTH: 25
<212> TYPE: DNA
<213> ORGANISM: Artificial Sequence
<220> FEATURE:
<223> OTHER INFORMATION: Forward primer

<400> SEQUENCE: 22
ctcgagatat ggtagtacag cacaa                                               25

<210> SEQ ID NO 23
<211> LENGTH: 26
<212> TYPE: DNA
<213> ORGANISM: Artificial Sequence
<220> FEATURE:
<223> OTHER INFORMATION: Reverse primer

<400> SEQUENCE: 23
cttagatctc tgtaataagg ataata                                              26

<210> SEQ ID NO 24
<211> LENGTH: 25
<212> TYPE: DNA
<213> ORGANISM: Artificial Sequence
```

```
<220> FEATURE:
<223> OTHER INFORMATION: Forward primer

<400> SEQUENCE: 24
ctcgagatat ggtggttaat cataa                                          25

<210> SEQ ID NO 25
<211> LENGTH: 27
<212> TYPE: DNA
<213> ORGANISM: Artificial Sequence
<220> FEATURE:
<223> OTHER INFORMATION: Reverse primer

<400> SEQUENCE: 25
cttagatctt ttcaaaatct caagcac                                        27

<210> SEQ ID NO 26
<211> LENGTH: 27
<212> TYPE: DNA
<213> ORGANISM: Artificial Sequence
<220> FEATURE:
<223> OTHER INFORMATION: Forward primer

<400> SEQUENCE: 26
gcaggatcca tgcgtggcgg agacaat                                        27

<210> SEQ ID NO 27
<211> LENGTH: 36
<212> TYPE: DNA
<213> ORGANISM: Artificial Sequence
<220> FEATURE:
<223> OTHER INFORMATION: Reverse primer

<400> SEQUENCE: 27
aatgtggtgg tggtggtggt gctgcagaat ctgcaa                              36

<210> SEQ ID NO 28
<211> LENGTH: 25
<212> TYPE: DNA
<213> ORGANISM: Artificial Sequence
<220> FEATURE:
<223> OTHER INFORMATION: Forward primer

<400> SEQUENCE: 28
ctcgagatat ggtagttaat cataa                                          25

<210> SEQ ID NO 29
<211> LENGTH: 27
<212> TYPE: DNA
<213> ORGANISM: Artificial Sequence
<220> FEATURE:
<223> OTHER INFORMATION: Reverse primer

<400> SEQUENCE: 29
cttagatctt tttaacattt ccaacac                                        27

<210> SEQ ID NO 30
<211> LENGTH: 26
<212> TYPE: DNA
<213> ORGANISM: Artificial Sequence
<220> FEATURE:
<223> OTHER INFORMATION: Reverse primer

<400> SEQUENCE: 30
cttagatctc tgtaacagag aaagta                                         26
```

<210> SEQ ID NO 31
<211> LENGTH: 27
<212> TYPE: DNA
<213> ORGANISM: Artificial Sequence
<220> FEATURE:
<223> OTHER INFORMATION: Forward primer

<400> SEQUENCE: 31
ccgggatcca tggtagtaca gcacaat                                             27

<210> SEQ ID NO 32
<211> LENGTH: 36
<212> TYPE: DNA
<213> ORGANISM: Artificial Sequence
<220> FEATURE:
<223> OTHER INFORMATION: Reverse primer

<400> SEQUENCE: 32
ttagtggtgg tgatgatgat gctgtaacag agaaag                                   36

<210> SEQ ID NO 33
<211> LENGTH: 1494
<212> TYPE: DNA
<213> ORGANISM: Roseburia intestinalis

<400> SEQUENCE: 33
atgcgtggcg agacaatag aaggagaaac agaatgagaa ttaattacaa tgtgtcagca          60
gcgattgcga ataaacattt acttggaatt gaggataatt taagtgcatc gatggaacgg        120
ctttcatcgg gacttaagat caaccattcc aaggacaatc cggcaggaat ggctatttcc        180
aacaagatga agcacagat tgatggttta accgggcttt cccagaatgc atcggatggt        240
atttctgtta ttcagatcgc agatggtgcg ctgagtgaaa cgaccagtat tttacagcgt        300
atgagagaac tttccgtgca ggcagcgagt gatgcaacaa tgacaccggc ggataaagaa        360
gcaatccaga agaaatcac ttcattaaaa gatgaagttg accgtatttc tacagataca        420
gagtataaca gcaaaacact tttagatggt tcattagata ccagggttta caccaaaaat        480
gcaacaagag tggacatttc tgatcatgtg aaagcaggac agtatcagct ttccattgat        540
actgcagcta cacaggccgg accggtaaca gcaaatcaga attataattc cacagcaccg        600
gtcggtgcgt ccggaacaat gagtattaat ggttctaaag tagagataga ggcagccgac        660
acctatgcgg aggcttttga agatcaga atgcagcag agactggtga acaaccgtt           720 aagattgaaa agaatggagc acttttcattt accgcagaac agtacggaat gtcaagcatc        780
ttagagatcg catttgatga taagcagctt gctaatgcac ttggatttac agcagacgga        840
ggaaacagtg ttgtagaaga tccagagaat aaaggcagct atgtatacgg acagattcag        900
aatggcaaag tgatcgtacc ttccggtaca gatgccgaag taacgctcac aaaaccgagt        960
gatggaaccg gatttggtga tacagctacg gtaaaaacag atggaaataa gattacggtt       1020
acagacagag ccggatttga tgtcatttt cttgctgatg caggttatac gggtaagctg       1080
gattttgatg tcacggatat cggaacgatg gcacttcata ttggagcaaa tgaggatcag       1140
gaaacaagag tgcgtattcc ggaggtttcc tgcaagagcc tttacattga tgatgcagac       1200
gtgacgactg taaatggagc aggcagaggt atcacacagt ttgacgatgc catttcaaag       1260
gtcagtgaag tgcgttcaag acttggtgca taccagaatc gtcttgagag tacggtatca       1320
agcctggata cgtttgaaga aaatatgaca ggagcccagt cacgactgac agatgcggat       1380

```
atggcatcgg aaatgacaga ttatacacat cagaatgtat taaatcaggc agcaatctct   1440
gttttgacac aggcaaacga tctgccacag caggtattgc agattctgca gtaa          1494
```

<210> SEQ ID NO 34
<211> LENGTH: 1626
<212> TYPE: DNA
<213> ORGANISM: Roseburia intestinalis

<400> SEQUENCE: 34

```
atggcaatgg tagtacagca caacatgtcc gcaatgaatg cgaacagaaa tttaggtgtt     60
acaacaggaa tgcaggcaaa atcatcagag aagttatctt ccggttacaa gatcaaccgt    120
gcagcagatg atgcagcagg actttctatt tctgagaaga tgagaagcca gatccgcggt    180
ttaaataaag catctgacaa tgcacaggat ggtatctctt taatccagac cgctgaggga    240
gcattaaatg agtcccactc tattttacag agaatgagag agttatccgt acaggcagcc    300
aacggtacag agacagatga cgaccgcgag gcagtacaga acgaggtttc ccagttacag    360
gaagagctga caagaatttc tgagacaaca gagttcaaca cgatgaagct gctggatggt    420
tctcagagtg gaagtacatc ttcaaccggg tcaggtccga agtttggtgt tgtagatgca    480
acattagacg gtgcacttgt aacatctaac gtgaaaggta ttaaagtagc aacagcagct    540
gccacaacaa caaaggcagg tcaggagact gctatctggg ctgctgatgg aaagacatta    600
actttaaatc tttcgaaaaa taaggtatat acacaggacg aaattgatga cttgatcgca    660
aatgcaaaac aggaagacag ttctgcaacg ggtgcaccgg ctgaagtgaa agtatcttta    720
aagaatggta ttttttaatgc agatgcagac acaactgccg gaactgtaac agccggtggt    780
gtgaaggcag tatctgatga aggaacagta actggatttg ttggtgcaga tacaatttca    840
tttacggcaa ataagtatgg agcagagttc aatgatactg tatttaaatt caaatttgat    900
aaggcagcag gcaaagaaga agtagagaca aatacagcaa ttgaaattga tggagcaaat    960
gcggtaacag caggtgaata tacaattcat cttgcagcag gcaaagaata tacggcagaa   1020
gatttagaag atgttcttaa aacggcagga ttcgactttg atgttaaatt aagtggaaat   1080
acaccagatg agccaaatac tttatttgca accagtggcg catcaactgt gactgatatt   1140
acaatgggtg ctggcaccgc cggagctggt cttggaagta cagatgctat gtggggcaa   1200 gctggttatg acagtgtatc ttctggtgct ggcattacct tgcagattgg tgcaaatgaa   1260
ggtcagacca tgagtttctc tatcgatgac atgagtgcaa gagcacttgg cgtagatggc   1320
aacaaagttg atttaagcac acaggctggc gcacagaaag caactgatac cattgatgca   1380
gcaatcaaga aagtatctgc acagcgtggt agaatgggtg cgatccagaa ccgtctggag   1440
cacaccatca gcaaccttga tacagcagca gagaataccc agactgcaga gtcccgtatc   1500
cgtgatacag atatggcaga agagatggtt gagtactcca agaacaacat tcttgcacag   1560
gcaggtcagt ctatgcttgc acaggcgaac cagtctacac agggtgtact ctccttatta   1620
cagtaa                                                              1626
```

POLYPEPTIDE AND IMMUNE MODULATION

CROSS-REFERENCE

This application is a divisional of U.S. application Ser. No. 14/249,710, filed Apr. 10, 2014, which claims the benefit of Great Britain Application No. 1306536.2, filed Apr. 10, 2013, all of which are hereby incorporated by reference in their entirety.

SEQUENCE LISTING

The instant application contains a Sequence Listing which has been submitted electronically in ANSI format and is hereby incorporated by reference in its entirety. Said ANSI copy is named "556865_DYY_009US_Sequence_Listing" and is 36,210 bytes in size.

FIELD OF THE INVENTION

The present invention relates to *Roseburia* flagellins, and/or polynucleotide sequences encoding said *Roseburia* flagellins, and/or vectors comprising said polynucleotide sequences, and/or host cells, including bacteria, comprising said vectors, and/or host cells, including bacteria, comprising said polynucleotide sequences, for various therapeutic and nutritional uses.

BACKGROUND

The human intestine is thought to be sterile in utero, but is exposed to a large variety of maternal and environmental microbes immediately after birth. Thereafter, a dynamic period of microbial colonization and succession occurs which is influenced by factors such as delivery mode, environment, diet and host genotype, all of which impact upon the composition of the gut microbiota, particularly during early life. Subsequently, the microbiota stabilizes and becomes adult-like (Spor, Koren & Ley 2011). The human gut microbiota contains more than 500-1000 different phylotypes belonging essentially to two major bacterial divisions, the Bacteroidetes and the Firmicutes (Eckburg et al. 2005). The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of byproducts providing an important nutrient source for the host. Similarly, the immunological importance of the gut microbiota is well-recognized and is exemplified in germfree animals which have an impaired immune system that is functionally reconstituted following the introduction of commensal bacteria (Macpherson et al. 2001, Macpherson, Martinic & Harris 2002, Mazmanian et al. 2005).

In sharp contrast to the production of secretory intestinal IgA, which is influenced by microbial colonization per se (Chung, Kasper 2010, Macpherson 2006), T cell development and differentiation seem to require colonization by specific commensal micro-organisms. *Clostridium* species, and in particular the spore-forming segmented filamentous bacteria (SFB), appear to be a potent stimulus for the differentiation and maturation of intestinal and colonic Th1, Th17 and Tregs (Gaboriau-Routhiau et al. 2009, Ivanov et al. 2009). Recent studies have now demonstrated that other gut bacteria, including those of *Clostridium* clusters IV and XIVa and the Altered Schaedler Flora (ASF), can induce de novo generation of Tregs while mono-colonization with *Bacteroides fragilis* can correct the Th1/Th2 imbalance in germfree mice by promoting the expansion of Tregs (Mazmanian et al. 2005, Geuking et al. 2011, Atarashi et al. 2011). These data infer important immune-regulatory effects of other resident gut bacteria. Clearly, the effects of commensal bacteria on T cell differentiation pathways is variable and as postulated previously may be influenced by the array of TLR ligands found associated with specific bacteria (Nutsch, Hsieh 2012). For example, the mechanism by which SFB influences T cell responses is currently unknown, but recent genome studies confirming the presence of flagellin genes suggest that innate responses mediated through TLR5-flagellin interactions may be important (Prakash et al. 2011, Sczesnak et al. 2011). Furthermore, the Treg-enhancing effects of *B. fragilis* have been linked with PSA and mediation by TLR2 signalling events (Round et al. 2011).

Dramatic changes in microbiota composition have been documented in gastrointestinal disorders such as inflammatory bowel disease (IBD). For example, the levels of *Clostridium* cluster XIVa bacteria are reduced in IBD patients whilst numbers of *E. coli* are increased, suggesting a shift in the balance of symbionts and pathobionts within the gut (Frank et al. 2007, Scanlan et al. 2006, Kang et al. 2010, Machiels K. et al. 2013). Interestingly, this microbial dysbiosis is also associated with imbalances in T effector cell populations.

*Roseburia* belongs to the phylogenetic cluster XIVa of the Firmicutes phylum. Currently, within the *Roseburia* genus, five species have been identified and characterised: *Roseburia cecicola*, *Roseburia faecis*, *Roseburia hominis*, *Roseburia intestinalis*, *Roseburia inulinivorans* (Stanton and Savage 1983, Duncan et al 2006). The bacteria are flagellated commensal anaerobes and are also major butyrate producers (Duncan et al. 2006). Although precise numbers of these bacteria colonizing the human gut have not been accurately estimated, *Roseburia* spp. are dominant in the healthy human gut and are under-represented in IBD patients (Machiels K. et al. 2013).

The roles of bacterial genes, in particular flagellin, participating in colonization and adaptation to the murine gut, as well as the host immune genes responding to colonization by *Roseburia* bacteria are disclosed. The inventors show that specific flagellin structures of *Roseburia* such as *R. hominis* and *R. intestinalis* induce distinct signalling responses in both epithelial cells and dendritic cells relative to other flagellate enteric bacteria. The importance of the TLR5-*Roseburia*, such as TLR5-*R. hominis*, interactions in directing the host adaptive response, in particular Treg responses is demonstrated. The complete genome sequence and annotation for *R. hominis* described herein is shown in GenBank under accession number CP003040 (version 1). For *R. intestinalis* (GenBank Accession Number for 16S rRNA gene strain L-82: AJ312385) described herein the reference genome sequence is shown in GenBank under accession number ABYJ02000000 (version 2) and consists of sequences ABYJ02000001-ABYJ02000409.

STATEMENTS OF INVENTION

Surprisingly, the present inventors found that *Roseburia* flagellin proteins are important in modulating the immune response.

In addition, the present inventors surprisingly found that the flagellin proteins derived or derivable from *Roseburia hominis* or *Roseburia intestinalis* are important in modulating the immune response.

The present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in modulating the inflammation of a tissue or an organ (such as the intestine) in a subject.

In another aspect, the present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in modulating the production of T cells (e.g. regulatory T cells such as regulatory T cells capable of expressing TLR5) in a subject.

The present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in restoring immunological tolerance.

In a further aspect, the present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in regulating the immune system of a subject.

In another aspect, the present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in treating a disorder in a subject, wherein said disorder is an inflammatory disorder and/or an autoimmune disorder.

The present invention, in another aspect, relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in modulating dendritic cells (such as bone marrow dendritic cells) and/or epithelial cells in a tissue or an organ of a subject.

The present invention, in a further aspect, relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in regulating the production of IL-10 and/or TGFβ in a cell or cells of a subject.

In a further aspect, the present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in regulating the production of cell surface markers involved in immune responses and antigen recognition such as CD40, I-A/I-E, CD317/BST-2, CD103, CD80, CD86, CD83 and/or Siglec-H and/or the species equivalent in a cell or cells of a subject.

In another aspect, the present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in regulating (e.g. downregulating) the expression of one of more Type I IFN genes (such as but not limited to one or more genes selected from the group consisting of IFN-β1, IFN-β, Ifi202b, Ifi203, IF144, IFTI, MXI, OASI, OAS2, OAS3, OASL, Irf3 and Irf4) in a cell or cells of a subject.

The present invention, in a further aspect, relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in regulating (e.g. downregulating) the expression of one or more pro-inflammatory genes (such as one or more genes selected from the group consisting of but not limited to IL1-β, IL4, IL5, IL6, IL8, IL12, IL13, IL17, IL21, IL22, IL23, IL27, IFNγ, CCL2, CCL3, CCL5, CCL20, CXCL5, CXCL10, CXCL12, CXCL13, and TNF-α) in a cell or cells of a subject.

The present invention, in another aspect, relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in improving intestinal microbiota in a subject.

In another aspect, the present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in regulating appetite in a subject.

In a further aspect, the present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in regulating (e.g. downregulating) the expression of the gene encoding cholecystokinin (Cck) and/or the expression of the gene encoding glucagon (Gcg) in a cell or cells of a subject.

The present invention, in a further aspect, relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in improving alimentary canal health in a subject.

The present invention, in another aspect, relates to a pharmaceutical composition comprising a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and a pharmaceutically acceptable excipient, carrier or diluent.

In another aspect, the present invention relates to a nutritional supplement comprising a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and a nutritional acceptable excipient, carrier or diluent.

In a further aspect, the present invention relates to a feedstuff, food product, dietary supplement, or food additive comprising a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*).

The present invention, in a further aspect, relates to a process for producing a pharmaceutical composition according to the present invention, said process comprising admixing a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), with a pharmaceutically acceptable excipient, carrier or diluent; optionally said *Roseburia* flagellin, and/or said polynucleotide sequence, and/or said vector, and/or said host cell comprising said vector, and/or said host cell comprising said polynucleotide sequence, and/or said *Roseburia* (such as the bacterial species *Roseburia hominis*, or the bacterial species *Roseburia intestinalis*), is encapsulated.

In a further aspect, the present invention relates to a process for producing a nutritional supplement according to the present invention, said process comprising admixing a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), with a nutritionally acceptable excipient, carrier or diluent; optionally said *Roseburia* flagellin, and/or said polynucleotide sequence, and/or said vector, and/or said host cell comprising said vector, and/or said host cell comprising said polynucleotide sequence, and/or said *Roseburia* (such as the bacterial species *Roseburia hominis*, or the bacterial species *Roseburia intestinalis*), is encapsulated.

In another aspect, the present invention relates to a method of modulating the inflammation of a tissue or an organ (such as the intestine) in a subject, said method comprising administering to the subject a *Roseburia* flagellin, or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein the inflammation of the tissue or organ (such as the intestine) in the subject is modulated.

The present invention, in another aspect, relates to a method of modulating the production of T cells (e.g. regulatory T cells such as regulatory T cells capable of expressing TLR5) in a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein the production of T cells (e.g. regulatory T cells such as regulatory T cells capable of expressing TLR5) in the subject is modulated.

The present invention, in a further aspect, relates to a method of regulating the immune system of a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein the immune system of the subject is regulated.

In a further aspect, the present invention relates to a method of treating a disorder in a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), wherein said disorder is an inflammatory disorder and/or an autoimmune disorder.

In another aspect, the present invention relates to a method of modulating dendritic cells (such as bone marrow dendritic cells) and/or epithelial cells in a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein dendritic cells (such as bone marrow dendritic cells) and/or epithelial cells in the subject are modulated.

In a further aspect, the present invention relates to a method of regulating the production of IL-10 and/or TGFβ in a cell or cells of a subject, said method comprising administering a *Roseburia* flagellin and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), to the subject, and wherein the production of IL-10 and/or TGFβ in a cell or cells of the subject is regulated.

The present invention, in another aspect, relates to a method of regulating the production of cell surface markers involved in immune responses and antigen recognition such as CD40, I-A/I-E, CD317/BST-2, CD103, CD80, CD86, CD83 and/or Siglec-H and/or the species equivalent in a cell or cells of a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), to the subject, and wherein the production of cell surface markers involved in immune responses and antigen recognition such as CD40, I-A/I-E, CD317/BST-2, CD103, CD80, CD86, CD83 and/or Siglec-H and/or the species equivalent in a cell or cells of the subject is regulated.

In another aspect, the present invention relates to a method of regulating (e.g. downregulating) the expression of one of more Type I IFN genes (such as one or more genes selected from the group consisting of but not limited to IFN-β1, IFN-β3, Ifi202b, Ifi203, IF144, IFTI, MXI, OASI, OAS2, OAS3, OASL, Irf3 and Irf4) in a cell or cells of a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), wherein the expression of one of more Type I IFN genes (such as one or more genes selected from the group consisting of but not limited to IFN-β1, IFN-β, Ifi202b, Ifi203, IF144, IFTI, MXI, OASI, OAS2, OAS3, OASL, Irf3 and Irf4) in a cell or cells of the subject is regulated.

In a further aspect, the present invention relates to a method of regulating (e.g. downregulating) the expression of one or more pro-inflammatory genes (such as one or more genes selected from the group consisting of but not limited to IL-β, IL4, IL5, IL6, IL8, IL2, IL13, IL17, IL21, IL22, IL23, IL27, IFNγ, CCL2, CCL3, CCL5, CCL20, CXCL5, CXCL10, CXCL12, CXCL13, and TNF-α in a cell or cells of a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), wherein the expression of one or more pro-inflammatory genes (such as one or more genes selected from the group consisting of but not limited to IL-β, IL4, IL5, IL6, IL8, IL12, IL13, IL17, IL21, IL22, IL23, IL27, IFNγ, CCL3, CCL5, CCL20, CXCL5, CXCL10, CXCL12, CXCL13, and TNF-α) in a cell or cells of the subject is regulated.

The present invention, in a further aspect, relates to a method of improving intestinal microbiota in a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein the intestinal microbiota in a subject is improved.

In another aspect, the present invention relates to a method of regulating appetite in a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein the appetite in the subject is regulated.

The present invention, in another aspect relates to a method of regulating (e.g. downregulating) the expression of the gene encoding cholecystokinin (Cck) and/or the expression of the gene encoding glucagon (Gcg) in a cell or cells of a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein the expression of the gene encoding cholecystokinin (Cck) and/or the expression of the gene encoding glucagon (Gcg) in a cell or cells of the subject is regulated.

In a further aspect, the present invention relates to a method of improving alimentary canal health in a subject, said method comprising administering a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein alimentary canal health in a subject is improved.

The present invention, in a further aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for modulating the inflammation of a tissue or an organ (such as the intestine) in a subject.

The present invention, in another aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for modulating the production of T cells (e.g. regulatory T cells such as regulatory T cells capable of expressing TLR5) in a subject.

In a further aspect, the present invention relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for regulating the immune system of a subject.

The present invention, in a further aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for the treatment of a disorder in a subject, wherein said disorder is an inflammatory disorder and/or an autoimmune disorder.

The present invention, in another aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for modulating dendritic cells (such as bone marrow dendritic cells) and/or epithelial cells in a tissue or an organ of a subject.

In another aspect, the present invention relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for regulating the production of IL-10 and/or TGFβ in a cell or cells of a subject.

The present invention, in a further aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for regulating the production of cell surface markers involved in immune responses and antigen recognition such as CD40, I-A/I-E, CD317/BST-2, CD103, CD80, CD86, CD83 and/or Siglec-H and/or the species equivalent in a cell or cells of a subject.

In a further aspect, the present invention relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for regulating (e.g. downregulating) the expression of one of more Type I IFN genes (such as one or more genes selected from the group consisting of but not limited to IFN-β1, IFN-β3, Ifi202b, Ifi203, IF144, IFTI, MXI, OASI, OAS2, OAS3, OASL, Irf3 and Irf4) in a cell or cells of a subject.

In another aspect, the present invention relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for regulating (e.g. downregulating) the expression of one or more pro-inflammatory genes (such as one or more genes selected from the group consisting of but not limited to IL1-β, IL4, IL5, IL6, IL8, IL12, IL3, IL17, IL21, IL22, IL23, IL27, IFNγ, CCL2, CCL3, CCL5, CCL20, CXCL5, CXCL10, CXCL12, CXCL13, and TNF-α) in a cell or cells of a subject.

The present invention, in a further aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for improving intestinal microbiota in a subject.

The present invention, in another aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for regulating appetite in a subject.

The present invention, in a further aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for regulating (e.g. downregulating) the expression of the gene encoding cholecystokinin (Cck) and/or the expression of the gene encoding glucagon (Gcg) in a cell or cells of a subject.

The present invention, in another aspect, relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for improving alimentary canal health in a subject.

In another aspect, the present invention relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in medicine.

In a further aspect, the present invention relates to a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for use in restoring immunological tolerance.

In another aspect, the present invention relates to use of a *Roseburia* flagellin, and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), for the manufacture of a medicament for restoring immunological tolerance in a subject.

The present invention relates to, in another aspect, a method of restoring immunological tolerance in a subject, said method comprising administering a *Roseburia* flagellin and/or a polynucleotide sequence encoding said *Roseburia* flagellin, and/or a vector comprising said polynucleotide sequence, and/or a host cell comprising said vector, and/or a host cell comprising said polynucleotide sequence, and/or *Roseburia* (such as the bacterial species *Roseburia hominis*, or the bacterial species *Roseburia intestinalis*), and wherein the immunological tolerance in a subject is restored.

FIGURES

FIGS. 1A-1B. Sequence and annotation of *R. hominis* genome. The complete genome sequence of *R. hominis* A2-183 was produced. It is represented by a single 3,592,125-bp chromosome with four ribosomal operons, 66 RNAs and 3,273 predicted proteins. FIG. 1A *R. hominis* circular genome map with the location of the PCR experiments (Table S1) indicated in the regions targeted by the primers. The tracks on the genome map, starting at the outer track 0, are: track 0 (blue)—Real-time PCR experiments indicated by numbered tick marks; track 1 (pale blue)—Forward CDS; track 2 (pale blue)—Reverse CDS; track 3 (grey)—rRNA; track 4 (green)—tRNA; track 5 (red)—STS marking regions targeted by Real-time PCR; graph 1—GC content; graph 2—GC bias. FIG. 1B Functional annotation of the *R. hominis* genome shows that the largest number of genes belong to Carbohydrates, Protein Metabolism and Amino acids and Derivatives.

FIGS. 2A-2D. *R. hominis* responds to the gut environment by up-regulating motility, mobilization and chemotaxis genes. Germfree GF C3H/HeN male mice were given *R. hominis* culture by gavage for 28 d, and compared to germfree control animals. At 14 d and 28 d, *R. hominis*-treated animals (N=5) and control animals (N=4) were sacrificed and ileum, colon and caecum were collected. FIG. 2A Real-time PCR validation of genes involved in conjugation/mobilization transfer. FIG. 2B Real-time PCR validation of genes involved in Motility and Chemotaxis. FIG. 2C Western blot of *R. hominis* grown in vitro in the presence of UV irradiated standard murine chow immuno-stained with affinity-purified Fla1 antibody, Fla2 specific antiserum and anti-DNA gyrase A antibody (lane 1: no diet, lane 2: 0.01 g diet/10 mL of *R. hominis* culture, lane 3: 0.02 g diet/10 mL, lane 4: 0.05 g diet/10 mL, lane 5: 0.1 g diet/10 mL, lane 6: 0.2 g diet/10 mL, lane 7: 0.5 g diet/10 mL, lane 8: 1 g diet/10 mL). Electron microscopy (EM) picture of *R. hominis* showing flagella (black arrows). Immunocytochemistry performed on bacteria from luminal contents of colonized mice and from *R. hominis* grown in vitro using FlaA1 and FlaA2 specific antiserum. Original magnification .times.1000. FIG. 2D Real-time PCR validation of genes involved in butyrate metabolism. FIG. 2E Real-time PCR analysis of *R. hominis* transcripts during in vitro exposure to human intestinal epithelial cells. Real-time PCR results are presented as fold change, *P<0.05, P<0.01, *P<0.001.

FIGS. 3A-3C. Identification of transcripts differentially expressed in the murine gut after mono-association with *R. hominis*. FIG. 3A Affymetrix microarray analysis of differentially expressed genes in *R. hominis*-colonized mice (N=5) relative to GF (N=4). Bar graphs represent number of genes higher and lower expressed after 14 and 28 days. FIG. 3B Heatmap generated from differentially expressed genes with functional significance between GF and *R. hominis*-colonized mice at 14 d and 28 d. FIG. 3C Real-time PCR validation of genes shown to be significantly different between *R. hominis*-colonized and GF mice. Real-time PCR results are presented as fold change, *P<0.05, P<0.01, *P<0.001.

FIG. 4. Induction of FoxP3+ Treg cells by *Roseburia hominis*. Flow cytometry analysis of FoxP3+ Treg cells in lamina propria (P=0.0425 between control and *R. hominis* treatment) and mesenteric lymph nodes (P=0.0683) of conventional C3H/HeN treated for 14 days with *R. hominis*.

FIGS. 5A-5E Colonic T cell markers are significantly induced by *R. hominis* mono-colonization. FIG. 5A is an Immunofluorescence analysis of ascending colon lamina propria cells with anti-CD3 and anti-FoxP3 in germfree and *R. hominis* mono-colonized C3H/HeN(N=8) and C57Bl/6 (N=3) mice. Immunofluorescence analysis of lamina propria cells labelled with FIG. 5B anti-Ly6G, FIG. 5C anti-CD11b, FIG. 5D anti-CD3, and FIG. 5E anti-CD3 and anti-FoxP3 in ascending colon of GF and *R. hominis*-treated C3H/HeN mice. Data expressed as number of positive cells per field of view in GF mice (N=7-8) and *R. hominis*-treated mice (N=8-10). *P<0.05. Original magnification .times.630.

FIGS. 6A-6G. *R. hominis* flagellin RH1 has specific effects on intestinal epithelial cells and murine bone marrow-derived dendritic cells. FIG. A depicts a heatmap generated from differentially expressed genes in Caco-2 intestinal epithelial cells (N=1) treated with different bacterial flagellins *Salmonella enteritidis* (SE), *E. coli* K12 (EC), RH1 and RH2. FIGS. 6B-6D depict expression of (FIG. 6B) CD40; (FIG. 6C) I-A/I-E and (FIG. 6D) CD103 by CD11c+ B220+CD317+Flt3L-derived dendritic cells from conventional C3H/HeN, control (blue) and after 24 hrs incubation with recombinant flagellin (SE, K12, RH1, RH2, RI1, RI2, RI3, RI4, Er; green) determined by flow cytometry. Histogram represents data from three experiments. FIG. 6E depicts frequencies of recombinant flagellin (SE, K12, RH1, RH2) treated Flt3L- and GMCSF-derived dendritic cell populations from conventional C3H/HeN gated on CD11c+ B220+CD317+ cells and CD11c+CD11b+B220-cells, respectively. Data presented as percentage of total, live and singlet cells, mean.+-.SEM from three experiments. FIG. 6F depicts Protein expression of cytokines IL-10 and IL-12 was measured by CBA in supernatants from control (unstimulated DCs; N=3) and RH1-treated DCs (N=3) derived from C3H/HeN and C5781/6. Data is presented as mean.+-.SD. ***P<0.001. (FIG. 6G depicts Quantitative analysis of immunofluorescent labelling of ascending colon lamina propria cells with anti-CD3 and anti-FoxP3 in germfree and *R. hominis* mono-colonized TLR5KO mice (N=2) (SE): *Salmonella enteritidis* flagellin; (K12): *Escherichia coli* K12 flagellin; (Rh1): *Roseburia hominis* Fla1; (Rh2): *Roseburia hominis* Fla2; (Ri1): *Roseburia intestinalis* Fla1; (Ri2): *Roseburia intestinalis* Fla2; (Ri3): *Roseburia intestinalis* Fla3; (Ri4): *Roseburia intestinalis* Fla4; (Er) *Eubacterium rectale* flagellin.

FIGS. 7A-7C. *R. hominis* attenuates inflammation in an experimental model of colitis. Twenty-two female C57BL/6 mice were used to assess the therapeutic effect of *R. hominis* during DSS-induced colitis. Treated mice were dosed daily with 10.sup.9 CFU *R. hominis* for 14 days. From day 8, mice were given DSS in their drinking water for 6 days. The animals were euthanized on day 14 and intestinal tissue sampling was performed. FIG. 7A Untreated DSS mice (N=8) had strong elevation of all genes compared to control mice (N=4), while differential gene expression was lower in *R. hominis*-treated animals (N=10). Real-time PCR results are presented as fold change, ***P<0.001. FIG. 7B Histopathology tissue scoring presented as mean percentage of fields of view at a given grade. DSS treatment significantly altered all fields of view at grades 0, 2, 3, and 4. *R. hominis* significantly reduced the % fields of view for grade 4 pathology (p=0.02) and increased the % fields of view for grade 0. Data is presented as mean.+−.SD. FIG. 7C Ascending colon (haematoxylin/eosin stained) of control, DSS-treated and DSS/*R. hominis*-treated IL-10KO animals. Images shown are representative fields of view from each treatment group. Original magnification .times.100.

SUPPLEMENTARY FIGURES

FIGS. 8A-8C *R. hominis* preferentially colonizes the ascending colon of mono-colonized mice. FIG. 8A *R. hominis* colonized the ascending colon of the mouse gut with close association of bacteria to the host epithelium, detected by FISH using A2-183 (*R. hominis*-specific probe; FITC), Eub338 (universal 16S probe; Cy3) and DAPI (nuclei; blue). Overlays of A2-183+Eub338 and Eub338+DAPI are also shown. The gamma for the red channel was increased in the Eub338+DAPI overlay to illustrate the labelled bacteria. Original magnification .times.630. FIG. 8B PCR using *R. hominis*-specific primers showed a strong positive signal in faecal DNA post-colonization, while faeces of GF animals were negative for the presence of any bacteria. FIG. 8C Real-time PCR analysis showing colonization levels of *R. hominis*/g faeces. Bacterial DNA isolated from faeces was compared against known standard concentrations of *R. hominis* grown in culture. Similar bacterial levels were detected in all mono-colonized mice, approximating .times.10.sup.10 bacteria/g faeces. Faeces of GF animals tested negative for the presence of any bacteria.

FIGS. 9A-C. Gene Ontology analysis performed on genes up-regulated at 28 days in the ascending colon. Gene Ontology (GO) based functional interpretation of the data was performed using DAVID (http://david.abcc.ncifcrf.gov). Significantly different transcripts (P<0.05) were allocated into the GO category 'Biological Process' to find significantly enriched GO terms. The GO biological processes for 'actin polymerization' (GO:0030041) and 'negative regulation of 1-kappaB kinase/NF-kappaB cascade' (GO:0043124) were affected.

FIGS. 10A-10C. Identification of transcripts differentially expressed in the murine gut after mono-association with *E. coli*. FIG. 10A Affymetrix microarray analysis of differentially expressed genes in *E. coli* and *R. hominis*-colonized mice over time. Bar graphs represent number of genes higher and lower expressed after 22 and 28 day, respectively. FIG. 10B Heatmap generated from differentially expressed genes with functional significance in *E. coli*-colonized mice at 22 d vs. 10 d.

FIGS. 11A-11D. Identification of transcripts differentially expressed in TLR5KO mouse gut after mono-association with *R. hominis*. FIG. 11A Heatmap generated from differentially expressed genes in ascending colon of *R. hominis*-colonized TLR5KO (N=3) and wildtype mice (N=3) at 28 d. FIG. 11B Heatmap generated from differentially expressed immune-associated genes in ascending colon of *R. hominis*-colonized TLR5KO and wildtype mice at 28 d. FIG. 11C Heatmap generated from differentially expressed genes in ileum of *R. hominis*-colonized TLR5KO and wildtype mice at 28 d. FIG. 11D Heatmap generated from differentially expressed immune-associated genes in ileum of *R. hominis*-colonized TLR5KO and wildtype mice at 28 d.

FIGS. 12A-J. Gene Ontology analysis performed on genes down-regulated at 28 days in the ascending colon. GO biological processes involved in appetite regulation, such as 'negative regulation of response to food' (GO:0032096), 'negative regulation of appetite' (GO:0032099) and 'regulation of catecholamine secretion' (GO:0050433) were mostly affected. FIG. 12K depicts an overview of the arrangement of FIGS. 12A-J.

FIGS. 13A-13B. *R. hominis* colonization influences satiety genes and body weight. Dry body weight and lipid carcass analysis was performed. FIG. 13A Dry carcass weights of *R. hominis*-associated mice were significantly heavier compared to GF animals. FIG. 13B Carcass lipid analysis showed that total adiposity was also significantly higher in *R. hominis*-treated animals at 14 d. Data is presented as mean.+−.SD.

FIG. 14 Representation of the cloning vector pCR-Blunt II-TOPO used for cloning recombinant flagellins insoluble after cell lysis. It allows high-efficiency DNA cloning of blunt-end PCR products. It encodes Kanamycin and Zeocin resistance genes for selection in *E. coli*, and the insert is flanked by multiples restriction sites for excision.

FIG. 15 Representation of the expression vector T7-MAT-Tag-FLAG-used for cloning recombinant flagellins insoluble after cell lysis. The multi cloning site (MCS) is flanked by MAT (Metal Affinity Tag) sequence and FLAG peptide (Asp-Tyr-Lys-Asp-Asp-Asp-Asp-Lys; SEQ ID NO: 13) sequence, which results in the production of double-tagged flagellin, which can be further purified by affinity columns. This expression vector also encodes a pT7/lac (phage T7 lac operon) promoter for IPTG inducible, high-level expression of MAT-ORF-FLAG recombinant flagellins, an internal lacI gene that represses transcription at basal state in any *E. coli* host, and an AmpR gene for ampicillin selection.

FIG. 16 Visualization on a SDS-PAGE of recombinant flagellin cloned with the pCR-Blunt II-TOPO cloning vector and expressed through the pT7-MAT-Tag-FLAG-2 expression vector. Description of lanes: 1, protein standard (kDa); 2, RH1.

FIGS. 18A and 18B show an SDS-Analysis of recombinant flagellins.

FIG. 18(A) K12 (*Escherichia coli* K12); ER (*Eubacterium rectale* 33656); RI1 (*Roseburia intestinalis* Fla1); RI2 (*Roseburia intestinalis* Fla2);

FIG. 18(B) RH1 (*Roseburia hominis* Fla1); RH2 (*Roseburia hominis* Fla 2); RI3 (*Roseburia intestinalis* Fla 3); RI4 (*Roseburia intestinalis* Fla 4).

FIGS. 19-22. Multiple sequence alignment confirming flagellin nucleotide sequence and accession number.

Figure 28:
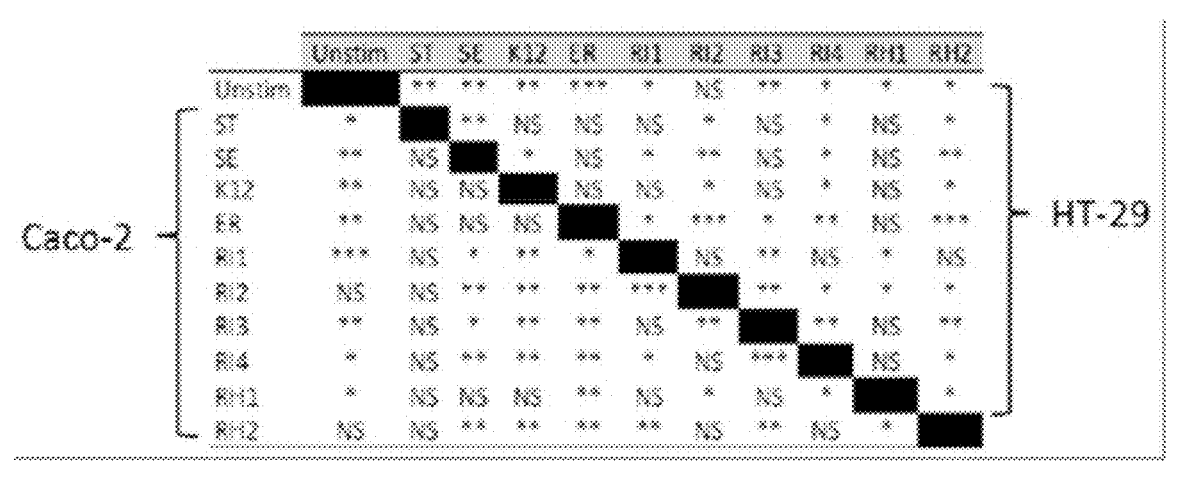

FIG. 23 Comparative analysis of CCL20 gene induction by different flagellins. HT-29 and Caco-2 cells were stimulated for 2 hours with a single recombinant flagellin at a concentration of 100 ng/mL. Total RNA was extracted and subjected to real time quantitative PCR analysis for the genes CCL20 and β-actin. Experiments were done in triplicate on three separate occasions. FIG. 28 indicates significant differences between each treatment calculated with paired t test in HT-29.

Figure 24:
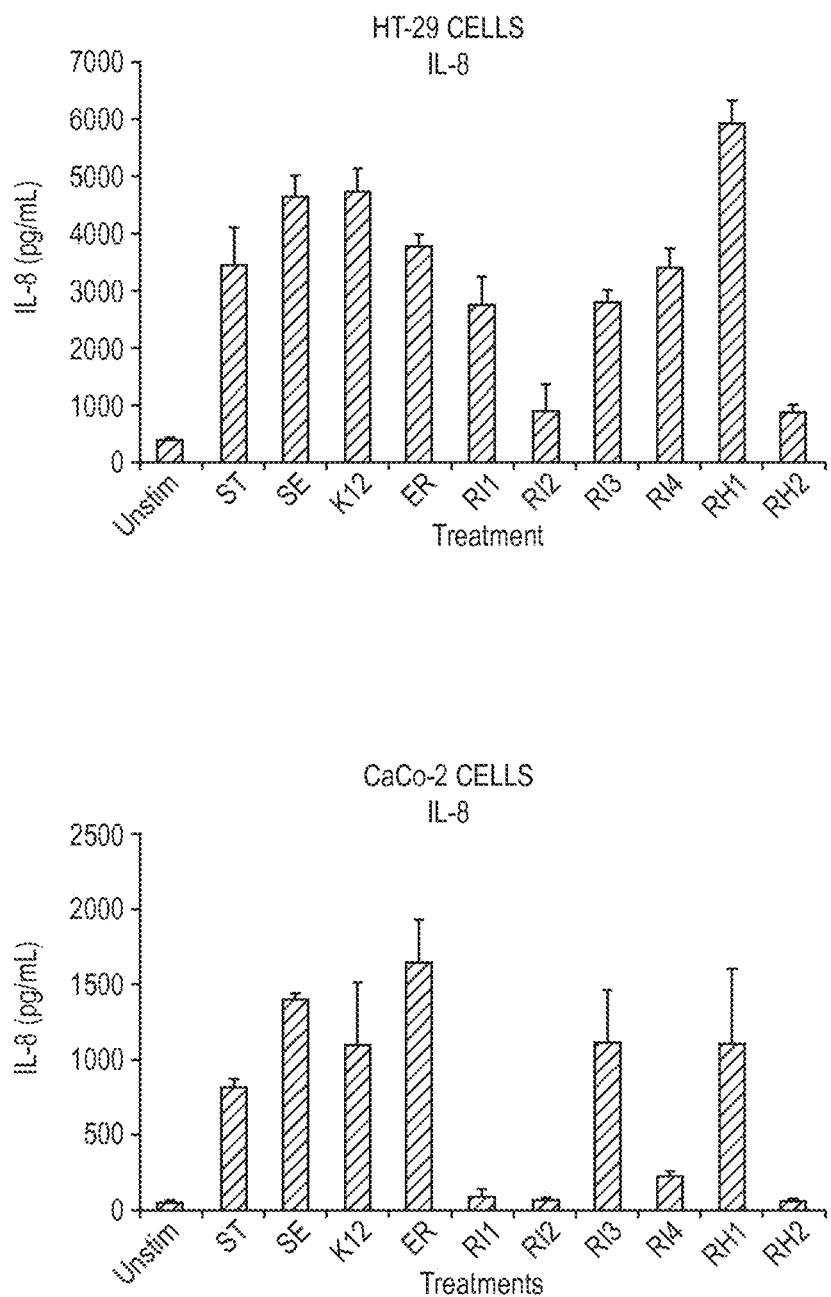
Figure 24:
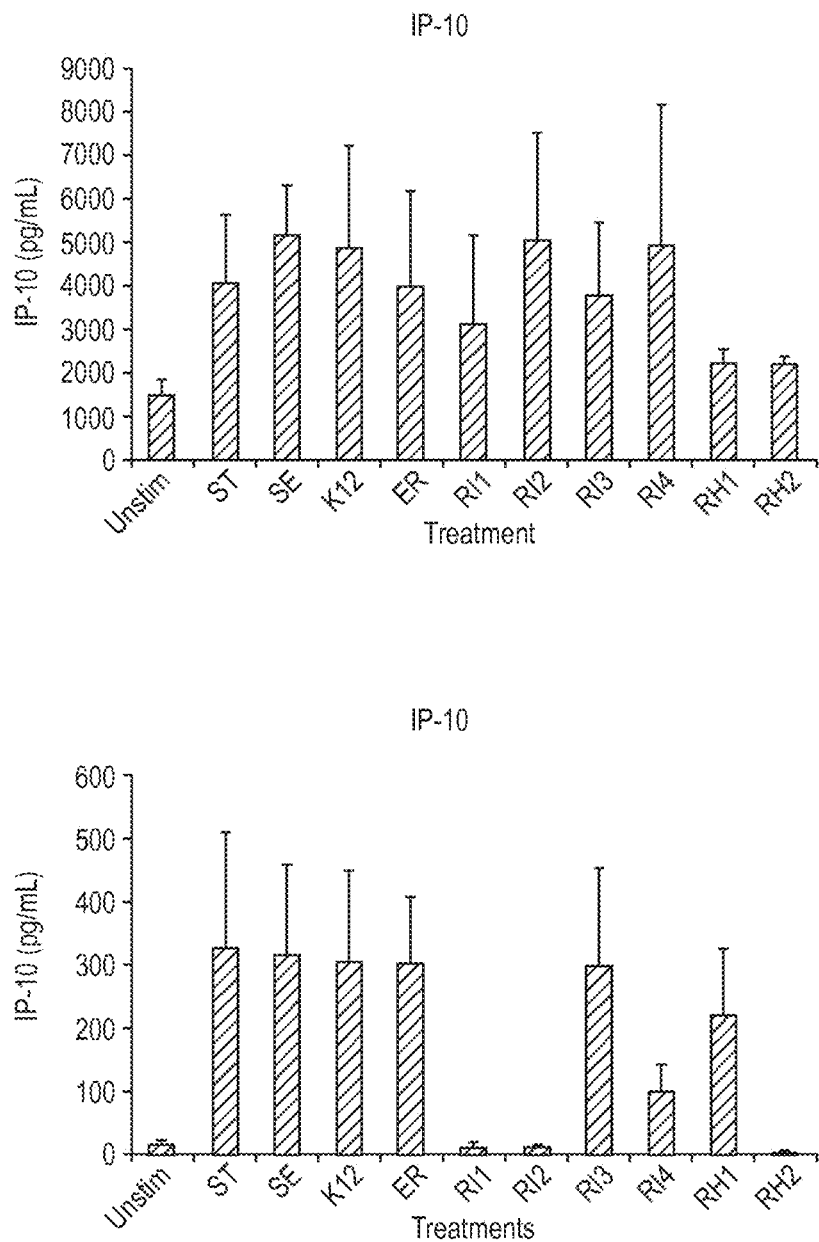

FIG. 24 Flagellin-mediated chemokine secretion in HT-29 and Caco-2 cells. FIGS. 29A-29D indicate significant differences between each treatment calculated with paired t test.

Figure 25:
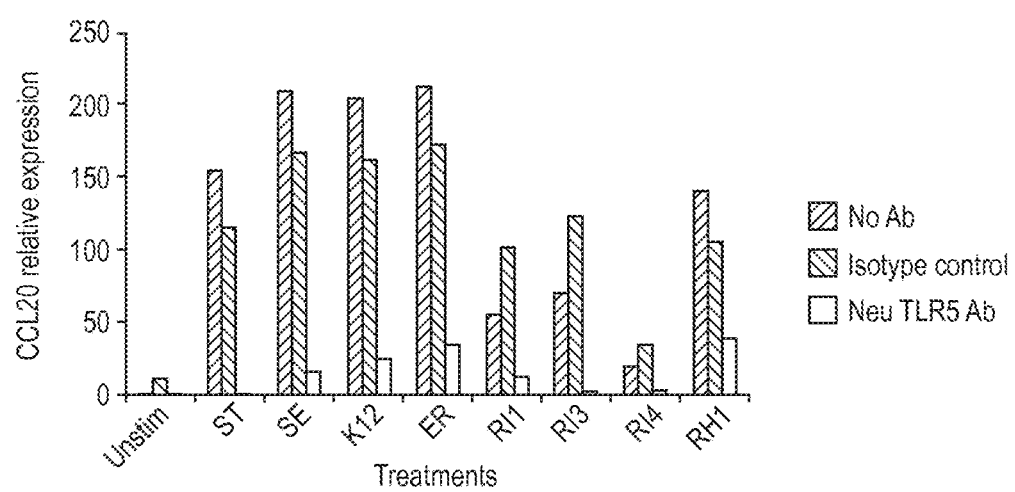

FIG. 25, neutralization of TLR5 with an anti-TLR5 specific antibody.

Figure 26A:
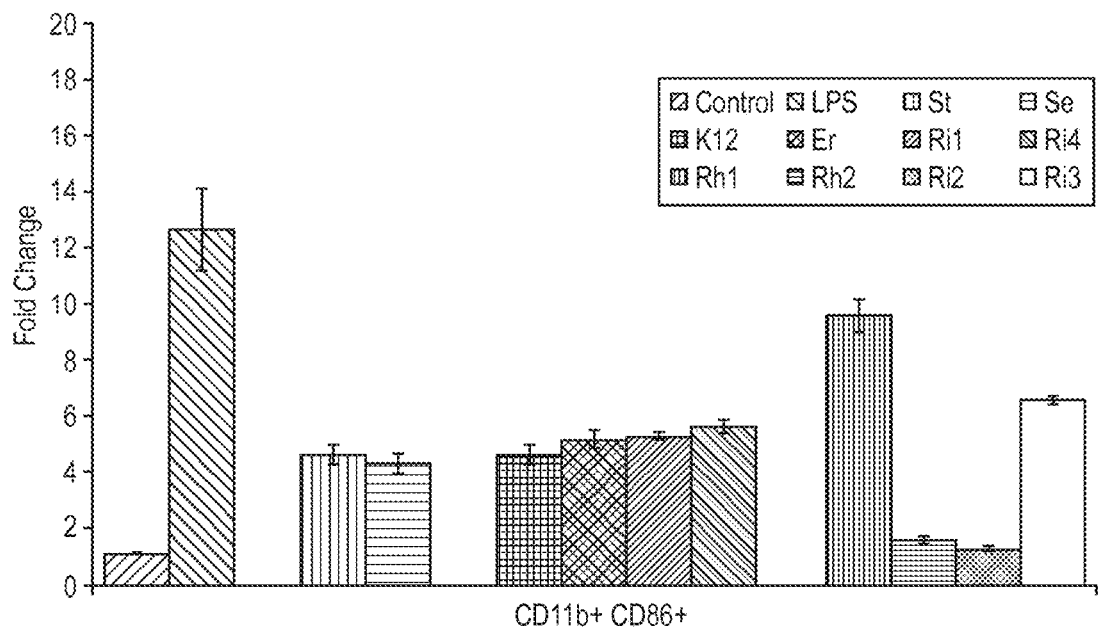

FIG. 26A: Frequencies of GM-CSF/IL-4 derived dendritic cells stimulated with recombinant flagellins, data shown as fold change compared to unstimulated GM-CSF/IL-4 derived dendritic cells.

Figure 26B:
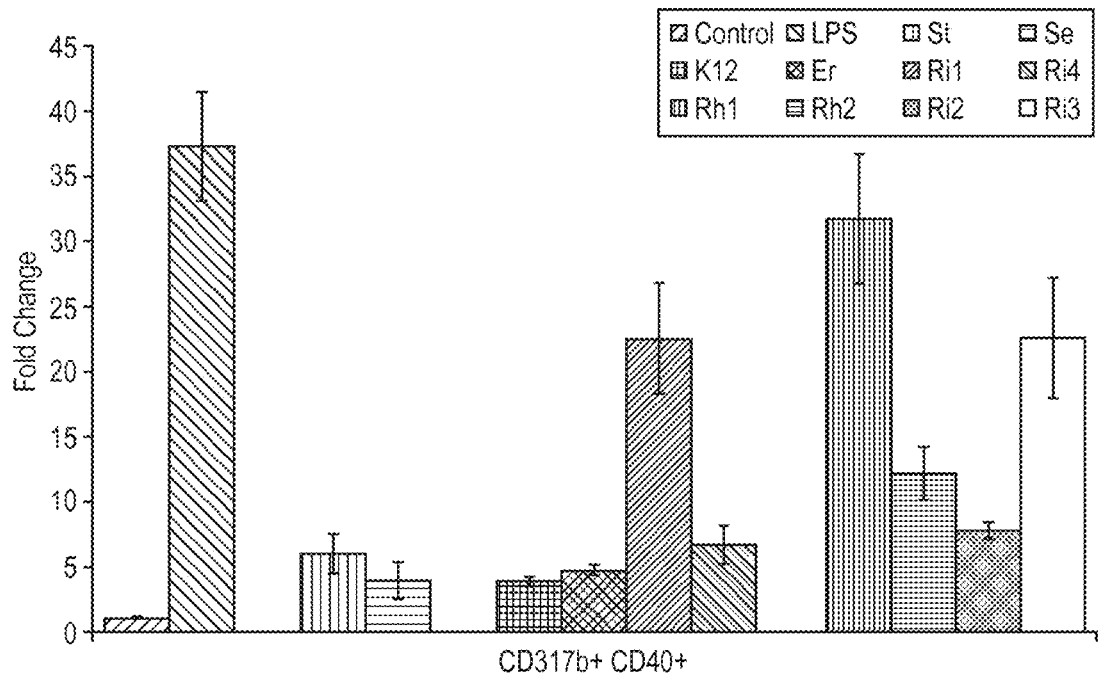

FIG. 26B: Frequencies of Flt3L derived dendritic cells stimulated with recombinant flagellins, data shown as fold change compared to unstimulated Flt3L derived dendritic cells.

Figure 27A:
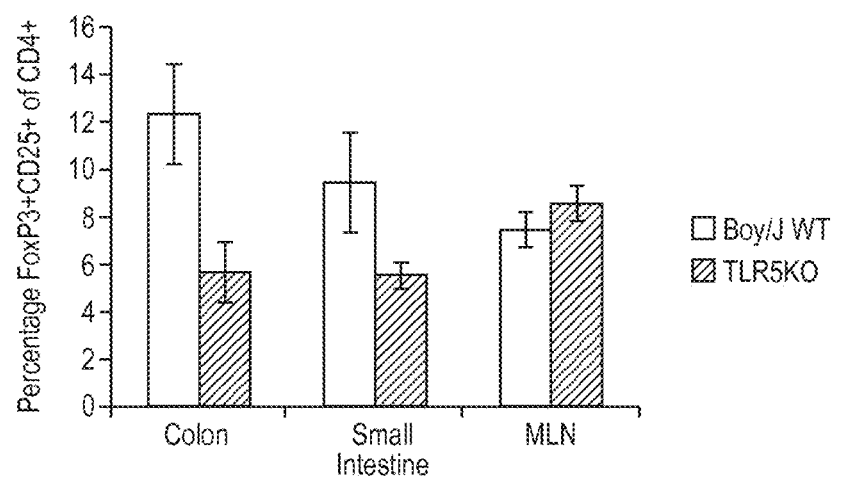
Figure 27B:
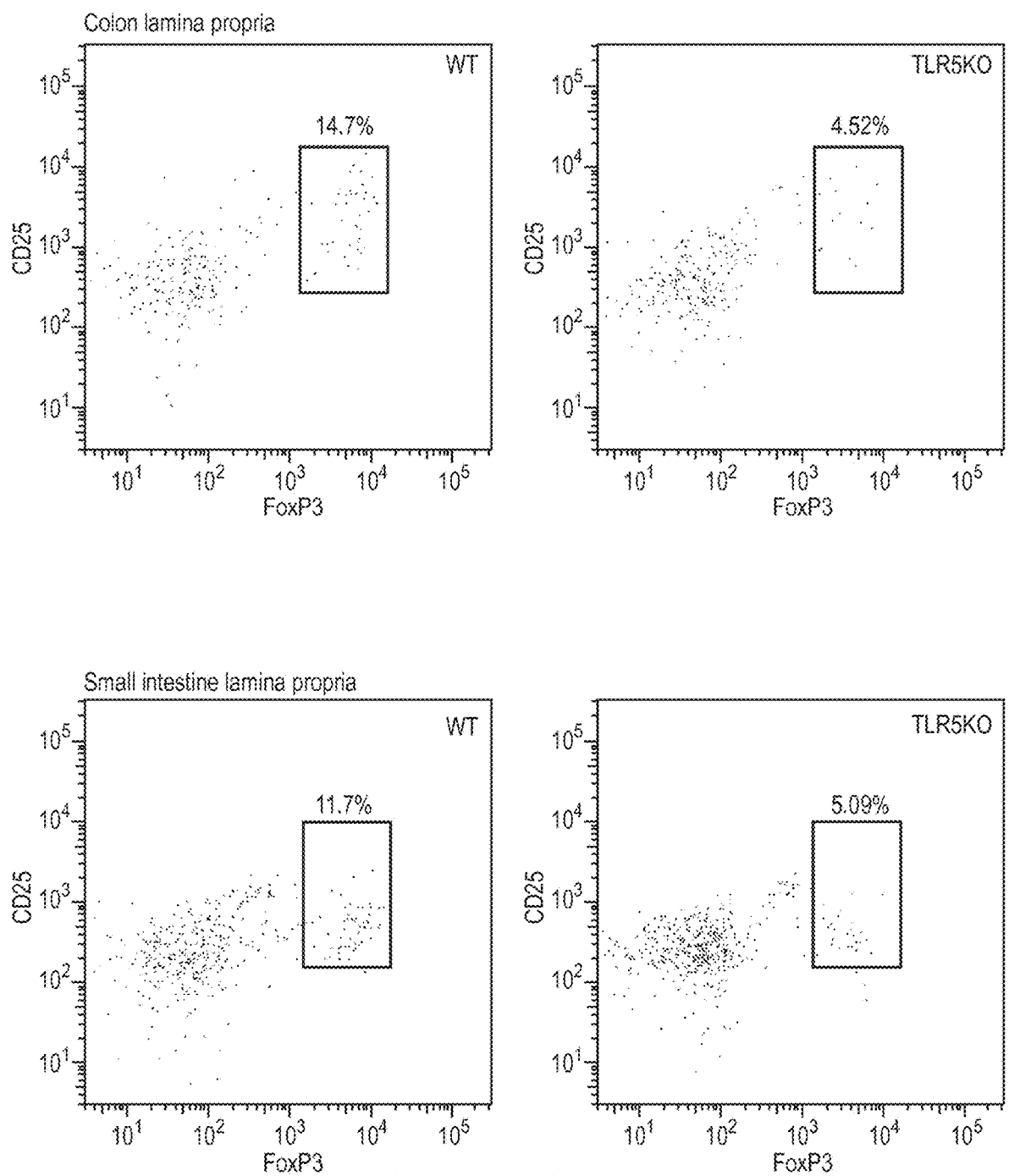

FIGS. 27A and 27B Flow cytometry analysis of FoxP3+ Tregs in lamina propria of BOY/J WT and TLR5KO mice treated with *R. hominis*.

FIG. 28 is a table indicating significant differences between each treatment calculated with paired t test in HT-29 (upper right) and Caco-2 (lower left). T tests used were unilateral to compare treatments to unstimulated cells (unstim) and bilateral to compare one treatment with another. NS (non significant); *(p<0.05); (p<0.01); *(p<0.001).

Figure 29A:
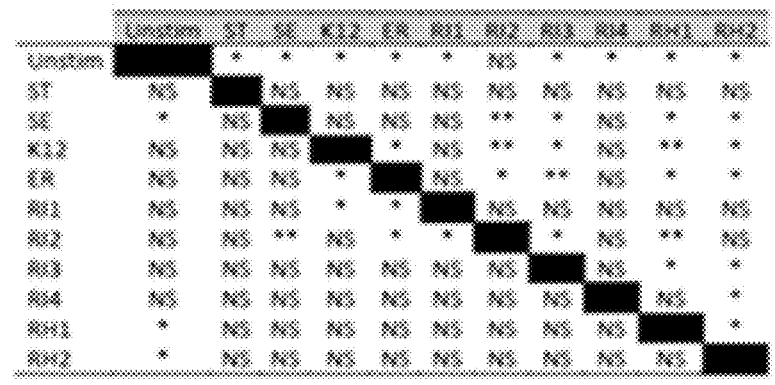
Figure 29B:
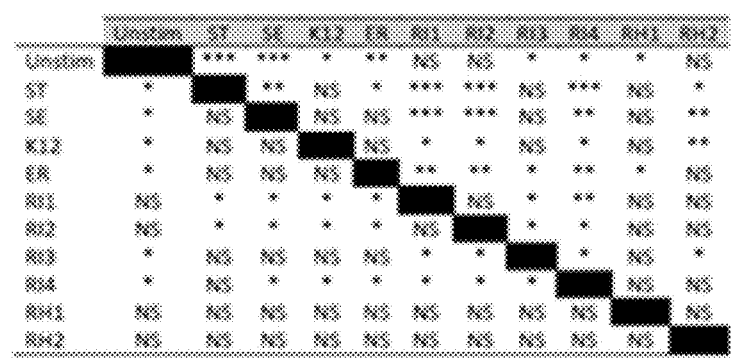
Figure 29C:
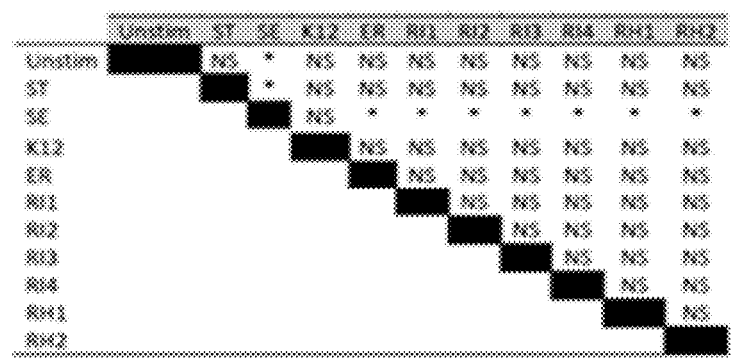
Figure 29D:
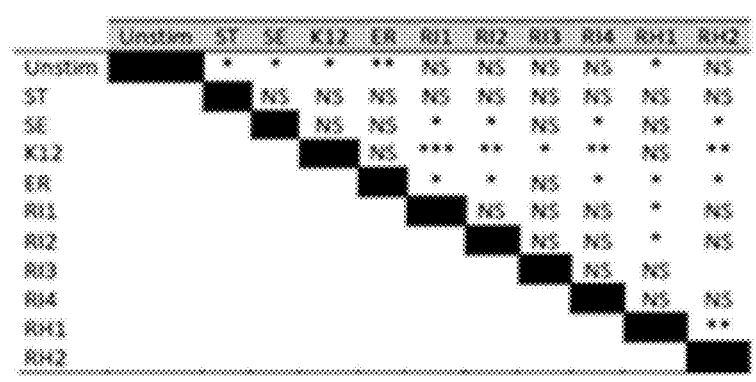

FIGS. 29A-29D are tables indicating significant differences between each treatment calculated with paired t test. The upper right side of FIGS. 29A and 29B give t values for IL-8 and the lower left side for IP-10, and FIGS. 29C and 29D give t values for MCP-1. NS (non significant); *(p<0.05); (p<0.01); *(p<0.001).

DETAILED DESCRIPTION

Flagellin

Flagellin is the principal substituent of bacterial flagellum, and is present in large amounts on nearly all flagellated bacteria. Typically, flagellins are globular proteins which arrange into a hollow cylinder to form the filament in bacterial flagellum.

The diversity of flagellin structural proteins and gene sequences is well recognized and vary according to bacterial species, geographical and clinical and environmental origins. There are thousands of flagellins and related flagellin genes. Some of the important ones in gut bacteria include the flagellins FLA, FliC, FlgC, FLiE, FlaB, MoA and FliG.

There are several types of FLA (Fla) polypeptides. FlaA1, FlaA2, FlaA3, FlaA4 and FlaB are examples of FLA polypeptides.

Polypeptide FlaA1

The term "polypeptide FlaA1" as used herein refers to the flagellin protein FlaA1. Examples of such polypeptides include the FlaA1 polypeptide of *Roseburia hominis, Roseburia cecicola, Roseburia faecis, Roseburia intestinalis,* and *Roseburia inulinivorans*; the polypeptide sequence shown as SEQ ID NO 2 or SEQ ID No 6; and polypeptides having at least 75%, 80%, 85%, 90%, 95%, 97%, 98%, or 99% identity to SEQ ID NO 2 or SEQ ID No 6 or variants, homologues, fragments or derivatives thereof.

SEQ ID NO 2 has the following sequence:

MVVQHNLTAMNANRQLGITTGAQAKSSEKLSSGYKINRAADDAAGLTISE

KMRSQVRGLNKASDNAQDGVSLIQVAEGALSETHSILQRMNELATQAAND

-continued
TNTTSDRTAVQQEINQLASEITRIASTTQFNTMNLIDGNFTSKKLQVGSL

CGQAITIDISDMSATGLGVSGLVVSSFSAAGKAMSAAQDAISYVSSMRSK

LGALQNRLEHTISHLDNISEHTSSAESRIRDTDMAEEMVEYSKNNILAQA

GQSMLAQANQSTQGVLSLLQ

SEQ ID NO 2 is deposited with NCBI under accession number AB148297.1.

The terms "polypeptide FlaA1" and "FlaA1 polypeptide" are used interchangeably herein.

The terms "FlaA1", "Fla1" and "RH1" may be used interchangeably herein.

In one embodiment, the polypeptide FlaA1 has at least 75%, 80%, 85%, 90%, 95%, 97%, 98%, or 99% identity to SEQ ID NO 2 or to variants, homologues, fragments or derivatives thereof. In one aspect, the amino acids at positions 79 to 117 and positions 408 to 439 as well as 411, 412, 420 of SEQ ID NO 2 (or equivalent thereof) are considered important. In one aspect, the amino acids at positions 411, 412, 420 of SEQ ID NO 2 (or equivalent thereof) are alanine (A), glutamine (Q) and serine (S) respectively.

In one embodiment, the polypeptide FlaA1 is the polypeptide shown as SEQ ID NO 2 or SEQ ID No 6.

FlaA1 polypeptides can be derived from certain microorganisms. In one aspect, the FlaA1 polypeptide is derived from a bacterium such as a Firmicute. In a further aspect, the FlaA1 polypeptide is derived from a *Roseburia* spp such as a *Roseburia hominis, Roseburia cecicola, Roseburia faecis, Roseburia intestinalis,* or *Roseburia inulinivorans.*

*Roseburia hominis* and *Roseburia intestinalis* are recently described commensal gut anaerobes of the phylogenetic cluster XIVa within the Firmicutes phylum, belonging to a dominant group of bacteria in the human gut and are also major butyrate producers. An example of *Roseburia hominis* is the strain deposited under the terms of the Budapest Treaty at National Collections of Industrial, Food and Marine Bacteria (NCIMB) at NCIMB Ltd, Ferguson Building, Craibstone Estate, Bucksburn, Aberdeen, UK, AB21 9YA, on 21 Oct. 2004 by the Rowett Research Institute under the accession number NCIMB 14029.sup.T *Roseburia hominis* A2-183.sup.T (DSM=16839.sup.T). Another example is the bacterial species is *Roseburia hominis* as described in Duncan, S. H., Aminov, R. I., Scott, K. P., Louis, P., Stanton, T. B., & Flint, H. J. (2006) Int. J. Syst. Evol. Microbiol. 56: 2437-2441. An example of *Roseburia intestinalis* is the strain deposited under the accession number NCIMB 13810 *Rosburia intestinalis* L1-82.sup.T (DSM=14610.sup.T) Another example is the bacterial species is *Roseburia hominis* as described in Duncan, S. H., Aminov, R. I., Scott, K. P., Louis, P., Stanton, T. B., & Flint, H. J. (2006) Int. J. Syst. Evol. Microbiol. 56: 2437-2441.

The term "polynucleotide sequence encoding the polypeptide FlaA1" as used herein refers a polynucleotide sequence encoding the flagellin protein FlaA1. Examples of such polynucleotide sequences include the gene FlaA1 of *R. hominis, Roseburia cecicola, Roseburia faecis, Roseburia intestinalis,* or *Roseburia inulinivorans*; the polynucleotide sequence shown as SEQ ID NO 1 or SEQ ID No 5; polynucleotide sequences encoding the polypeptide shown as SEQ ID NO 2 or SEQ ID No 6; polynucleotides sequences having at least 75%, 80%, 85%, 90%, 95%, 97%, 98%, or 99% identity to SEQ ID NO 1 or SEQ ID No 5 or variants, homologues, fragments or derivatives thereof; and polynucleotides sequences encoding the polypeptide shown as SEQ ID NO 2 or SEQ ID No 6 or encoding a polypeptide having at least 75%, 80%, 85%, 90%, 95%, 97%, 98%, or 99% identity to the polypeptide shown as SEQ ID NO 2 or SEQ ID No 6 or variants, homologues, fragments or derivatives thereof.

SEQ ID NO 1 has the following sequence:

ATGGTAGTACAGCACAATCTTACAGCAATGAACGCTAACAGACAGTTAGG

TATCACAACAGGCGCACAGGCTAAGTCTTCTGAGAAGTTATCTTCTGGTT

ACAAGATCAACCGCGCAGCAGATGACGCAGCAGGTCTTACGATTTCCGAG

AAGATGAGAAGCCAGGTTAGAGGCTTAAATAAAGCTTCTGACAACGCACA

GGATGGTGTATCCCTTATTCAGGTAGCTGAGGGTGCATTAAGTGAGACAC

ACTCCATCTTACAGCGTATGAATGAGTTAGCAACTCAGGCAGCAAACGAT

ACCAATACAACCTCAGACAGAACTGCAGTTCAGCAGGAGATCAACCAGTT

AGCATCTGAGATCACCAGAATCGCTTCTACAACTCAGTTCAACACAATGA

ACCTGATCGATGGTAACTTCACAAGTAAGAAGCTTCAGGTAGGTTCCCTT

TGCGGACAGGCTATCACAATCGATATCTCTGATATGTCTGCTACAGGTCT

TGGCGTTAGCGGATTAGTAGTATCTTCCTTCTCTGCAGCTGGTAAGGCAA

TGTCTGCAGCTCAGGATGCTATCAGCTACGTATCTTCTATGCGTTCTAAG

CTGGGTGCATTACAGAACAGACTTGAGCACACAATCTCCCACCTGGACAA

CATTTCTGAGCACACATCTTCTGCAGAGTCTCGTATCCGTGATACAGATA

TGGCTGAAGAGATGGTTGAGTACAGCAAGAACAACATCCTTGCTCAGGCA

GGACAGTCTATGCTTGCTCAGGCTAACCAGTCTACTCAGGGTGTATTATC

CTTATTACAGTAA

SEQ ID NO 1 is deposited with NCBI under accession number DQ789140.1.

In one embodiment, the polynucleotide sequence encoding the polypeptide FlaA1 has at least 75%, 80%, 85%, 90%, 95%, 97%, 98%, or 99% identity to the polynucleotide sequence shown as SEQ ID NO 1 or SEQ ID No 5 or to variants, homologues, fragments or derivatives thereof.

In one embodiment, the polynucleotide sequence encoding the polypeptide FlaA1 encodes a polypeptide shown as SEQ ID NO 2 or SEQ ID No 6 or a polypeptide having at least 75%, 80%, 85%, 90%, 95%, 97%, 98%, or 99% identity to the polypeptide shown as SEQ ID NO 2 or SEQ ID No 6 or to variants, homologues, fragments or derivatives thereof.

In one embodiment, the polypeptide FlaA1 is a truncated FlaA1 polypeptide. For example, the truncated polypeptide comprises at least 20, 30, 40, 50, 75, 100, 125, 150, 175 or 200 amino acids of polypeptide shown as SEQ ID NO 2 or SEQ ID No 6.

Without wishing to be bound by theory, two essential regions of flagellin protein involved in the recognition and activation of TLR5 are amino acids 79-117 of SEQ ID NO 2 (N-D1 domain) and amino acids 408-439 of SEQ ID NO 2 (C—D1 domain). Without wishing to be bound by theory, amino acid: A411, Q412, S420 are important amino acids.

Examples of truncated FlaA1 polypeptides include: polypeptides which comprise amino acids 79-117 and amino acids 408-439 of SEQ ID NO 2; polypeptides having at least 75%, 80%, 85%, 90%, 95%, 97%, 98%, or 99% identity to amino acids 79-117 and amino acids 408-439 of SEQ ID NO 2; polypeptides having at least 75%, 80%, 85%, 90%, 95%, 97%, 98%, or 99% identity to amino acids 79-117 and amino acids 408-439 of SEQ ID NO 2 wherein the amino acid at position 411 (or equivalent thereto) is alanine (A) and/or the amino acid at position 214 is glutamine (Q) and/or the amino acid at position 420 is serine (S); polypeptides comprising amino acids 79-439 of SEQ ID NO 2; polypeptides comprising amino acids 79-439 of SEQ ID NO 2 wherein the amino acid at position 411 (or equivalent thereto) is alanine (A); polypeptides having at least 75%, 80%, 85%, 90%, 95%, 97%, 98%, or 99% identity to amino acids 79-439 of SEQ ID NO 2; and polypeptides having at least 75%, 80%, 85%, 90%, 95%, 97%, 98%, or 99% identity to amino acids 79-439 of SEQ ID NO 2 wherein the amino acid at position 411 (or equivalent thereto) is alanine (A) and/or the amino acid at position 214 is glutamine (Q) and/or the amino acid at position 420 is serine (S).

In one aspect, the amino acids at positions 411, 412, 420 of SEQ ID NO 2 (or equivalent thereof) in a truncated FlaA1 polypeptide are alanine (A), glutamine (Q) and serine (S) respectively.

In one embodiment, the polynucleotide sequence encoding the polypeptide FlaA1 encodes a truncated FlaA1 polypeptide.

In one embodiment, the polypeptide FlaA1 is a fusion polypeptide. For example, the polypeptide is fused to glutathione S-transferase (GST).

*Roseburia* Genus

*Roseburia* bacteria are slightly curved rod-shaped cells that are strictly anaerobic and indigenous to the mammalian intestine. The bacteria are butyrate-producing and are actively motile through multiple flagella present along the concave side and in a cluster at one end (Stanton and Savage 1983). Currently, within the *Roseburia* genus, five species have been identified and characterised: *Roseburia* cecicola, *Roseburia* faecis, *Roseburia* hominis, *Roseburia* intestinalis, and *Roseburia* inulinivorans (Stanton and Savage 1983, Duncan et al 2006).

Stanton and Savage (1983—*Roseburia* cecicola gen. nov., sp. nov., a motile, obligately anaerobic bacterium from a mouse cecum. Int J. Syst. Bacteriol., 1983, 33, 618-627.) describe *Roseburia* cecicola.

Duncan et al. (2006—Proposal of *Roseburia* faecis sp. nov., *Roseburia* hominis sp. nov. and *Roseburia* inulinivorans sp. nov., based on isolates from human faeces. Int. J. Syst. Evol. Microbiol., 2006, 56, 2437-2441) describe *Roseburia faecis*.

Duncan et al. (2006—Proposal of *Roseburia* faecis sp. nov., *Roseburia* hominis sp. nov. and *Roseburia* inulinivorans sp. nov., based on isolates from human faeces. Int. J. Syst. Evol. Microbiol., 2006, 56, 2437-2441) describe *Roseburia hominis*.

Duncan et al. (2002—*Roseburia* intestinalis sp. nov., a novel saccharolytic, butyrate-producing bacterium from human faeces. Int. J. Syst. Evol. Microbiol., 2002, 52, 1615-1620) describe *Roseburia intestinalis*.

Duncan et al. (2006—Proposal of *Roseburia* faecis sp. nov., *Roseburia* hominis sp. nov. and *Roseburia* inulinivorans sp. nov., based on isolates from human faeces. Int. J. Syst. Evol. Microbiol., 2006, 56, 2437-2441) describe *Roseburia inulinivorans*.

*Roseburia* Flagellin

The term "*Roseburia* flagellin" as used herein refers to a flagellin protein derived or derivable from a *Roseburia* bacterium such as *Roseburia. hominis, Roseburia cecicola, Roseburia faecis, Roseburia intestinalis*, and *Roseburia inulinivorans*.

The *Roseburia* flagellin may be flaA1, flaA2, flaA3, flaA4 or combinations thereof.

The terms "FlaA1", "Fla1", "flaA1" and "fla1" are used interchangeably herein.

The terms "FlaA2", "Fla2", "flaA2" and "fla2" are used interchangeably herein.

The term Fla is used herein to encompass the polypeptides that may be flaA1, flaA2, flaA3 flaA4 or fliC.

In one embodiment, the present invention encompasses the use of at least one *Roseburia* flagellin. For example, the present invention encompasses the use of a combination of at least two, at least three, at least four, or at least five *Roseburia* flagellins.

In some embodiments, the combination of *Roseburia* flagellins comprises flagellins which are derived or derivable from at least two, three, four or five different *Roseburia* species.

Examples of *Roseburia* flagellins include flagellins derived or derivable from *Roseburia* bacterium such as *Roseburia hominis, Roseburia cecicola, Roseburia faecis, Roseburia intestinalis*, and *Roseburia inulinivorans*. In one embodiment, the flagellin is derived or derivable from *Roseburia hominis*. In another embodiment, the flagellin is derived or derivable from *Roseburia intestinalis*.

Examples of *Roseburia* flagellins include polypeptide sequences having at least 75%, 80%, 85%,90%, 95%,97%, 98%, or 99% identity to SEQ ID NO 2, SEQ ID NO 4, SEQ ID NO 6, SEQ ID NO 8, SEQ ID NO 10 or SEQ ID NO 12 or variants, homologues, fragments or derivatives thereof.

In one embodiment, the *Roseburia* flagellin has the polypeptide sequence shown as SEQ ID NO 2, SEQ ID NO 4, SEQ ID NO 6, SEQ ID NO 8, SEQ ID NO 10 or SEQ ID NO 12.

Examples of *Roseburia hominis* flagellins are *Roseburia hominis* Fla1 and Fla2.

An example of *Roseburia hominis* Fla1 is shown as SEQ ID NO 2. *Roseburia hominis* Fla1 is also referred herein as RhFlaA1, RHFlaA1, RhFla1, RHFla1, RH1 or Rh1.

SEQ ID NO 2 has the following sequence:

MVVQHNLTAMNANRQLGITTGAQAKSSEKLSSGYKINRAADDAAGLT

ISEKMRSQVRGLNKASDNAQDGVSLIQVAEGALSETHSILQRMNELA

TQAANDTNTTSDRTAVQQEINQLASEITRIASTTQFNTMNLIDGNFT

SKKLQVGSLCGQAITIDISDMSATGLGVSGLVVSSFSAAGKAMSAAQ

DAISYVSSMRSKLGALQNRLEHTISHLDNISEHTSSAESRIRDTDMA

EEMVEYSKNNILAQA GQSMLAQANQSTQGVLSLLQ

SEQ ID NO 2 is deposited with NCBI under accession number AB148297.1.

An example of *Roseburia hominis* Fla2 is shown as SEQ ID NO 4. *Roseburia hominis* Fla2 is also referred herein as RhFlaA2, RHFlaA2, RhFla2, RHFla2, Rh2 or RH2.

SEQ ID NO 4 has the following sequence:

MVVNHNMAAICESRQLRYNVKKMEKSSKKLATGYKLNTANDDAAGL

QISETMRHHVKGLNKASRNSQDGISMLQTADAALQETQDVLDRMVE

LTTQAANDINTDSDRRAIQDELDQLNKEVDRIAYTTHFNQQYMLAE

GTPQAAPGYYRIQSGALNGQAIDIHFVNASKESLGTDKVNVSSHAK

ASESITMVQDAIEQAALWRDEFGSQQERLEHAVRNTDNTSQNTQSA

ESGIRDTNMNMEMVLYSTNRILVHASQSILAQYNDDAKSVLEILK

Examples of *Roseburia intestinalis* flagellins include *Roseburia intestinalis* Fla1, Fla2, Fla3 and Fla4.

An example of *Roseburia intestinalis* Fla1 is shown as SEQ ID No 6. *Roseburia intestinalis* is also referred herein as RiFlaA1, RiFlaA1, RiFla1, RIFla1, Ri1 or RI1.

SEQ ID NO 6 has the following sequence:

MRINYNVSAAIANKHLLGIEDNLSASMERLSSGLKINHSKDNPAGM

AISNKMKAQIDGLNRASQNASDGISVIQIADGALSETTSILQRMRE

LSVQAASDATMTPADKEAIQKEITSLKDEVDRISTDTEYNSKTLLD

GSLDTRVYTKNATRVDISDHVKAGQYQLSIDTAATQAGPVTANQNY

NSTAPVGASGTMSINGSKVEIEAADTYAEAFEKIRNAAETGETTVK

IEKNGALSFTAEQYGMSSILEIAFDDKQLANALGFTADGGNSVVED

PENKGSYVYGQIQNGKVIVPSGTDAEVTLTKPSDGTGFGDTATVKT

DGNKITVTDRAGFEMSFLADAGYTGKLDFDVTDIGTMALHIGANED

QETRVRIPEVSCKSLYIDDADVTTVNGAGRGITQFDDAISKVSEVR

SRLGAYQNRLESTVSSLDTFEENMTGAQSRLTDADMASEMTDYTHQ

NVLNQAAISVLTQANDLPQ

An example of *Roseburia intestinalis* Fla2 is shown as SEQ ID No 8. *Roseburia intestinalis* Fla2 is also referred herein as RiFlaA2 or RIFlaA2 or Ri2 or RI2.

SEQ ID NO 8 has the following sequence:

MVVNHNMALICESRQLRCNVKNMEKSSKKLATGYKLLGANDDAAGL

QISETMRHQTRGLNKASRNSQDGISMLQTADAALQETQEVLDRMTD

LTTQAANDINTDADRRAIQDEIDQLNQEVDRIAYTTNFNQQYILAD

GTPQARPGYYMIQTGSLAGQGIEIKFVNASKESLGVDKVDVSSHAK

ATESIAVVQNAIEKAASFRDTFGAQQERLEHALRGTDNTSESTQRA

ESSRRDTNMNMEMVQYSTNRILVQASQSILAQYNDDAKYVLEMLKQ

VLQILQ

An example of *Roseburia intestinalis* Fla3 is shown as SEQ ID No 10. *Roseburia intestinalis* Fla3 is also referred herein as RiFla3 or RIFla3 or Ri3 or RI3.

SEQ ID NO 10 has the following sequence:

MVVQHNMTAMNANRMLGVTTSAQAKSSEKLSSGYRINRAGDDAAGL

TISEKMRSQIRGLNKASDNAQDGISLIQVAEGALSETHSILQRMNE

LATQAANDTNTTADRGAIQDEINQLTSEINRISSTTQFNTQNLIDG

TFANKNLQVGSICGQRITVSIDSMSAGSLNVSANLVKVNTFSAAGE

AMSNIQGAISAISTQRSYLGALQNRLEHTISNLDNISENTQSAESR

IRDTDMAEEMVTYSKNNILAQAGQSMLAQANQSTQGVLSLLQ

An example of *Roseburia intestinalis* Fla4 is shown as SEQ ID No 12. *Roseburia intestinalis* Fla4 is also referred herein as RiFla4 or RIFla4 or Ri4 or RI4.

SEQ ID NO 12 has the following sequence:

MAMVVQHNMSAMNANRNLGVTTGMQAKSSEKLSSGYKINRAADDAA

GLSISEKMRSQIRGLNKASDNAQDGISLIQTAEGALNESHSILQRM

```
RELSVQAANGTETDDDREAVQNEVSQLQEELTRISETTEFNTMKLL

DGSQSGSTSSTGSGPKFGVVDATLDGALVTSNVKGIKVATAAATTT

KAGQETAIWAADGKTLTLNLSKNKVYTQDEIDDLIANAKQEDSSAT

GAPAEVKVSLKNGIFNADADTTAGTVTAGGVKAVSDEGTVTGFVGA

DTISFTANKYGAEFNDTVFKFKFDKAAGKEEVETNTAIEIDGANAV

TAGEYTIHLAAGKEYTAEDLEDVLKTAGFDFDVKLSGNTPDEPNTL

FATSGASTVTDITMGAGTAGAGLGSTDAMWGQAGYDSVSSGAGITL

QIGANEGQTMSFSIDDMSARALGVDGNKVDLSTQAGNAQKATDTID

AAIKKVSAQRGRMGAIQNRLEHTISLDTAAENTQTAESRIRDTDMA

EEMVEYSKNNILAQAGQSMLAQANQSTQGVLSLLQ
```

The terms "polypeptide FlaA1", "FlaA1 polypeptide", "polypeptide Fla1" and "Fla1 polypeptide" are used interchangeably herein. The terms "polypeptide Fla2" and "Fla2 polypeptide" are used interchangeably herein. The terms "polypeptide Fla3" and "Fla3 polypeptide" are used interchangeably herein. The terms "polypeptide Fla4" and "Fla4 polypeptide" are used interchangeably herein.

In one aspect, the *Roseburia* flagellin is selected from the group consisting of Fla1, Fla2, Fla3 and Fla4. In one embodiment, the *Roseburia* flagellin is selected from the group consisting of Fla2, Fla1, Fla4 and combinations thereof. In a further embodiment, the *Roseburia* flagellin is Fla2.

In one aspect, the *Roseburia* flagellin is selected from the group consisting of *Roseburia hominis* Fla1, *Roseburia hominis* Fla2, *Roseburia intestinalis* Fla1, *Roseburia intestinalis* Fla2, *Roseburia intestinalis* Fla3 and *Roseburia intestinalis* Fla4. In one embodiment, the *Roseburia* flagellin is selected from the group consisting of *Roseburia hominis* Fla2, *Roseburia intestinalis* Fla2, *Roseburia intestinalis* Fla1, *Roseburia intestinalis* Fla4 and combinations thereof. In a further embodiment, the *Roseburia* flagellin is selected from the group consisting of *Roseburia hominis* Fla2, *Roseburia intestinalis* Fla2 and combinations thereof. In another embodiment, the *Roseburia* flagellin is *Roseburia intestinalis* Fla2.

In one embodiment, the present invention encompasses the use of at least one polynucleotide sequence encoding a *Roseburia* flagellin. For example, the present invention encompasses the use of a combination of at least two, at least three, at least four, or at least five polynucleotide sequences encoding *Roseburia* flagellins.

In one embodiment, the present invention encompasses the use of a polynucleotide sequence encoding at least one *Roseburia* flagellin. For example, the present invention encompasses the use of a polynucleotide sequence encoding a combination of at least two, at least three, at least four, or at least five polypeptide sequences encoding *Roseburia* flagellins.

The polynucleotide sequence encoding a *Roseburia* flagellin may encode flaA1, flaA2, fla3, fla4 or combinations thereof.

In some embodiments, the combination of polynucleotide sequences encoding *Roseburia* flagellins comprises polynucleotide sequences encoding flagellins which are derived or derivable from at least two, three, four or five different *Roseburia* species.

In some embodiments, the polynucleotide sequence encodes a combination of *Roseburia* flagellins which are derived or derivable from at least two, three, four or five different *Roseburia* species.

In another embodiment, the present invention encompasses the use of a combination of at least one *Roseburia* flagellin and at least one polynucleotide sequence encoding a *Roseburia* flagellin.

Examples of polynucleotide sequence encoding *Roseburia* flagellins include flagellins derived or derivable from *Roseburia* bacterium such as *Roseburia hominis*, *Roseburia cecicola*, *Roseburia faecis*, *Roseburia intestinalis*, and *Roseburia inulinivorans*. In one embodiment, the polynucleotide sequence encodes a *Roseburia* flagellin derived or derivable from *Roseburia hominis*. In another embodiment, the polynucleotide sequence encodes a *Roseburia* flagellin derived or derivable from *Roseburia intestinalis*.

Examples of polynucleotide sequences encoding *Roseburia* flagellin include the polynucleotide sequences encoding a polypeptide which has at least 75% identity to SEQ ID NO 2, SEQ ID NO 4, SEQ ID NO 6, SEQ ID NO 8, SEQ ID NO 10 or SEQ ID NO 12 or variants, homologues, fragments or derivatives thereof and polynucleotide sequences having at least 75% identity to SEQ ID NO 1, SEQ ID NO 3, SEQ ID NO 5, SEQ ID NO 7, SEQ ID NO 9 or SEQ ID NO 11 or variants, homologues, fragments or derivatives thereof.

In one embodiment, the polynucleotide sequence encoding *Roseburia* flagellin has the polynucleotide sequence encoding a polypeptide which has the sequence shown as SEQ ID NO 2, SEQ ID NO 4, SEQ ID NO 6, SEQ ID NO 8, SEQ ID NO 10 or SEQ ID NO 12.

In one embodiment, the polynucleotide sequence encoding the *Roseburia* flagellin has the polynucleotide sequence shown as SEQ ID NO 1, SEQ ID NO 3, SEQ ID NO 5, SEQ ID NO 7, SEQ ID NO 9 or SEQ ID NO 11.

Examples of polynucleotide sequences encoding *Roseburia hominis* flagellins are polynucleotide sequences encoding *Roseburia hominis* Fla1 and Fla2.

An example of a polynucleotide sequence encoding *Roseburia hominis* Fla1 is shown as SEQ ID NO 1.

SEQ ID No 1 has the following sequence:

```
ATGGTAGTACAGCACAATCTTACAGCAATGAACGCTAACAGACAGT

TAGGTATCACAACAGGCGCACAGGCTAAGTCTTCTGAGAAGTTATC

TTCTGGTTACAAGATCAACCGCGCAGCAGATGACGCAGCAGGTCTT

ACGATTTCCGAGAAGATGAGAAGCCAGGTTAGAGGCTTAAATAAAG

CTTCTGACAACGCACAGGATGGTGTATCCCTTATTCAGGTAGCTGA

GGGTGCATTAAGTGAGACACACTCCATCTTACAGCGTATGAATGAG

TTAGCAACTCAGGCAGCAAACGATACCAATACAACCTCAGACAGAA

CTGCAGTTCAGCAGGAGATCAACCAGTTAGCATCTGAGATCACCAG

AATCGCTTCTACAACTCAGTTCAACACAATGATACCTGATCGATGG

AACTTCACAAGTAAGAAGCTTCAGGTAGGTTCCCTTTGCGGACAGG

CTATCACAATCGATATCTCTGATATGTCTGCTACAGGTCTTGGCGT

TAGCGGATTAGTAGTATCTTCCTTCTCTGCAGCTGGTAAGGCAATG

TCTGCAGCTCAGGATGCTATCAGCTACGTATCTTCTATGCGTTCTA

AGCTGGGTGCATTACAGAACAGACTTGAGCACACAATCTCCCACCT

GGACAACATTTCTGAGCACACATCTTCTGCAGAGTCTCGTATCCGT

GATACAGATATGGCTGAAGAGATGGTTGAGTACAGCAAGAACAACA

TCCTTGCTCAGGCAGGACAGTCTATGCTTGCTCAGGCTAACCAGTC

TACTCAGGGTGTATTATCCTTATTACAGTAA
```

An example of a polynucleotide sequence encoding *Roseburia hominis* Fla2 is shown as SEQ ID NO 3.

SEQ ID No 3 has the following sequence:

ATGGTGGTTAATCATAATATGGCGGCAATCTGTGAGAGCAGGCAGC

TGCGCTATAACGTGAAGAAGATGGAAAAATCTTCCAAAAAGCTTGC

GACAGGGTACAAGCTGAACACAGCAAATGATGATGCGGCAGGCTTG

CAGATATCAGAGACGATGCGGCATCATGTGAAAGGGCTGAACAAAG

CCTCCCGGAATTCACAGGACGGCATCAGTATGCTGCAGACGGCGGA

TGCAGCGCTCCAAGAGACGCAGGATGTTCTCGATCGTATGGTGGAG

CTGACGACGCAGGCAGCCAATGACATCAACACAGACTCGGATCGCA

GGGCTATTCAGGATGAGTTGGATCAGCTGAACAAGGAAGTGGACCG

CATCGCCTATACGACGCACTTCAATCAGCAGTATATGTTGGCGGAG

GGAACGCCGCAGGCGGCACCGGGATATTACCGCATACCAGTCCGGG

GCACTGAAGGACAGGCGATAGATATCCATTTTGTAAATGCGAGCAA

GGAGAGCCTTGGCACAGACAAAGTGAATGTATCTTCGCATGCGAAG

GCGTCGGAATCCATCACGATGGTTCAGGACGCGATTGAACAGGCGG

CGCTCTGGAGAGACGAGTTCGGCAGCCAGCAGGAGCGTCTGGAACA

TGCCGTGCGCAATACGGACAACACATCACAAAATACGCAGAGTGCG

GAGTCAGGGATCAGAGACACCAACATGAATATGGAGATGGTATTAT

ATTCGACCAACCGGATTCTGGTGCATGCATCCCAGAGTATTCTGGC

ACAGTATAATGATGATGCAAAATCAGTGCTTGAGATTTTGAAATAG

Examples of polynucleotide sequences encoding *Roseburia intestinalis* flagellins are polynucleotide sequences encoding *Roseburia intestinalis* Fla1, Fla2, Fla3 and Fla4.

An example of a polynucleotide sequence encoding *Roseburia intestinalis* Fla1 is shown as SEQ ID NO 5.

SEQ ID No 5 has the following sequence:

ATGCGTGGCGGAGACAATAGAAGGAGAAACAGAATGAGAATTAATTA

CAATGTGTCAGCAGCGATTGCGAATAAACATTTACTTGGAATTGAGG

ATAATTTAAGTGCATCGATGGAACGGCTTTCATCGGGACTTAAGATC

AACCATTCCAAGGACAATCCGGCAGGAATGGCTATTTCCAACAAGAT

GAAAGCACAGATGTGATGGTTTAAACCGGGCTTCCCAGAATGCATCG

GATGTATTTCTGTTATTCAGATCGCAGATGGTGCGCTGAGTGAAACGA

CCAGTATTTTACAGCGTATGAGAGAACTTTCCGTGCAGGCAGCGAGTG

ATGCAACAATGACACCGGCAGGATAAGAAGCAATCCAGAAAGAAATCA

CTTCATTAAAAGATGAAGTTGACCGTATTTCTACAGATACAGAGTATA

ACAGCAAACACTTTTAGATGGTTCATTAGATACCAGGGTTTACACCA

AAAATGCAACAAGAGTGGACATTTCTGATCATGTGAAAGCAGGACAGT

ATCAGCTTTCCATTGATACTGCAGCTACACAGGCCGGACCGGTAACAG

CAAATCAGAATTATAATTCCACAGCACCGGTCGGTGCGTCCGGAACAA

TGAGTATTAATGGTTCTAAAGTAGAGATAGAGGCAGCCGACACCTATG

CGGAGGCTTTTGAGAAGATCAGAAATGCAGCAGAGACTGGTGAAACAA

CCGTTAAGATTGAAAAGAATGGAGCACTTTCATTTACCGCAGAACAGT

ACGGAATGTCAAGCATCTTAGAGATCGCATTNNTGATGATAAGCAGCT

TGCTAATGCACTTGGATTTACAGCAGACGGAGGAAACAGTGTTGTAGA

AGATCCAGAGAATAAAGGCAGCTATGTATACGGACAGATTCAGAATGG

CAAAGTGATCGTACCTTCCGGTACAGATGCCGAAGTAACGCTCACAAA

ACCGAGTGATGGAACCGGATTTGGTGATACAGCTACGGTAAAAACAGA

TGGAAATAAGATTACGGTTACAGACAGAGCCGGATTTGAGATGTCATA

TCGTTCTTGCTGATGCAGGTTATACGGGTAAGCTGGATTTTGATGTCA

CGGATGAACGATGGCACTTCATATTGGAGCAAATGAGGATCAGGAAAC

AAGAGTGCGTATTCCGGAGGTTTCCTGCAAGAGCCTTTACATTGATGA

TGCAGACGTGACGACTGTAAATGGAGCAGGCAGAGGTATCACACAGTT

TGACGATGCCATTTCAAAGGTCAGTGAAGTGCGTTCAAGACTTGGTGC

ATACCAGAATCGTCTTGAGAGTACGGTATCAAGCCTGGATACGTTTGA

AGAAAATATGACAGGAGCCCAGTCACGACTGACAGATGCGGATATGGC

ATCGGAAATGACAGATTATACACATCAGAATGTATTAAATCAGGCAGC

AATCTCTGTTTTGACACAGGCAAACGATCTGCCACAGCAGGTATTGCA

GATTCTGCAGTAA

An example of a polynucleotide sequence encoding *Roseburia intestinalis* Fla2 is shown as SEQ ID NO 7.

SEQ ID No 7 has the following sequence:

ATGGTAGTTAATCATAATATGGCATTGATCTGTGAGAGTAGACAGT

TACGATGTAATGTGAAGAACATGGAGAAGTCTTCAAAAAAGCTGGC

AACAGGTTATAAATTGCTTGGAGCAAATGATGATGCAGCAGGATTA

CAGATATCAGAAACCATGCGTCATCAGACCAGAGGTCTTAACAAAG

CATCCAGAAATTCGCAAGATGGAATTAGTATGCTGCAGACAGCAGA

TGCAGCATTACAGGAGACACAGGAAGTGTTGGATCGAATGACGGAT

CTGACAACACAGGCAGCTAATGATATCAATACGGATGCGGATCGTC

GTGCAATTCAGGATGAAATCGATCAGTTAAATCAGGAAGTGGATCG

TATTGCATATACGACGAATTTTAATCAGCAGTATATATTAGCGGAT

GGAACTCCGCAGGCAAGACCAGGATACTATATGATACAGACAGGAA

GTCTTGCGGGACAGGGAATAGAGATTAAGTTTGTTAATGCGAGCAA

AGAGAGCTTGGGTGTGGACAAGGTTGATGTATCATCGCATGCAAAA

GCGACAGAATCTATAGCAGTGGTACAGAATGCAATTGAAAAGGCAG

CTTCGTTTAGAGATACATTTGGGGCACAACAGGAGCGGTTAGAACA

CGCATTGCGTGGAACGGATAATACATCAGAAAGTACACAGAGGGCA

GAATCAAGTAGACGCGATACCAACATGAATATGGAGATGGTACAAT

ATTCTACAAACCGTATTTTAGTACAGGCATCTCAGAGTATTTTAGC

ACAGTACAATGATGATGCAAAATATGTGTTGGAAATGTTAAAATAG

An example of a polynucleotide sequence encoding *Roseburia intestinalis* Fla3 is shown as SEQ ID NO 9.

SEQ ID No 9 has the following sequence:

ATGGTAGTACAGCACAATATGACCGCAATGAATGCGAACAGAATGT

TAGGCGTTACAACAAGCGCACAGGCAAAATCTTCAGAGAAATTATC

TTCTGGTTACAGAATCAACCGTGCAGGTGATGACGCTGCTGGTTTA

ACAATTTCTGAGAAGATGAGAAGCCAGATCCGTGGATTAAACAAAG

CTTCTGACAACGCACAGGATGGTATTTCCTTAATCCAGGTTGCTGA

GGGTGCATTATCTGAGACACATTCTATCTTACAGCGTATGAATGAG

TTAGCTACTCAGGCTGCTAACGATACCAATACAACTGCTGATAGAG

GAGCTATTCAGGATGAGATCAACCAGTTAACATCTGAGATTAACAG

AATCTCTTCTACAACTCAGTTCAATACTCAGAACCTCATCGATGGT

ACATTCGCAAATAAAAACCTTCAGGTTGGTTCTATCTGTGGACAGA

GAATTACTGTTTCTATCGACAGTATGTCTGCTGGTAGCTTAAATGT

ATCTGCTAACTTAGTAAAGGTTAACACTTTCAGTGCAGCAGGTGAA

GCAATGTCCAATATTCAGGGTGCTATTTCTGCAATTTCTACACAGC

GTTCTTACTTAGGAGCTCTTCAGAATCGTCTGGAGCATACAATCTC

CAACTTGGACAACATTTCTGAGAATACTCAGTCTGCTGAATCTCGT

ATCCGTGATACAGATATGGCTGAAGAGATGGTTACTTACAGCAAGA

ACAATATTCTTGCTCAGGCAGGACAGTCTATGCTTGCTCAGGCTAA

CCAGTCTACTCAGGGTGTACTTTCTCTGTTACAGTAA

An example of a polynucleotide sequence encoding *Roseburia intestinalis* Fla4 is shown as SEQ ID NO 11.

SEQ ID No 11 has the following sequence:

ATGGCAATGGTAGTACAGCACAACATGTCCGCAATGAATGCGAACA

GAAATTTAGGTGTTACAACAGGAATGCAGGCAAAATCATCAGAGAA

GTTATCTTCCGGTTACAAGATCAACCGTGCAGCAGATGATGCAGCA

GGACTTTCTATTTCTGAGAAGATGAGAAGCCAGATCCGCGGTTTAA

ATAAAGCATCTGACAATGCACAGGATGGTATCTCTTTAATCCAGAC

CGCTGAGGGAGCATTAAATGAGTCCCACTCTATTTTACAGAGAATG

AGAGAGTTATCCGTACAGGCAGCCAACGGTACAGAGACAGATGACG

ACCGCGAGGCAGTACAGAACGAGGTTTCCCAGTTACAGGAAGAGCT

GACAAGAATTTCTGAGACAACAGAGTTCAACACGATGAAGCTGCTG

GATGGTTCTCAGAGTGGAAGTACATCTTCAACCGGGTCAGGTCCGA

AGTTTGGTGTTGTAGATGCAACATTAGACGGTGCACTTGTAACATC

TAACGTGAAAGGTATTAAAGTAGCAACAGCAGCTGCCACAACAACA

AAGGCAGGTCAGGAGACTGCTATCTGGGCTGCTGATGGAAAGACAT

TAACTTTAAATCTTTCGAAAAATAAGGTATATACACAGGACGAAAT

TGATGACTTGATCGCAAATGCAAAACAGGAAGACAGTTCTGCAACG

GGTGCACCGGCTGAAGTGAAAGTATCTTTAAAGAATGGTATTTTA

ATGCAGATGCAGACACAACTGCCGGAACTGTAACAGCCGGTGGTGT

GAAGGCAGTATCTGATGAAGGAACAGTAACTGGATTTGTTGGTGCA

GATACAATTTCATTTACGGCAAATAAGTATGGAGCAGAGTTCAATG

ATACTGTATTTAAATTCAAATTTGATAAGGCAGCAGGCAAAGAAGA

AGTAGAGACAAATACAGCAATTGAAATTGATGGAGCAAATGCGGTA

ACAGCAGGTGAATATACAATTCATCTTGCAGCAGGCAAAGAATATA

CGGCAGAAGATTTAGAAGATGTTCTTAAAACGGCAGGATTCGACTT

TGATGTTAAATTAAGTGGAAATACACCAGATGAGCCAAATACTTTA

TTTGCAACCAGTGGCGCATCAACTGTGACTGATATTACAATGGGTG

CTGGCACCGCCGGAGCTGGTCTTGGAAGTACAGATGCTATGTGGGG

GCAAGCTGGTTATGACAGTTATCTTCTGGTGCTGGCATTACCTTGC

AGATTGGTGCAAATGAAGGTCAGACCATGAGTTTCTCTATCGATGA

CATGAGTGCAAGAGCACTTGGCGTAGATGGCAACAAAGTTGATTTA

AGCACACAGGCTGGCGCACAGAAAGCAACTGATACCATTGATGCAG

CAATCAAGAAAGTATCTGCACAGCGTGGTAGAATGGGTGCGATCCA

GAACCGTCTGGAGCACACCATCAGCAACCTTGATACAGCAGCAGAG

AATACCCAGACTGCAGAGTCCCGTATCCGTGATACAGATATGGCAG

AAGAGATGGTTGAGTACTCCAAGAACAACATTCTTGCACAGGCAGG

TCAGTCTATGCTTGCACAGGCGAACCAGTCTACACAGGGTGTACTC

TCCTTATTACAGTAA

In one aspect, the polynucleotide sequence encodes a *Roseburia* flagellin selected from the group consisting of Fla1, Fla2, Fla3 and Fla4. In one embodiment, the polynucleotide sequence encodes a *Roseburia* flagellin selected from the group consisting of Fla2, Fla1, Fla4 and combinations thereof. In a further embodiment, the polynucleotide sequence encodes the *Roseburia* flagellin Fla2.

In one aspect, the polynucleotide sequence encoding *Roseburia* flagellin is selected from the group consisting of a polynucleotide sequence encoding *Roseburia hominis* Fla1, a polynucleotide sequence encoding *Roseburia hominis* Fla2, a polynucleotide sequence encoding *Roseburia intestinalis* Fla1, a polynucleotide sequence encoding *Roseburia intestinalis* Fla2, a polynucleotide sequence encoding *Roseburia intestinalis* Fla3 and a polynucleotide sequence encoding *Roseburia intestinalis* Fla4. In one embodiment, the polynucleotide sequence encoding *Roseburia* flagellin is selected from the group consisting of a polynucleotide sequence encoding *Roseburia hominis* Fla2, a polynucleotide sequence encoding *Roseburia intestinalis* Fla2, a polynucleotide sequence encoding *Roseburia intestinalis* Fla1, a polynucleotide sequence encoding *Roseburia intestinalis* Fla4 and combinations thereof. In a further embodiment, the polynucleotide sequence encoding *Roseburia* flagellin is selected from the group consisting of a polynucleotide sequence encoding *Roseburia hominis* Fla2, a polynucleotide sequence encoding *Roseburia intestinalis* Fla2 and combinations thereof. In another embodiment, the polynucleotide sequence encoding *Roseburia* flagellin is a polynucleotide sequence encoding *Roseburia intestinalis* Fla2.

The therapeutic effect of flagellins were evaluated by the inventors by functional assays.

In one embodiment, the *Roseburia* flagellin is a truncated *Roseburia* flagellin. For example, the truncated *Roseburia* flagellin comprises at least 20, 30, 40, 50, 75, 100, 125, 150, 175 or 200 amino acids of polypeptide shown as SEQ ID NO 2, SEQ ID NO 4, SEQ ID NO 6, SEQ ID NO 8, SEQ ID NO 10 or SEQ ID NO 12.

In one embodiment, the truncated *Roseburia* flagellin is a truncated *Roseburia hominis* flagellin or a truncated *Roseburia intestinalis* flagellin.

In one embodiment, the polynucleotide sequence encoding the *Roseburia* flagellin encodes a truncated FlaA1, Fla2, Fla3 or Fla4. For example, the polynucleotide sequence encodes a truncated *Roseburia* flagellin comprising at least 20, 30, 40, 50, 75, 100, 125, 150, 175 or 200 amino acids of polypeptide shown as SEQ ID NO 2, SEQ ID NO 4, SEQ ID NO 6, SEQ ID NO 8, SEQ ID NO 10 or SEQ ID NO 12.

In one embodiment, the polynucleotide sequence encoding the *Roseburia* flagellin encodes a truncated FlaA1 or Fla3.

In one embodiment, the *Roseburia* flagellin is a fusion polypeptide. For example, the polypeptide is fused to glutathione S-transferase (GST).

TABLE A

Summary of the Roseburia sequences described herein and the bacterial strain from which they may be derived.

| Bacteria and strain | Abbreviation | Nucleotide Sequence ID | Nucleotide Sequence | Amino Acid Sequence ID | Amino Acid Sequence |
|---|---|---|---|---|---|
| Roseburia hominis A2-183 (fla 1) | RhFlaA1 or RHFlaA1 or RhFla1 or Rh1 or RH1 | SEQ ID 1 | ATGGTAGTACAGCACAATCTTACAGCAATGAACG CTAACAGACAGTTAGGTATCACACAGGCGCACA GGCTAAGTCTTCTGAGAAGTTATCTTCTGGTTACA AGATCAACCGCGCAGCAGATGACGCAGAGTCT TACGCATTCCGAGAAGATGAGAAGCCAGGTTAGA GGCTTAAATAAAGCTTCTGACAACGCACAGGATG GTGTATCCCTTATTCAGTGAGTGAGGGTGCATTA AGTGAGACACACTCCATCTTACAGCGTATGAATG AGTTAGCACTCAGGCAGCAAACGATACCAATAC AACCTCAGACAGAACTGCAGTTCAGCAGGAGATC AACCAGTTAGCATCTGAGATCACCAGAATCGCTTC TACAACTTCAGTTCAACACAATGAACCTGATCGATG GTAACTTCACAAGTAAGAAGCTTCAGGTAGGTTC CCTTTGCGACAGGCTATCACAATCGATAATCTCTG ATATGTCTGCTACAGGTCTTGCGTTAGCGGATTA GTAGTATCTTCCTTCTTCTGCAGTTGGTAAGGCAAT GTCTGCAGCTCAGGATGCTATCAGCTACGTATCTT CTATGCGTTCTAAGCTGGGTGCATTACAGAACAG ACTTGAGGCACACAATCTTCTGCAGAGCTCGTATCCGT CTGAGCACACATCTTCTGCAGAGTCTCGTATCCGT GATACAGATATGGCTGAAGAGATGGTTGAGTACA GCAAGAACACATCCCTTGCTCAGGCAGGACAGTC TATGCTTGCTCAGGCTAACCAGTCTACTCAGGGTG TATTATCCTTATTACAGTAA | SEQ ID 2 | MVVQHNLTAMNANRQLGITTGAQAKS SEKLSSGYKINRAADDAAGLTISEKMRSQ VRGLNKASDNAQDGVSLIQVAEGALSET HSIIQRMNELATQAANDTNTTSDRTAV QQEINQLASEITRAISTTQPFNTMNLIDGN FTSKKLQVGSLCGQAITIDSDMSATGLG VSGLVVSFPSAAGKAMSAAQDAISYVSS ESRIRDTDMAEEMVEYSKNNILAQAGQS MLAQANQSTQQGVLSLLQ |
| Roseburia hominis As-183 (fla 2) | RhFlaA2 or RHFlaA2 or RhFla2 or RhFla2 or Rh2 or RH2 | SEQ ID 3 | ATGGTGGTTAATCATAATATGGCGCAATCTGT AGAGCAGGCAGCTGCCTATAACGTGAAGAAGA TGGAAAAATCTTCCAAAAAGCTTGCGACAGGGTA CAAGCTGAACACAGCAAATGATGATGCGGCAGGC TTGCAGATATCGAGAGACGATGCGGCATCATGTGA AAGGGCTGAACAAAGCCTCCCGGAATTCACAGGA CGGCATCAGTATGCTGCAGACGGCGATGCAGC GCTCCAAGAGACCGGAGGATGTTCTGATCGTATG GTGGAGCTGACGACCGGAGGCAGCCAATGACATCA ACACAGACTCGGATCGCAGGGCTATTCAGGATGA GTTGGATCAGCTGAACAAGGAAGTTGGACCGCATC GCCTATACGACGCACTTCAATCAGCAGTATATGTT GGCGCAGGGAACCGCCGGCGGCACCCGGATA TTACCGCATACAGTCCGGGGCACTGAACGACAG GCGATAGATATCCATTTTGTAAATGCGAGCAAGG AGAGCCTTGGCACAGACAAAGTGAATGTATCTTC GCATGCCGAAGGCGTCGGAATCCATCACCATGGTT | SEQ ID 4 | MVVNHNMAAICESRQLRYNVKKMEKSS KKLATGYKLNTANDDAAGLQISETMRHH VKGLNKASRNSQDGISMLQTADAALQE TQDVLDRMVELTTQAANDINTDSDRRAI QDELDQLNKEVDRIAYTTHFNQQYMLA EGTPQAAPGYRIQSGALNGQAIDIHFV NASKESLGTDKVNVSSHAKASESITMVQ DAIEQAALWRDEFGSQQERLEHAVRNT DNTSQNTQSAESGIRDTNMNMEMVLY STNRILVHASQSILAQYNDDAKSVLEILK |

TABLE A-continued summary of the Roseburia sequences described herein and the bacterial strain from which they may be derived.

| Bacteria and strain | Abbreviation | Nucleotide Sequence ID Nucleotide Sequence | Amino Acid Sequence ID Amino Acid Sequence |
|---|---|---|---|
| | | CAGGACGCGATTGAACAGGCGCGCTCTGGAGA GACGAGTTCGGCAGCCAGGAGCGTCTGAAA CATGCCGTGCGCAATACCGACAACACATCACAAA ATACGCAGAGTGCGGAGTCAGGATCAGAGACA CCAACATGAATATGGAGATGGTATTATATTCGACC AACCGGATTCTGTGCATGCATCCCAGAGTATTCT GGCACAGTATAATGATGATGCAAAATCAGTGCTT GAGTTTTGAAATAG | |
| Roseburia intestinalis L1-82 (fla1) | RiFlaA1 or RiFlaA1 RiFla1 or RiFla1 or Ri1 or Ri1 | SEQ ID 5 ATGCGTGCGGAGCAATAGAGAGGAGAAACAGA ATGAGAATTAATTACATGTCAGCAGCGATTG CGAATAAACATTTACTTGGAATTGAGGATAATTTA AGTGCATCGATGGAACGGCTTTCATCGGACTTA AGATCAACCATTCCAAGGACAATCCGGCAGGAAT GGCTATTTCCAACAAGATGAAAGCACAGATTGAT GGTTTAAACCGGGCTTCCAGAATGCATCGATG GTATTTCTGTTATTCAGATCGCAGATGGTGCGCTG AGTGAAACGACCAGTATTTTACAGCGTATGAGAG AACTTTCCGTGCAGGCAGCGAGTGATGCAACAAT GACACCGGCGGATAAAGAAGCAATCCAGAAAGA AATCACTTCATTAAAAGATGAAGTTGACCGTATTT CTACAGATACAGAGTATATACAGCAAAACACTTTA GATGGTTCATTAGATACATCCAGGGTTTACACCAAA ATGCAACAAGAGTGGACATTTCTGATCATGTCAA AGCAGGACAGTATCAGCTTTCCATTGATACTGCA GCTACACAGGCCGGACCCGGTAACGCAAATCAGA ATTATAATTCCAAGCACCGGTCGTGCTCCGG AACAATGAGTATTAATGGTTCTAAAGTAGAGAT GAGGCAGCCGACACCTATGCGGAGGCTTTTGAGA AGATCAGAATGCAGCAGAGACTGGTGAAACAA CCGTTAAGATTGAAAAGAATGGAGCACTTTCATTT ACCGCAGAACGATACGGAATGTCAAGCATCTTAG AGATCGCATTNNTGATGATAAGCAGTTCGCTAAT GCACTTGGATTTACAGCAGACGGAGGAAACAGTG TTGTAGAAGATCCAGAGATAAAGGCAGCTATGT ATACGGACAGATTCAGAATGGCAAAGTGATCGTA CCTTCCGGTACAGATGCCGAAGTAACGCTCACAA AACCGAGTGATGGAACCGGATTTGGTGATACAGC TACGGTAAAAACAGATGAAATAAGATTACGGTT ACAGACAGAGCCGATTTGAGATGTCATTTCTTG CTGATGCAGGTTATACGGGTAAGCTGGATTTTGA TGTCACGGATATCGGAACGATGGCACTTCATATT GGAGCAAATGAGGATCAGGAAACAAGAGTGCGT ATTCCGGAGGTTTCCTGCAAGAGCCTTTACATTGA | SEQ ID 6 MRINYNVSAAIANKHLLGIEDNLSASME RLSSGLKINHSKDNPAGMAISNKMKAQI DGLNRASQNASDGISVIQIADGALSETTS ILQRMRELSVQAASDATMTPADKEAIQK EITLSKDEVDRISTDTEYNSKTLLDGSLDT RVYTKNATRVDISDHVKAGQYQLSIDTA ATQAGPVTANQNYNSTAPVGASGTMSI NGSKVEIEAADTYAEAFEKIRNAAETGET TVKIEKNGALSFTAEQYGMSSILEIAFDDK QLANALGFTADGGNSVVEDPENKGSYV YGQIGNGKVIVPSGTDAEVTLTKPSDGT GFGDTATVKTDGNKITVDRAAGFEMSFL ADAGYGKLDFDVTDIGTMALHIGANED QETRVRIPEVSCKSLYIDDADVTVNGAG RGITQPFDDAISKVSEVRSRLGAYQNRLES TVSSLDTFENMTGAQSRLTDADMASE MTDYTHQNVLNQAAISVLTQANDLPQ |

TABLE A-continued summary of the Roseburia sequences described herein and the bacterial strain from which they may be derived.

| Bacteria and strain | Abbreviation | Nucleotide Sequence ID | Nucleotide Sequence | Amino Acid Sequence ID | Amino Acid Sequence |
|---|---|---|---|---|---|
| | | | TGATGCAGACGTGACGACTGTAAATGGAGCAGG CAGAGGTATCACACAGTTTGACGATGCCATTTCAA AGTTCAGTGAAGTGCGTTCAAGACTTGGTGCATA CCAGAATCGTCTTGAGAGTACGGTATCCAAGCCTG GATACGTTTGAAGAAAATATGACAGGAGCCCAGT CACGACTGACAGATGCGGATATGATGGCATCGGAAAT GACAGATTATACACATCAGAATGTATTAAATCAG GCAGCAATCTCTGTTTTGACACAGGCAAACGATCT GCCCACAGGTATTGCAGATTCTGCAGTAA | | |
| Roseburia intestinalis L1-82 (fla2) | RiFla1 or RiFla2 or Ri2 or RI2 | SEQ ID 7 | ATGGTAGTTAATCATAATATGGCATTGATCTGTGA GAGTAGACAGTTACGATGTAATGTGAAGAACATG GAGAAGTCTTCAAAAAAGCTGGCAACAGGTTATA AATTGCTTGGACGAAATGATGCAGCAGGATT ACAGATATCAGAAACCATGCGTCATCAGACCAGA GGTCTTAACAAAGCATCCAGAATTCGCAAGATG GAATTAGTATGTCGAGACAGCAGATGCAGCATT ACAGGAGACACAGGAAGTGTTGATCAGATGAC GGATCTGACAACACAGGCAGCTAATGATATCAAT ACGGATGCGGATCGTCTGCAATTCAGGATGAAA TCGATCAGTTAAATCAGGAAGTGGATCGTATTGC ATATACGACGAATTTAATCAGCAGTATATATTAG CGGATGGAACTCCGCAGGCAAGACCAGGATACTA TATGATACAGACAGGAGTCTTGCGGACAGGG AATAGAGATTAAGTTTGTTAATGCGAGCAAAGAG AGCTTGGGTGTGACAAGGTTGATGTATCATCGC ATGCAAAAGCACAGAATCTATAGCAGTGGTACA GAATGCAATTGAAAAGGCAGCTTCGTTTAGAGAT ACATTTGGGCACAAACAGGAGCGGTTAGAACACG CATTGCGTGGAACGGATAATAACATCAGAAAGTAC ACAGAGGCAGAATCAAGTAGACGCGATACCAA CATGAATATGGAGATGTACAATATTCTACAAACC GTATTTAGTACAGGCATCTCAGAGTATTTTAGCA CAGTACAATGATGATGCAAAATATGTTGGAAA TGTTAAATAG | SEQ ID 8 | MVVNHNMALICESRQLRCNVKNMEKSS KKLATGYKLLGANDDAAGLQISETMRHQ TRGLNKASRNSQDGISMLQTADAALQE TQEVLDRMTDLTTQAANDINTDADRRAI QDEIDQLNQEVDRIAYTTNFNQQYILAD GTPQARPGYYMIQTGSLAGQGIEIKFVN ASKESLGVDKDVSSHAKATESIAVVQN TSESTQRAESSRRDTNMNMEMVQYST NRIILVQASQSILAQYNDDAKYVLEMLKQ VLQILQ |
| Roseburia intestinalis L1-82 (fla3) | RiFla3 or RiFla3 or Ri3 or RI3 | SEQ ID 9 | ATGGTAGTACAGCACAATATGACCGCAATGAATG CGAACAGAATGTTAGGCGTTACAACAGCCACA GGCAAAATCTTCAGAGAATTATCTTCTGGTTACA GAATCAACCGTGCAGGTGATGAGAAGCCAGATCCGT AACAATTTCTGAGAGATGAGAAGCCAGATCCGT GGATTAAACAAAGCTTCTGACAACGCACAGGATG | SEQ ID 10 | MVVQHNMTAMNANRMLGVTTSAQAK SSEKLSSGYRINRAGDDAAGLTISEKMRS QIRGLNKASDNAQDGISLIQVAEGALSET HSIIQRMNELATQAANDTNTTADRGAI QDEINQLTSEINRISSTTQPNTQNLIDGTF ANKNLQVGSICGQRITVSIDSMSAGSLN |

TABLE A-continued summary of the Roseburia sequences described herein and the bacterial strain from which they may be derived.

| Bacteria and strain | Abbreviation | Nucleotide Sequence ID | Nucleotide Sequence | Amino Acid Sequence ID | Amino Acid Sequence |
|---|---|---|---|---|---|
| | | | GTATTCCTTAATCCAGTTGCTGAGGTGCATTA TCTGAGACACATTCTATCTTACAGCGTATGAATGA GTTAGCTACTCAGGCTGCTAACGATACCAATACAA CTGCTGATAGAGGAGCTATTCAGGATGAGATCAA CCAGTTAACATCTGAGATTAACAGAGAATCTCTCTA CAACTCAGTTCAATACTCAGAACCTCATCGATGGT ACATTCGCAAATAAAAACCTTCAGGTTGGTTCTAT CTGTGGACAGAGAATTACTGTTTCTATCGACAGTA TGTCTGCTGGTAGCTTAAATGTATCTGCTAACTTA GTAAAAGGTTAACACTTTCAGTGCAGCAGGTGAAG CAATGTCCAATATTCAGGGTGCTATTTCTGCAATT TCTACACAGCGTTCTTACTTAGGAGCTCTTCAGAA TTTCTGAGAATACTCAGTCTGCTGAATCTGTATC CGTGATACAGATATGGCTGAAGAGATGGTTACTT ACAGCAAGAACAATATTCTTGCTCAGGCAGGACA GTCTATGCTTGCTCAGGTAACCAGTCTACTCAGG GTCTACTTTCTCTGTTACAGTAA | | VSANLVKVNTFSAAGEAMSNIQGAISAIS TQRSYLGALQNRLEHTISNLDNISENTQS AESRIRDTDMAEEMVTYSKNNILAQAG QSMLAQANQSTQGVLSLLQ |
| Roseburia intestinalis L1-82 (fla4) | RiFla4 or RiFla4 or Ri4 or RI4 | SEQ ID 11 | ATGGCAATGGTAGTACAGCACAACATGTCCGCAA TGAATGCGAACAAATTAGGTGTTACAACAGG AATGCAGGCAAAATCATCAGAGAGTTATCTTCC GGTTACAAGATCAACCGTGCAGCAGATGATGCAG CAGGACTTTCTATTTCTGAGAAGATGAAGCCA GATCCGCCGGTTAAATAAAGCATCTGACAATGCA CAGGATGCTATCTCTTTAATCCAGACCCCTGAGG GAGCATTAAATGAGTCCCACTCTATTTTACAGAGA ATGAGAGAGTTATCCGTACAGGCAGCCAACGTA CAGAGACAGATGACGACCCGGAGGCAGTACAGA ACGAGGTTTCCCAGTTACAGGAAGAGCTGACAAG AATTTCTGAGACAACACAGAGTTCAACACGATGAAG CTGCTGGATGGTTCTCAGATGGAAGTACATCTTC AACCGGGTCAGGTCCGAAGTTTGGTGTTGTAGAT GCAACATTAGACGGTGCACTTGTAACATCTAACGT GAAAGTATTAAAGTAGCAACAGCAGGCTTGCCACA ACAACAAAGGCAGGTCAGGAGAGCTGCTATCTGGG CTGCTGATGGAAAGACATTAACTTAAATCTTTCG AAAAATAAGGTATATACACAGGACGAAATTGATG ACTTGATCGAAAATCAAGAGGAAGACAGTTC TGCAACGGGTGCACCGGCTGAAGTGAAAGTATCT TTAAAGAATGGTATTTTTAATGCAGATGCAGACAC AACTGCCCGGACTGTAACAGCCGGTGGTGTGAAG GCAGTATCTGAAGGAACAGTAACTGGATTTG TTGGTCAGATACAATTTCATTACGGCAAATAAG | SEQ ID 12 | MAMVVQHNMSAMNANRNLGVTTGM QAKSSEKLSSGYKINRAADDAAGLSISEK MRSQIRGLNKASDNAQDGISLIQTAEGA LNESHSILQRMRESLVQAANGTETDDDR EAVQNEVSQLQEELTRISETTEFNTMKLL DGSQSGSTSSTGSGPKFGVVDATLDGAL VTSNVKGIKVATAAATTTKAGQETAIWA ADGKTLTLNLSKNKVYTQDEIDDLIANKAK QEDSSATGAPAEVKVSLKNGIFNADADT TAGTVTAGGVKAVSDEGTVTGFVGADTI SFTANKYGAEFNDTVFKFKPDKAAGKEE VETNTAIEIDGANAVTAGEYTIHLAAGKE YTAEDLEDVLKTAGPFDFDVKLSGNTPDE PNTLFATSGASTVTDITMGAGTAGAGLG STDAMWGQAGYDSVSSGAGITLQIGAN EGQTMSFSIDDMSARALGVDGNKVDLS TQAGAQKATDTIDAAIKKVSAQRGRMG AIQNRLEHTISNLDTAAENTQTAESRIRD TDMAEEMVEYSKNNILAQAGQSMLAQ ANQSTQGVLSLLQ |

TABLE A-continued summary of the Roseburia sequences described herein and the bacterial strain from which they may be derived.

| Bacteria and strain Abbreviation | Nucleotide Sequence ID Nucleotide Sequence | Amino Acid Sequence ID Amino Acid Sequence |
|---|---|---|
| | TATGGAGCAGAGTTCAATGATACTGTATTAAATT<br>CAAATTGATAAGGCAGCAGGCAAAGAAGAAGT<br>AGAGACAAATACAGCAATTGAAATTGATGGAGCA<br>AATGCGGTAACAGCAGTGAATATACAATTCATC<br>TTGCAGCAGGCAAAGAATATACGGCAGAAGATTT<br>AGAAGATGTTCTTAAAACGGCAGGATTCGACTTT<br>GATGTTAAATTAAGTGGAAATACACCAGATGAGC<br>CAAATACTTTATTTGCAACCAGTGGCCATCAACT<br>GTGACTGATATTACAATGGGTGCTGGCACCGCCG<br>GAGCTGGTCTTGGAAGTACAGATGCTATGTGGGG<br>GCAAGCTGGTTATGACAGTTATCTTCTGGTGCTGG<br>CATTACCTTGCAGATTGTGCAAATGAAGGTCAG<br>ACCATGAGTTTCTCTATCGATGACATGAGTGCAAG<br>AGCACTTGGCGTAGATGCAACAAAGTTGATTTA<br>CCATTGATGCAGCAATCAAGAAAGTATCTGCACA<br>GCGTGGTAGAATGGGTGCGATCCAGAACCGTCTG<br>GAGCACACCATCAGCAACCTTGATACAGCAGCAG<br>AGAATACCCAGACTGCAGAGTCCCGTATCCGTGA<br>TACAGATATGGCAGAAGAGATGGTTGAGTACTCC<br>AAGAACAACATTCTTGCACAGGCAGGTCAGTCTA<br>TGCTTGCACAGGCGAACCAGTCTACACAGGGTGT<br>ACTCTCCTTATTACAGTAA | |

Modulation/Regulation

The terms "modulation" and "regulation" may be used interchangeably herein.

In one embodiment, the term "modulation" refers to an increase and/or induction and/or promotion and/or activation. In an alternative embodiment, the term "modulation" refers to a decrease and/or reduction and/or inhibition.

In one embodiment, the term "regulation" refers to an upregulation. In an alternative embodiment, the term "regulation" refers to a downregulation.

In one embodiment, the *Roseburia* flagellin, and/or Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), reduces the inflammation of a tissue or an organ.

For example, inflammation of the alimentary canal or part thereof (such as the intestine) is reduced.

The term "inflammation" as used herein refers to one or more of the following: redness, swelling, pain, tenderness, heat, and disturbed function of a tissue or organ due to an inflammatory process triggered by over-reaction of the immune system.

A reduction in inflammation in a subject can be determined by determining the levels of pro-inflammatory cytokines and chemokines in tissue, serum and/or faecal samples in a subject before, and after, the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. For example, the levels of one or more of the following can be monitored: IL-I, IL-4, IL5, IL6,IL-8, IL-12, IL-13, IL-17, IL-21, IL-22, IL23, TNFα, IFNγ, CXCL1, CXCL10, CCL2, CCL20 serum and faecal calprotectin, SA1009/SA1008 calcium binding proteins, and Type 1 interferons, CD markers such as CD163, CD14, inflammatory transcription factors such as NF-kB, STAT, and MAPkinases, c-reactive protein (CRP), erythrocyte sedimentation rate (ESR), complement proteins, serum albumin, histological evaluation of target tissues and organs, disease activity indices. Further, in human studies quality of life (QoL) questionnaires can be carried out before, and after, the *Roseburia* flagellin, and/or polypeptide Fla (such as FlaA1 or FlaA2), and/or the polynucleotide sequence encoding said *Roseburia* flagellin and/or polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the amount of a tissue or organ which is inflamed in a subject is at least 10%, 20%, 30%, 40% or 50% lower when compared to the amount of tissue or organ which is inflamed in a subject before the *Roseburia* flagellin, and/or polypeptide Fla (such as FlaA1 or FlaA2), and/or the polynucleotide sequence encoding said *Roseburia* flagellin and/or polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the *Roseburia* flagellin, and/or Fla (such as FlaA1 or FlaA2) polypeptide, and/or the polynucleotide sequence encoding the *Roseburia* flagellin and/or Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), reduces the inflammation by epithelial cells of the tissue or the organ.

For example, the epithelial cells are epithelial cells of the alimentary canal or part thereof (such as the intestine).

In one embodiment, the *Roseburia* flagellin, and/or Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), increases the production of T cells in a subject.

In one embodiment, the T cells are regulatory T cells (also referred to as Tregs) such as regulatory T cells capable of expressing TLR5 (Toll-like receptor 5).

Without wishing to be bound by theory, an increase in Treg numbers will combat the effects of other effector T cells (also referred to as Teffs), such as Th1, Th17 and Th2 which drive inflammation, autoimmunity and allergic/atopic conditions. Hence this property of the *Roseburia* flagellin, and/or the Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), can be exploited to address many diseases where Teff/Treg cell balance is lost, e.g. Crohn's and ulcerative colitis.

In one embodiment, the production of T cells in a subject is increased such that there are at least 10%, 20%, 30%, 40% or 50% more T cells, or greater than 100% more T cells, when compared to the number of T cells in the subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "immune system" as used herein may refer to the adaptive immune system and/or the innate immune system.

In one aspect, the invention relates to the *Roseburia* flagellin, and/or the Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), for use in regulating the adaptive immune system of a subject.

As used herein, the term "adaptive immune system", otherwise known as the "specific immune system" refers to highly specialized, systemic cells and processes that eliminate or prevent pathogenic growth. The adaptive immune response provides the vertebrate immune system with the ability to recognize and remember specific pathogens (to generate immunity), and to mount stronger attacks each time the pathogen is encountered.

As used herein, the term "regulating the adaptive immune system" means inducing the activity of the adaptive immune system, and/or promoting immune homeostatic mechanisms by increasing the level of activity relative to the baseline level of activity. Preferably, the adaptive immune system is modulated towards immune regulation (and not immune activation therefore reducing inflammation).

Defects and disorders associated with the adaptive immune system, particularly related to the function of T cells, are associated with many inflammatory and autoimmune diseases. T cell responses associated with Th1, Th2 and Th17 are associated with atopic, inflammatory and autoimmune diseases. Therapies which improve or increase T regulatory (Tregs) cell populations are important in controlling diseases driven by excessive Th1, Th2 and Th17 cell responses.

Another aspect of the invention relates to the *Roseburia* flagellin, and/or the Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), for use in regulating the innate immune system of a subject.

As used herein, the term "innate immune system", also known as the non-specific immune system, comprises the cells and mechanisms that provide the host with immediate defense against infection by other organisms in a non-specific manner. This means that the cells of the innate system recognize and respond to pathogens in a generic way, but unlike the adaptive immune system, it does not confer long-lasting or protective immunity to the host.

As used herein, the term "regulating the innate immune system" means inducing the activity of the innate immune system, and/or increasing the level of activity relative to the baseline level of activity such that it promotes immune homeostasis.

Loss or dysregulation of the innate immune function, either due to loss of epithelial barrier, innate immune peptides such as defensins, chemokines and cytokines or defective TLR signalling are associated with increased risk of inflammatory diseases, in several body organs including the gut. Such diseases include inflammatory bowel disease.

In one embodiment, the *Roseburia* flagellin, and/or the Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), restores immunological tolerance.

As used herein, the term "immunological tolerance" refers to the process by which the immune system does not attack an antigen such as a self-antigen.

As used herein the term "restoring immunological tolerance" refers to a restoration in immunological tolerance to one or more antigens (such as a self-antigen) in a subject such that the level of immunological tolerance to the antigen is higher when compared to the levels in a subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the *Roseburia* flagellin, and/or the Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), activates dendritic cells and/or epithelial cells.

As used herein the term "activates dendritic cells" refers to an up-regulation of one or more cells markers (such as I-A/I-E cell markers, CD80 and CD86 and CD40) and/or an increase in the production of one or more cytokines (such as IL-10 and TGFβ) by cells (such as dendritic cells) in a subject when compared to the levels in a subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "I-A/1-E" as used herein refers to cell markers of MHC class II.

CD40 has an essential role in immunity, and is one of the best characterized of the costimulatory molecules. This receptor, a member of the tumor necrosis factor receptor family, is expressed by professional antigen-presenting cells, such as dendritic cells. CD40 binds its ligand CD40L, which is transiently expressed on T cells and other non-immune cells under inflammatory conditions.

CD40L is an example of a T cell marker. CD3, CD4, CD25, FoxP3, CTLA-4, Ly6g and CD11b are further examples of T cell markers.

CD80 and CD86 are expressed on antigen-presenting cells (such as dendritic cells) and are required for the development and costimulation of T cell responses. The CD28 and CTLA-4 molecules on T cells serve as receptors for the CD80 and CD86 costimulatory antigens.

CD3, CD4, CD25, FoxP3, CTLA-4, Ly6g and CD11b are examples of markers of colonic T regulatory cells.

Without wishing to be bound by theory, the depletion of Ly6g (e.g. Ly6g6c and ly6g6e) increases infection risk, both gut and respiratory tract and is associated with diseases such as neutropenia. Thus, in one embodiment, the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is for use in treating neutropenia.

Another aspect of the invention relates to the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), for use in maintaining immune homeostasis in a subject. As used herein "maintaining immune homeostasis" refers to the self-regulation of the body's immune system to maintain oral tolerance or immune stability in response to changing conditions. Oral tolerance refers to the normal immune responses to food and commensal bacteria in a healthy gut. These are lost in coeliac disease and Inflammatory Bowel Diseases such as Crohn's disease and ulcerative colitis. Thus, in one aspect, the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is for use in treating coeliac disease and Inflammatory Bowel Diseases such as Crohn's disease and ulcerative colitis.

In one embodiment, the numbers of a cell marker on the cell(s) of a subject are up-regulated such that there are at least 10%, 20%, 30%, 40% or 50% more of the cell marker on the cell(s), or greater than 100% more of the cell marker on the cell(s), when compared to the number of the cell marker on the cell(s) of the subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have the cell marker are increased such that there are at least 10%, 20%, 30%, 40% or 50% more cells which have the cell marker, or greater than 100% more cells which have the cell marker, when compared to the number of cell with the cell marker in the subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one aspect, the cells are T cells.

In another aspect, the cells are cells of the alimentary canal (such as cells of the intestine).

In a further aspect, the cells are colonic and/or small intestinal T regulatory cells and may be either CD4 or CD8 positive.

In one aspect, the cell marker is a T cell marker. In another aspect, the cells marker is a colonic T cell marker.

Markers which are type I-A/I-E are examples of a cell marker. CD40 is another example of a cell marker both found on dendritic cells.

In one embodiment, the level of a cytokine in a subject is increased such that the cytokine level is at least 10%, 20%, 30%, 40% or 50% higher, or greater than 100% higher, when compared to the cytokine level in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

Examples of dendritic cells include bone marrow dendritic cells and gut mucosal dendritic cells.

As used herein the term "activates epithelial cells" refers to an increase in the expression of one or more pro-inflammatory genes by epithelial cells in a subject when compared to the expression levels in a subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "pro-inflammatory gene" as used herein refers to a gene which, when expressed, promotes inflammation. Examples of pro-inflammatory genes include genes encoding but not limited to IL1-β, IL4, IL5, IL6, IL8, IL12, IL13, IL17, IL21, IL22, IL23, IL27, IFNγ, CCL2, CCL3, CCL5, CCL20, CXCL5, CXCL10, CXCL12, CXCL13, and TNF-α.

In one embodiment, the *Roseburia* flagellin, and/or the Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), upregulates the production of a cytokine.

The term "upregulates the production of a cytokine" as used herein refers to an increase in the level of a cytokine in a subject compared to the level of the cytokine in a subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the level of the cytokine is increased such that the level is at least 10%, 20%, 30%, 40% or 50% higher, or greater than 100% higher, when compared to the level in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In another embodiment, the *Roseburia* flagellin, and/or the Fla (such as FlaA1 or FlaA2) polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), upregulates the production of IL-10 and/or TGFs.

The term "upregulates the production of IL-10" as used herein refers to an increase in the level of IL-10 in a subject compared to the level of IL-10 in a subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the level of IL-10 is increased such that the level is at least 10%, 20%, 30%, 40% or 50% higher, or greater than 100% higher, when compared to the level in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In some aspects, IL-10 is produced by dendritic cells such as bone marrow derived dendritic cells and gut mucosal dendritic cells in particular CD103+ subsets.

In one embodiment, the *Roseburia* flagellin, and/or the Fla polypeptide, and/or the polynucleotide sequence encoding the *Roseburia* flagellin and/or the Fla (such as FlaA1 or FlaA2) polypeptide, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), upregulates the production cell surface markers involved in immune responses and antigen recognition in a cell or cells of a subject.

Examples of cell surface markers involved in immune responses and antigen recognition include CD40, I-A/I-E, CD317/BST-2, CD103, CD80, CD86, CD83 and/or Siglec-H and/or the species equivalent.

Cell surface markers (e.g. CD317/BST-2) may be referred by different names in different species or the cell surface marker may not yet have been identified on the cells of a particular species. The term "species equivalent" as used herein encompasses these cell surface markers.

The term "upregulates the production CD40" as used herein refers to an increase in the level of CD40 in a subject compared to the level of CD40 in a subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. For example, the number of cells bearing the cell marker CD40 is increased and/or the number of CD40 markers on a cell is increased.

In one embodiment, the numbers of the CD40 cell marker on the cell(s) of a subject are up-regulated such that there are at least 10%, 20%, 30%, 40% or 50% more of the cell marker on the cell(s), or greater than 100% more of the cell marker on the cell(s), when compared to the number of the cell marker on the cell(s) of the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have the cell marker CD40 are increased such that there are at least 10%, 20%, 30%, 40% or 50% more cells which have the cell marker, or greater than 100% more cells which have the cell marker, when compared to the number of cell with the cell marker in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "upregulates the production I-A/I-E" as used herein refers to an increase in the level of I-A/l-E in a subject compared to the level of I-A/l-E in a subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. For example, the number of cells bearing one or more I-A/I-E cell markers is increased and/or the number of I-A/I-E cell markers on a cell is increased.

In one embodiment, the numbers of the I-A/I-E cell markers on the cell(s) of a subject are up-regulated such that there are at least 10%, 20%, 30%, 40% or 50% more of I-A/I-E cell markers on the cell(s), or greater than 100% more of I-A/I-E cell markers on the cell(s), when compared to the number of I-A/I-E cell markers on the cell(s) of the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have I-A/I-E cell markers are increased such that there are at least 10%, 20%, 30%, 40% or 50% more cells which have I-A/I-E cell markers, or greater than 100% more cells which have I-A/I-E cell markers, when compared to the number of cell with I-A/I-E cell markers in the subject before the *Roseburia* flagellin, and/or the polypeptide Fla (such as FlaA1 or FlaA2), and/or the polynucleotide sequence encoding said *Roseburia* flagellin and/or said Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "upregulates the production of CD317/BST-2" as used herein refers to an increase in the level of CD317/BST-2 in a subject compared to the level of CD317/BST-2 in a subject before the *Roseburia* flagellin, and/or the polypeptide Fla, and/or the polynucleotide sequence encoding said *Roseburia* flagellin and/or the polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. For example, the number of cells bearing one or more CD317/BST-2 cell markers is increased and/or the number of CD317/BST-2 cell markers on a cell is increased.

In one embodiment, the numbers of the CD317/BST-2 cell markers on the cell(s) of a subject are up-regulated such that there are at least 10%, 20%, 30%, 40% or 50% more of CD317/BST-2 cell markers on the cell(s), or greater than 100% more of CD317/BST-2 cell markers on the cell(s), when compared to the number of CD317/BST-2 cell markers on the cell(s) of the subject before the *Roseburia* flagellin, and/or the polypeptide Fla, and/or the polynucleotide sequence encoding said *Roseburia* flagellin and/or said polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have CD317/BST-2 cell markers are increased such that there are at least 10%, 20%, 30%, 40% or 50% more cells which have CD317/BST-2 cell markers, or greater than 100% more cells which have CD317/BST-2 cell markers, when compared to the number of cell with CD317/BST-2 cell markers in the subject before the *Roseburia* flagellin, and/or the polypeptide Fla (such as FlaA1 or FlaA2), and/or the polynucleotide sequence encoding said *Roseburia* flagellin and/or said Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "upregulates the production of CD103" as used herein refers to an increase in the level of CD103 in a subject compared to the level of CD103 in a subject before the *Roseburia* flagellin, and/or the polypeptide Fla, and/or the polynucleotide sequence encoding said *Roseburia* flagellin and/or the polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. For example, the number of cells bearing one or more CD103 cell markers is increased and/or the number of CD103 cell markers on a cell is increased.

In one embodiment, the numbers of the CD103 cell markers on the cell(s) of a subject are up-regulated such that there are at least 10%, 20%, 30%, 40% or 50% more of CD103 cell markers on the cell(s), or greater than 100% more of CD103 cell markers on the cell(s), when compared to the number of CD103 cell markers on the cell(s) of the subject before the *Roseburia* flagellin, and/or the polypeptide Fla, and/or the polynucleotide sequence encoding said *Roseburia* flagellin and/or said polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have CD103 cell markers are increased such that there are at least 10%, 20%, 30%, 40% or 50% more cells which have CD103 cell markers, or greater than 100% more cells which have CD103 cell markers, when compared to the number of cell with CD103 cell markers in the subject before the *Roseburia* flagellin, and/or the polypeptide Fla (such as FlaA1 or FlaA2), and/or the polynucleotide sequence encoding said *Roseburia* flagellin and/or said Fla (such as FlaA1 or FlaA2), and/or the vector comprising said polynucleotide sequence, and/or the host cell comprising said polynucleotide sequence, and/or *Roseburia* (such as the bacterial species *Roseburia hominis*, or the bacterial species *Roseburia intestinalis*), is administered to the subject.

The term "upregulates the production of CD80" as used herein refers to an increase in the level of CD80 in a subject compared to the level of CD80 in a subject before the *Roseburia* flagellin, and/or the polypeptide Fla, and/or the polynucleotide sequence encoding said *Roseburia* flagellin and/or the polypeptide Fla, and/or the vector comprising said polynucleotide sequence, and/or the host cell comprising said polynucleotide sequence, and/or *Roseburia* (such as the bacterial species *Roseburia hominis*, or the bacterial species *Roseburia intestinalis*), is administered to the subject. For example, the number of cells bearing one or more CD80 cell markers is increased and/or the number of CD80 cell markers on a cell is increased.

In one embodiment, the numbers of the CD80 cell markers on the cell(s) of a subject are up-regulated such that there are at least 10%, 20%, 30%, 40% or 50% more of CD80 cell markers on the cell(s), or greater than 100% more of CD80 cell markers on the cell(s), when compared to the number of CD80 cell markers on the cell(s) of the subject before the *Roseburia* flagellin, and/or the polypeptide Fla, and/or the polynucleotide sequence encoding said *Roseburia* flagellin and/or said polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have CD80 cell markers are increased such that there are at least 10%, 20%, 30%, 40% or 50% more cells which have CD80 cell markers, or greater than 100% more cells which have CD80 cell markers, when compared to the number of cell with CD80 cell markers in the subject before the *Roseburia* flagellin, and/or the polypeptide Fla (such as FlaA1 or FlaA2), and/or the polynucleotide sequence encoding said *Roseburia* flagellin and/or said Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "upregulates the production of CD86" as used herein refers to an increase in the level of CD86 in a subject compared to the level of CD86 in a subject before the *Roseburia* flagellin, and/or the polypeptide Fla, and/or the polynucleotide sequence encoding said *Roseburia* flagellin and/or the polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. For example, the number of cells bearing one or more CD86 cell markers is increased and/or the number of CD86 cell markers on a cell is increased.

In one embodiment, the numbers of the CD86 cell markers on the cell(s) of a subject are up-regulated such that them are at least 10%, 20%, 30%, 40% or 50% more of CD86 cell markers on the cell(s), or greater than 100% more of CD86 cell markers on the cell(s), when compared to the number of CD86 cell markers on the cell(s) of the subject before the *Roseburia* flagellin, and/or the polypeptide Fla, and/or the polynucleotide sequence encoding said *Roseburia* flagellin and/or said polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have CD86 cell markers are increased such that there are at least 10%, 20%, 30%, 40% or 50% more cells which have CD86 cell markers, or greater than 100% more cells which have CD86 cell markers, when compared to the number of cell with CD86 cell markers in the subject before the *Roseburia* flagellin, and/or the polypeptide Fla, and/or the polynucleotide sequence encoding said *Roseburia* flagellin and/or said Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "upregulates the production of CD83" as used herein refers to an increase in the level of CD83 in a subject compared to the level of CD83 in a subject before the *Roseburia* flagellin, and/or the polypeptide Fla, and/or the polynucleotide sequence encoding said *Roseburia* flagellin and/or the polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. For example, the number of cells bearing one or more CD83 cell markers is increased and/or the number of CD83 cell markers on a cell is increased.

In one embodiment, the numbers of the CD83 cell markers on the cell(s) of a subject are up-regulated such that there are at least 10%, 20%, 30%, 40% or 50% more of CD83 cell markers on the cell(s), or greater than 100% more of CD83 cell markers on the cell(s), when compared to the number of CD83 cell markers on the cell(s) of the subject before the *Roseburia* flagellin, and/or the polypeptide Fla, and/or the polynucleotide sequence encoding said *Roseburia* flagellin and/or said polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have CD83 cell markers are increased such that there are at least 10%, 20%, 30%, 40% or 50% more cells which have CD83 cell markers, or greater than 100% more cells which have CD83 cell markers, when compared to the number of cell with CD83 cell markers in the subject before the *Roseburia* flagellin, and/or the polypeptide Fla, and/or the polynucleotide sequence encoding said *Roseburia* flagellin and/or said Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "upregulates the production of Siglec-H" as used herein refers to an increase in the level of Siglec-H in a subject compared to the level of Siglec-H in a subject before the *Roseburia* flagellin, and/or the polypeptide Fla, and/or the polynucleotide sequence encoding said *Roseburia* flagellin and/or the polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. For example, the number of cells bearing one or more Siglec-H cell markers is increased and/or the number of Siglec-H cell markers on a cell is increased.

In one embodiment, the numbers of the Siglec-H cell markers on the cell(s) of a subject are up-regulated such that there are at least 10%, 20%, 30%, 40% or 50% more of Siglec-H cell markers on the cell(s), or greater than 100% more of Siglec-H cell markers on the cell(s), when compared to the number of Siglec-H cell markers on the cell(s) of the subject before the *Roseburia* flagellin, and/or the polypeptide Fla, and/or the polynucleotide sequence encoding said

*Roseburia* flagellin and/or said polypeptide Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition or alternatively, the number of cells in a subject which have Siglec-H cell markers are increased such that there are at least 10%, 20%, 30%, 40% or 50% more cells which have Siglec-H cell markers, or greater than 100% more cells which have Siglec-H cell markers, when compared to the number of cell with Siglec-H cell markers in the subject before the *Roseburia* flagellin, and/or the polypeptide Fla, and/or the polynucleotide sequence encoding said *Roseburia* flagellin and/or said Fla, and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In some aspects, the production of CD40 I-A/I-E, CD317/BST-2, CD80, CD86, CD83 and/or Siglec-His by dendritic cells (such as tolerogenic CD103.sup.+ dendritic cells expanded by FLT3L.).

In one embodiment, the expression of one or more Type I IFN genes in a cell or cells of a subject is down-regulated.

In one embodiment, the expression level of one or more Type I IFN genes is decreased such that the level is at least 10%, 20%, 30%, 40% or 50% lower when compared to the level in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

Examples of Type I IFN genes include but not limited to IFN-β1, IFN-β, Ifi202b, Ifi203, IF144, IFTI, MXI, OASI, OAS2, OAS3, OASL, Irf3 and Irf4.

In one embodiment, the expression of one or more pro-inflammatory genes in a cell or cells of a subject is down-regulated.

In one embodiment, the expression level of one or more pro-inflammatory genes is decreased such that the level is at least 10%, 20%, 30%, 40% or 50% lower when compared to the level in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "intestinal microbiota" as used herein refers to microorganisms that live in the digestive tract of the host animals. These microorganisms perform a wide variety of metabolic, structural, protective and other beneficiary functions.

As used herein, the term "improving intestinal microbiota" refers to increasing the number and/or type of microorganisms present in the intestine of a subject (e.g. the host), and/or increasing the activity of said microorganisms in terms of their metabolic, structural, protective and other beneficiary functions. For example, the numbers (i.e. levels) of *Clostridium* cluster XIVa bacteria are increased and the numbers of *E. coli* are reduced; such an improvement in intestinal microbiota may occur in subjects with inflammatory bowel disease (IBD) once the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), has been administered to the subject.

In one embodiment, the number of microorganisms present in the intestine of a subject (e.g. the host), is increased such that the number of microorganisms is at least 10%, 20%, 30%, 40% or 50% higher, or greater than 100% higher, when compared to the level in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition, or alternatively, the types of microorganisms present in the intestine of a subject (e.g. the host), are increased such that there are at least 5%, 10%, or 15% more types of microorganisms when compared to the types in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

As used herein, the term "regulating appetite" refers to the ability to modulate (i.e. increase or decrease) the desire for a subject to eat food.

In one embodiment, the appetite in the subject is stimulated (i.e. increased).

Without wishing to be bound by theory, the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), exerts a stimulatory effect on the appetite of a subject by downregulating the expression of genes associated with the suppression of appetite (such as genes encoding satiety hormones). Agt, Cartpt, Cck, Cxcl12 and Gcg are examples of genes associated with regulating appetite and the downregulation of one or more of these genes is associated with the suppression of appetite.

Cck and Gcg are examples of satiety hormones.

In one aspect, the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), stimulates the appetite in the subject such that the subject consumes at least 5%, 10%, or 15% more food when compared to the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject. In addition, or alternatively, the *Roseburia* flagellin, and/or the polypeptide Fla (such as FlaA1 or FlaA2), and/or the polynucleotide sequence encoding said *Roseburia* flagellin and/or polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), stimulates the appetite in the subject such that after 1 month from administration the weight of the subject is at least 2%, 5%, or 10% higher when compared to the subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), reduces the level of cholecystokinin (Cck) and/or glucagon (Gcg) in the blood of a subject.

In one aspect, the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), reduces the level of cholecystokinin (Cck) and/or glucagon (Gcg) in the blood of a subject by at least 5%, 10%, 15% or 20% when compared to the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the *Roseburia* flagellin, and/or the polypeptide Fla (such as FlaA1 or FlaA2), and/or a polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), downregulates the expression of the gene encoding cholecystokinin (Cck) and/or the expression of the gene encoding glucagon (Gcg) in a cell or cells of a subject.

In one aspect, the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), decreases the expression of the gene encoding cholecystokinin (Cck) such that the expression level is at least 5%, 10%, 15% or 20% lower when compared to the expression level in the subject before the *Roseburia* flagellin and/or the polypeptide Fla (such as FlaA1 or FlaA2) and/or the polynucleotide sequence encoding said *Roseburia* flagellin and/or the polypeptide Fla (such as FlaA1 or FlaA2) and/or *Roseburia* (such as the bacterial species *Roseburia hominis*, or the bacterial species *Roseburia intestinalis*), is administered to the subject.

In one aspect, the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), decreases the expression of the gene encoding glucagon (Gcg) such that the expression level is at least 5%, 10%, 15% or 20% lower when compared to the expression level in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

The term "improving alimentary canal health" as used herein refers to reducing the level of inflammation in the alimentary canal or part thereof and/or improving intestinal microbiota.

In one embodiment, the level of inflammation in the alimentary canal is at least 10%, 20%, 30%, 40% or 50% lower when compared to the level of inflammation in the alimentary canal of a subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/ or *Roseburia* (such as the bacterial species *Roseburia hominis*, or the bacterial species *Roseburia intestinalis*), is administered to the subject.

In one embodiment, the *Roseburia* flagellin, and/or the polypeptide Fla (such as FlaA1 or FlaA2), and/or a polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), regulates the expression of at least one gene selected from Tlr5, Tlr1, Vnn1, Defb37, Pla2g, Muc16, Itln, Sprr1a, Cldn4, Pmp22, Crb3, Magi3, Marveld3, Mpp7, Defcr20, Pcgf2, Ltbp4, Igsf8 and Tcfe2a. Many of these genes are gut barrier genes and antimicrobials and hence work to reduce invasiveness of gut pathogens and also reduce the numbers of viable pathogens.

In one embodiment, the expression of one or more genes selected from the group consisting of TLR-related genes (e.g. Tlr5, Tlr1, and Vnn1), genes encoding anti-microbial peptides (e.g. Defb37, Pla2g, Muc16, and Itln), gut barrier function genes (e.g. Sprr1a, Cldn4, Pmp22, Crb3, and Magi3), innate immune genes (e.g. Defcr20, Pcgf2, Ltbp4, Igsf8 and Tcfe2a) in a cell or cells of a subject is upregulated.

In one embodiment, the expression of one or more genes selected from the group consisting of TLR-related genes (e.g. Tlr5, Tlr1, and Vnn1), genes encoding anti-microbial peptides (e.g. Defb37, Pla2g, Muc16, and Inn), gut barrier function genes (e.g. Sprr1a, Cldn4, Pmp22, Crb3, and Magi3), innate immune genes (e.g. Defcr20, Pcgf2, Ltbp4, Igsf8 and Tcfe2a) is increased such that the level is at least 10%, 20%, 30%, 40% or 50% higher, or greater than 100% higher, when compared to the level in the subject before the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the expression of one or more genes selected from the group consisting of Tlr5, Tlr1, Vnn1, Defb37, Pla2g, Muc16, Itln, Sprr1a, Cldn4, Pmp22, Crb3, Magi3, Marveld3, Mpp7, Defcr20, Pcgf2, Ltbp4, Igsf8 and Tcfe2a in a cell or cells of a subject is upregulated.

In one embodiment, the expression level of one or more genes selected from the group consisting of Tlr5, Tlr1, Vnn1, Defb37, Pla2g, Muc16, Itln, Sprr1a, Cldn4, Pmp22, Crb3, Magi3, Marveld3, Mpp7, Defcr20, Pcgf2, Ltbp4, Igsf8 and Tcfe2a is increased such that the level is at least 10%, 20%, 30%, 40% or 50% higher, or greater than 100% higher, when compared to the level in the subject before the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In one embodiment, the expression of one or more genes selected from the group consisting of genes encoding acetyl-CoA acetyltransferase, 3-hydroxyacyl-CoA dehydrogenase, butyryl-CoA dehydrogenase and phosphoenolpyruvate carboxykinase [ATP] in a cell or cells of a subject is modulated.

In one embodiment, the expression level of one or more genes selected from the group consisting of genes encoding acetyl-CoA acetyltransferase, 3-hydroxyacyl-CoA dehydrogenase, butyryl-CoA dehydrogenase and phosphoenolpyruvate carboxykinase [ATP] is modulated such that the level is at least 10%, 20%, 30%, 40% or 50% higher or lower when compared to the level in the subject before the *Roseburia* flagellin, and/or the polypeptide Fla (such as FlaA1 or FlaA2), and/or the polynucleotide sequence encoding said *Roseburia* flagellin and/or polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is administered to the subject.

In a further aspect, the present invention relates to a transformed microorganism (such as a Firmicutes e.g. a *Roseburia* spp such as *R. hominis* or *R. intestinalis*) in which the expression of a flagellin (e.g. *Roseburia* flagellin) such as FlaA1 or FlaA2 is enhanced compared to the equivalent microorganism prior to transformation, and uses thereof for various therapeutic and nutritional uses as described herein. For example, the transformed microorganism may have been transformed with a nucleotide sequence (such as a promoter) such that the microorganism is capable of upregulating the expression of the gene encoding a flagellin (e.g. *Roseburia* flagellin) such as FlaA1 or FlaA2. In another example, the transformed microorganism may have be transformed with an expression vector comprising a nucleotide sequence encoding a flagellin (e.g. *Roseburia* flagellin) such as FlaA1 or FlaA2 operably linked to a regulatory sequence (such as a promoter) such that the microorganism is capable of overexpressing the gene encoding the flagellin (e.g. *Roseburia* flagellin) such as FlaA1 or FlaA2.

As used herein, the term "expression vector" refers to a DNA construct containing a DNA coding sequence (e.g., gene sequence) that is operably linked to one or more suitable control sequence(s) capable of affecting expression of the coding sequence in a host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the description is intended to include such other forms of expression vectors that serve equivalent functions and which are, or become, known in the art.

The term "operably linked" refers to juxtaposition wherein the elements are in an arrangement allowing them to be functionally related. For example, a promoter is operably linked to a coding sequence if it controls the transcription of the coding sequence.

Tissues

In one embodiment, the tissue or organ is the alimentary canal or a section thereof (e.g. the oesophagus, the stomach or the intestine such as the small intestine or the large intestine and colon) or another mucosal sites (such as the nasal passages and the lungs).

In one embodiment, the tissue or organ is the alimentary canal or part thereof.

Examples of parts of the alimentary canal include the oesophagus, the stomach and the intestine (such as the small intestine (e.g. the duodenum, the jejunum and the ileum) and/or the large intestine (e.g. the caecum, ascending colon, transverse colon, descending colon, and sigmoid colon)).

Subject

In one embodiment, the subject is a monogastric animal.

Examples of monogastric animals include poultry, humans, rats, pigs, dogs, cats, horses and rabbits.

In another embodiment, the subject is a mammal such as a monogastric mammal.

Examples of monogastric mammals include omnivores (such as humans, rats, and pigs), carnivores (such as dogs and cats), and herbivores (such as horses and rabbits).

In one embodiment, the subject is a human.

Typically, TLR5 is capable of being expressed in the cells of said subject.

Disorders

*Roseburia* flagellin, and/or polypeptide Fla (such as FlaA1 or FlaA2), and/or a polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), may be used in treating a disorder in a subject, wherein said disorder is an inflammatory disorder and/or an autoimmune disorder.

In one embodiment, the inflammatory disorder and/or an autoimmune disorder affects the alimentary canal, or a section thereof, of said subject.

In one embodiment, the inflammatory disorder and/or an autoimmune disorder affects a mucosal site of a subject. Examples of mucosal sites include the alimentary canal or a section thereof (e.g. the oesophagus, the stomach or the intestine such as the small intestine or the large intestine and colon), the nasal passages and the lungs.

In one embodiment, the inflammatory disorder and/or an autoimmune disorder is selected from the group consisting of rheumatoid arthritis, psoriasis, multiple sclerosis, type I diabetes, coeliac disease, atopic dermatitis, rhinitis, irritable bowel syndrome (IBS), colitis, inflammatory bowel disorder (IBD), ulcerative colitis, pouchitis, Crohn's disease, functional dyspepsia, atopic diseases, necrotising enterocolitis, and combinations thereof.

In one aspect, the inflammatory disorder is colitis. In a further aspect, the inflammatory disease is Crohn's disease, ulcerative colitis or pouchitis.

In one aspect, the inflammatory disorder and/or an autoimmune disorder affects the intestine.

In one aspect, the intestinal disorder is IBS. The precise pathophysiology of IBS remains to be elucidated. Recent studies have described mucosal inflammation and alterations in intestinal microbiota in IBS patients and a disease correlation with intestinal infections.

In a further aspect, the intestinal disorder is Crohn's disease.

In one aspect, the disorder is an autoimmune disorder.

In one aspect, the autoimmune disorder is selected from the group consisting of ulcerative colitis, pouchitis, rheumatoid arthritis, psoriasis, multiple sclerosis, type I diabetes, allergies (including coeliac disease), atopic dermatitis and rhinitis.

In particular due to its function in restoring immune tolerance, the autoimmune diseases, rheumatoid arthritis, psoriasis, multiple sclerosis, type I diabetes are of particular relevance.

As used herein, the term "medicament" encompasses medicaments for both human and animal usage in human and veterinary medicine. In addition, the term "medicament" as used herein means any substance, which provides a therapeutic and/or beneficial effect. The term "medicament" as used herein is not necessarily limited to substances, which need Marketing Approval, but may include substances which, can be used in cosmetics, nutraceuticals, food (including feeds and beverages for example), probiotic cultures, nutritional supplements and natural remedies. In addition, the term "medicament" as used herein encompasses a product designed for incorporation in animal feed, for example livestock feed and/or pet food.

Prophylactic Applications

The *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), according to the invention may also be used in prophylactic applications. In prophylactic applications, the *Roseburia* flagellin, and/or the polypeptide Fla (such as FlaA1 or FlaA2), and/or the polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), according to the invention are administered to a patient susceptible to, or otherwise at risk of, a particular disease in an amount that is sufficient to at least partially reduce the risk of developing a disease. Such an amount is defined to be "a prophylactic effective dose". The precise amounts depend on a number of specific factors such as the subject's state of health and weight.

Encapsulation

In one embodiment, the *Roseburia* flagellin, and/or the polypeptide Fla (such as FlaA1 or FlaA2), and/or the polynucleotide sequence encoding said *Roseburia* flagellin of the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is encapsulated.

In a further embodiment, the pharmaceutical composition comprising the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, or the host cell comprising said polynucleotide sequence, and/or *Roseburia* (such as the bacterial species *Roseburia hominis*, or the bacterial species *Roseburia intestinalis*), is encapsulated.

In another embodiment, the nutritional supplement comprising the *Roseburia* flagellin, and/or the polypeptide Fla (such as FlaA1 or FlaA2), and/or the polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), is encapsulated.

In a further embodiment, the feedstuff, food product, dietary supplement, or food additive is encapsulated.

The term "encapsulated" as used here refers to a means for protecting the polypeptide, and/or polynucleotide sequence, and/or the vector, and/or the host cell, and/or *Roseburia* (such as the bacterial species *Roseburia hominis*, or the bacterial species *Roseburia intestinalis*), from an incompatible environment by physical separation so that it can be delivered to the target site (e.g. the intestine) without degradation or significant degradation in order that the polypeptide, and/or polynucleotide sequence, and/or the vector, and/or the host cell, and/or the *Roseburia* (such as the bacterial species *Roseburia hominis*, or the bacterial species *Roseburia intestinalis*), can have an effect on the target site. An example is an enteric coated capsule.

Even when the objective of the encapsulation is the isolation of the polypeptide, and/or polynucleotide sequence, and/or the vector, and/or the host cell, and/or the *Roseburia* (such as the bacterial species *Roseburia hominis*, or the bacterial species *Roseburia intestinalis*), from its surroundings, the protective coating or shell must be ruptured at the time of desired action. The rupturing of the protective coating or shell is typically brought about through the application of chemical and physical stimuli such as pressure, enzyme attack, chemical reaction and physical disintegration.

For example, the encapsulation ensures that the polypeptide, and/or polynucleotide sequence, and/or the vector, and/or the host cell, and/or the *Roseburia* (such as the bacterial species *Roseburia hominis*, or the bacterial species *Roseburia intestinalis*), can be ingested so that the polypeptide, and/or polynucleotide sequence, and/or the vector, and/or the host cell and/or the *Roseburia* (such as the bacterial species *Roseburia hominis*, or the bacterial species *Roseburia intestinalis*), can be delivered to the intestine (i.e. the target site) in an amount which is effective to produce an effect in the intestine.

Pharmaceutical Composition

The pharmaceutical composition may be any pharmaceutical composition. In one aspect, the pharmaceutical composition is to be administered orally, enterally or rectally. For example, the composition may be an edible composition. "Edible" means a material that is approved for human or animal consumption.

The pharmaceutical compositions may be for human or animal usage in human and veterinary medicine.

Examples of such suitable excipients for the various different forms of pharmaceutical compositions described herein may be found in the "Handbook of Pharmaceutical Excipients, 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavouring agents may be provided in the pharmaceutical composition. Examples of preservatives include sodium benzoate, sorbic acid and esters of p-hydroxybenzoic acid. Antioxidants and suspending agents may be also used.

Nutritional Supplements

Nutritionally acceptable carriers, diluents and excipients include those suitable for human or animal consumption and that are used as standard in the food industry. Typical nutritionally acceptable carriers, diluents and excipients will be familiar to the skilled person in the art.

Feedstuff/Products

A further aspect of the invention relates to feedstuffs, food products, dietary supplements and food additives containing *Roseburia* flagellin, and/or the polypeptide Fla (such as FlaA1 or FlaA2), and/or a polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*).

The terms "feedstuff", "food product" "food additive" and "dietary supplement" as used herein are intended to cover all consumable products that can be solid, jellied or liquid.

Suitable food products may include, for example, functional food products, food compositions, pet food, livestock feed, health foods, feedstuffs and the like. In one aspect, the food product is a health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional—e.g. medical or physiological benefit—other than a purely nutritional effect.

Examples of specific food products that are applicable to the present invention include milk-based products, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

In one aspect, the feedstuff, food product, dietary supplement or food additive according to the present invention are intended for humans, pets or livestock such as monogastric animals. The feedstuff, food product, dietary supplement or food additive may be intended for animals selected from the group consisting of dogs, cats, pigs, horses, or poultry. In a further embodiment, the food product, dietary supplement or food additive is intended for adult species, in particular human adults.

The term "milk-based product" as used herein means any liquid or semi-solid milk or whey based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

The feedstuffs, food products, dietary supplements or food additives of the present invention may be—or may be added to—food supplements, also referred to herein as dietary or nutritional supplements or food additives.

The feedstuffs, food products, dietary supplements or food additives according to the invention may also be used in animal nutrition (e.g. in pig nutrition), particularly in the early-weaned period and growing fattening period. The feedstuffs, food products, dietary supplements or food additives are expected to enhance immune function reduce and prevent infectious diseases, beneficially alter the microbiota composition, and improve growth and performance of animals, for example, through increased feed conversion efficiency.

Probiotics or Live Biotherapeutic Product

The *Roseburia* flagellin, and/or the polypeptide Fla (such as FlaA1 or FlaA2), and/or a polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), may be used in a probiotic or live biotherapeutic product.

Another aspect of the invention relates to a probiotic composition comprising the *Roseburia* flagellin, and/or the polypeptide Fla (such as FlaA1 or FlaA2), and/or a polynucleotide sequence encoding said *Roseburia* flagellin and/or said polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*).

As used herein, the term "probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

In one aspect, the probiotic composition is an orally administrable composition of metabolically active, i.e., live and/or or lyophilized, or non-viable heat-killed, irradiated or lysed probiotic bacteria. The probiotic composition may contain other ingredients. The probiotic composition can be administered orally, i.e., in the form of a tablet, capsule or powder. The probiotic composition may comprise the bacterial species *R. hominis* or *R. intestinalis*. Encapsulated products are favoured for *R. hominis* and *R. intestinalis* as they are anaerobes. Other ingredients (such as vitamin C, for example), may be included as oxygen scavengers and prebiotic substrates (such as these improve the colonisation and survival in vivo). Alternatively, the probiotic composition of the invention may be administered orally as a food or nutritional product, such as milk or whey based fermented dairy product, or as a pharmaceutical product.

A suitable daily dose of the probiotic bacteria is from about $1 \times 10^3$ to about $1 \times 10^{11}$ colony forming units (CFU); for example, from about $1 \times 10^7$ to about $1 \times 10^{10}$ CFU; in another example from about $1 \times 10^6$ to about $1 \times 10^{10}$ CFU.

In one aspect, the probiotic composition contains the bacterial species and/or cellular components thereof, as active ingredients, in an amount of from about $1 \times 10^6$ to about $1 \times 10^1$ CFU/g, respect to the weight of the composition; for example, from about $1 \times 10^8$ to about $1 \times 10^{10}$ CFU/g. The dose may be of 1 g, 3 g, 5 g, and 10 g.

Typically, a probiotic is optionally combined with at least one suitable prebiotic compound. A prebiotic is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In one aspect, the probiotic composition of the present invention includes a prebiotic in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

Administration

The pharmaceutical compositions, the nutritional supplements, feedstuffs, food products, dietary supplements or food additives of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

In one aspect, the pharmaceutical compositions, the nutritional supplements, feedstuffs, food products, dietary supplements or food additives of the present invention are adapted for oral, rectal, vaginal, parenteral, nasal, buccal or sublingual routes of administration.

In a further aspect, the pharmaceutical compositions, the nutritional supplements, feedstuffs, food products, dietary supplements or food additives of the present invention are adapted for oral administration.

For oral administration, particular use is made of compressed tablets, pills, tablets, gellules, drops, and capsules.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. In another example, the active ingredient can also be incorporated into an ointment consisting of a white wax or white soft paraffin base together with such stabilisers and preservatives as may be required.

Pharmaceutical compositions, the nutritional supplements, feedstuffs, food products, dietary supplements or food additives may be formulated in unit dosage form, i.e., in the form of discrete portions containing a unit dose, or a multiple or sub-unit of a unit dose.

Dosage

A person of ordinary skill in the art can easily determine an appropriate dose of the *Roseburia* flagellin, and/or the polypeptide Fla (such as FlaA1 or FlaA2), and/or a polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), to administer to a subject without undue experimentation. Typically, a physician will determine the actual dosage which will be most suitable for an individual patient and it will depend on a variety of factors including the activity of the specific bacterial strain employed, the metabolic stability and length of action of that strain, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Combinations

In one aspect, the *Roseburia* flagellin, and/or the polypeptide Fla (such as FlaA1 or FlaA2), and/or a polynucleotide sequence encoding said *Roseburia* flagellin and/or the polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), are administered in combination with at least one or two, or three or four or five other active agents. In such cases, the *Roseburia* flagellin, and/or the polypeptide Fla (such as FlaA1 or FlaA2), and/or a polynucleotide sequence encoding said *Roseburia* flagellin and/or polypeptide Fla (such as FlaA1 or FlaA2), and/or the vector comprising said polynucleotide sequence, and/or the host cell comprising said vector, and/or the host cell comprising said polynucleotide sequence, and/or *Roseburia* (such as the bacterial species *Roseburia hominis*, or the bacterial species *Roseburia intestinalis*), may be administered consecutively, simultaneously or sequentially with the one or more other active agents.

The at least one or two, or three or four or five other active agents may be selected from the group consisting of: *Roseburia* flagellins, the polypeptide Fla (such as FlaA1 or FlaA2), polynucleotide sequence(s) encoding said *Roseburia* flagellin, polynucleotide sequence(s) encoding said polypeptide Fla (such as FlaA1 or FlaA2), vector(s) comprising said polynucleotide sequence(s), host cell(s) comprising said vector(s), host cell(s) comprising said polynucleotide sequence(s), and microorganisms (e.g. *Roseburia* such as *R. hominis* and/or *R. intestinalis*).

The at least one or two, or three or four or five other active agents may be a microorganism (e.g. a *Roseburia* such as *R. hominis* and/or *R. intestinalis*). Examples of suitable microorganisms include: *Roseburia hominis* A2-183 and *Roseburia intestinalis* L1-82.

Sequence Identity or Sequence Homology

The terms "polypeptide", "polypeptide sequence", "protein" and "amino acid sequence" are used interchangeably herein.

The terms "polynucleotide sequence" and "nucleotide sequence" are used interchangeably herein.

The present invention also encompasses the use of sequences having a degree of sequence identity or sequence homology with amino acid sequence(s) of a polypeptide described herein (e.g. variants, homologues and derivatives) or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

In the present context, a homologous sequence is taken to include an amino acid or a nucleotide sequence which may be at least 50, 60, 70, 75, 80, 85 or 90% identical, in some embodiments at least 95, 96, 97, 98 or 99% identical to the subject sequence. Although homology can also be considered in terms of similarity (i.e. amino acid residues having similar chemical properties/functions), in the context of the present invention it is preferred to express homology in terms of sequence identity.

In some embodiments, a homologous sequence is taken to include an amino acid sequence or nucleotide sequence which has one or several additions, deletions and/or substitutions compared with the subject sequence.

In some embodiments, the present invention relates to the use of a protein whose amino acid sequence is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In some embodiments, the present invention relates to the use of a nucleic acid sequence (or gene) encoding a protein whose amino acid sequence is represented herein or encoding a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In the present context, a homologous sequence is taken to include a nucleotide sequence which may be at least 50, 60, 70, 75, 85 or 90% identical, in some embodiments at least 95, 96, 97, 98 or 99% identical to a nucleotide sequence encoding a polypeptide described herein (the subject sequence). Typically, the homologues will comprise the same or equivalent sequences that code for the domain(s) etc. as the subject sequence. Although homology can also be considered in terms of similarity (i.e. amino acid residues having similar chemical properties/functions), in the context of the present invention it is preferred to express homology in terms of sequence identity.

The homologous amino acid sequence and/or nucleotide sequence may provide and/or encode a polypeptide which retains the functional activity and/or enhances the activity of the polypeptide.

In some aspects, an amino acid sequence as described herein has at least 50, 60, 70, 75, 80, 85 or 90% identity, in some embodiments at least 95, 96, 97, 98 or 99% identity to the subject sequence.

In some aspects, a nucleotide sequence as described herein has at least 50, 60, 70, 75, 80, 85 or 90% identity, in some embodiments at least 95, 96, 97, 98 or 99% identity to the subject sequence.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment so that, for the same number of identical amino acids, a sequence alignment with as few gaps as possible-reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps. Most alignment programs allow the gap penalties to be modified. Typically the default values are used when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed-Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate homology, for example % sequence identity. The software typically does this as part of the sequence comparison and generates a numerical result.

Should Gap Penalties be used when determining sequence identity, then the following parameters can be used for pairwise alignment for example:

| FOR BLAST | | | |
|---|---|---|---|
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

In one embodiment, the degree of identity with regard to a nucleotide sequence is determined over at least 20 contiguous nucleotides, for example over at least 30 contiguous nucleotides, for example over at least 40 contiguous nucleotides, for example over at least 50 contiguous nucleotides, for example over at least 60 contiguous nucleotides, for example over at least 100 contiguous nucleotides, for example over at least 200 contiguous nucleotides, for example over at least 300 contiguous nucleotides.

In one embodiment, the degree of identity with regard to a nucleotide sequence may be determined over the whole sequence.

Recombinant

In one aspect the *Roseburia* flagellin polypeptide and/or polynucleotide sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, Molecular Cloning: A Laboratory Manual, Second Edition, Books 1-3, Cold Spring Harbor Laboratory Press.

Synthetic

In one aspect the *Roseburia* flagellin polynucleotide sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

Expression of Enzymes

The nucleotide sequence for use in the present invention may be incorporated into a recombinant replicable vector. The vector may be used to replicate and express the nucleotide sequence, in protein form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

In one aspect, the present invention relates to a vector (such as an expression vector) comprising at least one polynucleotide sequence encoding at least one Roseburia flagellin.

The term "expression vector" means a construct capable of in vivo or in vitro expression.

In one embodiment, the expression vector is incorporated into the genome of a suitable host organism. The term "incorporated" in one aspect covers stable incorporation into the genome.

The nucleotide sequence of the present description may be present in a vector in which the nucleotide sequence is operably linked to regulatory sequences capable of providing for the expression of the nucleotide sequence by a suitable host cell or host organism.

The vectors for use in the present invention may be transformed into a suitable host cell or host organism as described herein to provide for expression of a polypeptide of the present description.

The choice of vector e.g. a plasmid, cosmid, or phage vector will often depend on the host cell into which it is to be introduced.

The vectors for use in the present invention may contain one or more selectable marker genes—such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the description provides a method of making nucleotide sequences of the present description by introducing a nucleotide sequence of the present description into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

An expression vector may comprise at least two, three, four or five polynucleotide sequences encoding Roseburia flagellins.

Examples of expression vectors include pGEX-6P-1, pCR-Blunt II-TOPO and T7-MAT-Tag-FLAG-.

The expression vector pGEX-6P-1 may be used for cloning recombinant flagellins. The expression vector pGEX-6P-1 comprises a tac promoter for chemically inducible, high-level expression of GST-tagged recombinant proteins, an internal lacI.sub.q gene for use in any E. coli host, an AmpR gene for ampicillin selection and a PreScission Protease site for cleaving, if desired, the protein from the fusion product.

The cloning vector pCR-Blunt II-TOPO may be used for cloning recombinant flagellins, in particular those which are insoluble after cell lysis. Typically this vector allows high-efficiency DNA cloning of blunt-end PCR products. The vector comprises Kanamycin and Zeocin resistance genes for selection in E. coli, and the insert is flanked by multiples restriction sites for excision.

Expression vector 17-MAT-Tag-FLAG—may be used for cloning recombinant flagellins, in particular those which insoluble after cell lysis. The multi cloning site (MCS) is flanked by MAT (Metal Affinity Tag) sequence and FLAG peptide (Asp-Tyr-Lys-Asp-Asp-Asp-Asp-Lys; SEQ ID NO: 13) sequence, which results in the production of double-tagged flagellin, which can be further purified by affinity columns. This expression vector also comprises a pT7/lac (phage T7 lac operon) promoter for IPTG inducible, high-level expression of MAT-ORF-FLAG recombinant flagellins, an internal lacI gene that represses transcription at basal state in any E. coli host, and an AmpR gene for ampicillin selection.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding a flagellin of the present description may also be achieved by the selection of heterologous regulatory regions, e.g. promoter, secretion leader and terminator regions.

In one embodiment, the nucleotide sequence according to the present description is operably linked to at least a promoter.

Other promoters may even be used to direct expression of the polypeptide of the present description.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present description. The same is true for the term "fused" in relation to the present description which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, the construct of the present description comprises at least the nucleotide sequence of the present description operably linked to a promoter.

Host Cells

The term "host cell"—in relation to the present description includes any cell that comprises the nucleotide sequence and/or an expression vector as described herein. Typically the host cell is capable of the recombinant production of a protein having the specific properties as defined herein.

Examples of host cells include bacteria such as *Roseburia* spp. and competent cells. Examples of *Roseburia* spp are *Roseburia hominis*, *Roseburia cecicola*, *Roseburia faecis*, *Roseburia intestinalis*, and *Roseburia inulinivorans*. Examples of competent cells include competent *E. coli* cells (such as *E. coli* BL21(DE3) pLysS and/or *E. coli* B21 Rosetta).

Thus, a further embodiment of the present description provides host cells transformed or transfected with a nucleotide sequence of the present description. In addition, or alternatively, a further embodiment of the present description provides host cells transformed or transfected with a nucleotide sequence (e.g. a promoter such as a heterologous promoter or an exogenous) that is capable of upregulating (overexpressing) the expression of a nucleotide sequence (e.g. gene—such as a homologous gene or an endogenous gene) encoding a flagellin of the present description when compared to the equivalent microorganism prior to transformation. The cells will be chosen to be compatible with the said vector and may for example be bacterial (e.g. prokaryotic), fungal, or yeast cells.

The nucleotide sequence encoding the flagellin of the present description may be heterologous or homologous to the host cell. Typically when the nucleotide sequence encoding the flagellin is homologous to the host cell the host cell comprises multiple copies of the nucleotide sequence. In addition or alternatively, the nucleotide sequence encoding the flagellin is operably linked to a heterologous promoter, typically said promoter is capable of upregulating (overexpressing) the homologous nucleotide sequence encoding the flagellin.

In one example, the host cell comprises the nucleotide sequence coding for the flagellin polypeptide of the present description (such as a homologous or endogenous nucleotide sequence) under the control of a heterologous or exogenous promoter.

In one embodiment, the host cell is transformed or transfected with one or more nucleotide sequences that encodes at least one flagellin (e.g. *Roseburia* flagellin) selected from the group consisting of Fla1, Fla2, Fla3 and Fla4. In another embodiment, the host cell is transformed or transfected with one or more nucleotide sequences that encode at least one flagellin (e.g. *Roseburia* flagellin) selected from the group consisting of Fla2, Fla1 and Fla4. In a further embodiment, the host cell is transformed or transfected with a nucleotide sequences that encodes the flagellin (e.g. *Roseburia* flagellin) Fla2.

The host cell may comprise multiple copies of polynucleotide sequences encoding *Roseburia* flagellins.

A host cell may comprise at least 1, 2, 3, 4 or 5 polynucleotide sequences encoding at least 1, 2, 3, 4 or 5 *Roseburia* flagellins.

In one embodiment, the host cell comprises a polynucleotide sequence encoding at least one *Roseburia* flagellin derived or derivable from one *Roseburia* species and at least one further polynucleotide sequence encoding at least one *Roseburia* flagellin derived or derivable from a different *Roseburia* species. For example, the host cell comprises at least one polynucleotide sequence encoding an *R. hominis* flagellin (e.g. Fla1 or Fla2) and at least one polynucleotide sequence encoding a *R. intestinalis* flagellin (e.g. Fla1 or Fla 2).

A host cell may comprise at least 1, 2, 3, 4 or 5 expression vectors comprising at least 1, 2, 3, 4 or 5 polynucleotide sequences encoding *Roseburia* flagellin.

In one embodiment, the host cell comprises an expression vector comprising a polynucleotide sequence encoding *Roseburia* flagellins derived or derivable from one *Roseburia* species and at least one further expression vector comprising a polynucleotide sequence encoding *Roseburia* flagellins derived or derivable from a different *Roseburia* species. For example, the host cell comprises at least one expression vector comprising a polynucleotide sequence encoding an *R. hominis* flagellin (e.g. Fla1 or Fla2) and at least one expression vector comprising a polynucleotide sequence encoding a *R. intestinalis* flagellin (e.g. Fla1 or Fla 2).

The nucleotide sequence encoding the flagellin may be endogenous or exogenous to the host cell. Typically when the nucleotide sequence encoding the flagellin is endogenous to the host cell the host cell comprises multiple copies of the nucleotide sequence. In addition or alternatively, the nucleotide sequence encoding the flagellin is operably linked to an exogenous promoter; typically said promoter is capable of upregulating (overexpressing) the endogenous nucleotide sequence encoding the flagellin.

Examples of suitable bacterial host organisms are gram positive or gram negative bacterial species.

In one embodiment, the host cell is a microorganism.

In one embodiment, the host cell is a lactic acid bacterium species, *Lactococcus* species, a *Bifidobacterium* species, a *Lactobacillus* species or a *Propionibacterium* species.

Examples of lactic acid bacteria include, but are not limited to, *Lactobacillus* spp., *Leuconostoc* spp., *Pediococcus* spp., *Lactococcus* spp., *Streptococcus* spp., *Aerococcus* spp., *Camobacterium* spp., *Enterococcus* spp., *Oenococcus* spp., *Sporolactobacillus* spp., *Tetragenococcus* spp., *Vagococcus* spp., and *Weisella* spp.

Examples of *Lactobacillus* spp include *Lactobacillus paracasei*, *L. acidophilus*, *L. fermentum*, *L. brevis*, *L. gasseri*, *L. plantarum*, *L. bulgaricus*, *L. helveticus*, *L. reuteri*, *L. casei*, *L. jensenii*, *L. rhamnosus*, *L. crispatus*, *L. johnsonii*, *L. salivarius*, *L. acetotolerans*, *L. acidifarinae*, *L. acidipiscis*, *L. agilis*, *L. algidus*, *L. alimentarius*, *L. amylolyticus*, *L. amylophilus*, *L. amylotrophicus*, *L. amylovorus*, *L. animalis*, *L. antri*, *L. apodemi*, *L. aviarius*, *L. bifermentans*, *L. buchneri*, *L. camelliae*, *L. catenaformis*, *L. ceti*, *L. coleohominis*, *L. collinoides*, *L. composti*, *L. concavus*, *L. coryniformis*, *L. crustorum*, *L. curvatus*, *L. delbrueckii* subsp. *delbrueckii*, *L. delbrueckii* subsp. *bulgaricus*, *L. delbrueckii* subsp. *lactis*, *L. dextrinicus*, *L. diolivorans*, *L. equi*, *L. equigenerosi*, *L. farraginis*, *L. farciminis*, *L. fomicalis*, *L. fructivorans*, *L. frumenti*, *L. fuchuensis*, *L. galUnarum*, *L. gastricus*, *L. ghanensis*, *L. graminis*, *L. hammesii*, *L. hamsteri*, *L. har-*

*binensis, L. hayakitensis, L. hilgardii, L. homohiochii, L. iners, L. ingluviei, L. intestinalis, L. kalixensis, L. kefuranofaciens, L. kefiri, L. kimchii, L. kitasatonis, L. kunkeei, L. leichmannii, L. lindneri, L. malefermentans, L. mail, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracollinoides, L. parafarraginis, L. parakefiri, L. paralimentarius, L. paraplantarum, L. pentosus, L. perolens, L. pontis, L. psittaci, L. rennini, L. rimae, L. rogosae, L. rossiae, L. ruminis, L. saerimneri, L. sakei, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae*, and *L. zymae.*

Examples of *Propionibacterium* include, but are not limited to *Propionibacterium freudenrechli* subsp. *shermanfi* (PAB), *Propionibacterium acidifaciens, Propionibacterium acidipropionici, Propionibacterium acnes, Propionibacterium australiense, Propionibacterium avidum, Propionibacterium cyclohexanicum, Propionibacterium freudenrelchli* subsp. *freudenrelchli, Propionibacterium granulosum, Propionibacterium jensenii, Propionibacterium microaerophilum, Propionibacterium propionicum*, and *Propionibacterium thoenii.*

In one embodiment, the *Propionibacterium* is *Propionibacterium freudenrechli* subsp. *shermanfi* (PAB).

Examples of *Bifidobacterium* include, but are not limited to, *Bifidobacterium adolescentis, B. breve, B. longum, B. animalis, B. infantis, B. thermophilum, B. bifidum, Bifidobacterium catenulatum, Bifidobacterium pseudocatenulatum, Bifidobacterium angulatum* and *B. lactis.*

In another embodiment, the host cell is a Firmicute—for example a *Roseburia* species such as *Roseburia hominis, Roseburia cecicola, Roseburia faecis, Roseburia intestinalis*, or *Roseburia inulinivorans*). In one embodiment, the host cell comprises at least one heterologous polynucleotide sequence encoding a *Roseburia* flagellin. In addition or alternatively, the host cell comprises at least two copies of a homologous polynucleotide sequence encoding a *Roseburia* flagellin; for instance, the host cell comprises at least 3, 4 or 5 homologous copies of a polynucleotide sequence encoding a *Roseburia* flagellin.

Depending on the nature of the nucleotide sequence encoding the polypeptide of the present description, and/or the desirability for further processing of the expressed protein, eukaryotic hosts such as yeasts or other fungi may be used. In general, yeast cells are used over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lipidation and tyrosine, serine or threonine phosphorylation) as may be needed to confer optimal biological activity on recombinant expression products of the present description.

The host cell may be a protease deficient or protease minus strain. This may for example be the protease deficient strain *Aspergillus oryzae* JaL 125 having the alkaline protease gene named "alp" deleted. This strain is described in WO97/35956.

The term "host cell" does not cover native nucleotide coding sequences in their natural environment when they are under the control of their native promoter which is also in its natural environment.

Organism

The term "organism" in relation to the present description includes any organism that could comprise the nucleotide sequence coding for the polypeptide according to the present description and/or products obtained therefrom, and/or wherein a promoter can allow expression of the nucleotide sequence according to the present description when present in the organism.

Suitable organisms may include a bacterium (such as a prokaryote), a fungus, a yeast or a plant.

The term "transgenic organism" in relation to the present description includes any organism that comprises the nucleotide sequence coding for the polypeptide according to the present description and/or the products obtained therefrom, and/or wherein a promoter can allow expression of the nucleotide sequence according to the present description within the organism. In one embodiment the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present description includes an organism comprising any one of, or combinations of, the nucleotide sequence coding for the polypeptide according to the present description, constructs according to the present description, vectors according to the present description, plasmids according to the present description, cells according to the present description, or the products thereof.

For example the transgenic organism may comprise the nucleotide sequence coding for the polypeptide of the present description (such as a homologous nucleotide sequence) under the control of a heterologous promoter.

Transformation of Host Cells/Organism

As indicated earlier, the host organism can be a prokaryotic or a eukaryotic organism. Examples of suitable prokaryotic hosts include *Roseburia hominis, Roseburia cecicola, Roseburia faecis, Roseburia intestinalis, Roseburia inulinivorans, E. coli* and *Bacillus subtilis.*

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation-such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (Annu Rev Plant Physiol Plant Mol Biol [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a mould. Examples of suitable such hosts include any member belonging to the genera *Thermomyces, Acremonium, Aspergillus, Penicillium, Mucor, Neurospora, Trichoderma* and the like.

In one embodiment, the host organism may be a filamentous fungus.

Transforming filamentous fungi is discussed in U.S. Pat. No. 5,741,665 which states that standard techniques for transformation of filamentous fungi and culturing the fungi are well known in the art. An extensive review of techniques as applied to *N. crassa* is found, for example in Davis and de Serres, Methods Enzymol (1971) 17A: 79-143.

Further teachings which may also be utilised in transforming filamentous fungi are reviewed in U.S. Pat. No. 5,674,707.

In addition, gene expression in filamentous fungi is taught in Punt et al. (2002) Trends Biotechnol 2002 May; 20(5): 200-6, Archer & Peberdy Crit Rev Biotechnol (1997) 17(4): 273-306.

The present description encompasses the production of transgenic filamentous fungi according to the present description prepared by use of these standard techniques.

In one aspect, the host organism can be of the genus *Aspergillus*, such as *Aspergillus niger*.

A transgenic *Aspergillus* according to the present description can also be prepared by following, for example, the teachings of Turner G. 1994 (Vectors for genetic manipulation. In: Martinelli S. D., Kinghorn J. R. (Editors) *Aspergillus:* 50 years on. Progress in industrial microbiology vol 29. Elsevier Amsterdam 1994. pp. 641-666).

Transformed Yeast

In another embodiment, the transgenic organism can be a yeast.

A review of the principles of heterologous gene expression in yeast are provided in, for example, Methods Mol Biol (1995), 49:341-54, and Curr Opin Biotechnol (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present description can be prepared by following the teachings of Hinnen et al., (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells may be selected using various selective markers—such as auxotrophic markers dominant antibiotic resistance markers.

Transformed Plants/Plant Cells

A host organism suitable for the present description may be a plant. In this respect, the basic principle in the construction of genetically modified plants is to insert genetic information in the plant genome so as to obtain a stable maintenance of the inserted genetic material. A review of the general techniques may be found in articles by Potrykus (Annu Rev Plant Physiol Plant Mol Biol [1991] 42:205-225) and Christou (Agro-Food-Industry Hi-Tech March/April 1994 17-27).

Direct infection of plant tissues by *Agrobacterium* is a simple technique which has been widely employed and which is described in Butcher D. N. et al., (1980), Tissue Culture Methods for Plant Pathologists, eds.: D. S. Ingrams and J. P. Helgeson, 203-208.

Other techniques for transforming plants include ballistic transformation, the silicon whisker carbide technique (see Frame B R, Drayton P R, Bagnaall S V, Lewnau C J, Bullock W P, Wilson H M, Dunwell J M, Thompson J A & Wang K (1994) Production of fertile transgenic maize plants by silicon carbide whisker-mediated transformation, The Plant Journal 6: 941-948) and viral transformation techniques (e.g. see Meyer P, Heidmann I & Niedenhof I (1992) The use of cassava mosaic virus as a vector system for plants, Gene 110: 213-217).

Further teachings on plant transformation may be found in EP-A-0449375.

Plant cells may be grown and maintained in accordance with well-known tissue culturing methods such as by culturing the cells in a suitable culture medium supplied with the necessary growth factors such as amino acids, plant hormones, vitamins, etc.

In a further aspect, the present description relates to a vector system which carries a nucleotide sequence or construct according to the present description and which is capable of introducing the nucleotide sequence or construct into the genome of an organism, such as a plant. The vector system may comprise one vector, but it may comprise two vectors. In the case of two vectors, the vector system is normally referred to as a binary vector system. Binary vector systems are described in further detail in Gynheung An et al., (1980), Binary Vectors, Plant Molecular Biology Manual A3, 1-19.

One extensively employed system for transformation of plant cells uses the Ti plasmid from *Agrobacterium tumefaciens* or a Ri plasmid from *Agrobacterium rhizogenes* An et al., (1986), Plant Physiol. 81, 301-305 and Butcher D. N. et al., (1980), Tissue Culture Methods for Plant Pathologists, eds.: D. S. Ingrams and J. P. Helgeson, 203-208. After each introduction method of the desired promoter or construct or nucleotide sequence according to the present description in the plants, the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1-46; and An et al., EMBO J. (1985) 4:277-284.

Culturing and Production

Host cells transformed with the nucleotide sequence of the present description and/or an expression vector of the present description may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

In some embodiments, the protein is secreted from the expression host into the culture medium from where the protein may be recovered. According to the present description, the secretion leader sequence may be selected on the basis of the desired expression host. Hybrid signal sequences may also be used with the context of the present description.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

The amino acid sequence for use according to the present description may be produced as a fusion protein, for example to aid in extraction and purification. Examples of fusion protein partners include glutathione-5-transferase (GST), 6.times.His, GAL4 (DNA binding and/or transcriptional activation domains) and (β-galactosidase). It may also be convenient to include a proteolytic cleavage site between the fusion protein partner and the protein sequence of interest to allow removal of fusion protein sequences.

Typically, the fusion protein will not hinder the activity of the protein sequence.

Gene fusion expression systems in *E. coli* have been reviewed in Curr Opin Biotechnol (1995)6(5):501-6.

In another embodiment, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The present invention is further described by way of the following non-limiting examples.

Examples

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; and E. M. Shevach and W. Strober, 1992 and periodic supplements, Current Protocols in Immunology, John Wiley & Sons, New York, N.Y. Each of these general texts is herein incorporated by reference.

Material and Methods

*Roseburia* Genus Flagellins

Flagellin Diversity

Flagellins from *Roseburia* genus bacteria, in particular, *Roseburia hominis* and *Roseburia intestinalis* were cloned, expressed, purified and analysed.

FIGS. 18A and 18B show an SDS-Analysis of recombinant flagellins.

Flagellin Protein Nomenclature:
  *Roseburia* Genus
  *Roseburia* Species
  *Roseburia hominis*
    *Roseburia hominis* FlaA1 (This is also referred herein as RhFlaA1 or Rh1)
    *Roseburia hominis* FlaA2 (This is also referred herein as RhFlaA2 or Rh2)
  *Roseburia intestinalis*
    *Roseburia intestinalis* FlaA1 (This is also referred herein as RiFlaA1 or Ri1 or RI1)
    *Roseburia intestinalis* FlaA2 (This is also referred herein as RiFlaA2 or Ri2 or RI2)
    *Roseburia intestinalis* FlaA3 (This is also referred herein as RiFlaA3 or Ri3 or RI3)
    *Roseburia intestinalis* FlaA4 (This is also referred herein as RiFlaA1 or Ri4 or RI4)

ELY, B., ELY, T. W., CRYMES, W. B., JR and MINNICH, S. A., 2000. A family of six flagellin genes contributes to the *Caulobacter crescentus* flagellar filament. *Journal of Bacteriology,* 182(17), pp. 5001-5004.

IBRAHIM, G. F., FLEET, G. H., LYONS, M. J. and WALKER, R. A., 1985. Method for the isolation of highly purified *Salmonella* flagellins. *Journal of clinical microbiology,* 22(6), pp. 1040-1044.

NEVILLE, B. A., FORDE, B. M., CLAESSON, M. J., DARBY, T., COGHLAN, A., NALLY, K., ROSS, R. P. and OTOOLE, P. W., 2012. Characterization of pro-inflammatory flagellin proteins produced by *Lactobacillus* ruminis and related motile Lactobacilli. *PloS one,* 7(7), pp. e40592.

NG, S. Y., CHABAN, B. and JARRELL, K. F., 2006. Archaeal flagella, bacterial flagella and type IV pili: a comparison of genes and posttranslational modifications. *Journal of Molecular Microbiology and Biotechnology*, 11(3-5), pp. 167-191.

WATSON, R. O. and GALAN, J. E., 2005. Signal transduction in *Campylobacter jejuni*-induced cytokine production. *Cellular microbiology*, 7(5), pp. 655-665.

Bacterial Growth Conditions

*R. hominis* A2-183.sup.T (=DSM 16839.sup.T=NCIMB 14029.sup.T) was grown anaerobically at 37° C. in YCFA media. The culture was spun down and the pellet was resuspended in one mL of YCFA media, supplemented with 2% cysteine (w/v, Sigma-Aldrich) and 3% ascorbic acid (w/v, Sigma-Aldrich).

*R. intestinalis* L1-82.sup.T (=DSM 14610.sup.T=NCIMB 13810.sup.T) was grown anaerobically at 37° C. in YCFA media. The culture was spun down and the pellet was resuspended in one mL of YCFA media, supplemented with 2% cysteine (w/v, Sigma-Aldrich) and 3% ascorbic acid (w/v, Sigma-Aldrich).

Mice

C3H/HeN and C57Bl/6 were purchased from Harlan Laboratories. GF C3H/HeN were provided and maintained in the INRA gnotobiotic rodent breeding facility at Jouy-en-Josas (ANAXEM plateform, Institut Micalis, INRA, Jouy-en-Josas, France). GF TLR5KO and wild type C57Bl/6 were provided by Andrew Gewirtz (Center for Inflammation, Immunity, and Infection and Department of Biology, Georgia State University, Atlanta, Ga. 30303, USA) and maintained in the INRA gnotobiotic rodent breeding facility at Jouy-en-Josas. Conventional TLR5KO and wild type BOY/J were provided by Adam Cunningham (MRC Centre for Immune Regulation, Institute of Microbiology and Infection, Division of Immunity and Infection University of Birmingham UK) The management and experimental procedures were approved by the respective Local Ethical Review Committees.

Animal Experiments

Germfree animal experiments were performed in the INRA gnotobiotic rodent breeding facility at Jouy-en-Josas (ANAXEM plateform, Institut Micalis, INRA, Jouy-en-Josas, France). GF C3H/HeN male mice were allocated into control (N=8) and treatment (N=10) groups and caged individually in plastic isolators. At day 0, 1 and 2, animals in the treatment group were given 100 µL of *R. hominis* culture by gavage, while control animals were given 100 µL YCFA media. Ileum, ascending colon and caecum samples were collected at 14 d and 28 d. Six GF C3H/HeN male mice were treated with *E. coli* MG1655 (K12) as described above, and three animals were sacrificed at 10 d and 22 d to give N=3. Three GF TLR5KO mice and three C57Bl/6 WT mice were inoculated with *R. hominis* culture as described above to evaluate the functional importance of *R. hominis* flagellins. After 28 d these animals were sacrificed together with their GF counterparts. Twenty-two female C57BL/6 mice were dosed daily with 50 µL of 10.sup.9 CFU *R. hominis* for 14 days. Control animals were dosed with culture medium alone. From day 8, mice were given DSS (MW 50 kDa, 30 g/l) in their drinking water for 6 days. The animals were euthanized on day 14 and tissue sampling was performed as described above.

Tissue Culture Experiments

Caco-2 (*Homo sapiens* epithelia; colorectal adenocarcinoma cells) and HT29 (*Homo sapiens* colorectal adenocarcinoma) cells were grown in transwell plates within an anaerobic workstation. *R. hominis* A2-183 culture or *R. intestinalis* L1-82.sup.T was harvested at exponential phase, and 100 µL of bacterial suspension (10.sup.8 CFU/mL) was added to experimental wells. Bacterial (non-adherent and adherent) and eukaryotic cells (Caco-2 and HT-29) were harvested after 2 h and 4 h incubation and stored in RNAlater. For tissue culture experiments with recombinant flagellins, 5.times.10.sup.4 Caco-2 cells were grown in 24-well plates at 37° C. in a 75% humidified atmosphere of 5% CO2. The cells reached confluence on day 5-6 and were used three days post-confluence. The cells were incubated with recombinant flagellins at a final concentration of 100 ng/µl for 2 hr at 37° C. in a 75% humidified atmosphere of 5% CO.sub.2.

FISH Analysis

FISH analysis was performed on neutral buffered formalin-fixed gut tissue sections using a general bacterial probe Eub338 and a newly designed *R. hominis* A2-183-specific probe and a *R. intestinalis* L1-82.sup.T specific probe.

*R. hominis* Library Construction

*R. hominis* chromosomal DNA for small-size library construction and pyrosequencing was isolated using an UltraClean™ Microbial DNA Isolation Kit (Mo Bio Laboratories Inc) and high-molecular-weight DNA for fosmid libraries was isolated using a Wizard Genomic DNA Purification kit (Promega).

Microarray Analyses

Bacterial Microarray

Bacterial RNA was isolated from mouse caecum contents and further processed using commercial kits following the manufacturer's recommendations. PCR products amplified from 6000 clones in the *E. coli* plasmid library of *R. hominis* were arrayed in duplicate on aminosilane-coated microscope slides (Corning) using a MicroGrid II TAS (BioRobotics).

Mouse Microarray Analysis

Total RNA was extracted from ileum and ascending colon tissue, processed into biotin-labelled cRNA/aRNA (depending on Affymetrix kit used), and hybridized to the GeneChip NuGO Mouse Array and GeneChip Mouse Genome Array (Affymetrix) using standard techniques. Data analysis was performed with the software packages R (http://www.r-project.org) and Bioconductor (http://www.bioconductor.org).

RT-PCR Analysis

The *R. hominis*-specific primers 5'-CCCACTGACAGAGTATGTAATGTAC-3'(SEQ ID NO: 14) and 5'-GCAC-CACCTGTCACCAC-3'(SEQ ID NO 15) were used for PCR analysis of faecal samples to validate gut colonization levels. Real-time PCR analysis was performed using a 7500 Fast Real-Time PCR System (Applied Biosystems) with the Power SYBR Green PCR Master Mix (Applied Biosystems). All samples were run in triplicate. GyrA was used as a reference gene for normalization. For host gene expression, total eukaryotic RNA isolated from the ileum and ascending colon was reverse-transcribed into cDNA using the High Capacity cDNA Reverse Transcription Kit (Applied Biosystems). Real-time PCR analysis was performed using a 7500 Fast Real-Time PCR System (Applied Biosystems) with the QuantiFast SYBR Green PCR Kit (Qiagen) and QuantiTect Primer Assays (Qiagen). All samples were run in triplicate. Hprt was selected as a reference gene for normalization. All RT-PCR data were analyzed on a logarithmic scale with base 2 by one-way ANOVA with a significance cut-off of $P<0.05$. Differences were back-transformed to calculate fold changes.

Western Blot

Immuno-purified rabbit polyclonal antibodies against *Roseburia hominis* FlaA1 and FlaA2 was produced as described in Duck et al. (Duck et al. 2007). For the western blot, *R. hominis* was grown in the presence of varying amounts (0.01 g to 1 g diet/10 mL of culture) of UV irradiated standard mouse chow for 3 hrs, filtered to remove dietary components and diluted in laemmli buffer containing 8M urea. Samples were loaded on a NuPAGE® Novex® 4-12% Bis-Tris gel (Invitrogen) and electrophoresed, followed by further processing using the WesternBreeze Chromogenic Immunodetection System (Invitrogen). FlaA1 and FlaA2 antibodies were used at 1:1000 and loading control anti-DNA gyrase A (Abcam) at 1:300, followed by alkaline phosphatase conjugated anti-rabbit. Detection was by substrate colour development relative to loading control colour development.

Immunofluorescence

Immuno-localization of *R. hominis* flagellin was examined in colon contents of mice using specific antisera raised against defined peptide sequences from both FlaA1 and FlaA2 flagellin proteins. Gut content smears were fixed in pre-cooled methanol, incubated with anti-FlaA1 or anti-FlaA2 rabbit antisera (CovaLabs) at 4° C. overnight and visualized using Alexa donkey anti rabbit 488 (Molecular Probes).

T cell markers were examined on sequential 8 μm cryosection. Fixed tissue sections were incubated with Ly6G-FITC, CD3-FITC, CD11b-FITC (BD Biosciences), double-labelled with FoxP3 (Abcam) and CD3-FITC (BD Biosciences) primary antibody or isospecific IgG. Sections were counterstained with DAPI and mounted with Vectashield (Vector Laboratories). For quantification of positive cells, a minimum of five fields of view from each mouse section was examined.

Cloning and Purification of Recombinant Flagellins

Flagellin genes were isolated from liquid bacterial cultures of *R. hominis*, *R. intestinalis*, *S. typhimurium*, *S. enteritidis*, *Eubacterium* rectale 33656 and *E. coli* K12 by PCR amplification and purification. Caco-2 cells were incubated with recombinant flagellins at a final concentration of 100 ng/μL for 2 h at 37° C. in a 75% humidified atmosphere of 5% CO2.

Isolation of Intestinal and MLN Cells

Cells were isolated from the small intestine and mesenteric lymph node as previously described with minor modifications (Monteleone et al. 2008). Briefly, cellular suspensions were incubated with 100 U/mL collagenase VIII (Sigma-Aldrich) in RPMI supplemented with 20% FBS at 37° C. for 20 min (mesenteric lymph nodes) or 1 hour (intestinal pieces). Single cell suspensions were then analyzed by flow cytometry (as described).

Generation of Bone Marrow-Derived Dendritic Cells and Cultures

Bone marrow was harvested from femur and tibia of C3H/HeN and C57l6 mice. For GMCSF-derived dendritic cells, bone marrow cells were resuspended at $1 \times 10^6$/mL in RPMI supplemented with 10% FCS and 20 ng/mL rmGM-CSF and seeded at 10 mL/plate in 100 mm$^2$ tissue culture plates. After three days culture, loosely adherent cells were collected and replated with GM-CSF supplemented media at $1 \times 10^6$/mL in 12 well tissue culture plates. At day 5, cells were stimulated with 100 ng/mL flagellins before being harvested on day 6. For Flt3L-derived dendritic cells, bone marrow cells were resuspended at $2 \times 10^6$/mL in RPMI supplemented with 10% FCS and 200 ng/mL rmFlt3 and seeded at 2 mL/well in 12-well tissue culture plates. Cells were cultured for 10 days with Flt3 supplemented media added to each well on day 4. At day 9, cells were stimulated with 100 ng/mL flagellins before being harvested on day 10 and analyzed by flow cytometry.

Flow Cytometry

Single cell suspensions of lamina propria cells and dendritic cells were incubated in blocking buffer (containing serum and CD16/CD32 antibody) at 4° C. for 15 min prior to staining with specific fluorochrome conjugated antibodies. Lamina propria cells were labelling with antibodies to mouse CD4-FITC and CD25-APC (eBioscience), CD8-APC-Cy7 and CD3-PerCP (Biolegend), and B220-BV570 (BD Biosciences). Intracellular FoxP3 labelling was performed after extracellular staining and cell fixation/permeabilisation according to the manufacturer's instructions (eBioscience). GMCSF-derived dendritic cells were labelled with antibodies CD11c-PE-Cy7, CD11-PerCP Cy5, I-A/I-E-APC-Cy7, CD80-PE, CD86-APC, CD8-FITC, B220-BV570. Flt3 derived dendritic cells were labelled with CD11c-PE-Cy7-, CD11b- or Siglec-H-PerCP Cy5-, I-A/I-E-APC-Cy7, CD317-PE, CD40-APC, CD103-FITC, B220-BV570 Cells were analyzed using a FACSArria (BD Biosciences) and FlowJo software version 7.2.5.

Cytometric Bead Array (CBA)

Bone marrow cells were isolated from femur and tibia with RPMI media of C3H/HeN and C57Bl/6 mice and Flt3L-expanded as described previously. Cells were stimulated with 100 ng/mL flagellin (e.g. *Roseburia* flagellin) after 9 days of culture, and supernatant was collected on day 10. The experiment was performed on three separate occasions to create N=3.

CBA analysis was performed on cell supernatants using the Cytometric Bead Array Mouse Enhanced Sensitivity Master Buffer Kit (BD Biosciences). Standards and samples were loaded onto a 96-well plate for measurement in a FACSArray (BD Biosciences). Results were analyzed using BD FCAP software (BD Biosciences).

Histology

Ascending colon tissue samples were fixed in neutral buffered formalin (Sigma), embedded in cold-curing resin, and 4 μm tissue sections were stained using standard haemotoxylin/eosin methods. A complete transverse cross sectional area of colon from each animal was imaged at .times.200 magnification on a Zeiss Axioskop microscope using a QImaging camera controlled by Image Pro Plus software. Each field of view was then scored from 0-4 according to a method based on Berg et al. (Berg et al. 1996). The mean percentage of fields of view at a given grade was calculated and treatment groups were compared using student t-test analysis.

Further detailed protocols are described in the supplementary Materials and Methods.

Supplementary Information (SI) Materials and Methods

Bacterial Growth Conditions

*R. hominis* A2-183.sup.T (=DSM 16839.sup.T=NCIMB 14029.sup.T) was grown anaerobically on synthetic YCFA or complex M2GSC media. Culture was inoculated from frozen stock into Hungate tubes and incubated overnight at 37° C. Bacteria were then grown on M2GSC agar plates for 48 h in a MACS-MG-1000 anaerobic workstation (Don Whitley Scientific) under 80% $N_2$, 10% $CO_2$, and 10% $H_2$ at 37° C. The effect of mucin was investigated by adding 0.5% (w/v) mucin from porcine stomach type III (Sigma-Aldrich) to the YCFA medium.

For colonization of germfree (GF) mice, *R. hominis* was grown in YCFA media overnight at 37° C. The culture was spun down and the pellet was resuspended in one mL of YCFA media, supplemented with 2% cysteine (w/v, Sigma-Aldrich) and 3% ascorbic acid (w/v, Sigma-Aldrich).

Mice

C3H/HeN and C57Bl/6 were purchased from Harlan Laboratories. Mice were housed within HEPA-filtered flexi-film isolators (Bell Isolation Systems) at the University of Aberdeen. GF C3H/HeN were provided and maintained in the INRA gnotobiotic rodent breeding facility at Jouy-en-Josas (ANAXEM plateform, Institut Micalis, INRA, Jouy-en-Josas, France). Germfree TLR5KO and wild type C57Bl/6 were provided by Andrew Gewirtz (Center for Inflammation, Immunity, and Infection and Department of Biology, Georgia State University, Atlanta, Ga. 30303, USA) and maintained in the INRA gnotobiotic rodent breeding facility at Jouy-en-Josas. The management and experimental procedures were approved by the respective Local Ethical Review Committees.

Mouse Experiments

Eighteen GF C3H/HeN male mice were allocated into control (N=8) and treatment (N=10) groups and caged individually in plastic isolators. The mice were fed ad libitum on a sterilized commercial diet (R03-40; UAR). At day 0, 1 and 2, animals in the treatment group were given 100 μL of R. hominis culture by gavage, while control animals were given 100 μL YCFA media. At 14 d and 28 d, four control animals and five R. hominis-treated animals were sacrificed. The ileum and ascending colon were divided into four equal parts and transferred to RNAlater (Ambion), neutral buffered formalin (NBF; Sigma-Aldrich) or liquid nitrogen. The whole caecum was transferred to RNAlater.

To demonstrate the specificity of the response to R. hominis, six GF C3H/HeN male mice were treated with E. coli MG1655 (K12), and three animals were sacrificed at 10 d and 22 d as described above to give N=3.

Three GF TLR5KO mice and three C57Bl/6 WT mice were inoculated with R. hominis culture as described above to evaluate the functional importance of R. hominis flagellins. After 28 d these animals were sacrificed together with their GF counterparts.

Twenty-two female C57BL/6 mice (6 weeks old) were used to evaluate the therapeutic effect of R. hominis during DSS-induced colitis. After an acclimatization period of 7-10 days, the mice were dosed daily with 50 μL of $10^9$ CFU R. hominis for 14 days. Control animals were dosed with culture medium alone. From day 8, mice were given DSS (MW 50 kDa, 30 g/l) in their drinking water for 6 days. The animals were euthanized on day 14 and tissue sampling was performed as described above.

Tissue Culture Experiments

All cell culture reagents, unless specified otherwise, were supplied by Sigma-Aldrich. For tissue culture experiments in anaerobic conditions, $2 \times 10^5$ Caco-2 or HT29 cells in 1.5 mL DMEM (high glucose, HEPES) medium supplemented with heat-inactivated fetal bovine serum (Gibco), penicillin, streptomycin, amphotericin B and L-glutamine were seeded into the upper compartments of a six-well transwell plate (Corning). The lower compartments contained 3.0 mL of the same medium. Cells were incubated at 37° C. in a 5% $CO_2$ atmosphere until three days post-confluence, washed with Hanks' solution to remove antibiotics and FCS and stepped down in DMEM supplemented with L-glutamine, sodium selenite and transferrin for 24 h without antibiotics. Transwell inserts were then transferred to an anaerobic culture box within the anaerobic workstation at 37° C. The upper compartment of each insert was filled with anaerobic DMEM cell medium, while the lower compartment was filled with oxygenated DMEM.

R. hominis A2-183 culture was harvested at exponential phase by centrifugation at $3,500 \times g$ for 5 min. The pellet was washed and resuspended in 0.8 mL anaerobic DMEM. One hundred microliters of bacterial suspension ($10^8$ CFU/mL) was added to experimental wells. The control wells received the same amount of medium without bacterial cells. Additional controls included bacterial cells incubated without Caco-2 or HT29 cells. Bacterial and eukaryotic cells were harvested after 2 h and 4 h incubation. Both non-adherent and adherent bacteria were aspirated and stored in RNAlater (Ambion). The viability of R. hominis cells was tested by plating onto YCFA plates. Caco-2 cells or HT-29 cells were harvested from the wells and also stored in RNAlater.

R. intestinalis L1-82$^T$ (=DSM 14610$^T$=NCIMB 13810$^T$) culture was harvested at exponential phase by centrifugation at $3,500 \times g$ for 5 min. The pellet was washed and resuspended in 0.8 mL anaerobic DMEM. One hundred microliters of bacterial suspension ($10^8$ CFU/mL) was added to experimental wells. The control wells received the same amount of medium without bacterial cells. Additional controls included bacterial cells incubated without Caco-2 or HT29 cells. Bacterial and eukaryotic cells were harvested after 2 h and 4 h incubation. Both non-adherent and adherent bacteria were aspirated and stored in RNAlater (Ambion). The viability of R. intestinalis cells was tested by plating onto YCFA plates. Caco-2 cells or HT-29 cells were harvested from the wells and also stored in RNAlater.

For tissue culture experiments with recombinant flagellins, $5 \times 10^4$ Caco-2 cells were seeded in 24-well plates in DMEM (high glucose, HEPES) medium supplemented with heat-inactivated fetal bovine serum (Gibco), penicillin, streptomycin, amphotericin B and L-glutamine at 37° C. in a 75% humidified atmosphere of 5% $CO_2$. The cells reached confluence on day 5-6 and were used 3 days post-confluency. Prior any treatment, cells were washed twice with Hanks' Balanced Salt Solution and kept in DMEM supplemented with L-Glutamine, selenium and transferrin for 24 hours.

R. hominis Library Construction

R. hominis chromosomal DNA for small-size library construction and pyrosequencing was isolated using an UltraClean™ Microbial DNA Isolation Kit (Mo Bio Laboratories Inc) and high-molecular-weight DNA for fosmid libraries was isolated using a Wizard Genomic DNA Purification Kit (Promega). DNA integrity was checked by gel electrophoresis.

DNA was mechanically sheared using a Nebulizer Kit (Invitrogen) and fractionated by gel electrophoresis. DNA fragments of desired size were excised from the gel and purified using a Wizard® SV Gel and PCR Clean-Up System (Promega). End-repair was done with a DNA Terminator End Repair Kit (Lucigen). 1.5-3.5 kb fragments were cloned using the CloneSmart® LCAmp Kit (Lucigen) and a 4-8 kb library was constructed using the pJAZZ®-OC Vector (Lucigen). Fosmid libraries were constructed using the CopyControl™ Fosmid Library Production Kit (Epicentre Biotechnologies). Colonies were picked using an automated colony picker (BioRobotics BioPick, Genomic Solutions) and archived into 384-well microtitre plates containing 70 μL 2×LB medium supplemented with 10% glycerol and corresponding antibiotic. Cells were grown overnight at 37° C. with shaking and stored at −80° C.

Sequencing, Assembly, and Annotation

Templates for sequencing of small-size libraries were generated by PCR using one µL of clone biomass and primers SL1 and SR2 surrounding the cloning site of pSMART-LCAmp. PCR products were purified using Multiscreen PCR Clean-up filter plates (Millipore). Recombinant DNA from the pJAZZ®-OC clones was isolated using the Wizard® SV 96 Plasmid DNA Purification System (Promega). Fosmid DNA was isolated using the Fosmid-MAX™ DNA Purification Kit (Epicentre). End-reads of DNA fragments from R. hominis WGS libraries with different insert sizes were obtained using CEQ8000 (Beckman Coulter) and ABI 3770 (Applied Biosystems) DNA sequencers. Genomic DNA from R. hominis was also sequenced using 454 GS20 (454 Life Sciences) and 454 FLX sequencers (Roche). The Sanger and 454 data were assembled with MIRA version 3 (http://chevreux.org/projects_mira.html; (1). The RAST annotation pipeline (http://rast.nmpdr.org; (2)) was used for automatic and manual annotation of the genome and for comparative genomic analyses. The annotated genomic sequence of R. hominis A2-183 was submitted to GenBank under the accession number CP003040.

Microarray Analyses

Bacterial Microarray

Bacterial RNA was isolated from mouse caecum contents using the RNeasy Mini Kit (Qiagen), and further processed with the MICROBEnrich™ Kit (Ambion), the MICROBExpress™ Bacterial mRNA Enrichment Kit (Ambion), and the MessageAmp™ II-Bacteria RNA Amplification Kit (Applied Biosystems). RNA was labelled with either dCTP-Cy3 or dCTP-Cy5 during cDNA synthesis (CyScribe First Strand cDNA Labelling Kit; Amersham). Labeled products were purified using the CyScribe GFX Purification Kit (Amersham). PCR products amplified from 6000 clones in the E. coli plasmid RA8 library of R. hominis were arrayed in duplicate on aminosilane-coated microscope slides (Corning) using a MicroGrid II TAS (BioRobotics). Amplified fragments of the housekeeping genes rpoD and gyrA were randomly distributed on the array as controls. Microarray hybridization was performed in the GeneTAC hybridization station (Genomic Solutions). Dye labelling was swapped for a second hybridization, and a separate RNA purification was also labelled and hybridized twice, to ensure reproducibility and to obtain statistically significant results. In total, four slides were hybridized for each comparison, for a total of 12 hybridizing spots per amplified clone. Fluorescence was measured in two channels using a GeneTAC LS IV (Genomic Solutions) with GeneTac Integrator version 3.0.1 software. Spot intensities were log-transformed and Loess normalization was applied to remove differences in probe labelling and hybridization efficiencies. The one-sample t-test was used on the log-ratio values to test for differential expression. Data was considered significant when fold change $>2$ and $P<0.05$.

Mouse Microarray Analysis

Ileum and ascending colon tissue was removed from RNAlater and lyzed in Trizol (Invitrogen). RNA was isolated using standard chloroform/isopropanol steps. Total RNA was further purified with the RNeasy Kit (Qiagen), including an RNase-free DNase I (Qiagen) digestion step. RNA integrity was determined using the Agilent 2100 Bioanalyzer (Agilent Technologies). Total RNA was processed into biotin-labelled cRNA using the One-Cycle Target Labeling Kit (Affymetrix) or biotin-labelled aRNA using the 3' IVT Express Kit (Affymetrix). Hybridization to the GeneChip NuGO Mouse Array and GeneChip Mouse Genome Array (Affymetrix) on a GeneChip Fluidics Station 450 (Affymetrix) was performed at the Institute of Medical Sciences Microarray Core Facility (University of Aberdeen, UK). Chips were scanned with an Affymetrix GeneChip Scanner 3000 (Affymetrix). Image quality analysis was performed using Gene Chip Operating Software (GCOS) (Affymetrix). Further data analysis was performed with the freely available software packages R (http://www.r-project.org) and Bioconductor (http:/www.bioconductor.org). The moderated F-test provided by the Bioconductor package limma was used to test for differential expression. Data was considered significant when $P<0.05$ using the Benjamini and Hochberg false discovery method. Statistical analysis was performed separately for each of the two time-points. All differentially expressed genes ($P<0.05$) were imported into MetaCore analytical software (GeneGo, St Joseph, Mich.) to generate pathway maps. Integrated pathway enrichment analysis was performed using the knowledge-based canonical pathways and endogenous metabolic pathways. Ranking of relevant integrated pathways was based on P-values calculated using hypergeometric distribution. P-values represented the probability of a given number of genes from the input list to match a certain number of genes in the map by chance, considering the numbers of genes in the experiment versus the number of genes in the map within the full set of all genes on maps.

Gene Ontology (GO) based functional interpretation of the data was performed using DAVID (http://david.abcc.ncifcrf.gov), an expanded version of the original web-accessible program (3). Significantly different transcripts ($P<0.05$) were allocated into the GO category 'Biological Process' to unearth patterns of gene expression significantly enriched for specific GO terms.

Microarray data were submitted to the National Center for Biotechnology Information (NCBI) Gene Expression Omnibus (accession number GSE25544; http://www.ncbi.nlm.nih.gov/geo).

RT-PCR Analysis

The R. hominis-specific primers 5'-CCCACTGACAGAGTATGTAATGTAC-3'(SEQ ID NO: 14) and 5'-GCACCACCTGTCACCAC-3'(SEQ ID NO: 15) were used for semi-quantitative and Real-time PCR analysis of faecal samples to validate gut colonization levels. Further bacterial PCR primers were designed using the on-line tool Primer3Plus (4) and purchased from Sigma-Aldrich. Real-time PCR analysis was performed using a 7500 Fast Real-Time PCR System (Applied Biosystems) with the Power SYBR Green PCR Master Mix (Applied Biosystems). PCR was performed as follows: one cycle at 95° C. for 10 min, followed by 40 cycles at 95° C. for 15 sec and 60° C. for 1 min, ending with a dissociation step. All samples were run in triplicate. GyrA was used as a reference gene for normalization due to its low variation between samples.

For host gene expression, 2 µg of total eukaryotic RNA isolated from the ileum and ascending colon was reverse-transcribed into cDNA using the High Capacity cDNA Reverse Transcription Kit (Applied Biosystems) with random primers. Real-time PCR analysis was performed using a 7500 Fast Real-Time PCR System (Applied Biosystems) with the QuantiFast SYBR Green PCR Kit (Qiagen) and QuantiTect Primer Assays (Qiagen). PCR cycling conditions were as follows: one cycle at 95° C. for 5 min, followed by 40 cycles at 95° C. for 10 seconds and at 600° C. for 30 seconds, ending with a dissociation step. All samples were run in triplicate. Hprt was selected as a reference gene for normalization because of its low variation between samples.

All RT-PCR data were analyzed on a logarithmic scale with base 2 by one-way ANOVA with a significance cut-off of $P<0.05$. Differences were back-transformed to calculate fold changes.

Western Blot

Immuno-purified rabbit polyclonal antibodies against *Roseburia hominis* Fla1 and Fla2 was produced as described in Duck et al. (5). In brief, New Zealand white female rabbits were immunized with synthetic peptide in complete Freund's adjuvant and boosted several times. For *R. hominis* Fla1, peptide NH2-CRSQVRGLNKASDNA-CONH$_2$ (SEQ ID NO: 16) and peptide NH2-IDGNFTSKKLQVGSLC-COOH (SEQ ID NO: 17) were used, while for *R. hominis* Fla2, peptide C-AQYNDDAKSVLEILK-COOH (SEQ ID NO: 18) and peptide C-GLNKASRNSQDGIS-CONH$_2$ (SEQ ID NO: 19) were used. Following immunization the antibodies were purified on an immunoaffinity column prepared by coupling the peptides to 1 mL of activated sepharose beads.

For the western blot, *R. hominis* was grown in the presence of varying amounts (0.01 g to 1 g diet/10 mL of culture) of UV irradiated standard mouse chow for 3 hrs, filtered to remove dietary components and diluted in laemmli buffer containing 8M urea. Thirty μL of each sample was loaded into wells of a NuPAGE® Novex® 4-12% Bis-Tris gel (Invitrogen) and electrophoresed, followed by further processing using the WesternBreeze Chromogenic Immunodetection System (Invitrogen). Fla1 and Fla2 antibodies were diluted 1:1000 and loading control anti-DNA gyrase A (Abcam) diluted 1:300 in antibody diluent and incubated overnight at 4° C., followed by 1 h at room temperature with alkaline phosphatase conjugated anti-rabbit. Detection was by substrate colour development relative to loading control colour development.

FISH Analysis

Tissues fixed in neutral buffered formalin were embedded in Technovit 8100 (Heraeus Kulzer). Two-micron sections were cut using a rotary microtome (Leica/Reichert Autocut). Three sections were taken per slide at 100 μm, 200 μm and 300 μm into the tissue, resulting in nine sections per animal.

Slides were dehydrated by consecutive incubations in 50% (v/v), 80% and 96% ethanol and dried at room temperature (RT). The 16S rRNA FISH probes used were a general bacterial probe Eub338 (GCTGCCTCCCGTAG-GAGT; Cy3; SEQ ID NO: 20) and a newly designed *R. hominis* A2-183-specific probe (GTACATTACATACTCT-GTCAGTG; FITC; SEQ ID NO: 21), which was extensively tested for specificity against a panel of intestinal bacterial isolates. Ten microliter probe (30 ng/μL) in 100 μL hybridization buffer was applied to the dehydrated sample and incubated at probe-specific temperature. The slides were washed in washing buffer at 50° C. for 30 min, dipped in ice-cold water to remove residual washing buffer and dried under compressed air flow. Counterstaining was performed with 4',6-diamidino-2-phenylindole (DAPI; Vector Laboratories Inc) and slides were mounted with Vectashield Mounting Medium for fluorescence (Vector Laboratories Inc) to prevent fading. Bacteria were visualized using a Leica DM RBE fluorescence microscope (Leitz GMBH) and photographed with a Penguin 600CL camera (Pixera) and Viewfinder 3.0 software (Studio Lite). High-magnification images (.times.630) were retrieved using the Apochromatics system (Leica).

Immunofluorescence

Immuno-localization of *R. hominis* flagellin was examined in colon contents of mice colonized with *R. hominis* using specific antisera raised against defined peptide sequences from both Fla1 and Fla2 flagellin proteins. Gut contents were diluted in PBS, smeared on glass slides and air dried. Smears were fixed in pre-cooled methanol for 5 min at −20° C., incubated with anti-Flat or anti-Fla2 rabbit antisera (1:125, CoveLabs) overnight at 4° C. and visualized using Alexa donkey anti rabbit 488 (1:1000, Molecular Probes).

Sections were fixed in pre-cooled methanol for 30 min at −20° C. Immuno-localization of T cell markers was examined on sequential cryosections (8 μm). Sections were fixed either in pre-cooled methanol for 30 min at −20° C. (Ly6G FITC, CD3 FITC, CD11b FITC, all at 1:50 (BD Biosciences)), or, for the double-labelled FoxP3 (1:500, Abcam) with CD3 FITC (1:100, BD Biosciences) fixed in 1% paraformaldehyde (PFA) for 2 min at RT followed by 3 min in 0.01% Triton X in PBS. All sections were blocked with 10% BSA (Sigma) containing 10% relevant pre-immune sera in PBS (pH 7.4). Methanol-fixed tissues were incubated with primary antibodies for 1 h at RT. PFA-fixed sections were incubated with antibodies overnight at 4° C. FoxP3 was visualized using Alexa goat anti rabbit 594 (1:1000, Molecular Probes). Sections were counter labelled with DAPI and mounted with Vectashield (Vector Laboratories). For quantification of positive cells, a minimum of five fields of view from each mouse section was examined, using imaging software and microscope settings described above.

Histology

Ascending colon tissue samples were fixed for three hours in neutral buffered formalin (Sigma) at room temperature with constant agitation. The samples rinsed in PBS and then transferred to 70% ethanol and stored at room temperature until orientated for transverse sectioning and embedded in cold-curing resin using Technovit 8100 (Heraeus Kulzer) according to the manufacturers instructions. The embedded tissue was mounted onto Histoblocs using Technovit 3040 (Heraeus Kulzer). Four micron sections were cut using a rotary microtome (Leica Autocut) fitted with a glass knife (TAAB Laboratories Equipment Ltd.). Tissue sections were stained using standard haemotoxylin/eosin methods. A complete transverse cross sectional area of an ascending colon from each animal was imaged at .times.200 magnification on a Zeiss Axioskop microscope using a QImaging camera controlled by Image Pro Plus software. Each field of view was then scored from 0-4 according to a method based on Berg et al. (6). Histopathology scores were O=Shallow crypts, no or few infiltrating inflammatory cells, intact epithelium, goblet cells appear full of mucin (no pathology); 1=Crypts may exhibit slight epithelial cell hyperplasia, some diffuse infiltrating inflammatory cells may be seen between crypts, luminal epithelium appears intact, goblet cells may appear slightly depleted of mucin; 2=Crypts appear deeper with distinct evidence of epithelial hyperplasia, depletion of mucin from goblet cells, infiltrating inflammatory cells evident and may be multifocal in nature, although infiltrates are not seen in the submucosa; 3=Lesions involve a larger area of the mucosa and/or are more frequent than seen in grade 2. Lesions do not involve the submucosa. Luminal epithelial cells exhibit small erosions. The lesions are not transmural; 4=Crypt epithelium appears eroded. Abscesses may be present. Luminal epithelial cells appear irregular, sometimes with complete loss. Transmural infiltrate is observed—often associated with complete loss of epithelial cells into the lumen.

The mean percentage of fields of view at a given grade was calculated and treatment groups were compared using student t-test analysis.

Cloning and Purification of Recombinant Flagellins

Flagellin genes were isolated from liquid bacterial cultures of *R. hominis*, *R. intestinalis*, *S. typhimurium*, *S. enteritidis*, *Eubacterium rectale* 33656 and *E. coli* K12 by PCR amplification and purification. The purified flagellin fragment from *R. hominis* was inserted into expression vector pT7-MAT-Tag-FLAG (Sigma) and flagellin fragments from *S. enteritidis* and *E. coli* K12 were inserted into expression vector pGEX-6P-1 (GE Healthcare). Recombinant flagellin was expressed by transformation of plasmid DNA into *E. coli* BL21 Rosetta and *E. coli* BL21 (DE3) cells, respectively and induction with 1 mM IPTG (isopropyl b-D-galactosidase). Flagellins were recovered from cell lysates with FLAG beads (Sigma) and Ni-NTA (nickel-nitriloacetic) beads (Clontech, Takara) as per the manufacturer's instructions. The purity of the preparation was assessed by SDS-PAGE stained with coomassie blue solution. Activity of the flagellins fragments was determined by Luciferase Assay (Promega) according to the manufacturer's instructions using the NF-.kappa.B transformed Caco-2 cell line.

Caco-2 cells were incubated with recombinant flagellins at a final concentration of 100 ng/μL for 2 h at 37° C. in a 75% humidified atmosphere of 5% CO2. After the treatment the cells were washed with PBS solution twice and harvested for total RNA isolation.

Isolation of Intestinal and MLN Cells

Cells were isolated from the small intestine and mesenteric lymph node as previously described with minor modifications (7). Briefly, cellular suspensions were incubated with 100 U/m collagenase VIII (Sigma-Aldrich) in RPMI supplemented with 20% FBS at 37° C. for 20 min (mesenteric lymph nodes) or 1 hour (intestinal pieces). Single cell suspensions were then analyzed by flow cytometry.

Generation of Bone Marrow-Derived Dendritic Cells and Cultures

Bone marrow was harvested from femur and tibia of C3H/HeN and C57Bl6 mice as previously described (8-11). For GMCSF-derived dendritic cells, bone marrow cells were resuspended at .times.10.sup.6/mL in RPMI supplemented with 10% FCS and 20 ng/mL rmGM-CSF and seeded at 10 mL/plate in 100 mm.sup.2 tissue culture plates. After three days culture, loosely adherent cells were collected and replated with GM-CSF supplemented media at 1.times.10.sup.6/mL in 12 well tissue culture plates. At day 5, cells were stimulated with 100 ng/mL flagellins before being harvested on day 6. For Flt3L-derived dendritic cells, bone marrow cells were resuspended at 2.times.10.sup.6/mL in RPMI supplemented with 10% FCS and 200 ng/mL rmFlt3 and seeded at 2 mL/well in 12-well tissue culture plates. Cells were cultured for 10 days with an additional 2 mL of Flt3 supplemented media added to each well on day 4. At day 9, cells were stimulated with 100 ng/mL flagellins before being harvested on day 10. Cells were harvested from plates by gentle pipetting and analyzed by flow cytometry.

Flow Cytometry

Single cell suspensions of lamina propria cells, mesenteric lymph node cells and dendritic cells were incubated in blocking buffer (containing serum and CD16/CD32 antibody) at 4° C. for 15 min prior to staining with specific fluorochrome conjugated antibodies. Lamina propria cells were labelled with antibodies to mouse CD4-FITC and CD25-APC (eBioscience), CD8-APC-Cy7, CD3-PerCP Cy5.5 and B220-BV570 (Biolegend). Intracellular FoxP3-PE (eBioscience) labelling was performed after extracellular staining and cell fixation/permeabilisation according to the manufacturer's instructions (eBioscience). GM-CSF derived dendritic cells were labelled with antibodies CD11b-PerCP Cy5.5 (BD Biosciences), CD11c-PE-Cy7, I-A/I-E-APC-Cy7, CD80-PE, CD86-APC, CD8-FITC, B220-BV570 (Biolegend). Flt3L derived dendritic cells were labelled with CD11c-PE-Cy7-, CD11b- or Siglec-H-PerCP Cy5.5 (Biolegend), I-A/1-E-APC-Cy7, CD317-PE, CD40-Alexa Fluor 647, CD103-FITC, B220-BV570. Cells were analyzed using a FACSAriaII (BD Biosciences) and FlowJo software version 7.2.5.

Cytometric Bead Array (CBA)

Bone marrow cells were isolated from femur and tibia with RPMI media of C3H/HeN and C57Bl/6 mice and Flt3L-expanded as described previously. Cells were stimulated with 100 ng/mL flagellin (e.g. *Roseburia* flagellin) after 9 days of culture, and supernatant was collected on day 10. The experiment was performed on three separate occasions to create N=3.

CBA analysis was performed on cell supernatants using the Cytometric Bead Array Mouse Enhanced Sensitivity Master Buffer Kit (BD Biosciences) according to the manufacturer's instructions. Standards and samples were loaded onto a 96-well plate for measurement in a FACSArray (BD Biosciences). Results were analyzed using BD FCAP software (BD Biosciences).

Dry Body Weight and Lipid Carcass Analysis

Eviscerated mouse carcass was weighed, lyophilized to constant weight and then milled for analysis. Lipid content was determined by extraction (1:100 w/v) with chloroform/methanol (2:1 v/v) as described previously (12).

Cloning of *Roseburia* Flagellins

Amplification by PCR of the Flagellin Gene from Liquid Bacteria Culture

*Roseburia hominis* A2-183 flagellin sequences were retrieved from the National Center for biotechnology Information (NCBI) website (http://www.ncbi.nm.nih.gov/).

*Roseburia intestinalis* L1-82.sup.T (NCIMB=13810; DSM=14610.sup.T) flagellin sequences were retrieved from the National Center for biotechnology Information (NCBI) website (http://www.ncbi.nlm.nih.gov/). Accession numbers for the flagellin genes and proteins are provided in Table B (Table B—summary of the accession numbers for *Roseburia* flagellins described herein)

Total RNA Isolation from Bacteria

Total RNA was isolated from 1 mL of log phase bacteria liquid culture using the RNAeasy minikit (Qiagen, Sussex, UK), coupled to RNase-free DNase I (Qiagen) digestion and based on manufacturer's protocol. In brief, one milliliter of liquid culture was place in a 1.5 mL tube, centrifuged at 5.000.times.g for 5 min at 4° C. and the supernatant was discarded. The bacterial pellet was resuspended in 100 μL of lysozyme-containing TE buffer (10 mM Tris-HCl, 1 mM EDTA, pH 8.0) and incubated at RT (room temperature). Gram-positive bacteria RH (*Roseburia hominis*) was incubated for 10 min with a lysozyme concentration of 3 mg/mL. Three hundred and fifty microliters of lysis buffer containing 1% β-mercapto-ethanol were then added to the tube to disrupt the cells by vortexing and 250 μL of 100% ethanol (Molecular grade, Merck) were added. Seven hundreds microliters of the resulting suspension was applied to the RNeasy mini column fitted with a catching tube, centrifuged for 15 seconds at 8.000.times.g and the catch emptied. Again, 350 μL of wash buffer was applied to the column, which was centrifuged for 15 s at 8.000.times.g and the flow-through discarded. DNA digestion was carried out by adding to each column, 30 units of DNase I mixed with 70 μL of RDD buffer, and incubating at RT for 15 min. The column was washed again as previously described with 350

µL of wash buffer, then twice with 500 µL of RPE buffer. After air-drying the column by centrifugation of the empty column for 1 min at 8.000.times.g, 40 µL of RNase-free water were added directly onto the column and incubated 1 min at RT to be centrifuged for 1 min at 8.000.times.g. The eluate containing the total RNA was measured spectrophotometrically using Nanodrop technique to determine the concentration. RNA integrity was checked by the RINH genomic department (University of Aberdeen, UK) with an Agilent 2100 Bioanalyzer (Agilent Technologies). RNA with integrity number (RIN) was between 9.5 and 10 was considered excellent quality. Total RNA was stored at −80° C. until later use.

Reverse Transcription

Total RNA was reverse transcribed using the Quantitect reverse Transcription kit (Qiagen), according to the manufacturer's instructions. Briefly, one microgram of total RNA in a total volume of 12 µL was incubated for 2 min at 42° C. with 1.times.gDNA wipeout buffer and further mixed with 1.times. Quantiscript RT buffer (3 µL), RT primer mix (2 µL) and Quantiscript reverse transcriptase (11 µL) in a final volume of 20 µL. The reverse transcription program was 15 min at 42° C. followed by 3 min at 95° C. to inactivate the enzyme. The resulting complementary DNA (cDNA) concentration was 50 ng/µL and the cDNA was stored at −20° C. until later use.

PCR Amplification of Flagellin Genes

To amplify the flagellin from genomic DNA, forward and reverse primers were manually designed and purchased to Sigma-Aldrich (Poole, UK). The amplification by PCR of flagellin fragments was performed with forward primer inserting a BglII restriction site at 5' end, and reverse primer inserting a XhoI restriction at the 3' end.

```
Roseburia hominis (fla1)
Forward primer (5'-3'):
                                              (SEQ ID NO: 22)
CTCGAGATATGGTAGTACAGCACAA Reverse primer (5'-3'):
                                              (SEQ ID NO: 23)
CTTAGATCTCTGTAATAAGGATAATA Roseburia hominis (fla2)
Forward primer (5'-3'):
                                              (SEQ ID NO: 24)
CTCGAGATATGGTGGTTAATCATAA Reverse primer (5'-3'):
                                              (SEQ ID NO: 25)
CTTAGATCTTTTCAAAATCTCAAGCAC Roseburia intestinalis (Fla1)
Forward primer (5'-3'):
                                              (SEQ ID NO: 26)
GCAGGATCCATGCGTGGCGGAGACAAT
Reverse primer (5'-3'):
                                              (SEQ ID NO: 27)
AATGTGGTGGTGGTGGTGCTGCAGAATCTGCAA Roseburia intestinalis (Fla2)
Forward primer (5'-3'):
                                              (SEQ ID NO: 28)
CTCGAGATATGGTAGTTAATCATAA Reverse primer (5'-3'):
                                              (SEQ ID NO: 29)
CTTAGATCTTTTTAACATTTCCAACAC Roseburia intestinalis (Fla3)
Forward primer (5'-3'):
                                              (SEQ ID NO: 22)
CTCGAGATATGGTAGTACAGCACAA
```

```
-continued
Reverse primer (5'-3'):
                                              (SEQ ID NO: 30)
CTTAGATCTCTGTAACAGAGAAAGTA Roseburia intestinalis (Fla4)
Forward primer (5'-3'):
                                              (SEQ ID NO: 31)
CCGGGATCCATGGTAGTACAGCACAAT Reverse primer (5'-3'):
                                              (SEQ ID NO: 32)
TTAGTGGTGGTGATGATGATGCTGTAACAGAGAAAG
```

Figure 14:
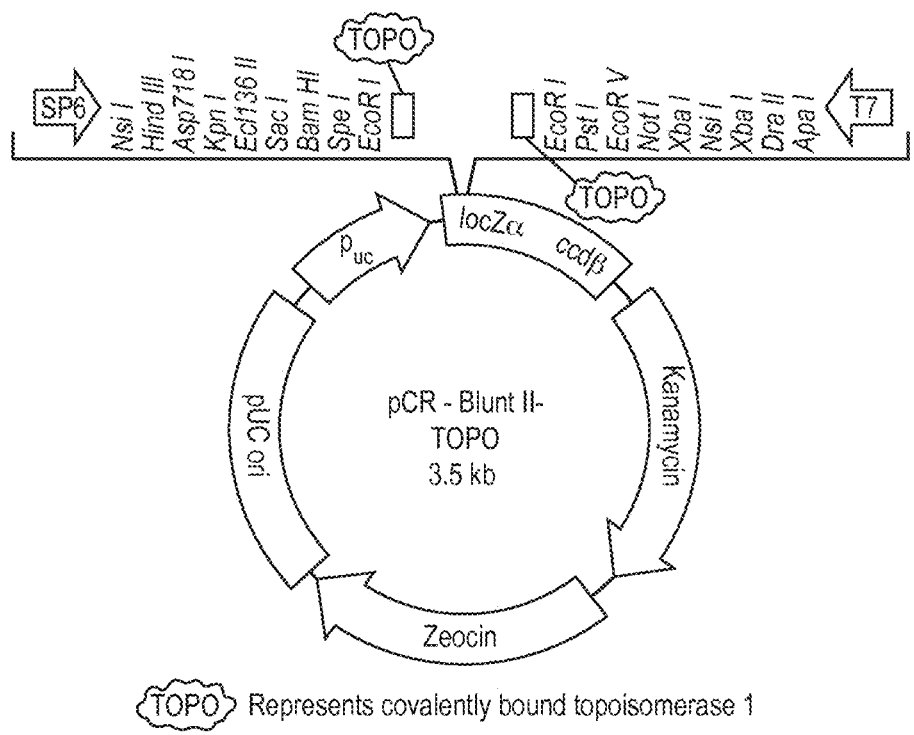

Using 1 µL of bacterial culture as a template, the flagellin genes were amplified by PCR. The thermal program for amplification was adapted from Fermentas (Fermentas GMBH, Germany) for optimum KOD polymerase (Novagen, Madison, Wis.) functions and was 95° C. for 2 min for polymerase activation followed by 34 cycles of amplification, 95° C. for 20 s, annealing temperature for 10 s and 70° C. for 20 s ending with 2 min at 70° C. using KOD polymerase. The details of the PCR mix are given in Table 1. The PCR products were run on a % agarose gel for 30 min at 120 V and the bands of interest were excised and purified. The insert was first cloned into the cloning vector pCRT™-Blunt II-TOPO using Zero Blunt TOPO PCR cloning kit (Invitrogen) according to the manufacturer's instructions and by mixing as described in FIG. 14 and Table 1.

TABLE-US-00019 TABLE 1 Composition of the mix for the insertion of PCR product into pCR-Blunt II-TOPO cloning vector. Salt solution and vector-enzyme mix were ready-to-use solutions.

TABLE 1

| Composition of the mix for the insertion of PCRproduct into pCR-Blunt II-TOPO cloning vector. Salt solution and vector-enzyme mix were ready-to-use solutions. | |
|---|---|
| Components | Volume (µL) |
| PCR product | 2 |
| Salt solution | 1 |
| H$_2$O | 2 |
| Vector-enzyme mix | 1 |
| Total | 6 |

Electrophoretic Separation and Purification of PCR Products

In order to view the isolated flagellin product amplified by PCR, the PCR reaction was mixed with 1.times. Blue-orange loading dye (Promega) and loaded onto a 1% agarose gel (made of agarose 1% diluted in TAE buffer (40 mM Tris base, 0.1% (v/v) acetic acid, 1 mM EDTA) boiled and poured in a gel tray) containing 0.5 µg/mL of Ethidium bromide to stain nucleic acids. Samples migrated for 30 min under 120 V using TAE as running buffer. When migration was finished, the gel was visualized under ultra-violet (UV) and the product was identified using a reference standard and excised with a clean scalpel. The gel slice was then transferred into a pre-weighed eppendorf tube and its weight recorded by subtraction from the empty tube weight. The PCR product was purified. Membrane binding solution was added to the gel slice in a ratio of 10 µL of solution per 10 mg of agarose gel slice. The mixture was then incubated at 65° C. for 10 min with frequent vortexing until the gel slice was completely dissolved. The tube was centrifuged briefly at RT to ensure all contents were at the bottom of the tube before progressing to DNA purification. From this point onward the purification PCR involved using Wizard® SV Gel and PCR Clean-up system (Promega, Southampton, UK) according to the manufacturer's instructions. One SV minicolumn per PCR product was placed into a collection tube. The PCR product were added to the SV minicolumn assembly and incubated for 1 min at room temperature (RT). The column was centrifuged at 16.000.times.g for 1 min, and the flow-through discarded. The column was then washed by adding 700 μL of membrane wash solution and centrifuged for 5 min at RT. The flow-through was discarded and the assembly spun again for 1 min and dried at RT for 2 min to evaporate any residual ethanol. The column was then transferred into a fresh 1.5 mL nuclease-free tube. To recover the PCR product, 25 μL of nuclease-free water was applied to the centre of the column and DNA was eluted by 1 min incubation at RT and 1 min spin at 16.000.times.g. The concentration of the eluate was measured spectrophotometrically using Nanodrop (Thermo Fisher Scientific) and stored at −20° C.

Digestion of the Flagellin and Expression Vector

Two hundred microliters of freshly thawed DH5a competent cells were kept on ice and 4 μL of the PCR product mix, and left on ice for 5 min. Heat shock was performed for 1 min at 42° C. and the cells returned on ice or 5 min, before addition of 400 μL of SOC medium. SOC Medium (Sigma) is a rich media used primarily in the recovery step of *Escherichia coli* competent cell transformations. Use of SOC maximizes the transformation efficiency of competent cells.

Figure 15:
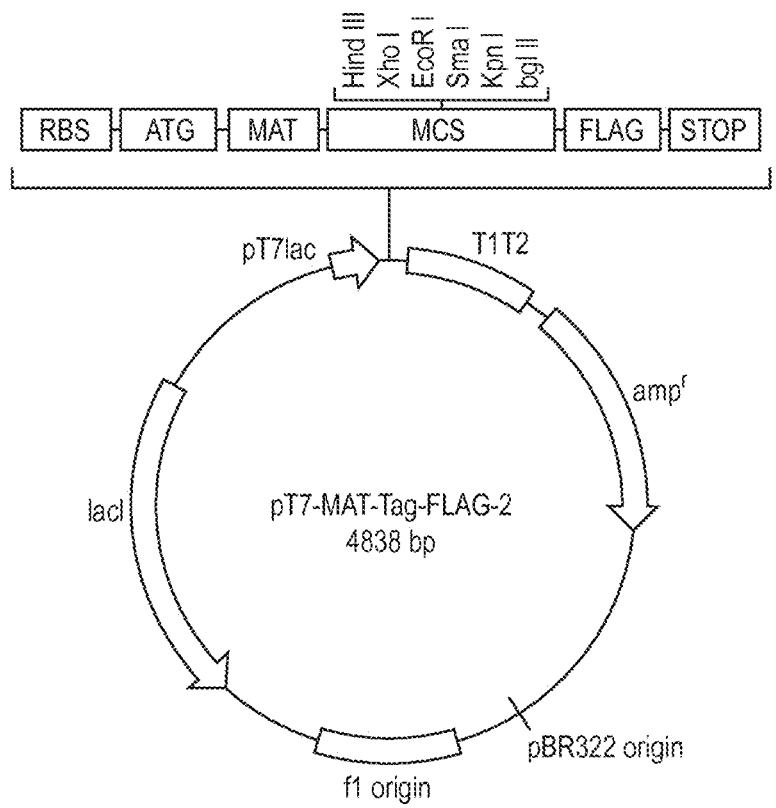

The cells grew at 37° C. for 1 hour, and 200 μL of the mix was plated on LB agar plate supplemented with Kanamycin 50 μg/mL. The positive clones were prepared as minipreps, nanodropped and digested with BamH1 and Xho1 for 2 hours to excise the flagellin. The expression vector pT7-MAT-Tag-FLAG-2 (Sigma), depicted in FIG. 15, was also digested with BamH1 and Xho1. After separation of the product on a 1% agarose gel and purification of the digested vector and fragment i.e. the vector and the insert were ligated at 4° C. overnight and transformed into *E. coli* DH5a. Ligation products were plated on LB agar supplemented with ampicillin 100 μg/mL. Positives clones were prepared as minipreps and transformed into *E. coli* BL21 (DE3) competent cells. The positives colonies were sequenced with appropriate primers to check the presence of the insert. Glycerol aliquots were made out the positive clones. The expression vectors encoding *Roseburia* flagellins were further prepared as minipreps and transformed into *E. coli* competent cells to improve the yield of the purification; for Rh1, Rh2 and Ri2 the *E. coli* competent cells were *E. coli* BL21 Rosetta and for RI3, Ri1 Ri4, Se, St, K12, and Er the *E. coli* competent cells were *E. coli* BL21 (DE3).

Expression and Purification of *Roseburia* Flagellins

Figure 16:
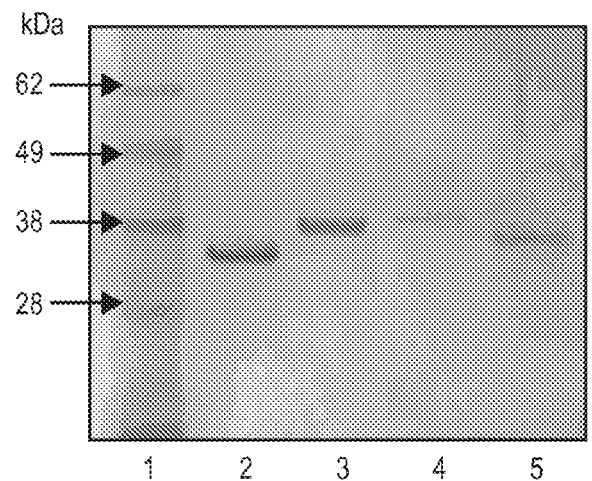

The transformed *E. coli* (e.g. BL21 Rosetta) encoding the flagellin gene (RH1 or FLaA1) were grown in I liter LB medium with ampicillin (100 μg/mL), and supplemented with chloramphenicol (50 μg/mL) for Rosetta cells, at 37° C. under shaking 180 rpm until log phase. The culture was induced for 3 hours with 1 mM IPTG under the same conditions, to allow the specific expression of flagellin protein. Bacteria were pelleted by centrifugation 4.000.times.g, 4° C., for 10 min and resuspended in 60 mL of buffer 1 (50 mM Tris (pH 7.4), 150 mM NaCl) and sonicated with a Soniprep 150 (Sanyo, Japan), for 1 min when using BL21 (DE3), or 3 min when using Rosetta with 1 min rest after each minute. Cell lysate was centrifuged at 9.000.times.g for 10 min at 4° C. and the supernatant discarded. The pellet, which contains insoluble proteins was resuspended in 60 mL of buffer 2 (50 mM Tris (pH 8.0), 100 mM NaCl, 5 mM EDTA, 0.5% Triton-X100, 1 mM DTT) sonicated again until complete resuspension, and centrifuged at 5.000.times.g for 15 min at 4° C. The insoluble fraction was washed a second and a third time with buffer 2. A last wash was carried out using buffer 2 without Tx-100 and DTT, as described above. To solubilise the proteins, the insoluble fraction was resuspended using sonication in 4 mL of urea buffer (2 M urea, 50 mM Tris (pH 7.4), 150 mM NaCl) and centrifuged at 5.000.times.g, 5 min at RT. The supernatant was discarded by decanting and the pellet was resuspended in 2 mL of 4 M urea, 50 mM Tris (pH7.4), 150 mM NaCl by sonication and centrifuged at 5.000.times.g, 5 min at RT. The supernatant was collected by decanting and the pellet was resuspended in 2 mL of 8 M urea, 50 mM Tris (pH7.4), 150 mM NaCl solution by sonication and centrifuged at 5.000.times.g, 5 min at RT. The supernatant was collected by decanting and mixed to the 4M urea fraction, to make a 6M urea solution containing solubilized flagellins. One milliliter of Talon resin (Clontech, Takara, UK) was washed twice with 2 mL of buffer 1 (50 mM Tris (pH7.4), 150 mM NaCl) and centrifugated at 1.000.times.g, 2 min at RT. The supernatant was discarded and the 6 M urea fraction containing flagellin was added, and left for rotation at 4° C. for 1 hour. After centrifugation at 1.000.times.g for 2 min at RT, the resin was washed twice with buffer containing 2 M urea, 50 mM Tris (pH 7.4), 150 mM NaCl, 15 mM immidazole. After centrifugation, the resin was incubated for 10 min with 300 μL of elution buffer (360 mM Tris-HCl, 680 mM imidazole, 360 mM NaCl, 0.35 N HCl, 1.43 M urea), gently mixed, and the eluate was collected after centrifugation at 2.000.times.g for 2 min at RT. The elution was repeated once and the two eluates mixed. A second purification step using anti-FLAG M2 magnetic beads (Sigma) was performed to improve the purity of the protein preparation. Four hundred microliters of ultra pure water were slowly added to the eluate of the Talon resin, to obtain a final concentration of 0.9 M urea, suitable for FLAG beads. Two hundred fifty microliters of FLAG magnetic beads were washed twice with 750 μL of buffer 1, by mixing and leaving on a magnetic stand (Ambion) to remove the supernatant. The Talon-eluate was added to the beads and rotated for 30 min at 4° C. The beads were washed five times with 1 mL of 0.9 M urea, 50 mM Tris (pH7.4), 150 mM NaCl. The elution consisted in adding to the beads 250 μL of 200 μg/mL FLAG peptide solution containing 0.9 M urea, 50 mM Tris (pH7.4), 150 mM NaCl, mixing well and incubating 30 min at RT. The tubes were placed on the magnetic stand and the final product was collected. This elution step was repeated once and 500 μL final products were further dialyzed in PBS with 0.9 M urea for 1 hour at 4° C., prepared as aliquots and stored at −80° C. The purity of the preparations was assessed by SDS-PAGE stained with coomassie blue solution (FIG. 16). Just before use, the protein aliquot was dialyzed 1 hour against PBS, changing the buffer twice, in slide-a-lyser of 20 kDa molecular weight cut off (Pierce, UK) and the protein concentration was measured using Bradford's method. Endotoxin measurement confirmed values were <0.25 EU/mL.

The nucleotide sequence encoding Fla1 is shown in SEQ ID NO 1 and the amino acid sequence of Fla1 is shown in SEQ ID NO 2.

```
                                                  (SEQ ID NO 1)
ATGGTAGTACAGCACAATCTTACAGCAATGAACGCTAACAGACAGTTAGG

TATCACAACAGGCGCACAGGCTAAGTCTTCTGAGAAGTTATCTTCTGGTT

ACAAGATCAACCGCGCAGCAGATGACGCAGCAGGTCTTACGATTTCCGAG
```

-continued

```
AAGATGAGAAGCCAGGTTAGAGGCTTAAATAAAGCTTCTGACAACGCACA

GGATGGTGTATCCCTTATTCAGGTAGCTGAGGGTGCATTAAGTGAGACAC

ACTCCATCTTACAGCGTATGAATGAGTTAGCAACTCAGGCAGCAAACGAT

ACCAATACAACCTCAGACAGAACTGCAGTTCAGCAGGAGATCAACCAGTT

AGCATCTGAGATCACCAGAATCGCTTCTACAACTCAGTTCAACACAATGA

ACCTGATCGATGGTAACTTCACAAGTAAGAAGCTTCAGGTAGGTTCCCTT

TGCGGACAGGCTATCACAATCGATATCTCTGATATGTCTGCTACAGGTCT

TGGCGTTAGCGGATTAGTAGTATCTTCCTTCTCTGCAGCTGGTAAGGCAA

TGTCTGCAGCTCAGGATGCTATCAGCTACGTATCTTCTATGCGTTCTAAG

CTGGGTGCATTACAGAACAGACTTGAGCACACAATCTCCCACCTGGACAA

CATTTCTGAGCACACATCTTCTGCAGAGTCTCGTATCCGTGATACAGATA

TGGCTGAAGAGATGGTTGAGTACAGCAAGAACAACATCCTTGCTCAGGCA

GGACAGTCTATGCTTGCTCAGGCTAACCAGTCTACTCAGGGTGTATTATC

CTTATTACAGTAA.
                                          (SEQ ID NO 2)
MVVQHNLTAMNANRQLGITTGAQAKSSEKLSSGYKINRAADDAAGLTISE

KMRSQVRGLNKASDNAQDGVSLIQVAEGALSETHSILQRMNELATQAAND

TNTTSDRTAVQQEINQLASEITRIASTTQFNTMNLIDGNFTSKKLQVGSL

CGQAITIDISDMSATGLGVSGLVVSSFSAAGKAMSAAQDAISYVSSMRSK

LGALQNRLEHTISHLDNISEHTSSAESRIRDTDMAEEMVEYSKNNILAQA

GQSMLAQANQSTQGVLSLLQ.
```

Figure 17:
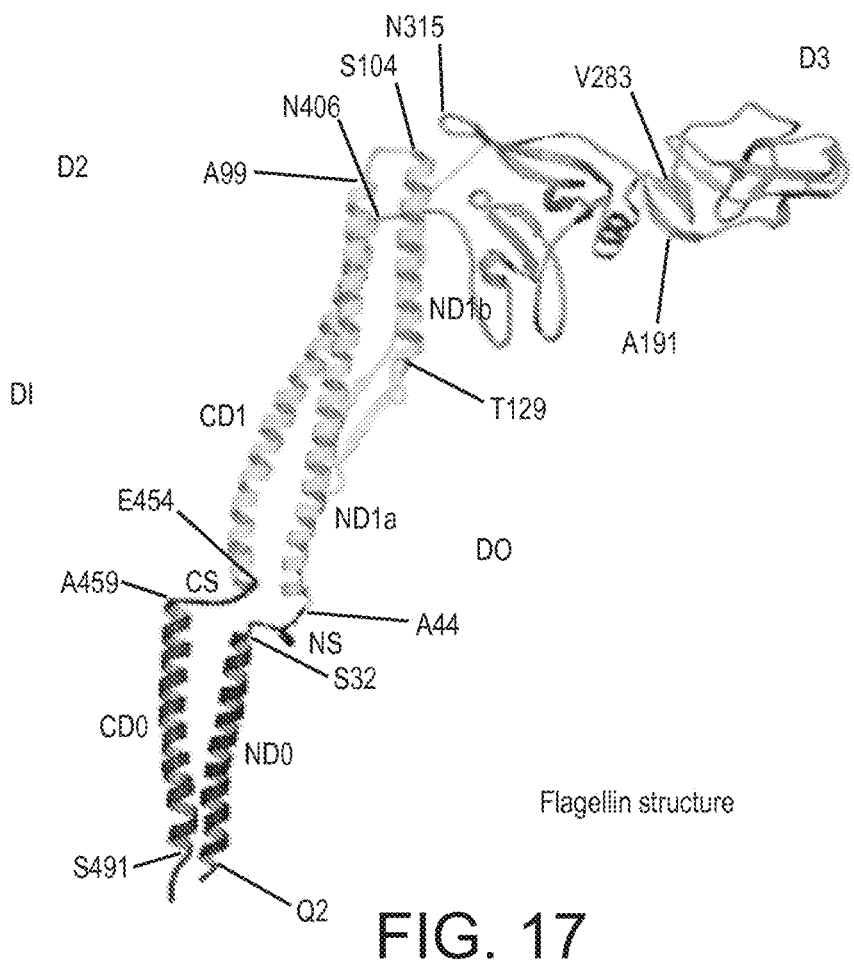
FIG. 17 depicts a ribbon structure of *R. hominis* Fla1. The flagellin structure consists of four domains: DO, D1, D2 and D3.

The flagellin structure consists of four domain DO, D1, D2 and D3. See FIG. 17.

D0: N-terminal α-helix starts from Gin 2 and extends up to Ser 32 (ND0). C-terminal α-helix starts from Ala 459 and extends down to Ser 491 (CD0).

The spoke region, which connects D0 and D1 domains, consists of two chains (Ns and Cs), one from Ser 32 to Ala 44 and the other from Glu 454 to Ala 459.

D1: N-terminal segment extends from Ala 44 to Gin 176 and the C-terminal segment from Asn 406 to Glu 454. N-terminal segment is made of an α-helix (from Ala 44 to Ala 99) (ND1a), followed up by a loop connecting to the second, shorter α-helix (ND1b) which goes down and the chain continues to two β-turns, a β-hairpin pointing down and an extended chain going up, and the rest of the chain finally goes into domain D2. The C-terminal α-helix in domain 1 (CD1) starts from Asn 406 and extends to Glu 454.

Domain D0 and D1 are packed into the protofilament structure so that N-D0 is oriented to the outside and C-D0 exposed to the central channel.

D2 domain comprises two segments: N-terminal segment from Lys 177 to Gly 189 and C-terminal segment from Ala 284 to Glu 405. It is made mostly of β strands excepting two helix 285-289 and 288-298.

D3 domain comprises a central segment from Tyr 190 to Val 283. Mostly made of β strands with one short stretch of helical fold (199-209).

Without wishing to be bound by theory, two essential regions of flagellin protein involved in the recognition and activation of TLR5 are thought to be amino acids at positions 79-117 of SEQ ID NO 2 (N-D1 domain) and amino acids at positions 408-439 of SEQ ID NO 2 (C-D1 domain), as well as the amino acid alanine (A) at position 411 of SEQ ID NO 2, the amino acid glutamine (Q) at position 412 of SEQ ID NO 2 and the amino acid serine (S) at position 420 of SEQ ID NO 2.

Examples

*R. hominis* Preferentially Colonizes the Colon

Figure 8A:
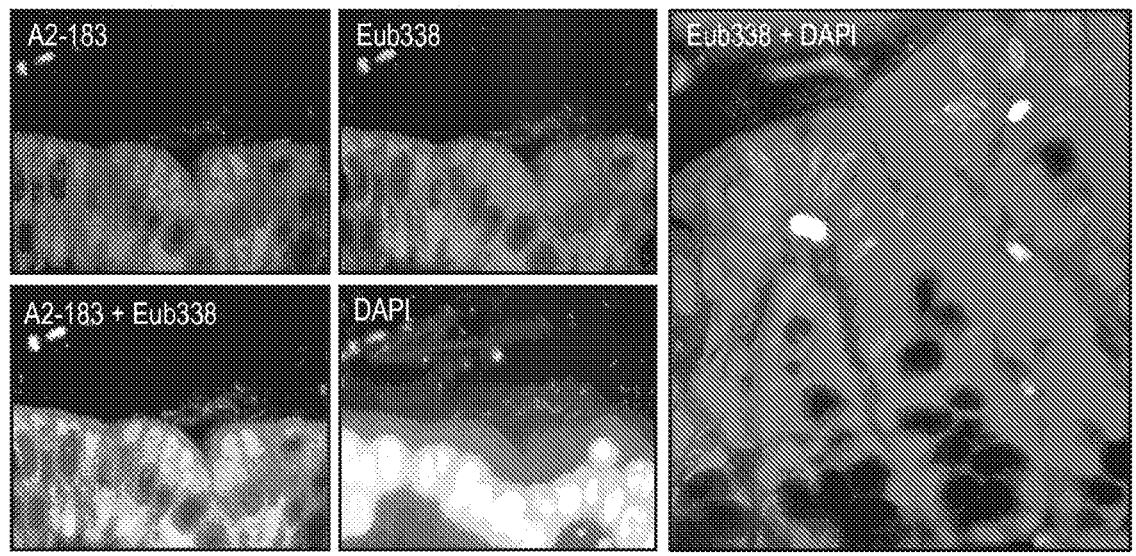
Figure 8B:
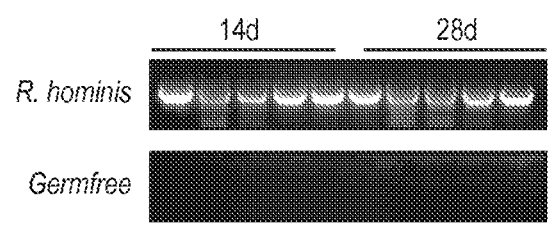
Figure 8C:
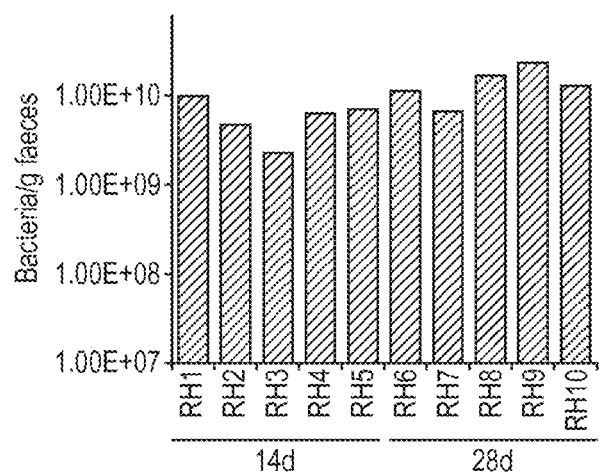

C3H/HeN germfree (GF) mice were inoculated with three gavages of *R. hominis* on consecutive days. The inventors report the first successful mono-colonization of germfree mice with a single bacterial species from the Firmicutes phylum. Successful colonization was achieved using an inoculation medium containing 3% ascorbic acid and 2% cysteine to protect this oxygen sensitive bacterium. Analysis of gut tissue by fluorescent in situ hybridization (FISH) revealed that *R. hominis* colonized both the ileum and colon, but was found in much higher numbers in the colon. Bacteria were also found closely associated with the colonic mucosa (FIG. 8A). Colonization was further validated and quantified by PCR using *R. hominis*-specific primers with numbers approximating 1.times.10.sup.10 bacteria/g faeces (FIG. 8B-C). Faeces of GF animals tested negative for the presence of any bacteria.

The *R. hominis* Genome Reveals Unique Genes Promoting Host Interactions

Figure 1A:
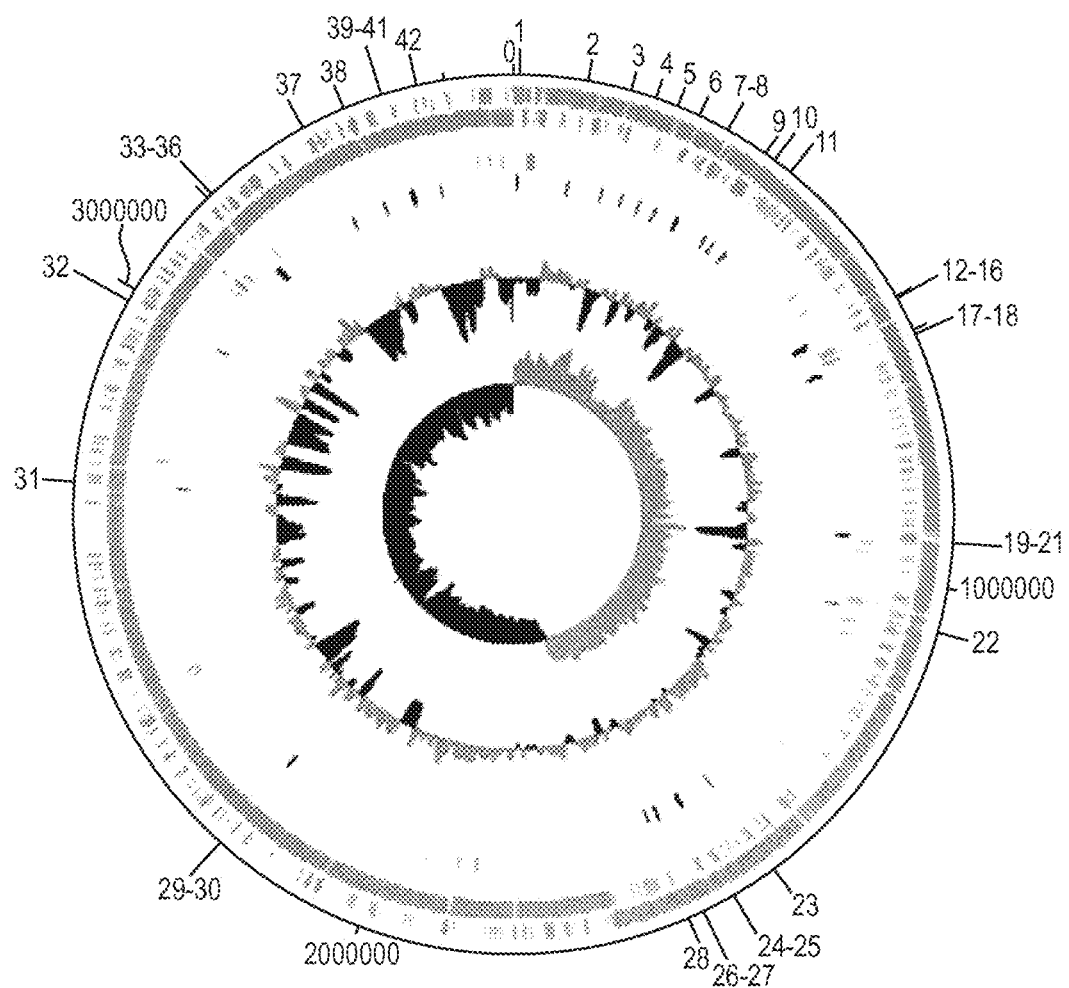
Figure 1B:
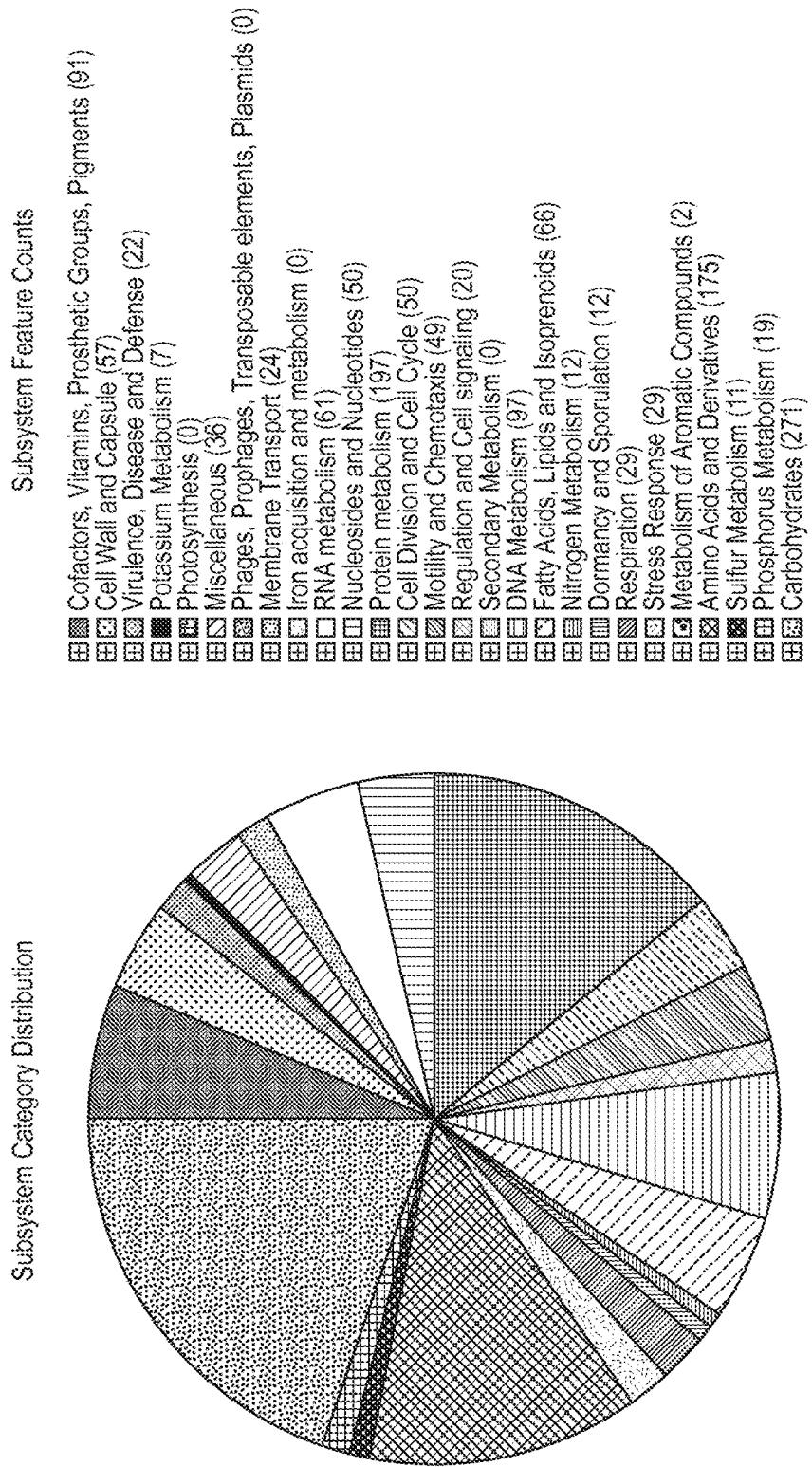

The complete genome sequence of *R. hominis* A2-183 was generated and is represented by a single 3,592,125-bp chromosome (FIG. 1A). Automated and manual annotation of the genome using the RAST platform revealed the presence of four ribosomal operons, 66 RNAs and 3,273 predicted proteins. The largest group of genes belonged to the Subsystem Category Carbohydrates (271 genes), encoding proteins involved in carbohydrate metabolism, followed by Protein Metabolism (197) and Amino acids and Derivatives (175) (FIG. 1B). Other important functional categories included Motility and Chemotaxis (49) and Dormancy and Sporulation (12). Comparative genomic analysis established that the closest relative in terms of genomic structure and function among the complete bacterial genomes is *Eubacterium rectale* (Mahowald et al. 2009), which is not surprising given the close taxonomical relatedness of these organisms (Duncan et al. 2006, Aminov et al. 2006). Comparative reconstruction of the two genomes with 1,095 genes revealed that they differed by approximately 25% of the genes. In particular, these differences encompassed genes encoding important functions for interaction with the host. For example, the Motility and Chemotaxis genes encoding type IV fimbrial assembly proteins PilB and PilC were present in *E. rectale* but absent in *R. hominis* whereas flagellar basal-body rod protein FlgC, flagellar hook-basal body complex protein FliE, flagellin protein FlaB and flagellar motor switch protein FliG were unique to *R. hominis* (Table S1). The two bacterial genomes also differed by 42 carbohydrate genes, reflecting their divergent nutritional requirements. Interestingly, *R. hominis* is unique in that it expresses two flagellin genes that are both FLA type as opposed to flagellins homologous to FliC expressed by *Salmonella* and *E. coli* bacterial species.

Table S1. Comparative Analysis of the *R. hominis* and *E. rectale* Genomes.

Comparative genomic analysis showed that *Eubacterium rectale* is the closest known relative of *R. hominis* in terms of genomic structure and function, and the two genomes differed by approximately 25% of the genes. (A) Genes present in *R. hominis* but absent in *E. rectale* and (B) genes present in *E. rectale* but absent in *R. hominis*.

TABLE S1A

Genes present in R. hominis but absent in E. rectale.

| Subcategory | Role |
|---|---|
| Amino Acids and Derivatives | |
| Alanine, serine, and glycine | L-serine dehydratase, alpha subunit |
| Alanine, serine, and glycine | L-serine dehydratase, beta subunit |
| Arginine; urea cycle, polyamines | Arginine pathway regulatory protein ArgR, repressor of arg |
| Arginine; urea cycle, polyamines | NADP-specific glutamate dehydrogenase |
| Arginine; urea cycle, polyamines | Ornithine decarboxylase |
| Arginine; urea cycle, polyamines | Spermidine Putrescine ABC transporter permease |
| Aromatic amino acids and derivatives | Biosynthetic Aromatic amino acid aminotransferase alpha |
| Branched-chain amino acids | Threonine dehydratase |
| Glutamine, glutamate, aspartate, asparagines | Aspartate aminotransferase |
| Glutamine, glutamate, aspartate, asparagine | L-asparaginase |
| Lysine, threonine, methionine, and cysteine | Sulfate permease |
| Lysine, threonine, methionine, and cysteine | Lysine decarboxylase |
| Lysine, threonine, methionine, and cysteine | Adenosylhomocysteinase |
| Lysine, threonine, methionine, and cysteine | Methionine ABC transporter ATP-binding protein |
| Lysine, threonine, methionine, and cysteine | Methionine ABC transporter permease protein |
| Lysine, threonine, methionine, and cysteine | Methionine ABC transporter substrate-binding protein |
| Lysine, threonine, methionine, and cysteine | S-ribosylhomocysteine lyase |
| Lysine, threonine, methionine, and cysteine | Predicted functional analog of homoserine kinase |
| Carbohydrates | |
| Aminosugars | Beta-hexosaminidase |
| Central carbohydrate metabolism | 6-phosphogluconolactonase |
| Central carbohydrate metabolism | Aldose 1-epimerase |
| Central carbohydrate metabolism | 4-Hydroxy-2-oxoglutarate aldolase |
| Central carbohydrate metabolism | Pyruvate:ferredoxin oxidoreductase, alpha subunit |
| Central carbohydrate metabolism | Pyruvate:ferredoxin oxidoreductase, beta subunit |
| Central carbohydrate metabolism | Pyruvate:ferredoxin oxidoreductase, delta subunit |
| Central carbohydrate metabolism | Pyruvate:ferredoxin oxidoreductase, gamma subunit |
| Central carbohydrate metabolism | Malate permease |
| Di- and oligosaccharides | Beta-glucoside bgl operon antiterminator, BglG family |
| Di- and oligosaccharides | Galactose operon repressor, GalR-LacI family of |
| Di- and oligosaccharides | Galactose/methyl galactoside ABC transport system, permease protein MglC |
| Di- and oligosaccharides | Multiple sugar ABC transporter, ATP-binding protein |
| Fermentation | Enoyl-CoA hydratase |
| Fermentation | D-lactate dehydrogenase |
| Monosaccharides | 2-dehydro-3-deoxygluconate kinase |
| Monosaccharides | 2-dehydro-3-deoxyphosphogluconate aldolase |
| Monosaccharides | 2-deoxy-D-gluconate 3-dehydrogenase |
| Monosaccharides | Alpha-glucosidase |
| Monosaccharides | Altronate hydrolases |
| Monosaccharides | Altronate oxidoreductase |
| Monosaccharides | Beta-glucuronidase |
| Monosaccharides | D-mannonate oxidoreductase |
| Monosaccharides | Mannonate dehydratase |
| Monosaccharides | Rhamnogalacturonides degradation protein RhiN |
| Monosaccharides | Uronate isomerase |
| Monosaccharides | Sugar diacid utilization regulator SdaR |
| Monosaccharides | Ribose ABC transport system, ATP-binding protein RbsA |
| Monosaccharides | Ribose ABC transport system, permease protein RbsC |
| Monosaccharides | Pyrimidine-nucleoside phosphorylase |
| Monosaccharides | Fructokinase |
| Monosaccharides | Transcriptional repressor of the fructose operon, DeoR family |
| Monosaccharides | Mannose-1-phosphate guanylyltransferase |
| Monosaccharides | Mannose-6-phosphate isomerase |
| Monosaccharides | Possible alpha-xyloside ABC transporter, substrate-binding |
| One-carbon Metabolism | Serine--pyruvate aminotransferase |
| Sugar alcohols | Glycerol uptake facilitator protein |
| Sugar alcohols | Glycerol-3-phosphate ABC transporter, periplasmic glycerol-3-phosphate-binding protein |
| No subcategory | Carbon storage regulator |
| Cell Wall and Capsule | |
| Capsular and extracellular polysacchrides | D,D-heptose 7-phosphate kinase |
| Capsular and extracellular polysacchrides | GDP-L-fucose synthetase |
| Capsular and extracellular polysacchrides | dTDP-4-dehydrorhamnose 3,5-epimerase |
| Capsular and extracellular polysacchrides | Peptidoglycan N-acetylglucosamine deacetylase |
| Capsular and extracellular polysacchrides | Polysaccharide deacetylase |
| Capsular and extracellular polysacchrides | Glucose-1-phosphate thymidylyltransferase |
| Capsular and extracellular polysacchrides | Teichoic acid translocation permease protein TagG |
| Capsular and extracellular polysacchrides | dTDP-4-dehydrorhamnose reductase |
| Capsular and extracellular polysacchrides | dTDP-glucose 4,6-dehydratase |
| Capsular and extracellular polysacchrides | TRAP-type transport system, small permease component, predicted N-acetylneuraminate transporter |

TABLE S1A-continued

Genes present in R. hominis but absent in E. rectale.

| Subcategory | Role |
|---|---|
| Capsular and extracellular polysacchrides | Glucose-1-phosphate cytidylyltransferase |
| No subcategory | N-acetylmuramoyl-L-alanine amidase |
| Clustering-based subsystems | |
| Chemotaxis, response regulators | diguanylate cyclase (GGDEF domain) with PAS/PAC sensor |
| Clustering-based subsystems | Stage II sporulation protein related to metaloproteases |
| Cytochrome biogenesis | Glutamate-1-semialdehyde aminotransferase |
| Protein export? | Membrane proteins related to metalloendopeptidases |
| Protein export? | NLP/P60 family protein |
| Protein export? | Peptide chain release factor 2 |
| Protein export? | hypothetical protein BH3604 |
| No subcategory | Cell division protein FtsW |
| No subcategory | FIG003307: hypothetical protein |
| No subcategory | SSU ribosomal protein S1p |
| Cofactors, Vitamins, Prosthetic Groups, Pigments | |
| Coenzyme A | 2-dehydropantoate 2-reductase |
| Coenzyme A | Pantothenate:Na+ symporter |
| Fe—S clusters | Iron-sulfur cluster assembly protein SufD |
| NAD and NADP | L-Aspartate dehydrogenase |
| Pyridoxine | Predicted transcriptional regulator of pyridoxine metabolism |
| Tetrapyrroles | Alpha-ribazole-5'-phosphate phosphatase |
| No subcategory | Predicted hydroxymethylpyrimidine transporter CytX |
| DNA Metabolism | |
| CRISPs | CRISPR-associated protein Cas2 |
| DNA repair | Uracil-DNA glycosylase, family 1 |
| DNA repair | Excinuclease ABC subunit A paralog of unknown function |
| DNA repair | A/G-specific adenine glycosylase |
| DNA repair | Exodeoxyribonuclease VII small subunit |
| DNA repair | Exonuclease SbcC |
| DNA repair | Exonuclease SbcD |
| DNA repair | putative ATP-dependent DNA helicase YjcD |
| DNA replication | DNA polymerase III subunits gamma and tau |
| DNA replication | DNA replication protein DnaC |
| No subcategory | DNA-binding protein HBsu |
| Dormancy and Sporulation | |
| Spore DNA protection | Small acid-soluble spore protein, beta-type SASP |
| No subcategory | Spore maturation protein A |
| No subcategory | Spore maturation protein B |
| Fatty Acids, Lipids, and Isoprenoids | |
| Fatty acids | 4'-phosphopantetheinyl transferase |
| Triacylglycerols | Lysophospholipase |
| Triacylglycerols | Lysophospholipase L2 |
| Triacylglycerols | Monoglyceride lipase |
| Membrane Transport | |
| ABC transporters | Phosphonate ABC transporter ATP-binding protein |
| ABC transporters | Phosphonate ABC transporter permease protein phnE1 |
| ABC transporters | Phosphonate ABC transporter permease protein phnE2 |
| ABC transporters | Dipeptide transport ATP-binding protein DppD |
| ABC transporters | Dipeptide transport ATP-binding protein DppF |
| ABC transporters | Dipeptide transport system permease protein DppB |
| ABC transporters | Dipeptide transport system permease protein DppC |
| ABC transporters | Dipeptide-binding ABC transporter, periplasmic substrate- |
| No subcategory | Duplicated ATPase component BL0693 of energizing |
| No subcategory | Duplicated ATPase component MtsB of energizing module of methionine-regulated ECF transporter |
| No subcategory | Substrate-specific component BL0695 of predicted ECF |
| No subcategory | Substrate-specific component MtsA of methionine-regulated |
| No subcategory | Substrate-specific component PdxU2 of predicted pyridoxin- |
| No subcategory | Substrate-specific component ThiT of thiamin ECF |
| No subcategory | Transmembrane component BL0694 of energizing module of |
| No subcategory | Transmembrane component MtsC of energizing module of |
| Miscellaneous | |
| Plant-Prokaryote DOE project | Aspartyl-tRNA(Asn) amidotransferase subunit A |
| Plant-Prokaryote DOE project | Aspartyl-tRNA(Asn) amidotransferase subunit B |
| Plant-Prokaryote DOE project | Glutamyl-tRNA(Gln) amidotransferase subunit A |
| Plant-Prokaryote DOE project | Glutamyl-tRNA(Gln) amidotransferase subunit B |
| Plant-Prokaryote DOE project | Phosphoglucosamine mutase |
| Plant-Prokaryote DOE project | Phosphomannomutase |
| Plant-Prokaryote DOE project | ABC transport system, sugar-binding protein |
| Plant-Prokaryote DOE project | Alpha-L-arabinofuranosidase II precursor |

TABLE S1A-continued

Genes present in R. hominis but absent in E. rectale.

| Subcategory | Role |
|---|---|
| Plant-Prokaryote DOE project | Alpha-N-arabinofuranosidase |
| Plant-Prokaryote DOE project | Alpha-N-arabinofuranosidase 2 |
| Plant-Prokaryote DOE project | COG3533 secreted protein |
| Plant-Prokaryote DOE project | L-arabinose isomerase |
| Plant-Prokaryote DOE project | Transcriptional repressor of the arabinose operon |
| Plant-Prokaryote DOE project | rhamnogalacturonan acetylesterase |
| No subcategory | Putative activity regulator of membrane protease YbbK |
| Motility and Chemotaxis | |
| Flagellar motility in Prokaryota | Flagellar basal-body rod protein FlgC |
| Flagellar motility in Prokaryota | Flagellar hook-basal body complex protein FliE |
| Flagellar motility in Prokaryota | Flagellin protein FlaB |
| No subcategory | Flagellar motor switch protein FliG |
| Nitrogen Metabolism | |
| No subcategory | Nitrogen regulatory protein P-II |
| No subcategory | Hcp transcriptional regulator HcpR (Crp/Fnr family) |
| Nucleosides and Nucleotides | |
| Purines | Adenine deaminase |
| Pyrimidines | Uridine kinase |
| No subcategory | Ribonucleotide reductase of class III (anaerobic), large |
| Phosphorus Metabolism | |
| No subcategory | Exopolyphosphatase |
| No subcategory | Phosphate transport system permease protein PstA |
| No subcategory | Phosphate transport system permease protein PstC |
| No subcategory | Sodium-dependent phosphate transporter |
| Potassium metabolism | |
| No subcategory | Potassium voltage-gated channel subfamily KQT |
| Protein Metabolism | |
| Protein biosynthesis | Probable GTPase related to EngC |
| Protein biosynthesis | Aspartyl-tRNA(Asn) synthetase |
| Protein biosynthesis | tRNA-Ala-CGC |
| Protein biosynthesis | tRNA-Gly-CCC |
| Protein biosynthesis | tRNA-Pro-GGG |
| Protein biosynthesis | tRNA-Ser-CGA |
| Protein biosynthesis | tRNA-Ser-GGA |
| Protein biosynthesis | tRNA-Val-CAC |
| Protein folding | Foldase protein PrsA precursor |
| Protein processing and modification | [NiFe] hydrogenase nickel incorporation protein HypA |
| Protein processing and modification | [NiFe] hydrogenase nickel incorporation-associated protein |
| RNA Metabolism | |
| RNA processing and modification | Peptidyl-prolyl cis-trans isomerase |
| RNA processing and modification | Ribonuclease P protein component |
| Transcription | Predicted transcriptional regulator of cysteine synthase, Rrf2 |
| Transcription | RNA polymerase sigma factor SigV |
| Regulation and Cell signaling | |
| Programmed Cell Death and Toxin-antitoxin Systems | YafQ toxin protein |
| No subcategory | Bifunctional autolysin Atl |
| No subcategory | Cell envelope-associated transcriptional attenuator LytR- |
| No subcategory | Aromatic hydrocarbon utilization transcriptional regulator |
| No subcategory | Catabolite control protein A |
| No subcategory | Catabolite repression HPr-like protein Crh |
| Respiration | |
| No subcategory | Ferredoxin |
| Stress Response | |
| Cold shock | Cold shock protein CspG |
| Virulence, Disease and Defense | |
| Resistance to antibiotics and toxic compounds | Probable Co/Zn/Cd efflux system membrane fusion protein |
| Resistance to antibiotics and toxic compounds | Transcriptional regulator, MerR family |
| Resistance to antibiotics and toxic compounds | Heavy metal-(Cd/Co/Hg/Pb/Zn)-translocating P-type |
| Resistance to antibiotics and toxic compounds | Vancomycin B-type resistance protein VanW |
| Resistance to antibiotics and toxic compounds | Tetracycline resistance protein TetW |

TABLE S1B

Genes present in E. rectale but absent in R. hominis.

| Subcategory | Role |
|---|---|
| *Amino Acids and Derivatives* | |
| Arginine; urea cycle, polyamines | Transcriptional regulator, MerR family, near polyamine |
| Lysine, threonine, methionine, and cysteine | Sulfate adenylyltransferase subunit 2 |
| Lysine, threonine, methionine, and cysteine | Sulfate and thiosulfate import ATP-binding protein CysA |
| Lysine, threonine, methionine, and cysteine | Sulfate transport system permease protein CysW |
| Lysine, threonine, methionine, and cysteine | Methionine transporter MetT |
| *Carbohydrates* | |
| Aminosugars | N-Acetyl-D-glucosamine ABC transport system, |
| Di- and oligosaccharides | Galactose/methyl galactoside ABC transport system, |
| Di- and oligosaccharides | Maltodextrin glucosidase |
| Di- and oligosaccharides | PTS system, maltose and glucose-specific II B |
| Di- and oligosaccharides | PTS system, maltose and glucose-specific liC I |
| Fermentation | NADH-dependent butanol dehydrogenase A |
| Fermentation | Alcohol dehydrogenase |
| Monosaccharides | Predicted beta-xyloside ABC transporter, substrate- |
| One-carbon Metabolism | Fumarate hydratase class I, aerobic |
| Organic acids | Serine--glyoxylate aminotransferase |
| Polysaccharides | Glycogen biosynthesis protein GlgD, glucose-1-phosphate adenylyltransferase family |
| Polysaccharides | glycogen debranching enzyme-related protein |
| Sugar alcohols | Glycerol dehydrogenase |
| *Cell Wall and Capsule* | |
| Gram-Positive cell wall components | Cell wall surface anchor family protein |
| Clustering-based subsystems | |
| Cell Division | FIG001960: FtsZ-interacting protein related to cell division |
| Isoprenoid/cell wall biosynthesis: predicted undecaprenyl diphosphate phosphatase | penicillin-binding protein, putative |
| Probably organic hydroperoxide resistance related hypothetical protein | Homoserine kinase |
| No subcategory | Cell division topological specificity factor MinE |
| No subcategory | Low molecular weight protein tyrosine phosphatase |
| *Cofactors, Vitamins, Prosthetic Groups, Pigments* | |
| Biotin | 3-ketoacyl-CoA thiolase |
| Biotin | Biotin synthase |
| Pyridoxine | Pyridoxine 4-hydroxythreonine-4-phosphate dehydrogenase |
| Pyridoxine | Pyridoxal kinase |
| Pyridoxine | Pyridoxine biosynthesis glutamine amidotransferase, |
| Pyridoxine | Pyridoxine biosynthesis glutamine amidotransferase, |
| Tetrapyrroles | Cob(I)alamin adenosyltransferase |
| Tetrapyrroles | Uroporphyrinogen-Ill methyltransferase |
| Tetrapyrroles | Vitamin B12 ABC transporter, B12-binding component |
| No subcategory | Sulfur carrier protein adenylyltransferase ThiF |
| No subcategory | Thiazole biosynthesis protein ThiG |
| No subcategory | Thiazole biosynthesis protein ThiH |
| *DNA Metabolism* | |
| CRISPs | CRISPR-associated protein Cas7 |
| DNA repair | Recombinational DNA repair protein Red T (prophage |
| DNA replication | ATP-dependent DNA helicase RecQ |
| *Fatty Acids, Lipids, and Isoprenoids* | |
| Phospholipids | CDP-diacylglycerol--serine 0-phosphatidyltransferase |
| Phospholipids | Diacylglycerol kinase |
| *Iron acquisition and metabolism* | |
| No subcategory | Sortase A, LPXTG specific |
| *Membrane Transport* | |
| No subcategory | Substrate-specific component FoIT of folate ECF transporter |
| *Motility and Chemotaxis* | |
| Social motility and nonflagellar swimming in bacteria | Type IV fimbrial assembly protein PiIC |
| Social motility and nonflagellar swimming in bacteria | Type IV fimbrial assembly. ATPase PilB |
| *Nucleosides and Nucleotides* | |
| Detoxification | Mutator mutT protein (7,8-dihydro-8-oxoguanine- |
| Purines | Uracil-xanthine permease |
| Purines | Adenine phosphoribosyltransferase |
| Purines | Adenosine deaminase |
| Pyrimidines | Uridine phosphorylase |

TABLE S1B-continued

Genes present in E. rectale but absent in R. hominis.

| Subcategory | Role |
|---|---|
| Phages, Prophages, Transposable elements, Plasmids | |
| Phages, Prophages | Phage tail length tape-measure protein |
| | Protein Metabolism |
| Protein biosynthesis | Similar to ribosomal large subunit pseudouridine synthase D, Bacillus subtilis YjbO type |
| Protein biosynthesis | tRNA (Guanine37-N1) -methyltransferase |
| Protein biosynthesis | Alanyl-tRNA synthetase family protein |
| Protein degradation | Aminopeptidase C |
| Protein degradation | Deblocking aminopeptidase |
| | RNA Metabolism |
| RNA processing and modification | COG1720: Uncharacterized conserved protein |
| RNA processing and modification | tRNA(Ile)-lysidine synthetase |
| | Respiration |
| Electron accepting reactions | Adenylylsulfate reductase alpha-subunit |
| Electron accepting reactions | Adenylylsulfate reductase beta-subunit |
| Electron accepting reactions | Dissimilatory sulfite reductase (desulfoviridin), alpha and |
| | Stress Response |
| Osmotic stress | Choline binding protein A |
| Osmotic stress | Sarcosine oxidase alpha subunit |
| No subcategory | Carbon starvation protein A |
| No subcategory | transcriptional regulator, PemK family |
| | Sulfur Metabolism |
| No subcategory | Beta-galactosidase large subunit |
| No subcategory | Beta-galactosidase small subunit |
| | Virulence Disease and Defense |
| Resistance to antibiotics and toxic | Aminoglycoside N6'-acetyltransferase |
| Resistance to antibiotics and toxic | Cytoplasmic copper homeostasis protein cutC |

TABLE-US-00022 TABLE S B Genes present in *E. rectale* but absent in *R. hominis*. Subcategory Role Amino Acids and Derivatives Arginine; urea cycle, polyamines Transcriptional regulator, MerR family, near polyamine Lysine, threonine, methionine, and cysteine Sulfate adenylyltransferase subunit 2 Lysine, threonine, methionine, and cysteine Sulfate and thiosulfate import ATP-binding protein CysA Lysine, threonine, methionine, and cysteine Sulfate transport system permease protein CysW Lysine, threonine, methionine, and cysteine Methionine transporter MetT Carbohydrates Aminosugars N-Acetyl-D-glucosamine ABC transport system, Di- and oligosaccharides Galactose/methyl galactoside ABC transport system, Di- and oligosaccharides Maltodextrin glucosidase Di- and oligosaccharides PTS system, maltose and glucose-specific IIB Di- and oligosaccharides PTS system, maltose and glucose-specific IIC Fermentation NADH-dependent butanol dehydrogenase A Fermentation Alcohol dehydrogenase Monosaccharides Predicted beta-xyloside ABC transporter, substrate-One-carbon Metabolism Fumarate hydratase class I, aerobic Organic acids Serine—glyoxylate aminotransferase Polysaccharides Glycogen biosynthesis protein GlgD, glucose-1-phosphate adenylyltransferase family Polysaccharides glycogen debranching enzyme-related protein Sugar alcohols Glycerol dehydrogenase Cell Wall and Capsule Gram-Positive cell wall components Cell wall surface anchor family protein Clustering-based subsystems Cell Division FIG001960: FtsZ-interacting protein related to cell division Isoprenoid/cell wall biosynthesis: predicted penicillin-binding protein, putative undecaprenyl diphosphatase Probably organic hydroperoxide resistance Homoserine kinase related hypothetical protein No subcategory Cell division topological specificity factor MinE No subcategory Low molecular weight protein tyrosine phosphatase Cofactors, Vitamins, Prosthetic Groups, Pigments Biotin 3-ketoacyl-CoA thiolase Biotin Biotin synthase Pyridoxine 4-hydroxythreonine-4-phosphate dehydrogenase Pyridoxine Pyridoxal kinase Pyridoxine Pyridoxine biosynthesis glutamine amidotransferase, Pyridoxine Pyridoxine biosynthesis glutamine amidotransferase, Tetrapyrroles Cob(I)alamin adenosyltransferase Tetrapyrroles Uroporphyrinogen-III methyltransferase Tetrapyrroles Vitamin B12 ABC transporter, B12-binding component No subcategory Sulfur carrier protein adenylyltransferase ThiF No subcategory Thiazole biosynthesis protein ThiG No subcategory Thiazole biosynthesis protein ThiH DNA Metabolism CRISPs CRISPR-associated protein Cas7 DNA repair Recombinational DNA repair protein RecT (prophage DNA replication ATP-dependent DNA helicase RecQ Fatty Acids, Lipids, and Isoprenoids Phospholipids CDP-diacylglycerol-serine O-phosphatidyltransferase Phospholipids Diacylglycerol kinase Iron acquisition and metabolism No subcategory Sortase A, LPXTG specific Membrane Transport No subcategory Substrate-specific component FolT of folate ECF transporter Motility and Chemotaxis Social motility and nonflagellar swimming in bacteria Type IV fimbrial assembly protein PilC Social motility and nonflagellar swimming in bacteria Type IV fimbrial assembly, ATPase PilB Nucleosides and Nucleotides Detoxification Mutator mutT protein (7,8-dihydro-8-oxoguanine-Purines Uracil-xanthine permease Purines Adenine phosphoribosyltransferase Purines Adenosine deaminase Pyrimidines Uridine phosphorylase Phages, Prophages, Transposable elements, Plasmids Phages, Prophages Phage tail length tape-measure protein Protein Metabolism Protein biosynthesis Similar to ribosomal large subunit pseudouridine synthase D, *Bacillus subtilis* YjbO type Protein biosynthesis tRNA (Guanine37-N1)-methyltransferase Protein biosynthesis Alanyl-tRNA synthetase family protein Protein degradation Aminopeptidase C Protein degradation Deblocking aminopeptidase RNA Metabolism RNA processing and modification COG1720: Uncharacterized conserved protein RNA processing and modification tRNA(Ile)-lysidine synthetase Respiration Electron accepting reactions Adenylylsulfate reductase alpha-subunit Electron accepting reactions Adenylylsulfate reductase beta-subunit Electron accepting reactions Dissimilatory sulfite reductase (desulfoviridin), alpha and Stress Response Osmotic stress Choline binding protein A Osmotic stress Sarcosine oxidase alpha subunit No subcategory Carbon starvation protein A No subcategory transcriptional regulator, PemK family Sulfur Metabolism No subcategory Beta-galactosidase large subunit No subcategory Beta-galactosidase small subunit Virulence, Disease and Defense Resistance to antibiotics and toxic Aminoglycoside N6'-acetyltransferase Resistance to antibiotics and toxic Cytoplasmic copper homeostasis protein cutC

*R. hominis* Responds to the Gut Environment by Up-Regulating Motility, Mobilization and Chemotaxis Genes To determine the genes differentially expressed by *R. hominis* in response to association with the host and diet, a microarray was constructed using 6,000 PCR fragments from the small-insert-size sequencing library. Subsequent Real-time PCR validation was performed on 42 differentially expressed genes (Tables S2 and S3), which cluster at specific regions of the *R. hominis* genome as illustrated in FIG. 1. To distinguish between the effects of gut environment and dietary components, bacterial RNA was isolated from four different experimental conditions: (i) in vivo, from the caecum of mono-associated mice; (ii) in vitro, from bacteria grown in culture media; (iii) in vitro, from bacteria grown in the presence of dietary components; and (iv) from bacteria incubated on the surface of confluent Caco-2 and HT-29 cells.

TABLE-US-00023 TABLE S2 Real-time PCR analysis on bacterial RNA using *R. hominis* specific primers. Bacterial PCR primers were designed for differentially expressed genes using Primer3Plus. All samples were run in triplicate. GyrA was used as a reference gene for normalization.

| Gene name | Rh14d-Control | | Rh28d-Control | | Rh14d-In Vitro + diet | | Rh28d-In Vitro + diet | | In Vitro + diet-In Vitro | |
|---|---|---|---|---|---|---|---|---|---|---|
| | FC | P-value | FC | P-value | FC | P-value | FC | P-value | FC | P-value |
| 3-hydroxyacyl-CoA dehydrogenase | 5.62 | 0.00393 | 8.62 | 0.00000 | −0.85 | 0.69927 | 1.30 | 0.38670 | 6.62 | 0.00124 |
| Acetyl-CoA acetyltransferase | 10.25 | 0.00304 | 18.27 | 0.00000 | 1.38 | 0.51556 | 2.46 | 0.01882 | 7.44 | 0.00048 |
| Aldose epimerase family protein | 7.20 | 0.00002 | 11.09 | 0.00001 | 22.65 | 0.03173 | 34.89 | 0.02105 | −0.32 | 0.30489 |
| ATP synthase alpha chain | 1.62 | 0.12713 | 2.50 | 0.00003 | 3.25 | 0.00645 | 5.00 | 0.00000 | −2.00 | 0.00147 |
| ATP synthase alpha chain2 | 11.94 | 0.00122 | 5.50 | 0.00001 | 2.71 | 0.18580 | 1.25 | 0.72876 | 4.41 | 0.06479 |
| ATP synthase beta chain | 1.85 | 0.08341 | 3.14 | 0.00056 | 4.00 | 0.00397 | 6.80 | 0.00001 | −2.16 | 0.00241 |
| ATP synthase beta chain2 | 8.27 | 0.00058 | 6.13 | 0.00025 | 1.64 | 0.33264 | 1.21 | 0.67923 | −5.05 | 0.01400 |
| ATP synthase gamma chain | 2.31 | 0.02994 | 3.58 | 0.00027 | 4.22 | 0.00238 | 6.52 | 0.00001 | −1.82 | 0.01276 |
| ATP synthase gamma chain2 | −9.59 | 0.00081 | −10.55 | 0.00013 | −1.59 | 0.40064 | −1.75 | 0.29398 | −6.02 | 0.01363 |
| Butyryl-CoA dehydrogenase | 13.31 | 0.00166 | 19.32 | 0.00000 | 1.48 | 0.39908 | 2.14 | 0.02840 | 9.03 | 0.00039 |
| Electron transfer flavoprotein, alpha subunit | 6.32 | 0.00729 | 15.55 | 0.00000 | −0.80 | 0.61916 | 1.96 | 0.03441 | 7.94 | 0.00030 |
| Electron transfer flavoprotein, beta subunit | 7.94 | 0.00414 | 12.31 | 0.00000 | 1.13 | 0.78504 | 1.76 | 0.08347 | 7.00 | 0.00078 |
| Flagellar motor rotation protein MotA | −0.94 | 0.71937 | 2.37 | 0.00023 | 1.69 | 0.02442 | 4.25 | 0.00001 | −0.56 | 1.00000 |
| Flagellar motor rotation protein MotB | −0.57 | 0.01030 | 1.19 | 0.00938 | −0.75 | 0.14601 | 1.58 | 0.01676 | −0.76 | 0.08011 |
| Flagellin protein FlaA1 | −3.05 | 0.00125 | −1.93 | 0.01193 | 3.13 | 0.01261 | 4.95 | 0.00249 | −9.57 | 0.00079 |
| Flagellin protein FlaA2 | 1.04 | 0.84732 | −1.28 | 0.05814 | 1.45 | 0.29909 | 1.09 | 0.77089 | −1.39 | 0.28105 |
| Flagellin protein FlaA3 | 1.14 | 0.41467 | 1.94 | 0.00312 | 1.63 | 0.08606 | 2.77 | 0.00477 | −1.43 | 0.17174 |
| Flagellin protein flaB | 1.02 | 0.97319 | −4.99 | 0.00568 | 1.96 | 0.40946 | −2.60 | 0.14359 | −1.92 | 0.25258 |
| Glucuronide permease | −9.34 | 0.00001 | −13.81 | 0.00022 | −13.97 | 0.00001 | −20.65 | 0.00003 | −1.50 | 0.13959 |
| L-threonine 3-O-phosphate decarboxylase | 1.62 | 0.00963 | 3.70 | 0.00002 | 1.66 | 0.07350 | 3.78 | 0.00186 | −0.98 | 0.92518 |
| Magnesium transporter | 372.00 | 0.00123 | 11.20 | 0.03391 | 4.42 | 0.32048 | −0.13 | 0.18758 | 84.10 | 0.01672 |
| Methyl-accepting chemotaxis protein1 | −1.18 | 0.54522 | −1.83 | 0.02731 | −2.90 | 0.01211 | −1.87 | 0.05778 | −0.21 | 0.00389 |
| Methyl-accepting chemotaxis protein2 | −2.46 | 0.00400 | −2.95 | 0.00154 | 1.48 | 0.10070 | 1.24 | 0.33586 | −3.65 | 0.00043 |
| Methyl-accepting chemotaxis protein3 | 1.13 | 0.54189 | 1.86 | 0.04504 | 3.17 | 0.00033 | 5.25 | 0.00055 | −2.81 | 0.00020 |
| Methyl-accepting chemotaxis sensory transducer1 | 1.33 | 0.01743 | 2.15 | 0.00001 | 1.58 | 0.05704 | 2.56 | 0.00396 | −1.19 | 0.38997 |
| Methyl-accepting chemotaxis sensory transducer2 | 2.03 | 0.00671 | 2.34 | 0.00017 | 4.94 | 0.00007 | 5.71 | 0.00003 | −2.44 | 0.00163 |
| MobA/MobL family protein4/putative conjugal transfer protein | 84.83 | 0.00177 | 5.77 | 0.01561 | 3.67 | 0.34227 | −4.00 | 0.29305 | 23.10 | 0.04583 |
| MobA/MobL protein1 | 257.93 | 0.00472 | 9.27 | 0.04437 | 8.72 | 0.25455 | −3.19 | 0.50297 | 29.57 | 0.07733 |
| MobA/MobL protein2 | 714.11 | 0.00172 | 11.64 | 0.08286 | 8.17 | 0.29225 | −7.51 | 0.31871 | 87.43 | 0.04300 |
| MobA/MobL protein3 | 362.26 | 0.00144 | 11.10 | 0.03880 | 7.77 | 0.27426 | −4.20 | 0.43208 | 46.62 | 0.06260 |
| MobA/MobL protein4 | 219.75 | 0.00147 | 6.52 | 0.08511 | 7.99 | 0.17452 | −4.22 | 0.34388 | 27.49 | 0.04519 |
| Oligopeptide ABC transporter, periplasmic oligopeptide-binding protein oppA | 1.26 | 0.49437 | 1.11 | 0.45125 | 1.28 | 0.49171 | 1.13 | 0.53525 | −1.02 | 0.92102 |

| Gene name | Rh14d-Control | | Rh28d-Control | | Rh14d-In Vitro + diet | | Rh28d-In Vitro + diet | | In Vitro + diet-In Vitro | |
|---|---|---|---|---|---|---|---|---|---|---|
| | FC | P-value | FC | P-value | FC | P-value | FC | P-value | FC | P-value |
| Oligopeptide transport ATP-binding protein oppD | −1.29 | 0.05256 | 1.08 | 0.40875 | −1.40 | 0.07422 | −1.00 | 0.98737 | 1.09 | 0.60319 |
| Osmosensitive K+ channel histidine kinase KdpD | 3.98 | 0.00004 | 7.07 | 0.00000 | 5.58 | 0.00005 | 9.91 | 0.00001 | −0.71 | 0.12049 |
| Phosphate regulon sensor protein PhoR | 2.73 | 0.00211 | 1.54 | 0.04166 | 3.80 | 0.00919 | 2.14 | 0.07191 | −1.39 | 0.34941 |
| Phosphoenolpyruvate carboxykinase [ATP] | 2.30 | 0.05000 | 3.22 | 0.00004 | 1.15 | 0.70105 | 1.61 | 0.04623 | 2.00 | 0.00988 |
| Potassium uptake protein, integral membrane component, KtrB | 7.74 | 0.00006 | 10.81 | 0.00002 | 50.92 | 0.02191 | 71.15 | 0.01638 | −0.15 | 0.15959 |
| Putative conjugal transfer protein MobA/MobL | 183.02 | 0.00023 | 9.49 | 0.01454 | 8.09 | 0.08695 | −2.39 | 0.44355 | 22.63 | 0.02615 |
| Pyruvate-flavodoxin oxidoreductase | −0.52 | 0.05848 | −0.92 | 0.52386 | −0.36 | 0.01504 | −0.65 | 0.09510 | 1.42 | 0.16352 |
| RNA polymerase sigma factor for flagellar operon | −0.76 | 0.02253 | 1.93 | 0.00032 | −0.82 | 0.08962 | 2.08 | 0.00013 | −0.93 | 0.40060 |

TABLE S3 Index of *R. hominis* PCR experiments plotted on circular genome map. List of *R. hominis* PCR experiments as shown on the circular genome map.

Fifty differentially express genes were identified in vivo vs. in vitro. The most surprising discovery was the high up-regulation in vivo of genes involved in conjugation/

Figure 2A:
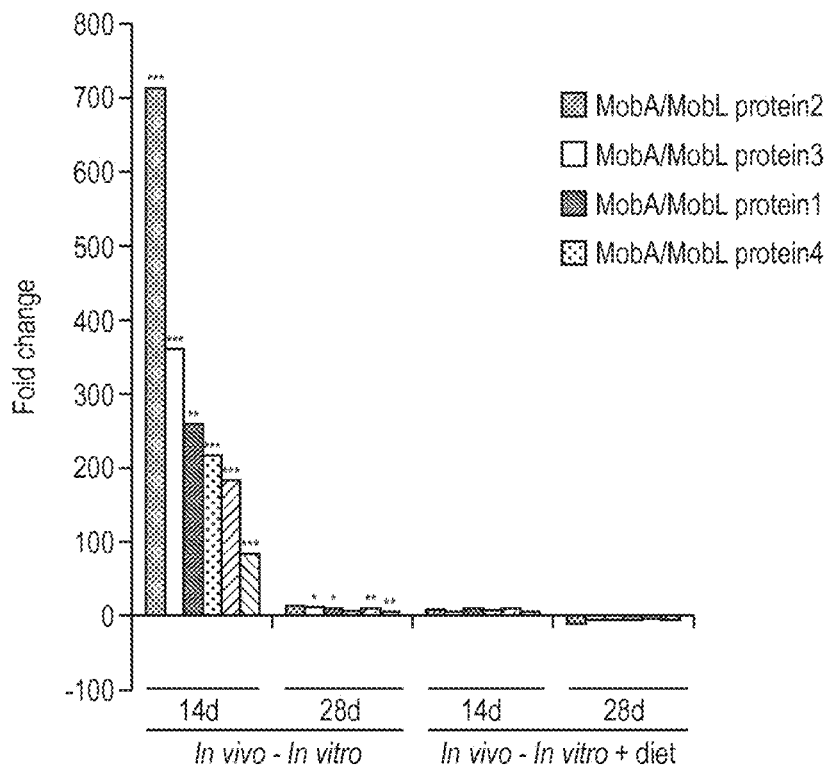

| Exp | Primer | Start | End | Length | Gene |
|---|---|---|---|---|---|
| 1 | gyrA-N-F | 7803 | 7889 | 87 bp | gyrA |
| 2 | 1602-F | 95664 | 95740 | 77 bp | Phosphate regulon sensor protein PhoR |
| 3 | 1653-F | 153403 | 153483 | 81 bp | Flagellin protein FlaA1 |
| 4 | 1686-F | 189295 | 189382 | 88 bp | Flagellin protein FlaA2 |
| 5 | 1718-F | 221205 | 221279 | 75 bp | Flagellin protein FlaA3 |
| 6 | 1735-F | 250582 | 250674 | 93 bp | Methyl-accepting chemotaxis protein1 |
| 7 | 1769-F | 290546 | 290628 | 83 bp | Methyl-accepting chemotaxis sensory transducer1 |
| 8 | 1770-F | 291722 | 291808 | 87 bp | Methyl-accepting chemotaxis protein2 |
| 9 | 1831-N-F | 348711 | 348810 | 100 bp | MobA/MobL protein4 |
| 10 | 1842-F | 364775 | 364851 | 77 bp | MobA/MobL protein2 |
| 11 | 1867-2652-F | 391044 | 391120 | 77 bp | MobA/MobL family protein4/putative conjugal transfer protein |
| 12 | 2055-F | 600837 | 600928 | 92 bp | Acetyl-CoA acetyltransferase |
| 13 | 2056-F | 602279 | 602363 | 85 bp | 3-hydroxyacyl-CoA dehydrogenase |
| 14 | 2057-F | 602961 | 603037 | 77 bp | Butyryl-CoA dehydrogenase |
| 15 | 2058-F | 604411 | 604504 | 94 bp | Electron transfer flavoprotein, beta subunit |
| 16 | 2059-F | 605434 | 605516 | 83 bp | Electron transfer flavoprotein, alpha subunit |
| 17 | 129-F | 653987 | 654066 | 80 bp | Oligopeptide ABC transporter, oligopeptide-binding protein oppA periplasmic |
| 18 | 132-F | 658435 | 658516 | 82 bp | Oligopeptide transport ATP-binding protein oppD |
| 19 | 805-R | 934310 | 934406 | 97 bp | Osmosensitive K+ channel histidine kinase KdpD |
| 20 | 807-R | 935306 | 935394 | 89 bp | Aldose epimerase family protein |
| 21 | 808-R | 936111 | 936190 | 80 bp | Potassium uptake protein, integral membrane component, KtrB |
| 22 | 909-F | 1053529 | 1053604 | 76 bp | Pyruvate-flavodoxin oxidoreductase |
| 23 | 1235-F | 1434705 | 1434785 | 81 bp | MobA/MobL protein3 |
| 24 | 1296-F | 1495460 | 1495544 | 85 bp | Methyl-accepting chemotaxis protein3 |
| 25 | 1297-R | 1497854 | 1497931 | 78 bp | L-threonine 3-0-phosphate decarboxylase |
| 26 | 1335-F | 1540579 | 1540671 | 93 bp | Flagellar motor rotation protein MotA |
| 27 | 1336-F | 1541416 | 1541511 | 96 bp | Flagellar motor rotation protein MotB |
| 28 | 1356-F | 1559143 | 1559227 | 85 bp | RNA polymerase sigma factor for flagellar operon |
| 29 | 3119-F | 2211612 | 2211705 | 94 bp | Phosphoenolpyruvate carboxykinase [ATP] |
| 30 | 3117-R | 2213046 | 2213139 | 94 bp | Methyl-accepting chemotaxis sensory transducer2 |
| 31 | 1867-2652-R | 2736100 | 2736176 | 77 bp | MobA/MobL family protein4/putative conjugal transfer protein |
| 32 | 1552M-R | 2984489 | 2984566 | 78 bp | Magnesium transporter |
| 33 | 397-R | 3153341 | 3153427 | 87 bp | ATP synthase beta chain2 |
| 34 | 398-R | 3153616 | 3153699 | 84 bp | ATP synthase gamma chain2 |
| 35 | 399-R | 3155799 | 3155898 | 100 bp | ATP synthase alpha chain2 |
| 36 | 404-R | 3159387 | 3159467 | 81 bp | Glucuronide permease |
| 37 | 2399-R | 3308172 | 3308265 | 94 bp | Putative conjugal transfer protein MobA/MobL |
| 38 | 2323-R | 3366526 | 3366615 | 90 bp | Flagellin protein flaB |
| 39 | 2281-R | 3416947 | 3417042 | 96 bp | ATP synthase beta chain |
| 40 | 2280-R | 3418736 | 3418824 | 89 bp | ATP synthase gamma chain |
| 41 | 2279-R | 3418857 | 3418942 | 86 bp | ATP synthase alpha chain |
| 42 | 641-R | 3467164 | 3467255 | 92 bp | MobA/MobL protein1 | mobilization transfer, the mobA- and mobL-like genes (FIG. 2A). The presence of such genes in the tanscriptional studies was surprising as no identifiable genes were assigned to Phages, Prophages, Transposable Elements and Plasmids in the Subsystem Category feature. This difference in gene detection and allocation is likely due to the recognized limitations of the Subsystem Category annotation. The stimulatory effect of dietary compounds was much less pronounced, suggesting that the gut environment per se is a major inducer of genes involved in horizontal gene transfer.

Figure 2B:
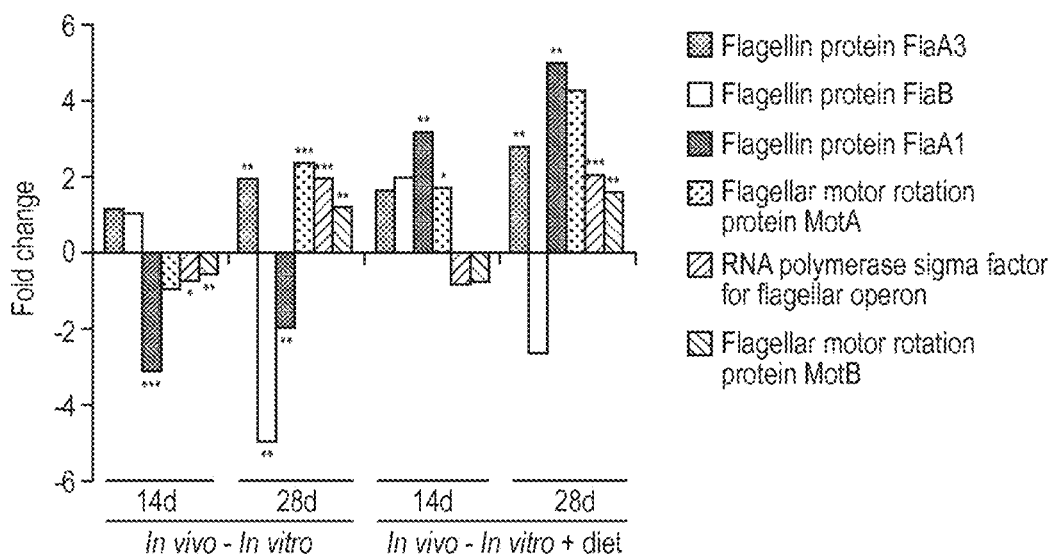
Figure 2D:
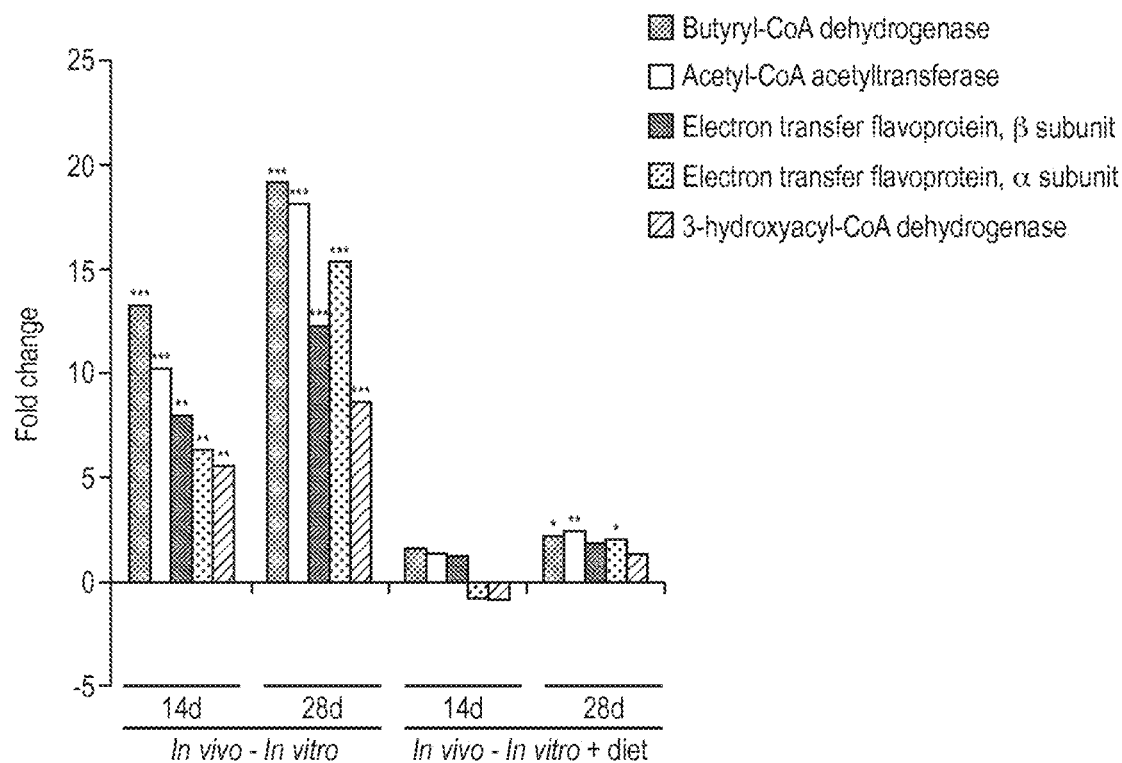

Other gut environment-induced subsystems included Membrane Transport, in particular magnesium transport, and Motility and Chemotaxis including multiple methyl-accepting chemotaxis proteins and genes of the flagellar operon (FIG. 2B). R. hominis possesses multiple flagellin genes flaA1, flaA2, flaA3, and flab. In the mouse gut environment, flagellin expression was verified by Western-blot and immunocytochemistry using bacteria isolated from both in vivo colonized mice and from in vitro cultures grown in the presence of diet, with specific antibodies raised against recombinant flagellin proteins FlaA1 and FlaA2 (RH1 and RH2) (FIG. 2C). This positive validation of flagellin expression in vivo is consistent with previous reports indicating that only certain subsets of Firmicutes produce flagella in vivo (Turnbaugh et al. 2008) unlike other bacterial species that actively down-regulate expression of the bacterial protein. The expression of catabolic metabolism genes in R. hominis in the gut environment was also affected by the gut environment (FIG. 2D). The genes involved included acetyl-CoA acetyltransferase, 3-hydroxyacyl-CoA dehydrogenase, butyryl-CoA dehydrogenase and phosphoenolpyruvate carboxykinase [ATP].

Figure 2E:
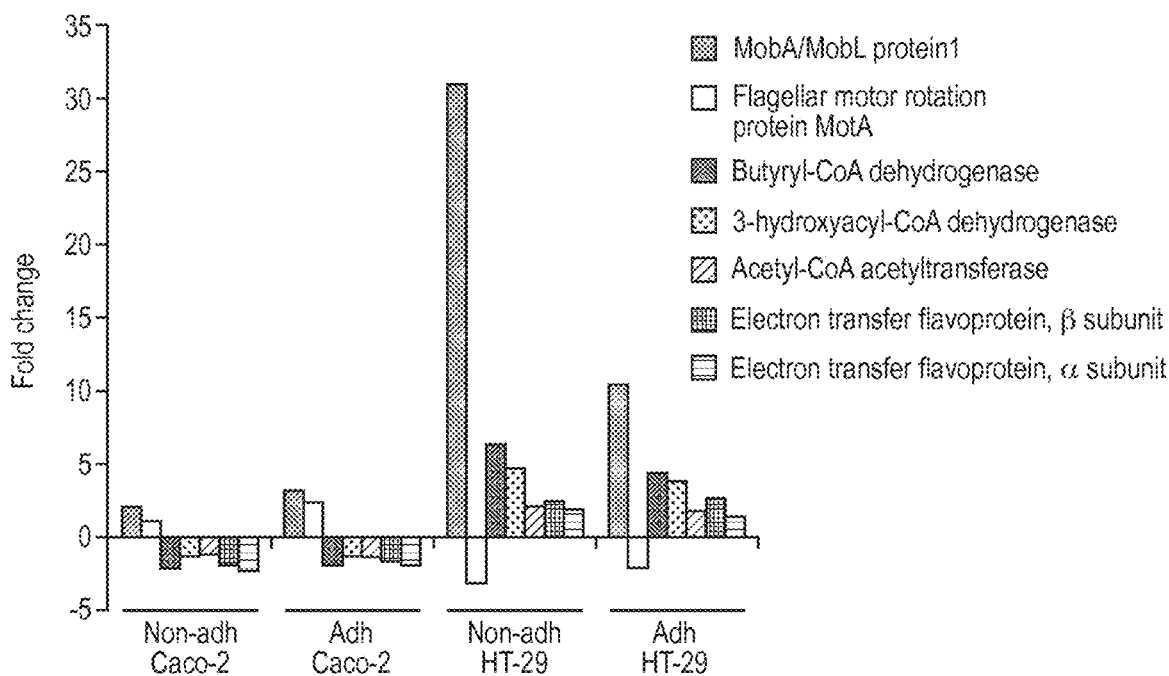

To further investigate the effects of host-adaptation on the R. hominis transcriptome, in vitro stimulation of human intestinal epithelial cells (Caco-2 and HT-29) was performed. This showed that the conjugation/mobilization transfer gene mobA/mobL protein1, which was induced by adaptation to the mouse gut, was also increased in both cell lines (FIG. 2E). Consistent with the in vivo data, the flagellin gene MotA was up-regulated in Caco-2 cells. Genes involved in butyrate metabolism showed differences between the two cell lines, with down-regulation seen in Caco-2 cells and up-regulation in HT-29 cells.

R. hominis Influences Host Innate Signalling Pathways Mostly in the Colon

Figure 3A:
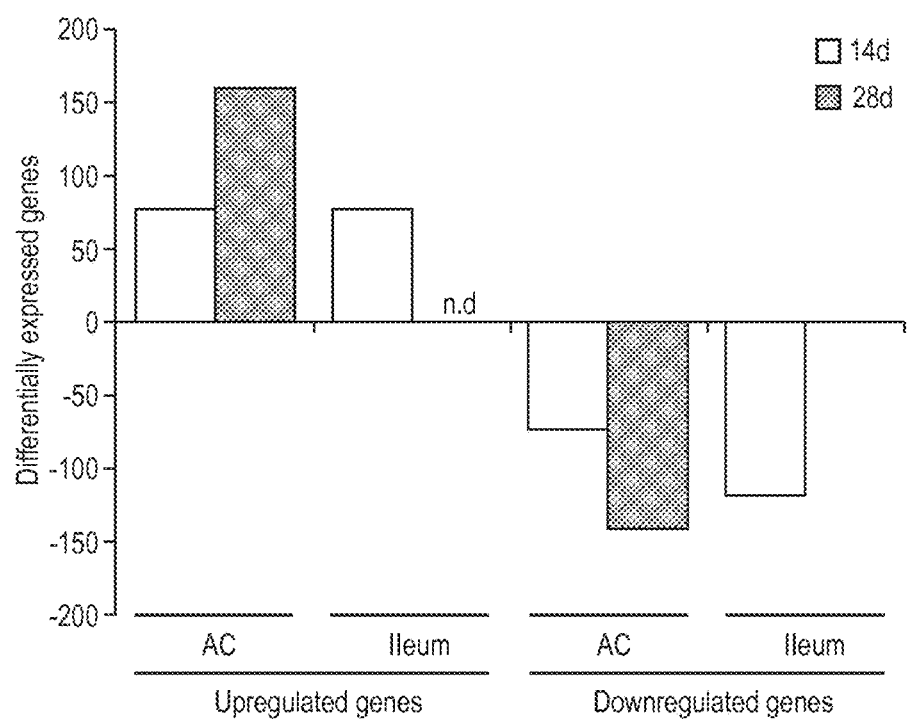
Figure 3B:
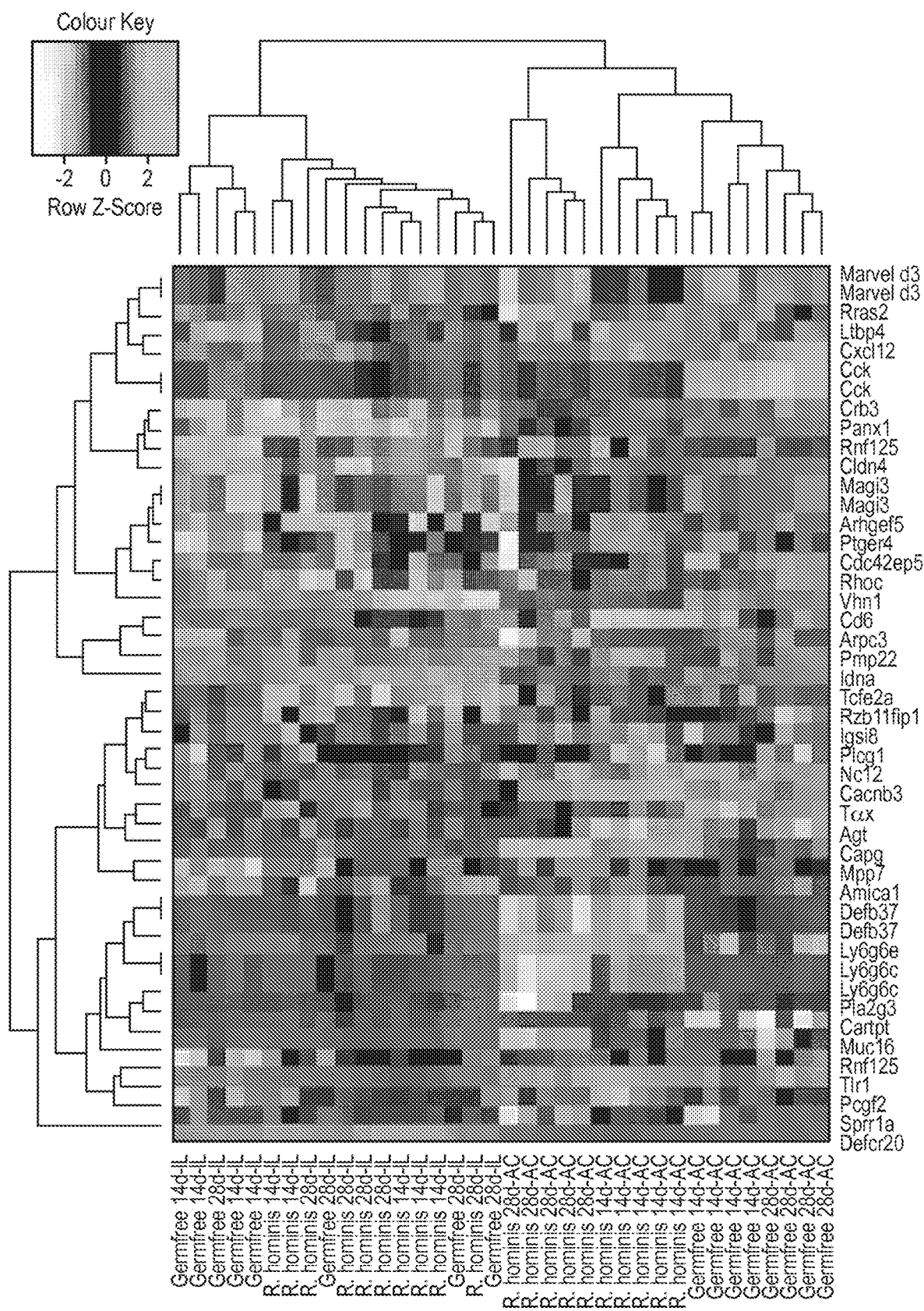
Figure 3C:
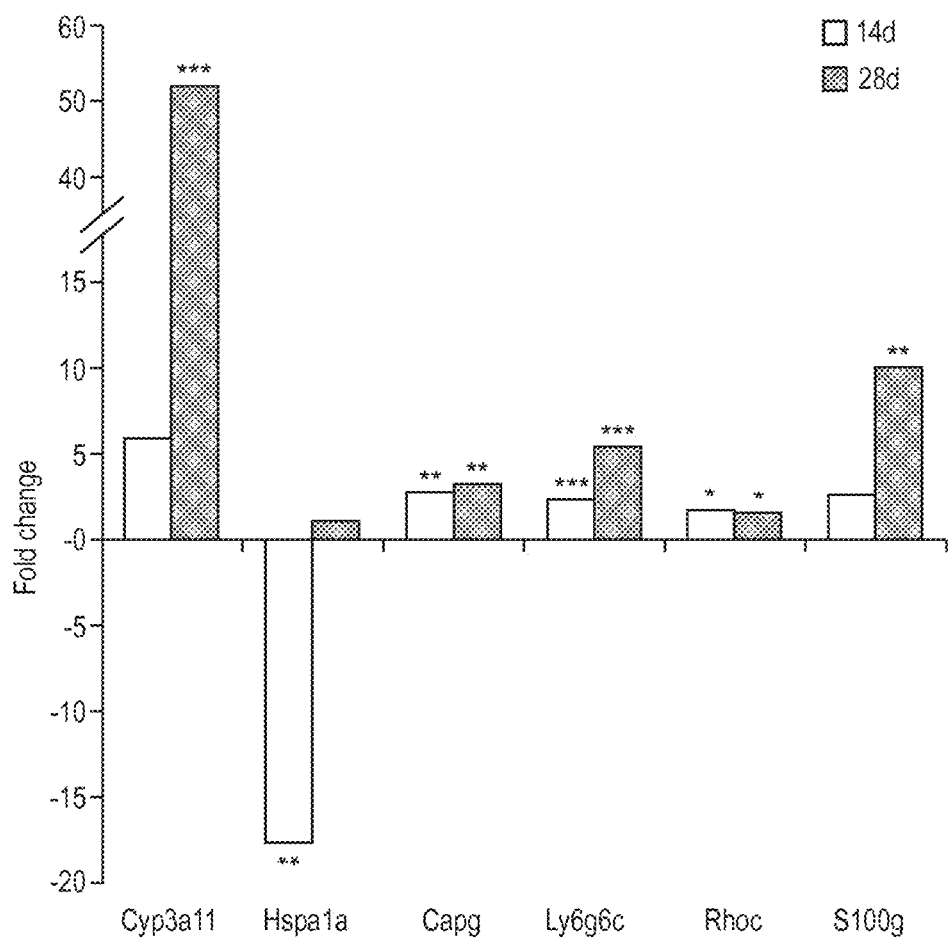

Colonization of GF mice with R. hominis correlated with increased host gene expression, which was highest in the colon (FIG. 3A and Table S4). Differential expression was most profound at 28 d after colonization, with 159 genes up-regulated and 143 genes down-regulated. The number of differentially expressed genes in the ileum at 14 d was similar to the ascending colon, with 79 genes up-regulated and 119 genes down-regulated. Differential expression in the ileum was very low at 28 d, consistent with reduced colonization levels. The transcriptomic response differed at the two time-points, as shown by the clear separation of significant transcripts by heatmap analysis (FIG. 3B). Positive Real-time PCR validation of Affymetrix data is shown in FIG. 3C.

Table S4. Affymetrix Data Between R. hominis Inoculated Animals and GF Animals.

Affymetrix microarray analysis was performed on RNA isolated from ascending colon and ileum tissue. Data was considered significant when P<0.05 using the Benjamini and Hochberg false discovery method. (A) Transcripts differentially expressed in the ascending colon at 14 d. (B) Transcripts differentially expressed in the ascending colon at 28 d. (C) Transcripts differentially expressed in the ileum at 14 d. (D) Transcripts differentially expressed in the ileum at 28 d.

TABLE S4A

Transcripts differentially expressed in the ascending colon at 14d between R. hominis inoculated animals and germfree animals.

| ID | Symbol | Name | FC | P-value | B |
|---|---|---|---|---|---|
| 1424973_at | Cyp3a25 | Cytochrome P450, family 3, subfamily a, polypeptide 25 | 26.35 | 4.09E−05 | 8.91 |
| 1449375_at | Ces6 | Carboxylesterase 6 | 22.80 | 5.71E−16 | 29.28 |
| 1428400_at | 2200002K05Rik | RIKEN cDNA 2200002K05 qene | 6.22 | 6.65E−09 | 17.20 |
| 1419393_at | Abcq5 | ATP-binding cassette, sub-family G (WHITE), member 5 | 5.81 | 0.002156 | 4.51 |
| 1429726_at | Slc16a9 | Solute carrier family 16 (monocarboxylic acid transporters), member 9 | 4.38 | 0.001103 | 5.26 |
| 1430641_at | 9030605I04Rik | RIKEN cDNA 9030605I04 gene | 4.36 | 0.000358 | 6.52 |
| 1436575_at | Grin3a | Glutamate receptor ionotropic, NMDA3A | 3.91 | 0.018503 | 1.71 |
| 1422749_at | Ly6g6c | Lymphocyte antiqen 6 complex, locus G6C | 3.71 | 0.004044 | 3.79 |
| NuGO_emt070648_at | Abca12 | ATP-binding cassette, sub-family A (ABC1), member 12 | 3.69 | 0.000333 | 6.62 |
| 1428682_at | Zc3h6 | Zinc finqer CCCH type containing 6 | 3.28 | 0.002747 | 4.26 |
| 1431554_a_at | Anxa9 | Annexin A9 | 3.00 | 3.25E−05 | 9.18 |
| 1423556_at | Akr1b7 | Aldo-keto reductase family 1, member B7 | 2.87 | 0.018503 | 1.70 |
| 1424451_at | Acaa1b | Acetyl-Coenzyme A acyltransferase 1B | 2.70 | 0.000404 | 6.33 |
| 1418486_at | Vnn1 | Vanin 1 | 2.66 | 0.001531 | 4.93 |
| 1418606_at | Hoxd10 | Homeo box D10 | 2.60 | 0.000102 | 7.97 |
| 1435207_at | Dixdc1 | DIX domain containing 1 | 2.55 | 0.014337 | 2.11 |
| 1427072_at | Stard8 | START domain containinq 8 | 2.48 | 0.027058 | 1.15 |
| 1442560_at | NA | NA | 2.42 | 0.006928 | 3.17 |
| 1420998_at | Etv5 | Ets variant gene 5 | 2.33 | 0.017697 | 1.81 |
| 1440925_at | Rhoq | Ras homolog gene family, member Q | 2.32 | 0.013564 | 2.22 |
| 1428902_at | Chst11 | Carbohydrate sulfotransferase 11 | 2.30 | 0.000154 | 7.46 |
| 1416607_at | 4931406C07Rik | RIKEN cDNA 4931406C07 qene | 2.28 | 7.26E−11 | 21.08 |
| 1435673_at | Hoxd3 | Homeo box D3 | 2.26 | 0.019944 | 1.60 |
| 1426663_s_at | Slc45a3 | Solute carrier family 45, member 3 | 2.21 | 0.007554 | 3.07 |
| 1419651_at | 2610200G18Rik | RIKEN cDNA 2610200G18 gene | 2.21 | 0.000406 | 6.29 |
| 1422188_s_at | NA | NA | 2.20 | 0.000397 | 6.39 |
| 1435468_at | D230025D16Rik | RIKEN cDNA D230025D16 gene | 2.15 | 0.018503 | 1.71 |
| 1417991_at | Dio1 | Deiodinase, iodothyronine, type I | 2.12 | 0.026066 | 1.24 |
| 1451557_at | Tat | Tyrosine aminotransferase | 2.11 | 0.046376 | 0.38 |
| 1428989_at | 0710001 D07Rik | RIKEN cDNA 0710001D07 gene | 2.03 | 0.04028 | 0.54 |

TABLE S4A-continued

Transcripts differentially expressed in the ascending colon at 14d between R. hominis inoculated animals and germfree animals.

| ID | Symbol | Name | FC | P-value | B |
|---|---|---|---|---|---|
| 1456680_at | B3gnt6 | UDP-GlcNAc:betaGal beta-1,3-N-acetylglucosaminyltransferase 6 (core 3 synthase) | 2.01 | 0.024447 | 1.35 |
| 1443235_at | Eif2ak4 | Eukaryotic translation initiation factor 2 alpha kinase 4 | 1.97 | 0.002156 | 4.51 |
| 1419759_at | Abcb1a | ATP-binding cassette, sub-family B (MDR/TAP), member 1A | 1.97 | 0.009639 | 2.79 |
| 1456389_at | Zeb2 | Zinc finger E-box binding homeobox 2 | 1.96 | 0.013795 | 2.16 |
| 1440840_at | D630004K10Rik | RIKEN cDNA D630004K10 gene | 1.96 | 0.017697 | 1.80 |
| 1457619_at | Ces6 | Carboxylesterase 6 | 1.94 | 0.04028 | 0.55 |
| 1449049_at | Tlr1 | Toll-like receptor 1 | 1.92 | 0.018503 | 1.72 |
| NuGO_emt049113_at | Ptprh | Protein tyrosine phosphatase, receptor type, H | 1.89 | 0.002961 | 4.17 |
| 1424376_at | Cdc42ep1 | CDC42 effector protein (Rho GTPase binding) 1 | 1.88 | 0.014337 | 2.10 |
| 1436566_at | Rab40b | Rab40b, member RAS oncogene family | 1.87 | 0.028805 | 1.04 |
| 1432590_at | LOC621549 | NA | 1.83 | 0.012459 | 2.38 |
| 1430543_at | Clip3 | CAP-GLY domain containing linker protein 3 | 1.82 | 6.24E−05 | 8.47 |
| 1435553_at | Pdzd2 | PDZ domain containing 2 | 1.81 | 0.048735 | 0.32 |
| 1428271_at | Acbd4 | Acyl-Coenzyme A binding domain containing 4 | 1.80 | 0.014378 | 2.09 |
| 1418059_at | Eltd1 | EGF, latrophilin seven transmembrane domain containing 1 | 1.79 | 0.005331 | 3.47 |
| 1456532_at | Pdgfd | Platelet derived growth factor, D polypeptide | 1.77 | 0.007554 | 3.05 |
| 1437393_at | AI875142 | Expressed sequence AI875142 | 1.77 | 0.03504 | 0.78 |
| 1428332_at | 1500004A08Rik | RIKEN cDNA 1500004A08 gene | 1.77 | 0.038684 | 0.61 |
| 1434015_at | Slc2a6 | Solute carrier family 2 (facilitated glucose transporter), member 6 | 1.75 | 0.000437 | 6.19 |
| 1449403_at | Pde9a | Phosphodiesterase 9A | 1.71 | 0.03504 | 0.79 |
| 1428260_at | Spg3a | Spastic paraplegia 3A homolog (human) | 1.69 | 0.011437 | 2.55 |
| 1417803_at | 1110032A04Rik | RIKEN cDNA 1110032A04 gene | 1.66 | 0.001103 | 5.27 |
| 1430245_at | Fxr1h | Fragile X mental retardation gene 1, autosomal homoloq | 1.66 | 0.012459 | 2.36 |
| 1422542_at | Gpr34 | G protein-coupled receptor 34 | 1.65 | 0.031372 | 0.95 |
| 1427020_at | Scara3 | Scavenger receptor class A, member 3 | 1.60 | 0.010425 | 2.69 |
| 1430211_at | 4930415O20Rik | RIKEN cDNA 4930415O20 gene | 1.57 | 0.045 | 0.42 |
| 1452809_at | 9030607L17Rik | RIKEN cDNA 9030607L17 gene | 1.53 | 0.013564 | 2.22 |
| NuGO_emt066282_at | Defb37 | Defensin beta 37 | 1.51 | 0.005422 | 3.44 |
| 1451498_at | BC004853 | cDNA sequence BC004853 | 1.50 | 0.037045 | 0.69 |
| 1434140_at | Mcf2l | Mcf,2 transforming sequence-like | 1.49 | 0.025597 | 1.30 |
| 1452650_at | Trim62 | Tripartite motif-containing 62 | 1.46 | 0.02652 | 1.19 |
| 1427492_at | Pof1b | Premature ovarian failure 1B | 1.46 | 0.004679 | 3.61 |
| 1426601_at | Slc37a1 | Solute carrier family 37 (glycerol-3-phosphate transporter), member 1 | 1.42 | 0.032433 | 0.90 |
| 1448188_at | Ucp2 | Uncoupling protein 2 (mitochondrial, proton carrier) | 1.42 | 0.008209 | 2.96 |
| 1460409_at | Cpt1a | Carnitine palmitoyltransferase 1a, liver | 1.40 | 0.025932 | 1.26 |
| 1460652_at | Esrra | Estrogen related receptor, alpha | 1.39 | 0.038182 | 0.65 |
| 1453869_at | LOC328277 | NA | 1.36 | 0.017271 | 1.86 |
| 1435985_at | Farp2 | FERM, RhoGEF and pleckstrin domain protein 2 | 1.34 | 0.037045 | 0.70 |
| 1454706_at | Uvrag | UV radiation resistance associated gene | 1.34 | 0.021704 | 1.51 |
| 1451232_at | Cd151 | CD151 antigen | 1.31 | 0.049274 | 0.31 |
| 1423570_at | Abcg1 | ATP-binding cassette, sub-family G (WHITE), member 1 | 1.30 | 0.04028 | 0.55 |
| 1418817_at | Chmp1b | Chromatin modifying protein 1B | 1.25 | 0.010981 | 2.61 |
| 1441059_at | 1700049G17Rik | RIKEN cDNA 1700049G17 gene | 1.25 | 0.028805 | 1.05 |
| NuGO_emt061346_at | NA | NA | 1.24 | 0.026697 | 1.17 |
| 1420503_at | Slc6a14 | Solute carrier family 6 (neurotransmitter transporter), member 14 | 1.22 | 0.012499 | 2.32 |
| NuGO_emt073103_x_at | NA | NA | 1.21 | 0.01946 | 1.63 |
| 1452592_at | Mgst2 | Microsomal glutathione S-transferase 2 | 1.18 | 0.038684 | 0.60 |
| 1441135_at | NA | NA | −1.10 | 0.01646 | 1.92 |
| 1428482_at | Akap10 | A kinase (PRKA) anchor protein 10 | −1.20 | 0.022427 | 1.47 |
| 1426679_at | Zfp706 | Zinc finger protein 706 | −1.26 | 0.028805 | 1.05 |
| 1415816_at | Cct7 | Chaporonin subunit 7 (eta) | −1.26 | 0.011936 | 2.47 |
| 1445024_at | Stard7 | START domain containing 7 | −1.27 | 0.03504 | 10.79 |
| 1453591_at | 5730437N04Rik | RIKEN cDNA 5730437N04 gene | −1.32 | 0.02652 | 1.19 |
| 1450788_at | Saa1 | Serum amyloid A 1 | −1.32 | 0.002156 | 4.54 |
| 1436157_at | Ccar1 | Cell division cycle and apoptosis regulator 1 | −1.33 | 0.034783 | 0.81 |
| 1450987_a_at | 2310004I24Rik | RIKEN cDNA 2310004I24 gene | −1.35 | 0.0361 | 0.73 |
| 1433850_at | Ppp4r2 | Protein phosphatase 4, regulatory subunit 2 | −1.36 | 0.018503 | 1.71 |
| 1434835_at | Wapal | Wings apart-like homolog (Drosophila) | −1.37 | +0.027058 | 1.14 |
| NuGO_emt090017_s_at | Cdk7 | Cyclin-dependent kinase 7 (homolog of Xenopus M015 cdk- activating kinase) | −1.37 | 0.044186 | 0.44 |
| 1422579_at | Hspe1 | Heat shock protein 1 (chaperonin 10) | −1.38 | 0.017697 | 1.81 |
| 1455726_at | Gm71 | Gene model 71, (NCBI) | −1.42 | 0.029302 | 1.02 |
| 1420461_at | Mst1r | Macrophage stimulating 1 receptor (c-met-related tyrosine kinase) | −1.49 | 0.046838 | 0.37 |
| 1453264_at | Marveld3 | MARVEL (membrane-associating) domain containing 3 | −1.49 | 0.005522 | 3.40 |
| 1425030_at | Zfp622 | Zinc finger protein 622 | −1.49 | 0.000586 | 5.89 |
| 1458507_at | 2810055G22Rik | RIKEN cDNA 2810055G22 gene | −1.50 | 0.032433 | 0.89 |
| 1443988_at | Rbm39 | RNA binding motif protein 39 | −1.51 | 0.037045 | 0.68 |
| 1460465_at | A930038C07Rik | RIKEN cDNA A930038C07 gene | −1.51 | 0.004627 | 3.64 |
| 1428784_at | Gmip | Gem-interacting protein | −1.51 | 0.045 | 0.42 |
| 1451621_at | 5830417C01Rik | RIKEN cDNA 5830417C01 gene | −1.65 | 0.014536 | 2.07 |
| 1422837_at | Sce1 | Sciellin | −1.68 | 0.0361 | 0.74 |
| 1454617_at | Arrdc3 | Arrestin domain containing 3 | −1.71 | 0.038496 | 0.62 |
| 1452047_at | Cacybp | Calcyclin binding protein | −1.72 | 0.018495 | 1.75 |
| 1434724_at | Usp31 | Ubiquitin specific peptidase 31 | −1.75 | 0.024018 | 1.39 |
| 1417032_at | Ube2g2 | Ubiquitin-conjugating enzyme E2G 2 | −1.76 | 0.04028 | 0.56 |

TABLE S4A-continued

Transcripts differentially expressed in the ascending colon at 14d between R. hominis inoculated animals and germfree animals.

| ID | Symbol | Name | FC | P-value | B |
|---|---|---|---|---|---|
| 1448628_at | Scg3 | Secretogranin III | −1.77 | 0.016351 | 1.93 |
| 1443877_a_at | Rapgef6 | Rap guanine nucleotide exchange factor (GEF) 6 | −1.82 | 0.004044 | 3.80 |
| 1427944_at | Caprin2 | Caprin family member 2 | −1.85 | 0.04248 | 0.49 |
| 1415909_at | Stipl | Stress-induced phosphoprotein 1 | −1.89 | 0.024018 | 1.38 |
| 1422452_at | Bag3 | Bcl2-associated athanogene 3 | −1.89 | 0.026066 | 1.24 |
| 1438041_at | Pde7a | Phosphodiesterase 7 A | −1.91 | 0.025597 | 1.29 |
| 1433927_at | Uspn | Ubiquitin specific peptidase like 1 | −1.92 | 0.024018 | 1.38 |
| 1422860_at | Nts | Neurotensin | −1.94 | 1.84E−07 | 14.1 |
| 1451194_at | Aldob | Aldolase 2, B isoform | −1.94 | 7.08E−06 | 10.5 |
| 1441662_at | Cyp4x1 | Cytochrome P450, family 4, subfamily x, polypeptide 1 | −1.95 | 0.00019 | 7.22 |
| 1445490_at | C77805 | Expressed sequence C77805 | −1.96 | 0.003479 | 4.00 |
| NuGO_emt066852_at | NA | NA | −2.07 | 0.013658 | 2.19 |
| 1442427_at | NA | NA | −2.11 | 0.033207 | 0.86 |
| 1430185_at | Akap13 | A kinase (PRKA) anchor protein 13 | −2.12 | 0.0361 | 0.74 |
| 1452462_a_at | Banp | Btg3 associated nuclear protein | −2.16 | 0.038182 | 0.64 |
| 1446158_at | Exoc6b | Exocyst complex component 6B | −2.19 | 0.010302 | 2.72 |
| 1418113_at | Cyp2d10 | Cytochrome P450, family 2, subfamily d, polypeptide 10 | −2.24 | 0.012383 | 2.42 |
| 1426645_at | Hsp90aa1 | Heat shock protein 90kDa alpha (cytosolic), class A member 1 | −2.30 | 0.012459 | 2.34 |
| 1420150_at | Spsbl | SplA/ryanodine receptor domain and SOCS box containing 1 | −2.36 | 0.015257 | 2.01 |
| 1452382_at | Dnm3os | Dynamin 3, opposite strand | −2.37 | 0.025932 | 1.26 |
| 1460645_at | Chordcl | Cysteine and histidine-rich domain (CHORD)-containing, zinc- binding protein 1 | −2.38 | 0.002156 | 4.53 |
| 1457477_at | NA | NA | −2.39 | 0.027058 | 1.14 |
| 1430175_at | Tmtc2 | Transmembrane and tetratricopeptide repeat containing 2 | −2.40 | 0.028805 | 1.05 |
| 1433266_at | 2810416A17Rik | RIKEN cDNA 2810416A17 gene | −2.43 | 0.0361 | 0.73 |
| 1416756_at | Dnajbl | DnaJ (Hsp40) homolog, subfamily B, member 1 | −2.50 | 0.013658 | 2.19 |
| 1415938_at | Spink3 | Serine peptidase inhibitor, Kazal type 3 | −2.53 | 0.012459 | 2.35 |
| 1429273_at | Bmper | BMP-binding endothelial regulator | −2.53 | 0.012459 | 2.34 |
| 1450518_at | Hnf4g | Hepatocyte nuclear factor 4, gamma | −2.53 | 0.019018 | 1.66 |
| 1440227_at | BF642829 | Expressed sequence BF642829 | −2.58 | 0.038494 | 0.63 |
| 1451924_a_at | Edn1 | Endothelin 1 | −2.63 | 0.011568 | 2.51 |
| 1425952_a_at | Gcg | Glucagon | −2.65 | 2.76E−06 | 11.57 |
| 1459253_at | Arrdc3 | Arrestin domain containing 3 | −2.69 | 0.026081 | 1.23 |
| 1416288_at | Dnaja1 | DnaJ (Hsp40) homoloq, subfamily A, member 1 | −2.75 | 0.000154 | 7.45 |
| 1435160_at | 1110064P04Rik | RIKEN cDNA 1110064P04 gene | −2.76 | 0.011568 | 2.52 |
| 1460179_at | Dnaja1 | DnaJ (Hsp40) homolog, subfamily A, member 1 | −2.78 | 0.000251 | 6.92 |
| 1419349_a_at | Cyp2d9 | Cytochrome P450, family 2, subfamily d, polypeptide 9 | −2.78 | 0.000134 | 7.68 |
| NuGO_emt044299_at | Sstr1 | Somatostatin receptor 1 | −2.80 | 3.73E−07 | 13.38 |
| 1449493_at | Insl5 | Insulin-like 5 | −2.91 | 5.33E−08 | 15.35 |
| NuGO_emt054105_at | D630013G24Rik | RIKEN cDNA D630013G24 gene | −2.99 | 0.004044 | 3.83 |
| 1419185_a_at | Mlxipl | MLX interacting protein-like | −3.16 | 4.43E−06 | 11.08 |
| 1449939_s_at | Dlk1 | Delta-like 1 homolog (Drosophila) | −3.29 | 9.19E−11 | 20.69 |
| 1458385_at | Hspa4l | Heat shock protein 4 like | −3.36 | 0.032433 | 0.90 |
| 1422639_at | Calcb | Calcitonin-related polypeptide, beta | −3.75 | 0.010981 | 2.62 |
| 1425993_a_at | Hsp110 | Heat shock protein 110 | −4.08 | 0.028805 | 1.05 |
| NuGO_emt091063_at | NA | NA | −6.03 | 3.11E−07 | 13.63 |
| 1419473_a_at | Cck | Cholecystokinin | −10.07 | 4.94E−11 | 21.66 |
| 1452388_at | Hspa1a | Heat shock protein 1A | −25.30 | 0.02652 | 1.19 |

TABLE S4B

Transcripts differentially expressed in the ascending colon at 28d between R. hominis inoculated animals and germfree animals.

| ID | Symbol | Name | FC | P-value | B |
|---|---|---|---|---|---|
| 1416809_at | Cyp3a11 | Cytochrome P450, family 3, subfamily a, polypeptide 11 | 89.84 | 1.45E−06 | 12.00 |
| 1424973_at | Cyp3a25 | Cytochrome P450, family 3, subfamily a, polypeptide 25 | 52.30 | 7.31.E−07 | 12.67 |
| 1419393_at | Abcg5 | ATP-binding cassette, sub-family G (WHITE), member 5 | 42.06 | 1.60E−09 | 18.55 |
| 1449375_at | Ces6 | Carboxylesterase 6 | 26.10 | 1.75E−16 | 31.66 |
| 1422749_at | Ly6g6c | Lymphocyte antigen 6 complex, locus G6C | 25.94 | 2.06E−10 | 20.64 |
| 1448964_at | S100g | S100 calcium binding protein G | 17.88 | 4.82E−07 | 13.11 |
| 1455540_at | Cps1 | Carbamoyl-phosphate synthetase 1 | 11.50 | 0.010507 | 1.76 |
| 1449133_at | Sprr1a | Small proline-rich protein 1A | 11.27 | 0.009303 | 1.97 |
| NuGO_emt070648_at | Abca12 | ATP-binding cassette, sub-family A (ABC1), member 12 | 7.97 | 4.05E−08 | 15.43 |
| 1448485_at | Ggt1 | Gamma-glutamyltransferase 1 | 7.45 | 0.020934 | 0.94 |
| 1417828_at | Aqp8 | Aquaporin 8 | 6.67 | 0.001582 | 4.30 |
| 1437060_at | Olfm4 | Olfactomedin 4 | 5.80 | 0.023469 | 0.77 |
| 1420437_at | Indo | Indoleamine-pyrrole 2,3 dioxyqenase | 5.18 | 0.000637 | 5.44 |
| 1425452_s_at | AW125753 | Expressed sequence AW125753 | 4.97 | 0.001639 | 4.20 |
| 1439934_at | Slc30a10 | Solute carrier family 30, member 10 | 4.68 | 0.000119 | 7.49 |
| 1430641_at | 9030605I04Rik | RIKEN cDNA 9030605I04 qene | 4.47 | 0.000199 | 6.89 |
| 1423556_at | Akr1b7 | Aldo-keto reductase family 1, member B7 | 4.36 | 0.000304 | 6.44 |
| 1428400_at | 2200002K05Rik | RIKEN cDNA 2200002K05 gene | 4.31 | 4.81E−07 | 13.18 |

TABLE S4B-continued

Transcripts differentially expressed in the ascending colon at 28d between R. hominis inoculated animals and germfree animals.

| ID | Symbol | Name | FC | P-value | B |
| --- | --- | --- | --- | --- | --- |
| 1424626_at | 2010003K11Rik | RIKEN cDNA 2010003K11 gene | 4.25 | 0.024887 | 0.68 |
| 1439727_at | Clca6 | Chloride channel calcium activated 6 | 4.09 | 0.000869 | 5.07 |
| 1450355_a_at | Capg | Capping protein (actin filament), gelsolin-like | 3.90 | 4.67E−05 | 8.59 |
| 1427119_at | Spink4 | Serine peptidase inhibitor, Kazal type 4 | 3.67 | 0.007507 | 2.25 |
| NuGO_emt092118_s_at | NA | NA | 3.51 | 0.040399 | −0.04 |
| 1451239_a_at | Slc26a1 | Solute carrier family 26 (sulfate transporter), member 1 | 3.36 | 0.004508 | 2.94 |
| 1418283_at | Cldn4 | Claudin 4 | 2.97 | 0.002809 | 3.51 |
| 1418165_at | Itlna | Intelectin a | 2.88 | 0.0005 | 5.82 |
| 1440192_at | 1810054D07Rik | RIKEN cDNA 1810054D07 gene | 2.86 | 0.000108 | 7.65 |
| 1426980_s_at | E130012A19Rik | RIKEN cDNA E130012A19 gene | 2.83 | 0.002052 | 3.91 |
| 1431042_at | Paqr8 | Progestin and odipoQ receptor family member VIII | 2.67 | 0.000637 | 5.46 |
| 1424688_at | Creb3l3 | cAMP responsive element binding protein 3-like 3 | 2.67 | 0.035165 | 0.19 |
| NuGO_emt049113_at | Ptprh | Protein tyrosine phosphatase, receptor type, H | 2.54 | 6.75E−06 | 10.55 |
| 1432358_at | Muc16 | Mucin 16 | 2.47 | 0.044391 | −0.20 |
| 1419759_at | Abcb1a | ATP-binding cassette, sub-family B (MDR/TAP), member 1A | 2.46 | 0.00017 | 7.13 |
| NuGO_emt033610_at | Nox1 | NADPH oxidase 1 | 2.43 | 0.035165 | 0.20 |
| 1418661_at | Abhd2 | Abhydrolase domain containing 2 | 2.41 | 0.043727 | −0.17 |
| 1420499_at | Gch1 | GTP cyclohydrolase 1 | 2.38 | 0.040391 | −0.03 |
| 1416607_at | 4931406C07Rik | RIKEN cDNA 4931406C07 gene | 2.31 | 3.39E−11 | 22.26 |
| 1417991_at | Dio1 | Deiodinase, iodothyronine, type I | 2.29 | 0.006845 | 2.39 |
| 1455455_at | Glt28d2 | Glycosyltransferase 28 domain containing 2 | 2.16 | 0.015457 | 1.33 |
| 1417164_at | Dusp10 | Dual specificity phosphatase 10 | 2.13 | 0.031006 | 0.40 |
| 1428937_at | Atp2b1 | ATPase, Ca++ transporting, plasma membrane 1 | 2.13 | 1.13E−05 | 9.98 |
| 1429833_at | Ly6g6e | Lymphocyte antigen 6 complex, locus G6E | 2.10 | 0.042694 | −0.12 |
| 1419582_at | Cyp2c55 | Cytochrome P450, family 2, subfamily c, polypeptide 55 | 2.06 | 0.022426 | 0.83 |
| 1448562_at | Upp1 | Uridine phosphorylase 1 | 2.06 | 0.007369 | 2.29 |
| 1444254_at | NA | NA | 2.05 | 0.009642 | 1.90 |
| 1428936_at | Atp2b1 | ATPase, Ca++ transporting, plasma membrane 1 | 2.05 | 0.000378 | 6.15 |
| 1421268_at | Ugcg | UDP-glucose ceramide glucosyltransferase | 2.05 | 0.035029 | 0.21 |
| 1419478_at | Sectm1b | Secreted and transmembrane 1B | 2.02 | 0.004814 | 2.83 |
| 1428336_at | Agpat4 | 1-acylglycerol-3-phosphate O-acyltransferase 4 (lysophosphatidic acid acyltransferase, delta) | 2.02 | 0.047797 | −0.32 |
| 1456231_at | Pla2g3 | Phospholipase A2, group III | 1.99 | 0.000365 | 6.21 |
| 1421709_a_at | Fmo5 | Flavin containing monooxygenase 5 | 1.97 | 0.02187 | 0.86 |
| 1455104_at | NA | NA | 1.95 | 0.010934 | 1.71 |
| 1417133_at | Pmp22 | Peripheral myelin protein | 1.95 | 0.027135 | 10.58 |
| 1418206_at | Sdf2l1 | Stromal cell-derived factor 2-like 1 | 1.94 | 0.045914 | −0.25 |
| 1436614_at | AI843639 | Expressed sequence AI843639 | 1.94 | 0.006795 | 2.41 |
| 1452070_at | Dedd2 | Death effector domain-containing DNA binding protein 2 | 1.92 | 0.046848 | −0.28 |
| 1417404_at | Elovl6 | ELOVL family member 6, elongation of long chain fatty acids (yeast) | 1.90 | 0.012549 | 1.55 |
| 1417277_at | Cyp4f16 | Cytochrome P450, family 4, subfamily f, polypeptide 16 | 1.87 | 0.000119 | 7.50 |
| 1422983_at | Itgb6 | Integrin beta 6 | 1.87 | 0.03266 | 0.33 |
| 1454746_at | Plekhm1 | Pleckstrin homology domain containing, family M (with RUN domain) member 1 | 1.86 | 0.001042 | 4.88 |
| 1425079_at | Tm6sf2 | Transmembrane 6 superfamily member 2 | 1.85 | 0.001269 | 4.60 |
| 1455099_at | Mogat2 | Monoacylglycerol O-acyltransferase 2 | 1.85 | 0.024887 | 0.68 |
| 1435749_at | Gda | Guanine deaminase | 1.82 | 0.002467 | 3.67 |
| 1416488_at | Ccng2 | Cyclin G2 | 1.81 | 0.003976 | 3.09 |
| 1418256_at | Srf | Serum response factor | 1.79 | 0.033108 | 0.26 |
| 1426744_at | Srebf2 | Sterol regulatory element binding factor 2 | 1.76 | 0.041026 | −0.07 |
| 1457253_at | Trim40 | Tripartite motif-containing 40 | 1.75 | 0.001269 | 4.61 |
| 1433556_at | Centa1 | Centaurin, alpha 1 | 1.75 | 0.009141 | 2.01 |
| NuGO_emt084792_x_at | NA | NA | 1.74 | 0.020944 | 0.92 |
| 1417823_at | Gcat | Glycine C-acetyltransferase (2-amino-3-ketobutyrate-coenzyme A ligase) | 1.74 | 0.049235 | −0.38 |
| NuGO_emt066282_at | Defb37 | Defensin beta 37 | 1.74 | 6.42E−05 | 8.25 |
| 1429550_at | Entpd8 | Ectonucleoside triphosphate diphosphohydrolase 8 | 1.73 | 0.004814 | 2.85 |
| 1430594_at | Rab11fip1 | RAB11 family interacting protein 1 (class I) | 1.73 | 0.033108 | 0.27 |
| 1420913_at | Slco2a1 | Solute carrier organic anion transporter family, member 2a1 | 1.73 | 0.001791 | 4.09 |
| NuGO_emt043440_at | 2210010C17Rik | RIKEN cDNA 2210010C17 gene | 1.73 | 0.01702 | 1.21 |
| 1430674_at | 1700016C15Rik | RIKEN cDNA 1700016C15 gene | 1.73 | 0.036022 | 0.14 |
| 1430890_at | 2210010C17Rik | RIKEN cDNA 2210010C17 gene | 1.72 | 0.011201 | 1.68 |
| 1417803_at | 1110032A04Rik | RIKEN cDNA 1110032A04 gene | 1.71 | 0.000358 | 6.25 |
| 1449873_at | Bmp8a | Bone morphogenetic protein 8a | 1.71 | 0.044796 | −0.22 |
| 1434130_at | Lhfpl2 | Lipoma HMGIC fusion partner-like 2 | 1.71 | 0.004814 | 2.83 |
| 1448605_at | Rhoc | Ras homolog gene family, member C | 1.70 | 0.001099 | 4.79 |
| 1432363_at | 2410018E23Rik | RIKEN cDNA 2410018E23 gene | 1.69 | 0.04853 | −0.34 |
| 1427878_at | 0610010012Rik | RIKEN cDNA 0610010012 gene | 1.68 | 2.48E−05 | 9.21 |
| 1416379_at | Panx1 | Pannexin 1 | 1.67 | 0.002404 | 3.74 |
| 1434059_at | B230312A22Rik | RIKEN cDNA B230312A22 gene | 1.65 | 0.001763 | 4.12 |
| 1452475_at | Pcsk5 | Proprotein convertase subtilisin/kexin type 5 | 1.65 | 0.036022 | 0.12 |
| 1454399_at | 2010003H20Rik | RIKEN cDNA 2010003H20 gene | 1.62 | 0.016629 | 1.24 |
| 1460550_at | Mtmr11 | Myotubularin related protein 11 | 1.62 | 0.010762 | 1.73 |
| NuGO_emt070892_at | NA | NA | 1.62 | 0.020773 | 0.95 |
| 1436710_at | Zswim4 | Zinc finger, SWIM domain containing 4 | 1.62 | 0.009718 | 1.88 |
| 1420663_at | Zbtb7b | Zinc finger and BTB domain containing 7B | 1.61 | 0.042694 | −0.13 |

TABLE S4B-continued

Transcripts differentially expressed in the ascending colon at 28d between R. hominis inoculated animals and germfree animals.

| ID | Symbol | Name | FC | P-value | B |
| --- | --- | --- | --- | --- | --- |
| 1418991_at | Bak1 | BCL2-antagonist/killer 1 | 1.61 | 0.01094 | 1.71 |
| 1417990_at | Ppp1r14d | Protein phosphatase 1, regulatory (inhibitor) subunit 14D | 1.59 | 0.003746 | 3.16 |
| 1452837_at | Lpin2 | Lipin 2 | 1.58 | 0.035702 | 0.16 |
| NuGO_emt021769_s_at | Slc17a4 | Solute carrier family 17 (sodium phosphate), member 4 | 1.57 | 0.015878 | 1.30 |
| 1418671_at | Capn5 | Calpain 5 | 1.57 | 0.041629 | −0.09 |
| 1417751_at | Stk10 | Serine/threonine kinase 10 | 1.57 | 0.027636 | 0.55 |
| 1452294_a1 | Pcdh1 | Protocadherin 1 | 1.56 | 0.003042 | 3.42 |
| 1429154_at | Slc35f2 | Solute carrier family 35, member F2 | 1.56 | 0.004185 | 3.02 |
| 1450982_at | Slc9a3r1 | Solute carrier family 9 (sodium/hydrogen exchanger), isoform 3 regulator 1 | 1.56 | 0.008755 | 2.06 |
| 1434015_at | Slc2a6 | Solute carrier family 2 (facilitated glucose transporter), member 6 | 1.55 | 0.005093 | 2.72 |
| 1418712_at | Cdc42ep5 | CDC42 effector protein (Rho GTPase binding) 5 | 1.55 | 0.003976 | 3.09 |
| 1424809_at | Crb3 | Crumbs homoloq 3 (Drosophila) | 1.53 | 0.014107 | 1.43 |
| 1428953_at | Otud7b | OTU domain containing 7B | 1.53 | 0.035702 | 0.17 |
| 1424090_at | Sdcbp2 | Syndecan binding protein (syntenin) 2 | 1.53 | 0.023574 | 0.76 |
| 1418215_at | Mep1b | Meprin 1 beta | 1.53 | 0.027636 | 0.55 |
| 1434456_at | Gm440 | gene model 440, (NCBI) | 1.53 | 0.032752 | 0.32 |
| 1423521_at | Lmnb1 | Lamin B1 | 1.53 | 0.007369 | 2.31 |
| 1425298_a_at | Naip1 | NLR family, apoptosis inhibitory protein 1 | 1.51 | 0.002438 | 3.70 |
| 1456619_at | Liph | Lipase, member H | 1.50 | 0.044796 | −0.22 |
| 1418976_s_at | Cideb | Cell death-inducing DNA fragmentation factor, alpha subunit-like effector B | 1.49 | 0.020944 | 0.93 |
| 1423376_a_at | Dok4 | Docking protein 4 | 1.49 | 0.005089 | 2.73 |
| 1415793_at | Pnpo | Pyridoxine 5'-phosphate oxidase | 1.48 | 0.00252 | 3.63 |
| 1435461_at | Magi3 | Membrane associated guanylate kinase, WW and PDZ domain containing 3 | 1.48 | 0.001623 | 4.23 |
| 1444951_at | BC042698 | cDNA sequence BC042698 | 1.45 | 0.042694 | −0.14 |
| 1452214_at | Skil | SKI-like | 1.45 | 0.020383 | 0.99 |
| 1426284_at | Krt20 | Keratin 20 | 1.43 | 0.021519 | 0.88 |
| 1460406_at | AI427122 | Expressed sequence AI427122 | 1.42 | 0.016225 | 1.27 |
| 1419331_at | Cdh17 | Cadherin 17 | 1.41 | 0.009399 | 1.94 |
| 1428509_at | Myo1e | Myosin IE | 1.41 | 0.043727 | −0.17 |
| 1429117_at | Tradd | TNFRSFIA-associated via death domain | 1.41 | 0.020944 | 0.91 |
| 1460681_at | Ceacam2 | CEA-related cell adhesion molecule 2 | 1.41 | 0.036022 | 0.14 |
| 1455678_at | NA | NA | 1.41 | 0.048555 | −0.36 |
| 1440218_at | BC040758 | cDNA sequence BC040758 | 1.41 | 0.026321 | 0.62 |
| 1416009_at | Tspan3 | Tetraspanin 3 | 1.40 | 0.002052 | 3.91 |
| 1456200_at | Ipmk | Inositol polyphosphate multikinase | 1.40 | 0.033108 | 0.28 |
| 1424126_at | Alas1 | Aminolevulinic acid synthase 1 | 1.39 | 0.040391 | −0.03 |
| 1434482_at | D4Ertd22e | DNA segment, Chr 4, ERATO Doi 22, expressed | 1.39 | 0.038213 | 0.05 |
| 1416690_at | Gtpbp2 | GTP binding protein 2 | 1.38 | 0.035702 | 0.16 |
| 1417895_a_at | Tmem54 | Transmembrane protein 54 | 1.38 | 0.001332 | 4.53 |
| 1424245_at | Ces2 | Carboxylesterase 2 | 1.37 | 0.020303 | 0.99 |
| 1434559_at | Stx3 | Syntaxin 3 | 1.37 | 0.032755 | 0.31 |
| 1426733_at | Itpk1 | Inositol 1,3,4-triphosphate 5/6 kinase | 1.35 | 0.010099 | 1.81 |
| 1451139_at | Slc39a4 | Solute carrier family 39 (zinc transporter), member 4 | 1.34 | 0.04853 | −0.34 |
| 1417398_at | Rras2 | Related RAS viral (r-ras) oncogene homolog 2 | 1.34 | 0.040085 | −0.02 |
| 1427203_at | Myo15b | Myosin XVB | 1.33 | 0.020944 | 0.92 |
| 1428331_at | 2210016F16Rik | RIKEN cDNA 2210016F16 gene | 1.32 | 0.047659 | −0.30 |
| 1427128_at | Rpn23 | Protein tyrosine phosphatase, non-receptor type 23 | 1.31 | 0.042694 | −0.13 |
| 1420426_at | Myo7b | Myosin VIIb | 1.30 | 0.036022 | 0.13 |
| 1452304_a_at | Arhgef5 | Rho guanine nucleotide exchange factor (GEF) 5 | 1.30 | 0.047797 | −0.31 |
| 1434303_at | Raph1 | Ras association (RalGDS/AF-6) and pleckstrin homology domains 1 | 1.29 | 0.024887 | 0.69 |
| 1433885_at | AI788777 | Expressed sequence AI788777 | 1.28 | 0.018321 | 1.10 |
| 1415765_at | Hnrpul2 | Heterogeneous nuclear ribonucleoprotein U-like 2 | 1.28 | 0.009181 | 2.00 |
| 1448110_at | Sema4a | Serna domain, immunoglobulin domain (Ig), transmembrane domain (TM) and short cytoplasmic domain, (semaphorin) 4A | 1.27 | 0.00151 | 4.40 |
| 1423960_at | Mboat5 | Membrane bound O-acyltransferase domain containing 5 | 1.27 | 0.043727 | −0.18 |
| 1415676_a_at | Psmb5 | Proteasome (prosome, macropain) subunit, beta type 5 | 1.27 | 0.040399 | −0.04 |
| 1434345_at | Clrn3 | Clarin 3 | 1.27 | 0.027133 | 0.59 |
| 1426014_a_at | Mucdh1 | Mucin and cadherin like | 1.27 | 0.036152 | 0.11 |
| 1420503_at | Slc6a14 | Solute carrier family 6 (neurotransmitter transporter), member 14 | 1.26 | 0.001582 | 4.31 |
| 1418817_at | Chmp1b | Chromatin modifying protein 1B | 1.25 | 0.004961 | 2.78 |
| 1423686_a_at | Prr13 | Proline rich 13 | 1.25 | 0.026919 | 0.60 |
| 1420826_at | Letm1 | Leucine zipper-EF-hand containing transmembrane protein 1 | 1.24 | 0.036022 | 0.13 |
| 1448618_at | Mvp | Major vault protein | 1.24 | 0.031006 | 0.39 |
| 1417178_at | Gipc2 | GIPC PDZ domain containing family, member 2 | 1.24 | 0.014863 | 1.38 |
| 1416627_at | Spint1 | Serine protease inhibitor, Kunitz type 1 | 1.23 | 0.048555 | −0.36 |
| 1428163_at | Sar1b | SAR1 gene homolog B (S, cerevisiae) | 1.22 | 0.036022 | 0.13 |
| 1416193_at | Car1 | Carbonic anhydrase 1 | 1.21 | 0.009728 | 1.87 |
| 1444884_at | Ppt1 | Palmitoyl-protein thioesterase 1 | 1.18 | 0.032755 | 0.31 |
| 1448279_at | Arpc3 | Actin related protein 2/3 complex, subunit 3 | 1.14 | 0.049367 | −0.38 |
| 1417282_at | Mmp23 | Matrix metallopeptidase 23 | −1.14 | 0.024366 | 0.72 |
| 1429615_at | Zfp91 | Zinc finger protein 91 | −1.22 | 0.038424 | 0.04 |
| 1453577_at | 2610018I03Rik | RIKEN cDNA 2610018I03 gene | −1.22 | 0.04853 | −0.35 |
| 1417999_at | Itm2b | Integral membrane protein 2B | −1.22 | 0.020944 | 0.91 |

TABLE S4B-continued

Transcripts differentially expressed in the ascending colon at 28d between R. hominis inoculated animals and germfree animals.

| ID | Symbol | Name | FC | P-value | B |
|---|---|---|---|---|---|
| 1454994_at | Klhl20 | Kelch-like 20 (Drosophila) | −1.24 | 0.040433 | −0.05 |
| 1435563_at | Mrps5 | Mitochondrial ribosomal protein S5 | −1.25 | 0.022222 | 0.84 |
| 1445561_at | NA | NA | −1.27 | 0.04853 | −0.34 |
| 1436854_at | Trpc2 | Transient receptor potential cation channel, subfamily C, member 2 | −1.27 | 0.002008 | 3.97 |
| 1416452_at | Oat | Ornithine aminotransferase | −1.27 | 0.009757 | 1.86 |
| 1415961_at | Itm2c | Integral membrane protein 2C | −1.28 | 0.007369 | 2.28 |
| 1448933_at | Pcdhb17 | Protocadherin beta 17 | −1.28 | 0.048555 | −0.35 |
| 1440391_at | Gcn1l1 | GCN1 general control of amino-acid synthesis 1-like 1 (yeast) | −1.29 | 0.030585 | 0.42 |
| 1450788_at | Saa1 | Serum amyloid A 1 | −1.31 | 0.001623 | 4.23 |
| 1444451_at | Pappa2 | Pappalysin 2 | −1.31 | 0.038548 | 0.03 |
| 1457029_at | C030010B13Rik | RIKEN cDNA C030010B13 gene | −1.31 | 0.023793 | 0.74 |
| 1417088_at | Zfp346 | Zinc finger protein 346 | −1.33 | 0.039077 | 0.01 |
| 1436220_at | Zfp287 | Zinc finger protein 287 | −1.33 | 0.022441 | 0.82 |
| 1445824_at | Zfp458 | Zinc finger protein 458 | −1.37 | 0.044011 | −0.18 |
| 1420191_s_at | D16Bwg1494e | DNA segment, Chr 16, Brigham & Women's Genetics 1494 expressed | −1.37 | 0.035165 | 0.19 |
| 1415871_at | Tgfbi | Transforming growth factor, beta induced | −1.38 | 0.039653 | 0.00 |
| 1442731_at | 9030416H16Rik | RIKEN cDNA 9030416H16 gene | −1.41 | 0.012107 | 1.59 |
| 1424889_at | Nupl2 | Nucleoporin like 2 | −1.42 | 0.001582 | 4.31 |
| 1416178_a_at | Plekhb1 | Pleckstrin homology domain containing, family B (evectins) member 1 | −1.44 | 0.047797 | −0.32 |
| 1447946_at | Adam23 | A disintegrin and metallopeptidase domain 23 | −1.44 | 0.017961 | 1.13 |
| NuGO_emt080869_at | NA | NA | −1.45 | 0.032755 | 0.31 |
| 1452050_at | Camk1d | Calcium/calmodulin-dependent protein kinase ID | −1.45 | 0.006002 | 2.56 |
| 1442447_at | Znrf3 | Zinc and ring finger 3 | −1.45 | 9.00E−06 | 10.24 |
| 1416865_at | Fgd1 | FYVE, RhoGEF and PH domain containing 1 | −1.46 | 0.049235 | −0.37 |
| 1442197_at | AI480624 | Expressed sequence AI480624 | −1.47 | 0.033108 | 0.27 |
| 1427020_at | Scara3 | Scavenger receptor class A, member 3 | −1.47 | 0.029906 | 0.45 |
| 1434961_at | Asb1 | Ankyrin repeat and SOCS box-containing protein 1 | −1.48 | 0.0093 | 1.97 |
| 1431873_a_at | Tubel | Epsilon-tubulin 1 | −1.48 | 0.033108 | 0.26 |
| 1424367_a_at | Homer2 | Homer homolog 2 (Drosophila) | −1.49 | 0.00269 | 3.56 |
| 1441662_at | Cyp4x1 | Cytochrome P450, family 4, subfamily x, polypeptide 1 | −1.50 | 0.028455 | 0.51 |
| 1429086_at | Grhl2 | Grainyhead-like 2 (Drosophila) | −1.51 | 0.04298 | −0.15 |
| 1439078_at | Klhl4 | Kelch-like 4 (Drosophila) | −1.52 | 0.020679 | 0.96 |
| 1451194_at | Aldob | Aldolase 2, B isoform | −1.54 | 0.002438 | 3.70 |
| 1449913_at | Zfp2 | Zinc finger protein 2 | −1.55 | 0.033108 | 0.29 |
| 1431820_at | 4632404H12Rik | RIKEN cDNA 4632404H12 gene | −1.56 | 0.036071 | 0.12 |
| 1437900_at | 4930523C07Rik | RIKEN cDNA 4930523C07 gene | −1.56 | 0.044391 | −0.20 |
| 1449462_at | 3110049J23Rik | RIKEN cDNA 3110049J23 gene | −1.57 | 0.041709 | −0.09 |
| 1457373_at | Cdh19 | Cadherin 19, type 2 | −1.57 | 0.032755 | 0.31 |
| 1423072_at | 6720475J19Rik | RIKEN cDNA 6720475J10 gene | 1.58 | 0.006244 | 2.51 |
| 1422542_at | Gpr34 | G protein-coupled receptor 34 | −1.58 | 0.040399 | −0.04 |
| 1448475_at | Olfml3 | Olfactomedin-like 3 | −1.58 | 0.032964 | 0.30 |
| 1417676_a_at | Ptpro | Protein tyrosine phosphatase, receptor type, O | −1.59 | 0.001623 | 4.24 |
| 1456763_at | AA536749 | Expressed sequence AA536749 | −1.59 | 0.017774 | 1.15 |
| 1417732_at | Anxa8 | Annexin A8 | −1.59 | 0.027267 | 0.57 |
| 1425510_at | Mark1 | MAP/microtubule affinity-regulating kinase 1 | −1.60 | 0.004814 | 2.85 |
| 1417234_at | Mmp11 | Matrix metallopeptidase 11 | −1.61 | 0.036152 | 0.11 |
| 1416194_at | Cyp4b1 | Cytochrome P450, family 4, subfamily b, polypeptide 1 | −1.62 | 0.002404 | 3.74 |
| 1429679_at | Fbxl13 | F-box and leucine-rich repeat protein 13 | −1.64 | 0.010507 | 1.76 |
| 1428260_at | Spg3a | Spastic paraplegia 3A homolog (human) | −1.68 | 0.007369 | 2.28 |
| 1426413_at | Neurod1 | Neurogenic differentiation 1 | −1.68 | 0.009718 | 1.88 |
| 1455500_at | Rnf213 | Ring finger protein 213 | −1.68 | 0.017961 | 1.13 |
| 1456532_at | Pdgfd | Platelet-derived growth factor, D polypeptide | −1.70 | 0.008375 | 2.11 |
| 1419754_at | Myo5a | Myosin Va | −1.71 | 0.020595 | 0.97 |
| 1460147_at | NA | NA | −1.71 | 0.037207 | 0.08 |
| 1440014_at | Pacs1 | Phosphofurin acidic cluster sorting protein 1 | −1.72 | 7.34E−05 | 8.05 |
| 1451342_at | Spon1 | Spondin 1, (f-spondin) extracellular matrix protein | −1.73 | 0.045023 | −0.23 |
| 1438530_at | Tfpi | Tissue factor pathway inhibitor | −1.76 | 0.001582 | 4.29 |
| 1449563_at | Cntn1 | Contactin 1 | −1.77 | 0.029208 | 0.48 |
| 1435829_at | B930008K04Rik | RIKEN cDNA B930008K04 gene | −1.78 | 0.004961 | 2.78 |
| NuGO_emt010210_at | Cacna2d2 | Calcium channel, voltage-dependent, alpha 2/delta subunit 2 | −1.80 | 0.035702 | 0.17 |
| 1455633_at | Zfp647 | Zinc finger protein 647 | −1.80 | 0.041245 | −0.08 |
| 1420416_at | Sema3a | Sema domain, immunoglobulin domain (Ig), short basic domain, secreted, (semaphorin) 3A | −1.81 | 0.000506 | 5.78 |
| 1417644_at | Sspn | Sarcospan | −1.83 | 0.003984 | 3.08 |
| 1419687_at | D930010J01Rik | RIKEN cDNA D930010J01 gene | −1.83 | 0.045963 | −0.25 |
| 1439618_at | Pde10a | Phosphodiesterase 10A | −1.83 | 0.017774 | 1.16 |
| 1440430_at | Elp4 | Elongation protein 4 homolog (S, cerevisiae) | −1.84 | 0.023065 | 0.79 |
| 1425069_at | BC018285 | cDNA sequence BC018285 | −1.84 | 0.042264 | −0.11 |
| 1419376_at | 1110018M03Rik | RIKEN cDNA 1110018M03 gene | −1.85 | 0.009718 | 1.88 |
| 1434194_at | Mtap2 | Microtubule-associated protein 2 | −1.85 | 0.007048 | 2.36 |
| 1459707_at | Pacs1 | Phosphofurin acidic cluster sorting protein 1 | −1.86 | 0.004814 | 2.86 |
| 1434475_at | Ppig | Peptidyl-prolyl isomerase G (cyclophilin G) | −1.86 | 0.045576 | −0.24 |
| 1449158_at | Kcnk2 | Potassium channel, subfamily K, member 2 | −1.87 | 0.004961 | 2.77 |
| 1460606_at | Hsd17b13 | Hydroxysteroid (17-beta) dehydrogenase 13 | −1.88 | 0.003153 | 3.38 |

TABLE S4B-continued

Transcripts differentially expressed in the ascending colon at 28d between R. hominis inoculated animals and germfree animals.

| ID | Symbol | Name | FC | P-value | B |
|---|---|---|---|---|---|
| 1436087_at | Dpp10 | Dipeptidylpeptidase 10 | 1.89 | 0.043727 | 0.17 |
| NuGO_emt029633_at | Npy2r | Neuropeptide Y receptor Y2 | −1.90 | 0.000199 | 6.88 |
| 1418606_at | HoxdIO | Homeo box D10 | −1.91 | 0.007866 | 2.18 |
| 1417411_at | Nap1l5 | Nucleosome assembly protein 1-like 5 | −1.91 | 0.047023 | −0.29 |
| NuGO_emt034831_at | Nr2e3 | Nuclear receptor subfamily 2, qroup E, member 3 | −1.91 | 0.040798 | −0.06 |
| 1434740_at | Scarf 2 | Scavenger receptor class F, member 2 | −1.91 | 0.046195 | −0.26 |
| 1420858_at | Pkia | Protein kinase inhibitor, alpha | −1.92 | 0.003616 | 3.21 |
| 1457072_at | Bcl11a | B-cell CLL/lymphoma 11A (zinc finger protein) | −1.93 | 0.04853 | −0.35 |
| 1428347_at | Cyfip2 | Cytoplasmic FMR1 interacting protein 2 | −1.93 | 0.000484 | 5.87 |
| 1448823_at | Cxcl12 | Chemokine (C-X-C motif) liqand 12 | −1.95 | 0.007369 | 2.28 |
| 1436051_at | Myo5a | Myosin Va | −1.95 | 0.000596 | 5.61 |
| 1425065_at | Oas2 | 2'-5' oliqoadenylate synthetase 2 | −1.96 | 0.032484 | 0.34 |
| 1454876_at | Rab23 | RAB23, member RAS oncoqene family | −1.97 | 0.029208 | 0.48 |
| NuGO_emt022150_at | Cartpt | CART prepropeptide | −1.98 | 0.008035 | 2.16 |
| 1423396_at | Agt | Anqiotensinogen (serpin peptidase inhibitor, clade A, member 8) | −1.98 | 0.017774 | 1.15 |
| 1418213_at | Krt23 | Keratin 23 | −1.99 | 0.031284 | 0.38 |
| 1444670_at | Smyd3 | SET and MYND domain containing 3 | −2.02 | 0.022766 | 0.80 |
| 1453251_at | Dhx30 | DEAH (Asp-Glu-Ala-His) box polypeptide 30 | −2.03 | 0.027622 | 0.56 |
| 1440925_at | Rhoq | Ras homoloq qene family, member Q | −2.05 | 0.031006 | 0.40 |
| 1422640_at | Pcdhb9 | Protocadherin beta 9 | −2.07 | 0.015304 | 1.34 |
| 1450708_at | Scg2 | Secretogranin II | −2.09 | 0.010099 | 1.81 |
| 1435673_at | Hoxd3 | Homeo box D3 | −2.09 | 0.029426 | 0.47 |
| 1416710_at | Tmem35 | Transmembrane protein 35 | −2.10 | 0.007507 | 2.24 |
| 1423150_at | Scg5 | Secretogranin V | −2.11 | 0.002438 | 3.69 |
| 1418392_a_at | Gbp3 | Guanylate nucleotide binding protein 3 | −2.11 | 0.020383 | 0.99 |
| 1436566_at | Rab40b | Rab40b, member RAS oncogene family | −2.12 | 0.003512 | 3.25 |
| 1441231_at | EG665123 | Predicted gene, EG665123 | −2.14 | 0.035789 | 0.15 |
| 1419349_a_at | Cyp2d9 | Cytochrome P450, family 2, subfamily d, polypeptide 9 | −2.14 | 0.003512 | 3.25 |
| 1445481_at | AI317158 | Expressed sequence AI317158 | −2.18 | 0.033108 | 0.26 |
| 1443698_at | Fbxo39 | F-box protein 39 | −2.19 | 0.009359 | 1.95 |
| 1424900_at | Slc29a4 | Solute carrier family 29 (nucleoside transporters), member 4 | −2.22 | 0.001105 | 4.77 |
| 1419185_a_at | Mlxipl | MLX interacting protein-like | −2.23 | 0.000867 | 5.09 |
| 1435504_at | Clip4 | CAP-GLY domain containing linker protein family, member 4 | −2.24 | 0.006244 | 2.51 |
| 1438868_at | Phf11 | PHD finger protein 11 | −2.24 | 0.000857 | 5.12 |
| 1422860_at | Nts | Neurotensin | −2.28 | 1.04E−09 | 19.02 |
| 1451860_a_at | Trim30 | Tripartite motif protein 30 | −2.28 | 0.038792 | 0.03 |
| 1434788_at | D930050A07Rik | RIKEN cDNA D930050A07 gone | −2.33 | 0.009359 | 1.95 |
| 1450684_at | Etv1 | Ets variant gene 1 | −2.38 | 0.000606 | 5.57 |
| 1433536_at | Lrp11 | Low density lipoprotein receptor-related protein 11 | −2.39 | 0.000793 | 5.21 |
| NuGO_emt060551_at | 9030421 J09Rik | RIKEN cDNA 9030421J09 gene | −2.44 | 0.044497 | −0.20 |
| 1428758_at | Tmem86a | Transmembrane protein 86A | −2.45 | 0.004961 | 2.76 |
| 1445881_at | NA | NA | −2.54 | 0.031006 | 0.39 |
| 1451426_at | D11Lgp2e | DNA segment, Chr 11, Lothar Hennighausen 2, expressed | −2.55 | 0.0093 | 1.98 |
| 1416639_at | Slc2a5 | Solute carrier family 2 (facilitated glucose transporter), member 5 | −2.67 | 0.006738 | 2.43 |
| 1429313_at | Ror1 | Receptor tyrosine kinase-like orphan receptor 1 | −2.70 | 0.001269 | 4.59 |
| 1433184_at | 6720477C19Rik | RIKEN cDNA 6720477C19 gene | −2.72 | 0.017774 | 1.16 |
| 1419136_at | Akr1c18 | Aldo-keto reductase family 1, member C18 | −2.77 | 0.0113 | 1.66 |
| 1418113_at | Cyp2d10 | Cytochrome P450, family 2, subfamily d, polypeptide 10 | −2.79 | 0.000483 | 5.90 |
| 1417988_at | Resp18 | Regulated endocrine-specific protein 18 | −2.83 | 0.003512 | 3.26 |
| 1453196_a_at | Oasl2 | 2'-5' oligoadenylate synthetase-like 2 | −2.84 | 0.011794 | 1.62 |
| 1423555_a_at | Ifi44 | Interferon-induced protein 44 | −2.86 | 0.042694 | −0.13 |
| 1449939_s_at | Dlk1 | Delta-like 1 homolog (Drosophila) | −2.99 | 5.20E−10 | 19.73 |
| NuGO_emt091063_at | NA | NA | −3.08 | 0.000637 | 5.49 |
| 1436998_at | Ankrd43 | Ankyrin repeat domain 43 | −3.13 | 0.001056 | 4.85 |
| 1418293_at | Ifit2 | Interferon-induced protein with tetratricopeptide repeats 2 | −3.14 | 0.000637 | 5.44 |
| NuGO_emt044299_at | Sstr1 | Somatostatin receptor 1 | −3.16 | 2.31E−08 | 16.00 |
| 1421492_at | Ptqds2 | Prostaqlandin D2 synthase 2, hematopoietic | −3.18 | 7.03E−05 | 8.13 |
| 1449025_at | Ifit3 | Interferon-induced protein with tetratricopeptide repeats 3 | −3.34 | 0.007674 | 2.21 |
| 1455528_at | NA | NA | −3.47 | 0.002046 | 3.94 |
| 1429273_at_1425952_a_at | Bmper | BMP-binding endothelial regulator Glucaqon | −3.68 | 3.98E−09 | 17.68 |
| 1448628_at | Scg3 | Secretogranin III | −3.77 | 1.61E−08 | 16.39 |
| 1448201_at | Sfrp2 | Secreted frizzled-related protein 2 | −4.18 | 0.000257 | 6.62 |
| 1418191_at | Usp18 | Ubiquitin specific peptidase 18 | −4.45 | 0.046848 | −0.28 |
| 1449493_at | Insl5 | Insulin-like 5 | −9.54 | 5.98E−16 | 30.51 |
| 1419473_a_at | Cck | Cholecystokinin | −11.97 | 1.17E−11 | 23.32 |

TABLE S4C

Transcripts differentially expressed in the ileum at 14d between *R. hominis* inoculated animals and germfree animals.

| ID | Symbol | Name | FC | P-value | B |
|---|---|---|---|---|---|
| 1427343_at | Rasd2 | RASD family, member 2 | 4.21 | 0.008352 | 3.02 |
| 1420673_a_at | Acox2 | Acyl-Coenzyme A oxidase 2, branched chain | 3.37 | 0.023445 | 1.29 |
| 1418174_at | Dbp | D site albumin promoter binding protein | 3.26 | 0.04708 | 0.16 |
| 1434116_at | Cbx2 | Chromobox homolog 2 (Drosophila Pc class) | 3.15 | 0.01298 | 2.21 |
| 1456284_at | Tmem171 | Transmembrane protein 171 | 2.94 | 0.011378 | 2.45 |
| 1460713_at | BC048355 | cDNA sequence BC048355 | 2.61 | 0.035037 | 0.67 |
| 1438689_at | 4632433K11Rik | RIKEN cDNA 4632433K11 gene | 2.41 | 0.04048 | 0.41 |
| 1460187_at | Sfrp1 | Secreted frizzled-related sequence protein 1 | 2.37 | 0.021033 | 1.51 |
| 1420645_at | Pcgf2 | Polycomb group ring finger 2 | 2.31 | 0.003987 | 4.19 |
| 1455547_at | Zc3h7b | Zinc finger CCCH type containing 7B | 2.16 | 0.008352 | 2.98 |
| 1416258_at | Tk1 | Thymidine kinase 1 | 2.12 | 0.017451 | 1.78 |
| 1449845_a_at | Ephb4 | Eph receptor B4 | 2.12 | 0.033002 | 0.77 |
| 1455120_at | Hpdl | 4-hydroxyphenylpyruvate dioxygenase-like | 2.07 | 0.023445 | 1.30 |
| 1417399_at | Gas6 | Growth arrest specific 6 | 2.06 | 0.000167 | 8.81 |
| 1452862_at | Rreb1 | Ras responsive element binding protein 1 | 2.05 | 0.03901 | 0.47 |
| 1455246_at | NA | NA | 2.02 | 0.032868 | 0.78 |
| 1434322_at | Micall2 | MICAL-like 2 | 1.99 | 0.009875 | 2.69 |
| 1428207_at | Bcl7a | B-cell CLL/lymphoma 7A | 1.99 | 0.04708 | 0.11 |
| 1420845_at | Mrps2 | Mitochondrial ribosomal protein S2 | 1.97 | 0.042267 | 0.36 |
| 1444254_at | NA | NA | 1.96 | 0.025132 | 1.19 |
| 1448656_at | Cacnb3 | Calcium channel, voltage-dependent, beta 3 subunit | 1.96 | 0.032019 | 0.86 |
| 1434908_at | AI480556 | Expressed sequence AI480556 | 1.95 | 0.029591 | 0.99 |
| 1424376_at | Cdc42ep1 | CDC42 effector protein (Rho GTPase binding) 1 | 1.89 | 0.01298 | 2.20 |
| 1430274_a_at | Stard3nl | STARD3 N-terminal like | 1.88 | 0.008596 | 2.92 |
| 1416513_at | Lamb2 | Laminin, beta 2 | 1.87 | 0.016398 | 1.89 |
| 1416536_at | Mum1 | Melanoma associated antigen (mutated) 1 | 1.86 | 0.025132 | 1.17 |
| NuGO_emt084041_s_at | Defcr20 | Defensin related cryptdin 20 | 1.84 | 0.020502 | 1.55 |
| 1418320_at | Prss8 | Protease, serine, 8 (prostasin) | 1.83 | 0.021033 | 1.49 |
| 1455163_at | Guf1 | GUF1 GTPase homolog (S. cerevisiae) | 1.80 | 0.02461 | 1.22 |
| 1436665_a_at | Ltbp4 | Latent transforming growth factor beta binding protein 4 | 1.80 | 0.036581 | 0.57 |
| 1420643_at | Lfng | Lunatic fringe gene homolog (Drosophila) | 1.79 | 0.003248 | 4.57 |
| 1428695_at | 9130227C08Rik | RIKEN cDNA 9130227C08Rik gene | 1.79 | 0.036167 | 0.59 |
| 1453018_at | Nvl | Nuclear VCP-like | 1.77 | 0.035037 | 0.65 |
| 1419101_at | Sin3a | Transcriptional regulator, SIN3A (yeast) | 1.76 | 0.030882 | 0.91 |
| 1424459_at | Aytl2 | Acyltransferase like 2 | 1.74 | 0.039921 | 0.43 |
| 1415935_at | Smoc2 | SPARC related modular calcium binding 2 | 1.73 | 0.04615 | 0.19 |
| 1424618_at | Hpd | 4-hydroxyphenylpyruvic acid dioxygenase | 1.73 | 0.03901 | 0.47 |
| 1426297_at | Tcfe2a | Transcription factor E2a | 1.73 | 0.002215 | 5.11 |
| 1425391_a_at | Osbpl5 | Oxysterol binding protein-like 5 | 1.73 | 0.04615 | 0.19 |
| 1455719_at | Tubb5 | Tubulin, beta 5 | 1.73 | 0.032477 | 0.82 |
| 1451912_a_at | Fgfrl1 | Fibroblast growth factor receptor-like 1 | 1.73 | 0.02321 | 1.33 |
| 1429582_at | Btbd14a | BTB (POZ) domain containing 14A | 1.72 | 0.003987 | 4.21 |
| 1454777_at | Slco2b1 | Solute carrier organic anion transporter family, member 2b1 | 1.70 | 0.01298 | 2.22 |
| 1424101_at | Hnrpl | Heterogeneous nuclear ribonucleoprotein L | 1.69 | 0.044481 | 0.25 |
| 1448691_at | Ubqln4 | Ubiquilin 4 | 1.65 | 0.016054 | 1.92 |
| 1417604_at | Camk1 | Calcium/calmodulin-dependent protein kinase I | 1.63 | 0.033233 | 0.74 |
| 1442757_at | Lrch1 | Leucine-rich repeats and calponin homology (CH) domain containing 1 | 1.63 | 0.007505 | 3.30 |
| 1460675_at | Igsf8 | Immunoglobulin superfamily, member 8 | 1.62 | 0.04708 | 0.13 |
| 1418671_at | Capn5 | Calpain 5 | 1.58 | 0.04708 | 0.15 |
| 1426897_at | Rcc2 | Regulator of chromosome condensation 2 | 1.57 | 0.035037 | 0.65 |
| 1417594_at | Gkap1 | G kinase anchoring protein 1 | 1.52 | 0.019831 | 1.60 |
| 1433539_at | Commd3 | COMM domain containing 3 | 1.51 | 0.009875 | 2.72 |
| 1435469_at | Qscn6l1 | Quiescin Q6-like 1 | 1.51 | 0.0414121 | 0.38 |
| 1448561_at | Ncf2 | Neutrophil cytosolic factor 2 | 1.51 | 0.044087 | 0.30 |
| 1427022_at | Ddx42 | DEAD (Asp-Glu-Ala-Asp) box polypeptide 42 | 1.50 | 0.01872 | 1.67 |
| 1416030_a_at | Mcm7 | Minichromosome maintenance deficient 7 (S. cerevisiae) | 1.49 | 0.02321 | 1.34 |
| 1450023_at | Gtpbp1 | GTP binding protein 1 | 1.48 | 0.044113 | 0.27 |
| 1417879_at | Nenf | Neuron derived neurotrophic factor | 1.48 | 0.03901 | 0.46 |
| 1424640_at | Arl8a | ADP-ribosylation factor-like 8A | 1.47 | 0.044113 | 0.28 |
| 1418982_at | Cebpa | CCAAT/enhancer binding protein (C/EBP), alpha | 1.47 | 0.036167 | 0.60 |
| 1428382_at | Smarcc2 | SWI/SNF related, matrix associated, actin dependent regulator of chromatin, subfamily c, member 2 | 1.47 | 0.044113 | 0.28 |
| 1434134_at | Wdr42a | WD repeat domain 42A | 1.45 | 0.009875 | 2.74 |
| 1450519_a_at | Prkaca | Protein kinase, cAMP dependent, catalytic, alpha | 1.44 | 0.008352 | 2.99 |
| 1451306_at | Cdca7l | Cell division cycle associated 7 like | 1.44 | 0.035037 | 0.65 |
| 1426724_at | Cnn3 | Calponin 3, acidic | 1.44 | 0.033105 | 0.76 |
| 1424644_at | Tbcc | Tubulin-specific chaperone c | 1.42 | 0.032128 | 0.85 |
| 1417266_at | Ccl6 | Chemokine (C-C motif) ligand 6 | 1.42 | 0.021206 | 1.47 |
| 1415975_at | Carhsp1 | Calcium regulated heat stable protein 1 | 1.38 | 0.014132 | 2.10 |
| 1448277_at | Pold2 | Polymerase (DNA directed), delta 2, regulatory subunit | 1.38 | 0.044481 | 0.24 |
| 1433736_at | Hcfc1 | Host cell factor C1 | 1.35 | 0.035162 | 0.64 |
| 1435149_at | Plcg1 | Phospholipase C, gamma 1 | 1.35 | 0.036167 | 0.59 |
| 1417500_a_at | Tgm2 | Transglutaminase 2, C polypeptide | 1.33 | 0.022457 | 1.39 |
| 1428125_at | 4921506J03Rik | RIKEN cDNA 4921506J03 gene | 1.32 | 0.030752 | 0.92 |
| 1452100_at | Dullard | Dullard homolog (Xenopus laevis) | 1.32 | 0.030391 | 0.94 |

TABLE S4C-continued

Transcripts differentially expressed in the ileum at 14d between *R. hominis* inoculated animals and germfree animals.

| ID | Symbol | Name | FC | P-value | B |
| --- | --- | --- | --- | --- | --- |
| 1448148_at | Grn | Granulin | 1.30 | 0.011783 | 2.33 |
| 1451984_at | Hnrpul1 | Heterogeneous nuclear ribonucleoprotein U-like 1 | 1.30 | 0.016884 | 1.85 |
| 1426401_at | Ppp3ca | Protein phosphatase 3, catalytic subunit, alpha isoform | 1.29 | 0.009875 | 2.72 |
| 1428380_at | 0610007C21Rik | RIKEN cDNA 0610007C21 gene | 1.26 | 0.043354 | 0.32 |
| 1418364_a_at | Ftl1 | Ferritin light chain 1 | 1.24 | 0.01702 | 1.82 |
| 1456854_at | Neurl | Neuralized-like homolog (Drosophila) | −1.18 | 0.031207 | 0.89 |
| 1448853_at | Synj2bp | Synaptojanin 2 binding protein | −1.19 | 0.04708 | 0.15 |
| 1416281_at | Wdr45l | Wdr45 like | −1.22 | 0.016971 | 1.84 |
| 1418843_at | Slc30a4 | Solute carrier family 30 (zinc transporter), member 4 | −1.30 | 0.037239 | 0.54 |
| 1459557_at | Zbtb16 | Zinc finger and BTB domain containing 16 | −1.31 | 0.001423 | 5.62 |
| 1418116_at | Ifig15 | Interferon alpha responsive gene | −1.32 | 0.038411 | 0.50 |
| 1448762_at | Rad17 | RAD17 homolog (S. pombe) | −1.32 | 0.044087 | 0.30 |
| 1435461_at | Magi3 | Membrane associated guanylate kinase, WW and PDZ domain containing 3 | −1.33 | 0.044113 | 0.26 |
| 1434835_at | Wapal | Wings apart-like homolog (Drosophila) | −1.33 | 0.046851 | 0.17 |
| 1444328_at | NA | NA | −1.34 | 0.010408 | 2.57 |
| NuGO_emt073151_at | Nlrp9b | NLR family, pyrin domain containing 9B | −1.34 | 0.045959 | 0.20 |
| 1427269_at | Sfrs11 | Splicing factor, arginine/serine-rich 11 | −1.35 | 0.02461 | 1.22 |
| 1436157_at | Ccar1 | Cell division cycle and apoptosis regulator 1 | −1.36 | 0.021206 | 1.46 |
| NuGO_emt081039_at | Eif4e1b | Eukaryotic translation initiation factor 4E family member 1B | −1.38 | 0.037239 | 0.54 |
| 1422217_a_at | Cyp1a1 | Cytochrome P450, family 1, subfamily a, polypeptide 1 | −1.38 | 0.005253 | 3.71 |
| 1434654_at | Cog3 | Component of oligomeric golgi complex 3 | −1.38 | 0.03901 | 0.46 |
| 1421680_at | NA | NA | −1.39 | 0.044113 | 0.28 |
| 1424296_at | Gclc | Glutamate-cysteine ligase, catalytic subunit | −1.41 | 0.023137 | 1.36 |
| 1440722_at | D19Ertd386e | DNA segment, Chr 19, ERATO Doi 386, expressed | −1.41 | 0.008352 | 3.15 |
| 1429849_at | 4632411B12Rik | RIKEN cDNA 4632411B12 gene | −1.44 | 0.015927 | 1.94 |
| 1451407_at | Jam4 | Junction adhesion molecule 4 | −1.44 | 0.015521 | 1.99 |
| 1424324_at | Esco1 | Establishment of cohesion 1 homolog 1 (S. cerevisiae) | −1.47 | 0.010277 | 2.60 |
| 1441403_at | 6430501K19Rik | RIKEN cDNA 6430501K19 gene | −1.47 | 0.019952 | 1.59 |
| 1453160_at | Thrap1 | Thyroid hormone receptor associated protein 1 | −1.48 | 0.034193 | 0.71 |
| 1432962_at | 2610024D14Rik | RIKEN cDNA 2610024D14 gene | −1.49 | 0.018436 | 1.70 |
| 1456896_at | 6720462K09Rik | RIKEN cDNA 6720462K09 gene | −1.50 | 0.011783 | 2.34 |
| 1444705_at | App | Amyloid beta (A4) precursor protein | −1.50 | 0.032477 | 0.80 |
| 1426886_at | Cln5 | Ceroid-lipofuscinosis, neuronal 5 | −1.52 | 0.01702 | 1.81 |
| 1459059_at | 2010308F09Rik | RIKEN cDNA 2010308F09 gene | −1.53 | 0.008352 | 2.97 |
| 1436616_at | R74740 | Expressed sequence R74740 | −1.55 | 0.011378 | 2.44 |
| 1453269_at | Unc5b | Unc-5 homolog B (C, elegans) | −1.55 | 0.018436 | 1.70 |
| 1424536_at | Oas1e | 2'-5' oligoadenylate synthetase 1E | −1.55 | 0.008352 | 3.08 |
| 1444565_at | NA | NA | −1.56 | 0.005253 | 3.70 |
| 1448049_at | Jmjd1c | Jumonji domain containing 1C | −1.58 | 0.02321 | 1.33 |
| 1441546_at | Mpp6 | Membrane protein, palmitoylated 6 (MAGUK p55 subfamily member 6) | −1.58 | 0.009875 | 2.70 |
| 1442605_at | Bach2 | BTB and CNC homology 2 | −1.59 | 0.032477 | 0.80 |
| 1451415_at | 1810011O10Rik | RIKEN cDNA 1810011O10 gene | −1.66 | 0.023445 | 1.29 |
| 1436637_at | Eif4h | Eukaryotic translation initiation factor 4H | −1.66 | 0.011571 | 2.40 |
| 1453457_at | Sri | Sorcin | −1.67 | 0.024152 | 1.25 |
| 1429GG0_at | Tra2a | Transformer 2 alpha homolog (Drosophila) | −1.68 | 0.033105 | 0.75 |
| 1429624_at | Sltm | SAFB-like, transcription modulator | −1.68 | 0.036906 | 0.56 |
| 1429870_at | Tnik | TRAF2 and NCK interacting kinase | −1.72 | 0.001356 | 5.94 |
| 1444065_at | Cyb5d2 | Cytochrome b5 domain containing 2 | −1.72 | 0.000237 | 8.03 |
| 1424208_at | Ptger4 | Prostaglandin E receptor 4 (subtype EP4) | −1.74 | 0.029592 | 0.98 |
| 1452837_at | Lpin2 | Lipin 2 | −1.74 | 0.011783 | 2.33 |
| 1448185_at | Herpud1 | Homocysteine-inducible, endoplasmic reticulum stress- inducible, ubiquitin-like domain member 1 | −1.75 | 0.002895 | 4.81 |
| 1432719_at | 4833412K13Rik | RIKEN cDNA 4833412K13 gene | −1.76 | 0.04708 | 0.13 |
| 1437868_at | BC023892 | cDNA sequence BC023892 | −1.76 | 0.044113 | 0.28 |
| 1433101_at | 9030419F21Rik | RIKEN cDNA 9030419F21 gene | −1.77 | 0.008596 | 2.90 |
| 1451621_at | 5830417C01Rik | RIKEN cDNA 5830417C01 gene | −1.77 | 0.00495 | 3.81 |
| 1432423_a_at | C530008M17Rik | RIKEN cDNA C530008M17 gene | −1.78 | 0.01164 | 2.38 |
| 1429399_at | Rnf125 | Ring finger protein 125 | −1.84 | 0.033002 | 0.77 |
| 1453264_at | Marveld3 | MARVEL (membrane-associating) domain containing 3 | −1.86 | 4.82E−05 | 10.38 |
| 1454343_at | Ppapdc1 | Phosphatidic acid phosphatase type 2 domain containing 1 | −1.88 | 0.003658 | 4.42 |
| 1435571_at | A530065I17Rik | RIKEN cDNA A530065I17 gene | −1.90 | 0.015795 | 1.96 |
| 1443164_at | NA | NA | −1.91 | 0.010163 | 2.63 |
| 1437776_at | Tmcc1 | Transmembrane and coiled coil domains 1 | −1.91 | 0.028192 | 1.04 |
| 1442111_at | D430033H22Rik | RIKEN cDNA D430033H22 gene | −1.91 | 0.007072 | 3.40 |
| 1424451_at | Acaa1b | Acetyl-Coenzyme A acyltransferase 1B | −1.92 | 0.035037 | 0.67 |
| 1459879_at | 4921513D23Rik | RIKEN cDNA 4921513D23 gene | −1.92 | 0.008352 | 2.99 |
| 1428776_at | Slc10a6 | Solute carrier family 10 (sodium/bile acid cotransporter family), member 6 | −1.92 | 0.011378 | 2.45 |
| 1458079_at | Usp40 | Ubiquitin specific peptidase 40 | −1.93 | 0.004696 | 3.98 |
| 1442897_at | 2610024E20Rik | RIKEN cDNA 2610024E20 gene | −1.95 | 0.00402 | 4.15 |
| 1455744_at | Tmem181 | Transmembrane protein 181 | −1.97 | 0.037843 | 0.52 |
| 1449385_at | Hsd17b6 | Hydroxysteroid (17-beta) dehydrogenase 6 | −1.98 | 0.025132 | 1.18 |
| 1443068_at | D130084N16Rik | RIKEN cDNA D130084N16 gene | −1.98 | 0.04708 | 0.11 |
| 1419582_at | Cyp2c55 | Cytochrome P450, family 2, subfamily c, polypeptide 55 | −1.99 | 0.042267 | 0.35 |

TABLE S4C-continued

Transcripts differentially expressed in the ileum at 14d between R. hominis inoculated animals and germfree animals.

| ID | Symbol | Name | FC | P-value | B |
|---|---|---|---|---|---|
| 1457801_at | 9930024M15Rik | RIKEN cDNA 9930024M15 gene | −2.01 | 0.04708 | 0.13 |
| 1438331_at | Ypel2 | Yippee-like 2 (Drosophila) | −2.02 | 0.037843 | 0.51 |
| 1428833_at | 4930406D14Rik | RIKEN cDNA 4930406D14 gene | −2.04 | 0.015418 | 2.01 |
| 1419388_at | Tm4sf20 | Transmembrane 4 L six family member 20 | −2.05 | 0.010163 | 2.65 |
| 1455510_at | Spop | Speckle-type POZ protein | −2.08 | 0.023445 | 1.29 |
| 1444178_at | ENSMUSG00000052976 | Predicted gene, ENSMUSG00000052976 | −2.09 | 0.029592 | 0.97 |
| 1443159_at | Txnrd1 | Thioredoxin reductase 1 | 2.10 | 0.04708 | 0.11 |
| 1457161_at | 9530029O12Rik | RIKEN cDNA 9530029O12 gene | −2.11 | 0.019032 | 1.65 |
| 1459887_at | NA | NA | −2.11 | 0.003987 | 4.29 |
| 1459005_at | NA | NA | −2.13 | 0.007384 | 3.34 |
| 1439283_at | NA | NA | −2.18 | 0.007823 | 3.24 |
| 1438338_at | Mdh1 | Malate dehydrogenase 1, NAD (soluble) | −2.21 | 0.001446 | 5.54 |
| 1458452_at | NA | NA | −2.21 | 0.010277 | 2.59 |
| 1442256_at | Prkcd | Protein kinase C, delta | −2.21 | 0.026633 | 1.11 |
| 1443969_at | Irs2 | Insulin receptor substrate 2 | −2.22 | 0.003987 | 4.22 |
| 1452462_a_at | Banp | Btg3 associated nuclear protein | −2.30 | 0.021033 | 1.52 |
| 1454558_at | 5430416B10Rik | RIKEN cDNA 5430416B10 gene | −2.32 | 1.71E-07 | 15.68 |
| 1430393_at | C030048B08Rik | RIKEN cDNA C030048B08 gene | −2.32 | 0.001388 | 5.78 |
| 1446929_at | Bach2 | BTB and CNC homology 2 | −2.32 | 0.027369 | 1.07 |
| NuGO_emt067737_at | 9130230L23Rik | RIKEN cDNA 9130230L23 gene | −2.34 | 0.04708 | 0.15 |
| 1441138_at | Foxn2 | Forkhead box N2 | −2.36 | 0.001356 | 6.01 |
| 1416041_at | Sgk | Serum/glucocorticoid regulated kinase | −2.40 | 0.04048 | 0.41 |
| 1454158_at | Mpp7 | Membrane protein, palmitoylated 7 (MAGUK p55 subfamily member 7) | −2.40 | 0.011571 | 2.40 |
| 1459253_at | Arrdc3 | Arrestin domain containing 3 | −2.46 | 0.044113 | 0.27 |
| 1444376_at | Sesn1 | Sestrin 1 | −2.48 | 0.036167 | 0.59 |
| 1430362_at | 5730409N24Rik | RIKEN cDNA 5730409N24 gene | −2.49 | 0.032477 | 0.83 |
| 1442069_at | D5Wsu178e | DNA segment, Chr 5, Wayne State University 178, expressed | −2.50 | 0.032477 | 0.80 |
| 1433203_at | 6030400A10Rik | RIKEN cDNA 6030400A10 gene | −2.56 | 0.000747 | 6.76 |
| 1456706_at | 1700109H08Rik | RIKEN cDNA 1700109H08 gene | −2.60 | 0.004825 | 3.89 |
| 1441561_at | Fbxl3 | F-box and leucine-rich repeat protein 3 | −2.60 | 0.034193 | 0.70 |
| 1437884_at | Arl5b | ADP-ribosylation factor-like 5B | −2.65 | 0.022457 | 1.40 |
| 1445843_at | Chd2 | Chromodomain helicase DNA binding protein 2 | −2.66 | 0.044481 | 0.24 |
| 1428306_at | Ddit4 | DNA-damage-inducible transcript 4 | −2.66 | 0.008352 | 3.09 |
| 1421009_at | Rsad2 | Radical S-adenosyl methionine domain containing 2 | −2.69 | 0.04708 | 0.14 |
| 1440227_at | BF642829 | Expressed sequence BF642829 | −2.69 | 0.026633 | 1.11 |
| 1453595_at | Bcl6 | B-cell leukemia/lymphoma 6 | −2.70 | 0.004825 | 3.89 |
| 1444775_at | 9930033D15Rik | RIKEN cDNA 9930033D15 gene | −2.71 | 0.003248 | 4.61 |
| 1439972_at | Etnk1 | Ethanolamine kinase 1 | −2.74 | 0.032477 | 0.83 |
| 1440536_at | Slc22a5 | Solute carrier family 22 (organic cation transporter), member 5 | −2.90 | 0.021033 | 1.49 |
| 1438660_at | Gcnt2 | Glucosaminyl (N-acetyl) transferase 2, I-branching enzyme | −2.95 | 0.018436 | 1.70 |
| 1437759_at | Pfkp | Phosphofructokinase, platelet | −2.97 | 0.008352 | 3.11 |
| NuGO_emt000020_at | Amica1 | Adhesion molecule, interacts with CXADR antigen 1 | −2.97 | 0.000981 | 6.41 |
| 1446950_at | Tox | Thymocyte selection-associated HMG box gene | −3.00 | 0.008352 | 2.98 |
| 1447141_at | AW107722 | Expressed sequence AW107722 | −3.14 | 0.013251 | 2.17 |
| 1459219_at | Rapgef2 | Rap guanine nucleotide exchange factor (GEF) 2 | −3.21 | 0.000747 | 6.75 |
| 1449496_at | 2010109I03Rik | RIKEN cDNA 2010109I03 gene | −3.22 | 0.000167 | 8.69 |
| 1458296_at | NA | NA | −3.23 | 0.001388 | 5.70 |
| 1440749_at | NA | NA | −3.38 | 0.001388 | 5.76 |
| 1440892_at | BC017647 | cDNA sequence BC017647 | −3.52 | 0.004881 | 3.85 |
| 1441115_at | Rnf125 | Ring finger protein 125 | −3.90 | 0.000237 | 8.14 |
| 1421365_at | Fst | Follistatin | −4.33 | 0.04708 | 0.12 |
| 1446972_at | D15Wsu126e | DNA segment, Chr 15, Wayne State University 126, expressed | −7.09 | 0.003054 | 4.72 |

TABLE S4D Transcripts differentially expressed in the ileum at 28 d between R. hominis inoculated animals and germfree animals.

TABLE S4D

Transcripts differentially expressed in the ileum at 28 d between R. hominis inoculated animals and germfree animals.

| ID | Symbol | Name | M | P-value | B |
|---|---|---|---|---|---|
| 1458427_at | Brip1 | BRCA1 interacting protein C-terminal helicase 1 | −1.72 | 0.002194 | 4.97 |

Genes involved in innate immunity and gut barrier function were significantly induced by the presence of R. hominis in the ascending colon. The GO-process 'innate immune response' (GO:0045087) was up-regulated and included the important TLR-related genes Tr5, Tlr1 and Vnn1. The up-regulation of Tlr5 was of particular interest, given the corresponding induction of flagellar genes and flagellin protein in R. hominis during gut colonization, and may infer a role for this innate signalling pathway in mediating innate and adaptive immune responses. Other innate immune genes affected in the colon by R. hominis included the antimicrobial peptides DeJb37, Pla2g3, Muc16 and Itln and the gut barrier function genes Sprr1a, Cldn4, Pmp22, Crb3 and Magi3. Innate immune genes showing up-regulation in the ileum in response to R. hominis included Defcr20, Pcgf2, Ltbp4, Igsf8 and Tcfe2a. Interestingly, herein it is shown negative regulation of the NF-κB pathway (GO:0043124) (FIG. 9A-9C) by R. hominis, which, like B. thetaiotaomicron (Kelly et al. 2004), may contribute to immune homeostasis by downregulating this inflammatory cascade.

Figure 10A:
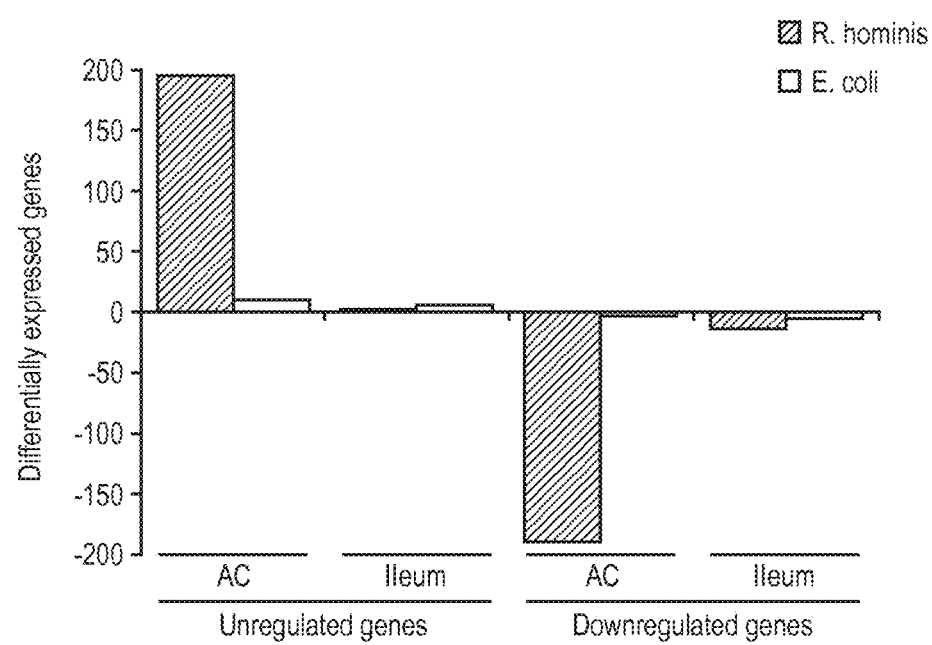
Figure 11A:
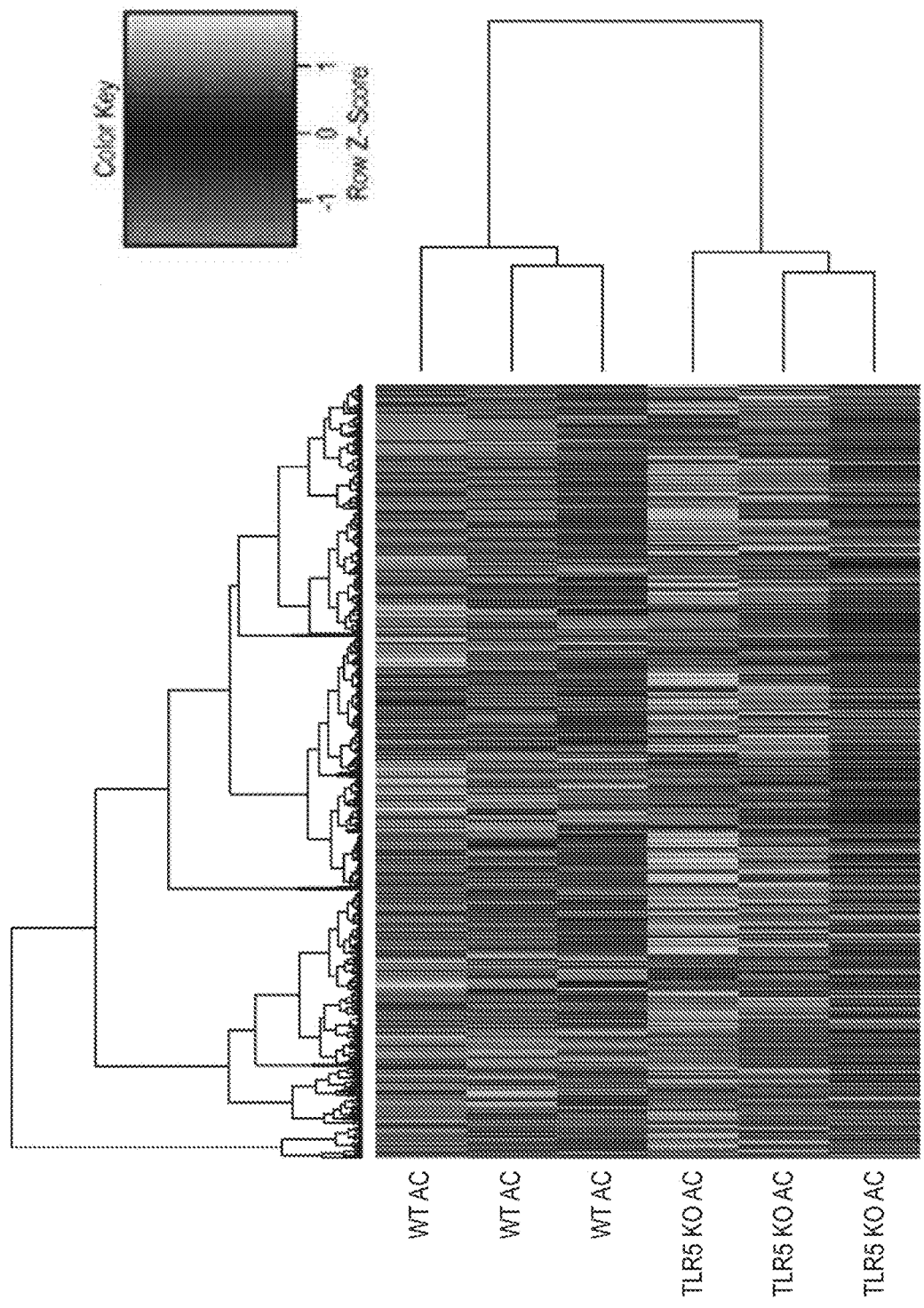
Figure 11B:
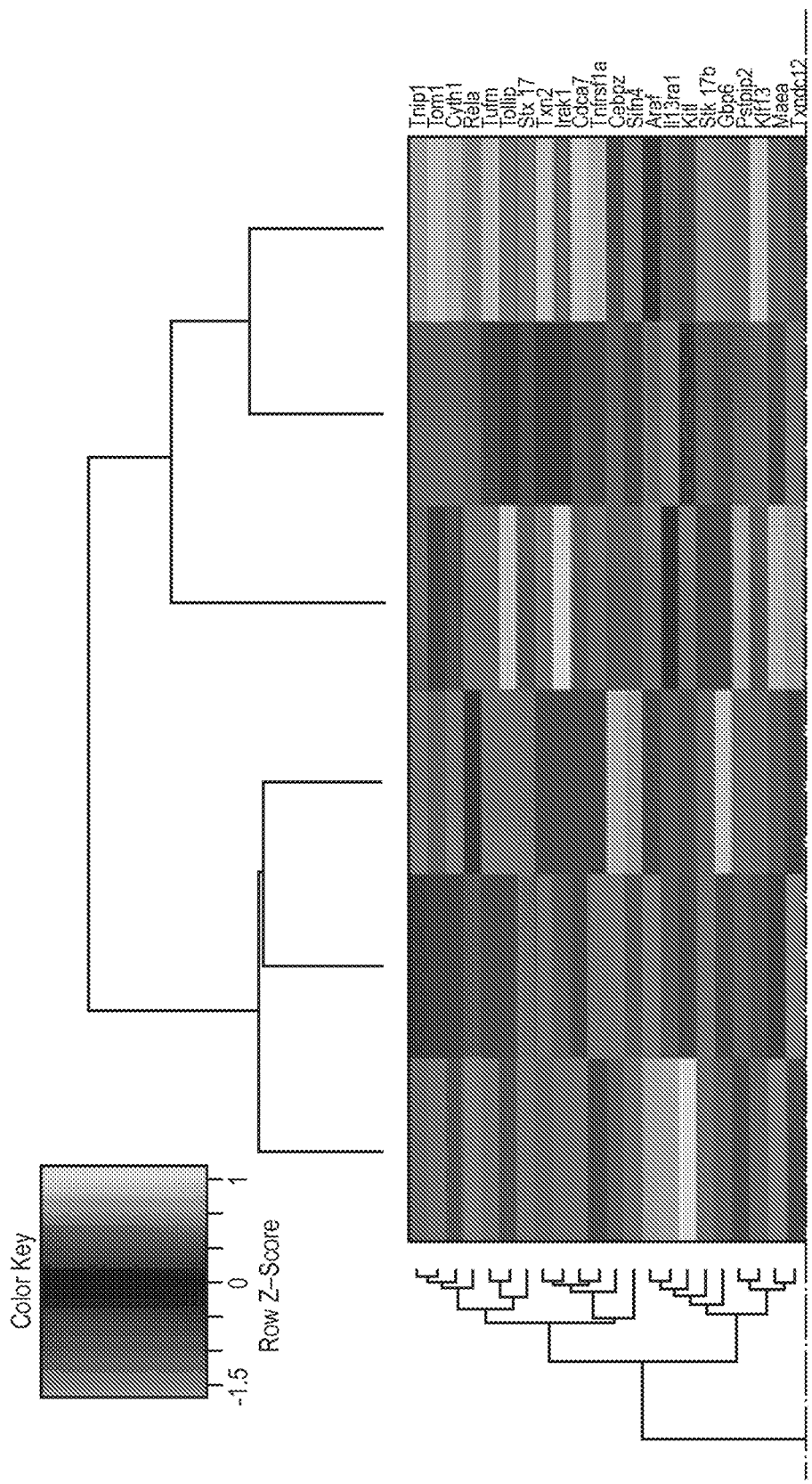
Figure 11B:
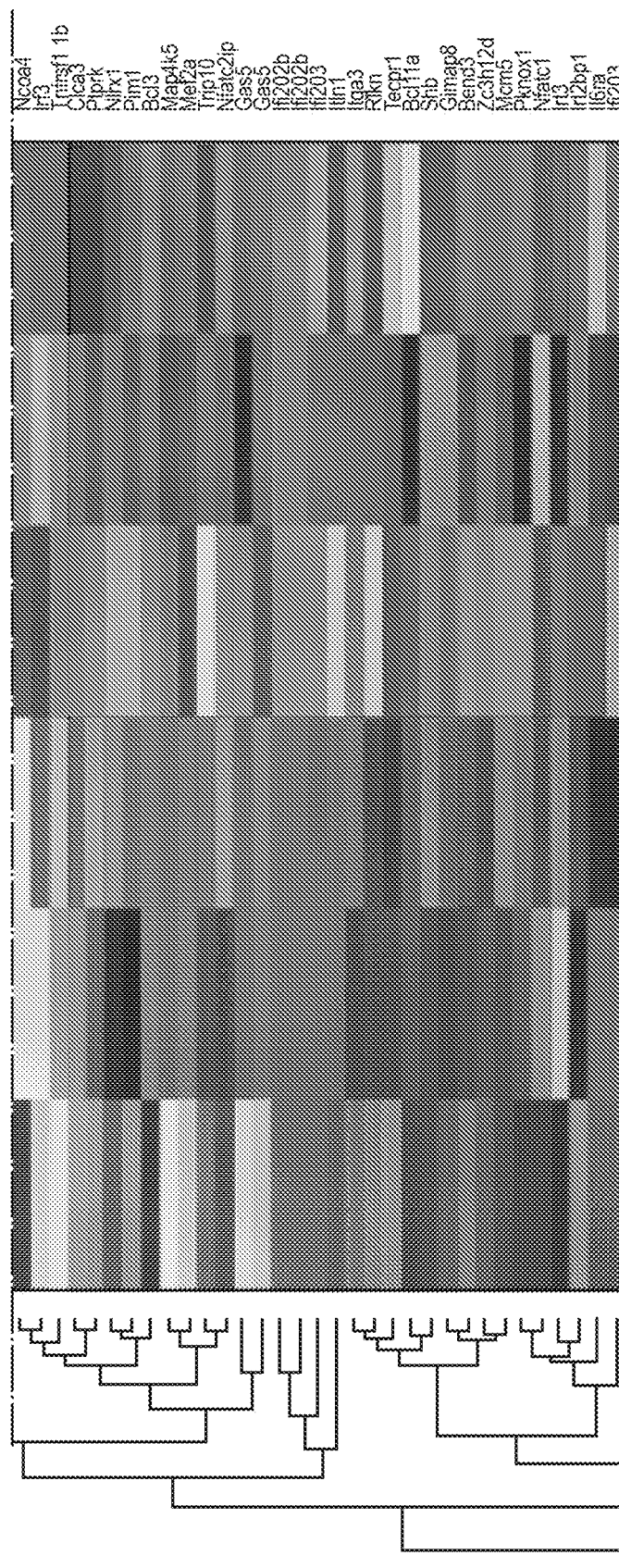
Figure 11B:
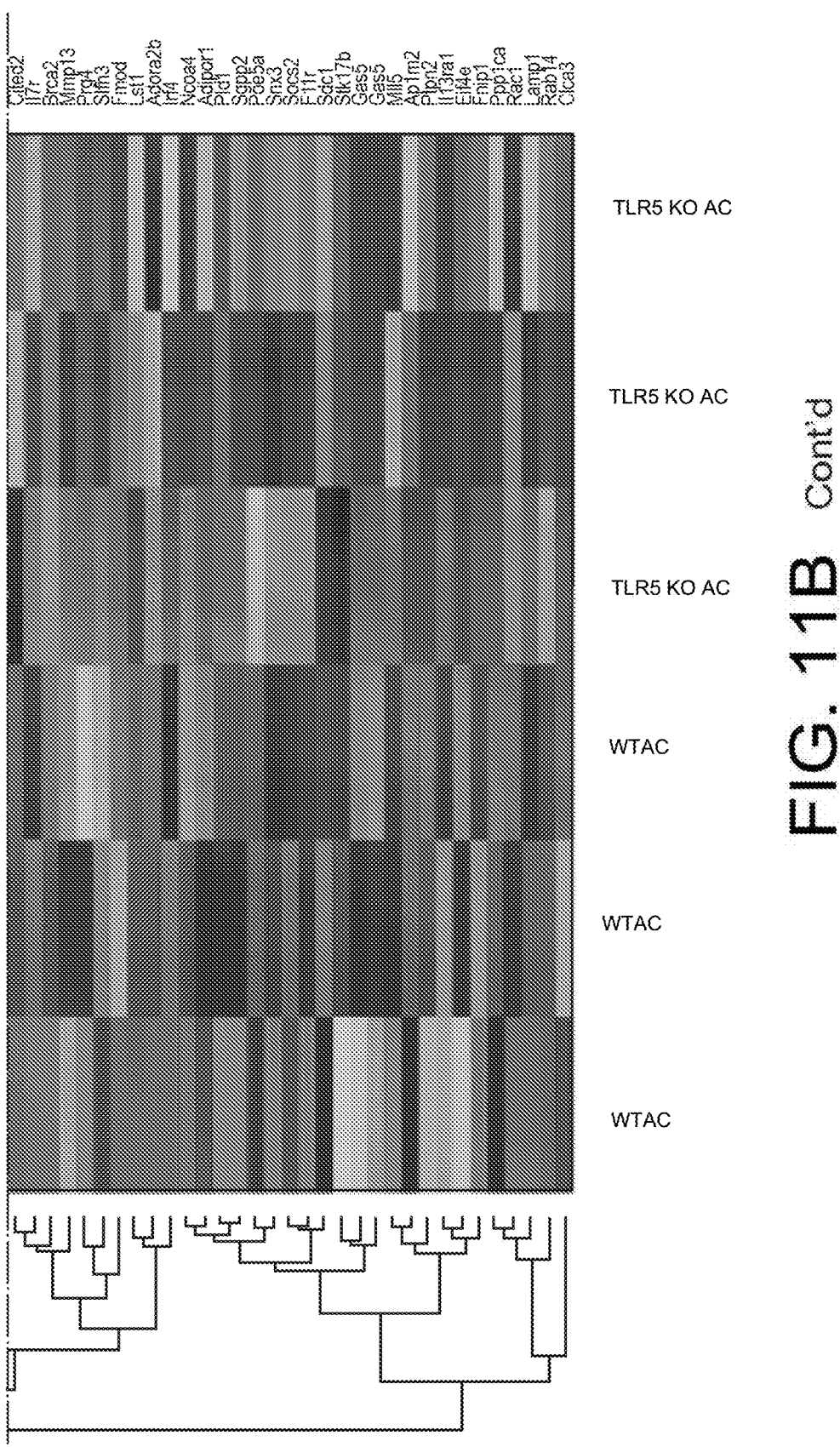
Figure 11C:
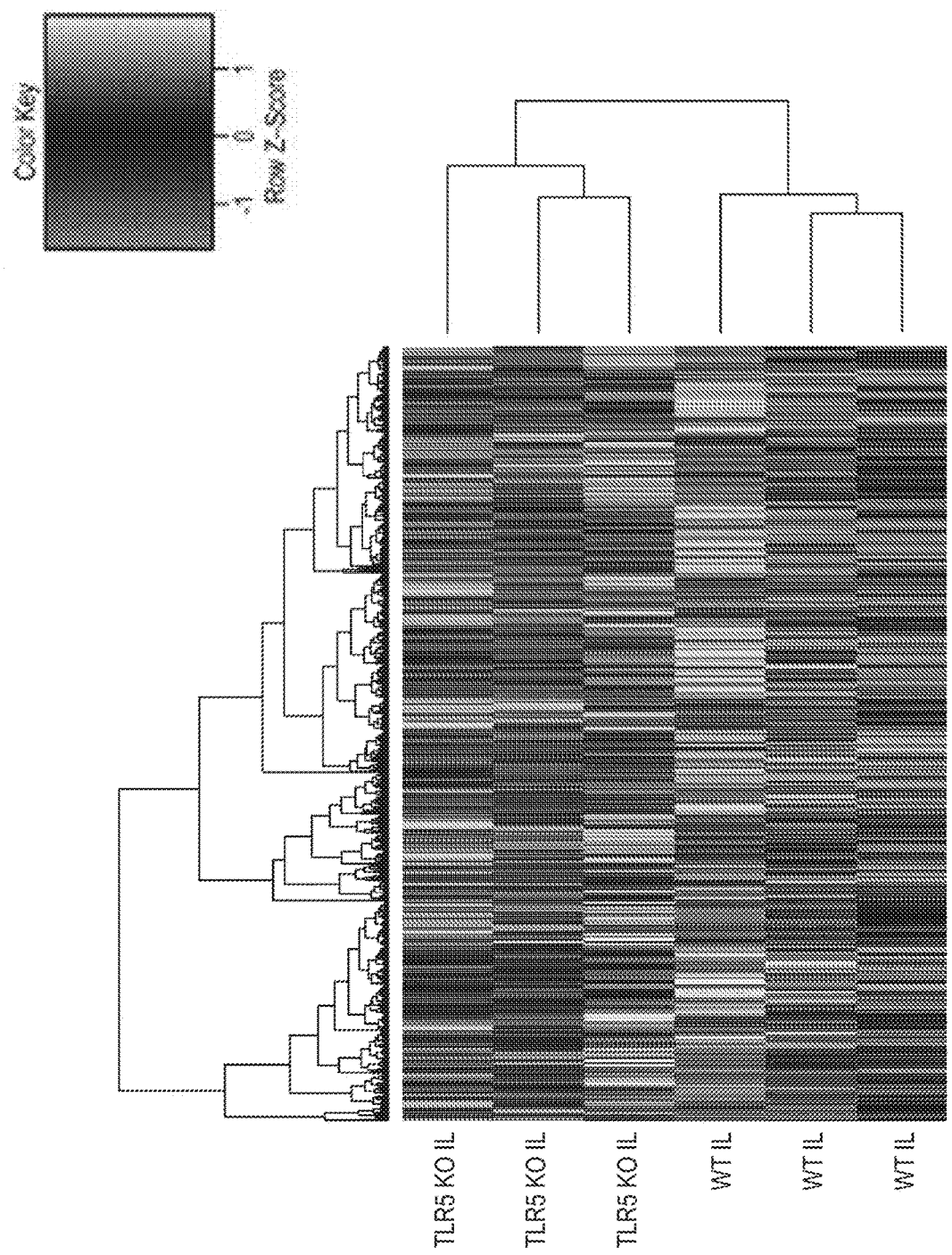
Figure 11D:
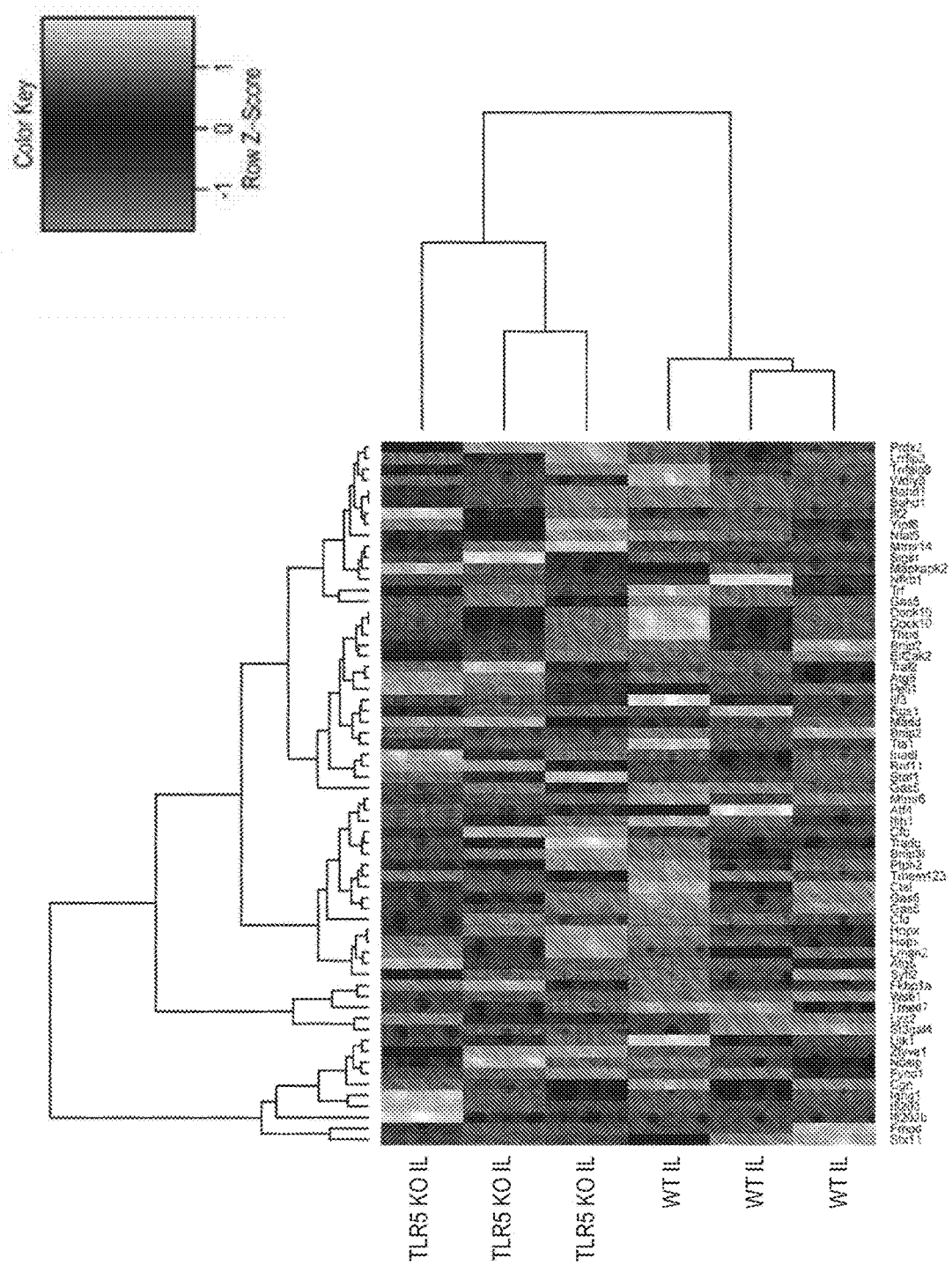
Figure 12A:
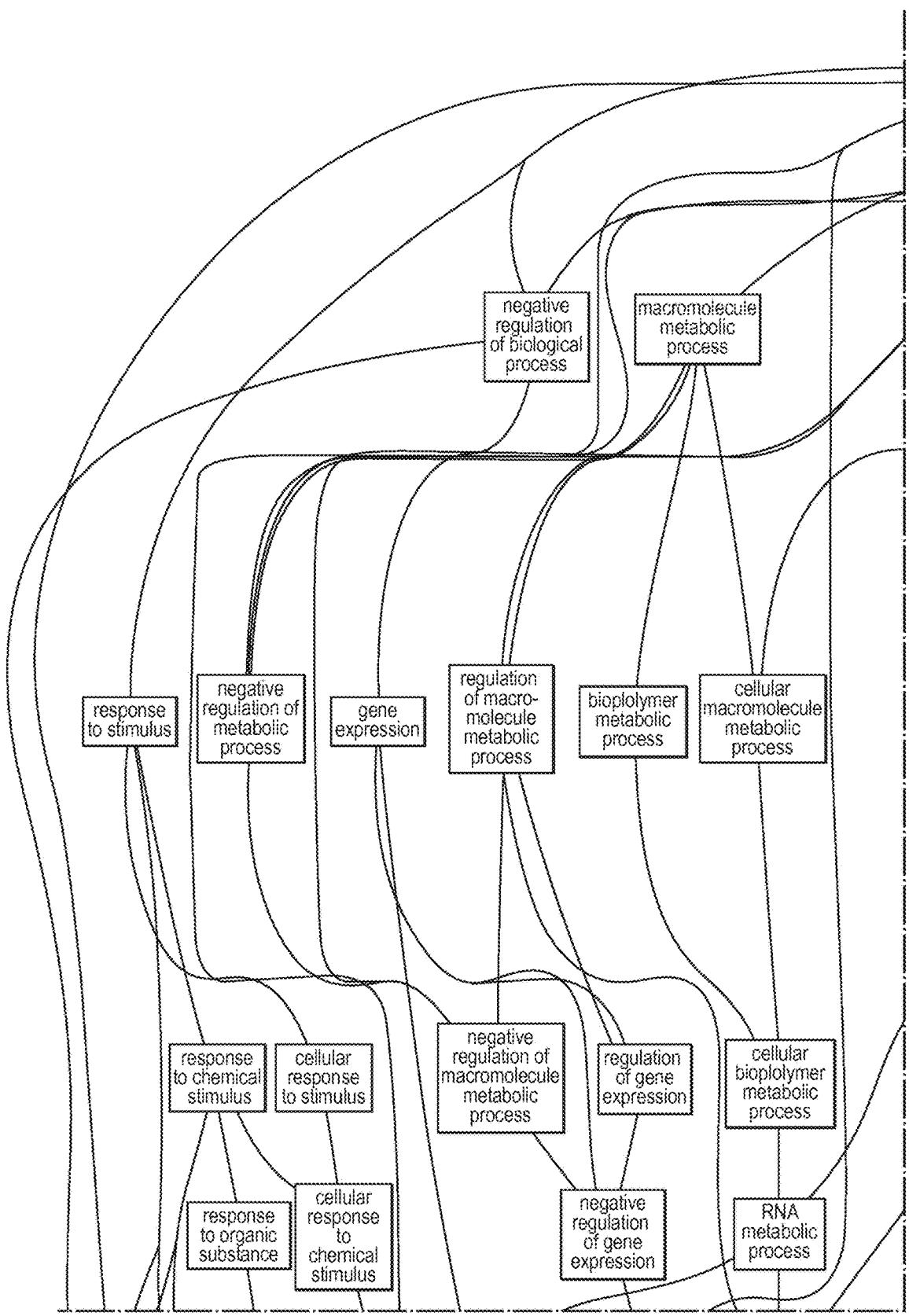
Figure 12B:
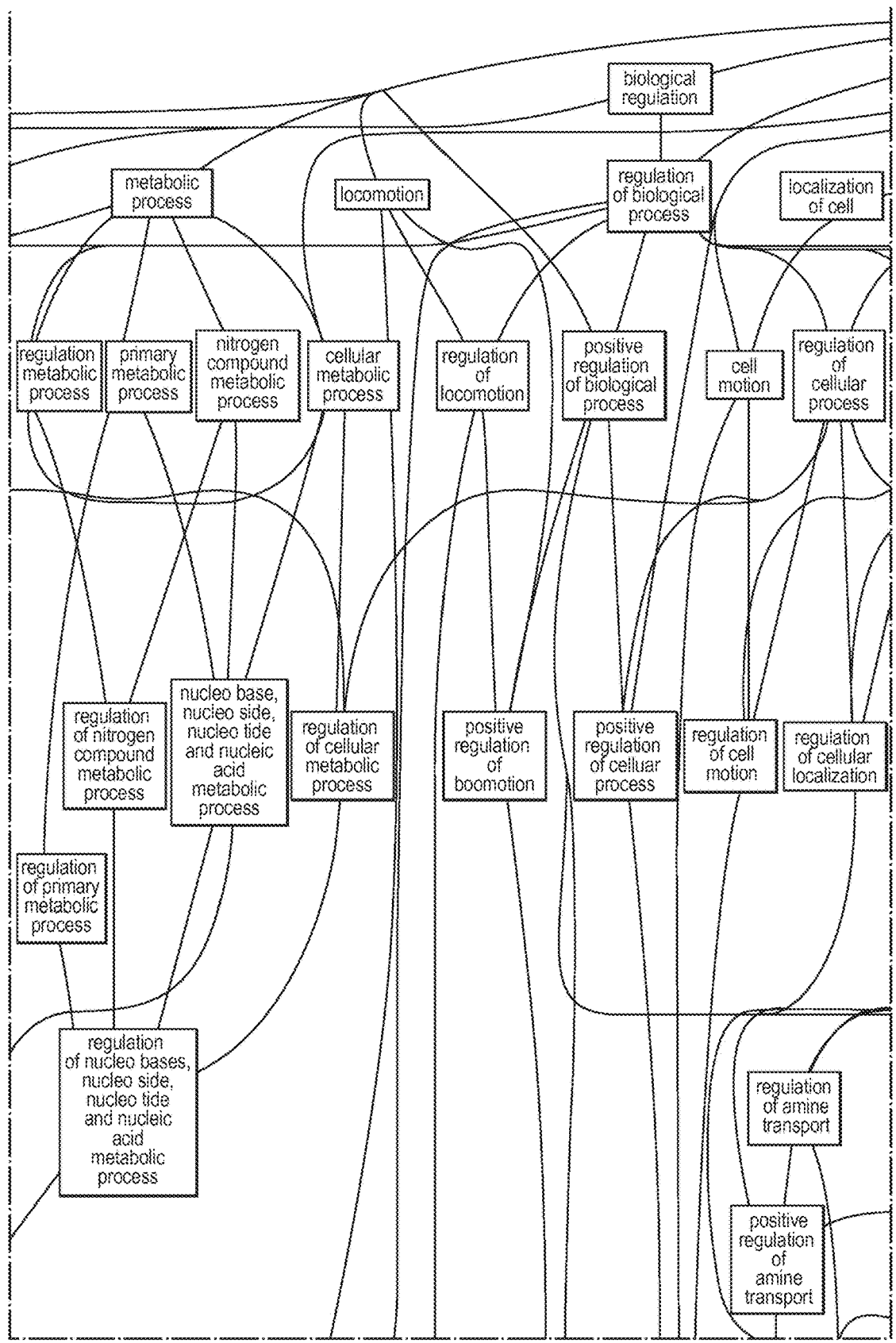
Figure 12C:
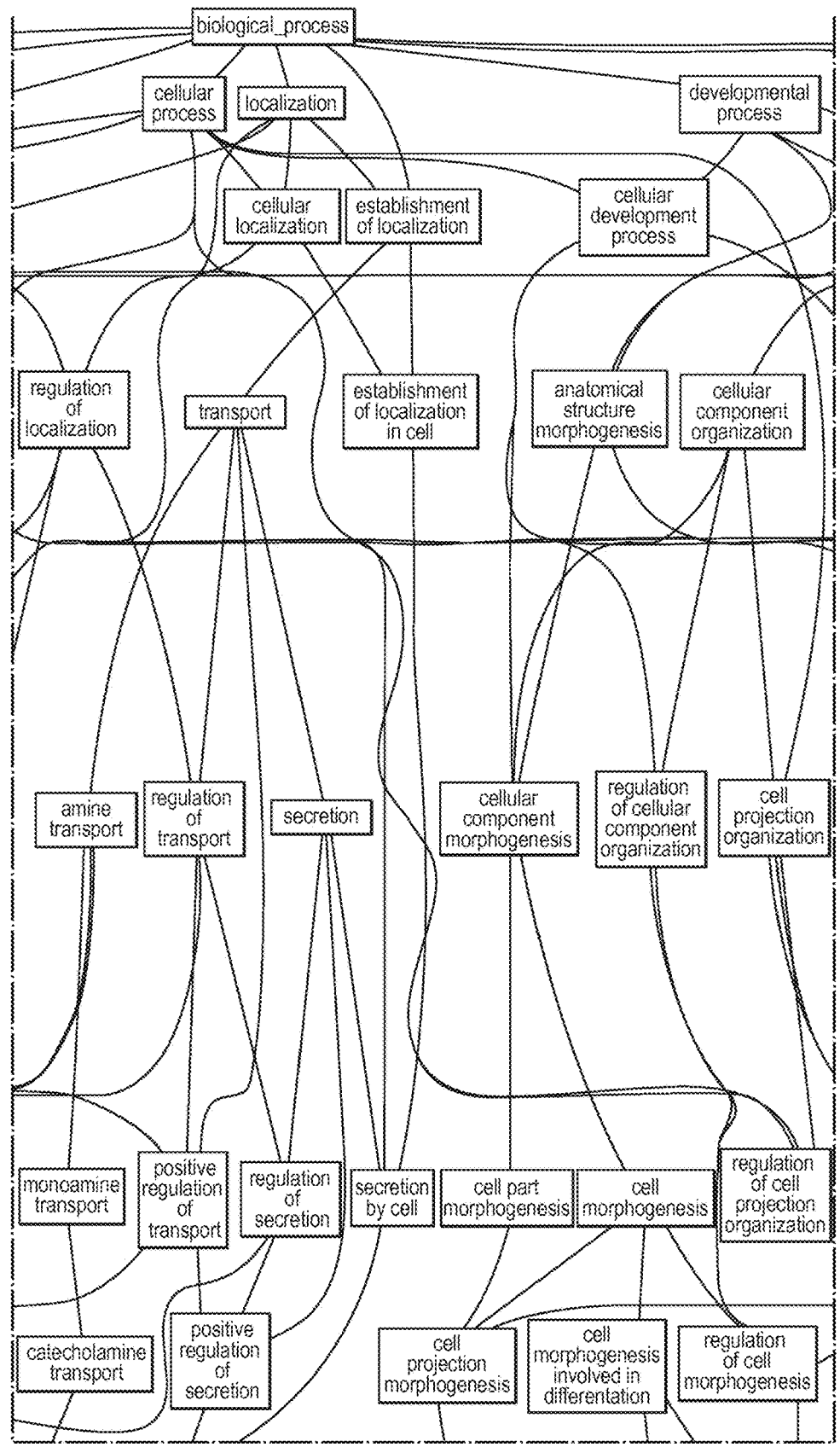
Figure 12D:
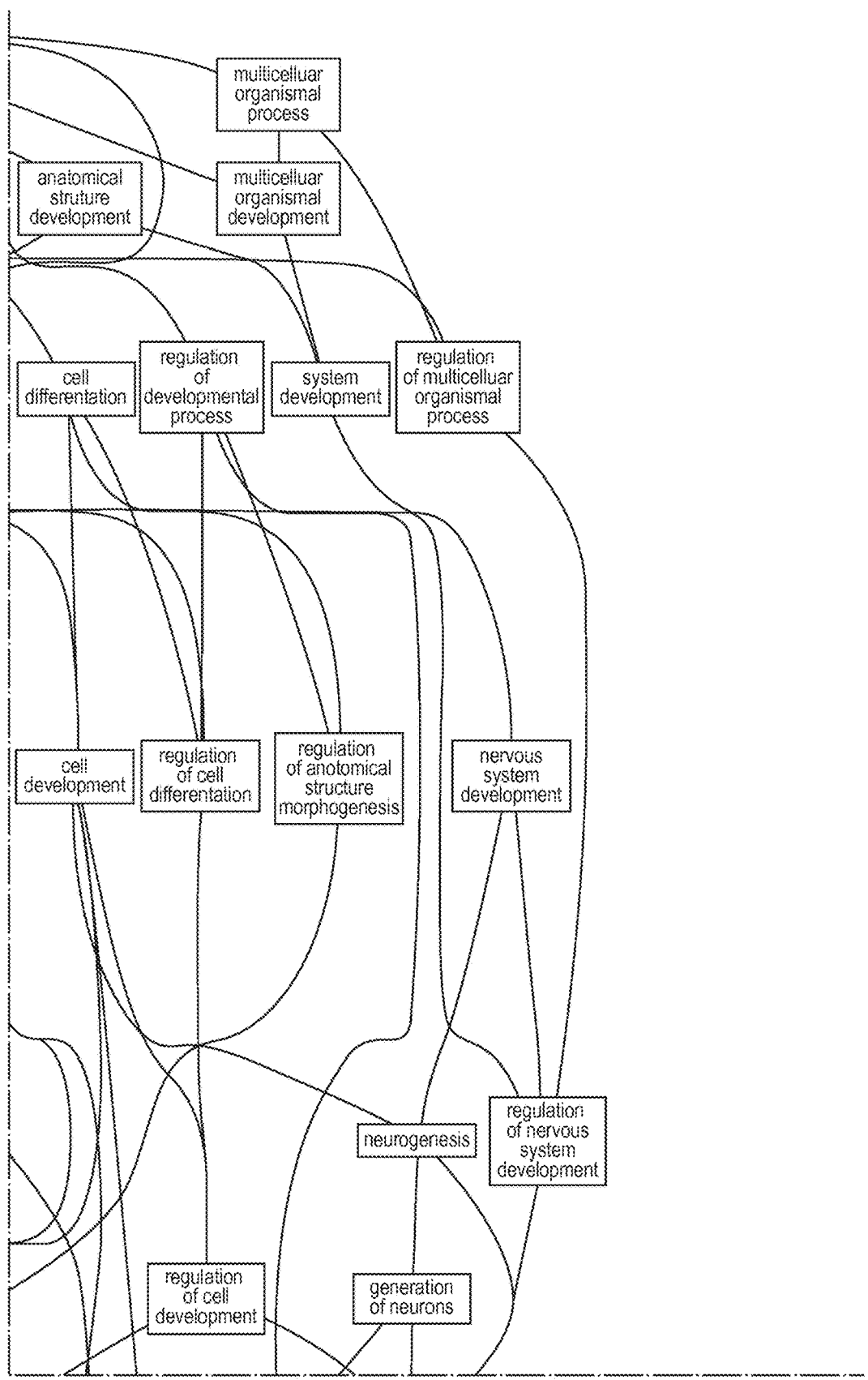
Figure 12E:
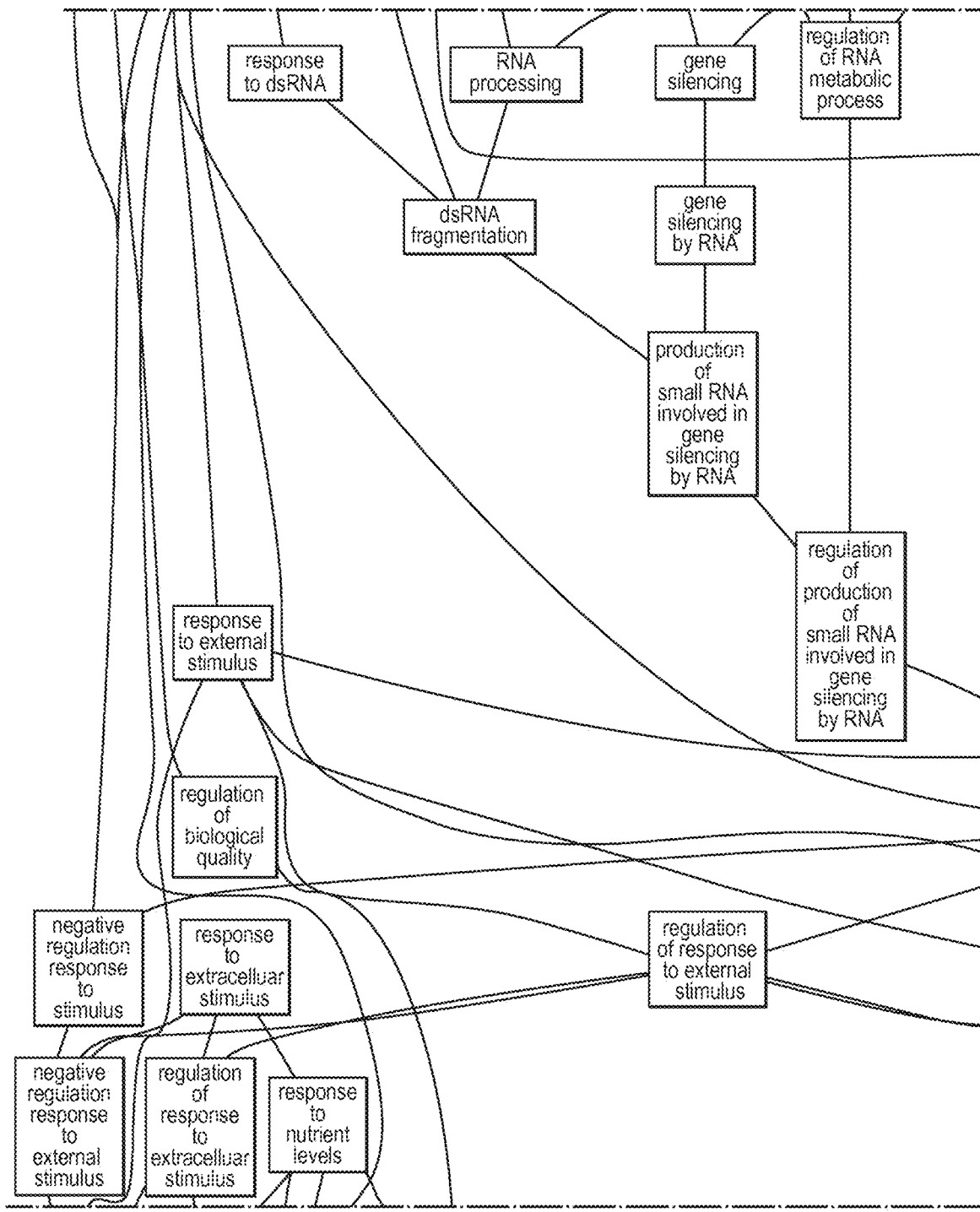
Figure 12F:
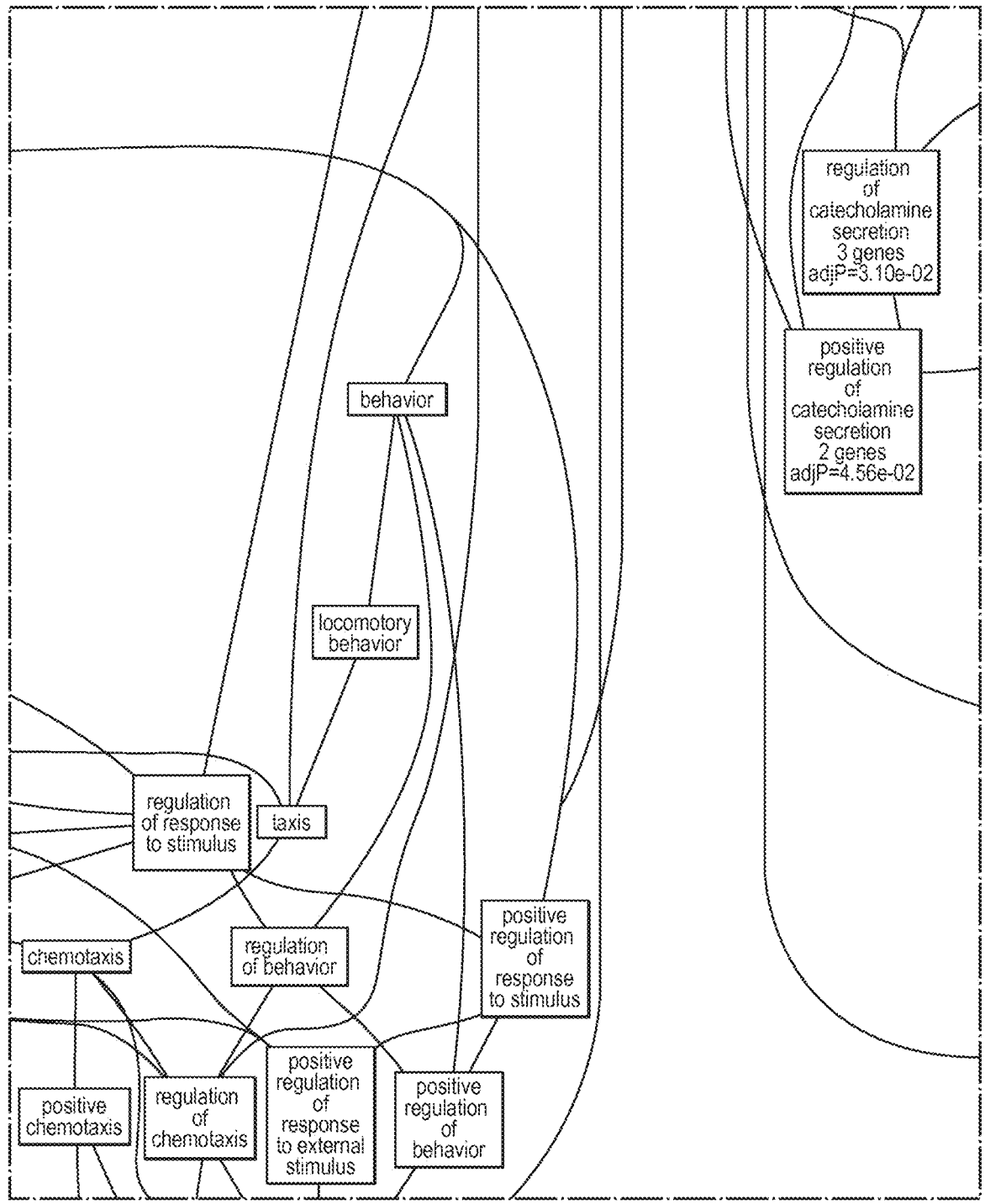
Figure 12G:
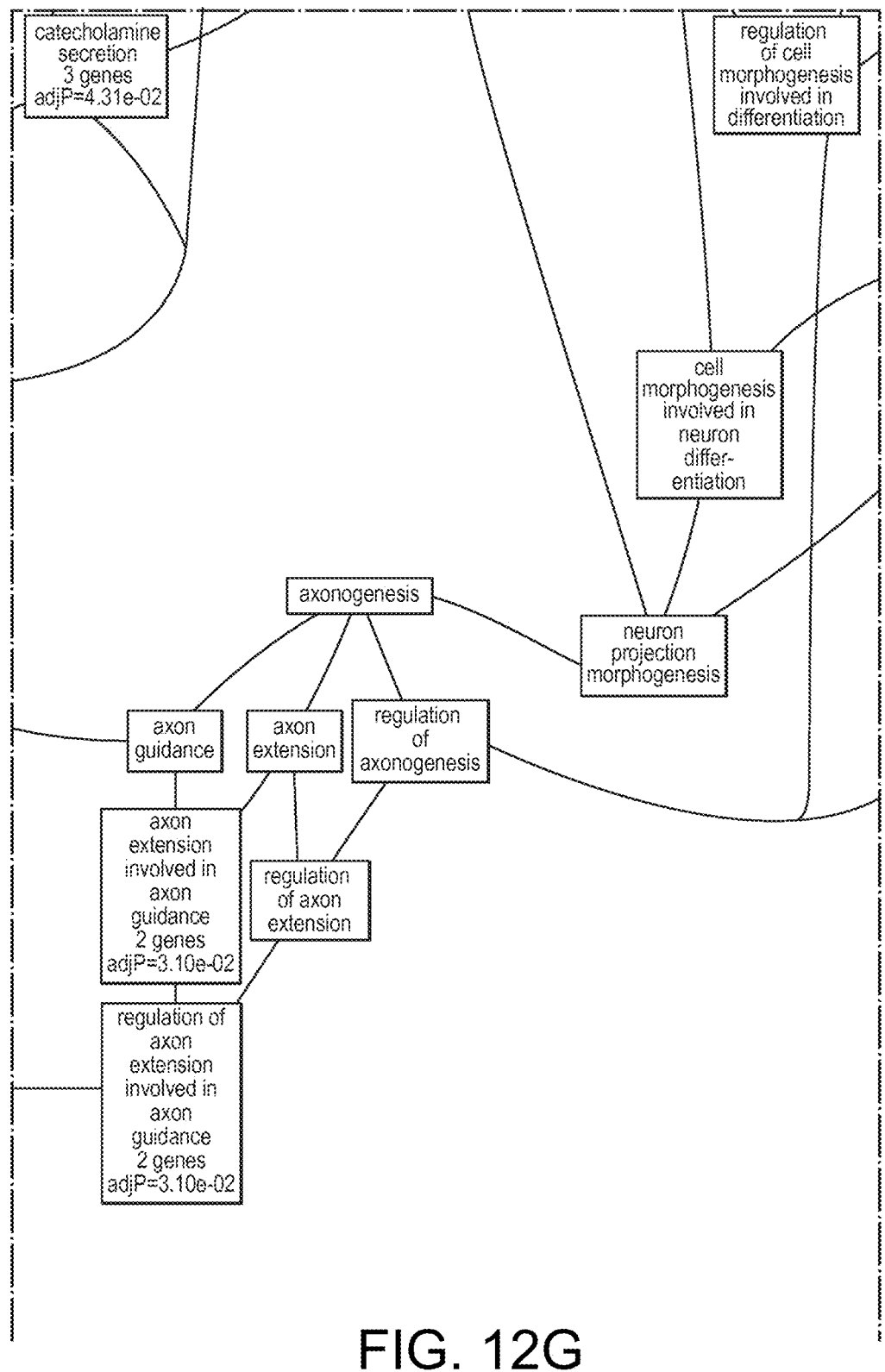
Figure 12H:
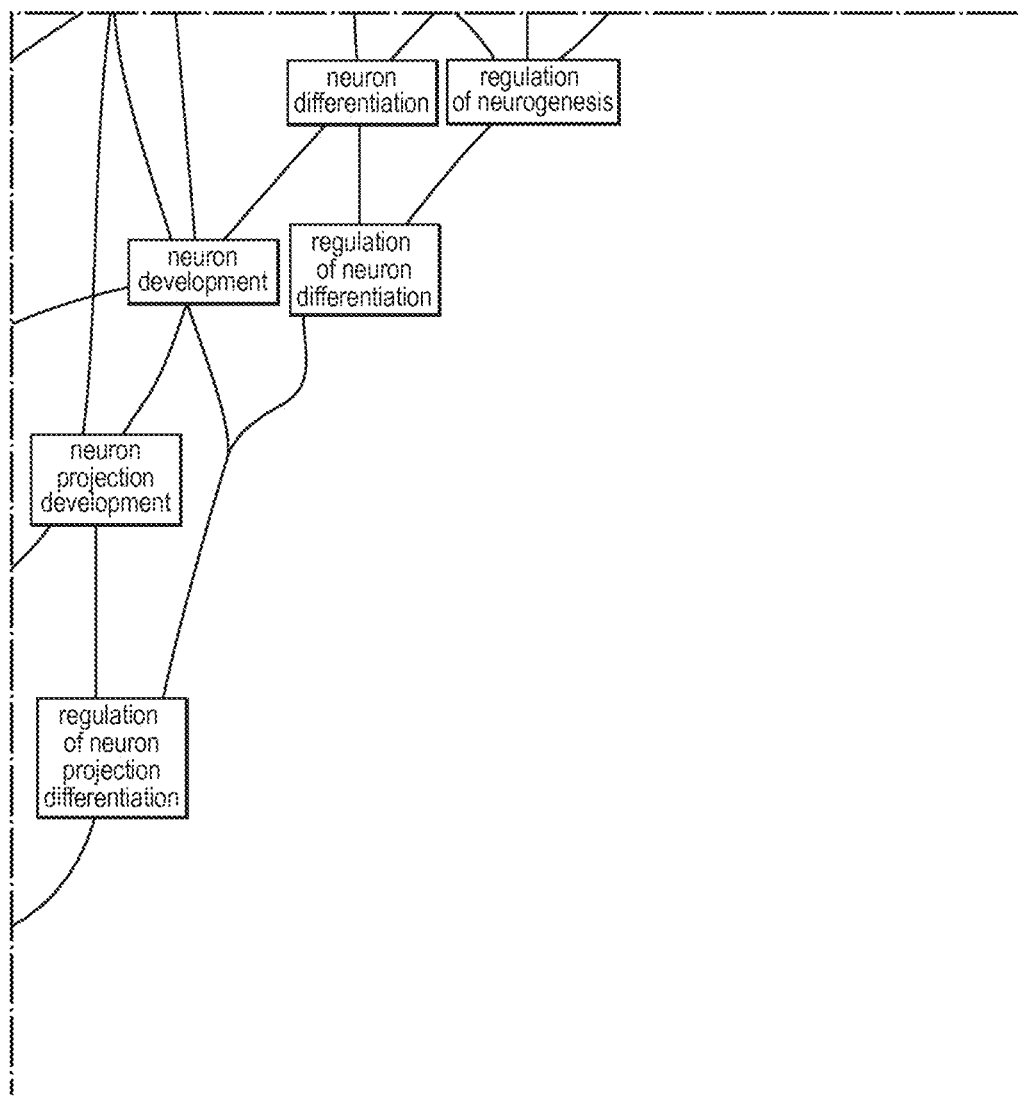
Figure 12I:
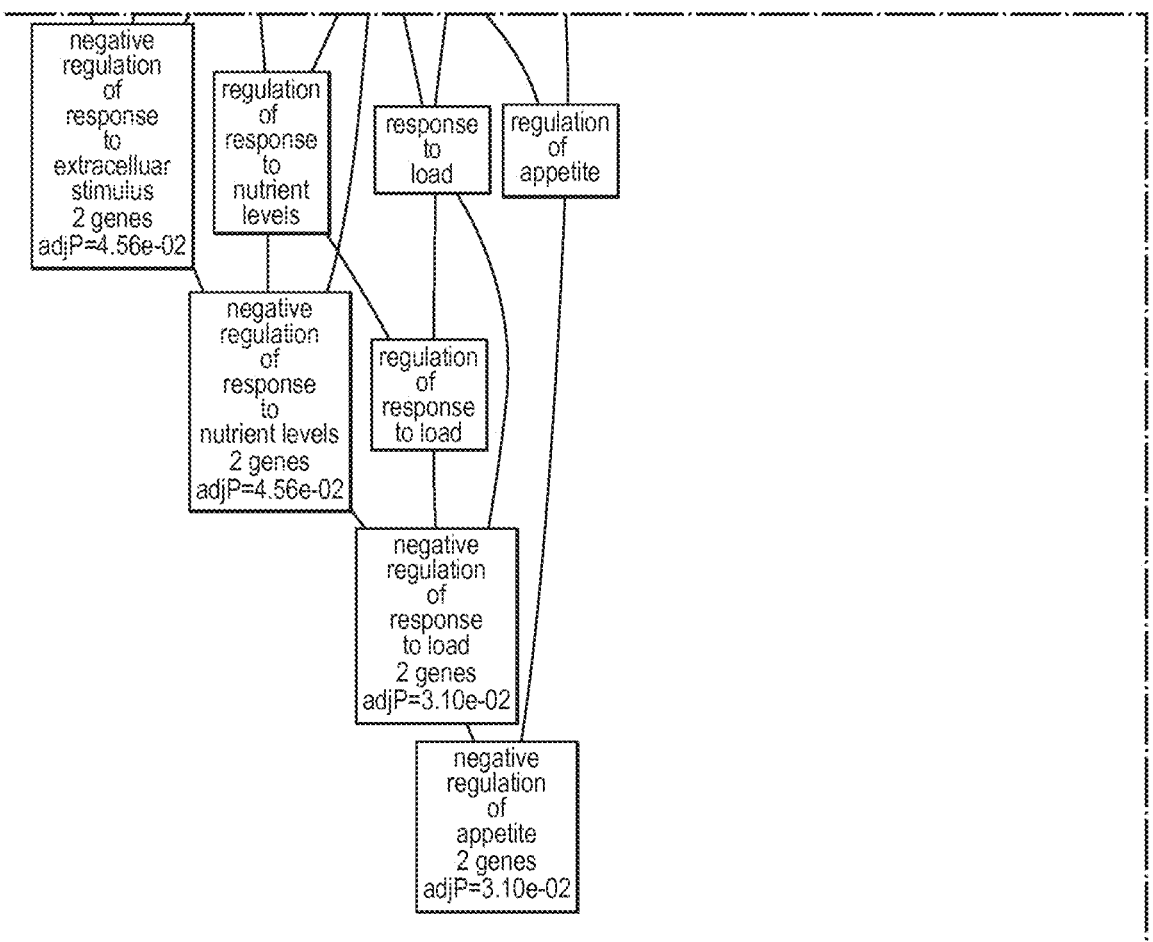
Figure 12J:
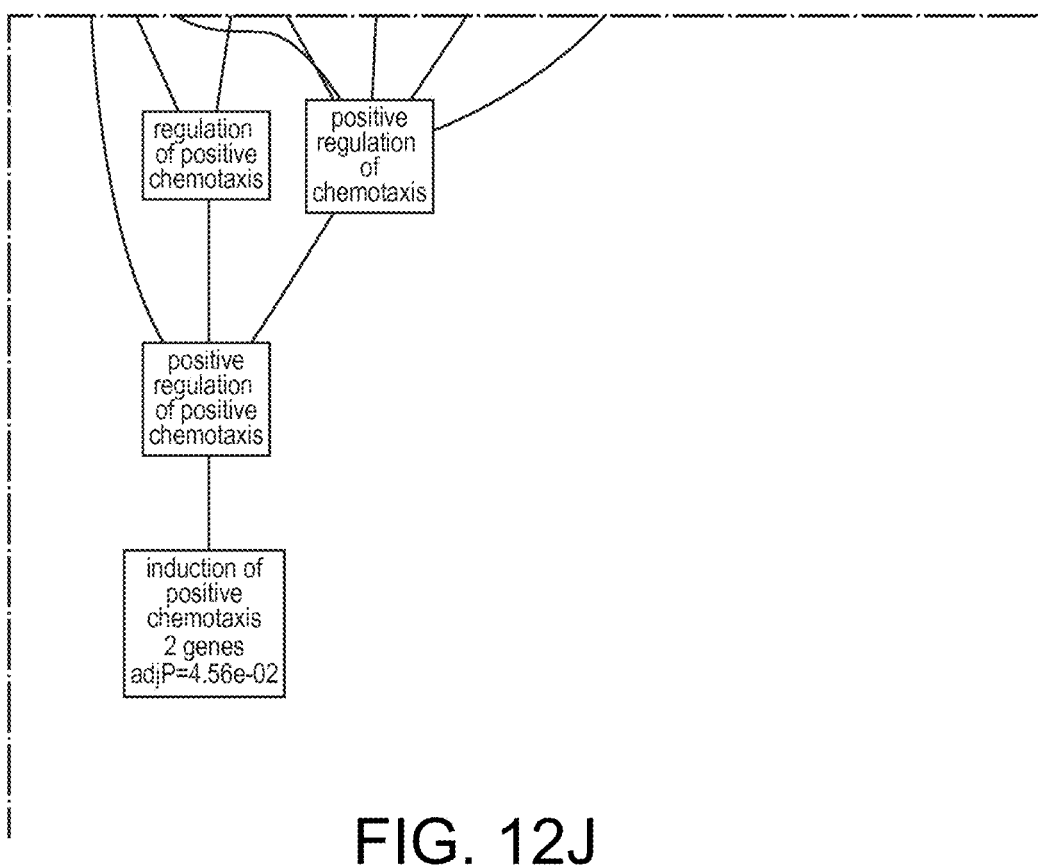
Figure 12K:
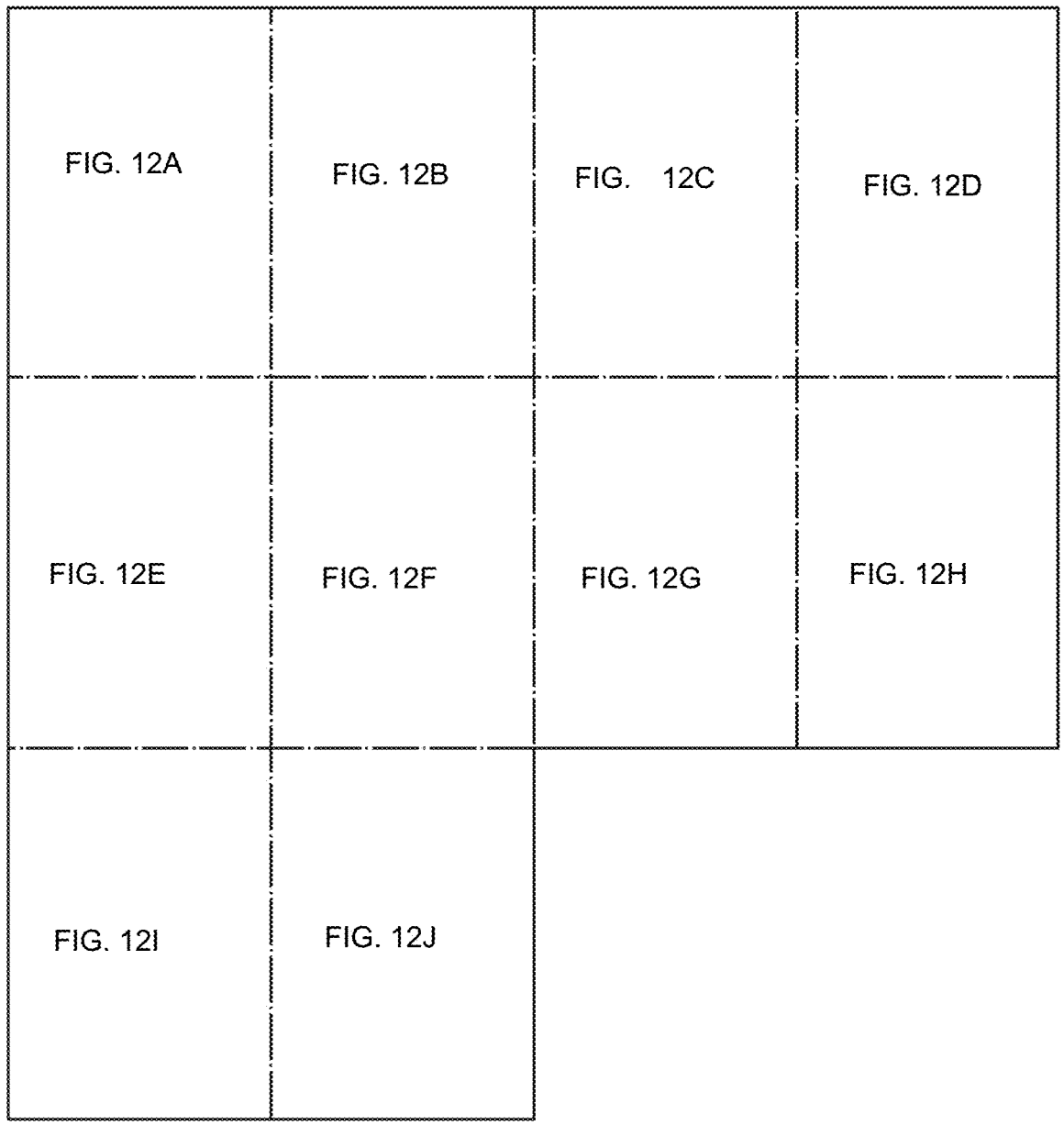

To demonstrate that these responses are specific to R. hominis, the response of germfree animals to another commensal bacterium was investigated. The gene expression responses to colonization with E. coli MG1655 (K12) were compared to R. hominis after 10-14d and 22-28d post-colonization. Over this time interval, large differences in gene expression were observed in response to R. hominis but not to E. coli, indicating that R. hominis is biologically very active in the gut, in contrast to the minimal impact of E. coli (FIG. 10). The response to E. coli deduced from the gene expression data in the ascending colon seemed to be mainly a B-cell mediated antibody response.

R. hominis Affects T Cell Pathways Mostly in the Colon

Figure 4:
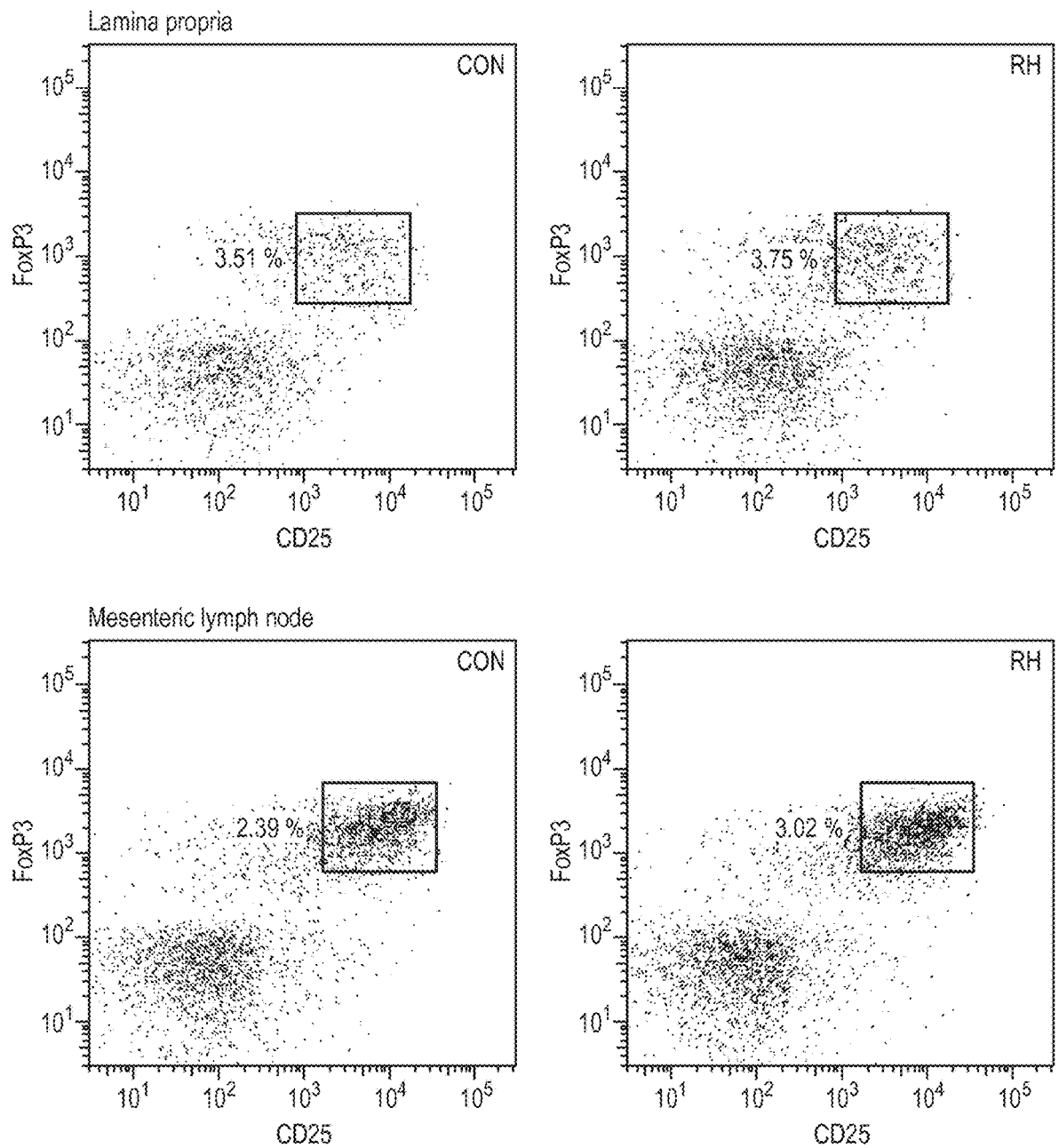
Figure 5A:
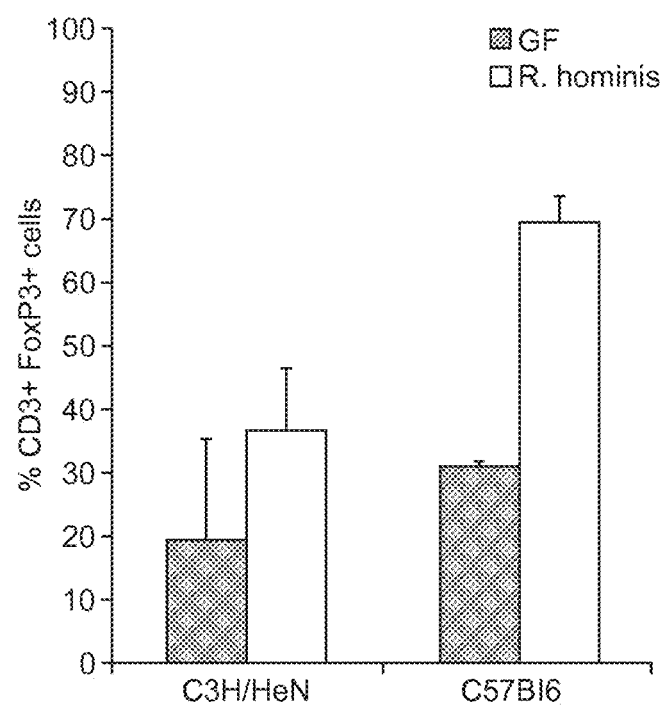
Figure 5B:
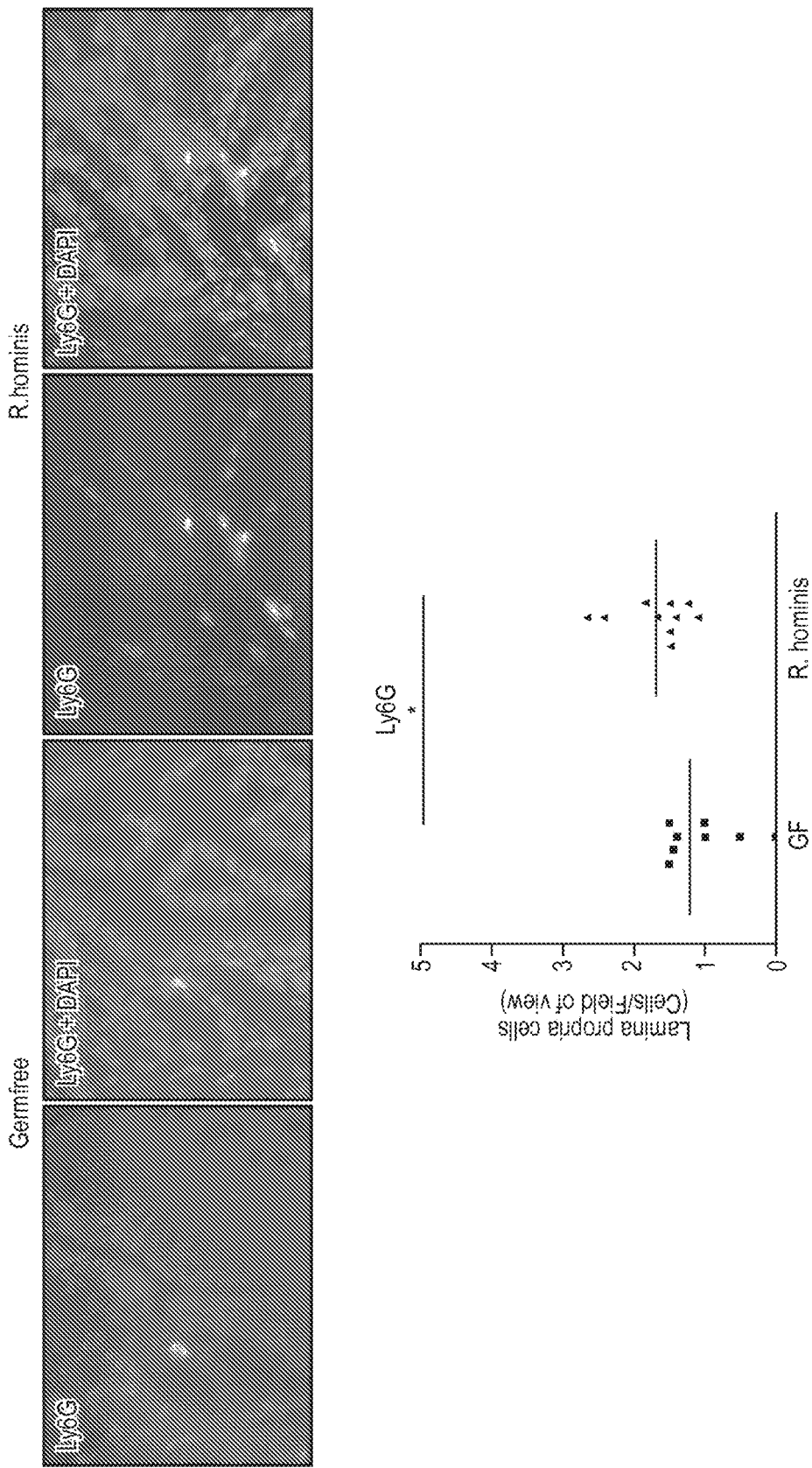
Figure 5C:
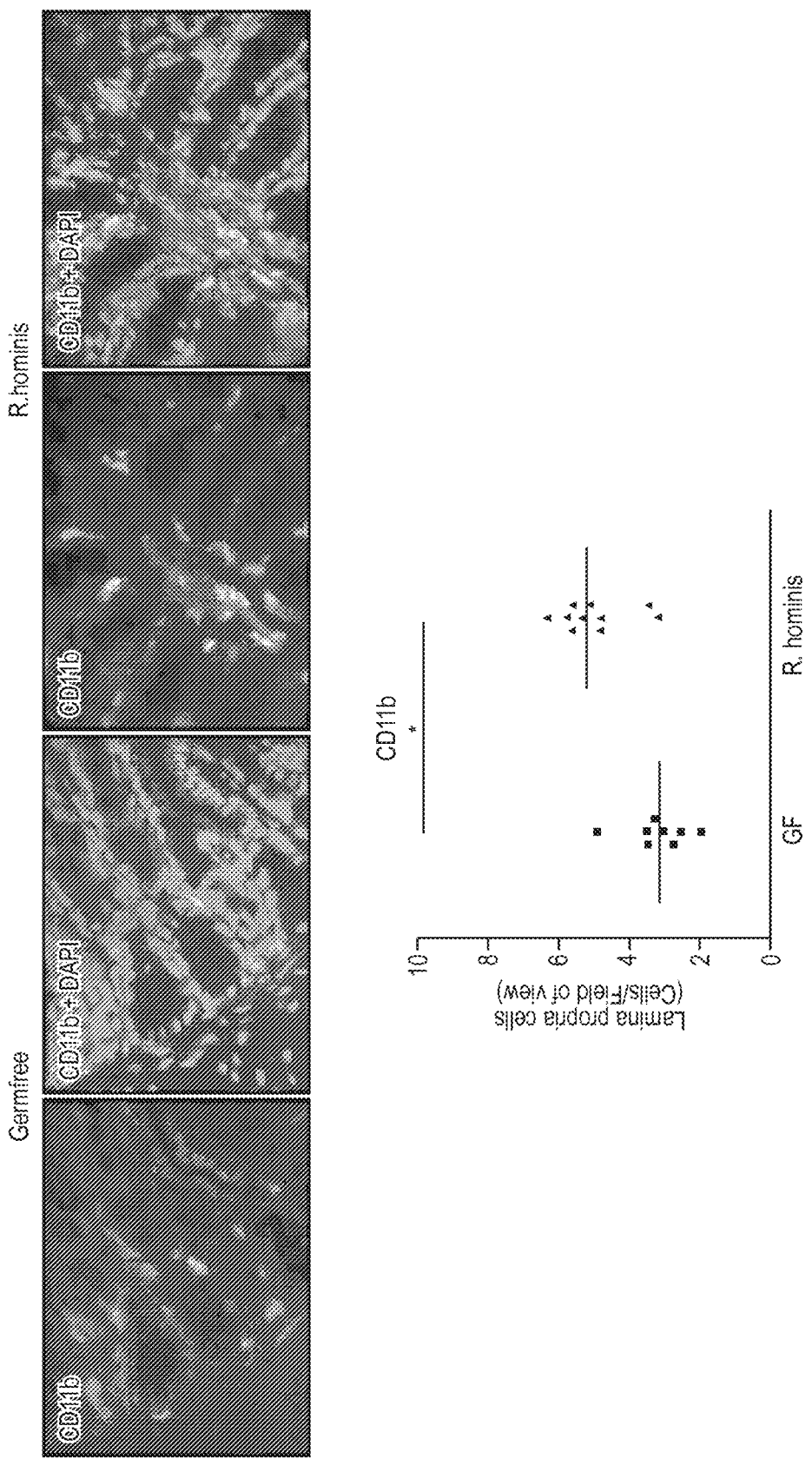
Figure 5D:
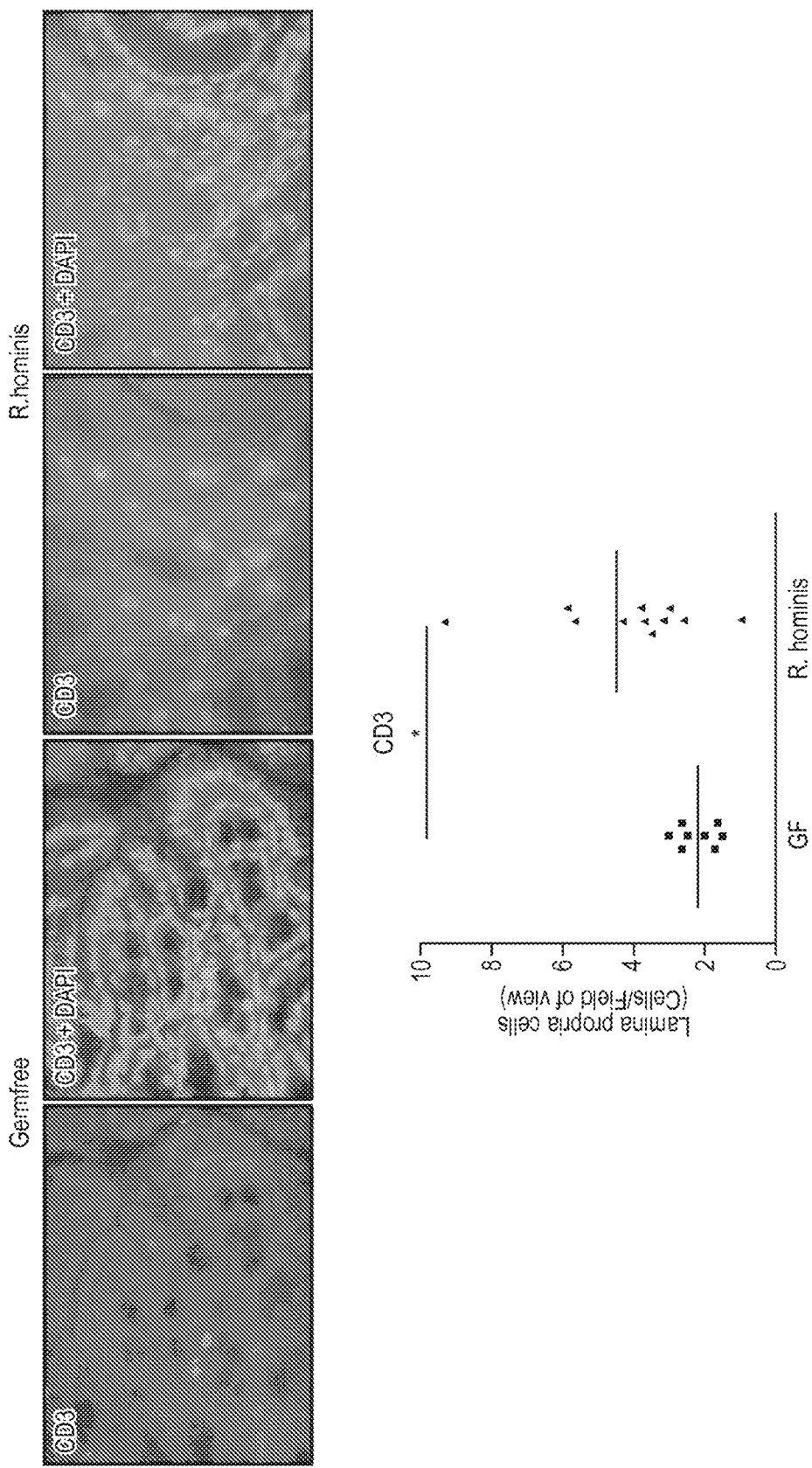
Figure 5E:
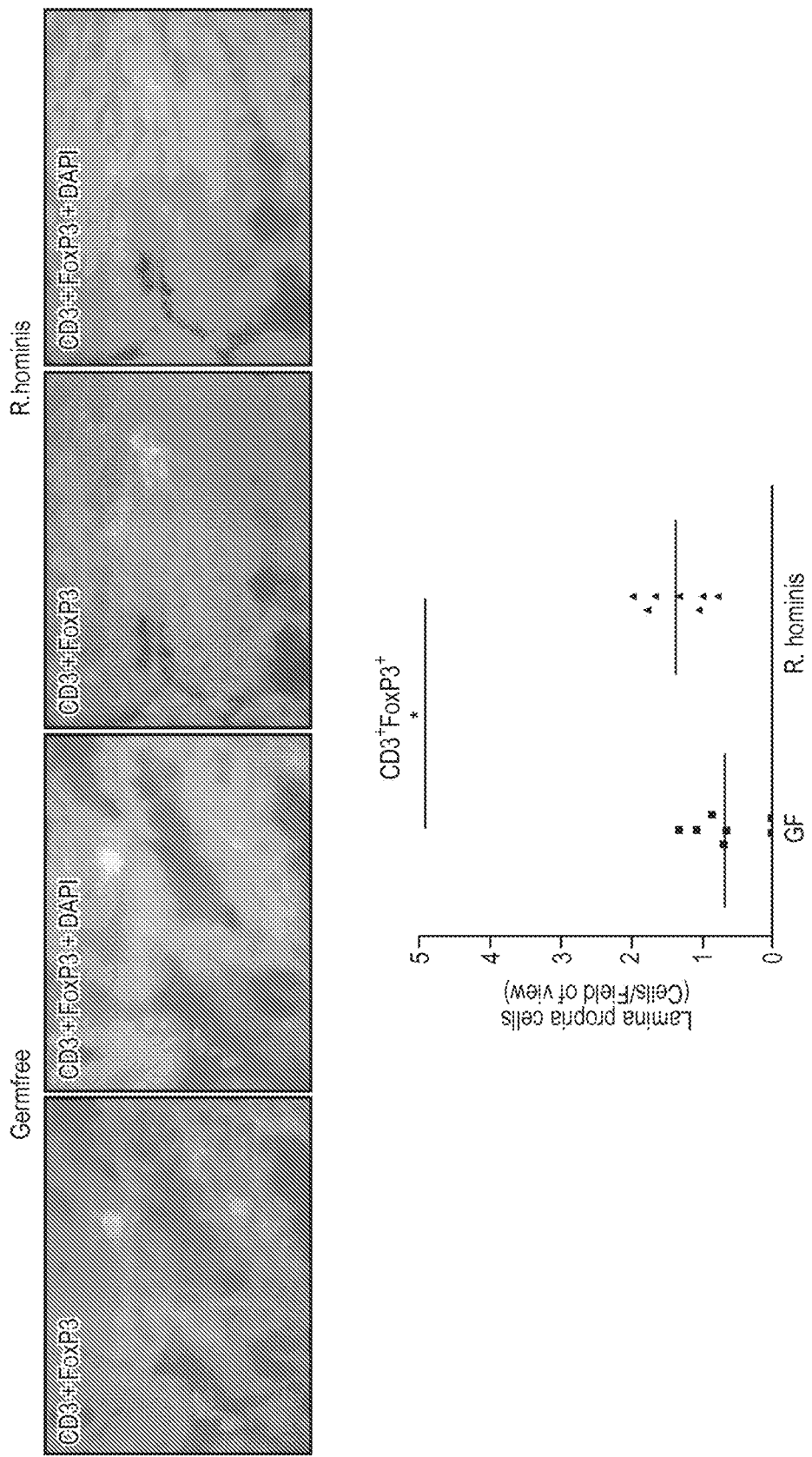
Figure 9A:
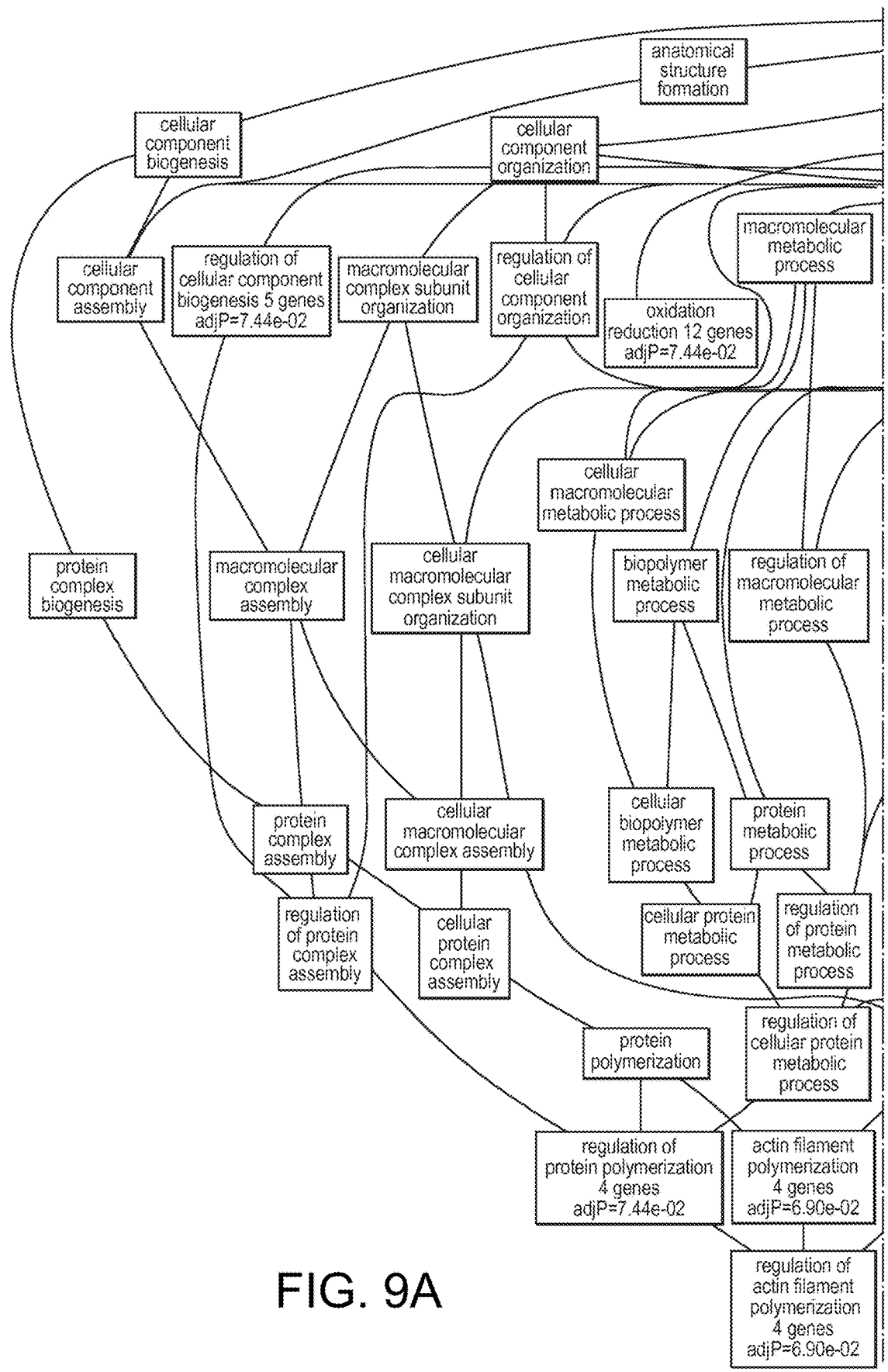
Figure 9B:
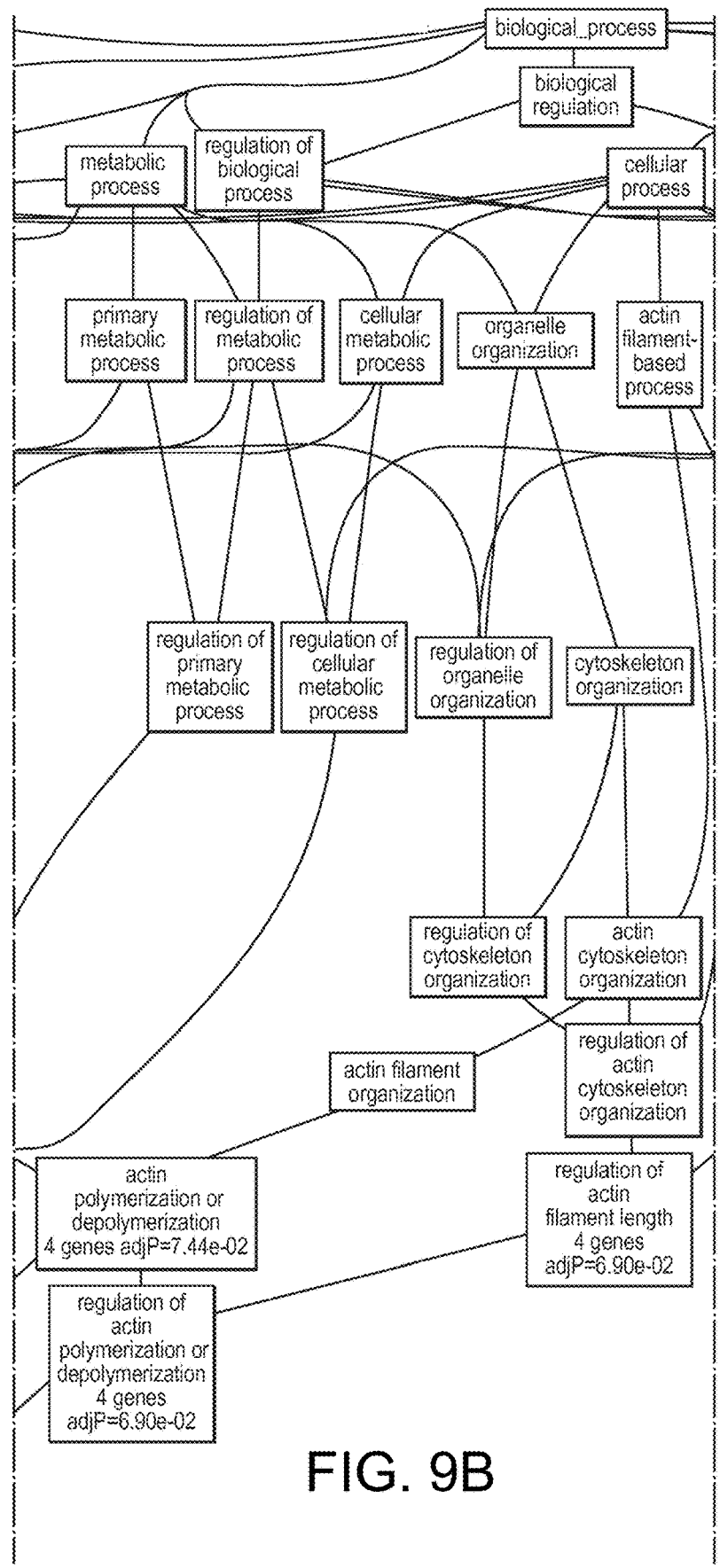
Figure 9C:
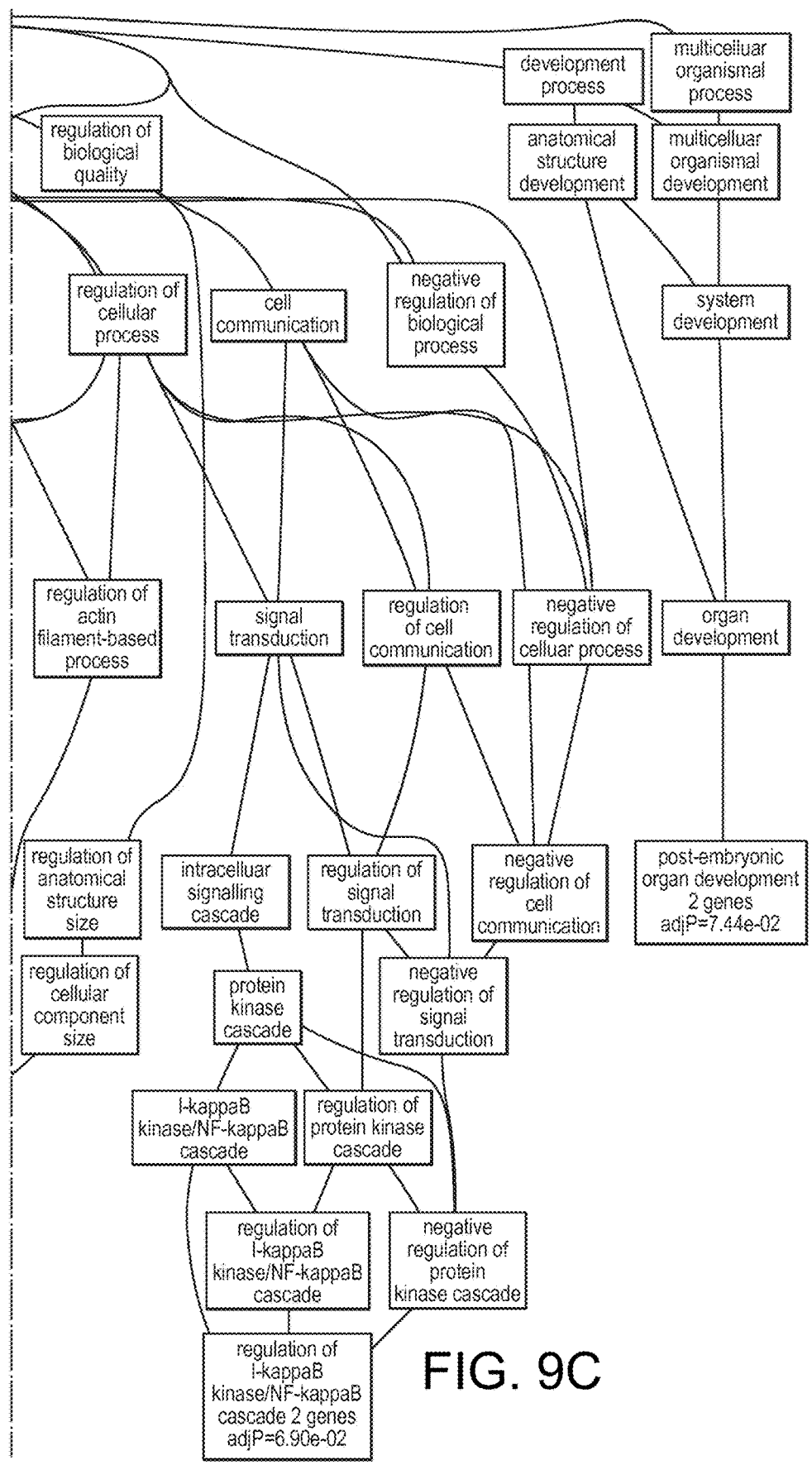

The majority of pathways affected at 14d grouped into the categories cell differentiation, cell cycle regulation and tissue remodelling. Importantly, immune response was a major pathway induced at 28d in the ascending colon. The significantly affected pathways in this category were mostly involved in T cell function, including IL-10 signalling and regulation of T cell function by CTLA-4 (Table S5). The genes involved in these pathways showed both up-regulation and down-regulation, so while these pathways were significantly affected by the presence of R. hominis, the precise net functional effects on T cell differentiation required further investigation. To clarify the role of R. hominis in relation to T cell differentiation, conventional mice with R. hominis were treated for 14 days and determined the impact on T cell subsets both in the lamina propria and mesenteric lymph nodes (MLN). Treatment with R. hominis increased the population of CD3'CD4$^+$CD25$^+$FoxP3$^+$ T cells in both locations (FIG. 4). An assessment was made of the numbers of double-positive CD3$^+$FoxP3$^+$ cells in the lamina propria of ascending and descending colon of mono-associated C3H/HeN and C57B16 animals and confirmed a significant increase in regulatory T cells in R. hominis-treated mice (FIG. 5A). The GO-process for 'actin polymerization' (GO: 0030041)(Arpc3, Capg, Cdc42ep5 and Rhoc) was up-regulated at 28d in the colon in R. hominis colonized mice (FIG. 9A-C). Actin polymerization at the immune synapse is required for T cell activation and effector function. Overall, this data indicates that R. hominis actively effects the adaptive immune response in the colon by positively influencing T cell regulation.

Table S5. Immune system response pathway analysis of transcripts differentially expressed in the ascending colon between R. hominis treated mice and germfree mice at 28d. Differentially expressed genes (P<0.05) were imported into GeneGo MetaCore analytical software to determine significantly enriched canonical pathways in each group. * The number of genes on each map that are differentially expressed in the specific treatment comparison. ** The total number of genes on each map.

TABLE S5

Immune system response pathway analysis of transcripts differentially expressed in the ascending colon between R. hominis treated mice and germfree mice at 28 d. Differentially expressed genes (P < 0.05) were imported into GeneGo MetaCore analytical software to determine significantly enriched canonical pathways in each group.

| Regulatory processes/ Immune system response pathway | P-value | Significant* | Total** |
|---|---|---|---|
| Immune response_IL-10 signaling pathway | 0.00125 | 10 | 26 |
| Immune response_IL-9 signaling pathway | 0.00592 | 11 | 36 |
| Immune response_HMGB1/RAGE signaling pathway | 0.00832 | 14 | 53 |
| Immune response_BCR pathway | 0.00992 | 14 | 54 |
| Development_GM-CSF signaling | 0.01258 | 13 | 50 |
| Development_PEDF signaling | 0.02618 | 12 | 49 |
| Immune response_IL-5 signalling | 0.02840 | 11 | 44 |
| Immune response_TCR and CD28 co-stimulation in activation of NF-kB | 0.03611 | 10 | 40 |
| Immune response_Regulation of T cell function by CTLA-4 | 0.04598 | 9 | 36 |
| Immune response_CD40 signaling | 0.04796 | 14 | 65 |
| Signal transduction_JNK pathway | 0.04921 | 10 | 42 |

*The number of genes on each map that are differentially expressed in the specific treatment comparison.
**The total number of genes on each map.

Related to these results was the induction of the Ly6 gene family in the ascending colon. In particular, the GPI-anchored gene product of Ly6g6c was up-regulated 25-fold, and the related gene Ly6g6e was up-regulated two-fold at 28 d. Most haematopoietic cells, including neutrophils and plasmacytoid dendritic cells, express one or more members of the Ly6 family. Furthermore, a possible role of Ly6 in T cell activation, differentiation and maturation has been proposed (Mallya, Campbell & Aguado 2006). Immunocytochemistry confirmed increased presence of Ly6G.sup.+, CD11b.sup.+ and CD3.sup.+ FoxP3.sup.+ cells in R. hominis-colonized mice (FIG. 5B-5E).

R. hominis Flagellins Modulate T Cell Differentiation

The influence of bacteria on the differentiation of T cells may reflect the array of TLR ligands displayed. For example, the coupling between TLR5 signalling and CD4+ T cell responses has recently been demonstrated for flagellate pathogens (Letran et al. 2011). Interestingly, depending upon the experimental setting, flagellin can prime a range of T cell responses including Th1, Th2, Th17 and Treg responses (Wilson et al. 2012).

The functionality of bacterial flagellins FlaA1 (RH1) and FlaA2 (RH2) was investigated using novel soluble recombinant flagellin proteins, generated against the unique R. hominis flagellin sequences. The ability of RH I and RH2 were compared and contrasted with various commensal and pathogenic flagellins, generated using identical protocols, to activate signalling responses in intestinal epithelial cell lines and bone marrow derived dendritic cells expanded with either FLT3L or GM-CSF.

Figure 6A:
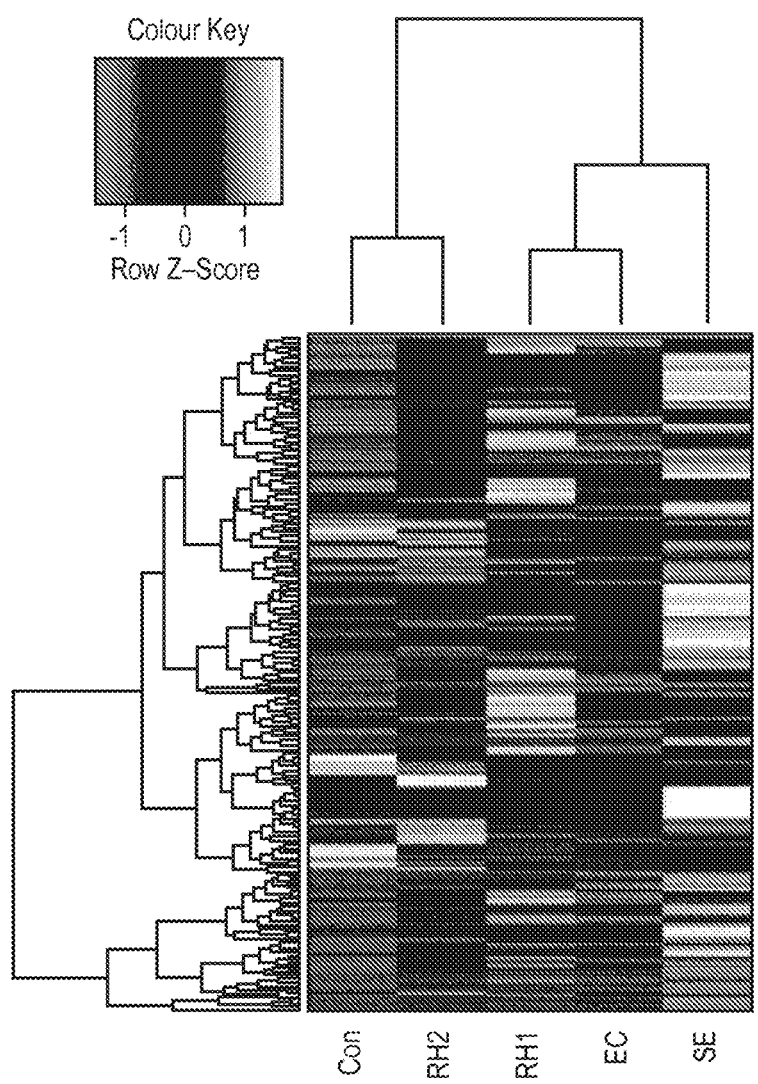
Figure 6B:
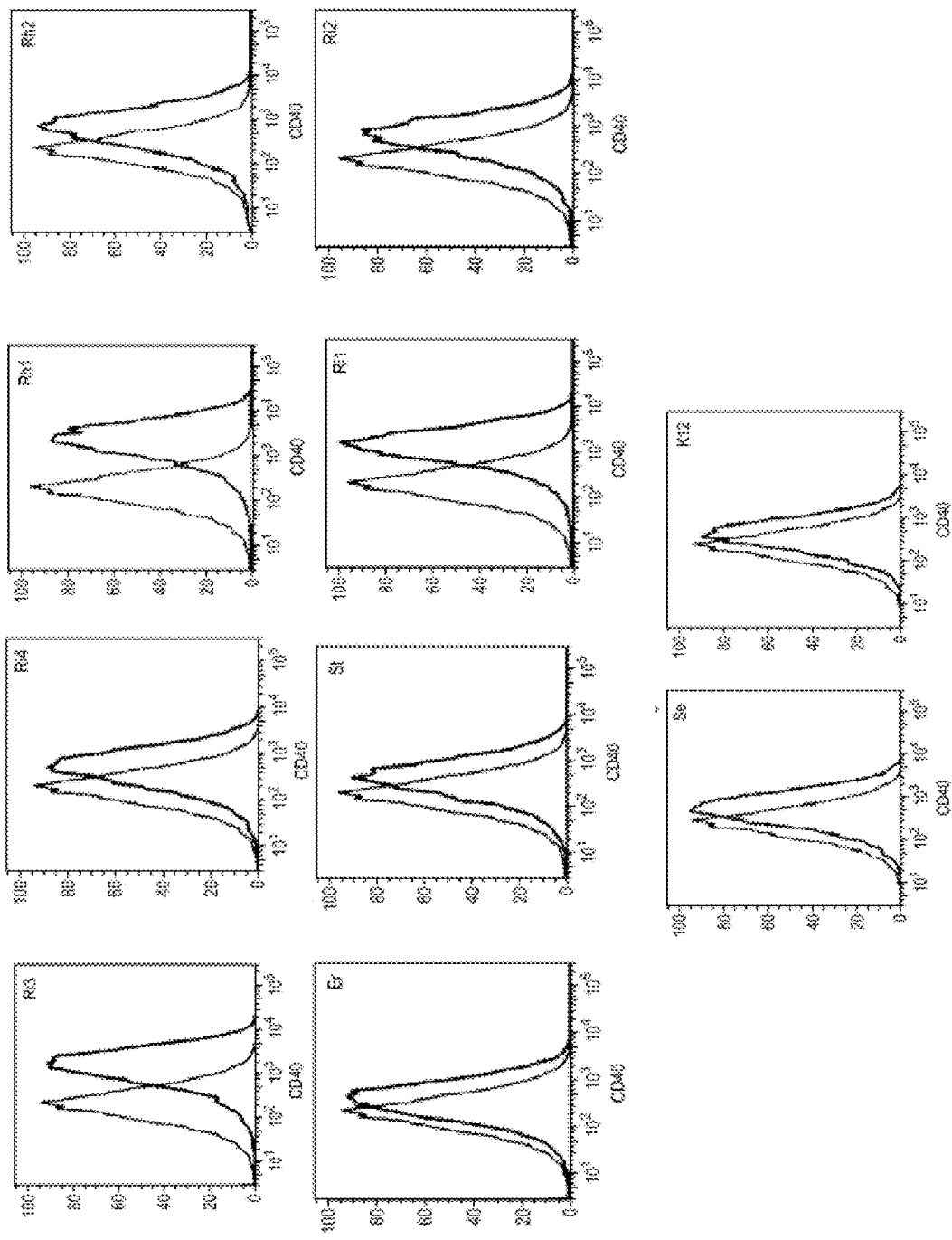
Figure 6C:
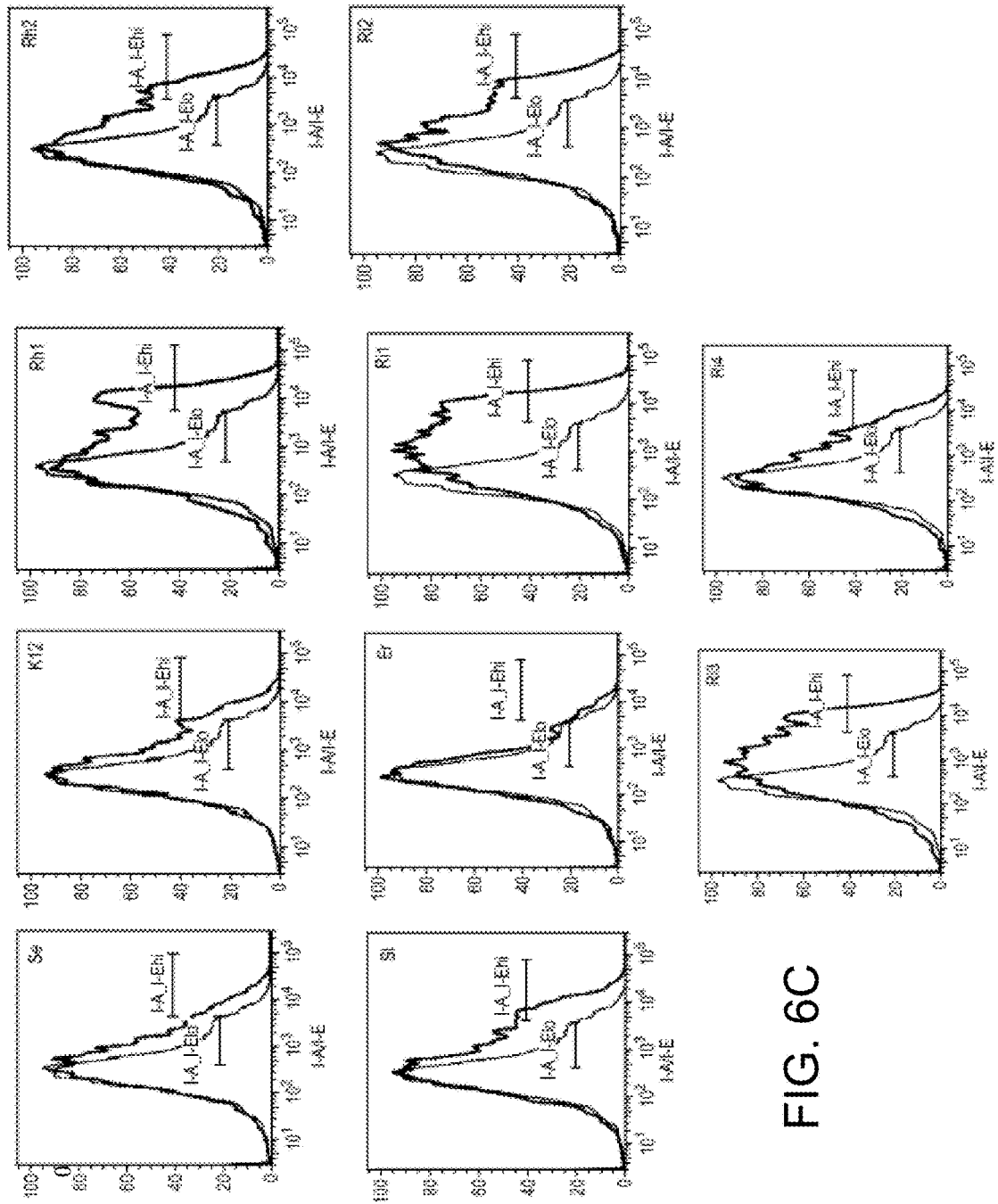
Figure 6D:
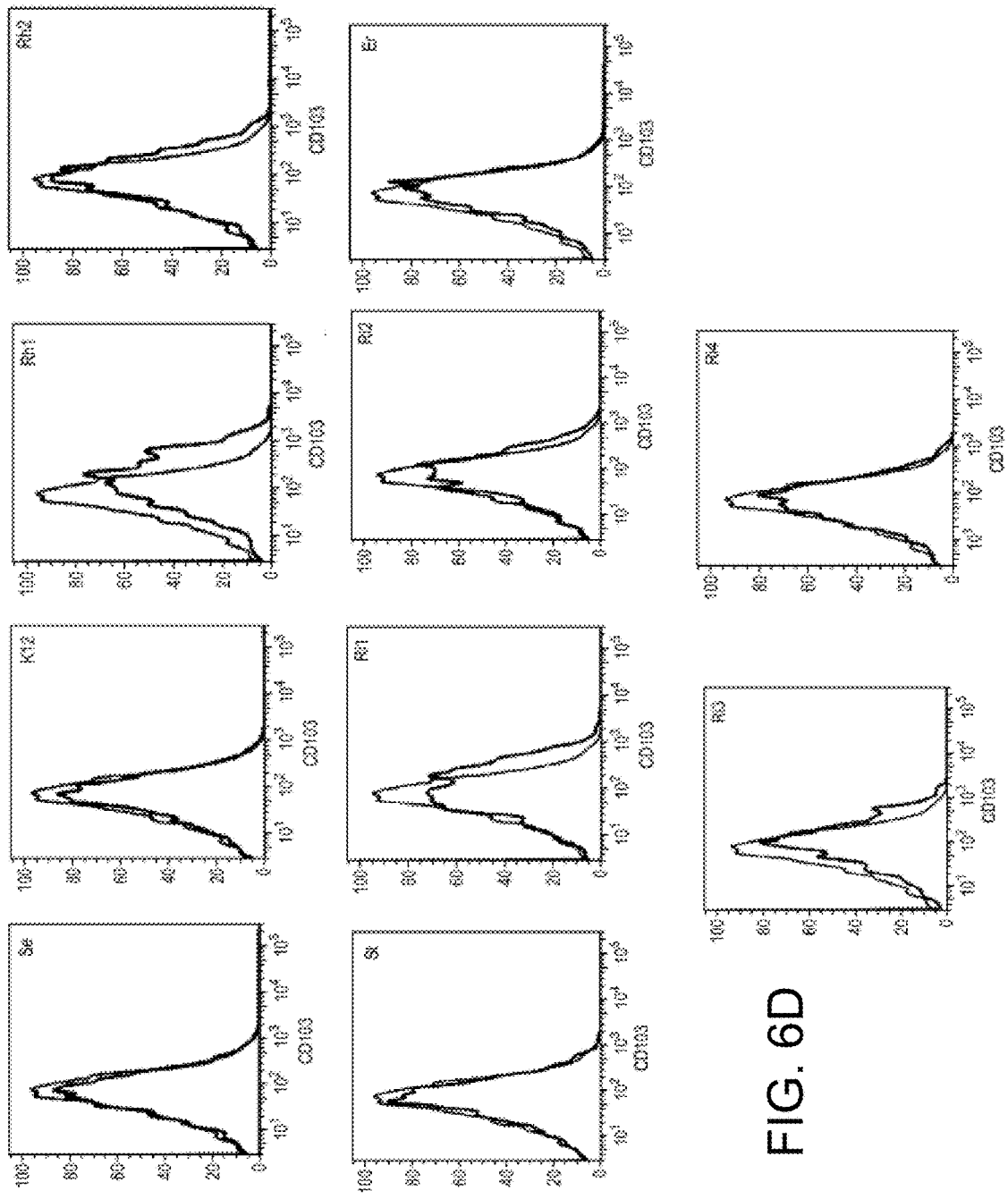
Figure 6E:
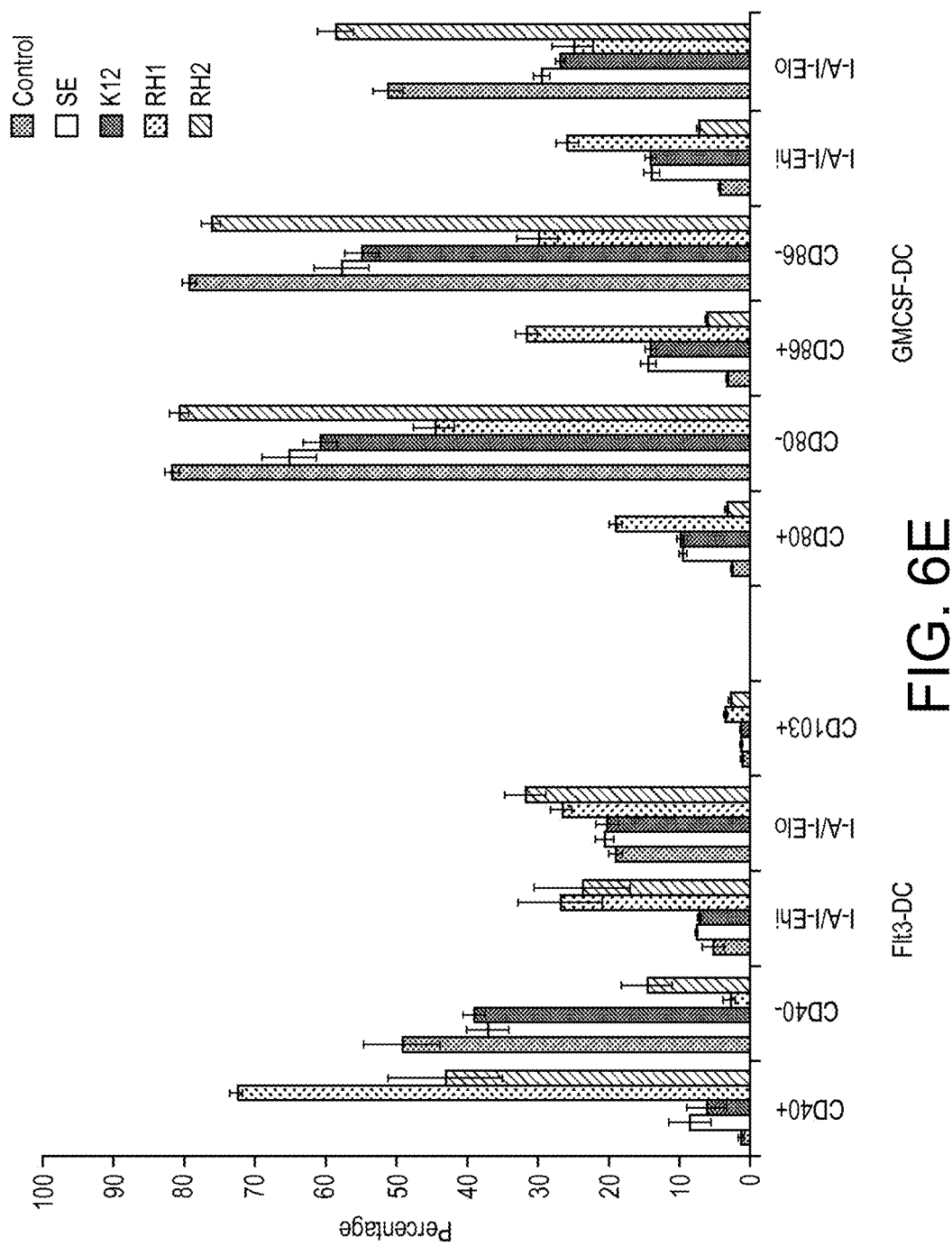
Figure 6F:
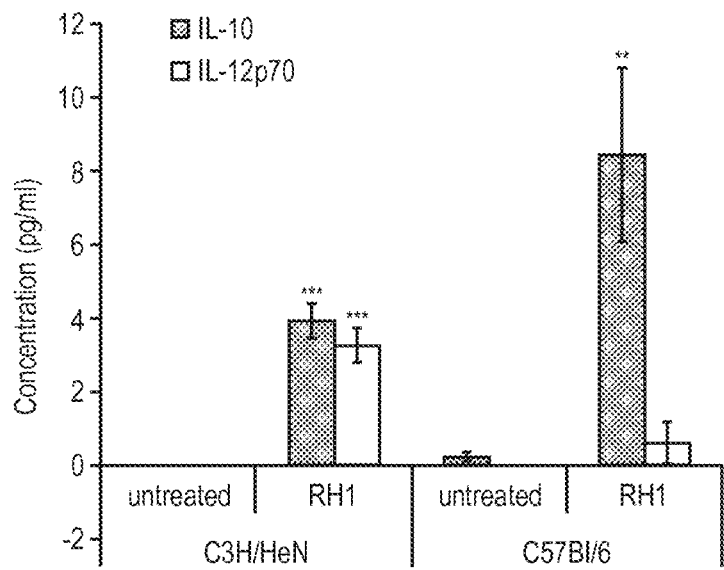

Epithelial cells treated with identical concentrations of different bacterial flagellins revealed distinct patterns of gene expression (FIG. 6A). Importantly, no endotoxin contamination was detected in the recombinant protein preparations. Salmonella enteritidis (SE) was more potent than E. coli K12 (EC) or RH flagellin. RH1 flagellin also showed a strong response but clustered in a distinct clad along with commensal EC. The responses were shown to be TLR5-dependent using epithelial cells expressing dominant-negative TLR5. In contrast, RH2 was shown to be minimally active; it was generally not pro-inflammatory nor did it activate the conserved gene signature (IL-8, CXCL-1, CXCL-2 and CXCL-10) induced by other recombinant bacterial flagellins. RH1 flagellin protein is more biologically active than RH2 in vitro; although both recombinant proteins were expressed in vivo, RH1 was also significantly up-regulated at the gene expression level in vivo. It was demonstrated that the RH1 flagellin from R. hominis induced different responses in Flt3L and GM-CSF derived dendritic cells relative to commensal *E. coli* and pathogenic *Salmonella enteritidis* (FIG. 6E). In particular, RH1 was unique in its ability to activate Flt3L-expanded DCs, with up-regulation of I-A/1-E and CD40 and the production of IL-10 by bone marrow derived DCs from both C3H/HeN and C57Bl/6 mice. The IL-10/IL-12 ratio was particularly elevated in C57BV6 DCs (FIG. 6F), which were found to be between TLR5 KO mice and WT mice, mono-colonized with *R. hominis*. Differentially expressed genes (P<0.05) were imported into GeneGo MetaCore analytical software to determine significantly enriched canonical pathways in each group. *The number of genes on each map that are differentially expressed in the specific treatment comparison. **The total number of genes on each map.

TABLE S6

Immune system response pathway analysis of transcripts differentially expressed in the ascending colon between TLR5 KO mice and WT mice, mono-colonized with *R. hominis*. Differentially expressed genes (P < 0.05) were imported into GeneGo MetaCore analytical software to determine significantly enriched canonical pathways in each group.

| # | Maps | pValue | | Ratio |
|---|---|---|---|---|
| 1 | Immune response_IL-9 signaling pathway | 0.00001 | 7 | 36 |
| 2 | Immune response_Histamine signaling in dendritic cells | 0.00008 | 7 | 50 |
| 3 | Immune response_HMGB1/RAGE signaling pathway | 0.00012 | 7 | 53 |
| 4 | Immune response_IL-6 signaling pathway | 0.00046 | 5 | 31 |
| 5 | Immune response_Histamine H1 receptor signaling in immune response | 0.00052 | 6 | 48 |
| 6 | Immune response_Oncostatin M signaling via MAPK in mouse cells | 0.00082 | 5 | 35 |
| 7 | Immune response_Oncostatin M signaling via MAPK in human cells | 0.00107 | 5 | 37 |
| 8 | Signal transduction_JNK pathway | 0.00191 | 5 | 42 |
| 9 | Immune response_IL-7 signaling in B lymphocytes | 0.00213 | 5 | 43 |
| 10 | Immune response_Signaling pathway mediated by IL-6 and IL-1 | 0.00362 | 4 | 30 |
| 11 | Development_GM-CSF signaling | 0.00415 | 5 | 50 |
| 12 | Immune response_T cell receptor signaling pathway | 0.00492 | 5 | 52 |
| 13 | Chemotaxis_Leukocyte chemotaxis | 0.00528 | 6 | 75 |
| 14 | Immune response_CCL2 signaling | 0.00579 | 5 | 54 |
| 15 | Immune response_CD28 signaling | 0.00579 | 5 | 54 |
| 16 | Immune response_Role of DAP12 receptors in NK cells | 0.00579 | 5 | 54 |
| 17 | Immune response_Fc epsilon RI pathway | 0.00626 | 5 | 55 |
| 18 | Immune response_Role of PKR in stress-induced antiviral cell response | 0.00728 | 5 | 57 |
| 19 | Immune response_HMGB1 release from the cell | 0.01114 | 4 | 41 |
| 20 | Immune response_IL-15 signaling | 0.01176 | 5 | 64 |
| 21 | Immune response_HTR2A-induced activation of cPLA2 | 0.01313 | 4 | 43 |
| 22 | Immune response_IL-4 signaling pathway | 0.01421 | 4 | 44 |
| 23 | Immune response_IL-5 signalling | 0.01421 | 4 | 44 |
| 24 | Immune response_Fc gamma R-mediated phagocytosis in macrophages | 0.01653 | 4 | 46 |
| 25 | Immune response_NF-AT signaling and leukocyte interactions | 0.01653 | 4 | 46 |
| 26 | Development_PEDF signaling | 0.02043 | 4 | 49 |
| 27 | Immune response_IL-2 activation and signaling pathway | 0.02043 | 4 | 49 |
| 28 | Immune response_NFAT in immune response | 0.02332 | 4 | 51 |
| 29 | Immune response_IL-3 activation and signaling pathway | 0.02803 | 3 | 31 |
| 30 | Immune response_BCR pathway | 0.02809 | 4 | 54 |
| 31 | Immune response_TLR signaling pathways | 0.02809 | 4 | 54 |
| 32 | Immune response_Immunological synapse formation | 0.03727 | 4 | 59 |
| 33 | Immune response_Th17 cell differentiation | 0.03836 | 3 | 35 |
| 34 | Immune response_Human NKG2D signaling | 0.04722 | 3 | 38 |

*The number of genes on each map that are differentially expressed in the specific treatment comparison.
**The total number of genes on each map.

CD103+ Siglec-H+. Consistent with the observations herein, a number of recent reports have also shown that flagellin can activate CD103+DC populations (Flores-Langarica et al. 2012, Kinnebrew et al. 2012).

Figure 6G:
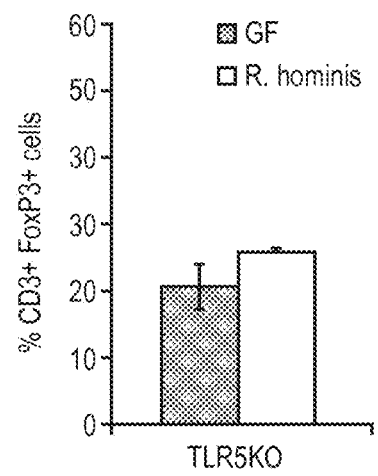

To evaluate the functional importance of *R. hominis* and its flagellins, germ-free TLR5KO and WT mice were mono-colonized. The heatmap showing differentially expressed genes for both TLR5KO and wild-type colonized with *R. hominis* revealed a very strong effect of TLR5 (FIG. 11). Although T cell pathways were still influenced by *R. hominis* colonization in TLR5KO mice, the responses were more related to IL4, IL5, IL-6, IL-9 pathways and not IL-10 and CTLA-4 (Table S6). Furthermore, the numbers of double-positive $CD3^+FoxP3^+$ cells in the lamina propria of TLR5KO mice were not increased by *R. hominis* treatment (FIG. 6G), in contrast to mono-associated C3H/HeN and C57B16 animals (FIG. 5A).

TABLE S6 Immune system response pathway analysis of transcripts differentially expressed in the ascending colon The observation herein that *R. hominis* influences Tregs in conventional and germ-free mice and not in TLR5KO is consistent with reports of flagellin-TLR5 interactions promoting $CD4^+CD25^+Foxp3^+$ regulatory Tcells (Crellin et al. 2005, Hossain et al. 2011). Similarly, the ability of a flagellin-ovalbumin fusion protein to suppress IL-4 production by OVA-T-cell receptor CD4(+) Tcells via an IL-10 dependent mechanism has recently been described (Schulke et al. 2011) indicating that flagellin can influence the directional differentiation of T cell subsets. In addition, the impact of the TLR5KO on T cells responses driven by *R. hominis* infers that RH1 (the signalling flagellin) was crucial in mediating the Treg responses and not RH2 (the non-signaling flagellin). Finally, an additional observation was the enhancement of Type I IFN genes in TLR5KO mice (including Ifi202b, Ifi203 and Irf4), which suggests that TLR5 signalling may dampen Type I interferon responses.

Figure 7A:
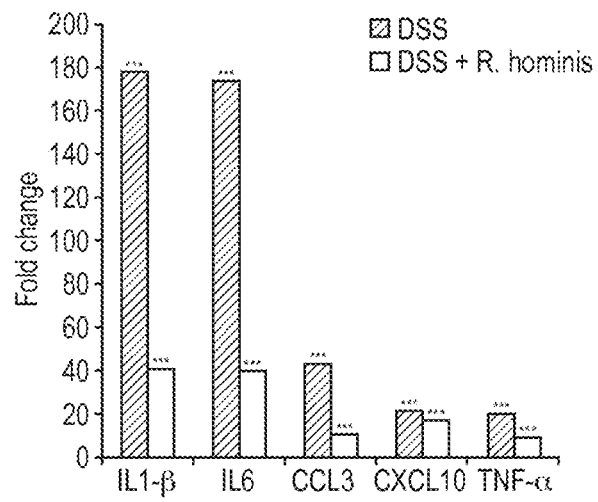
Figure 7B:
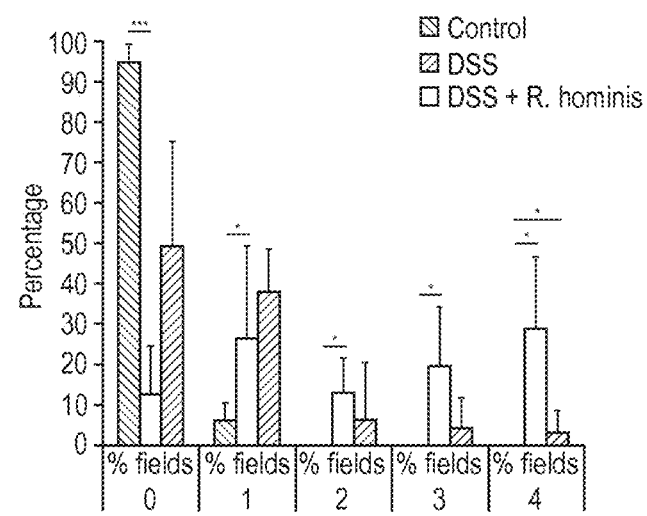
Figure 7C:
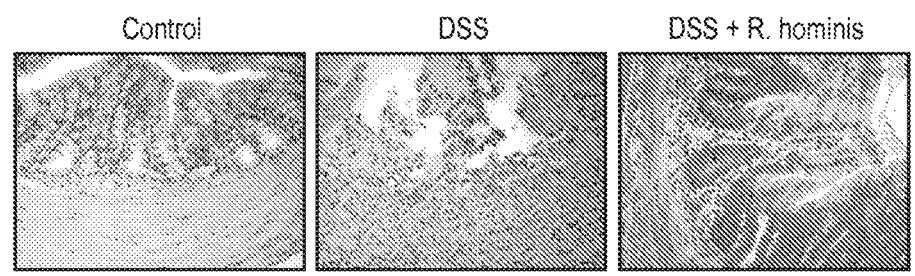

*R. hominis* Modulates Innate Immune Response Genes in Both the Ileum and Colon and Attenuates Colitis in DSS-Treated Mice The DSS mouse model was used to test the therapeutic efficacy of *R. hominis*, due to the control of inflammatory pathways as well as the positive effects on Treg induction in mono-associated mice. Mice were dosed (.about.50 µL, $10.\sup 9$ CFU) daily for a period of 14 days, and given DSS (MW 50 kDa, 30 g/l) in their drinking water from day 8 onwards. Gene expression of a panel of pro-inflammatory biomarkers showed that untreated DSS mice had strong elevation of all investigated genes compared to wild-type mice, with gene induction ranging from 4- to 49-fold (FIG. 7A). Pro-inflammatory gene induction was significantly lower in *R. hominis*-treated compared to untreated mice, indicating strong therapeutic benefits of oral administration of *R. hominis*. Histological analysis showed the presence of severe inflammation in the ascending colon of untreated DSS, while the colonic mucosa of *R. hominis*-treated animals was normal, with low-level inflammation, consistent with the reduced inflammatory gene expression (FIGS. 7B and C).

*R. hominis* Colonization Influences Body Composition and Expression of Satiety Genes Significant metabolic actions of *R. hominis* in mono-associated mice were also evident. The GO-processes 'negative regulation of response to food' (GO:0032096), 'negative regulation of appetite' (GO:0032099), and 'regulation of catecholamine secretion' (GO:0050433) were all down-regulated in the ascending colon after colonization with *R. hominis* (FIGS. 12A-J). This data infers that *R. hominis* exerts a stimulatory effect on host appetite. The genes involved in these processes were Agt, Cartpt, Cck and Cxcl12, with fold-changes ranging from 2- to 12-fold. Cck, in particular, plays a major role in digestion and satiety as a hunger suppressant. Gcg also showed down-regulation at this gut site.

Figure 13A:
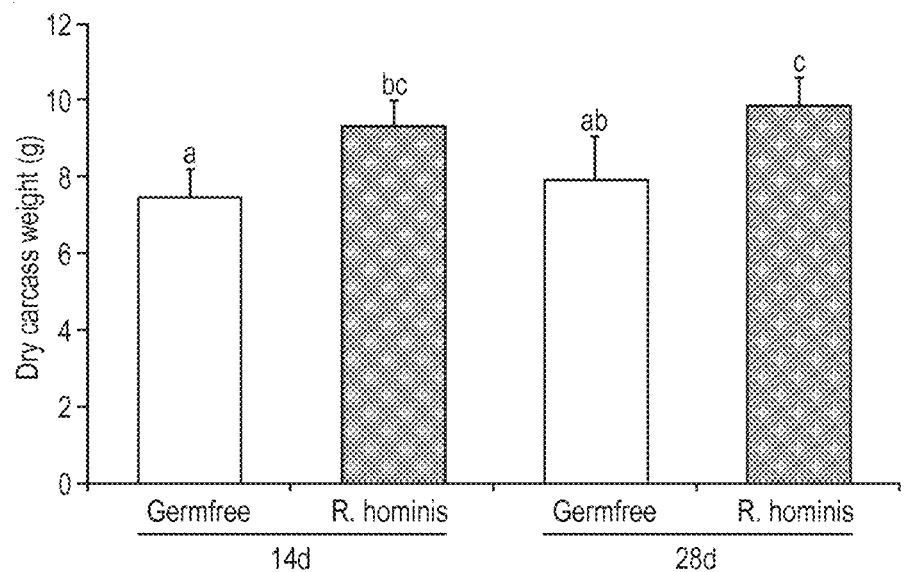
Figure 13B:
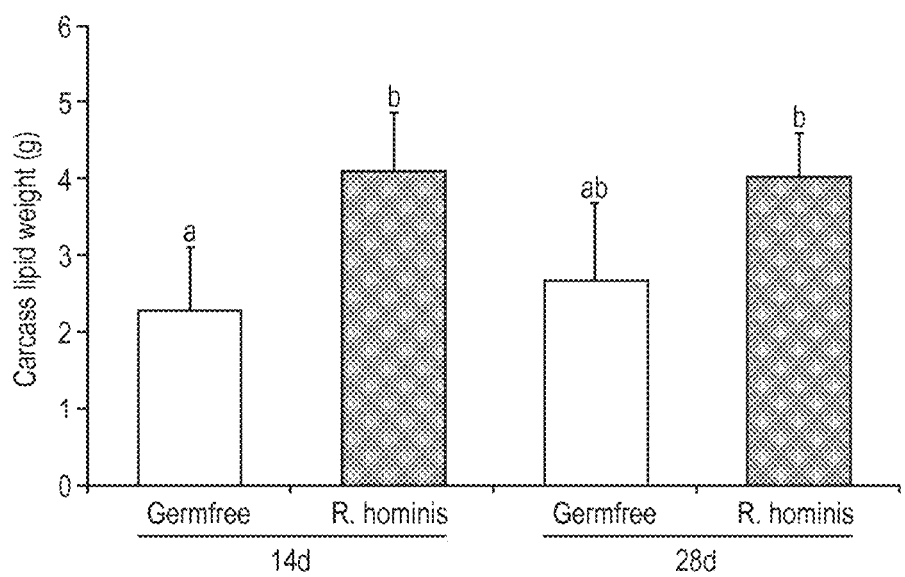

To establish whether these gene changes had physiological relevance in relation to food intake and body composition, dry carcass weight and composition analyses were performed. The dry carcass weights of *R. hominis*-associated mice were significantly heavier compared to GF animals, and the differences were most discernible at 14 d (FIG. 13A). Further carcass lipid analysis showed that total adiposity was also significantly higher in *R. hominis*-treated animals at 14 d (FIG. 13B). These findings are consistent with recent data revealing the role of Firmicutes in energy harvest through dietary fermentation, but also support the notion that gut bacteria can in fact modulate the brain-gut axis and appetite-regulating hormones.

Discussion

The long-term co-evolution of host-microbe mutualism has likely driven the selection of functionally important bacterial species in the gut, the majority of which are not highly represented in other ecosystems. Currently, there is limited information regarding the contribution of individual members of the microbial community to intestinal functions, particularly in relation to development of the mucosal immune system.

Recent work using a reversible colonization model based on *E. coli* (HA 107) has demonstrated that live bacteria are required in numbers approaching $10.\sup 8$ CFUs per gram of content for the immune-inducing effects on IgA (Hapfelmeier et al. 2010). The specific functions of SFB and *Bacteroides fragilis* have been investigated in the mouse gut to define their individual contributions to T cell biology and both these bacteria have been shown to be potent inducers of Tregs and Th17 cells (Mazmanian et al. 2005, Gaboriau-Routhiau et al. 2009, Ivanov et al. 2009). The effects of individual members of the cluster XIVa Firmicutes have not been reported previously, although their presence in the ASF and the contribution of a mixed culture of 46 Clostridial strains, which also affects T cell differentiation has been noted (Geuking et al. 2011, Atarashi et al. 2011).

Reported here is the first successful mono-association of the germ-free mouse gut with an anaerobic bacterium, *R. hominis*, which is a member of the Firmicutes phylum. The extreme oxygen sensitivity of bacteria like *Roseburia* requires strict anaerobic culture techniques, making it difficult to perform functional characterization. The stable mono-colonization of *R. hominis* in germfree mice has been established and the complete annotated genomic sequence to uncover its metabolic organization, physiology, and symbiotic properties has been produced. It was found that the transcriptional responses of *R. hominis* following colonization could be attributed to both the host gut environment and diet. The host-driven effects dominated the response of *R. hominis* following mono-association. These included gene transfer, membrane transport, chemotaxis and motility subsystems. The strong up-regulation of genes involved in mobilization transfer supports the view that the gut environment is highly conducive to horizontal gene exchange between members of the gut microbiota. Thus, this environment may accelerate the dissemination of genes important for bacterial survival, colonization and function within the gut ecosystem. The role of motility and flagellar apparatus in host colonization is well-elaborated for pathogenic bacteria but much less is known about the role of flagellar proteins in commensal bacteria. In vivo experiments revealed a stimulatory effect of the host intestinal environment on the expression of flagellin genes.

A clear role for *R. hominis* in promoting gut barrier function and innate immunity in the mouse colon has been established. Tight junctions, gap junctions and adherens junctions operate to limit bacterial translocation to the subepithelial layer (Werth et al. 2010). Both Crohn's disease and ulcerative colitis are characterized by loss of barrier function and tight junction integrity. Interestingly, dysbiosis of the gut microbiota in IBD is associated with a reduction in Firmicutes (Spor, Koren & Ley 2011, Qin et al. 2010). The observation herein that *R. hominis* actively enhances the expression of barrier genes suggests that theft loss in IBD patients may be functionally significant. Activation of tight junction complexes is not just the prerogative of *R. hominis*; other commensals, such as *Bacteroides* thetaiotaomicron and *Lactobacillus acidophilus*, also enhance mucosal barrier function (Hooper et al. 2001, Ukena et al. 2007), inferring probiotic opportunities with these bacteria in human IBD.

The effects of *R. hominis* on the gut immune system are intriguing. The strongest effects were noted in the ascending colon and genes such as Ly6g6c were strongly up-regulated, as well as pathways involved in T cell regulation and differentiation and actin polymerization at the immune synapse, which are implicated in T cell activation and effector functions. The most affected T cell pathways included those related to IL-10, ICOS and CTLA-4, which are all involved in supporting Treg differentiation. Importantly, it has been demonstrated that significant increases in CD3+CD4+ CD25+FoxP3+ cells in the colons of germ-free mice and conventional mice colonized with *R. hominis* using both flow cytometry and immunocytochemistry. These findings complement the recent data on other *Clostridium* species that drive Treg differentiation. Clearly, *R. hominis* can as a single bacterial species promote mucosal T cell expansion and impact on T cell differentiation.

Flagellin signals are perceived by host TLR5 receptors and many pathogenic flagellin structures induce strong pro-inflammatory responses (Hayashi et al. 2001). Signalling through TLR5 in response to resident flagellated commensals may be important for homeostasis, since deletion of TLR5 results in spontaneous colitis in mice (Vijay-Kumar et al. 2007). The enhanced expression of R. hominis flagellin FlaA1 (RH1) in vivo and its potency in activating epithelial cells and BMDCs is of great interest. Other work has shown that E. coli flagellin mutants have a colonization advantage over wild-type flagellated strains, possibly due to absence of innate recognition by TLR5 signalling (De Paepe et al. 2011, Giraud et al. 2008). Herein it is shown that for certain Firmicutes, the expression or possibly up-regulation of flagellin is a natural response to gut colonization. R. hominis flagellin protein remains expressed in vivo and correlates with sustained colonization, absence of overt inflammation and expansion of T cells of regulatory phenotype. The recent confirmation of flagellin genes in SFB (Prakash et al. 2011, Sczesnak et al. 2011) may correlate with the host T cell responses induced by this bacterium (Gaboriau-Routhiau et al. 2009, Ivanov et al. 2009). Interestingly, RH1 induced a unique effect on both epithelial and DC cultures compared to other flagellins, although all tested structures possess the conserved Arg90 associated with flagellins that bind and activate TLR5 (Yoon et al. 2012) suggesting that other sequence/structural differences may account for the unique signalling responses mediated by RH1. The significance of flagellin-TLR5 signalling in Treg responses induced by R. hominis was confirmed using TLR5KO. Without wishing to be bound by theory, certain commensal flagellin structures may help to direct immune tolerance responses through TLR5 expressed on either CD103+DC or Treg subsets (Flores-Langarica et al. 2012, Kinnebrew et al. 2012, Crellin et al. 2005). Furthermore, the immune homeostatic effect of R. hominis was confirmed in DSS-treated mice, although other signalling moieties, such as butyrate, may also contribute to immune tolerance. This data suggests a potential therapeutic benefit of R. hominis in IBD.

An interesting additional biological effect of R. hominis colonization was the regulation of genes influencing responses to food and control of appetite. In particular, the satiety hormones Cck and Gcg were significantly reduced. The effects of Cck on food intake are mediated via a vagal afferent pathway. This is the major neural pathway by which information about ingested nutrients reaches the central nervous system to influence both gut function and feeding behaviour. Cck acts on the vagal system to decrease expression of molecules that stimulate appetite and feeding, and to increase expression of molecules that inhibit feeding and decrease appetite (Npy2r and Cartpt, both down-regulated two-fold in the current study). No link between Cck, Gcg and commensal bacteria has been reported thus far, however, both fatty acids and proteins are potent inducers of Cck and Gcg (Geraedts et al. 2010). R. hominis produces short-chain fatty acids such as butyrate with aliphatic tails of less than six carbons; this metabolic activity has been reported to reduce the stimulatory effect on plasma Cck observed with longer chain fatty acids (McLaughlin et al. 1999). Carcass weight analysis revealed that both body weight and lipid content was indeed significantly increased with R. hominis, consistent with body weight increases observed in conventionalization of germfree mice (Turnbaugh et al. 2006). Whether this is a direct effect of a reduction in satiety hormones as seen in the current study remains to be seen, as the involvement of Cck and Gcg has not been reported previously. However, it is important to acknowledge that a link between microbiota colonization and energy harvest from the diet, in part through release of SCFAs, has been shown previously (Turnbaugh et al. 2006) (Tremaroli, Kovatcheva-Datchary & Backhed 2010). Given that R. hominis is a major butyrate producer, this mechanism is likely also to contribute to the metabolic efficiency observed following R. hominis treatment.

In summary, mono-association of the murine gut with R. hominis induced strong bi-directional gene expression events culminating in commensal bacterial adaptation and host tolerance. The flagellin product RH1 seems to exert a unique signaling effect, which preferentially drives expansion of Tregs. The importance of TLR5 in directing Treg differentiation and expansion has been demonstrated. Collectively, this data highlights additional functionality of commensal flagellins, TLR5 signaling and the net direction of the mucosal T cell response.

Functional Assays
In Vitro Model
Analysis of the Response of Intestinal Epithelial Cells (IECs) to Different Recombinant Flagellins Molecular analysis of CCL20 gene expression (a pro-inflammatory gene) after stimulation of IECs to different recombinant flagellins (FIG. 23) pathogenic flagellins (SE, ST, LF, and HM) induced similar but not identical levels of CCL20 mRNA, commensal flagellins displayed much more variable levels of induction. ER (Eubacterium rectale 33656), K12 (Escherichia coli K12), RH1 and RI3 flagellins induced CCL20 at similar levels to pathogenic flagellins, RI1 and RI4 had intermediate stimulatory activity, RH2 revealed as a low inducer of CCL20 in HT-29 and was devoid of agonistic potential in Caco-2 cells, and RI2 had no observable activity in both cell lines. In conclusion, the inventors distinguished three categories of TLR5 agonists (i) those with no or very low immunostimulatory activity, (ii) those with intermediate immunostimulatory activity and (iii) those with high immunostimulatory activity.

FIG. 28 indicates significant differences between each treatment calculated with paired t test in HT-29 (upper right) and Caco-2 (lower left). T tests used were unilateral to compare treatments to unstimulated cells (unstim) and bilateral to compare one treatment with another. NS (non significant); *($p<0.05$); ($p<0.01$); *($p<0.001$).

Cellular and immunological analysis of the effects of the recombinant flagellins on the IECs was determined by measurement of cytokines, CXCL8, CXCL10 and CCL2 (MCP-1) secreted. IECS were stimulated for 24 hrs with recombinant flagellins (FIG. 24).

The flagellins ST, SE, K12, ER, RI3 and RH1 induced the secretion of variable but similar levels of IL-8, IP-10 and MCP-1 chemokines, while RI1, RI2, RI4 and RH2, especially in Caco-2 behaved as low agonists of TLR5, inducing significantly lower amounts of secreted chemokines.

FIGS. 29A-29D indicate significant differences between each treatment calculated with paired t test. The upper right side of FIGS. 29A and 29B give t values for IL-8 and the lower left side for IP-10, and FIGS. 29C and 29D give t values for MCP-1. NS (non significant); *($p<0.05$); ($p<0.01$); *($p<0.001$).

As shown in FIG. 25, neutralization of TLR5 with an anti-TLR5 specific antibody abolished the flagellin-mediated inflammatory response, independent of the commensal or pathogenic origin of flagellin. Therefore, the pro-inflammatory effects of flagellin observed in Caco-2 cells are dependent on TLR5 activation.

Generation of Bone Marrow-Derived Dendritic Cells and Cultures

Bone marrow was harvested from femur and tibia of C3H/HeN and C57B16 mice. For GMCSF-derived dendritic cells, bone marrow cells were resuspended at $.\text{times}.10.\text{sup}.6/\text{mL}$ in RPMI supplemented with 10% FCS and 20 ng/mL rmGM-CSF and seeded at 10 mL plate in 100 mm.sup.2 tissue culture plates. After three days culture, loosely adherent cells were collected and replated with GM-CSF supplemented media at $.\text{times}.10.\text{sup}.6/\text{mL}$ in 12 well tissue culture plates. At day 5, cells were stimulated with 100 ng/mL flagellins before being harvested on day 6. For Flt3L-derived dendritic cells, bone marrow cells were resuspended at $2.\text{times}.10.\text{sup}.6/\text{mL}$ in RPMI supplemented with 10% FCS and 200 ng/mL rmFlt3 and seeded at 2 mL/well in 12-well tissue culture plates. Cells were cultured for 10 days with Flt3 supplemented media added to each well on day 4. At day 9, cells were stimulated with 100 ng/mL flagellins before being harvested on day 10 and analyzed by flow cytometry.

Figure 27B:
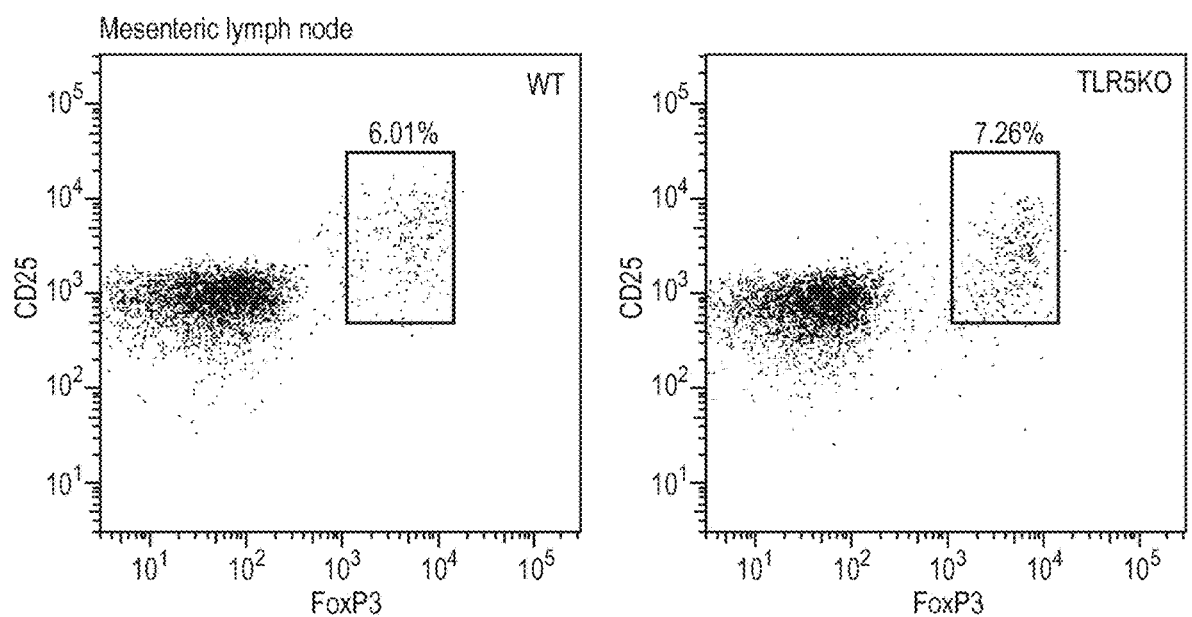

Flow Cytometry Analysis of GM-CSF/IL-4 derived dendritic cells (FIG. 26) and Flt3L derived dendritic cells (FIG. 27) stimulated with recombinant flagellins was carried out. Flagellin Rh1 was most potent at inducing cellular response in GM-CSF/IL-4 derived dendritic cells with Ri4 and Ri3 having a similar response to commensal flagellins K12 and Er and pathogenic flagellins SE and ST. In contrast Rh2, and Ri2 did not induce cellular response with the GM-CSF/IL-4 derived dendritic cells but significantly increase cellular responses to Flt3L derived dendritic cells. These flagellins and in particular Ri1, are distinctive in their ability to elicit difference in responses with the activation of Flt3L-derived dendritic cells. This response signifies the specificity of the flagellins to a specific subset of dendritic cells. These Flt3L derived dendritic cells are categorised as plasmocytoid dendritic cells which play an important role in immunological tolerance.

In Vivo Model

BOY/J WT and TLR5KO mice were used to evaluate the functional importance of R. hominis and its flagellins. The mice were colonised with R. hominis. The animals were euthanized and intestinal tissue sampling was performed. Small intestine was collected for immunological analysis by flow cytometry.

Flow cytometry analysis of T cell populations, in particular, T regulatory (Treg) cells, in small intestine lamina propria was carried out (FIGS. 6 A and B). The percentage of FoxP3+CD25+ cells in CD4+ T cell population was significantly higher in the BOY/J WT mice in comparison to the TLR5KO mice. This indicates that R. hominis and more specifically the flagellins influences T regs by promoting CD4+FoxP3+CD25+ regulatory T cells Therefore it can be concluded that flagellins are important in directing host immune response through TLR5 interactions.

Summary Clauses

The present invention is defined in the claims and the accompanying description. For convenience other aspects of the present invention are presented herein by way of numbered clauses.

1. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/ or a polynucleotide encoding said *Roseburia* flagellin, and/ or a vector comprising said polynucleotide sequence, and/or a host cell comprising said vector, and/or a host cell comprising said polynucleotide sequence, for use in regulating the immune system of a subject.

2. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, according to clause 1 for use in regulating the adaptive immune system of a subject.

3. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, according to clause 1 for use in regulating the innate immune system of a subject.

4. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/ or the polynucleotide encoding said *Roseburia* flagellin, and/or a vector comprising said polynucleotide sequence, and/or a host cell comprising said vector, and/or a host cell comprising said polynucleotide sequence, for use in maintaining immune homeostasis in a subject.

5. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/ or a polynucleotide encoding said *Roseburia* flagellin, and/ or a vector comprising said polynucleotide sequence, and/or a host cell comprising said vector, and/or a host cell comprising said polynucleotide sequence, for use in treating an immune disorder in a subject.

6. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to clause 5, wherein the immune disorder is selected from ulcerative colitis, pouchitis, other autoimmune conditions including rheumatoid arthritis, psoriasis, multiple sclerosis, allergies including coeliac disease, atopic dermatitis and rhinitis.

7. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/ or a polynucleotide encoding said *Roseburia* flagellin, and/ or a vector comprising said polynucleotide sequence, and/or a host cell comprising said vector, and/or a host cell comprising said polynucleotide sequence, for use in treating a disorder selected from an inflammatory disorder, an immune disorder and an intestinal disorder in a subject.

8. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to clause 7, wherein the disorder is selected from irritable bowel syndrome (IBS), colitis, inflammatory bowel disorder (IBD), including Crohn's disease and ulcerative colitis, pouchitis, functional dyspepsia, functional constipation, functional diarrhoea (including antibiotic associated diarrhoea, traveller's diarrhoea and pediatric diarrhoea), functional abdominal pain, functional bloating, Epigastric Pain Syndrome, Postprandial Distress Syndrome, gastrointestinal reflux disease (GERD), autoimmune diseases such as diabetes, arthritis, multiple sclerosis and psoriasis allergies, atopic diseases e.g. atopic dermatitis, necrotising enterocolitis, other infections, and combinations thereof.

9. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, for use in improving intestinal microbiota in a subject.

10. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, for use in regulating appetite in a subject.

11. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, for use in promoting gut health in a subject.

12. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, for use in promoting Tregs cells and tolerance mechanisms in the immune system of a subject.

13. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to any one of clauses 1 to 12, which regulates the induction and/or expression of at least one mobilization or chemotaxis gene.

14. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to clause 13, which upregulates the expression of at least one mobilization or chemotaxis gene, and wherein said gene is selected from MobA and MobL.

15. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to any preceding clause, which regulates at least one gene selected from FlaA1, Fla2, FlaA3, and FlaB.

16. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to any preceding clause, which regulates the expression of at least one of the following: acetyl-CoA acetyltransferase, 3-hydroxyacyl-CoA dehydrogenase, butyryl-CoA dehydrogenase, electron transfer flavoprotein beta subunit, electron transfer flavoprotein alpha subunit.

17. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to any preceding clause, which downregulates the expression of at least one gene selected from Agt, Cartpt, Cck, Cxcl12 and Gcg.

18. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to any preceding clause, which activates at least one immune response gene in the colon or ileum.

19. *Roseburia* (such as the bacterial species *Roseburia hominis*, or the bacterial species *Roseburia intestinalis*), and/or the polypeptide FlaA1 and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to any preceding clause, which activates the adaptive immune response by regulating the induction and/or expression of genes associated with T-cell regulation.

20. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to any preceding clause which upregulates expression of at least one gene selected from Ly6g6c and Ly6g6e in the ascending colon.

21. *Roseburia* (such as the bacterial species *Roseburia hominis*, or the bacterial species *Roseburia intestinalis*), and/or the polypeptide FlaA1 and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, for use according to any preceding clause which regulates the expression of at least one gene selected from Tlr5, Tlr1, Vnn1, Defb37, Pla2g, Muc16, Inn, Sprr1a, Cldn4, Pmp22, Crb3, Magi3, Marveld3, Mpp7, Defcr20, Pcgf2, Ltbp4, Igsf8 and Tcfe2a.

22. Use of *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, in the preparation of a medicament for regulating the immune system of a subject.

23. Use of *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, according to clause 22 in the preparation of a medicament for regulating the innate immune system of a subject.

24. Use of *Roseburia* (such as a bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or the polynucleotide encoding said *Roseburia* flagellin, and/or the vector, and/or the host cell comprising said vector, and/or the host cell comprising said polynucleotide sequence, according to clause 22 in the preparation of a medicament for regulating the adaptive immune system of a subject.

25. Use of *Roseburia* (such as the bacterial species *Roseburia hominis*, or the bacterial species *Roseburia intestinalis*), and/or a polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, in the preparation of a medicament for maintaining immune homeostasis in a subject.

26. Use of *Roseburia* (such as the bacterial species *Roseburia hominis*, or the bacterial species *Roseburia intestinalis*), and/or polypeptide FlaA1 and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, in the preparation of a medicament for treating an immune disorder in a subject.

27. A method of regulating the immune system of a subject, said method comprising administering to the subject a composition comprising *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence.

28. A method of activating the innate immune system of a subject, said method comprising administering to the subject a composition comprising *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence.

29. A method of activating the adaptive immune system of a subject, said method comprising administering to the subject a composition comprising *Roseburia* (such as the bacterial species *Roseburia hominis*, or the bacterial species *Roseburia intestinalis*), and/or polypeptide FlaA1 and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence.

30. A method of treating an immune disorder in a subject, said method comprising administering to the subject a pharmaceutically effective amount of *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence.

31. *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or a polynucleotide encoding said *Roseburia* flagellin, and/or the vector, and/or the host cell comprising said vector, and/or the host cell comprising said polynucleotide sequence for use according to any one of clauses 1 to 21, or a method according to any one of clauses 27 to 30, or a use according to any one of clauses 22 to 26, wherein the subject is a mammal.

32. *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, for use in medicine.

33. A pharmaceutical composition comprising *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, and a pharmaceutically acceptable excipient, carrier or diluent.

34. A nutritional supplement comprising *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence, and a nutritionally acceptable excipient, carrier or diluent.

35. A probiotic composition comprising *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence.

36. A feedstuff, food product, dietary supplement, nutritional supplement or food additive comprising *Roseburia* (such as the bacterial species *Roseburia hominis*, or the bacterial species *Roseburia intestinalis*), and/or polypeptide FlaA1, and/or a polynucleotide sequence encoding said polypeptide, and/or *Roseburia* flagellin, and/or a polynucleotide encoding said *Roseburia* flagellin, and/or a vector comprising said polynucleotide sequence, and/or a host cell comprising said vector, and/or a host cell comprising said polynucleotide sequence.

37. A process for producing a pharmaceutical composition according to clause 32, said process comprising admixing *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or a polynucleotide encoding said *Roseburia* flagellin, and/or the vector, and/or the host cell comprising said vector, and/or the host cell comprising said polynucleotide sequence, with a pharmaceutically acceptable excipient, carrier or diluent.

38. A process for producing a nutritional supplement according to clause 33, said process comprising admixing *Roseburia* (such as the bacterial species *Roseburia hominis*, or the bacterial species *Roseburia intestinalis*), and/or the polypeptide FlaA1, and/or the polynucleotide sequence encoding said polypeptide, and/or *Roseburia* flagellin, and/or a polynucleotide encoding said *Roseburia* flagellin, and/or the vector, and/or the host cell comprising said vector, and/or the host cell comprising said polynucleotide sequence, with a nutritionally acceptable excipient, carrier or diluent.

Summary Paragraphs

For convenience other aspects of the present invention are presented herein by way of numbered paragraphs.

1. Polypeptide FlaA1 or a polynucleotide sequence encoding said polypeptide for use in modulating the inflammation of a tissue or an organ in a subject.

2. The polypeptide or the polynucleotide according to paragraph 1 wherein said polypeptide or polynucleotide reduces the inflammation of the tissue or the organ.

3. The polypeptide or the polynucleotide according to paragraph 2 wherein said polypeptide or polynucleotide reduces the inflammation by epithelial cells of the tissue or the organ.

4. The polypeptide or the polynucleotide according to paragraph 3 wherein said epithelial cells are epithelial cells of the alimentary canal.

5. Polypeptide FlaA1 or a polynucleotide sequence encoding said polypeptide for use in modulating the production of T cells in a subject; preferably, the polypeptide or the polynucleotide increases the production of T regulatory cells in a subject.

6. Polypeptide FlaA1 or a polynucleotide sequence encoding said polypeptide for use in restoring immunological tolerance.

7. Polypeptide FlaA1 or a polynucleotide sequence encoding said polypeptide for use in regulating the immune system and restoring immunological tolerance of a subject.

8. The polypeptide or the polynucleotide according to paragraph 7 for use in regulating the adaptive immune system of a subject.

9. The polypeptide or the polynucleotide according to paragraph 7 for use in regulating the innate immune system of a subject.

10. Polypeptide FlaA1 or a polynucleotide sequence encoding said polypeptide for use in treating a disorder in a subject, wherein said disorder is an inflammatory disorder and/or an autoimmune disorder.

11. The polypeptide or the polynucleotide according to paragraph 10 wherein said disorder affects the alimentary canal or a section thereof of said subject.

12. The polypeptide or the polynucleotide according to paragraph 10 wherein said disorder is selected from the group consisting of rheumatoid arthritis, psoriasis, multiple sclerosis, type I diabetes, coeliac disease, atopic dermatitis, rhinitis, irritable bowel syndrome (IBS), colitis, inflammatory bowel disorder (IBD), ulcerative colitis, pouchitis, Crohn's disease, functional dyspepsia, atopic diseases, necrotising enterocolitis, and combinations thereof.

13. Polypeptide FlaA1 or a polynucleotide sequence encoding said polypeptide for use in modulating dendritic cells and/or epithelial cells in a tissue or an organ of a subject.

14. The polypeptide or the polynucleotide according to paragraph 13 wherein said polypeptide or polynucleotide activates dendritic cells and/or epithelial cells.

15. Polypeptide FlaA1 or a polynucleotide sequence encoding said polypeptide for use in regulating the production of IL-10 and/or TGFβ in a cell or cells of a subject.

16. The polypeptide or the polynucleotide according to paragraph 15 wherein the production of IL-10 is by dendritic cells.

17. The polypeptide or the polynucleotide according to paragraph 15 or 16 wherein said polypeptide or polynucleotide upregulates the production of IL-10 and/or TGFβ.

18. Polypeptide FlaA1 or a polynucleotide sequence encoding said polypeptide for use in regulating the production of CD40 and/or I-A/I-E in a cell or cells of a subject.

19. The polypeptide or the polynucleotide according to paragraph 18 wherein the production of CD40 and/or I-A/I-E is by dendritic cells.

20. The polypeptide or the polynucleotide according to paragraph 18 or 19 wherein said polypeptide or polynucleotide upregulates the production CD40 and/or I-A/I-E.

21. Polypeptide FlaA1 or a polynucleotide sequence encoding said polypeptide for use in regulating the expression of one or more Type I IFN genes in a cell or cells of a subject.

22. Polypeptide FlaA1 or a polynucleotide sequence encoding said polypeptide for use in regulating the expression of one or more pro-inflammatory genes in a cell or cells of a subject.

23. Polypeptide FlaA1 or a polynucleotide sequence encoding said polypeptide for use in improving intestinal microbiota in a subject.

24. Polypeptide FlaA1 or a polynucleotide sequence encoding said polypeptide for use in regulating appetite in a subject.

25. The polypeptide or polynucleotide according to paragraph 24 wherein said polypeptide or polynucleotide stimulates the appetite in the subject.

26. The polypeptide or polynucleotide according to paragraph 24 or 25 wherein the level of cholecystokinin (Cck) and/or glucagon (Gcg) is reduced in the blood of a subject.

27. Polypeptide FlaA1 or a polynucleotide sequence encoding said polypeptide for use in regulating the expression of the gene encoding cholecystokinin (Cck) and/or the expression of the gene encoding glucagon (Gcg) in a cell or cells of a subject.

28. Polypeptide FlaA1 or a polynucleotide sequence encoding said polypeptide for use in improving alimentary canal health in a subject.

29. The polypeptide or polynucleotide according to any one of paragraphs I to 28 wherein said polypeptide or polynucleotide is encapsulated.

30. A pharmaceutical composition comprising polypeptide FlaA1 or a polynucleotide sequence encoding said polypeptide and a pharmaceutically acceptable excipient, carrier or diluent.

31. The pharmaceutical composition according to paragraph 30 wherein said polypeptide or polynucleotide is encapsulated.

32. A nutritional supplement comprising polypeptide FlaA1 or a polynucleotide sequence encoding said polypeptide and a nutritional acceptable excipient, carrier or diluent.

33. The nutritional supplement according to paragraph 32 wherein said polypeptide or polynucleotide is encapsulated.

34. A feedstuff, food product, dietary supplement, or food additive comprising polypeptide FlaA1 or a polynucleotide sequence encoding said polypeptide.

35. The feedstuff, food product, dietary supplement, or food additive according to paragraph 34 wherein said feedstuff, food product, dietary supplement, or food additive is encapsulated.

36. A process for producing a pharmaceutical composition according to paragraph 30, said process comprising admixing said polypeptide or polynucleotide with a pharmaceutically acceptable excipient, carrier or diluent; optionally said polypeptide or polynucleotide is encapsulated.

37. A process for producing a nutritional supplement according to paragraph 32, said process comprising admixing said polypeptide or polynucleotide with a nutritionally acceptable excipient, carrier or diluent; optionally said polypeptide or polynucleotide is encapsulated.

38. A method of modulating the inflammation of a tissue or an organ in a subject, said method comprising administering to the subject polypeptide FlaA1 or a polynucleotide sequence encoding said polypeptide, and wherein the inflammation of the tissue or organ in the subject is modulated.

39. A method of modulating the production of T cells in a subject, said method comprising administering polypeptide FlaA1 or a polynucleotide sequence encoding said polypeptide, and wherein the production of T cells in the subject is modulated, in particular T regulatory cells.

40. A method of regulating the immune system of a subject, said method comprising administering polypeptide FlaA1 or a polynucleotide sequence encoding said polypeptide, and wherein the immune system of the subject is regulated.

41. A method of treating a disorder in a subject, said method comprising administering polypeptide FlaA1 or a polynucleotide sequence encoding said polypeptide, wherein said disorder is an inflammatory disorder and/or an autoimmune disorder.

42. A method of modulating dendritic cells and/or epithelial cells in a subject, said method comprising administering polypeptide FlaA1 or a polynucleotide sequence encoding said polypeptide, and wherein dendritic cells and/or epithelial cells in the subject are modulated.

43. A method of regulating the production of IL-10 and/or TGFβ in a cell or cells of a subject, said method comprising administering polypeptide FlaA1 or a polynucleotide sequence encoding said polypeptide to the subject, and wherein the production of IL-10 and/or TGFβ in a cell or cells of the subject is regulated.

44. A method of regulating the production of CD40 and/or I-A/I-E in a cell or cells of a subject, said method comprising administering polypeptide FlaA1 or a polynucleotide sequence encoding said polypeptide to the subject, and wherein the production of CD40 and/or I-A/I-E in a cell or cells of the subject is regulated.

45. A method of regulating the expression of one of more Type I IFN genes in a cell or cells of a subject, said method comprising administering polypeptide FlaA1 or a polynucleotide sequence encoding said polypeptide wherein the expression of one of more Type I IFN genes in a cell or cells of the subject is regulated.

46. A method of regulating the expression of one or more pro-inflammatory genes in a cell or cells of a subject, said method comprising administering polypeptide FlaA1 or a polynucleotide sequence encoding said polypeptide, wherein the expression of one or more pro-inflammatory genes in a cell or cells of the subject is regulated.

47. A method of improving intestinal microbiota in a subject, said method comprising administering polypeptide FlaA1 or a polynucleotide sequence encoding said polypeptide and wherein the intestinal microbiota in a subject is improved.

48. A method of regulating appetite in a subject, said method comprising administering polypeptide FlaA1 or a polynucleotide sequence encoding said polypeptide and wherein the appetite in the subject is regulated.

49. A method of regulating the expression of the gene encoding cholecystokinin (Cck) and/or the expression of the gene encoding glucagon (Gcg) in a cell or cells of a subject, said method comprising administering polypeptide FlaA1 or a polynucleotide sequence encoding said polypeptide and wherein the expression of the gene encoding cholecystokinin (Cck) and/or the expression of the gene encoding glucagon (Gcg) in a cell or cells of the subject is regulated.

50. A method of improving alimentary canal health in a subject, said method comprising administering polypeptide FlaA1 or a polynucleotide sequence encoding said polypeptide, and wherein alimentary canal health in a subject is improved.

51. Use of polypeptide FlaA1 or a polynucleotide sequence encoding said polypeptide for the manufacture of a medicament for modulating the inflammation of a tissue or an organ in a subject.

52. Use of polypeptide FlaA1 or a polynucleotide sequence encoding said polypeptide for the manufacture of a medicament for modulating the production of T cells in a subject.

53. Use of polypeptide FlaA1 or a polynucleotide sequence encoding said polypeptide for the manufacture of a medicament for regulating the immune system of a subject.

54. Use of polypeptide FlaA1 or a polynucleotide sequence encoding said polypeptide for the manufacture of a medicament for the treatment of a disorder in a subject, wherein said disorder is an inflammatory disorder and/or an autoimmune disorder.

55. Use of polypeptide FlaA1 or a polynucleotide sequence encoding said polypeptide for the manufacture of a medicament for modulating dendritic cells and/or epithelial cells in a tissue or an organ of a subject.

56. Use of polypeptide FlaA1 or a polynucleotide sequence encoding said polypeptide for the manufacture of a medicament for regulating the production of IL-10 and/or TGFβ in a cell or cells of a subject.

57. Use of polypeptide FlaA1 or a polynucleotide sequence encoding said polypeptide for the manufacture of a medicament for regulating the production of CD40 and/or I-A/I-E in a cell or cells of a subject.

58. Use of polypeptide FlaA1 or a polynucleotide sequence encoding said polypeptide for the manufacture of a medicament for regulating the expression of one of more Type I IFN genes in a cell or cells of a subject.

59. Use of polypeptide FlaA1 or a polynucleotide sequence encoding said polypeptide for the manufacture of a medicament for regulating the expression of one or more pro-inflammatory genes in a cell or cells of a subject.

60. Use of polypeptide FlaA1 or a polynucleotide sequence encoding said polypeptide for the manufacture of a medicament for improving intestinal microbiota in a subject.

61. Use of polypeptide FlaA1 or a polynucleotide sequence encoding said polypeptide for the manufacture of a medicament for regulating appetite in a subject.

62. Use of polypeptide FlaA1 or a polynucleotide sequence encoding said polypeptide for the manufacture of a medicament for regulating the expression of the gene encoding cholecystokinin (Cck) and/or the expression of the gene encoding glucagon (Gcg) in a cell or cells of a subject.

63. Use of polypeptide FlaA1 or a polynucleotide sequence encoding said polypeptide for the manufacture of a medicament for improving alimentary canal health in a subject.

64. Use of polypeptide FlaA1 or a polynucleotide sequence encoding said polypeptide for the manufacture of a medicament for restoring immunological tolerance in a subject.

65. A method of restoring immunological tolerance in a subject, said method comprising administering polypeptide FlaA1 or a polynucleotide sequence encoding said polypeptide and wherein the immunological tolerance in a subject is restored.

REFERENCES

Aminov, R. I., Walker, A. W., Duncan, S. H., Harmsen, H. J., Welling, G. W. & Flint, H. J. 2006, "Molecular diversity, cultivation, and improved detection by fluorescent in situ hybridization of a dominant group of human gut bacteria related to *Roseburia* spp. or *Eubacterium rectale*", Applied and Environmental Microbiology, vol. 72, no. 9, pp. 6371-6376.

Atarashi, K., Tanoue, T., Shima, T., Imaoka, A., Kuwahara, T., Momose, Y., Cheng, G., Yamasaki, S., Saito, T., Ohba, Y., Taniguchi, T., Takeda, K., Hori, S., Ivanov, I. I., Umesaki, Y., Itoh, K. & Honda, K. 2011, "Induction of colonic regulatory T cells by indigenous *Clostridium* species", Science (New York, N.Y.), vol. 331, no. 6015, pp. 337-341.

Berg, D. J., Davidson, N., Kuhn, R., Muller, W., Menon, S., Holland, G., Thompson-Snipes, L., Leach, M. W. & Rennick, D. 1996. "Enterocolitis and colon cancer in interleukin-10-deficient mice are associated with aberrant cytokine production and CD4(+) TH1-like responses", The Journal of clinical investigation, 98, no. 4, pp. 1010-1020.

Chung, H. & Kasper, D. L. 2010, "Microbiota-stimulated immune mechanisms to maintain gut homeostasis", Current opinion in immunology, vol. 22, no. 4, pp. 455-460.

Crellin, N. K., Garda, R. V., Hadisfar, O., Allan, S. E., Steiner, T. S. & Levings, M. K. 2005, "Human CD4+ T cells express TLR5 and its ligand flagellin enhances the suppressive capacity and expression of FOXP3 in CD4+ CD25+T regulatory cells", Journal of immunology (Baltimore. Md.: 1950), vol. 175, no. 12, pp. 8051-8059.

De Paepe, M., Gaboriau-Routhiau, V., Rainteau, D., Rakotobe, S., Taddei, F. & Ceri-Bensussan, N. 2011, "Trade-off between bile resistance and nutritional competence drives *Escherichia coli* diversification in the mouse gut", PLoS genetics, vol. 7, no. 6, pp. 0002107.

Duck, L. W., Walter, M. R., Novak, J., Kelly, D., Tomasi, M., Cong, Y. & Elson, C. O. 2007, "Isolation of flagellated bacteria implicated in Crohn's disease", Inflammatory bowel diseases, vol. 13, no. 10, pp. 1191-1201.

Duncan, S. H., Aminov, R. I., Scott, K. P., Louis, P., Stanton, T. B. & Flint, H. J. 2006, "Proposal of *Roseburia* faecis sp. nov., *Roseburia hominis* sp. nov. and *Roseburia inulinivorans* sp. nov., based on isolates from human faeces", International Journal of Systematic and Evolutionary Microbiology, vol. 56, no. Pt 10, pp. 2437-2441.

Eckburg, P. B., Bik, E. M., Bernstein, C. N., Purdom, E., Dethlefsen, L., Sargent, M., Gill, S. R., Nelson, K. E. & Reiman, D. A. 2005, "Diversity of the human intestinal microbial flora", Science (New York, N.Y.), vol. 308, no, 5728, pp. 1635-1638.

Flores-Langarica, A., Marshall, J. L., Hitchcock, J., Cook, C., Jobanputra, J., Bobat, S., Ross, E. A., Coughlan, R. E., Henderson, I. R., Uematsu, S., Akira, S. & Cunningham, A. F. 2012, "Systemic flagellin immunization stimulates mucosal CD103+ dendritic cells and drives Foxp3+ regulatory CELL and IgA responses in the mesenteric lymph node", Journal of immunology (Baltimore, Md.: 1950), vol. 189, no. 12, pp. 5745-5754.

Frank, D. N., St Amand, A. L., Feldman, R. A., Boedeker, E. C., Harpaz, N. & Pace, N. R. 2007, "Molecular-phylogenetic characterization of microbial community imbalances in human inflammatory bowel diseases", Proceedings of the National Academy of Sciences of the United States of America, vol. 104, no. 34, pp. 13780-13785.

Gaboriau-Routhiau, V., Rakotobe, S., Lecuyer, E., Mulder, I., Lan, A., Bridonneau, C., Rochet, V., Pisi, A., De Paepe, M., Brandi, G., Eberl, G., Snel, J., Kelly, D. Cerf-Bensussan, N. 2009, "The key role of segmented filamentous bacteria in the coordinated maturation of gut helper T cell responses", Immunity, vol. 31, no. 4, pp. 677-689.

Geraedts, M. C., Troost, F. J., Tinnemans, R., Soderholm, J. D., Brummer, R. J. & Saris, W. H. 2010, "Release of satiety hormones in response to specific dietary proteins is different between human and murine small intestinal mucosa", Annals of Nutrition & Metabolism, vol. 56, no. 4, pp. 308-313.

Geuking, M. P., Cahenzli, J., Lawson, M. A., Ng, D. C., Slack, E., Hapfelmeier, S., McCoy, K. D. & Macpherson, A. J. 2011, "Intestinal bacterial colonization induces mutualistic regulatory T call responses", Immunity, vol. 34, no. 5, pp. 794-806.

Giraud, A., Arous, S., De Paepe, M., Gaboriau-Routhiau, V., Bambou, J. C., Rakotobe, S., Lindner, A. B., Taddei, F. & Cert-Bensussan, N. 2008, "Dissecting the genetic components of adaptation of *Escherichia coli* to the mouse gut", PLoS genetics, vol. 4, no. 1, pp. e2.

Hapfelmeier, S., Lawson, M. A., Slack, E., Kirundi, J. K., Stoel, M., Heikenwalder, M., Cahenzii, J., Veiykoredko, Y., Balmer, M. L., Endt, K., Geuking, M. B., Curtiss, R., 3rd, McCoy, K. D. & Macpherson, A. J. 2010, "Reversible microbial colonization of germ-free mice reveals the dynamics of IgA immune responses", Science (New York, N.Y.), vol. 328, no. 5986, pp. 1705-1709.

Hayashi, F., Smith, K. D., Ozinsky, A., Hawn, T. R., Yi, E. C., Goodlett, D. R., Eng, J. K., Akira, S., Underhill, D. M. & Aderem, A. 2001, "The innate immune response to bacterial flagellin is mediated by Toll-like receptor 5", Nature, vol. 410, no. 6832, pp. 1099-1103.

Hooper, L. V., Wong, M. H., Thelin, A., Hansson, L., Falk, P. G. & Gordon, J. I., 2001, "Molecular analysis of commensal host-microbial relationships in the intestine", Science (New York, N.Y.), vol. 291 no. 5505, pp. 881-884, Hossain, M. S., Jaye, D. L., Pollack, B. P., Farris, A. B., Tselanyane, M. L., David, E., Roback, J. D., Gewirtz, A. T. & Waller, E. K. 2011, "Flagellin, a TLR5 agonist, reduces graft-versus-host disease in allogeneic hematopoietic stem cell transplantation recipients while enhancing antiviral immunity", Journal of immunology (Baltimore, Md., 1950), vol. 187, no. 10, pp. 5130-5140.

Ivanov, I.I., Atarashi, K., Manel, N., Brodie, E. L., Shima, T., Karaoz, U., Wei, D., Goldfarb, K. C., Santee, C. A., Lynch, S. V., Tanoue, T., Imaoka, A., Itoh, K., Takeda, K., Umesaki, Y., Honda, K. & Littman, D. R. 2009, "induction of intestinal Th17 cells by segmented filamentous bacteria", Cell, vol. 139, no. 3, pp. 485-498.

Kang, S., Denman, S. E., Morrison, M., Yu, Z., Dore, J., Leclerc, M. & McSweeney, C. S. 2010, "Dysbiosis of fecal microbiota in Crohn's disease patients as revealed by a custom phylogenetic microarray", Inflammatory bowel diseases, vol. 16, no. 12, pp. 2034-2042.

Kelly, D., Campbell, J. I., King, T. E., Grant, G., Jansson, E. A., Coutts, A. G., Pettersson, S. & Conway, S. 2004, "Commensal anaerobic gut bacteria attenuate inflammation by regulating nuclear-cytoplasmic shuttling of PPAR-gamma and RelA", Nature immunology, vol. 5, no. 1, pp. 104-112.

Kinnebrew, M. A., Butfie, C. G., Diehl, G. E., Zenewicz, L. A., Leiner, I., Hohl, T. M., Flavell, B. A., Littman, D. R. & Perrier, E. G. 2012, "Interleukin 23 production by intestinal CD103(+)CD11b(+) dendritic cells in response to bacterial flagellin enhances mucosal innate immune defense", Immunity, vol. 36, no. 2, pp. 276-287.

Letran, S. E., Lee, S. J., Atif, S. M., Flores-Langarica, A., Uematsu, S., Akira, S., Cunningham, A. F. & McSorley, S. J. 2011, "TLR5-deficient mice lack basal inflammatory and metabolic defects but exhibit impaired CD4 T cell responses to a flagellated pathogen", Journal of immunology (Baltimore, Md.: 1950), vol. 188, no. 9, pp. 5406-5412.

Machiels K., Joossens M., Sabino J., De Prater V., Arijs I., Ballet V., Claes K., Verhaegen J., Van Assche G., Rutgeerts P. & Vermeire S. 2013, "Predominant dysbiosis in patients with ulcerative colitis is different from Crohn's disease patients", Inflammatory Bowel Diseases. 8th Congress of ECCO, Feb. 14-16, 2013.

Macpherson, A. J. 2006, "IgA adaptation to the presence of commensal bacteria in the intestine", Current topics in microbiology and immunology, vol. 308, pp. 117-136.

Macpherson, A. J., Hunziker, L., McCoy, K. & Lamarre, A. 2001. "IgA responses in the intestinal mucosa against pathogenic and non-pathogenic microorganisms", Microbes and infection/Institut Pasteur, vol. 3, no. 12, pp. 1021-1035.

Macpherson, A. J., Martinic, M. M. & Harris, N. 2002, "The functions of mucosal T cells in containing the indigenous commensal flora of the intestine", Cellular and molecular life sciences: CMLS, vol. 59, no. 12, pp. 2088-2096.

Mahowald, M. A., Rey, F. E., Seedort, H., Tumbaugh, P. J., Fulton, R. S., Wollam A., Shah, N., Wang, C., Magrini, V., Wilson, R. K., Cantarel, B. L., Coutinho, P. M., Henrissat, B., Crock, L. W., Russell, A., Verberkmoes, N. C., Hettich, R. L. & Gordon, J.I. 2009, "Characterizing a model human gut microbiota composed of members of its two dominant bacterial phyla", Proceedings of the National Academy of Sciences of the United States of America, vol. 106, no. 14, pp. 5859-5864.

Mallya, M., Campbell, R. D. & Aguado, B. 2006, "Characterization of the five novel Ly-6 superfamily members encoded in the MHC, and detection of cells expressing their potential ligands", Protein science: a publication of the Protein Society, vol. 15, no. 10, pp. 2244-2256.

Mazmanian, S. K., Liu, C. H., Tzianabos, A. O. & Kasper, D. L. 2005, "An immunomodulatory molecule of symbiotic bacteria directs maturation of the host immune system", Cell, vol. 122, no. 1, pp. 107-118.

McLaughlin, J., Grazia Luca, M., Jones, M. N., D'Amato, M., Dockray, C. J. & Thompson, D. G. 1999, "Fatty acid chain length determines cholecystokinin secretion and effect on human gastric motility", Gastroenterology, vol. 116, no. 1, pp. 46-53.

Monteleone, ., Platt, A. M., Jaensson, E., Agace, W. W. & Mowat, A. M. 2008, "IL-10-dependent partial refractoriness to Toll-like receptor stimulation modulates gut mucosal dendritic cell function", European journal of immunology, vol. 38, no. 6, pp. 1533-1547.

Nutsch, K. M. & Hsieh, C. S. 2012, "T cell tolerance and immunity to commensal bacteria", Current opinion in immunology, vol. 24, no 4, pp. 385-391.

Prakash, T., Oshima, K., Morita, H., Fukuda, S., Imaoka, A., Kumar, N., Sharma, V. K., Kim, S. W., Takahashi, M., Saitou, N., Taylor, T. D., Ohno, H., Umesaki, Y. & Hattori, M. 2011, "Complete genome sequences of rat and mouse segmented filamentous bacteria, a potent inducer of th17 cell differentiation", Cell host & microbe, vol. 10, no. 3, pp. 273-284.

Qin, J., Li, R., Rees, J., Arumugam, M., Burgdorf, K. S., Manichanh, C., Nielsen, T., Pons, N., Levenez, F., Yamada, T., Mende, D. R., Li, J., Xu, J., Li, S., Li, D., Cao, J., Wang, B., Liang, H., Zheng, H., Xie, Y., Tap, J., Lepage, P., Bertalan, M., Batto, J. M., Hansen, T., Le Paslier, D., Linneberg, A., Nielsen, H. B., Pelletier, E., Henault, P., Sicheritz-Ponten, T., Turner, K., Zhu, H., Yu, C., Li, S., Jian, M., Zhou, Y., Li, Y., Zhang, X., Li, S., Qin, N., Yang, H., Wang, J., Brunak, S., Dore, J., Guarner, F., Kristiansen, K., Pedersen, O., Parkhill, J., Weissenbach, J., MetaHIT Consortium, Bork, P., Ehrlich, S. D. & Wang, J. 2010, "A human gut microbial gene catalogue established by metagenomic sequencing", Nature, vol. 464, no. 7285, pp. 59-65.

Round, J. L., Lee, S. M., Li, J., Tran, G., Jabri, B., Chatila, T. A. & Mazmanian, S. K. 2011, "The Toll-like receptor 2 pathway establishes colonization by a commensal of the human microbiota", Science (New York, N.Y.), vol. 332, no. 6032, pp. 974-977.

Scanlan, P. D., Shanahan, F., O'Mahony, C. & Marchesi, J. R. 2006, "Culture-independent analyses of temporal variation of the dominant fecal microbiota and targeted bacterial subgroups in Crohn's disease", Journal of clinical microbiology, vol. 44, no. 11, pp. 3980-3988.

Schulke, S., Burggraf, M., Waibier, Z., Wangorsch, A., Wolfheimer, S., Kalinke, U., Vieths, S., Toda, M. & Scheurer, S. 2011, "A fusion protein of flagellin and ovalbumin suppresses the TH2 response and prevents murine intestinal allergy", The Journal of allergy and clinical immunology, vol. 128, no. 6, pp. 1340-1348. e12, Sczesnak, A., Segata, N., Qin, X., Severs, D., Petrosino, J. F., Huttenhower, C., Littman, D. R. & Ivanov, I. I. 2011, "The genome of th17 cell-inducing segmented filamentous bacteria reveals extensive auxotrophy and adaptations to the intestinal environment". Cell host & microbe, vol. 10, no. 3, pp. 260-272.

Spor, A., Koren, O. & Ley, R. 2011, "Unravelling the effects of the environment and host genotype on the gut microbiome", Nature reviews. Microbiology, vol. 9, no. 4, pp. 279-290, Tremaroli, V., Kovatcheva-Datchary, P. & Backhed, F. 2010, "A role for the gut microbiota energy harvesting?", Gut, vol. 59, no. 12, pp. 1589-1590.

Turnbaugh, P. J., Backhed, F., Fulton, L. & Gordon, J. I. 2008, "Diet-induced obesity is linked to marked but reversible alterations in the mouse distal gut microbiome", Cell host & microbe, vol. 3, no. 4, pp. 213-223.

Turnbaugh, P. J., Ley, R. E., Mahowald, M. A., Magrini, V., Mardis, E. R. & Gordon, J. I. 2006, "An obesity-associated gut microbiome, with increased capacity for energy harvest", Nature, vol. 444, no. 7122, pp. 1027-1031, Ukena, S. N., Singh, A., Dringenberg, U., Engelhardt, R., Seidler, U., Hansen, W., Bleich, A., Bruder, D., Franzke, A., Roger, G., Suerbaum, S., Buer, J., Gunzer, F. & Westendorf, A. M. 2007, "Probiotic *Escherichia coli* Nissle 1917 inhibits leaky gut by enhancing mucosal integrity", PloS one, vol. 2, no, 12, pp. e1308.

Vijay-Kumar, M. Sanders, C. J., Taylor, R. T., Kumar, A., Aitken, J. D., Sitaraman, S. V., Neish, A. S., Uematsu, S., Akira, S., Williams, I. R. & Gewirtz, A. T. 2007, "Deletion of TLR5 results in spontaneous colitis in mice", The Journal of clinical investigation, vol. 117, no. 12, pp. 3909-3921.

Werth, M., Walentin, K., Aue, A., Schonheit, J., Wuebken, A., Pode-Shakked, N., Vilianovitch, L., Erdmann, B., Dekel, B., Bader, M., Barasch, J., Rosenbauer, F., Luft, F. C. & Schmidt-Ott, K. M. 2010, "The transcription factor grainyhead-like 2 regulates the molecular composition of the epithelial apical junctional complex", Development (Cambridge, England), vol. 137, no. 22, pp. 3835-3845.

Wilson, R. H., Maruoka, S., Whitehead, G. S., Foley, J. F., Hake, C. P., Sever, M. L., Zeldin, D. C., Kraft, M., Garantziotis, S., Nakano, H. & Cook, D. N. 2012. "The Toll-like, receptor 5 ligand flagellin promotes asthma by priming allergic responses to indoor allergens", Nature medicine, vol. 18, no. 11, pp. 1705-1710.

Yoon, S. I., Kurnasov, O., Natarajan, V., Hong, M., Gudkov, A. V., Osterman, A. L. & Wilson, I. A. 2012, "Structural basis of TLR5-flagellin recognition and signaling". Science (New York, N.Y.), vol. 335, no. 6070, pp. 859-864.

REFERENCE LIST FOR SUPPLEMENTARY INFORMATION (1) Genome sequence assembly using trace signals and additional sequence information. Computer Science and Biology: Proceedings of the German Conference on Bioinformatics (GCB); 1999.

(2) Aziz R K. Bartels D, Best A A, DeJongh M, Disz T, Edwards R A, et al. The RAST Server: rapid annotations using subsystems technology. BMC Genomics 2008 Feb. 8; 9:75-2164-9-755.

(3) Dennis G, Jr, Sherman B T, Hosack D A, Yang J, Gao W, Lane H C, et al. DAVID: Database for Annotation, Visualization, and Integrated Discovery. Genome Biol 2003; 4(5):P3.

(4) Untergasser A, Nijveen H, Rao X, Bisseling T, Geurts R, Leunissen J A. Primer3Plus, an enhanced web interface to Primer3. Nucleic Acids Res 2007 July; 35(Web Server issue):W71-4.

(5) Duck L W, Walter M R, Novak J, Kelly D, Tomasi M, Cong Y, et al. Isolation of flagellated bacteria implicated in Crohn's disease. Inflamm Bowel Dis 2007 October; 13(10):1191-1201.

(6) Berg D J, Davidson N, Kuhn R, Muller W, Menon S, Holland G, Thompson-Snipes L, Leach M W, Rennick D. Enterocolitis and colon cancer in interleukin-10-deficient mice are associated with aberrant cytokine production and CD4(+) TH1-like responses. J. Clin. Invest., 1996, 98, 4, 1010-1020.

(7) Monteleone I, Platt A M, Jaensson E, Agace W W, Mowat A M. IL-10-dependent partial refractoriness to Toll-like receptor stimulation modulates gut mucosal dendritic cell function. Eur J Immunol. 2008 38(6):1533-47

(8) Inaba K, Inaba M, Romani N, Aya H, Deguchi M, Ikehara S, et al. Generation of large numbers of dendritic cells from mouse bone marrow cultures supplemented with granulocyte/macrophage colony-stimulating factor. J Exp Med 1992 Dec. 1; 176(6):1693-702.

(9) Brasel K, De Smedt T, Smith J L, Maliszewski C R. Generation of murine dendritic cells from flt3-ligand-supplemented bone marrow cultures. Blood 2000 Nov. 1; 96(9):3029-3039,

(10) Weigel B J, Nath N, Taylor P A, Panoskaltsis-Mortari A, Chen W, Krieg A M, et al. Comparative analysis of murine marrow-derived dendritic cells generated by Flt3L or GM-CSF/IL-4 and matured with immune stimulatory agents on the in vivo induction of antileukemia responses. Blood 2002 Dec. 1; 100(12):4169-4176.

(10) Xu Y, Zhan Y, Lew A M, Naik S H, Kershaw M H, Differential development of murine dendritic cells by GM-CSF versus Flt3 ligand has implications for inflammation and trafficking. J Immunol 2007 Dec. 1; 179(11): 7577-7584.

(12) Olivera L, Canul R R, Pereira-Pacheco F, Cockburn J, Soldani F, McKenzie N H, et al, Nutritional and physiological responses of young growing rats to diets containing raw cowpea seed meal, protein isolate (globulins), or starch. J Agric Food Chem 2003 Jan. 1; 51(1):319-325.

All publications mentioned in the above specification are herein incorporated by reference. Various modifications and variations of the described methods and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention which are obvious to those skilled in biochemistry and molecular biology or related fields are intended to be within the scope of the following claims.

The invention claimed is:

1. A pharmaceutical composition that comprises:
an isolated, recombinant *Roseburia* flagellin polypeptide in a unit dose comprising a therapeutically effective amount sufficient to reduce inflammation by increasing a level of IL-10 when the unit dose is administered to a subject suffering from a gastrointestinal inflammatory disorder or an autoimmune disorder, relative to an extent inflammation prior to the administering, wherein the isolated, recombinant *Roseburia* flagellin polypeptide comprises:

a polypeptide sequence having at least 85% identity to the polypeptide sequence of SEQ ID NO: 2, as determined by a sequence alignment performed using BLAST, wherein said polypeptide sequence comprises a region that has at least 90% identity to the polypeptide sequence of amino acids 79-117 of SEQ ID NO: 2, as determined by a sequence alignment performed using BLAST; and a preservative or stabilizer, and wherein the isolated, recombinant *Roseburia* flagellin polypeptide binds to TLR5.

2. A method of making the pharmaceutical composition according to claim 1, the method comprising:

expressing the recombinant *Roseburia* flagellin polypeptide;

purifying the expressed recombinant *Roseburia* flagellin polypeptide to produce the isolated, recombinant *Roseburia* flagellin polypeptide; and admixing the isolated, recombinant *Roseburia* flagellin polypeptide with the preservative or stabilizer to form the pharmaceutical composition.

3. The pharmaceutical composition of claim 1, wherein the isolated, recombinant *Roseburia* flagellin polypeptide is a FlaA1 polypeptide.

4. The pharmaceutical composition of claim 1, wherein the isolated, recombinant *Roseburia* flagellin polypeptide comprises a *Roseburia hominis* flagellin polypeptide or a *Roseburia intestinalis* flagellin polypeptide.

5. The pharmaceutical composition of claim 1, wherein the isolated, recombinant *Roseburia* flagellin polypeptide comprises a polypeptide sequence that has at least 95% sequence identity to the polypeptide sequence of SEQ ID NO: 2, as determined by a sequence alignment performed using BLAST, and at least 95% identity to amino acids 79-117 of SEQ ID NO: 2, as determined by a sequence alignment performed using BLAST.

6. The pharmaceutical composition of claim 1, wherein the isolated, recombinant *Roseburia* flagellin polypeptide comprises the polypeptide sequence of SEQ ID NO: 2.

7. The pharmaceutical composition of claim 1, wherein the isolated, recombinant *Roseburia* flagellin polypeptide comprises at least 50 contiguous amino acids of the polypeptide sequence of SEQ ID NO: 2 within the sequence having at least 85% identity to the polypeptide sequence of SEQ ID NO: 2, as determined by a sequence alignment performed using BLAST.

8. The pharmaceutical composition of claim 1, wherein the isolated, recombinant *Roseburia* flagellin polypeptide comprises at least 100 contiguous amino acids of the polypeptide sequence of SEQ ID NO: 2 within the sequence having at least 85% identity to the polypeptide sequence of SEQ ID NO: 2, as determined by a sequence alignment performed using BLAST.

9. The pharmaceutical composition of claim 1, wherein the isolated, recombinant *Roseburia* flagellin polypeptide comprises at least 150 contiguous amino acids of the polypeptide sequence of SEQ ID NO: 2 having at least 85% identity to the polypeptide sequence of SEQ ID NO: 2, as determined by a sequence alignment performed using BLAST.

10. The pharmaceutical composition of claim 1, wherein the isolated, recombinant *Roseburia* flagellin polypeptide comprises at least 175 contiguous amino acids of the polypeptide sequence of SEQ ID NO: 2 having at least 85% identity to the polypeptide sequence of SEQ ID NO: 2, as determined by a sequence alignment performed using BLAST.

11. The pharmaceutical composition of claim 1, wherein the pharmaceutical composition is a solid composition.

12. The pharmaceutical composition of claim 11, wherein the pharmaceutical composition is in the form of one or more tablets or capsules.

13. The pharmaceutical composition of claim 1, wherein the pharmaceutical composition is an enteric formulation.

14. The pharmaceutical composition of claim 1, wherein the isolated, recombinant *Roseburia* flagellin polypeptide is comprised in a fusion protein.

15. The pharmaceutical composition of claim 1, wherein the isolated recombinant *Roseburia* flagellin polypeptide has at least 98% identity to the polypeptide sequence of SEQ ID NO: 2, as determined by a sequence alignment performed using BLAST, and at least 98% identity to amino acids 79-117 of SEQ ID NO: 2, as determined by a sequence alignment performed using BLAST.

16. The pharmaceutical composition of claim 1, wherein the isolated, recombinant *Roseburia* flagellin polypeptide has at least 99% identity to the polypeptide sequence of SEQ ID NO: 2, as determined by a sequence alignment performed using BLAST.

17. The pharmaceutical composition of claim 1, wherein the isolated, recombinant *Roseburia* flagellin polypeptide increases a level of IL-10 by at least 5-fold after contacting the isolated, recombinant *Roseburia* flagellin polypeptide with a bone marrow dendritic cell in an amount of about 100 ng/mL in vitro, relative to a level of IL-10 prior to the contacting.

* * * * *